United States Patent
Dragoli et al.

(10) Patent No.: US 11,858,959 B2
(45) Date of Patent: Jan. 2, 2024

(54) GLYCYRRHETINIC ACID DERIVATIVES FOR USE IN TREATING HYPERKALEMIA

(71) Applicant: ARDELYX, INC., Fremont, CA (US)

(72) Inventors: Dean Dragoli, Fremont, CA (US); Gary Luehr, Fremont, CA (US); Tao Chen, Fremont, CA (US); Jason Lewis, Fremont, CA (US); Michael Leadbetter, Fremont, CA (US)

(73) Assignee: Ardelyx, Inc., Fremont, CA (US)

( * ) Notice: Subject to any disclaimer, the term of this patent is extended or adjusted under 35 U.S.C. 154(b) by 120 days.

(21) Appl. No.: 17/429,599

(22) PCT Filed: Feb. 6, 2020

(86) PCT No.: PCT/US2020/017077
§ 371 (c)(1),
(2) Date: Aug. 9, 2021

(87) PCT Pub. No.: WO2020/163642
PCT Pub. Date: Aug. 13, 2020

(65) Prior Publication Data
US 2022/0106354 A1 Apr. 7, 2022

Related U.S. Application Data

(60) Provisional application No. 62/802,210, filed on Feb. 7, 2019.

(51) Int. Cl.
| | | |
|---|---|---|
| *C07J 63/00* | (2006.01) | |
| *A61P 3/12* | (2006.01) | |
| *A61K 31/56* | (2006.01) | |
| *A61P 5/40* | (2006.01) | |
| *A61K 31/58* | (2006.01) | |

(52) U.S. Cl.
CPC ............ *C07J 63/008* (2013.01); *A61K 31/56* (2013.01); *A61K 31/58* (2013.01); *A61P 3/12* (2018.01); *A61P 5/40* (2018.01)

(58) Field of Classification Search
CPC . A61K 31/56; A61K 31/58; A61P 3/12; A61P 5/40; C07J 63/008
See application file for complete search history.

(56) References Cited

U.S. PATENT DOCUMENTS

2015/0218206 A1  8/2015  Yoon

FOREIGN PATENT DOCUMENTS

| WO | 2005027882 A1 | 3/2005 |
| WO | 2007105015 A2 | 9/2007 |
| WO | 2010103046 A1 | 9/2010 |

OTHER PUBLICATIONS

Database CA, "Triterpenoids. XXV. PMR spectra of glycyrrhetic acid derivatives", Accession No. 1971:420694 Abstract, 1 page (1971).
Gaware, R, et al., "Synthesis of new glycyrrhetinic acid derived ring A azepanone, 29-urea and 29-hydroxamic acid derivatives as selective 11 beta-hydroxysteroid dehydrogenase 2 inhibitors", Bioorganic Med Chem 19, 1866-1880 (2011).
Kratschmar, D, et al., "Characterization of activity and binding mode of glycyrrhetinic acid derivatives inhibiting 11 beta-hydroxysteroid dehydrogenase type 2", Journal of Steroid Biochemistry & Molecular Biology 125, 129-142 (2011).
Patent Cooperation Treaty, International Searching Authority, Search Report and Written Opinion for PCT/US2020/017077, 15 pages, dated May 13, 2020.
Schuster, D, et al., "The Discovery of New 11β-Hydroxysteroid Dehydrogenase Type 1 Inhibitors by Common Feature Pharmacophore Modeling and Virtual Screening", J Med Chem 49, 3454-3466 (2006).
Stanetty, C, et al., "Synthesis of novel 3-amino and 29-hydroxamic acid derivatives of glycyrrhetinic acid as selective 11β-hydroxysteroid dehydrogenase 2 inhibitors", Bioorganic & Medicinal Chemistry 18, 7522-7541 (2010).
Yoon, Y, et al., "Discovery of ursolic acid prodrug (NX-201): Pharmacokinetics and in vivo antitumor effects in PANC-1 pancreatic cancer", Bioorganic Medicinal Chemistry Letters 26, 5524-5527 (2016).

*Primary Examiner* — Theodore R. Howell
(74) *Attorney, Agent, or Firm* — Viksnins Harris Padys Malen LLP

(57) ABSTRACT

The present invention provides a compound of formula (I) or a salt thereof: (Formula (I)) wherein X, L, V, $R_1$; $R_2$, $R_3$ and $R_4$, are as defined herein. The claimed compounds inhibit the enzyme 11-hydroxysteroid dehydrogenase type 2 (11-HSD2) and as a result are useful in the treatment of hyperkalemia by preventing cortisol from being oxidised to cortisone and thus allowing it to occupy the mineralocorticoid receptor, thus stimulating potassium excretion.

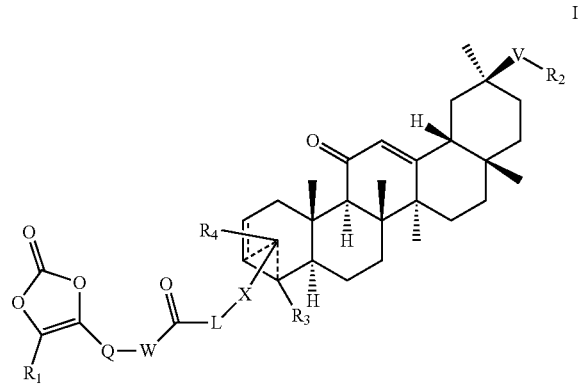

22 Claims, 3 Drawing Sheets

GLYCYRRHETINIC ACID DERIVATIVES FOR USE IN TREATING HYPERKALEMIA

CROSS-REFERENCE TO RELATED APPLICATIONS

This application claims priority to U.S. Provisional Application No. 62/802,210 that was filed on 7 Feb. 2019. The entire contents of the application referenced above are hereby incorporated by reference herein.

FIELD OF THE INVENTION

The present invention relates to compounds that inhibit 11β-hydroxysteroid dehydrogenase 2 and methods of using these compounds to remove potassium from the gastrointestinal tract, including methods of treating hyperkalemia.

BACKGROUND OF THE INVENTION

Potassium is the most abundant cation in the intracellular fluid and plays an important role in normal human physiology, especially with regard to the firing of action potential in nerve and muscle cells. Total body potassium content is about 50 mmol/kg of body weight, which translates to approximately 3500 mmols of potassium in a 70 kg adult. The bulk of total body potassium is intracellular (~98%), with only approximately 70 mmol (~2%) in the extracellular space. This large differential between intracellular potassium (~120-140 mmol/L) and extracellular potassium (~4 mmol/L) largely determines the resting membrane potential of cells. As a consequence, very small absolute changes in the extracellular potassium concentration will have a major effect on this ratio and consequently on the function of excitable tissues (muscle and nerve). Extracellular potassium levels are therefore tightly regulated.

Two separate and cooperative systems participate in potassium homeostasis, one regulating external potassium balance (the body parity of potassium intake vs. potassium elimination) while the other regulates internal potassium balance (distribution between intracellular and extracellular fluid compartments. Intracellular/extracellular balance provides short-term management of changes in serum potassium, and is primarily driven physiologically by the action of $Na^+$, $K^+$-ATPase "pumps," which use the energy of ATP hydrolysis to pump $Na^+$ and $K^+$ against their concentration gradients. Almost all cells possess a $Na^+$, $K^+$-ATPase. Body parity is managed by elimination mechanisms via the kidney and gastrointestinal tract: in healthy kidneys, 90-95% of the daily potassium load is excreted through the kidneys with the balance eliminated in the feces.

Due to the fact that intracellular/extracellular potassium ratio ($K_i$:$K_e$ ratio) is the major determinant of the resting membrane potential of cells, small changes in $K_e$ (i.e., serum [K]) have profound effects on the function of electrically active tissues, such as muscle and nerve. Potassium and sodium ions drive action potentials in nerve and muscle cells by actively crossing the cell membrane and shifting the membrane potential, which is the difference in electrical potential between the exterior and interior of the cell. In addition to active transport, $K^+$ can also move passively between the extracellular and intracellular compartments. An overload of passive $K^+$ transport, caused by higher levels of blood potassium, depolarizes the membrane in the absence of a stimulus. Excess serum potassium, known as hyperkalemia, can disrupt the membrane potential in cardiac cells that regulate ventricular conduction and contraction.

Clinically, the effects of hyperkalemia on cardiac electrophysiology are of greatest concern because they can cause arrhythmias and death. Since the bulk of body parity is maintained by renal excretion, it is therefore to be expected that as kidney function declines, the ability to manage total body potassium becomes impaired.

Hyperkalemia is defined as a serum potassium level above the normal range, typically >5.0 mmol/L. Moderate hyperkalemia (serum potassium above 6.0 mEq/L) has been reported to have a 1-day mortality rate up to 30 times higher than that of patients with serum potassium less than 5.5 mEq/L. Severe hyperkalemia (serum K+ of at least 6.5 mmol/L) is a potentially life-threatening electrolyte disorder that has been reported to occur in 1% to 10% of all hospitalized patients and constitutes a medical emergency requiring immediate treatment. Hyperkalemia is caused by deficiencies in potassium excretion, and since the kidney is the primary mechanism of potassium removal, hyperkalemia commonly affects patients with kidney diseases such as chronic kidney disease (CKD) or end-stage renal disease (ESRD). However, episodes of hyperkalemia can occur in patients with normal kidney function, where it is still a life-threatening condition. For example, in hospitalized patients, hyperkalemia has been associated with increased mortality in patients both with and without CKD. While CKD is the most common predisposing condition for hyperkalemia, the mechanisms driving hyperkalemia typically involve a combination of factors, such as increased dietary potassium intake, disordered distribution of potassium between intracellular and extracellular compartments and abnormalities in potassium excretion. These mechanisms can be modulated by a variety of factors with causality outside of CKD. These include the presence of other comorbidities, such as type 2 diabetes mellitus (T2DM), cardiovascular disease (CVD) or the use of co-medications that can disrupt potassium homeostasis as side effects, such as blockade of the renin-angiotensin-aldosterone system (RAAS), for example, with angiotensin-converting-enzyme (ACE) inhibitors and angiotensin-receptor blockers (ARBs).

Serum potassium can be lowered by two general mechanisms: the first is by shifting potassium intracellularly using agents such as insulin, albuterol or sodium bicarbonate. The second is by excreting it from the body using 1 of 4 routes: the stool with K binding resins such as sodium polystyrene sulfonate (Na PSS), the urine with diuretics, the blood with hemodialysis or the peritoneal fluid with peritoneal dialysis. Other than Na PSS, the medications that treat hyperkalemia, such as insulin, diuretics, beta agonists and sodium bicarbonate, simply cause hypokalemia as a side effect and are not suitable as chronic treatments. Definitive therapy necessitates the removal of potassium from the body. Studies have confirmed that reducing serum potassium levels in hyperkalemia patients actually reduces the mortality risk, further solidifying the role of excess potassium in the risk of death. While Na PSS is the current standard of care treatment for potassium reduction in the U.S., the calcium salt of PSS (Ca PSS) is also commonly used in other parts of the world, including Europe (e.g., Resonium) and Japan. Kayexalate/Na PSS is poorly tolerated causing a high incidence of GI side effects including nausea, vomiting, constipation and diarrhea. In addition, Kayexalate is a milled product and consists of irregularly shaped particles ranging in size from about 1-150 µm in size, and has sand-like properties in the human mouth: on ingestion, it gives a strong sensation of foreign matter on the palate and this sensation contributes negatively to patient compliance. In total, the physical properties and associated side-effects of Kayexalate lead to poor compliance and render the drug suboptimal for chronic use. Due to these properties, there has been a long felt need to provide an optimal drug for chronic use.

The mineralocorticoid receptor (or MR, MLR, MCR), also known as the aldosterone receptor or nuclear receptor subfamily 3, group C, member 2, (NR3C2) is a protein that in humans is encoded by the NR3C2 gene that is located on chromosome 4q31.1-31.2. MR is a receptor with equal affinity for mineralocorticoids and glucocorticoids including cortisol. It belongs to the nuclear receptor family where the ligand diffuses into cells, interacts with the receptor and results in a signal transduction affecting specific gene expression in the nucleus. MR is expressed in many tissues, such as the kidney, colon, heart, central nervous system (hippocampus), brown adipose tissue and sweat glands. Activation of the mineralocorticoid receptor by ligands aldosterone and cortisol in epithelial tissues promotes excretion of potassium. In intact animals, the MR is "protected" from the greater concentration of cortisol (100-1000 fold) by co-localization of an enzyme, 1 ip-hydroxysteroid dehydrogenase 2; (also referred to herein as 11β-HSD2 and HSD2 herein), that oxidizes cortisol to the inactive metabolite cortisone. HSD2, thus prevents MR activation and therefore inhibits excretion of potassium.

Accordingly, inhibition of HSD2 to prevent inactivation of cortisol activation of the MR is a promising mechanism for promoting potassium excretion, for example, in the treatment of hyperkalemia.

SUMMARY OF THE INVENTION

In one aspect of the present invention there is provided a compound of formula I or a salt thereof:

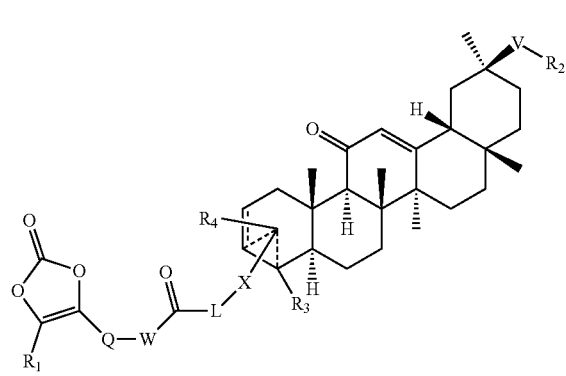

I wherein,
X is a bond, —O—, —C(O)—, —N($R_x$)—, —C(O)N($R_x$)—, —N($R_x$)—C(O)—, —S(O)$_n$—N($R_x$)— or —N($R_x$)—S(O)$_n$—;
L is a bond, alkylene wherein one or more non-adjacent methylene groups of said alkylene are replaced with —O—; divalent aryl or divalent heteroaryl; or L is alkylene-Y-alkylene wherein Y is O, N$R_x$, S, SO, $SO_2$ or a divalent heterocycle; wherein said alkylene groups are optionally substituted with OH, —C(O)O—$R_1$, alkyl or alkyl substituted with OH or —C(O)O—$R_1$; and wherein a carbon of said alkylene groups and $R_x$ optionally together form a heterocycle; provided that when X is other than a bond, then L is other than a bond;

W is O or S;
Q is a bond or alkylene;
$R_1$ is H, alkyl, a carbocycle or a heterocycle wherein said alkyl, carbocycle and heterocycle are each optionally substituted with halogen, OH, amino, oxo, carboxy, acyloxy, alkoxycarbonyl, alkoxyacyloxy, alkoxycarbonyloxy, aminocarbonyl, a carbocycle optionally substituted with alkyl, haloalkyl, oxo, amino and halogen and a heterocycle optionally substituted with alkyl, oxo, amino and halogen; and a carbocycle or heterocycle optionally substituted with alkyl, haloalkyl, oxo, amino and halogen;
V is —C(O)O—, —C(O)O—($CHR_5$)—O—C(O)—, —C(O)O—($CHR_5$)—O—C(O)—O—, —C(O)N($R_5$)—, —C(O)N($R_5$)O—, —NH—C(O)—N($R_5$)— or NH—S(O)$_n$—;
$R_2$ is H or $R_5$;
$R_3$ is absent or alkyl;
$R_4$ is absent, H, OH, =O, —$R_6$, —O—$R_6$, —C(O)O—$R_6$, —O—C(O)—$R_6$, —O—C(O)—O—$R_6$, —O—C(O)—NR$_5$R$_6$, —NR$_5$R$_6$, —NR$_5$—C(O)—$R_6$, —NR$_5$—C(O)—O—$R_6$, —NR$_5$—SO$_2$—$R_6$, =N—O—$R_5$;
$R_5$ is H or alkyl optionally substituted with a carbocycle or heterocycle wherein said carbocycle and heterocycle are optionally substituted with halogen, OH, oxo and alkyl;
$R_6$ is H, alkyl, a carbocycle, a heterocycle wherein said alkyl, carbocycle and heterocycle are optionally substituted with halogen, OH, SH, alkylthio, —S(O)-alkyl, —SO$_2$-alkyl, amino, —NHC(O)-alkyl, oxo, alkyl, carboxyl, acyl, acyloxy, alkoxy, alkoxycarbonyl, a carbocycle optionally substituted with halogen, OH, amino or alkyl, or a heterocycle optionally substituted with halogen, OH, amino or alkyl; and wherein one or more non-adjacent methylene groups in each of said alkyl groups of $R_6$ are optionally replaced with —O— or —S—;
$R_x$ is H, —C(O)O—$R_1$, or alkyl optionally substituted with —C(O)O—$R_1$; and
n is 1 or 2.

In another aspect of the invention, there are provided compositions comprising compounds of Formula I and a carrier, diluent or excipient.

In another aspect of the invention, there is provided a method of inhibiting conversion of cortisol to cortisone by HSD2 comprising contacting HSD2 with a compound of Formula I.

In another aspect of the invention, there is provided a method for promoting activation MR in a mammal, comprising administering to said mammal an effective amount of a compound of Formula I.

In another aspect of the invention, there is provided a method of reducing potassium levels in plasma of a mammal, comprising administering to said mammal an effective amount of a compound of Formula I.

In another aspect of the invention, there is provided a method for promoting potassium ion secretion into the colonic lumen of a mammal, comprising administering to said mammal an effective amount of a compound of Formula I. In another aspect of the invention, there is provided a method for treating hyperkalemia in a mammal, comprising administering to said mammal an effective amount of a compound of Formula I.

In another aspect of the invention, there is provided a method for treating or preventing hyperkalemia in a mammal comprising coadministering a compound of Formula I with an inhibitor of the renin-angiotensin-aldosterone system (RAAS).

DETAILED DESCRIPTION OF THE INVENTION

Figure 1:
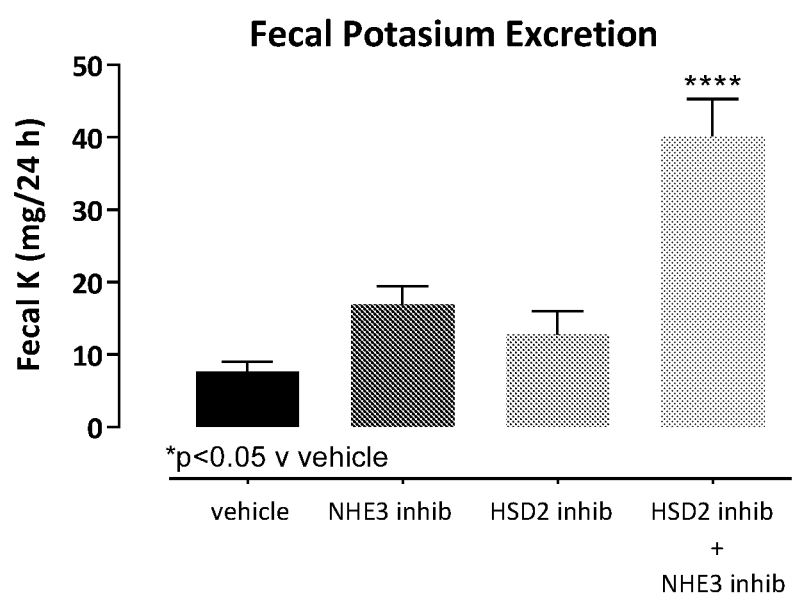
FIG. 1 illustrates the synergistic effect on potassium excretion in feces upon administration of an HSD2 inhibitor in combination with an NHE3 inhibitor.
Figure 2:
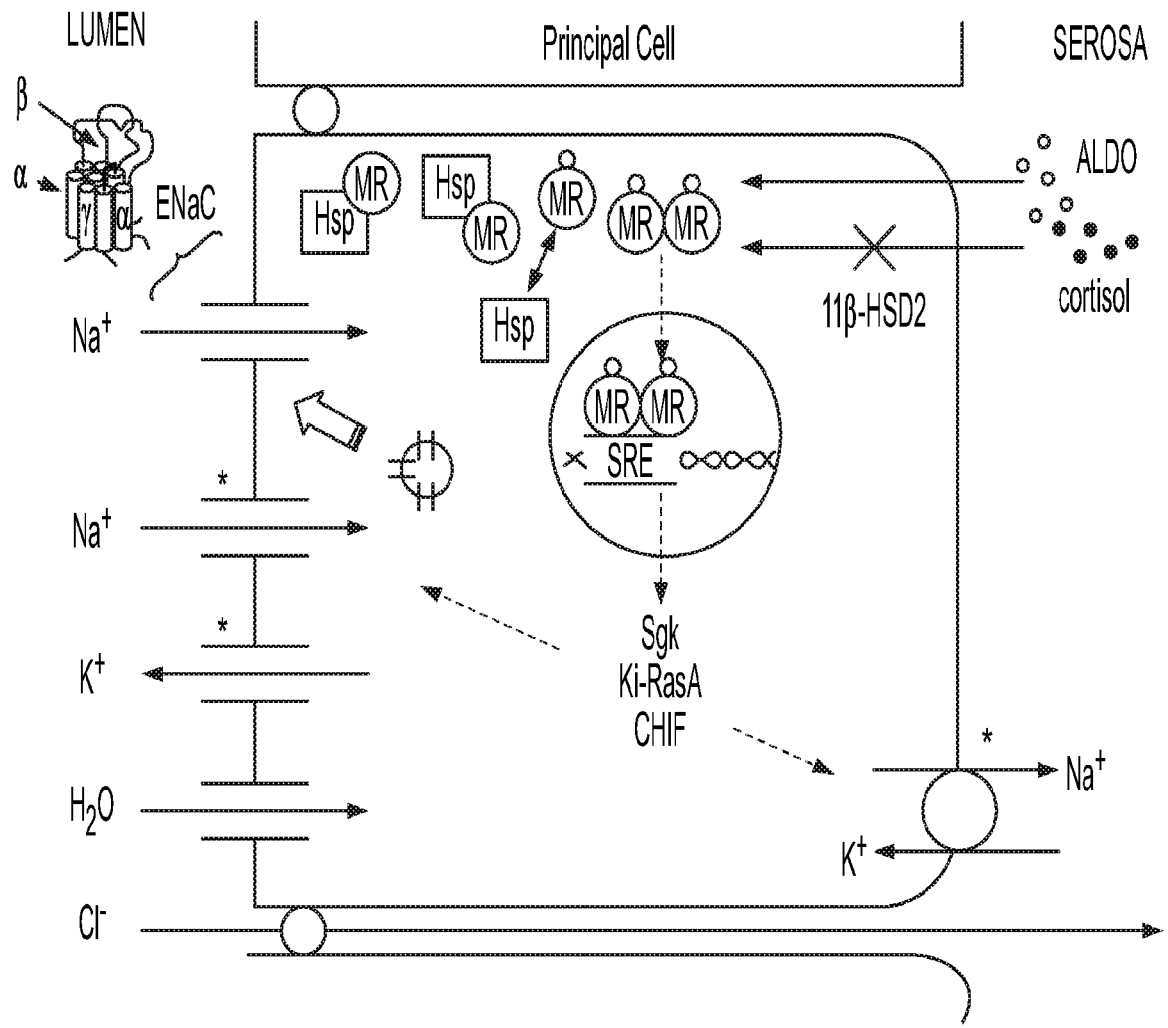
FIG. 2 is an illustration of HSD2 inhibition in an epithelial cell allowing cortisol to activate the mineralocorticoid receptor (MR) which facilitates excretion of potassium into the lumen.

Glycyrrhizin (or glycyrrhizic acid or glycyrrhizinic acid) is extract of the plant called Glycyrrhiza which is derived from the ancient Greek term 'glykos', meaning sweet, and 'rhiza', meaning root. Glycyrrhiza was indulged upon by many prophets and pharaohs. Licorice extract has been utilized in the battlefields and the desert where soldiers and travelers drank it to suppress their thirst sensation on long marches. Glycyrrhetic acid, the active metabolite in licorice, inhibits HSD2 with a resultant cortisol-induced mineralocorticoid effect and the tendency towards the reduction of potassium levels. While glycyrrhetic acid lowers potassium levels, it is associated with abnormal heart rhythms, hypertension, edema, lethargy, congestive heart failure, hypokalemia and rhabdomyolysis. Accordingly, it would be desirable to provide a compound that promotes potassium excretion in patients suffering from hyperkalemia like glycyrrhetinic acid without the undesirable side effects.

The present invention provides a compound of formula I or a salt thereof:

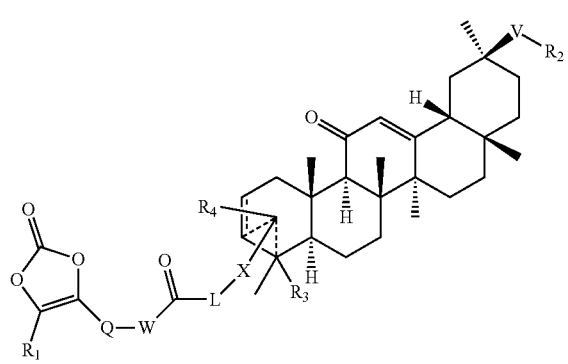

I wherein,
X is a bond, —O—, —C(O)—, —N($R_x$)—, —C(O)N($R_x$)—, —N($R_x$)—C(O)—, —S(O)$_n$—N($R_x$)— or —N($R_x$)—S(O)$_n$—;
L is a bond, alkylene wherein one or more non-adjacent methylene groups of said alkylene are replaced with —O—; divalent aryl or divalent heteroaryl; or L is alkylene-Y-alkylene wherein Y is O, N$R_x$, S, SO, SO$_2$ or a divalent heterocycle; wherein said alkylene groups are optionally substituted with OH, —C(O)O—$R_1$, alkyl or alkyl substituted with OH or —C(O)O—$R_1$; and wherein a carbon of said alkylene groups and $R_x$ optionally together form a heterocycle; provided that when X is other than a bond, then L is other than a bond;
W is O or S;
Q is a bond or alkylene;
$R_1$ is H, alkyl, a carbocycle or a heterocycle wherein said alkyl, carbocycle and heterocycle are each optionally substituted with halogen, OH, amino, oxo, carboxy, acyloxy, alkoxycarbonyl, alkoxyacyloxy, alkoxycarbonyloxy, aminocarbonyl, a carbocycle optionally substituted with alkyl, haloalkyl, oxo, amino and halogen and a heterocycle optionally substituted with alkyl, oxo, amino and halogen; and a carbocycle or heterocycle optionally substituted with alkyl, haloalkyl, oxo, amino and halogen;
V is —C(O)O—, —C(O)O—(CHR$_5$)—O—C(O)—, —C(O)O—(CHR$_5$)—O—C(O)—O—, —C(O)N(R$_5$)—, —C(O)N(R$_5$)O—, —NH—C(O)—N(R$_5$)— or NH—S(O)$_n$—;
$R_2$ is H or $R_1$;
$R_3$ is absent or alkyl;
$R_4$ is absent, H, OH, =O, —R$_6$, —O—R$_6$, —C(O)O—R$_6$, —O—C(O)—R$_6$, —O—C(O)—O—R$_6$, —O—C(O)—NR$_5$R$_6$, —NR$_5$R$_6$, —NR$_5$—C(O)—R$_6$, —NR$_5$—C(O)—O—R$_6$, —NR$_5$—SO$_2$—R$_6$, =N—O—R$_5$;
$R_5$ is H or alkyl;
$R_6$ is H, alkyl, a carbocycle, a heterocycle wherein said alkyl, carbocycle and heterocycle are optionally substituted with halogen, OH, SH, alkylthio, —S(O)-alkyl, —SO$_2$-alkyl, amino, —NHC(O)-alkyl, oxo, alkyl, carboxyl, acyl, acyloxy, alkoxy, alkoxycarbonyl, a carbocycle optionally substituted with halogen, OH, amino or alkyl, or a heterocycle optionally substituted with halogen, OH, amino or alkyl; and wherein one or more non-adjacent methylene groups in each of said alkyl groups of $R_6$ are optionally replaced with —O— or —S—;
$R_x$ is H, —C(O)O—$R_1$, or alkyl optionally substituted with —C(O)O—$R_1$; and
n is 1 or 2.

Figure 3:
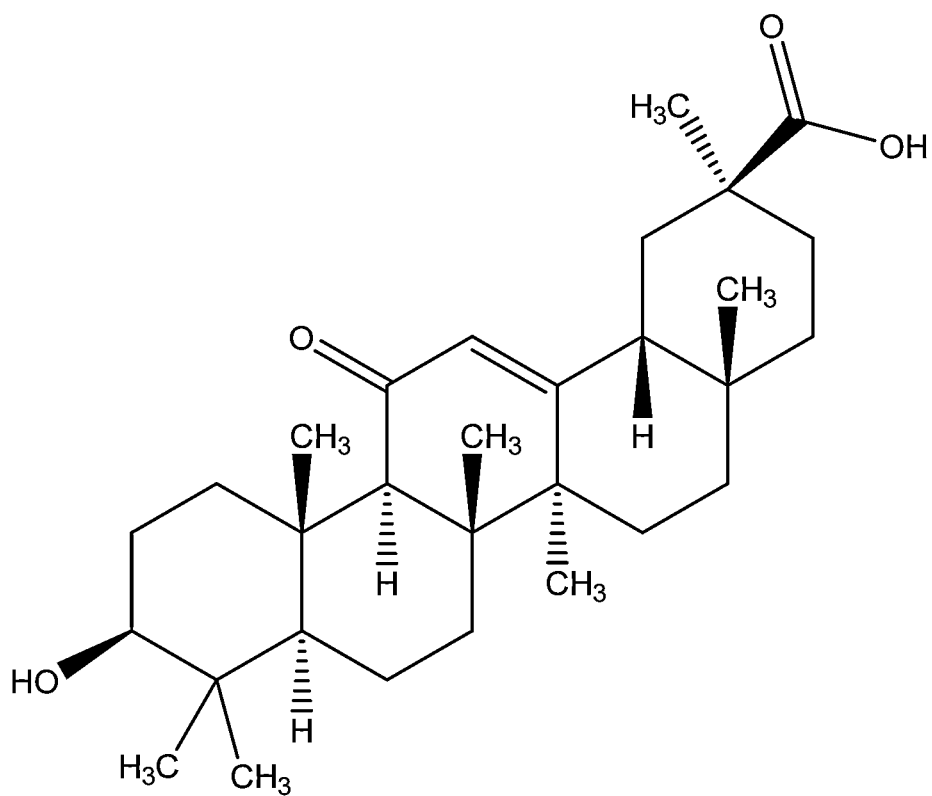
FIG. 3 depicts the structure of glycyrrhetinic acid with the numbering of the carbon atoms.

The dashed lines between the 2- and 3-positions of the fused ring system indicate alternatively a single or double bond. The dashed lines converging inside the fused ring system indicate that $R_4$, when present, and the group comprising —X-L-C(O)-Q- (and a dioxalone ring) may be attached alternatively at the 3-position (e.g. as in Formula Ie) or 4-position (e.g. as in Formula Ic) of the fused ring system. Fused ring numbering convention is shown in FIG. 3. In a particular embodiment, compounds of the invention have the group comprising the dioxolone ring pending from the 4-position of the fused ring system. In an embodiment, following administration to a subject of a compound of the invention, the ester moiety is metabolized in plasma or liver to a less active acid form. In another embodiment, the compound of the invention has equal or greater HSD2 inhibitory activity than glycyrrhetinic acid. In another embodiment, the compound of the invention has greater HSD2 inhibitory activity than glycyrrhetinic acid.

"Acyl" means a carbonyl containing substituent represented by the formula —C(O)—R in which R is H, alkyl, a carbocycle, a heterocycle, carbocycle-substituted alkyl or heterocycle-substituted alkyl, wherein the alkyl, alkoxy, carbocycle and heterocycle are as defined herein. Acyl groups include alkanoyl (e.g., acetyl), aroyl (e.g., benzoyl), and heteroaroyl.

"Alkyl" means a branched or unbranched, saturated or unsaturated (i.e. alkenyl, alkynyl) aliphatic hydrocarbon group, having up to 12 carbon atoms unless otherwise specified. When used as part of another term, for example, "alkylamino", "cycloalkyl", "alkylene" etc., the alkyl portion may be a saturated hydrocarbon chain, however also includes unsaturated hydrocarbon carbon chains such as "alkenylamino" and "alkynylamino. Examples of particular alkyl groups are methyl, ethyl, n-propyl, isopropyl, n-butyl, iso-butyl, sec-butyl, tert-butyl, n-pentyl, 2-methylbutyl, 2,2-dimethylpropyl, n-hexyl, 2-methylpentyl, 2,2-dimethylbutyl, n-heptyl, 3-heptyl, 2-methylhexyl, and the like. The terms "lower alkyl" "$C_1$-$C_4$ alkyl" and "alkyl of 1 to 4 carbon atoms" are synonymous and used interchangeably to mean methyl, ethyl, 1-propyl, isopropyl, cyclopropyl, 1-butyl, sec-butyl or t-butyl. Unless specified, substituted, alkyl groups may contain, for example, one, two, three or four substituents, which may be the same or different. Examples of substituents are, unless otherwise defined, halogen, amino, hydroxyl, protected hydroxyl, mercapto, carboxy, alkoxy, nitro, cyano, amidino, guanidino, urea, sulfonyl, sulfinyl, aminosulfonyl, alkylsulfonylamino, arylsulfonylamino, aminocarbonyl, acylamino, alkoxy, acyl, acyloxy, a carbocycle, and a heterocycle. Examples of the above substituted alkyl groups include, but are not limited to; cyanomethyl, nitromethyl, hydroxymethyl, trityloxymethyl, propionyloxymethyl, aminomethyl, carboxymethyl, carboxyethyl, carboxypropyl, alkyloxycarbonylmethyl, allyloxycarbonylaminomethyl, carbamoyloxymethyl, methoxymethyl, ethoxymethyl, t-butoxymethyl, acetoxymethyl, chloromethyl, bromomethyl, iodomethyl, trifluoromethyl, 6-hydroxyhexyl, 2,4-dichloro(n-butyl), 2-amino(isopropyl), 2-carbamoyloxyethyl and the like. The alkyl group may also be substituted with a carbocycle group. Examples include cyclopropylmethyl, cyclobutylmethyl, cyclopentylmethyl, and cyclohexylmethyl groups, as well as the corresponding -ethyl, -propyl, -butyl, -pentyl, -hexyl groups, etc. Substituted alkyls include substituted methyls, e.g., a methyl group substituted by the same substituents as the "substituted $C_n$-$C_m$ alkyl" group. Examples of the substituted methyl group include groups such as hydroxymethyl, protected hydroxymethyl (e.g., tetrahydropyranyloxymethyl), acetoxymethyl, carbamoyloxymethyl, trifluoromethyl, chloromethyl, carboxymethyl, bromomethyl and iodomethyl. In an embodiment, alkyl is saturated. In an embodiment, alkyl is unsaturated. In an embodiment, alkyl is partially unsaturated.

"Amidine" means the group —C(NH)—NHR in which R is H, alkyl, a carbocycle, a heterocycle, carbocycle-substituted alkyl or heterocycle-substituted alkyl wherein the alkyl, alkoxy, carbocycle and heterocycle are as defined herein. A particular amidine is the group —NH—C(NH)—NH$_2$.

"Amino" means primary (i.e. —NH$_2$), secondary (i.e. —NRH) and tertiary (i.e. —NRR) amines in which R is H, alkyl, a carbocycle, a heterocycle, carbocycle-substituted alkyl or heterocycle-substituted alkyl wherein the alkyl, alkoxy, carbocycle and heterocycle are as defined herein. Particular secondary and tertiary amines are alkylamine, dialkylamine, arylamine, diarylamine, aralkylamine and diaralkylamine, wherein the alkyl is as herein defined and optionally substituted. Particular secondary and tertiary amines are methylamine, ethylamine, propylamine, isopropylamine, phenylamine, benzylamine dimethylamine, diethylamine, dipropylamine and diisopropylamine.

"Amino-protecting group" as used herein refers to a derivative of the groups commonly employed to block or protect an amino group while reactions are carried out on other functional groups on the compound. Examples of such protecting groups include carbamates, amides, alkyl and aryl groups, imines, as well as many N-heteroatom derivatives which can be removed to regenerate the desired amine group. Suitable amino-protecting groups (NH-Pg) include acetyl, trifluoroacetyl, t-butyloxy carbonyl ("Boc"), benzyloxy carbonyl ("CBz") and 9-fluorenylmethyleneoxycarbonyl ("Fmoc"). Further examples of these groups are found in Wuts. *Greene's Protective Groups in Organic Synthesis*. 5th ed. New York: John Wiley & Sons, Inc., 2014. The term "protected amino" refers to an amino group substituted with one of the above amino-protecting groups.

"Aryl" when used alone or as part of another term means a carbocyclic aromatic group whether or not fused having the number of carbon atoms designated or if no number is designated, up to 14 carbon atoms. Particular aryl groups are phenyl, naphthyl, biphenyl, phenanthrenyl, naphthacenyl, and the like (see e.g., Dean, J. A., ed. *Lange's Handbook of Chemistry*, 13th ed. New York: McGraw-Hill, 1985, Table 7-2). A particular aryl is phenyl. Substituted phenyl or substituted aryl means a phenyl group or aryl group substituted with one, two, three, four or five substituents, for example 1-2, 1-3 or 1-4 substituents chosen, unless otherwise specified, from halogen (F, Cl, Br, I), hydroxy, protected hydroxy, cyano, nitro, alkyl (for example $C_1$-$C_6$ alkyl), alkoxy (for example $C_1$-$C_6$ alkoxy), benzyloxy, carboxy, protected carboxy, carboxymethyl, protected carboxymethyl, hydroxymethyl, protected hydroxymethyl, aminomethyl, protected aminomethyl, trifluoromethyl, alkylsulfonylamino, alkylsulfonylaminoalkyl, arylsulfonylamino, arylsulonylaminoalkyl, heterocyclylsulfonylamino, heterocyclylsulfonylaminoalkyl, heterocyclyl, aryl, or other groups specified. One or more methyne (CH) and/or methylene (CH$_2$) groups in these substituents may in turn be substituted with a similar group as those denoted above. Examples of the term "substituted phenyl" includes but is not limited to a mono- or di(halo)phenyl group, such as 2-chlorophenyl, 2-bromophenyl, 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a mono- or di(hydroxy)phenyl group such as 4-hydroxyphenyl, 3-hydroxyphenyl, 2,4-dihydroxyphenyl, the protected-hydroxy derivatives thereof and the like; a nitrophenyl group such as 3- or 4-nitrophenyl; a cyanophenyl group, for example, 4-cyanophenyl; a mono- or di(lower alkyl)phenyl group such as 4-methylphenyl, 2,4-dimethylphenyl, 2-methylphenyl, 4-(isopropyl)phenyl, 4-ethylphenyl, 3-(n-propyl)phenyl and the like; a mono or di(alkoxy) phenyl group, for example, 3,4-dimethoxyphenyl, 3-methoxy-4-benzyloxyphenyl, 3-methoxy-4-(1-chloromethyl)benzyloxy-phenyl, 3-ethoxyphenyl, 4-(isopropoxy) phenyl, 4-(t-butoxy)phenyl, 3-ethoxy-4-methoxyphenyl and the like; 3- or 4-trifluoromethylphenyl; a mono- or dicarboxyphenyl or (protected carboxy)phenyl group such as 4-carboxyphenyl; a mono- or di(hydroxymethyl)phenyl or (protected hydroxymethyl)phenyl such as 3-(protected hydroxymethyl)phenyl or 3,4-di(hydroxymethyl)phenyl; a mono- or di(aminomethyl)phenyl or (protected aminomethyl)phenyl such as 2-(aminomethyl)phenyl or 2,4-(protected aminomethyl)phenyl; a mono- or di(N-(methylsulfonylamino))phenyl such as 3-(N-methylsulfonylamino))phenyl; disubstituted phenyl groups such as 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl; trisubstituted phenyl groups such as 3-methoxy-4-benzyloxy-6-methyl sulfonylamino, 3-m ethoxy-4-benzyl oxy-6-phenyl sulfonylamino; and tetrasubstituted phenyl groups such as 3-methoxy-4-benzyloxy-5-methyl-6-phenyl sulfonylamino. Particular substituted phenyl groups include the 2-chlorophenyl, 2-aminophenyl, 2-bromophenyl, 3-methoxyphenyl, 3-ethoxy-phenyl, 4-benzyloxyphenyl, 4-methoxyphenyl, 3-ethoxy-4-benzyloxyphenyl, 3,4-diethoxyphenyl, 3-methoxy-4-benzyloxyphenyl, 3-methoxy-4-(1-chloromethyl)benzyloxy-phenyl, 3-methoxy-4-(1-chloromethyl) benzyloxy-6-methyl sulfonyl aminophenyl groups. Fused aryl rings may also be substituted with any, for example 1, 2 or 3, of the substituents specified herein in the same manner as substituted alkyl groups.

"Carbocyclyl", "carbocyclic", "carbocycle" and "carbocyclo" alone and when used as a moiety in a complex group such as a carbocycloalkyl group, refer to a mono-, bi-, or tricyclic aliphatic ring having 3 to 14 carbon atoms, for example 3 to 7 carbon atoms or 3 to 6 carbon atoms, which may be saturated or unsaturated, aromatic or non-aromatic. Particular saturated carbocyclic groups are cyclopropyl, cyclobutyl, cyclopentyl and cyclohexyl groups. A particular saturated carbocycle is cyclopropyl. Another particular saturated carbocycle is cyclohexyl. Particular unsaturated carbocycles are aromatic e.g. aryl groups as previously defined, for example phenyl. The terms "substituted carbocyclyl", "carbocycle" and "carbocyclo" mean these groups substituted by the same substituents as the "substituted alkyl" group.

"Carboxy-protecting group" as used herein refers to one of the ester derivatives of the carboxylic acid group commonly employed to block or protect the carboxylic acid group while reactions are carried out on other functional groups on the compound. Examples of such carboxylic acid protecting groups include 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, alkyl such as t-butyl or t-amyl, trityl, 4-methoxytrityl, 4,4'-dimethoxy trityl, 4,4',4"-trimethoxytrityl, 2-phenylprop-2-yl, trimethylsilyl, t-butyl dimethylsilyl, phenacyl, 2,2,2-trichloroethyl, beta-(trimethylsilyl)ethyl, beta-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl, and like moieties. The species of carboxy-protecting group employed is not critical so long as the derivatized carboxylic acid is stable to the condition of subsequent reaction(s) on other positions of the molecule and can be removed at the appropriate point without disrupting the remainder of the molecule. In particular, it is important not to subject a carboxy-protected molecule to strong nucleophilic bases, such as lithium hydroxide or NaOH, or reductive conditions employing highly activated metal hydrides such as $LiAlH_4$. Such harsh removal conditions are also to be avoided when removing amino-protecting groups and hydroxy-protecting groups, discussed below. Particular carboxylic acid protecting groups are the alkyl (e.g., methyl, ethyl, t-butyl), allyl, benzyl and p-nitrobenzyl groups. Similar carboxy-protecting groups used in the cephalosporin, penicillin and peptide arts can also be used to protect carboxy group substituents. Further examples of these groups are found in Greene, T. W., and P. G. M. Wuts. *Protective Groups in Organic Synthesis.* 2nd ed. New York: John Wiley & Sons, Inc. 1991, Chapter 5; Haslam, E. *Protective Groups in Organic Chemistry.* New York: Plenum Press 1973, Chapter 5; and Greene, T. W. *Protective Groups in Organic Synthesis.* New York: John Wiley & Sons, Inc. 1981, Chapter 5. The term "protected carboxy" refers to a carboxy group substituted with one of the above carboxy-protecting groups.

"Alkoxycarbonyl" means the group —C(=O)OR in which R is alkyl. A particular group is $C_1$-$C_6$ alkoxycarbonyl, wherein the R group is $C_1$-$C_6$ alkyl.

"Guanidine" means the group —NH—C(NH)—NHR in which R is hydrogen, alkyl, a carbocycle, a heterocycle, carbocycle-substituted alkyl or heterocycle-substituted alkyl, wherein the alkyl, alkoxy, carbocycle and heterocycle are as defined herein. A particular guanidine is the group —NH—C(NH)—$NH_2$.

"Hydroxy-protecting group" as used herein refers to a derivative of the hydroxy group commonly employed to block or protect the hydroxy group while reactions are carried out on other functional groups on the compound. Examples of such protecting groups include tetrahydropyranyloxy, benzoyl, acetoxy, carbamoyloxy, benzyl, and silylethers (e.g., TBS, TBDPS) groups. Further examples of these groups are found in Greene, T. W., and P. G. M. Wuts. *Protective Groups in Organic Synthesis.* 2nd ed. New York: John Wiley & Sons, Inc. 1991, Chapters 2-3; Haslam, E. *Protective Groups in Organic Chemistry,* New York: Plenum Press 1973, Chapter 5; and Greene, T. W. *Protective Groups in Organic Synthesis.* New York: John Wiley & Sons, Inc. 1981. The term "protected hydroxy" refers to a hydroxy group substituted with one of the above hydroxy-protecting groups.

"Heterocyclic group", "heterocyclic", "heterocycle", "heterocyclyl", or "heterocyclo" alone and when used as a moiety in a complex group such as a heterocycloalkyl group, are used interchangeably and refer to any mono-, bi-, or tricyclic, saturated or unsaturated, aromatic (heteroaryl) or non-aromatic ring having the number of atoms designated, generally from 5 to about 14 ring atoms, where the ring atoms are carbon and at least one heteroatom (nitrogen, sulfur or oxygen), for example 1 to 4 heteroatoms. Heterocyclic groups include four to seven membered cyclic groups containing one, two or three heteroatoms selected from the group consisting of nitrogen, oxygen and sulfur. Typically, a 5-membered ring has 0 to 2 double bonds and 6- or 7-membered ring has 0 to 3 double bonds. The nitrogen or sulfur heteroatoms may optionally be oxidized (e.g., SO, $SO_2$), and any nitrogen heteroatom may optionally be quaternized. Particular non-aromatic heterocycles are morpholinyl (morpholino), pyrrolidinyl, oxiranyl, oxetanyl, tetrahydrofuranyl, 2,3-dihydrofuranyl, 2H-pyranyl, tetrahydropyranyl, thiiranyl, thietanyl, tetrahydrothietanyl, aziridinyl, azetidinyl, 1-methyl-2-pyrrolyl, piperazinyl and piperidinyl. A "heterocycloalkyl" group is a heterocycle group as defined above covalently bonded to an alkyl group as defined above. Particular 5-membered heterocycles containing a sulfur or oxygen atom and one to three nitrogen atoms are thiazolyl, in particular thiazol-2-yl and thiazol-2-yl N-oxide, thiadiazolyl, in particular 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Particular 5-membered ring heterocycles containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Particular benzo-fused 5-membered heterocycles are benzoxazol-2-yl, benzthiazol-2-yl and benzimidazol-2-yl. Particular 6-membered heterocycles contain one to three nitrogen atoms and optionally a sulfur or oxygen atom, for example pyridyl, such as pyrid-2-yl, pyrid-3-yl, and pyrid-4-yl;

pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are a particular group. Substituents for "optionally substituted heterocycles", and further examples of the 5- and 6-membered ring systems discussed above can be found in W. Druckheimer et al., U.S. Pat. No. 4,278,793. In a particular embodiment, such optionally substituted heterocycle groups are substituted with hydroxyl, alkyl, alkoxy, acyl, halogen, mercapto, oxo, carboxyl, acyl, halo-substituted alkyl, amino, cyano, nitro, amidino and guanidino.

"Heteroaryl" alone and when used as a moiety in a complex group such as a heteroaralkyl group, refers to any mono-, bi-, or tricyclic aromatic ring system having the number of atoms designated where at least one ring is a 5-, 6- or 7-membered ring containing from one to four heteroatoms selected from the group nitrogen, oxygen, and sulfur, and in a particular embodiment at least one heteroatom is nitrogen (Lange's Handbook of Chemistry, supra). In one example, the heteroaryl is a five to six membered aromatic ring containing one, two or three heteroatoms selected from nitrogen, oxygen and sulfur. Included in the definition are any bicyclic groups where any of the above heteroaryl rings are fused to a benzene ring. Particular heteroaryls incorporate a nitrogen or oxygen heteroatom. The following ring systems are examples of the heteroaryl (whether substituted or unsubstituted) groups denoted by the term "heteroaryl": thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, thiazinyl, oxazinyl, triazinyl, thiadiazinyl, oxadiazinyl, dithiazinyl, dioxazinyl, oxathiazinyl, tetrazinyl, thiatriazinyl, oxatriazinyl, dithiadiazinyl, imidazolinyl, dihydropyrimidyl, tetrahydropyrimidyl, tetrazolo[1,5-b]pyridazinyl and purinyl, as well as benzo-fused derivatives, for example benzoxazolyl, benzofuryl, benzothiazolyl, benzothiadiazolyl, benzotriazolyl, benzoimidazolyl and indolyl. A particular "heteroaryl" may be selected from: 1,3-thiazol-2-yl, 4-(carboxymethyl)-5-methyl-1,3-thiazol-2-yl, 4-(carboxymethyl)-5-methyl-1,3-thiazol-2-yl, 1,2,4-thiadiazol-5-yl, 3-methyl-1,2,4-thiadiazol-5-yl, 1,3,4-triazol-5-yl, 2-methyl-1,3,4-triazol-5-yl, 2-hydroxy-1,3,4-triazol-5-yl, 2-carboxy-4-methyl-1,3,4-triazol-5-yl, 1,3-oxazol-2-yl, 1,3,4-oxadiazol-5-yl, 2-methyl-1,3,4-oxadiazol-5-yl, 2-(hydroxymethyl)-1,3,4-oxadiazol-5-yl, 1,2,4-oxadiazol-5-yl, 1,3,4-thiadiazol-5-yl, 2-thiol-1,3,4-thiadiazol-5-yl, 2-(methylthio)-1,3,4-thiadiazol-5-yl, 2-amino-1,3,4-thiadiazol-5-yl, 1H-tetrazol-5-yl, 1-methyl-1H-tetrazol-5-yl, 1-(1-(dimethylamino)eth-2-yl)-1H-tetrazol-5-yl, 1-(carboxymethyl)-1H-tetrazol-5-yl, 1-(carboxymethyl)-1H-tetrazol-5-yl, 1-(methylsulfonic acid)-1H-tetrazol-5-yl, 1-(methylsulfonic acid)-1H-tetrazol-5-yl, 2-methyl-1H-tetrazol-5-yl, 1,2,3-triazol-5-yl, 1-methyl-1,2,3-triazol-5-yl, 2-methyl-1,2,3-triazol-5-yl, 4-methyl-1,2,3-triazol-5-yl, pyrid-2-yl N-oxide, 6-methoxy-2-(n-oxide)-pyridaz-3-yl, 6-hydroxypyridaz-3-yl, 1-methylpyrid-2-yl, 1-methylpyrid-4-yl, 2-hydroxypyrimid-4-yl, 1,4,5,6-tetrahydro-5,6-dioxo-4-methyl-as-triazin-3-yl, 1,4,5,6-tetrahydro-4-(formylmethyl)-5,6-dioxo-as-triazin-3-yl, 2,5-dihydro-5-oxo-6-hydroxy-astriazin-3-yl, 2,5-dihydro-5-oxo-6-hydroxy-as-triazin-3-yl, 2,5-dihydro-5-oxo-6-hydroxy-2-methyl-astriazin-3-yl, 2,5-dihydro-5-oxo-6-hydroxy-2-methyl-as-triazin-3-yl, 2,5-dihydro-5-oxo-6-methoxy-2-methyl-as-triazin-3-yl, 2,5-dihydro-5-oxo-as-triazin-3-yl, 2,5-dihydro-5-oxo-2-methyl-as-triazin-3-yl, 2,5-dihydro-5-oxo-2,6-dimethyl-as-triazin-3-yl, tetrazolo[1,5-b]pyridazin-6-yl and 8-aminotetrazolo[1,5-b]-pyridazin-6-yl. An alternative group of "heteroaryl" includes; 4-(carboxymethyl)-5-methyl-1,3-thiazol-2-yl, 4-(carboxymethyl)-5-methyl-1,3-thiazol-2-yl, 1,3,4-triazol-5-yl, 2-methyl-1,3,4-triazol-5-yl, 1H-tetrazol-5-yl, 1-methyl-1H-tetrazol-5-yl, 1-(1-(dimethylamino)eth-2-yl)-1H-tetrazol-5-yl, 1-(carboxymethyl)-1H-tetrazol-5-yl, 1-(carboxymethyl)-1H-tetrazol-5-yl, 1-(methylsulfonic acid)-1H-tetrazol-5-yl, 1-(methylsulfonic acid)-1H-tetrazol-5-yl, 1,2,3-triazol-5-yl, 1,4,5,6-tetrahydro-5,6-dioxo-4-methyl-as-triazin-3-yl, 1,4,5,6-tetrahydro-4-(2-formylmethyl)-5,6-dioxo-as-triazin-3-yl, 2,5-dihydro-5-oxo-6-hydroxy-2-methyl-as-triazin-3-yl, 2,5-dihydro-5-oxo-6-hydroxy-2-methyl-as-triazin-3-yl, tetrazolo[1,5-b]pyridazin-6-yl, and 8-aminotetrazolo[1,5-b]pyridazin-6-yl. Heteroaryl groups are optionally substituted as described for heterocycles.

"Inhibitor" means a compound which reduces or prevents the enzymatic conversion of cortisol to cortisone by HSD2.

"Optionally substituted" unless otherwise specified means that a group may be unsubstituted or substituted by one or more (e.g., 0, 1, 2, 3 and/or 4) of the substituents listed for that group, as valency allows, in which said substituents may be the same or different. In one embodiment, an optionally substituted group has 1 substituent. In another embodiment, an optionally substituted group has 2 substituents. In another embodiment, an optionally substituted group has 3 substituents.

"Pharmaceutically acceptable salts" include both acid and base addition salts. "Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly base addition salts are the ammonium, potassium, sodium, calcium and magnesium salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly organic non-toxic bases are isopropylamine, diethylamine, ethanolamine, trimethamine, dicyclohexylamine, choline, and caffeine.

"Sulfanyl" means —S—R group in which R is alkyl, a carbocycle, a heterocycle, carbocycle-substituted alkyl or heterocycle-substituted alkyl, wherein the alkyl, alkoxy, carbocycle and heterocycle are as defined herein. Particular sulfanyl groups are alkylsulfanyl (i.e., —SO$_2$-alkyl), for example methyl sulfanyl; arylsulfanyl, for example phenylsulfanyl; aralkylsulfanyl, for example benzylsulfanyl.

"Sulfinyl" means —SO—R group in which R is hydrogen, alkyl, a carbocycle, a heterocycle, carbocycle-substituted alkyl or heterocycle-substituted alkyl, wherein the alkyl, alkoxy, carbocycle and heterocycle are as defined herein. Particular sulfonyl groups are alkylsulfinyl (i.e., —SO-alkyl), for example methyl sulfinyl; arylsulfinyl, for example phenyl sulfinyl; aralkylsulfinyl, for example benzylsulfinyl.

"Sulfonyl" means a —SO$_2$—R group in which R is hydrogen, alkyl, a carbocycle, a heterocycle, carbocycle-substituted alkyl or heterocycle-substituted alkyl, wherein the alkyl, alkoxy, carbocycle and heterocycle are as defined herein. Particular sulfonyl groups are alkylsulfonyl (i.e. —SO$_2$-alkyl), for example methylsulfonyl; arylsulfonyl, for example phenyl sulfonyl; aralkylsulfonyl, for example benzylsulfonyl.

The phrase "and salts and solvates thereof" as used herein means that compounds of the inventions may exist in one or a mixture of salts and solvate forms. For example a compound of the invention may be substantially pure in one particular salt or solvate form or else may be mixtures of two or more salt or solvate forms.

In particular embodiments of the invention, compounds of Formula I have the structures defined by Formula Ia-Ip:

Ia

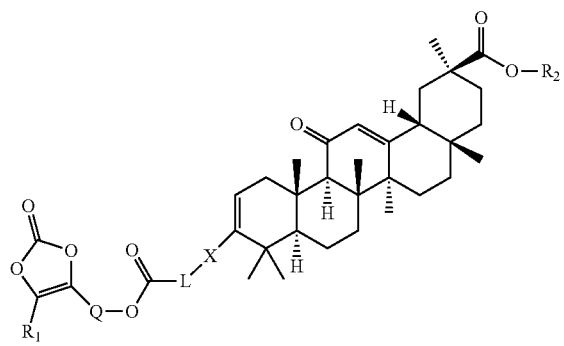

Ib

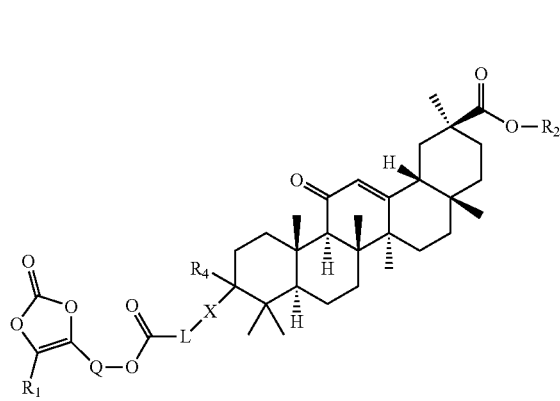

Ic

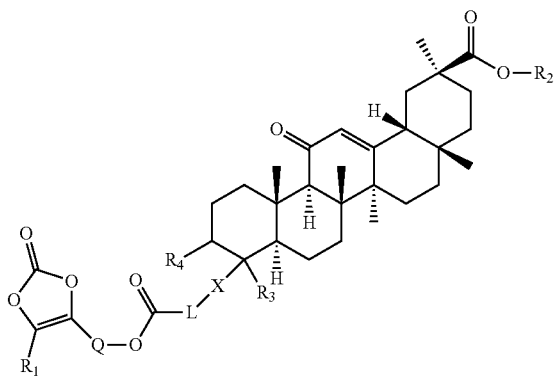

Id

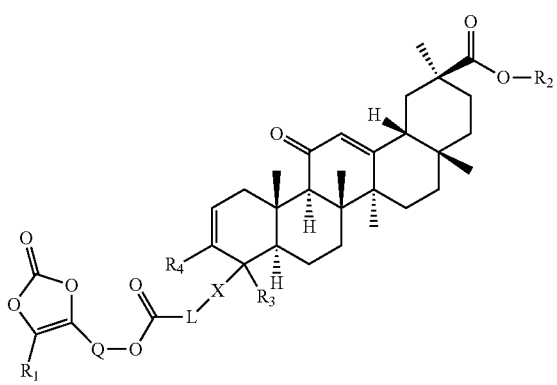

Ie

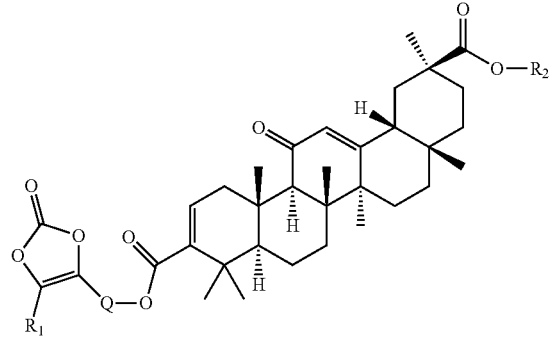

If

15
-continued
Ig
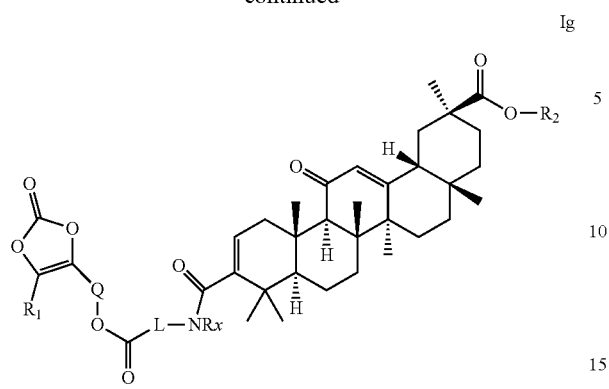
Ih
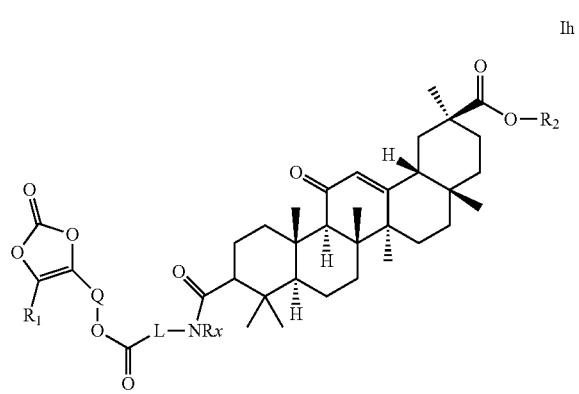
Ii
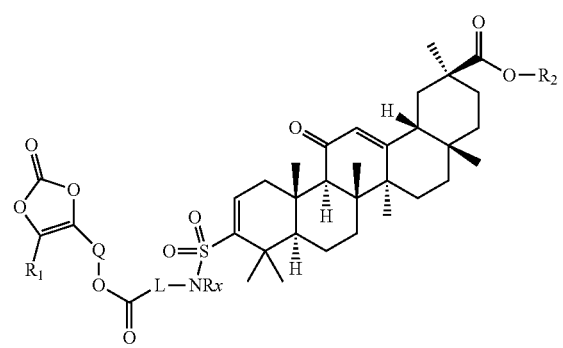
Ij
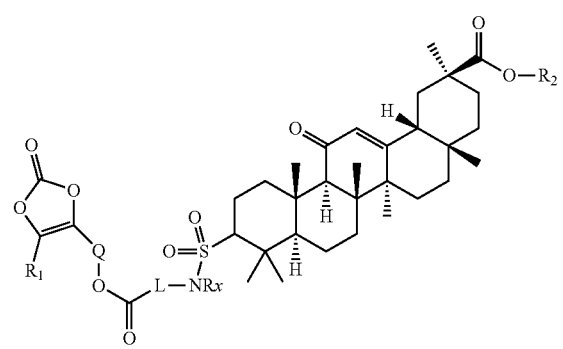
16
-continued
Ik
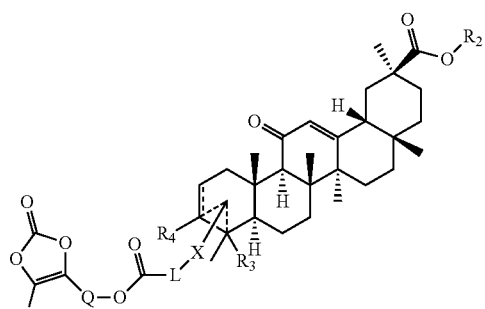
Il
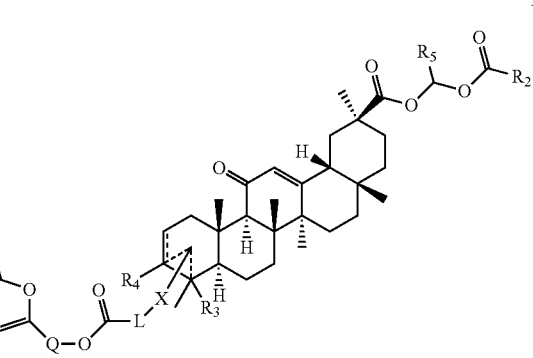
Im
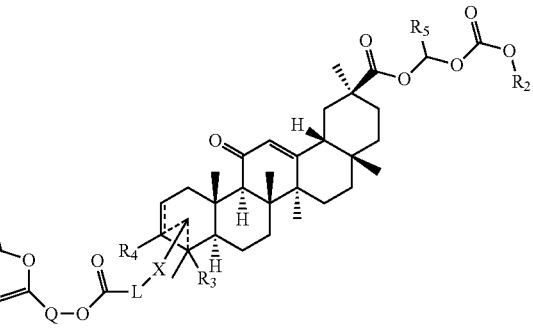
In
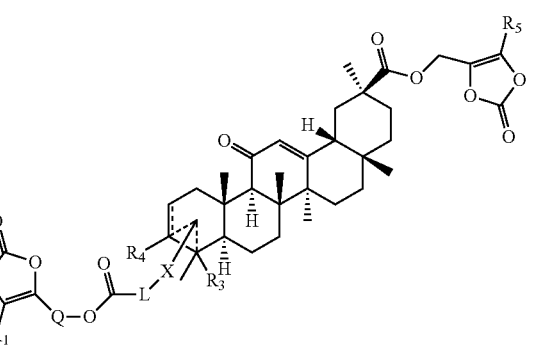

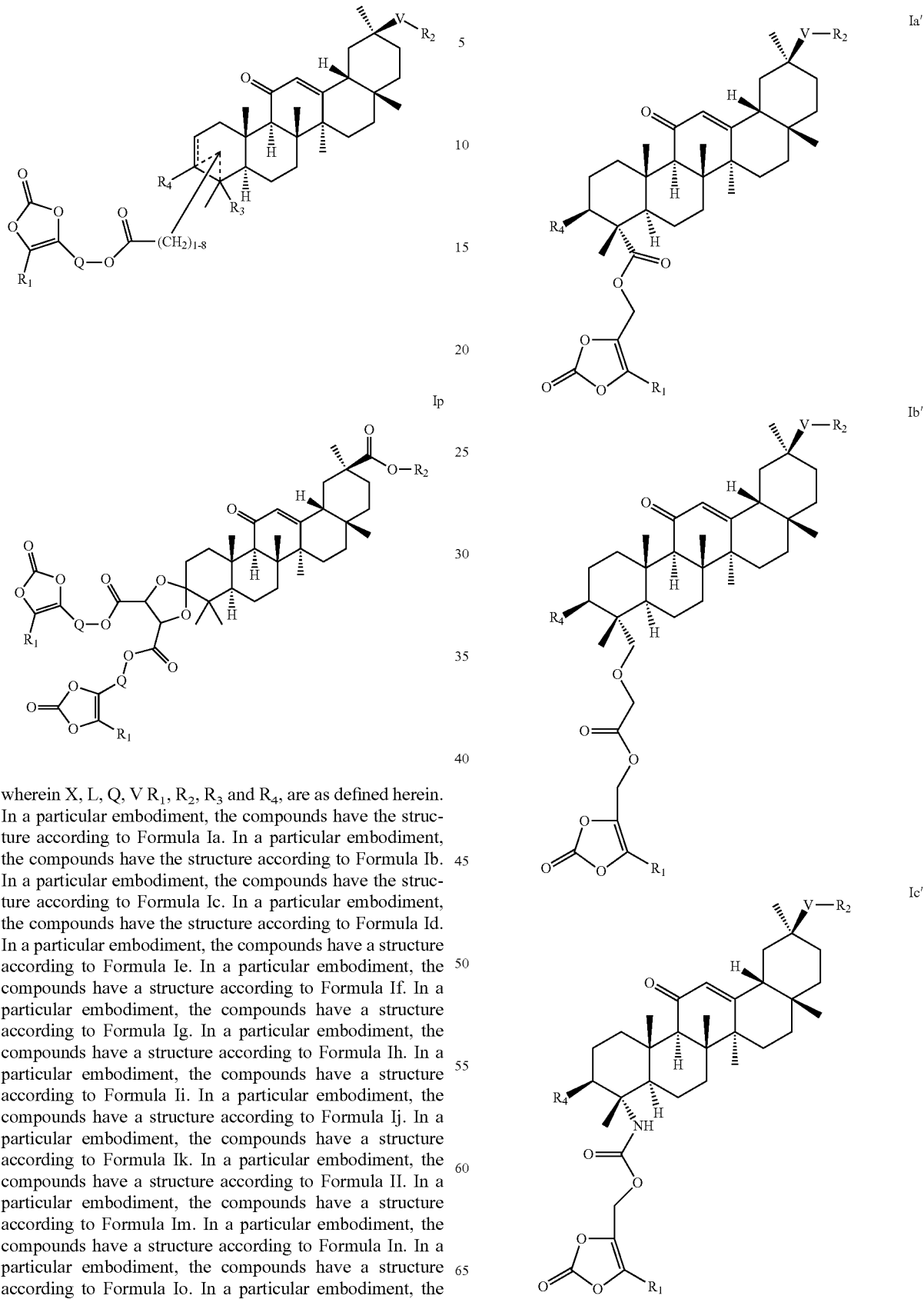

wherein X, L, Q, V R$_1$, R$_2$, R$_3$ and R$_4$, are as defined herein. In a particular embodiment, the compounds have the structure according to Formula Ia. In a particular embodiment, the compounds have the structure according to Formula Ib. In a particular embodiment, the compounds have the structure according to Formula Ic. In a particular embodiment, the compounds have the structure according to Formula Id. In a particular embodiment, the compounds have a structure according to Formula Ie. In a particular embodiment, the compounds have a structure according to Formula If. In a particular embodiment, the compounds have a structure according to Formula Ig. In a particular embodiment, the compounds have a structure according to Formula Ih. In a particular embodiment, the compounds have a structure according to Formula Ii. In a particular embodiment, the compounds have a structure according to Formula Ij. In a particular embodiment, the compounds have a structure according to Formula Ik. In a particular embodiment, the compounds have a structure according to Formula Il. In a particular embodiment, the compounds have a structure according to Formula Im. In a particular embodiment, the compounds have a structure according to Formula In. In a particular embodiment, the compounds have a structure according to Formula Io. In a particular embodiment, the compounds have a structure according to Formula Ip.

In particular embodiments of the invention, compounds of Formula I have the structures defined by Formula Ia'-If:

-continued

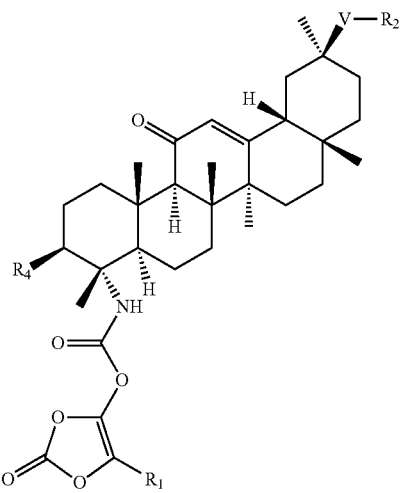

Id'

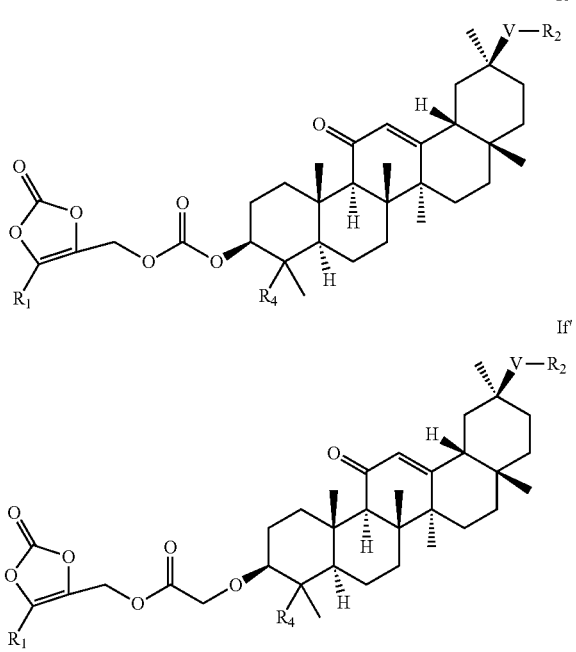

Ie'

If' wherein X, L, V, R$_1$, R$_2$, R$_3$, R$_4$ and R$_5$ are as defined herein. In a particular embodiment, the compounds have the structure according to Formula Ib'. In a particular embodiment, the compounds have the structure according to Formula Ic'. In a particular embodiment, the compounds have the structure according to Formula Id'. In a particular embodiment, the compounds have the structure according to Formula If.

In an embodiment, the compound of the invention has a formula of any one of formula I In an embodiment, X is a bond, —O—, —N(R$_x$)—, —C(O)N(R$_x$)—, —N(R$_x$)—C(O)—, —S(O)$_n$—N(R$_x$)— or —N(R$_x$)—S(O)$_n$—; wherein R$_x$ is H, —C(O)O—R$_1$, or alkyl optionally substituted with —C(O)O—R$_1$; In an embodiment, X is a bond. In an embodiment, X is —O—. In an embodiment, X is —N(R$_x$)—. In an embodiment, X is —NH—. In an embodiment, X is —C(O)N(R$_x$)—. In an embodiment, X is —C(O)NH—. In an embodiment, X is —N(R$_x$)—C(O)—. In an embodiment, X is —NH—C(O)—. In an embodiment, X is —S(O)$_n$—N(R$_x$)—. In an embodiment, X is —S(O)—NH—. In an embodiment, X is —S(O)$_2$—NH—. In an embodiment, X is —N(R$_x$)—S(O)$_n$—. In an embodiment, X is —NH—S(O)—. In an embodiment, X is —NH—S(O)$_2$—.

W is O or S. In an embodiment, W is O. In another embodiment, W is S.

Q is a bond or alkylene. In an embodiment, Q is a bond. In an embodiment, Q is methylene. In an embodiment, Q is ethylene.

V is —C(O)O—, —C(O)O—(CHR$_5$)—O—C(O)—, —C(O)O—(CHR$_5$)—O—C(O)—O—, —C(O)N(R$_5$)—, —C(O)N(R$_5$)O—, —NH—C(O)—N(R$_5$)— or NH—S(O)$_n$—.

In an embodiment, V is —C(O)O—. In an embodiment, V is —C(O)O— and R$_2$ is H. In an embodiment, V is —C(O)O— and R$_2$ is a prodrug group. In an embodiment, V is —C(O)O— and R$_2$ is alkyl. In an embodiment, V is —C(O)O— and R$_2$ is methyl. In another embodiment V is —C(O)O— and R$_2$ is alkyl optionally substituted with oxo, acyloxy, alkoxycarbonyl, alkoxyacyloxy, alkoxycarbonyloxy, a carbocycle optionally substituted with alkyl and oxo, and a heterocycle optionally substituted with alkyl and oxo.

In an embodiment, V is —C(O)N(R$_5$)—. In an embodiment, V is —C(O)N(R$_5$)— and both R$_2$ and R$_5$ are H. In an embodiment, V is —C(O)N(R$_5$)— and R$_2$ and R$_5$ are independently H and alkyl optionally substituted with OH. In an embodiment, V is —C(O)N(R$_5$)— and R$_5$ is H and R$_2$ is hydroxy ethyl.

In an embodiment, V is —C(O)N(R$_5$)O—. In an embodiment, V is —C(O)N(R$_5$)O— and R$_2$ and R$_5$ are independently H or alkyl. In an embodiment, V is —C(O)N(R$_5$)O— and R$_2$ is methyl and R$_5$ is H.

In an embodiment, V is —NH—C(O)—N(R$_5$)— and R$_2$ and R$_5$ are independently H or alkyl. In an embodiment, V is —NH—C(O)—N(R$_2$)— and R$_2$ is methyl and R$_5$ is H. In an embodiment, V is —NH—C(O)—N(R$_5$)— and both R$_2$ and R$_5$ are H.

In an embodiment, V is NH—S(O)$_n$—. In an embodiment, V is NH—S(O)$_2$—. In an embodiment, V is NH—S(O)$_2$— and R$_2$ is alkyl. In an embodiment, V is NH—S(O)$_2$— and R$_2$ is methyl.

L is a bond, alkylene wherein one or more non-adjacent methylene groups of said alkylene are replaced with —O—; divalent aryl or divalent heteroaryl; or L is alkyl ene-Y-alkyl ene wherein Y is O, NR$_x$, S, SO, SO$_2$ or a divalent heterocycle; wherein said alkylene groups are optionally substituted with OH, —C(O)O—R$_1$, alkyl or alkyl substituted with OH or —C(O)O—R$_1$; and wherein a carbon of said alkylene groups and R$_x$ optionally together form a heterocycle; provided that when X is other than a bond, then L is other than a bond;

In an embodiment, L is a bond or alkylene wherein one or more non-adjacent methylene groups of said alkylene are replaced with —O—. In an embodiment, L is a bond. In an embodiment, L is alkylene. In an embodiment, L is alkylene. In an embodiment, L is alkylene in which one or more non-adjacent methylene groups of said alkylene are replaced with —O—. In an embodiment, L is —[(CH$_2$)$_2$—O]$_{1-5}$—. In an embodiment, L is —(CH$_2$)$_2$—O—. In an embodiment, L is —[(CH$_2$)$_2$—O]$_2$—. In an embodiment, L is —[(CH$_2$)$_2$—O]$_3$—. In an embodiment, L is —[(CH$_2$)$_2$—O]$_4$—. In an embodiment, L is —[(CH$_2$)$_2$—O]$_5$—.

In an embodiment, L is alkylene-Y-alkylene wherein Y is O, NR$_x$, S, SO, SO$_2$ or a divalent heterocycle; wherein said alkylene groups are optionally substituted with OH, —C(O)O—R$_1$, alkyl or alkyl substituted with OH or —C(O)O—R$_1$; and wherein a carbon of said alkylene groups and R$_x$ optionally together form a heterocycle; provided that when X is other than a bond, then L is other than a bond. In an embodiment, L is alkylene-Y-alkylene wherein Y is O. In an embodiment, L is alkylene-Y-alkylene wherein Y is $NR_x$. In an embodiment, L is alkylene-Y-alkylene wherein Y is $NR_x$ wherein a carbon of said alkylene groups and $R_x$ together form a heterocycle. In an embodiment, L is alkylene-Y-alkylene wherein Y is S. In an embodiment, L is alkylene-Y-alkylene wherein Y is SO. In an embodiment, L is alkylene-Y-alkylene wherein Y is $SO_2$. In an embodiment, L is alkylene-Y-alkylene wherein Y is divalent heterocycle. In an embodiment, L is a aryl. In an embodiment, L is phenyl. In an embodiment, L is 1,4-phenylene. In an embodiment, L is heteroaryl. In an embodiment, L is triazole. In an embodiment, L is isoxazole.

$R_1$ is H, alkyl, a carbocycle or a heterocycle wherein said alkyl, carbocycle and heterocycle are each optionally substituted with halogen, OH, amino, oxo, carboxy, acyloxy, alkoxycarbonyl, alkoxyacyloxy, alkoxycarbonyloxy, aminocarbonyl, a carbocycle optionally substituted with alkyl, haloalkyl, oxo, amino and halogen and a heterocycle optionally substituted with alkyl, oxo, amino and halogen; and a carbocycle or heterocycle optionally substituted with alkyl, haloalkyl, oxo, amino and halogen. In an embodiment, $R_1$ is H. In an embodiment, $R_1$ is alkyl. In an embodiment, $R_1$ is methyl. In an embodiment, $R_1$ is ethyl. In an embodiment, $R_1$ is n-propyl. In an embodiment, $R_1$ is i-propyl. In an embodiment, $R_1$ is cyclohexyl. In an embodiment, $R_1$ is alkyl substituted with OH. In an embodiment, $R_1$ is alkyl substituted with oxo. In an embodiment, $R_1$ is alkyl substituted with carboxy. In an embodiment, $R_1$ is alkyl substituted with acyloxy. In an embodiment, $R_1$ is alkyl substituted with alkoxycarbonyl. In an embodiment, $R_1$ is alkyl substituted with alkoxyacyloxy. In an embodiment, $R_1$ is alkyl substituted with alkoxycarbonyloxy. In an embodiment, $R_1$ is alkyl substituted with aminocarbonyl. In an embodiment, $R_1$ is methyl. In an embodiment, $R_1$ is propyl. In an embodiment, $R_1$ is hydroxyethyl.

In an embodiment, $R_2$ is H or $R_5$. In an embodiment, $R_2$ is H. In an embodiment, $R_2$ is $R_5$. In an embodiment, $R_2$ is methyl. In an embodiment, $R_2$ is t-butyl. In an embodiment, $R_2$ is benzhydryl. In an embodiment, $R_2$ is benzyl.

$R_3$ is absent or alkyl. In an embodiment, $R_3$ is methyl. In an embodiment, $R_3$ is absent.

$R_4$ is absent, H, OH, =O, —$R_6$, —O—$R_6$, —C(O)O—$R_6$, —O—C(O)—$R_6$, —O—C(O)—O—$R_6$, —O—C(O)—$NR_5R_6$, —$NR_5R_6$, —$NR_5$—C(O)—$R_6$, —$NR_5$—C(O)—O—$R_6$, —$NR_5$—$SO_2$—$R_6$, =N—O—$R_5$. In an embodiment, $R_4$ is H. In an embodiment, $R_4$ is OH. In an embodiment, $R_4$ is =O. In an embodiment, $R_4$ is —O—$R_6$. In an embodiment, $R_4$ is —C(O)O—$R_6$. In an embodiment, $R_4$ is —O—C(O)—$R_6$. In an embodiment, $R_4$ is —O—C(O)—O—$R_6$. In an embodiment, $R_4$ is —O—C(O)—$NR_5R_6$. In an embodiment, $R_4$ is —$NR_5R_6$. In an embodiment, $R_4$ is —$NR_5$—$SO_2$—$R_6$. In an embodiment, $R_4$ is =N—O—$R_5$. In an embodiment, $R_4$ is as defined and the carbon from which it depends is part of a double bond. In an embodiment, $R_4$ is H and the carbon from which it depends is not part of a double bond. In an embodiment, $R_4$ is —$R_6$.

$R_5$ is H or alkyl optionally substituted with a carbocycle or heterocycle wherein said carbocycle and heterocycle are optionally substituted with halogen, OH, oxo and alkyl. In an embodiment, $R_5$ is H. In an embodiment, $R_5$ is alkyl. In an embodiment, $R_5$ is methyl.

$R_6$ is H, alkyl, a carbocycle, a heterocycle wherein said alkyl, carbocycle and heterocycle are optionally substituted with halogen, OH, SH, alkylthio, —S(O)-alkyl, —$SO_2$-alkyl, amino, —NHC(O)-alkyl, oxo, alkyl, carboxyl, acyl, acyloxy, alkoxy, alkoxycarbonyl, a carbocycle optionally substituted with halogen, OH, amino or alkyl, or a heterocycle optionally substituted with halogen, OH, amino or alkyl; and wherein one or more non-adjacent methylene groups in each of said alkyl groups of $R_6$ are optionally replaced with —O— or —S—.

In an embodiment, $R_6$ is H. In an embodiment, $R_6$ is alkyl. In an embodiment, $R_6$ is methyl. In an embodiment, $R_6$ is ethyl. In an embodiment, $R_6$ is cyclopropyl. In an embodiment, $R_6$ is allyl. In an embodiment, $R_6$ is vinyl. In an embodiment, $R_6$ is OH. In an embodiment, $R_6$ is alkoxycarbonyl. In an embodiment, $R_6$ is methyloxycarbonyl. In an embodiment, $R_6$ is ethyloxycarbonyl. In an embodiment, $R_6$ is amino. In an embodiment, $R_6$ is $NH_2$. In an embodiment, $R_6$ is alkoxy. In an embodiment, $R_6$ is polyalkoxyalkyl. In an embodiment, $R_6$ is oxo. In an embodiment, $R_6$ is alkylthio. In an embodiment, $R_6$ is —S-Me. In an embodiment, $R_6$ is —S-Et.

In an embodiment, $R_x$ is H. In an embodiment, $R_x$ is —C(O)O—$R_1$. In an embodiment, $R_x$ is alkyl. In an embodiment, $R_x$ is alkyl optionally substituted with —C(O)O—$R_1$.

In an embodiment 'n' is 1. In another embodiment, 'n' is 2.

In a further aspect of the invention, there is provided a compound of formula II

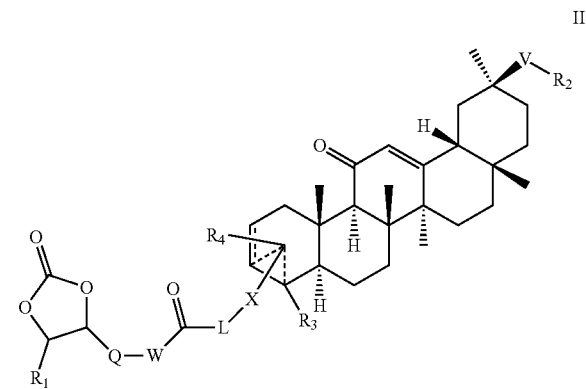

wherein R1, R2, R3, R4, L, X, Q, V and W are as defined for compounds of formula I. Furthermore, particular embodiments of formula II are analogous to those embodiments specified herein for formula I. For example, particular embodiments of formula II include compounds according to formula Ia-Ip, Ia'-If except that the dioxolone ring is saturated.

In an embodiment, the compound of the invention is selected from the group consisting of:
(2S,4aS,6aS,6bR,8aR,9S,10S,12aS,12bR,14bR)-10-Hydroxy-2,4a,6a,6b,9,12a-hexamethyl-13-oxo-1,2,3,4,4a,5,6,6a,6b,7,8,8a,9,10,11,12,12a,12b,13,14b-icosahydropicene-2,9-dicarboxylic acid (122-3); (2S,4aS,6aS,6bR,8aS,10S,12aS,12bR,14bR)-2,4a,6a,6b,9,9,12a-Heptamethyl-10-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic acid (176-2);
(2S,4aS,6aS,6bR,8aS,10S,12aS,12bR,14bR)-2,4a,6a,6b,9,9,12a-Heptamethyl-10-(((5-methyl-2-oxo-1,3-dioxolan-4-yl)methoxy)carbonyl)-13-oxo-1,2,3,4,4a,5,6,6a,6b,7,8,8a,9,10,11,12,12a,12b,13,14b-icosahydropicene-2-carboxylic acid (178-1); (2S,4aS,6aS,6bR,8aR,9S,10S,12aS,12bR,14bR)-2,4a,6a,6b,9,12a-Hexamethyl-9-(((5- methyl-2-oxo-1,3-dioxol-4-yl)methoxy)carbonyl)-10-(2-(methylthio)acetoxy)-13-oxo-1,2,3,4,4a,5,6,6a,6b,7,8,8a,9,10,11,12,12a,12b,13,14b-icosahydropicene-2-carboxylic acid (194-10);

(2S,4aS,6aS,6bR,8aR,9S,10S,12aS,12bR,14bR)-2,4a,6a,6b,9,12a-Hexamethyl-9-(((5-methyl-2-oxo-1,3-dioxol-4-yl)methoxy)carbonyl)-10-(2-(methylsulfonyl)acetoxy)-13-oxo-1,2,3,4,4a,5,6,6a,6b,7,8,8a,9,10,11,12,12a,12b,13,14b-icosahydropicene-2-carboxylic acid (195-2);

(2S,4aS,6aS,6bR,8aR,9S,10S,12aS,12bR,14bR)-10-((L-Valyl)oxy)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic acid (196-2);

(2S,4aS,6aS,6bR,8aR,9S,10S,12aS,12bR,14bR)-10-(Benzoyloxy)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic acid (197-2);

(2S,4aS,6aS,6bR,8aR,9S,10S,12aS,12bR,14bR)-10-((Cyclopropanecarbonyl)oxy)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic acid (198-2);

(2S,4aS,6aS,6bR,8aR,9S,10S,12aS,12bR,14bR)-10-(((R)-2-Methoxypropanoyl)oxy)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic acid (203-2);

(2S,4aS,6aS,6bR,8aR,9S,10S,12aS,12bR,14bR)-10-(((S)-2-Methoxypropanoyl)oxy)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic acid (204-2);

(2S,4aS,6aS,6bR,8aR,9S,10S,12aS,12bR,14bR)-10-(Methoxymethoxy)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic acid (205-2);

(2S,4aS,6aS,6bR,8aR,9S,10S,12aS,12bR,14bR)-10-((Ethylcarbamoyl)oxy)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic acid (206-2);

(2S,4aS,6aS,6bR,8aR,9S,10S,12aS,12bR,14bR)-10-((butylcarbamoyl)oxy)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic acid (207-2);

(2S,4aS,6aS,6bR,8aR,9S,10S,12aS,12bR,14bR)-2,4a,6a,6b,9,12a-hexamethyl-9-(((5-methyl-2-oxo-1,3-dioxol-4-yl)methoxy)carbonyl)-13-oxo-10-((pyrrolidine-1-carbonyl)oxy)-1,2,3,4,4a,5,6,6a,6b,7,8,8a,9,10,11,12,12a,12b,13,14b-icosahydropicene-2-carboxylic acid (208-2);

(2S,4aS,6aS,6bR,8aR,9S,10S,12aS,12bR,14bR)-10-acetoxy-9-(((5-isopropyl-2-oxo-1,3-dioxol-4-yl)methoxy)carbonyl)-2,4a,6a,6b,9,12a-hexamethyl-13-oxo-1,2,3,4,4a,5,6,6a,6b,7,8,8a,9,10,11,12,12a,12b,13,14b-icosahydropicene-2-carboxylic acid (209-3);

(2S,4aS,6aS,6bR,8aR,9S,10S,12aS,12bR,14bR)-2,4a,6a,6b,9,12a-hexamethyl-9-(((5-methyl-2-oxo-1,3-dioxol-4-yl)methoxy)carbonyl)-13-oxo-10-(propionyloxy)-1,2,3,4,4a,5,6,6a,6b,7,8,8a,9,10,11,12,12a,12b,13,14b-icosahydropicene-2-carboxylic acid (211-1);

(2S,4aS,6aS,6bR,8aR,9S,10S,12aS,12bR,14bR)-10-((cyclopentanecarbonyl)oxy)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic acid (212-1);

(2S,4aS,6aS,6bR,8aR,9S,10S,12aS,12bR,14bR)-2,4a,6a,6b,9,12a-hexamethyl-9-(((5-methyl-2-oxo-1,3-dioxol-4-yl)methoxy)carbonyl)-13-oxo-10-((3-(piperidin-1-yl)propanoyl)oxy)-1,2,3,4,4a,5,6,6a,6b,7,8,8a,9,10,11,12,12a,12b,13,14b-icosahydropicene-2-carboxylic acid (215-1);

(2S,4aS,6aS,6bR,8aR,9S,10S,12aS,12bR,14bR)-10-((isopropoxycarbonyl)oxy)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic acid (216-2);

(2S,4aS,6aS,6bR,8aR,9S,10S,12aS,12bR,14bR)-10-(2,2-Difluoroacetoxy)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic acid (223-1);

(2S,4aS,6aS,6bR,8aR,9R,10S,12aS,12bR,14bR)-10-Hydroxy-2,4a,6a,6b,9,12a-hexamethyl-9-((2-((5-methyl-2-oxo-1,3-dioxol-4-yl)methoxy)-2-oxoethoxy)methyl)-13-oxo-1,2,3,4,4a,5,6,6a,6b,7,8,8a,9,10,11,12,12a,12b,13,14b-icosahydropicene-2-carboxylic acid (240-8);

(2S,4aS,6aS,6bR,8aR,9S,10S,12aS,12bR,14bR)-10-Acetoxy-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic acid (243-1);

(2S,4aS,6aS,6bR,8aR,9S,10S,12aS,12bR,14bR)-10-(2-Hydroxyacetoxy)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic acid (244-1);

(2S,4aS,6aS,6bR,8aR,9S,10S,12aS,12bR,14bR)-10-(2-Methoxyacetoxy)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic acid (245-1);

(2S,4aS,6aS,6bR,8aR,9S,10S,12aS,12bR,14bR)-10-((2,5,8,11-Tetraoxadodecanoyl)oxy)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic acid (246-3); (2S,4aS,6aS,6bR,8aR,9S,10S,12aS,12bR,14bR)-10-Methoxy-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic acid (249-5);

(2S,4aS,6aS,6bR,8aR,9S,10S,12aS,12bR,14bR)-9-(((5-Isopropyl-2-oxo-1,3-dioxol-4-yl)methoxy)carbonyl)-10-methoxy-2,4a,6a,6b,9,12a-hexamethyl-13-oxo-1,2,3,4,4a,5,6,6a,6b,7,8,8a,9,10,11,12,12a,12b,13,14b-icosahydropicene-2-carboxylic acid (252-2);

(2S,4aS,6aS,6bR,8aR,9R,12aS,12bR,14bR)-2,4a,6a,6b,9,12a-Hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic acid (253-4);

(2S,4aS,6aS,6bR,8aR,9S,10S,12aS,12bR,14bR)-10-Acetoxy-2,4a,6a,6b,9,12a-hexamethyl-9-((((5-methyl-2-oxo-1,3-dioxol-4-yl)methoxy)carbonyl)amino)-13-oxo-1,2,3,4,4a,5,6,6a,6b,7,8,8a,9,10,11,12,12a,12b,13,14b-icosahydropicene-2-carboxylic acid (254-3);

(2S,4aS,6aS,6bR,8aR,9S,10S,12aS,12bR,14bR)-10-Acetoxy-9-((((5-isopropyl-2-oxo-1,3-dioxol-4-yl)methoxy)carbonyl)amino)-2,4a,6a,6b,9,12a-hexamethyl-13-oxo-1,2,3,4,4a,5,6,6a,6b,7,8,8a,9,10,11,12,12a,12b,13,14b-icosahydropicene-2-carboxylic acid (255-2);

(2S,4aS,6aS,6bR,8aR,9S,10S,12aS,12bR,14bR)-10-(2,2-Difluoroacetoxy)-9-(((5-isopropyl-2-oxo-1,3-dioxol-4-yl)methoxy)carbonyl)-2,4a,6a,6b,9,12a-hexamethyl-13-oxo-1,2,3,4,4a,5,6,6a,6b,7,8,8a,9,10,11,12,12a,12b,13,14b-icosahydropicene-2-carboxylic acid (256-2);

(2S,4aS,6aS,6bR,8aR,9S,10S,12aS,12bR,14bR)-9-(((5-Isopropyl-2-oxo-1,3-dioxol-4-yl)methoxy)carbonyl)-10-(methoxymethoxy)-2,4a,6a,6b,9,12a-hexamethyl-13-oxo-1,2,3,4,4a,5,6,6a,6b,7,8,8a,9,10,11,12,12a,12b,13,14b-icosahydropicene-2-carboxylic acid (258-2);

(2S,4aS,6aS,6bR,8aR,9S,10S,12aS,12bR,14bR)-10-((2,5,8,11-tetraoxatetradecan-14-oyl)oxy)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic acid (264-1);

(2S,4aS,6aS,6bR,8aR,9S,10S,12aS,12bR,14bR)-10-((2,5,8,11-tetraoxatetradecan-14-oyl)oxy)-2,4a,6a,6b,9,12a-hexamethyl-9-(((5-methyl-2-oxo-1,3-dioxolan-4-yl)methoxy)carbonyl)-13-oxo-1,2,3,4,4a,5,6,6a,6b,7,8,8a,9,10,11,12,12a,12b,13,14b-icosahydropicene-2-carboxylic acid (265-2)

(2S,4aS,6aS,6bR,8aR,10S,12aS,12bR,14bR)-2,4a,6a,6b,9,9,12a-heptamethyl-10-(2-((5-methyl-2-oxo-1,3-dioxol-4-yl)methoxy)-2-oxoethoxy)-13-oxo-1,2,3,4,4a,5,6,6a,6b,7,8,8a,9,10,11,12a,12b,13,14b-icosahydropicene-2-carboxylic acid (279-2);

(2S,4aS,6aS,6bR,8aR,9S,10S,12aS,12bR,14bR)-10-amino-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic acid (280-7); (2S,4aS,6aS,6bR,8aR,9S,10S,12aS,12bR,14bR)-10-((methoxycarbonyl)amino)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic acid (281-3);

(2S,4aS,6aS,6bR,8aR,9S,10S,12aS,12bR,14bR)-2,4a,6a,6b,9,12a-hexamethyl-9-(((5-methyl-2-oxo-1,3-dioxol-4-yl)methoxy)carbonyl)-13-oxo-10-(pentanoyloxy)-1,2,3,4,4a,5,6,6a,6b,7,8,8a,9,10,11,12,12a,12b,13,14b-icosahydropicene-2-carboxylic acid (282-2);

(2S,4aS,6aS,6bR,8aR,9S,10S,12aS,12bR,14bR)-2,4a,6a,6b,9,12a-hexamethyl-9-(((5-methyl-2-oxo-1,3-dioxol-4-yl)methoxy)carbonyl)-10-(2-(4-methylpiperazin-1-yl)acetoxy)-13-oxo-1,2,3,4,4a,5,6,6a,6b,7,8,8a,9,10,11,12,12a,12b,13,14b-icosahydropicene-2-carboxylic acid (283-2);

(2S,4aS,6aS,6bR,8aR,9S,10S,12aS,12bR,14bR)-2,4a,6a,6b,9,12a-hexamethyl-9-(((5-methyl-2-oxo-1,3-dioxol-4-yl)methoxy)carbonyl)-10-((3-morpholinopropanoyl)oxy)-13-oxo-1,2,3,4,4a,5,6,6a,6b,7,8,8a,9,10,11,12,12a,12b,13,14b-icosahydropicene-2-carboxylic acid (284-2);

(2S,4aS,6aS,6bR,8aR,9S,10S,12aS,12bR,14bR)-2,4a,6a,6b,9,12a-hexamethyl-9-(((5-methyl-2-oxo-1,3-dioxol-4-yl)methoxy)carbonyl)-10-(methyl sulfonamido)-13-oxo-1,2,3,4,4a,5,6,6a,6b,7,8,8a,9,10,11,12,12a,12b,13,14b-icosahydropicene-2-carboxylic acid (285-2);

(2S,4aS,6aS,6bR,8aR,9S,10S,12aS,12bR,14bR)-2,4a,6a,6b,9,12a-hexamethyl-9-(((5-methyl-2-oxo-1,3-dioxol-4-yl)methoxy)carbonyl)-10-(((2-morpholinoethyl)carbamoyl)oxy)-13-oxo-1,2,3,4,4a,5,6,6a,6b,7,8,8a,9,10,11,12,12a,12b,13,14b-icosahydropicene-2-carboxylic acid (286-4);

(2S,4aS,6aS,6bR,8aR,9S,10S,12aS,12bR,14bR)-2,4a,6a,6b,9,12a-hexamethyl-9-(((5-methyl-2-oxo-1,3-dioxol-4-yl)methoxy)carbonyl)-10-(2-(methylsulfinyl)acetoxy)-13-oxo-1,2,3,4,4a,5,6,6a,6b,7,8,8a,9,10,11,12,12a,12b,13,14b-icosahydropicene-2-carboxylic acid (289-2);

(2S,4aS,6aS,6bR,8aR,9S,10S,12aS,12bR,14bR)-10-((dimethylglycyl)oxy)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic acid (290-2);

(2S,4aS,6aS,6bR,8aR,9S,10S,12aS,12bR,14bR)-10-((acetylglycyl)oxy)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic acid (291-2);

(2S,4aS,6aS,6bR,8aR,9S,10S,12aS,12bR,14bR)-10-acetamido-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic acid;

(2S,4aS,6aS,6bR,8aR,9S,10S,12aS,12bR,14bR)-10-(allyloxy)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic acid (297-5);

(2S,4aS,6aS,6bR,8aR,9S,10S,12aS,12bR,14bR)-10-(3-methoxy-3-oxopropanamido)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic acid (298-2);

(2S,4aS,6aS,6bR,8aR,9S,10S,12aS,12bR,14bR)-10-(4-methoxy-4-oxobutanamido)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic acid (299-2);

(2S,4aS,6aS,6bR,8aR,9S,10S,12aS,12bR,14bR)-10-((butoxycarbonyl)amino)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic acid (300-1); (2S,4aS,6aS,6bR,8aR,9S,10S,12aS,12bR,14bR)-9-(((5-isopropyl-2-oxo-1,3-dioxol-4-yl)methoxy)carbonyl)-10-((methoxycarbonyl)oxy)-2,4a,6a,6b,9,12a-hexamethyl-13-oxo-1,2,3,4,4a,5,6,6a,6b,7,8,8a,9,10,11,12,12a,12b,13,14b-icosahydropicene-2-carboxylic acid (301-2);

(2S,4aS,6aS,6bR,8aR,9S,10S,12aS,12bR,14bR)-2,4a,6a,6b,9,12a-hexamethyl-9-(((5-methyl-2-oxo-1,3-dioxol-4-yl)methoxy)carbonyl)-10-((((5-methyl-2-oxo-1,3-dioxol-4-yl)methoxy)carbonyl)oxy)-13-oxo-1,2,3,4,4a,5,6,6a,6b,7,8,8a,9,10,11,12,12a,12b,13,14b-icosahydropicene-2-carboxylic acid (302-3);

(2S,4aS,6aS,6bR,8aR,9S,10S,12aS,12bR,14bR)-2,4a,6a,6b,9,12a-hexamethyl-10-((((5-methyl-2-oxo-1,3-dioxol-4-yl)methoxy)carbonyl)oxy)-13-oxo-1,2,3,4,4a,5,6,6a,6b,7,8,8a,9,10,11,12,12a,12b,13,14b-icosahydropicene-2,9-dicarboxylic acid (307-2);

(2S,4aS,6aS,6bR,8aR,9S,10S,12aS,12bR,14bR)-9-(((5-Isopropyl-2-oxo-1,3-dioxol-4-yl)methoxy)carbonyl)-10-(2-methoxyacetoxy)-2,4a,6a,6b,9,12a-hexamethyl-13-oxo-1,2,3,4,4a,5,6,6a,6b,7,8,8a,9,10,11,12,12a,12b,13,14b-icosahydropicene-2-carboxylic acid (308-2);

(2S,4aS,6aS,6bR,8aR,9S,10S,12aS,12bR,14bR)-10-(2,2-Difluoroacetamido)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic acid (309-2);

(2S,4aS,6aS,6bR,8aR,9S,10S,12aS,12bR,14bR)-10-((cyclopropanecarbonyl)oxy)-2,4a,6a,6b,9,12a-hexamethyl- 9-(((((5-methyl-2-oxo-1,3-dioxol-4-yl)methoxy)carbonyl) amino)-13-oxo-1,2,3,4,4a,5,6,6a,6b,7,8,8a,9,10,11,12, 12a,12b,13,14b-icosahydropicene-2-carboxylic acid (314-4);

(2S,4aS,6aS,6bR,8aR,9S,10S,12aS,12bR,14bR)-10-((cyclopropanecarbonyl)oxy)-9-(((((5-ethyl-2-oxo-1,3-dioxol-4-yl)methoxy)carbonyl)amino)-2,4a,6a,6b,9,12a-hexamethyl-13-oxo-1,2,3,4,4a,5,6,6a,6b,7,8,8a,9,10,11,12,12a, 12b,13,14b-icosahydropicene-2-carboxylic acid (315-2);

(2S,4aS,6aS,6bR,8aR,9S,10S,12aS,12bR,14bR)-10-acetoxy-9-((((5-ethyl-2-oxo-1,3-dioxol-4-yl)methoxy)carbonyl)-2,4a,6a,6b,9,12a-hexamethyl-13-oxo-1,2,3,4,4a,5, 6,6a,6b,7,8,8a,9,10,11,12,12a,12b,13,14b-icosahydropicene-2-carboxylic acid (316-1);

(2S,4aS,6aS,6bR,8aR,9S,10S,12aS,12bR,14bR)-2,4a,6a,6b, 9,12a-hexamethyl-9-(((((5-methyl-2-oxo-1,3-dioxol-4-yl) methoxy)carbonyl)amino)-13-oxo-10-(propionyloxy)-1, 2,3,4,4a,5,6,6a,6b,7,8,8a,9,10,11,12,12a,12b,13,14b-icosahydropicene-2-carboxylic acid (317-6); (2S,4aS, 6aS,6bR,8aR,9S,10S,12aS,12bR,14bR)-9-(((((5-ethyl-2-oxo-1,3-dioxol-4-yl)methoxy)carbonyl)amino)-2,4a,6a, 6b,9,12a-hexamethyl-13-oxo-10-(propionyloxy)-1,2,3,4, 4a,5,6,6a,6b,7,8,8a,9,10,11,12,12a,12b,13,14b-icosahydropicene-2-carboxylic acid (318-1);

(2S,4aS,6aS,6bR,8aR,9S,10S,12aS,12bR,14bR)-2,4a,6a,6b, 9,12a-hexamethyl-9-(((((5-methyl-2-oxo-1,3-dioxol-4-yl) methoxy)carbonyl)amino)-13-oxo-10-(propionyloxy)-1, 2,3,4,4a,5,6,6a,6b,7,8,8a,9,10,11,12,12a,12b,13,14b-icosahydropicene-2-carboxylic acid (319-1);

(3S,4S,4aR,6aR,6bS,8aS,11S,12aR,14aR,14bS)-4-(((((5-ethyl-2-oxo-1,3-dioxol-4-yl)methoxy)carbonyl)amino)-4, 6a,6b,8a,11,14b-hexamethyl-11-(methylcarbamoyl)-14-oxo-1,2,3,4,4a,5,6,6a,6b,7,8,8a,9,10,11,12,12a,14,14a, 14b-icosahydropicen-3-yl propionate (320-1);

(2S,4aS,6aS,6bR,8aR,9S,10S,12aS,12bR,14bR)-10-((cyclopropanecarbonyl)oxy)-9-(((((5-isopropyl-2-oxo-1,3-dioxol-4-yl)methoxy)carbonyl)amino)-2,4a,6a,6b,9,12a-hexamethyl-13-oxo-1,2,3,4,4a,5,6,6a,6b,7,8,8a,9,10,11, 12,12a,12b,13,14b-icosahydropicene-2-carboxylic acid (321-1);

(2S,4aS,6aS,6bR,8aR,9S,10S,12aS,12bR,14bR)-2,4a,6a,6b, 9,12a-hexamethyl-9-(((((5-methyl-2-oxo-1,3-dioxol-4-yl) methoxy)carbonyl)amino)-13-oxo-10-propoxy-1,2,3,4, 4a,5,6,6a,6b,7,8,8a,9,10,11,12,12a,12b,13,14b-icosahydropicene-2-carboxylic acid (322-6);

(2S,4aS,6aS,6bR,8aR,9S,10S,12aS,12bR,14bR)-9-((((5-isopropyl-2-oxo-1,3-dioxol-4-yl)methoxy)carbonyl) amino)-2,4a,6a,6b,9,12a-hexamethyl-13-oxo-10-propoxy-1,2,3,4,4a,5,6,6a,6b,7,8,8a,9,10,11,12,12a,12b, 13,14b-icosahydropicene-2-carboxylic acid (323-1);

(2S,4aS,6aS,6bR,8aR,9S,10S,12aS,12bR,14bR)-10-methoxy-2,4a,6a,6b,9,12a-hexamethyl-9-(((((5-methyl-2-oxo-1,3-dioxol-4-yl)methoxy)carbonyl)amino)-13-oxo-1, 2,3,4,4a,5,6,6a,6b,7,8,8a,9,10,11,12,12a,12b,13,14b-icosahydropicene-2-carboxylic acid (324-3);

(2S,4aS,6aS,6bR,8aR,9S,10S,12aS,12bR,14bR)-9-((((5-isopropyl-2-oxo-1,3-dioxol-4-yl)methoxy)carbonyl) amino)-10-m ethoxy-2,4a, 6a,6b, 9,12a-hexamethyl-13-oxo-1,2,3,4,4a,5,6,6a,6b,7,8,8a,9,10,11,12,12a,12b,13, 14b-icosahydropicene-2-carboxylic acid (325-1);

(2S,4aS,6aS,6bR,8aR,9S,10S,12aS,12bR,14bR)-10-acetoxy-9-(((((5-ethyl-2-oxo-1,3-dioxol-4-yl)methoxy)carbonyl)amino)-2,4a,6a,6b,9,12a-hexamethyl-13-oxo-1,2, 3,4,4a,5,6,6a,6b,7,8,8a,9,10,11,12,12a,12b,13,14b-icosahydropicene-2-carboxylic acid (326-1);

(2S,4aS,6aS,6bR,8aR,9S,10S,12aS,12bR,14bR)-10-(4,4-difluoropiperidin-1-yl)-9-(((((5-isopropyl-2-oxo-1,3-dioxol-4-yl)methoxy)carbonyl)amino)-2,4a,6a,6b,9,12a-hexamethyl-13-oxo-1,2,3,4,4a,5,6,6a,6b,7,8,8a,9,10,11,12,12a, 12b,13,14b-icosahydropicene-2-carboxylic acid (327-8);

(2S,4aS,6aS,6bR,8aR,9S,10S,12aS,12bR,14bR)-10-acetoxy-9-(((((5-ethyl-2-oxo-1,3-dioxol-4-yl)methoxy)carbonyl)amino)-2,4a,6a,6b,9,12a-hexamethyl-13-oxo-1,2, 3,4,4a,5,6,6a,6b,7,8,8a,9,10,11,12,12a,12b,13,14b-icosahydropicene-2-carboxylic acid (326-1);

(2S,4aS,6aS,6bR,8aR,9S,10S,12aS,12bR,14bR)-10-(4,4-difluoropiperidin-1-yl)-9-(((((5-isopropyl-2-oxo-1,3-dioxol-4-yl)methoxy)carbonyl)amino)-2,4a,6a,6b,9,12a-hexamethyl-13-oxo-1,2,3,4,4a,5,6,6a,6b,7,8,8a,9,10,11,12,12a, 12b,13,14b-icosahydropicene-2-carboxylic acid (327-8);

(2S,4aS,6aS,6bR,8aR,9S,10S,12aS,12bR,14bR)-2,4a,6a,6b, 9,12a-hexamethyl-9-(((5-methyl-2-oxo-1,3-dioxol-4-yl) methoxy)carbonyl)-13-oxo-10-(1H-pyrrol-1-yl)-1,2,3,4, 4a,5,6,6a,6b,7,8,8a,9,10,11,12,12a,12b,13,14b-icosahydropicene-2-carboxylic acid (328-2);

(2S,4aS,6aS,6bR,8aR,9S,10S,12aS,12bR,14bR)-2,4a,6a,6b, 9,12a-hexamethyl-9-(((5-methyl-2-oxo-1,3-dioxol-4-yl) methoxy)carbonyl)-13-oxo-10-(1H-pyrazol-1-yl)-1,2,3,4, 4a,5,6,6a,6b,7,8,8a,9,10,11,12,12a,12b,13,14b-icosahydropicene-2-carboxylic acid;

(2S,4aS,6aS,6bR,8aR,9S,10S,12aS,12bR,14bR)-9-(((5-isopropyl-2-oxo-1,3-dioxol-4-yl)methoxy)carbonyl)-2,4a, 6a,6b,9,12a-hexamethyl-13-oxo-10-(1H-pyrazol-1-yl)-1, 2,3,4,4a,5,6,6a,6b,7,8,8a,9,10,11,12,12a,12b,13,14b-icosahydropicene-2-carboxylic acid (330-1);

(2S,4aS,6aS,6bR,8aR,9S,10S,12aS,12bR,14bR)-2,4a,6a,6b, 9,12a-hexamethyl-10-(5-methyl-1H-pyrazol-1-yl)-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13, 14b-icosahydropicene-2-carboxylic acid (331-2);

(2S,4aS,6aS,6bR,8aR,9S,10S,12aS,12bR,14bR)-2,4a,6a,6b, 9,12a-hexamethyl-10-(3-methyl-1H-pyrazol-1-yl)-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13, 14b-icosahydropicene-2-carboxylic acid (332-2);

(2S,4aS,6aS,6bR,8aR,9S,10S,12aS,12bR,14bR)-9-(((((5-ethyl-2-oxo-1,3-dioxol-4-yl)methoxy)carbonyl)amino)-2, 4a,6a,6b,9,12a-hexamethyl-13-oxo-10-(propionyloxy)-1, 2,3,4,4a,5,6,6a,6b,7,8,8a,9,10,11,12,12a,12b,13,14b-icosahydropicene-2-carboxylic acid (333-1);

(2S,4aS,6aS,6bR,8aR,9S,10S,12aS,12bR,14bR)-10-(4-(ethoxycarbonyl)-1H-pyrazol-1-yl)-2,4a,6a,6b,9,12a-hexamethyl-9-(((5-methyl-2-oxo-1,3-dioxol-4-yl) methoxy)carbonyl)-13-oxo-1,2,3,4,4a,5,6,6a,6b,7,8,8a,9, 10,11,12,12a,12b,13,14b-icosahydropicene-2-carboxylic acid (334-8);

(2S,4aS,6aS,6bR,8aR,9S,10S,12aS,12bR,14bR)-10-(4-(ethoxycarbonyl)-1H-pyrazol-1-yl)-2,4a,6a,6b,9,12a-hexamethyl-9-(((5-methyl-2-oxo-1,3-dioxol-4-yl) methoxy)carbonyl)-13-oxo-1,2,3,4,4a,5,6,6a,6b,7,8,8a,9, 10,11,12,12a,12b,13,14b-icosahydropicene-2-carboxylic acid (335-1);

(2S,4aS,6aS,6bR,8aR,9S,10S,12aS,12bR,14bR)-10-(5-(ethoxycarbonyl)-3-methyl-1H-pyrazol-1-yl)-2,4a,6a,6b, 9,12a-hexamethyl-9-(((5-methyl-2-oxo-1,3-dioxol-4-yl) methoxy)carbonyl)-13-oxo-1,2,3,4,4a,5,6,6a,6b,7,8,8a,9, 10,11,12,12a,12b,13,14b-icosahydropicene-2-carboxylic acid (336-2);

(2S,4aS,6aS,6bR,8aR,9S,10S,12aS,12bR,14bR)-10-(3-(ethoxycarbonyl)-5-methyl-1H-pyrazol-1-yl)-2,4a,6a,6b, 9,12a-hexamethyl-9-(((5-methyl-2-oxo-1,3-dioxol-4-yl) methoxy)carbonyl)-13-oxo-1,2,3,4,4a,5,6,6a,6b,7,8,8a,9, 10,11,12,12a,12b,13,14b-icosahydropicene-2-carboxylic acid (337-2);

(2S,4aS,6aS,6bR,8aR,9S,10S,12aS,12bR,14bR)-2,4a,6a,6b,9,12a-hexamethyl-10-(4-methyl-1H-pyrazol-1-yl)-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic acid (338-4);

(2S,4aS,6aS,6bR,8aR,9S,10S,12aS,12bR,14bR)-9-(((5-ethyl-2-oxo-1,3-dioxol-4-yl)methoxy)carbonyl)-2,4a,6a,6b,9,12a-hexamethyl-10-(4-methyl-1H-pyrazol-1-yl)-13-oxo-1,2,3,4,4a,5,6,6a,6b,7,8,8a,9,10,11,12,12a,12b,13,14b-icosahydropicene-2-carboxylic acid (339-1);

(2S,4aS,6aS,6bR,8aR,9S,10S,12aS,12bR,14bR)-10-((2-methoxy-2-oxoethyl)amino)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic acid (341-2);

(2S,4aS,6aS,6bR,8aR,9S,10S,12aS,12bR,14bR)-10-((2-amino-2-oxoethyl)amino)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic acid (342-1);

(2S,4aS,6aS,6bR,8aR,9S,10S,12aS,12bR,14bR)-10-((2-methoxy-2-oxoethyl)amino)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic acid (343-3);

(2S,4aS,6aS,6bR,8aR,9S,10S,12aS,12bR,14bR)-10-(allyl(2-methoxy-2-oxoethyl)amino)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic acid (344-1);

(2S,4aS,6aS,6bR,8aR,9S,10S,12aS,12bR,14bR)-10-(((S)-1-methoxy-1-oxopropan-2-yl)amino)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic acid (345-2);

(2S,4aS,6aS,6bR,8aR,9S,10S,12aS,12bR,14bR)-2,4a,6a,6b,9,12a-hexamethyl-9-(((5-methyl-2-oxo-1,3-dioxol-4-yl)methoxy)carbonyl)-10-(1-methyl cyclopropane-1-carboxamido)-13-oxo-1,2,3,4,4a,5,6,6a,6b,7,8,8a,9,10,11,12,12a,12b,13,14b-icosahydropicene-2-carboxylic acid (346-2);

(2S,4aS,6aS,6bR,8aR,9S,10S,12aS,12bR,14bR)-2,4a,6a,6b,9,12a-hexamethyl-9-(((5-methyl-2-oxo-1,3-dioxol-4-yl)methoxy)carbonyl)-13-oxo-10-(2-oxopyrrolidin-1-yl)-1,2,3,4,4a,5,6,6a,6b,7,8,8a,9,10,11,12,12a,12b,13,14b-icosahydropicene-2-carboxylic acid (347-4);

(2S,4aS,6aS,6bR,8aR,9S,10S,12aS,12bR,14bR)-9-(((5-ethyl-2-oxo-1,3-dioxol-4-yl)methoxy)carbonyl)-10-((S)-2-(methoxycarbonyl)pyrrolidin-1-yl)-2,4a,6a,6b,9,12a-hexamethyl-13-oxo-1,2,3,4,4a,5,6,6a,6b,7,8,8a,9,10,11,12,12a,12b,13,14b-icosahydropicene-2-carboxylic acid (348-11);

(2S,4aS,6aS,6bR,8aR,9S,10S,12aS,12bR,14bR)-10-((S)-2-(methoxycarbonyl)pyrrolidin-1-yl)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic acid (349-1);

(2S,4aS,6aS,6bR,8aR,9S,10S,12aS,12bR,14bR)-9-(((5-isopropyl-2-oxo-1,3-dioxol-4-yl)methoxy)carbonyl)-10-((S)-2-(methoxycarbonyl)pyrrolidin-1-yl)-2,4a,6a,6b,9,12a-hexamethyl-13-oxo-1,2,3,4,4a,5,6,6a,6b,7,8,8a,9,10,11,12,12a,12b,13,14b-icosahydropicene-2-carboxylic acid (350-1);

(2S,4aS,6aS,6bR,8aR,9S,10S,12aS,12bR,14bR)-9-(((5-isopropyl-2-oxo-1,3-dioxol-4-yl)methoxy)carbonyl)-10-((R)-2-(methoxycarbonyl)pyrrolidin-1-yl)-2,4a,6a,6b,9,12a-hexamethyl-13-oxo-1,2,3,4,4a,5,6,6a,6b,7,8,8a,9,10,11,12,12a,12b,13,14b-icosahydropicene-2-carboxylic acid (351-1);

(2S,4aS,6aS,6bR,8aR,9S,10S,12aS,12bR,14bR)-10-((S)-2-(ethoxycarbonyl)pyrrolidin-1-yl)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic acid (352-1);

(2S,4aS,6aS,6bR,8aR,9S,10S,12aS,12bR,14bR)-10-((R)-2-(ethoxycarbonyl)pyrrolidin-1-yl)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic acid (353-1);

(2S,4aS,6aS,6bR,8aR,9S,10S,12aS,12bR,14bR)-2,4a,6a,6b,9,12a-hexamethyl-9-(((5-methyl-2-oxo-1,3-dioxol-4-yl)methoxy)carbonyl)-13-oxo-10-(piperidin-1-yl)-1,2,3,4,4a,5,6,6a,6b,7,8,8a,9,10,11,12,12a,12b,13,14b-icosahydropicene-2-carboxylic acid (356-2);

(2S,4aS,6aS,6bR,8aR,9S,10S,12aS,12bR,14bR)-10-(4,4-difluoropiperidin-1-yl)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic acid (357-7);

(2S,4aS,6aS,6bR,8aR,9S,10S,12aS,12bR,14bR)-10-((R)-3-(ethoxycarbonyl)pyrrolidin-1-yl)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic acid (358-7);

(2S,4aS,6aS,6bR,8aR,9S,10S,12aS,12bR,14bR)-10-((R)-3-(ethoxycarbonyl)piperidin-1-yl)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic acid (359-1);

(2S,4aS,6aS,6bR,8aR,9S,10S,12aS,12bR,14bR)-10-((S)-3-(ethoxycarbonyl)piperidin-1-yl)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic acid (360-1);

(2S,4aS,6aS,6bR,8aR,9S,10S,12aS,12bR,14bR)-10-(4-(ethoxycarbonyl)piperidin-1-yl)-9-(((5-ethyl-2-oxo-1,3-dioxol-4-yl)methoxy)carbonyl)-2,4a,6a,6b,9,12a-hexamethyl-13-oxo-1,2,3,4,4a,5,6,6a,6b,7,8,8a,9,10,11,12,12a,12b,13,14b-icosahydropicene-2-carboxylic acid (361-1);

(2S,4aS,6aS,6bR,8aR,9S,10S,12aS,12bR,14bR)-10-(4-(ethoxycarbonyl)piperidin-1-yl)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic acid (362-1);

(2S,4aS,6aS,6bR,8aR,9S,10S,12aS,12bR,14bR)-9-acetamido-2,4a,6a,6b,9,12a-hexamethyl-10-((((5-methyl-2-oxo-1,3-dioxol-4-yl)methoxy)carbonyl)oxy)-13-oxo-1,2,3,4,4a,5,6,6a,6b,7,8,8a,9,10,11,12,12a,12b,13,14b-icosahydropicene-2-carboxylic acid (363-5);

(2S,4aS,6aS,6bR,8aR,9S,10S,12aS,12bR,14bR)-9-acetamido-2,4a,6a,6b,9,12a-hexamethyl-10-((((5-methyl-2- oxo-1,3-dioxol-4-yl)methoxy)carbonyl)oxy)-13-oxo-1,2,
3,4,4a,5,6,6a,6b,7,8,8a,9,10,11,12,12a,12b,13,14b-
icosahydropicene-2-carboxylic acid (363-5);
(2S,4aS,6aS,6bR,8aR,9S,10S,12aS,12bR,14bR)-2,4a,6a,6b,
9,12a-hexamethyl-9-(((5-methyl-2-oxo-1,3-dioxol-4-yl)
methoxy)carbonyl)-10-((R)-5-methyl-2-oxooxazolidin-3-
yl)-13-oxo-1,2,3,4,4a,5,6,6a,6b,7,8,8a,9,10,11,12,12a,
12b,13,14b-icosahydropicene-2-carboxylic acid (364-5);
(2S,4aS,6aS,6bR,8aR,9S,10S,12aS,12bR,14bR)-10-(2,5-di-
oxoimidazolidin-1-yl)-2,4a,6a,6b,9,12a-hexamethyl-9-
(((5-methyl-2-oxo-1,3-dioxol-4-yl)methoxy)carbonyl)-
13-oxo-1,2,3,4,4a,5,6,6a,6b,7,8,8a,9,10,11,12,12a,12b,
13,14b-icosahydropicene-2-carboxylic acid (365-8);
(2S,4aS,6aS,6bR,8aR,9S,10S,12aS,12bR,14bR)-2,4a,6a,6b,
9,12a-hexamethyl-10-((R)-4-methyl-2,5-dioxoimidazoli-
din-1-yl)-9-(((5-methyl-2-oxo-1,3-dioxol-4-yl)methoxy)
carbonyl)-13-oxo-1,2,3,4,4a,5,6,6a,6b,7,8,8a,9,10,11,12,
12a,12b,13,14b-icosahydropicene-2-carboxylic acid
(366-1);
2-(3-((1-PEG$_{5K}$-1H-1,2,3-triazol-4-yl)methoxy)-4-ni-
trobenzyl) 9-((5-methyl-2-oxo-1,3-dioxol-4-yl)methyl)
(2S,4aS,6aS,6bR,8aR,9S,10S,12aS,12bR,14bR)-10-((2,
5,8,11-tetraoxatetradecan-14-oyl)oxy)-2,4a, 6a, 6b,
9,12a-h exam ethyl-13-oxo-1,2,3,4,4a,5,6,6a,6b,7,8,8a,9,
10,11,12,12a,12b,13,14b-icosahydropicene-2,9-dicar-
boxylate (605-2);
(2S,4aS,6aS,6bR,8aS,10S,12aS,12bR,14bR)-2,4a,6a,6b,9,9,
12a-heptamethyl-13-oxo-10-{[(2-oxo-1,3-dioxolan-4-yl)
methoxy]carbonyl}-1,2,3,4,4a,5,6,6a,6b,7,8,8a,9,10,11,
12,12a,12b,13,14b-icosahydropicene-2-carboxylic acid
(cmpd 700-1);
(2S,4aS,6aS,6bR,8aR,9S,10S,12aS,12bR,14bR)-2,4a,6a,6b,
9,12a-hexamethyl-10-{[2-(methylsulfanyl)acetyl]oxy}-
13-oxo-9-({[2-oxo-5-(propan-2-yl)-2H-1,3-dioxol-4-yl]
methoxy}carbonyl)-1,2,3,4,4a,5,6,6a,6b,7,8,8a,9,10,11,
12,12a,12b,13,14b-icosahydropicene-2-carboxylic acid
(cmpd 701-1);
(2S,4aS,6aS,6bR,8aR,9S,10R,12aS,12bR,14bR)-10-(acety-
loxy)-2,4a,6a,6b,9,10,12a-heptamethyl-13-oxo-9-({[2-
oxo-5-(propan-2-yl)-2H-1,3-dioxol-4-yl]
methoxy}carbonyl)-1,2,3,4,4a,5,6,6a,6b,7,8,8a,9,10,11,
12,12a,12b,13,14b-icosahydropicene-2-carboxylic acid
(cmpd 702-1);
(2S,4aS,6aS,6bR,8aR,9S,10R,12aS,12bR,14bR)-10-(acety-
loxy)-9-{[(5-ethyl-2-oxo-2H-1,3-dioxol-4-yl)methoxy]
carbonyl}-2,4a, 6a,6b, 9,10,12a-heptamethyl-13-oxo-1,2,
3,4,4a,5,6,6a,6b,7,8,8a,9,10,11,12,12a,12b,13,14b-
icosahydropicene-2-carboxylic acid (cmpd 703-1);
(2S,4aS,6aS,6bR,8aR,9S,10R,12aS,12bR,14bR)-10-(acety-
loxy)-2,4a,6a,6b,9,10,12a-heptamethyl-9-{[(5-methyl-2-
oxo-2H-1,3-dioxol-4-yl)methoxy]carbonyl}-13-oxo-1,2,
3,4,4a,5,6,6a,6b,7,8,8a,9,10,11,12,12a,12b,13,14b-
icosahydropicene-2-carboxylic acid (cmpd 704-1);
(2S,4aS,6aS,6bR,8aR,9S,10S,12aS,12bR,14bR)-10-(acety-
loxy)-9-{[(5-tert-butyl-2-oxo-2H-1,3-dioxol-4-yl)
methoxy]carbonyl}-2,4a,6a,6b,9,12a-hexamethyl-13-
oxo-1,2,3,4,4a,5,6,6a,6b,7,8,8a,9,10,11,12,12a,12b,13,
14b-icosahydropicene-2-carboxylic acid (cmpd 705-1);
(2S,4aS,6aS,6bR,8aR,9S,10S,12aS,12bR,14bR)-10-(acety-
loxy)-2,4a,6a,6b,9,12a-hexamethyl-13-oxo-9-{[(2-oxo-5-
propyl-2H-1,3-dioxol-4-yl)methoxy]carbonyl}-1,2,3,4,
4a,5,6,6a,6b,7,8,8a,9,10,11,12,12a,12b,13,14b-
icosahydropicene-2-carboxylic acid (cmpd 706-1);
(2S,4aS,6aS,6bR,8aR,9S,10S,12aS,12bR,14bR)-10-(acety-
loxy)-2,4a,6a,6b,9,12a-hexamethyl-13-oxo-9-{[(2-oxo-5-
phenyl-2H-1,3-dioxol-4-yl)methoxy]carbonyl}-1,2,3,4,
4a,5,6,6a,6b,7,8,8a,9,10,11,12,12a,12b,13,14b-
icosahydropicene-2-carboxylic acid (cmpd 707-1);
(2S,4aS,6aS,6bR,8aR,9S,10S,12aS,12bR,14bR)-10-[(2-
methoxyacetyl)oxy]-2,4a,6a,6b,9,12a-hexamethyl-13-
oxo-9-({[2-oxo-5-(propan-2-yl)-2H-1,3-dioxol-4-yl]
methoxy}carbonyl)-1,2,3,4,4a,5,6,6a,6b,7,8,8a,9,10,11,
12,12a,12b,13,14b-icosahydropicene-2-carboxylic acid
(cmpd 708-1);
(2S,4aS,6aS,6bR,8aR,9S,10S,12aS,12bR,14bR)-10-[(2-
methoxyacetyl)oxy]-2,4a,6a,6b,9,12a-hexamethyl-9-{
[(5-methyl-2-oxo-2H-1,3-dioxol-4-yl)methoxy]carbo-
nyl}-13-oxo-1,2,3,4,4a,5,6,6a,6b,7,8,8a,9,10,11,12,12a,
12b,13,14b-icosahydropicene-2-carboxylic acid (cmpd
709-1);
(2S,4aS,6aS,6bR,8aR,10S,12aS,12bR,14bR)-2,4a,6a,6b,9,
9,12a-heptamethyl-13-oxo-10-(2-oxo-2-{[2-oxo-5-(2,5,
8-trioxa-11-thiadodecan-12-yl)-2H-1,3-dioxol-4-yl]
methoxy}ethoxy)-1,2,3,4,4a,5,6,6a,6b,7,8,8a,9,10,11,12,
12a,12b,13,14b-icosahydropicene-2-carboxylic acid
(cmpd 710-1);
(2S,4aS,6aS,6bR,8aR,10S,12aS,12bR,14bR)-10-(2-{[5-
(hydroxymethyl)-2-oxo-2H-1,3-dioxol-4-yl]methoxy}-2-
oxoethoxy)-2,4a,6a,6b,9,9,12a-heptamethyl-13-oxo-1,2,
3,4,4a,5,6,6a,6b,7,8,8a,9,10,11,12,12a,12b,13,14b-
icosahydropicene-2-carboxylic acid (cmpd 711-1);
(2S,4aS,6aS,6bR,8aR,10S,12aS,12bR,14bR)-2,4a,6a,6b,9,
9,12a-heptamethyl-10-{2-[(5-methyl-2-oxo-2H-1,3-di-
oxol-4-yl)methoxy]-2-oxoethoxy}-13-oxo-1,2,3,4,4a,5,6,
6a,6b,7,8,8a,9,10,11,12,12a,12b,13,14b-
icosahydropicene-2-carboxylic acid (cmpd 712-1); and
(2S,4aS,6aS,6bR,8aR,9S,10S,12aS,12bR,14bR)-10-[4-
(ethoxycarbonyl)-5-methoxy-1H-pyrazol-1-yl]-2,4a,6a,
6b,9,12a-hexamethyl-9-{[(5-methyl-2-oxo-2H-1,3-di-
oxol-4-yl)methoxy]carbonyl}-13-oxo-1,2,3,4,4a,5,6,6a,
6b,7,8,8a,9,10,11,12,12a,12b,13,14b-icosahydropicene-
2-carboxylic acid (cmpd 713-1).

Compounds of the invention are "soft drugs" which in parent form are active inhibitors of 11b-HSD2 in the gastrointestinal tract of a patient but upon uptake into plasma are enzymatically converted to inactive, or less active, metabolites. This effect provides a desired preferential inhibition of HSD2 in the GI tract relative to HSD2 in kidney. Compounds of the invention disclosed herein were tested in the assays described in examples 112 and were found to inhibit HSD2 by measuring the amount of cortisol before and after contacting cell lysate human or a colon monolayer organoid derived from human colon tissue. Furthermore, each of the compounds tested were found to be more potent HSD2 inhibitors than their corresponding metabolites.

Compounds of the invention may contain one or more asymmetric or chiral centers. Accordingly, the compounds may exist as diastereomers, enantiomers or mixtures thereof. The syntheses of the compounds may employ racemates, diastereomers or enantiomers as starting materials or as intermediates. Diastereomeric compounds may be separated by chromatographic or crystallization methods. Similarly, enantiomeric mixtures may be separated using the same techniques or others known in the art. Unless specified, each of the asymmetric centers may be in the R or S configuration and both of these configurations are within the scope of the invention. It is intended that all stereoisomeric forms of the compounds described herein, including but not limited to, diastereomers, enantiomers and atropisomers, as well as mixtures thereof, such as racemic mixtures, form part of the present compounds.

It will also be appreciated that certain compounds of Formula I may be used as intermediates for further compounds of Formula I. It will be further appreciated that the compounds described herein may exist in unsolvated, as well as solvated forms with pharmaceutically acceptable solvents, such as water, ethanol, and the like, and it is intended that the compounds embrace both solvated and unsolvated forms.

Compounds of the invention are prepared using standard organic synthetic techniques from commercially available starting materials and reagents. It will be appreciated that synthetic procedures employed in the preparation of compounds of the invention will depend on the particular substituents present in a compound and that various protection and deprotection steps that are standard in organic synthesis may be required but may not be illustrated in the following general schemes. The starting materials are generally available from commercial sources or are readily prepared using methods well known to those skilled in the art. For example, compounds of the invention may be prepared from glycyrrhetinic acid shown in FIG. 3. For illustrative purposes, schemes herein show general methods for preparing the compounds of the invention, as well as key intermediates. Those skilled in the art will appreciate that other synthetic routes may be used to synthesize the compounds. Although specific starting materials and reagents are depicted in the Schemes and discussed below, other starting materials and reagents can be substituted to provide a variety of derivatives and/or reaction conditions. In addition, many of the compounds prepared by the methods described below can be further modified in light of this disclosure using conventional chemistry well known to those skilled in the art. As illustrated in Scheme I, the compounds of the invention in which -Q-W—C(O)-L-X— form an ester linkage —$CH_2$—O—C(O)— to the dioxalone may be prepared starting with a carboxylic acid derivative of glycyrrhetinic acid (either at the 3- or 4-position) and reacting with, for example, a halogenated dioxalone.

Scheme 1

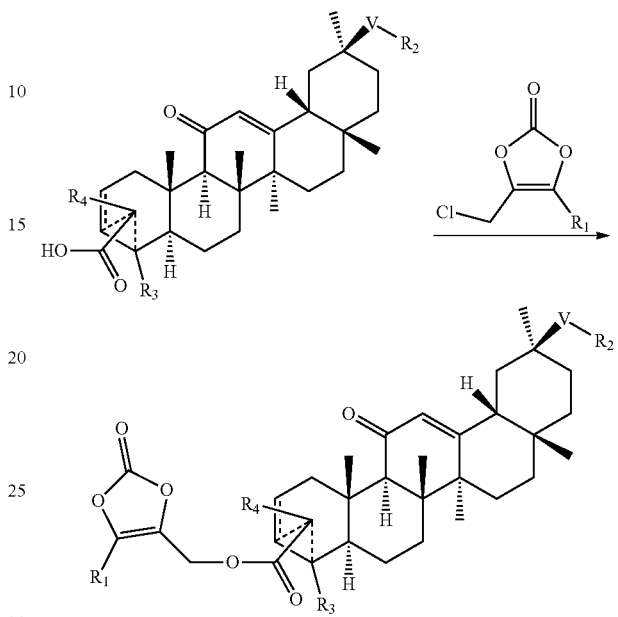

Compounds of the invention in which -Q-W—C(O)-L-X— form a linkage —$CH_2$—O—C(O)—O— to the dioxalone may be according to the general Scheme 2.

Scheme 2

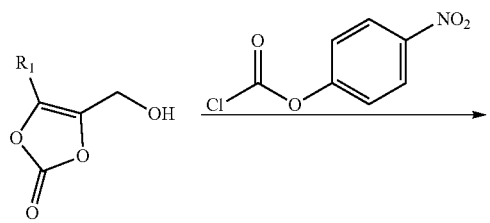

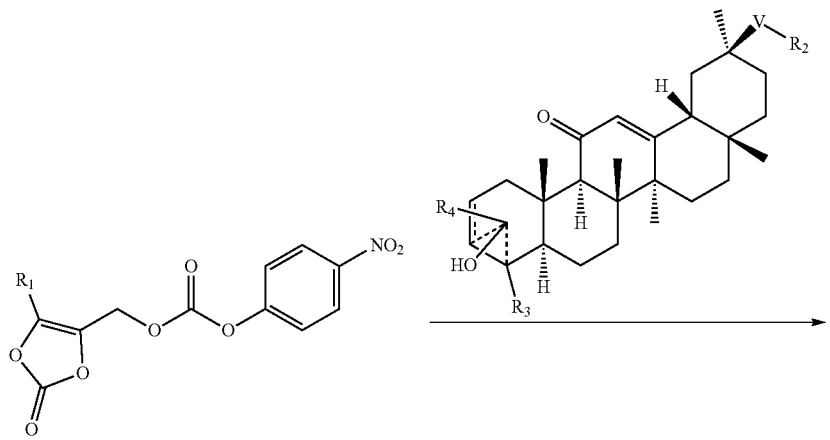

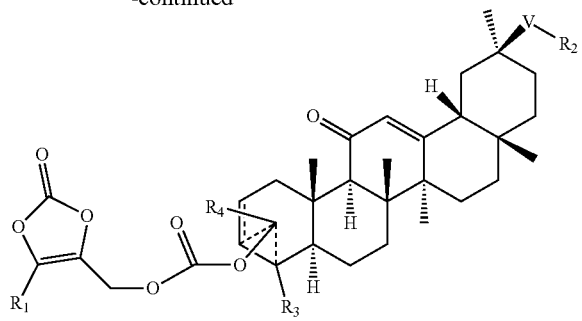

Compounds of the invention in which -Q-W—C(O)-L-X— form an amide linkage —CH$_2$—O—C(O)—NH— to the dioxalone may be prepared starting by reacting an isocyanate at the 3- or 4-position of the fused ring system with a hydroxylated dioxalone as illustrated in Scheme 3.

Scheme 3

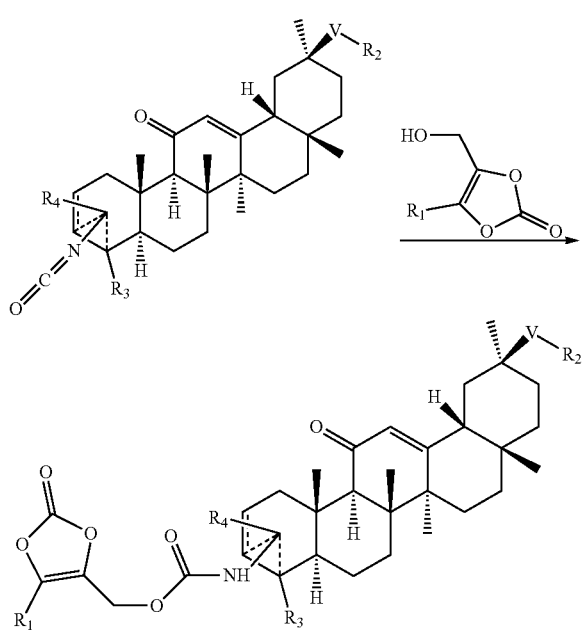

In preparing compounds of the invention, protection of remote functionalities (e.g., primary or secondary amines, etc.) of intermediates may be necessary. The need for such protection will vary depending on the nature of the remote functionality and the conditions of the preparation methods. The need for such protection is readily determined by one skilled in the art. For a general description of protecting groups and their use, see Greene, T. W., and P. G. M. Wuts. *Greene's Protective Groups in Organic Synthesis.* 4th ed. New York: Wiley-Interscience, 2006.

It may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed ("SMB") and preparative thin or thick layer chromatography, as well as techniques of small scale thin layer and flash chromatography. One skilled in the art will apply techniques most likely to achieve the desired separation.

Diastereomeric and enantiomeric mixtures can be separated into their individual stereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column.

The invention also includes pharmaceutical compositions or medicaments containing the compounds of the invention and a therapeutically inert carrier, diluent or excipient, as well as methods of using the compounds of the invention to prepare such compositions and medicaments. Typically, the compounds of Formula I used in the methods of the invention are formulated by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range anywhere from about 3 to about 8. Formulation in an acetate buffer at pH 5 is a suitable embodiment. In one embodiment, formulations comprising compounds of the invention are sterile. The compounds ordinarily will be stored as a solid composition, although lyophilized formulations or aqueous solutions are acceptable.

Compositions comprising compounds of the invention will be formulated, dosed, and administered in a fashion consistent with good medical practice. Factors for consideration in this context include the particular disorder being treated, the particular mammal being treated, the clinical condition of the individual patient, the cause of the disorder, the site of administration, the method of administration, the scheduling of administration, and other factors known to medical practitioners. The "effective amount" of the compound to be administered will be governed by such considerations, and is the minimum amount necessary to inhibit conversion of cortisol to cortisone by HSD2. Such amount may be below the amount that is toxic to normal cells, or the mammal as a whole.

The compound of the invention may be administered by any suitable means. In a particular embodiment, the compounds are administered orally. In a particular embodiment, the compounds are administered rectally.

Generally, the initial pharmaceutically effective amount of the compound of the invention administered parenterally per dose will be in the range of about 0.01-1,000 mg/kg/day, for example about 0.1 to 100 mg/kg of patient body weight per day, with the typical initial range of compound used being 0.5 to 50 mg/kg/day. Oral unit dosage forms, such as tablets and capsules, may contain from about 25 to about 1000 mg of the compound of the invention. In a particular embodiment, an effective amount is the amount of the compound of the invention sufficient to enhance colonic potassium secretion by about 15 mmol/day. In a particular embodiment, an effective amount is the amount of the compound of the invention sufficient to enhance colonic potassium secretion by about 1 mmol/day. In a particular embodiment, an effective amount is the amount of the compound of the invention sufficient to enhance colonic potassium secretion by about 5 mmol/day. In a particular embodiment, an effective amount is the amount of the compound of the invention sufficient to enhance colonic potassium secretion by about 10 mmol/day. In a particular embodiment, an effective amount is the amount of the compound of the invention sufficient to enhance colonic potassium secretion by about 15 mmol/day. In a particular embodiment, an effective amount is the amount of the compound of the invention sufficient to enhance colonic potassium secretion by about 20 mmol/day.

The compounds may be administered in any convenient administrative form, e.g., tablets, capsules, solutions, dispersions, suspensions, syrups, suppositories, gels, emulsions etc. An example of a suitable oral dosage form is a tablet containing about 25 mg, 50 mg, 100 mg, 250 mg, or 500 mg of the compound of the invention compounded with about 90-30 mg anhydrous lactose, about 5-40 mg sodium croscarmellose, about 5-30 mg polyvinylpyrrolidone ("PVP") K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment.

Another formulation may be prepared by mixing a compound described herein and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington; The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound described herein or pharmaceutical composition thereof) or aid in the manufacturing of the pharmaceutical product (i.e., medicament).

In an embodiment, the formulation releases the compound in response to contact with colonic enzyme, for example, enzymes created by enterobacteria. Certain starch-based capsule coatings may be used that are resistant to digestion in the stomach and small intestine but are degraded by microbial (normal gut flora) enzymes once the dosage form reaches the colon.

In an embodiment, the compound of the invention is administered orally. In another embodiment, the compound is formulated for colonic delivery. Colonic delivery may be effected in response to pH time, microbes, and pressure. In an embodiment, the formulation releases the compound in response to colonic pH. Release of the compound is triggered by the pH increase as the formulation travels through the GI tract. Formulations are based on polymers that are insoluble at the lower pH in the stomach and upper small intestine and soluble in the higher pH found in the distal small intestine, for example, polymers that are derivatives of acrylic acid and cellulose which withstand an environment as low as pH ~1.2. Suitable enteric polymers include, polyvinyl acetate phthalate (PVAP) e.g. Coateric®, cellulose acetate trimellitate (CAT), hydroxypropyl methylcellulose phthalate (HPMCP) e.g. HP-50, HP-55, HP-55S, hydroxypropylmethylcellulose acetate succinate (HPMCAS) e.g. LF grade, MF grade or HF grade, methacrylic acid copolymer e.g. Eudragit® L100-55, L30D-55, L-1000, L12.5, S-100, S12.5, FS30D, cellulose acetate phthalate (CAP) e.g. Aquateric®, and shellac e.g. MarCoat® 125 or 125N.

In an aspect of the invention, there is provided a method of inhibiting conversion of cortisol to cortisone by HSD2 comprising contacting HSD2 with a compound of Formula I. In another aspect of the invention, there is provided a method for promoting activation MR in a mammal, comprising administering to said mammal an effective amount of a compound of Formula I. In another aspect of the invention, there is provided a method of reducing potassium levels in plasma of a mammal, comprising administering to said mammal an effective amount of a compound of Formula I. In another aspect of the invention, there is provided a method for promoting potassium ion secretion into the colonic lumen of a mammal, comprising administering to said mammal an effective amount of a compound of Formula I.

In an aspect of the invention, there is provided a method for treating and/or preventing hyperkalemia in a mammal, comprising administering to said mammal an effective amount of a compound of Formula I. Hyperkalemia occurs especially frequently in patients with chronic kidney disease (CKD), hypertension, heart failure and diabetes. Accordingly, in an embodiment of the invention the methods of treating and/or preventing hyperkalemia is in a patient having CKD hypertension, heart failure and diabetes. Patients suffering for these conditions are often treated with certain classes of medications, such as angiotensin-converting-enzyme (ACE) inhibitors, angiotensin-receptor blockers (ARBs) or other inhibitors of the renin-angiotensin-aldosterone system (RAAS) in order to regulate blood pressure. However such medications promote potassium retention. Accordingly, there is provided a method of treating and/or preventing hyperkalemia in a mammal comprising administering a compound of formula I in combination with an inhibitor of the RAAS system. In an embodiment, the RAAS inhibitor is an ACE inhibitor.

The compounds described herein and stereoisomers, diastereomers, enantiomers, tautomers and pharmaceutically acceptable salts thereof may be employed alone or in combination with other anti-hyperkalemia agents that works by a different mechanism of action. The compound of the invention may be administered together with the other anti-hyperkalemia agent in a unitary pharmaceutical composition or separately and, when administered separately this may occur simultaneously or sequentially in any order. Such sequential administration may be close in time or remote in time.

In an embodiment, the other anti-hyperkalemic compound is a potassium ion binder such as a cross-lined polystyrene sulfonate (PSS) polymer resins. In an embodiment, the PSS resin is crosslinked with divinylbenzene (DVB) co-polymer. DVB-crosslinked PSS is the most common agent used in the management of hyperkalemia in hospitalized patients. PSS is typically provided as a sodium or calcium salt, and in the lumen of the intestine it exchanges sodium or calcium ions for secreted potassium ions. Most of this takes place in the colon, the site of most potassium secretion in the gut. In an embodiment, the anti-hyperkalemic PSS resin is described in WO2016111855 (incorporated herein by reference). In an embodiment, the PSS resin is a calcium salt of a PSS polymer resins crosslinked with DVB co-polymer. In an embodiment, the PSS resin is cross-linked with from 1.0 to 1.9 percent of DVB. In an embodiment, the PSS resin is cross-linked with from 1.6 to 1.9 percent of DVB. In an embodiment, the PSS resin is cross-linked with about 1.8 percent of DVB.

In an embodiment, the other anti-hyperkalemia agent is Kayexalate®, Argamate®, Kionex®, Resonium® or RDX7675. In another embodiment, the other anti-hyperkalemia agent is a fluoroacrylate polymer incorporating a potassium-binding carboxylate group e.g. patiromer (Veltassa®). In an embodiment, the other anti-hyperkalemia agent is an insoluble, non-absorbed zirconium-sodium silicate that traps potassium ions within its crystalline lattice structure e.g. ZS-9 (Lokelma®). In an embodiment, the other anti-hyperkalemia agent is a crosslinked polyacrylic acid e.g. CLP-1001.

In another aspect of the invention, it has been found unexpectedly that HSD2 inhibition in combination with inhibition of sodium-hydrogen exchanger (NHE) synergistically increase excretion of potassium into feces. NHE is found in the tubulus proximal of the nephron of the kidney and in the apical membrane of enterocytes of the intestine. The isoform known as NHE3 is primarily responsible for maintaining the balance of sodium and also indirectly linked to buffering of blood pH. The NHE3 antiporter imports one sodium ion into the cytosol of a cell as it ejects one hydrogen ion from the cell into the intestinal lumen and proximal tubule lumen. As shown in FIG. 1, it has been demonstrated that there is a synergistic effect on fecal potassium excretion when inhibiting HSD2 and NHE. Accordingly, there is provided a method for removing potassium from plasma and/or tissue of a mammal comprising administering to said mammal an effective amount of an HSD2 inhibitor or an MR agonist in combination with a compound that increases fluid volume in the colon. There is also provided a method for removing potassium from plasma and/or tissue of a mammal comprising administering to said mammal an effective amount of an HSD2 inhibitor or an MR agonist in combination with a compound that removes sodium from plasma and/or tissue. There is also provided a method for removing potassium from plasma and/or tissue of a mammal comprising administering to said mammal an effective amount of an HSD2 inhibitor or an MR agonist in combination with a compound that promotes excretions of sodium into the gastrointestinal tract. In an embodiment, the compound is a laxative that increases fluid in the colon. In an embodiment, the laxative is bisacodyl. In an embodiment, the laxative is picosulfate. In an embodiment, the laxative is MgOH. In an embodiment, the laxative is MiraLAX® (PEG 3350). In an embodiment, the laxative is lactulose. In an embodiment, the compound is an activator of intestinal guanylate cyclase. In an embodiment the guanylate cyclase agonist is linaclotide. In an embodiment, the guanylate cyclase agonist is plecanatide. In an embodiment, the compound is an activator of intestinal C1C-2 chloride channel. In an embodiment, the C1C-2 chloride channels activator is lubiprostone.

There is also provided a method for removing potassium from plasma and/or tissue of a mammal comprising administering to said mammal an effective amount of an HSD2 inhibitor or an MR agonist in combination with a an NHE inhibitor. In an embodiment, the HSD2 inhibitor or MR agonist and the NHE inhibitor compounds are administered concurrently. In an embodiment, the HSD2 or MR agonist and the NHE inhibitor compounds are administered sequentially. In an embodiment, the HSD2 inhibitor or MR agonist is administered prior to the NHE inhibitor or MR agonist. In an embodiment, the NHE inhibitor or MR agonist compound is administered prior to the HSD2 inhibitor or MR agonist. In an embodiment, the NHE inhibitor is an NHE3 inhibitor.

In another aspect of the invention, there is provided a pharmaceutical composition comprising an HSD2 inhibitor and an NHE inhibitor. In another aspect, there is provided a pharmaceutical composition comprising an MR agonist and an NHE inhibitor.

In another aspect, there is provided a method for treating hyperkalemia in a mammal comprising administering to said mammal an effective amount of an HSD2 inhibitor or an MR agonist in combination with an NHE inhibitor. In an embodiment, the NHE inhibitor is an NHE3 inhibitor.

In an embodiment, the MR agonist is fludrocortisone.

In another aspect, there is provided a method for treating hyperkalemia in a mammal comprising administering to said mammal an effective amount of an HSD2 inhibitor in combination with an NHE inhibitor. In an embodiment, the NHE inhibitor is an NHE3 inhibitor. In another aspect, there is provided a composition comprising an HSD2 inhibitor and an NHE inhibitor. In an embodiment, the composition is a pharmaceutical composition. In an embodiment there is an effective amount of HSD2 inhibitor compound and the NHE inhibitor compound. In an embodiment, the composition further comprises a pharmaceutically acceptable carrier, excipient and/or diluent. In an embodiment, the HSD2 inhibitor is glycyrrhetinic acid or an analogue thereof. In an embodiment, the HSD2 inhibitor is glycyrrhetinic acid. In an embodiment, the HSD2 inhibitor is glycyrrhizin. In an embodiment, the HSD2 inhibitor is a compound according to formula I herein. In an embodiment, the NHE inhibitor is an NHE3 inhibitor. In an embodiment the NHE3 inhibitor is a compound described in: U.S. Pat. Nos. 5,866,610; 6,399,824; 6,911,453; 6,703,405; 6,005,010; 6,736,705; 6,887,870; 6,737,423; 7,326,705; 5,824,691 (WO94/026709); 6,399,824 (WO02/024637); U.S. Pat. Pub. Nos. 2004/0039001 (WO02/020496); 2005/0020612 (WO03/055490); 2004/0113396 (WO03/051866); 2005/0020612; 2005/0054705; 2008/0194621; 2007/0225323; 2004/0039001; 2004/0224965; 2005/0113396; 2007/0135383; 2007/0135385; 2005/0244367; 2007/0270414; International Publication Nos. WO 01/072742; WO 01/021582 (CA2387529); WO97/024113 (CA02241531) WO2010078449; WO2014029983; WO2014029984; and European Pat. No. EP0744397 (CA2177007); each of which is incorporated herein by reference in their entirety.

In an embodiment, the NHE inhibitor is a compound that is minimally systemic, i.e., it inhibits NHE in the intestine and is substantially non-bioavailable. In an embodiment, the NHE inhibitor is a compound Formula (I) or (IX):

wherein:
NHE is a NHE-binding small molecule that comprises (i) a hetero-atom containing moiety, and (ii) a cyclic or heterocyclic scaffold or support moiety bound directly or indirectly thereto, the heteroatom-containing moiety being selected from a substituted guanidinyl moiety and a substituted heterocyclic moiety, which may optionally be fused with the scaffold or support moiety to form a fused bicyclic structure; and, Z is a moiety having at least one site thereon for attachment to the NHE-binding small molecule, the resulting NHE-Z molecule possessing overall physicochemical properties that render it substantially impermeable or substantially systemically non-bioavailable; and, E is an integer having a value of 1 or more.

In certain embodiments, the total number of freely rotatable bonds in the NHE-Z molecule is at least about 10. In certain embodiments, the total number hydrogen bond donors in the NHE-Z molecule is at least about 5. In some embodiments, the total number of hydrogen bond acceptors in the NHE-Z molecule is at least about 10. In certain embodiments, the total number of hydrogen bond donors and hydrogen bond acceptors in the NHE-Z molecule is at least about 10. In some embodiments, the Log P of the NHE-Z binding compound is at least about 5. In certain embodiments, the log P of the NHE-Z binding compound is less than about 1, or less than about 0. In certain embodiments, the scaffold is a 5-member or 6-member cyclic or heterocyclic moiety. In certain embodiments, the scaffold is aromatic.

In some embodiments, the scaffold of the NHE-binding small molecule is bound to the moiety, Z, the compound having the structure of Formula (II):

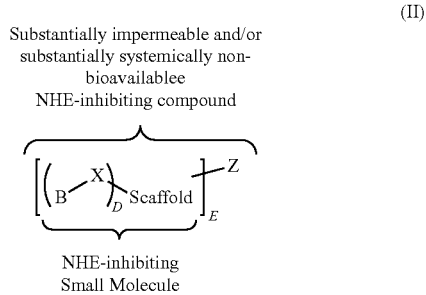

wherein:
Z is a Core having one or more sites thereon for attachment to one or more NHE-binding small molecules, the resulting NHE-Z molecule possessing overall physicochemical properties that render it substantially impermeable or substantially systemically non-bioavailable;

B is the heteroatom-containing moiety of the NHE-binding small molecule, and is selected from a substituted guanidinyl moiety and a substituted heterocyclic moiety, which may optionally be fused with the Scaffold moiety to form a fused, bicyclic structure;

Scaffold is the cyclic or heterocyclic scaffold or support moiety of the NHE-binding small molecule, which is bound directly or indirectly to heteroatom-containing moiety, B, and which is optionally substituted with one or more additionally hydrocarbyl or heterohydrocarbyl moieties;

X is a bond or a spacer moiety selected from a group consisting of substituted or unsubstituted hydrocarbyl or heterohydrocarbyl moieties, and in particular substituted or unsubstituted $C_{1-7}$ hydrocarbyl or heterohydrocarbyl, and substituted or unsubstituted, saturated or unsaturated, cyclic or heterocyclic moieties, which links B and the Scaffold; and D and E are integers, each independently having a value of 1 or more.

In some embodiments, the compound is an oligomer, dendrimer or polymer, and further wherein Z is a Core moiety having two or more sites thereon for attachment to multiple NHE-binding small molecules, either directly or indirectly through a linking moiety, L, the compound having the structure of Formula (X):

wherein L is a bond or linker connecting the Core to the NHE-binding small molecule, and n is an integer of 2 or more, and further wherein each NHE-binding small molecule may be the same or differ from the others.

In some embodiments, the NHE-binding small molecule has the structure of Formula (IV):

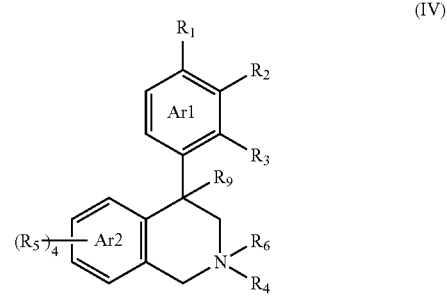

or a stereoisomer, prodrug or pharmaceutically acceptable salt thereof, wherein:

each $R_1$, $R_2$, $R_3$, $R_5$ and $R_9$ are independently selected from H, halogen, —$NR_7(CO)R_8$, —$(CO)NR_7R_8$, —$SO_2$—$NR_7R_8$, —$NR_7SO_2R_8$, —$NR_7R_8$, —$OR_7$, —$SR_7$, —$O(CO)NR_7R_8$, —$NR_7(CO)OR_8$, and —$NR_7SO_2NR_8$, where $R_7$ and $R_8$ are independently selected from H or a bond linking the NHE-binding small molecule to L, provided at least one is a bond linking the NHE-binding small molecule to L;

$R_4$ is selected from H, $C_1$-$C_7$ alkyl, or a bond linking the NHE-binding small molecule to L;

$R_6$ is absent or selected from H and $C_1$-$C_7$ alkyl; and

Ar1 and Ar2 independently represent an aromatic ring or a heteroaromatic ring.

In certain embodiments, the NHE-binding small molecule has the following structure:

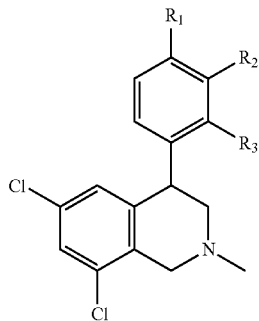

or a stereoisomer, prodrug or pharmaceutically acceptable salt thereof, wherein:

each $R_1$, $R_2$ and $R_3$ are independently selected from H, halogen, —$NR_7(CO)R_8$, —$(CO)NR_7R_8$, —$SO_2$—$NR_7R_8$, —$NR_7SO_2R_8$, —$NR_7R_8$, —$OR_7$, —$SR_7$, —$O(CO)NR_7R_8$, —$NR_7(CO)OR_8$, and —$NR_7SO_2NR_8$, where $R_7$ and $R_8$ are independently selected from H or a bond linking the NHE-binding small molecule to L, provided at least one is a bond linking the NHE-binding small molecule to L.

In some embodiments, the NHE-binding small molecule has one of the following structures:

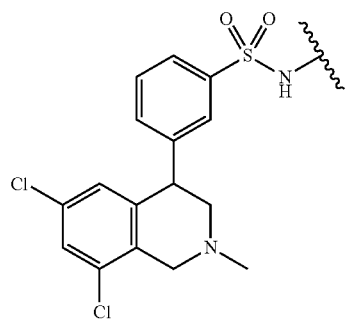

or

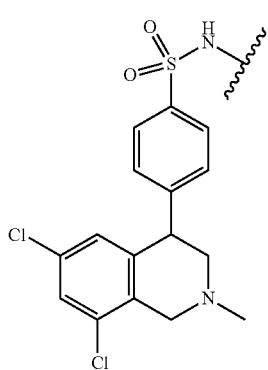

or a stereoisomer, prodrug or pharmaceutically acceptable salt thereof. In certain embodiments, L is a polyalkylene glycol linker. In certain embodiments, L is a polyethylene glycol linker. In some embodiments, n is 2.

In certain embodiments, the Core has the following structure:

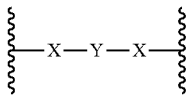

wherein:
X is selected from the group consisting of a bond, —O—, —NH—, —S—, $C_{1-6}$alkylene, —NHC(=O)—, —C(=O)NH—, —NHC(=O)NH—, —$SO_2NH$—, and —$NHSO_2$—;
Y is selected from the group consisting of a bond, optionally substituted $C_{1-8}$alkylene, optionally substituted aryl, optionally substituted heteroaryl, a polyethylene glycol linker, —$(CH_2)_{1-6}O(CH_2)_{1-6}$— and —$(CH_2)_{1-6}NY_1(CH_2)_{1-6}$—; and
$Y_1$ is selected from the group consisting of hydrogen, optionally substituted $C_{1-8}$alkyl, optionally substituted aryl or optionally substituted heteroaryl.

In some embodiments, the Core is selected from the group consisting of:

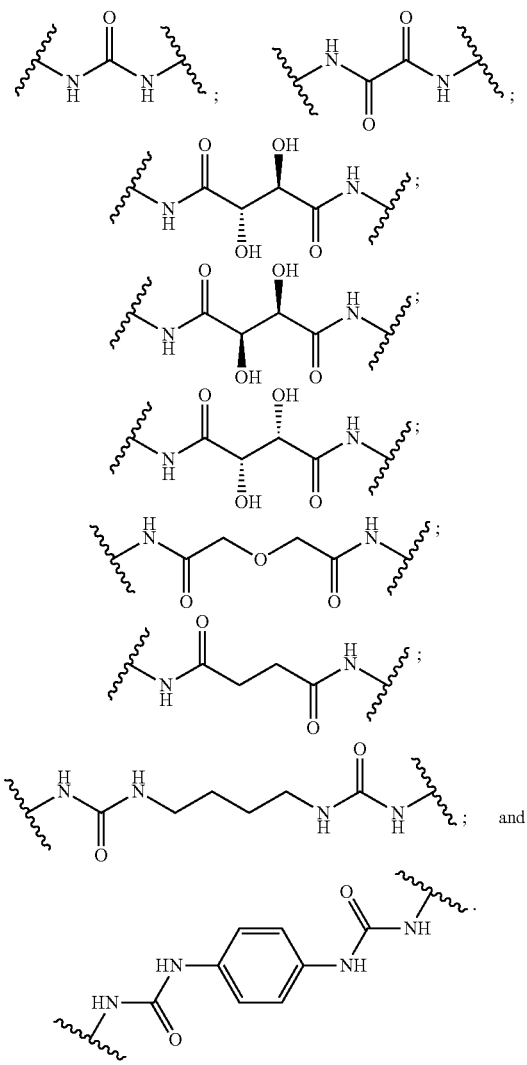

wherein: L is a bond or a linking moiety; NHE is a NHE-binding small molecule; and n is a non-zero integer.

In an embodiment, the NHE inhibitor is:

N,N',N''-(2,2',2''-nitrilotris(ethane-2,1-diyl))tris(3-(6,8-dichloro-2-methyl-1,2,3,4-tetrahydroisoquinolin-4-yl)benzenesulfonamide);

N,N'-(2,2'-(ethane-1,2-diylbis(oxy))bis(ethane-2,1-diyl))bis(3-(6,8-dichloro-2-methyl-1,2,3,4-tetrahydroisoquinolin-4-yl)benzenesulfonamide);

N,N'-(1,4-phenylenebis(methylene))bis(3-(6,8-di chloro-2-methyl-1,2,3,4-tetrahydroisoquinolin-4-yl)benzenesulfonamide);

N,N'-(1,4-phenylenebis(methylene))bis(3-(6,8-di chloro-2-methyl-1,2,3,4-tetrahydroisoquinolin-4-yl)benzenesulfonamide);

N,N'-(butane-1,4-diyl)bis(3-(6,8-dichloro-2-methyl-1,2,3,4-tetrahydroisoquinolin-4-yl)benzenesulfonamide);

N,N'-(dodecane-1,12-diyl)bis(3-(6,8-dichloro-2-methyl-1,2,3,4-tetrahydroisoquinolin-4-yl)benzenesulfonamide);

N,N',N'',N'''-(3,3',3'',3'''-(butane-1,4-diylbis(azanetriyl))tetrakis(propane-3,1-diyl))tetrakis(3-(6,8-dichloro-2-methyl-1,2,3,4-tetrahydroisoquinolin-4-yl)benzenesulfonamide);

N,N'-(butane-1,4-diyl)bis(4-(6,8-dichloro-2-methyl-1,2,3,4-tetrahydroisoquinolin-4-yl)benzenesulfonamide);

N,N'-(dodecane-1,12-diyl)bis(4-(6,8-dichloro-2-methyl-1,2,3,4-tetrahydroisoquinolin-4-yl)benzenesulfonamide);

N,N',N''-(2,2',2''-nitrilotris(ethane-2,1-diyl))tris(4-(6,8-dichloro-2-methyl-1,2,3,4-tetrahydroisoquinolin-4-yl)benzenesulfonamide);

N,N',N'',N'''-(3,3',3'',3'''-(butane-1,4-diylbis(azanetriyl))tetrakis(propane-3,1-diyl))tetrakis(4-(6,8-dichloro-2-methyl-1,2,3,4-tetrahydroisoquinolin-4-yl)benzenesulfonamide);

N,N'-(1,4-phenylenebis(methylene))bis(4-(6,8-dichloro-2-methyl-1,2,3,4-tetrahydroisoquinolin-4-yl)benzenesulfonamide);

N,N'-(2,2'-(ethane-1,2-diylbis(oxy))bis(ethane-2,1-diyl))bis(4-(6,8-dichloro-2-methyl-1,2,3,4-tetrahydroisoquinolin-4-yl)benzenesulfonamide);

N1,N8-bis(2-(2-(2-(2-(3-(6,8-dichloro-2-methyl-1,2,3,4-tetrahydroisoquinolin-4-yl)phenylsulfonamido)ethoxy)ethoxy)ethyl)octanediamide;

2-(N-(4-(6,8-dichloro-2-methyl-1,2,3,4-tetrahydroisoquinolin-4-yl)phenyl)sulfamoylamino)ethylphosphonic acid;

2-(N-(3-(6,8-dichloro-2-methyl-1,2,3,4-tetrahydroisoquinolin-4-yl)phenyl)sulfamoylamino)ethylphosphonic acid;

N,N'-(butane-1,4-diyl)bis[(E)-N-(diaminomethylene)-3-(3,5-difluoro-4-(4-sulfamoylphenoxy)phenyl)-2-methylacrylamide];

N,N'-(1,4-phenylenebis(methyl ene))bis[(E)-N-(diaminomethylene)-3-(3,5-difluoro-4-(4-sulfamoylphenoxy)phenyl)-2-methylacrylamide];

N,N'-(2,2'-(ethane-1,2-diylbis(oxy))bis(ethane-2,l-diyl))bis[(E)-N-(diaminomethylene)-3-(3,5-difluoro-4-(4-sulfamoylphenoxy)phenyl)-2-methylacrylamide];

N,N'-(2,2'-(2,2'-oxybis(ethane-2,l-diyl)bis(oxy))bis(ethane-2,l-diyl))bis[(E)-N-(diaminomethylene)-3-(3,5-difluoro-4-(4-sulfamoylphenoxy)phenyl)-2-methylacrylamide]
(E)-3-(4-(4-(N-(2-(2-(2-(2-aminoethoxy)ethoxy)ethoxy)ethyl)sulfamoyl)phenoxy)-3,5-difluorophenyl)-N-(diaminomethylene)-2-methylacrylamide;

N,N'-(13-oxo-3,6,9,17,20,23-hexaoxa-12,14-diazapentacosane-1,25-diyl)bis[(E)-N-(diaminomethylene)-3-(3,5-difluoro-4-(4-sulfamoylphenoxy)phenyl)-2-methylacrylamide];

N,N'-(13,20 dioxo-3, 6, 9, 24, 27, 30-hexaoxa-12, 21-diazadotricontane-1,32-diyl)bis[(E)-N-(diaminomethylene)-3-(3,5-difluoro-4-(4-sulfamoylphenoxy)phenyl)-2-methylacrylamide];

N,N'-(2,2'-(2,2'-(2,2'-(2,2'-(4,4'-oxybis(methylene)bis(1H-1,2,3-triazole-4,1-diyl))bis(ethane-2,1-diyl))bis(oxy)bis(ethane-2,l-diyl))bis(oxy)bis(ethane-2,l-diyl))bis(oxy)bis(ethane-2,l-diyl))bis[(E)-N-(diaminomethylene)-3-(3,5-difluoro-4-(4-sulfamoylphenoxy)phenyl)-2-methylacrylamide];

N,N'-(2,2'-(2,2'-(2,2'-(2,2'-(4,4'-oxybis(methylene)bis(1H-1,2,3-triazole-4,1-diyl))bis(ethane-2,1-diyl))bis(oxy)bis(ethane-2,l-diyl))bis(oxy)bis(ethane-2,l-diyl))bis(oxy)bis(ethane-2,l-diyl))bis(3-(6,8-dichloro-2-methyl-1,2,3,4-tetrahydroisoquinolin-4-yl)benzenesulfonamide)

1-(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)-1H-1,2,3-triazole-4,5-dicarboxylic acid;

N1,N4-bis(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)-2,3-dihydroxysuccinamide;

N1,N4-bis(2-(2-(2-(2-(4-(6,8-dichloro-2-methyl-1,2,3,4-tetrahydroisoquinolin-4-yl)phenylsulfonamido)ethoxy)ethoxy)ethoxy)ethyl)-2,3-dihydroxysuccinamide;

N1,N31-bis(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)-4,7,10,13,16,19,22,25,28-nonaoxahentriacontane-1,31-diamide;

N1,N31-bis(2-(2-(2-(2-(4-(6,8-dichloro-2-methyl-1,2,3,4-tetrahydroisoquinolin-4-yl)phenylsulfonamido)ethoxy)ethoxy)ethoxy)ethyl)-4,7,10,13,16,19,22,25,28-nonaoxahentriacontane-1,31-diamide;

N,N'-(13-oxo-3,6,9,17,20,23-hexaoxa-12,14-diazapentacosane-1,25-diyl)bis(3-(6,8-dichloro-2-methyl-1,2,3,4-tetrahydroisoquinolin-4-yl)benzenesulfonamide);

N1,N31-bis(2-(2-(2-(2-(4-(4-((E)-3-(diaminomethyleneamino)-2-methyl-3-oxoprop-1-enyl)-2,6-difluorophenoxy)phenylsulfonamido)ethoxy)ethoxy)ethoxy)ethyl)-4,7,10,13,16,19,22,25,28-nonaoxahentriacontane-1,31-diamide;

N,N'-(13-oxo-3,6,9,17,20,23-hexaoxa-12,14-diazapentacosane-1,25-diyl)bis(4-(6,8-dichloro-2-methyl-1,2,3,4-tetrahydroisoquinolin-4-yl)benzenesulfonamide);

N1,N4-bis(20-(4-(4-((E)-3-(diaminomethyleneamino)-2-methyl-3-oxoprop-1-enyl)-2,6-difluorophenoxy)phenylsulfonamido)-3,6,9,12,15,18-hexaoxaicosyl)-2,3-dihydroxysuccinamide;

N1,N4-bis(2-(3-(6,8-dichloro-2-methyl-1,2,3,4-tetrahydroiso-quinolin-4-yl)phenylsulfonamido)ethyl)-2,3-dihydroxysuccinamide;

N1,N4-bis(2-(2-(2-(2-(3-(6,8-dichloro-2-ethyl-1,2,3,4-tetrahydroisoquinolin-4-yl)phenylsulfonamido)ethoxy)ethoxy)ethoxy)ethyl)-2,3-dihydroxysuccinamide;

3,3'-(2,2'-(2,2'-(2,2'-oxybis(ethane-2,l-diyl)bis(oxy))bis(ethane-2,l-diyl))bis(6,8-dichloro-1,2,3,4-tetrahydroisoquinoline-4,2-diyl))dianiline;

N1,N4-bis(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)-2,3-dihydroxysuccinamide;

N1,N4-bis(2-(2-(2-(2-(3-(6,8-dichloro-2-methyl-1,2,3,4-tetrahydroisoquinolin-4-yl)phenylamino)ethoxy)ethoxy)ethoxy)ethyl)-2,3-dihydroxysuccinamide;

N1,N4-bis(1-(3-(6,8-dichloro-2-methyl-1,2,3,4-tetrahydroisoquinolin-4-yl)phenylamino)-1-oxo-5,8,11-trioxa-2-azatridecan-13-yl)-2,3-dihydroxysuccinamide;

N1,N2-bis(2-(2-(2-(4-(6,8-dichloro-2-methyl-1,2,3,4-tetrahydroisoquinolin-4-yl)phenylsulfonamido)ethoxy)ethoxy)ethyl)oxalamide;
N1,N4-bis(2-(2-(3-(6,8-dichloro-2-methyl-1,2,3,4-tetrahydroisoquinolin-4-yl)phenylsulfonamido)ethoxy)ethyl)-2,3-dihydroxysuccinamide;
N1,N4-bis(2-(2-(2-(4-(6,8-dichloro-2-methyl-1,2,3,4-tetrahydroisoquinolin-4-yl)phenylsulfonamido)ethoxy)ethoxy)ethyl)succinamide;
2,2'-oxybis(N-(2-(2-(2-(4-(6,8-dichloro-2-methyl-1,2,3,4-tetrahydroisoquinolin-4-yl)phenylsulfonamido)ethoxy)ethoxy)ethyl)acetamide;
(2R,3R)—N1,N4-bis(2-(2-(2-(3-(3-(6,8-dichloro-2-methyl-1,2,3,4-tetrahydroisoquinolin-4-yl)phenylamino)-3-oxopropoxy)ethoxy)ethoxy)ethyl)-2,3-dihydroxysuccinamide;
N1,N2-bis(2-(2-(2-(2-(3-(6,8-dichloro-2-methyl-1,2,3,4-tetrahydroisoquinolin-4-yl)phenylsulfonamido)ethoxy)ethoxy)ethyl)oxal amide;
N1,N4-bis(2-(2-(2-(2-(3-(6,8-dichloro-2-methyl-1,2,3,4-tetrahydroisoquinolin-4-yl)phenylsulfonamido)ethoxy)ethoxy)ethyl)succinamide;
N1,N3-bis(2-(2-(2-(2-(3-(6,8-dichloro-2-methyl-1,2,3,4-tetrahydroisoquinolin-4-yl)phenylsulfonamido)ethoxy)ethoxy)ethyl)-2,2-dimethylmalonamide;
N1,N3-bis(2-(2-(2-(4-(6,8-dichloro-2-methyl-1,2,3,4-tetrahydroisoquinolin-4-yl)phenylsulfonamido)ethoxy)ethoxy)ethyl)-2,2-dimethylmalonamide;
N,N'-(2,2'-(2,2'-(2,2'-(pyridine-2,6-diylbis(oxy))bis(ethane-2,1-diyl))bis(oxy)bis(ethane-2,1-diyl))bis(oxy)bis(ethane-2,1-diyl))bis(3-(6,8-dichloro-2-methyl-1,2,3,4-tetrahydroisoquinolin-4-yl)benzenesulfonamide);
2,2'-(methylazanediyl)bis(N-(2-(2-(2-(4-(6,8-dichloro-2-methyl-1,2,3,4-tetrahydroisoquinolin-4-yl)phenylsulfonamido)ethoxy)ethoxy)ethyl)acetamide) tris(2,2,2-trifluoroacetate);
5-amino-N1,N3-bis(2-(2-(2-(4-(6,8-dichloro-2-methyl-1,2,3,4-tetrahydroisoquinolin-4-yl)phenylsulfonamido)ethoxy)ethoxy)ethyl)isophthalamide tris(2,2,2-trifluoroacetate);
2,2'-oxybis(N-(2-(2-(2-(2-(3-(6,8-dichloro-2-methyl-1,2,3,4-tetrahydroisoquinolin-4-yl)phenylsulfonamido)ethoxy)ethoxy)ethyl)acetamide);
5-bromo-N1,N3-bis(2-(2-(2-(4-(6,8-dichloro-2-methyl-1,2,3,4-tetrahydroisoquinolin-4-yl)phenylsulfonamido)ethoxy)ethoxy)ethyl)isophthalamide bis(2,2,2-trifluoroacetate);
N1,N3-bis(2-(2-(2-(4-(6,8-dichloro-2-methyl-1,2,3,4-tetrahydroisoquinolin-4-yl)phenylsulfonamido)ethoxy)ethoxy)ethyl)-2-hydroxymalonamide bis(2,2,2-trifluoroacetate);
N1,N2-bis(2-(2-(2-(3-(6,8-dichloro-2-methyl-1,2,3,4-tetrahydroisoquinolin-4-yl)phenylsulfonamido)ethoxy)ethoxy)ethyl)oxal amide;
N1,N4-bis(2-(2-(2-(3-(6,8-dichloro-2-methyl-1,2,3,4-tetrahydroisoquinolin-4-yl)phenylsulfonamido)ethoxy)ethoxy)ethyl)succinamide;
3,5-bis(2-(2-(2-(4-(6,8-dichloro-2-methyl-1,2,3,4-tetrahydroisoquinolin-4-yl)phenylsulfonamido)ethoxy)ethoxy)ethylcarbamoyl)benzenesulfonic acid;
N1,N3-bis(2-(2-(2-(4-(6,8-dichloro-2-methyl-1,2,3,4-tetrahydroisoquinolin-4-yl)phenylsulfonamido)ethoxy)ethoxy)ethyl)-5-hydroxyisophthalamide;
(2R,3R)—N1,N4-bis(3-((3-(3-(6,8-dichloro-2-methyl-1,2,3,4-tetrahydroisoquinolin-4-yl)phenylsulfonamido)propyl)(methyl)amino)propyl)-2,3-dihydroxysuccinamide;
2,2'-oxybis(N-(2-(2-(2-(3-(6,8-dichloro-2-methyl-1,2,3,4-tetrahydroisoquinolin-4-yl)phenylsulfonamido)ethoxy)ethoxy)ethyl)acetamide);
N1,N3-bis(2-(2-(2-(3-(6,8-dichloro-2-methyl-1,2,3,4-tetrahydroisoquinolin-4-yl)phenylsulfonamido)ethoxy)ethoxy)ethyl)-2,2-dimethylmalonamide;
N1,N2-bis(2-(2-(2-(2-(4-(6,8-dichloro-2-methyl-1,2,3,4-tetrahydroisoquinolin-4-yl)phenylsulfonamido)ethoxy)ethoxy)ethyl)oxalamide;
2,2'-oxybis(N-(2-(2-(2-(2-(4-(6,8-dichloro-2-methyl-1,2,3,4-tetrahydroisoquinolin-4-yl)phenylsulfonamido)ethoxy)ethoxy)ethyl)acetamide);
N1,N4-bis(2-(2-(2-(2-(4-(6,8-dichloro-2-methyl-1,2,3,4-tetrahydroisoquinolin-4-yl)phenylsulfonamido)ethoxy)ethoxy)ethyl)succinamide;
N1,N4-bis(2-(2-(2-(4-((S or R)-6,8-dichloro-2-methyl-1,2,3,4-tetrahydroisoquinolin-4-yl)phenylsulfonamido)ethoxy)ethoxy)ethyl)succinamide;
2,2'-oxybis(N-(2-(2-(2-(4-((S or R)-6,8-dichloro-2-methyl-1,2,3,4-tetrahydroisoquinolin-4-yl)phenylsulfonamido)ethoxy)ethoxy)ethyl)acetamide);
(S or R)—N,N'-(10,17-dioxo-3,6,21,24-tetraoxa-9,11,16,18-tetraazahexacosane-1,26-diyl)bis(3-((S)-6,8-dichloro-2-methyl-1,2,3,4-tetrahydroisoquinolin-4-yl)benzenesulfonamide);
(S or R)—N,N'-(2,2'-(2,2'-(2,2'-(1,4-phenylenebis(azanediyl))bis(oxomethylene)bis(azanediyl)bis(ethane-2,1-diyl))bis(oxy)bis(ethane-2,1-diyl))bis(oxy)bis(ethane-2,1-diyl))bis(3-((S or R)-6,8-dichloro-2-methyl-1,2,3,4-tetrahydroisoquinolin-4-yl)benzenesulfonamide);
N,N'-(butane-1,4-diyl)bis(2-(2-(2-(4-(6,8-dichloro-2-methyl-1,2,3,4-tetrahydroisoquinolin-4-yl)phenylsulfonamido)acetamido)acetamido)acetamide);
N1,N4-bis(2-(2-(2-(4-(6,8-dichloro-2-methyl-1,2,3,4-tetrahydroisoquinolin-4-yl)phenylsulfonamido)ethoxy)ethoxy)ethyl)-2,3-dihydroxysuccinamide;
N,N'-(2,2'-(2,2'-(2,2'-(1,4-phenyl enebis(methylene))bis(azanediyl)bis(ethane-2,1-diyl))bis(oxy)bis(ethane-2,1-diyl))bis(oxy)bis(ethane-2,1-diyl))bis(3-(6,8-dichloro-2-methyl-1,2,3,4-tetrahydroisoquinolin-4-yl)benzenesulfonamide);
(2R,3R)—N1,N4-bis(2-(2-(2-(4-(6,8-dichloro-2-methyl-1,2,3,4-tetrahydroisoquinolin-4-yl)phenylsulfonamido)ethoxy)ethoxy)ethyl)-2,3-dihydroxysuccinamide;
N,N'-(13,20-dioxo-3,6,9,24,27,30-hexaoxa-12,14,19,21-tetraazadotriacontane-1,32-diyl)bis(3-(6,8-dichloro-2-methyl-1,2,3,4-tetrahydroisoquinolin-4-yl)benzenesulfonamide);
N,N'-(1,1'-(1,4-phenylenebis(azanediyl))bis(1-oxo-5,8,11-trioxa-2-azatridecane-13,1-diyl))bis(3-(6,8-dichloro-2-methyl-1,2,3,4-tetrahydroisoquinolin-4-yl)benzenesulfonamide);
(2R,3R)—N1,N4-bis(20-(4-(4-((E)-3-(diaminomethyleneamino)-2-methyl-3-oxoprop-1-enyl)-2,6-difluorophenoxy)phenylsulfonamido)-3,6,9,12,15,18-hexaoxaicosyl)-2,3-dihydroxysuccinamide;
(E)-3-(4-(4-(N-(20-amino-3,6,9,12,15,18-hexaoxaicosyl)sulfamoyl)phenoxy)-3,5-difluorophenyl)-N-(diaminomethylene)-2-methylacrylamide;
(2R,3R)—N1,N4-bis(2-(2-(2-(2-(4-(4-((E)-3-(diaminomethyleneamino)-2-methyl-3-ox oprop-1-enyl)-2,6-difluorophenoxy)phenylsulfonamido)ethoxy)ethoxy)ethoxy)ethyl)-2,3-dihydroxysuccinamide;
2,2',2''-nitrilotris(N-(2-(2-(2-(3-(6,8-dichloro-2-methyl-1,2,3,4-tetrahydroisoquinolin-4-yl)phenylsulfonamido)ethoxy)ethoxy)ethoxy)ethyl)acetamide);

N-(32-amino-3,6,9,12,15,18,21,24,27,30-decaoxadotriacontyl)-3-(6,8-dichloro-2-methyl-1,2,3,4-tetrahydroisoquinolin-4-yl)benzenesulfonamide;

N1,N3,N5-tris(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)benzene-1,3,5-tricarboxamide;

N1,N4-bis(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)terephthalamide;

N1,N31-bis(32-(3-(6,8-dichloro-2-methyl-1,2,3,4-tetrahydroisoquinolin-4-yl)phenylsulfonamido)-3,6,9,12,15,18,21,24,27,30-decaoxadotriacontyl)-4,7,10,13,16,19,22,25,28-nonaoxahentriacontane-1,31-diamide;

2R,3R)—N1,N4-bis(2-(2-(2-(3-(6,8-dichloro-2-methyl-1,2,3,4-tetrahydroisoquinolin-4-yl)phenylsulfonamido)ethoxy)ethoxy)ethyl)-2,3-dihydroxysuccinamide;

N1,N3-bis(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)benzene-1,3-di sulfonamide;

N4,N4'-bis(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)biphenyl-4,4'-disulfonamide;

(14R,15R)-1-(3-(6,8-dichloro-2-methyl-1,2,3,4-tetrahydroisoquinolin-4-yl)phenylsulfonamido)-14,15-dihydroxy-13-oxo-3,6,9-trioxa-12-azahexadecan-16-oic acid;

(2S,3S)—N1,N4-bis(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)-2,3-dihydroxysuccinamide;

N1,N4-bis(2-(2-(2-(2-(3-((R)-6,8-dichloro-2-methyl-1,2,3,4-tetrahydroisoquinolin-4-yl)phenylsulfonamido)ethoxy)ethoxy)ethoxy)ethyl)-2,3-dihydroxysuccinamide;

N1,N4-bis(2-(2-(2-(2-(3-((S or R)-6,8-dichloro-2-methyl-1,2,3,4-tetrahydroisoquinolin-4-yl)phenylsulfonamido)ethoxy)ethoxy)ethoxy)ethyl)-2,3-dihydroxysuccinamide;

N1,N4-bis(2-(2-(2-(2-(4-((S or R)-6,8-dichloro-2-methyl-1,2,3,4-tetrahydroisoquinolin-4-yl)phenylsulfonamido)ethoxy)ethoxy)ethoxy)ethyl)-2,3-dihydroxysuccinamide;

N1,N4-bis(2-(2-(2-(2-(4-((R or S)-6,8-dichloro-2-methyl-1,2,3,4-tetrahydroisoquinolin-4-yl)phenylsulfonamido)ethoxy)ethoxy)ethoxy)ethyl)-2,3-dihydroxysuccinamide;

N1,N4-bis(2-(2-(2-(2-(4-(6,8-dichloro-2-methyl-1,2,3,4-tetrahydroisoquinolin-4-yl)phenylsulfonamido)ethoxy)ethoxy)ethoxy)ethyl)-2,3-dihydroxysuccinamide;

N1,N3-bis(2-(2-(2-(3-(6,8-dichloro-2-methyl-1,2,3,4-tetrahydroisoquinolin-4-yl)phenylsulfonamido)ethoxy)ethoxy)ethyl)isophthalamide;

(2R,3S)—N1,N4-bis(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)-2,3-dihydroxysuccinamide;

N1,N2-bis(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)phthalamide;

N1,N4-bis(2-(2-(2-(4-(6,8-dichloro-2-methyl-1,2,3,4-tetrahydroisoquinolin-4-yl)phenylsulfonamido)ethoxy)ethoxy)ethyl)terephthalamide;

N,N'-(10-oxo-3,6,14,17-tetraoxa-9,11-diazanonadecane-1,19-diyl)bis(4-(6,8-dichloro-2-methyl-1,2,3,4-tetrahydroisoquinolin-4-yl)benzenesulfonamide);

N1,N4-bis(2-(2-(2-(2-(4-(6,8-dichloro-2-methyl-1,2,3,4-tetrahydroisoquinolin-4-yl)phenylsulfonamido)ethoxy)ethoxy)ethoxy)ethyl)terephthalamide;

N1,N4-bis(2-(2-(2-(3-(6,8-dichloro-2-methyl-1,2,3,4-tetrahydroisoquinolin-4-yl)phenylsulfonamido)ethoxy)ethoxy)ethyl)terephthalamide;

N,N'-(10-oxo-3,6,14,17-tetraoxa-9,11-diazanonadecane-1,19-diyl)bis(3-(6,8-dichloro-2-methyl-1,2,3,4-tetrahydroisoquinolin-4-yl)benzenesulfonamide);

N,N'-(10,17-di oxo-3,6,21,24-tetraoxa-9,11,16,18-tetraazahexacosane-1,26-diyl)bis(3-(6,8-dichloro-2-methyl-1,2,3,4-tetrahydroisoquinolin-4-yl)benzenesulfonamide);

N,N'-(2,2'-(2,2'-(2,2'-(1,4-phenylenebis(azanediyl))bis(oxomethylene)bis(azanediyl)bis(ethane-2,1-diyl))bis(oxy)bis(ethane-2,1-diyl))bis(oxy)bis(ethane-2,1-diyl))bis(3-(6,8-dichloro-2-methyl-1,2,3,4-tetrahydroisoquinolin-4-yl)benzenesulfonamide);

N,N'-(10,17-di oxo-3,6,21,24-tetraoxa-9,11,16,18-tetraazahexacosane-1,26-diyl)bis(4-(6,8-dichloro-2-methyl-1,2,3,4-tetrahydroisoquinolin-4-yl)benzenesulfonamide);

phenylenebis(azanediyl))bis(oxomethylene)bis(azanediyl)bis(ethane-2,1-diyl))bis(oxy)bis(ethane-2,1-diyl))bis(oxy)bis(ethane-2,1-diyl))bis(4-(6,8-dichloro-2-methyl-1,2,3,4-tetrahydroisoquinolin-4-yl)benzenesulfonamide);

(2S,3S)—N1,N4-bis(2-(2-(2-(2-(3-((S or R)-6,8-dichloro-2-methyl-1,2,3,4-tetrahydroisoquinolin-4-yl)phenylsulfonamido)ethoxy)ethoxy)ethoxy)ethyl)-2,3-dihydroxysuccinamide;

(2R,3R)—N1,N4-bis(2-(2-(2-(2-(3-((S or R)-6,8-dichloro-2-methyl-1,2,3,4-tetrahydroisoquinolin-4-yl)phenylsulfonamido)ethoxy)ethoxy)ethoxy)ethyl)-2,3-dihydroxysuccinamide;

(2S,3S)—N1,N4-bis(2-(2-(2-(2-(4-((S or R)-6,8-dichloro-2-methyl-1,2,3,4-tetrahydroisoquinolin-4-yl)phenylsulfonamido)ethoxy)ethoxy)ethoxy)ethyl)-2,3-dihydroxysuccinamide;

(2R,3R)—N1,N4-bis(2-(2-(2-(2-(4-((S or R)-6,8-dichloro-2-methyl-1,2,3,4-tetrahydroisoquinolin-4-yl)phenylsulfonamido)ethoxy)ethoxy)ethoxy)ethyl)-2,3-dihydroxysuccinamide;

(S or R)—N,N'-(13,20-dioxo-3,6,9,24,27,30-hexaoxa-12,14,19,21-tetraazadotriacontane-1,32-diyl)bis(3-((S or R)-6,8-dichloro-2-methyl-1,2,3,4-tetrahydroisoquinolin-4-yl)benzenesulfonamide);

(S or R)—N,N'-(1,1'-(1,4-phenylenebis(azanediyl))bis(1-oxo-5,8,11-trioxa-2-azatridecane-13,1-diyl))bis(3-((S or R)-6,8-dichloro-2-methyl-1,2,3,4-tetrahydroisoquinolin-4-yl)benzenesulfonamide);

N1,N4-bis(2-(2-(2-(2-(4-((S or R)-6,8-dichloro-2-methyl-1,2,3,4-tetrahydroisoquinolin-4-yl)phenylsulfonamido)ethoxy)ethoxy)ethyl)-terephthalamide;

N1-(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)succinamide;

N,N'-(13,20-dioxo-3,6,9,24,27,30-hexaoxa-12,14,19,21-tetraazadotriacontane-1,32-diyl)bis(4-(6,8-dichloro-2-methyl-1,2,3,4-tetrahydroisoquinolin-4-yl)benzenesulfonamide);

N,N'-(1,1'-(1,4-phenylenebis(azanediyl))bis(1-oxo-5,8,11-trioxa-2-azatridecane-13,1-diyl))bis(4-(6,8-dichloro-2-methyl-1,2,3,4-tetrahydroisoquinolin-4-yl)benzenesulfonamide);

(S or R)—N,N'-(13-oxo-3,6,9,17,20,23-hexaoxa-12,14-diazapentacosane-1,25-diyl)bis(4-((S or R)-6,8-dichloro-2-methyl-1,2,3,4-tetrahydroisoquinolin-4-yl)benzenesulfonamide);

(S or R)—N,N'-(13,20-dioxo-3,6,9,24,27,30-hexaoxa-12,14,19,21-tetraazadotriacontane-1,32-diyl)bis(4-((S or R)-6,8-dichloro-2-methyl-1,2,3,4-tetrahydroisoquinolin-4-yl)benzenesulfonamide); or (S or R)—N,N'-(1,1'-(1,4-phenylenebis(azanediyl))bis(1-oxo-5,8,11-trioxa-2-azatridecane-13,1-diyl))bis(4-((S or R)-6,8-dichloro-2-methyl-1,2,3,4-tetrahydroisoquinolin-4-yl)benzenesulfonamide).

In an embodiment, the NHE inhibitor is:

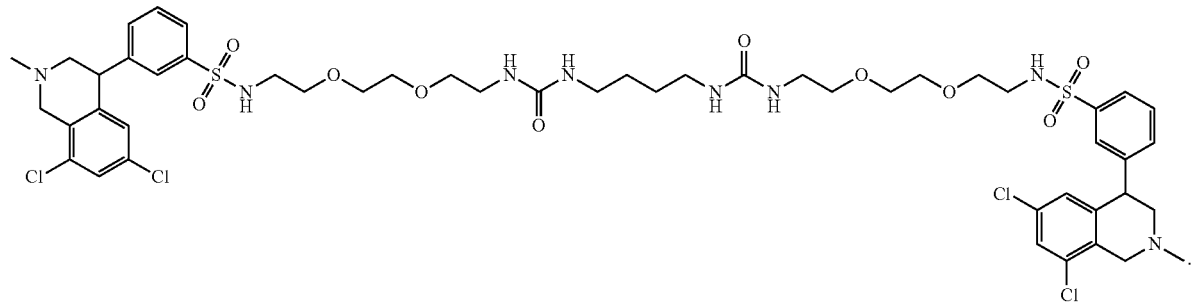

In some embodiments, the compound has the following structure of Formula (I-H):

(I-H)

or a stereoisomer, prodrug or pharmaceutically acceptable salt thereof,
wherein:
(a) n is an integer of 2 or more;
(b) Core is a Core moiety having two or more sites thereon for attachment to two or more NHE-binding small molecule moieties;
(c) L is a bond or linker connecting the Core moiety to the two or more NHE-binding small molecule moieties; and
(d) NHE is a NHE-binding small molecule moiety having the following structure of Formula (XI-H):

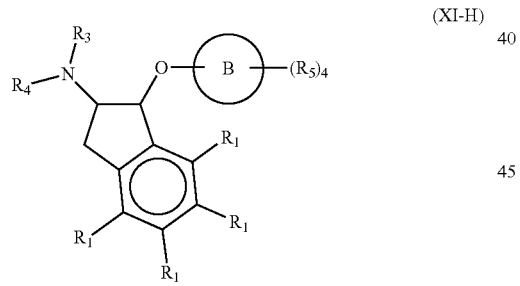

(XI-H)

wherein:
B is selected from the group consisting of aryl and heterocyclyl;
each $R_5$ is independently selected from the group consisting of hydrogen, halogen, optionally substituted $C_{1-4}$alkyl, optionally substituted $C_{1-4}$alkoxy, optionally substituted $C_{1-4}$thioalkyl, optionally substituted heterocyclyl, optionally substituted heterocyclylalkyl, optionally substituted aryl, optionally substituted heteroaryl, hydroxyl, oxo, cyano, nitro, —$NR_7R_8$, —$NR_7C(=O)R_8$, —$NR_7C(=O)OR_8$, —$NR_7C(=O)NR_8R_9$, —$NR_7SO_2R_8$, —$NR_7S(O)_2NR_8R_9$, —$C(=O)OR_7$, —$C(=O)R_7$, —$C(=O)NR_7R_8$, —$S(O)_{1-2}R_7$, and —$SO_2NR_7R_8$, wherein $R_7$, $R_8$, and $R_9$ are independently selected from the group consisting of hydrogen, $C_{1-4}$alkyl, or a bond linking the NHE-binding small molecule moiety to L, provided at least one is a bond linking the NHE-binding small molecule moiety to L;
$R_3$ and $R_4$ are independently selected from the group consisting of hydrogen, optionally substituted $C_{1-4}$alkyl, optionally substituted cycloalkyl, optionally substituted cycloalkylalkyl, optionally substituted aryl, optionally substituted aralkyl, optionally substituted heterocyclyl and optionally substituted heteroaryl; or
$R_3$ and $R_4$ form together with the nitrogen to which they are bonded an optionally substituted 4-8 membered heterocyclyl; and
each $R_1$ is independently selected from the group consisting of hydrogen, halogen, optionally substituted $C_{1-6}$alkyl and optionally substituted $C_{1-6}$alkoxy. In some embodiments, n is 2. In certain embodiments, L is a polyalkylene glycol linker. In certain embodiments, L is a polyethylene glycol linker.

In certain embodiments, the Core has the following structure:

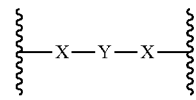

wherein:
X is selected from the group consisting of a bond, —O—, —NH—, —S—, $C_{1-6}$alkylene, —NHC(=O)—, —C(=O)NH—, —NHC(=O)NH—, —$SO_2$NH—, and —$NHSO_2$—;
Y is selected from the group consisting of a bond, optionally substituted $C_{1-8}$alkylene, optionally substituted aryl, optionally substituted heteroaryl, a polyethylene glycol linker, —$(CH_2)_{1-6}O(CH_2)_{1-6}$— and —$(CH_2)_{1-6}NY_1(CH_2)_{1-6}$—; and
$Y_1$ is selected from the group consisting of hydrogen, optionally substituted $C_{1-8}$alkyl, optionally substituted aryl or optionally substituted heteroaryl.

In some embodiments, the Core is selected from the group consisting of

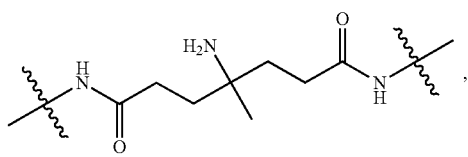

-continued

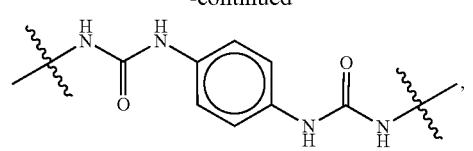

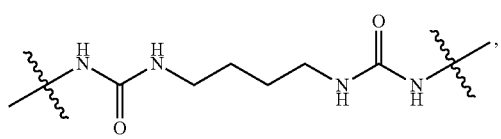

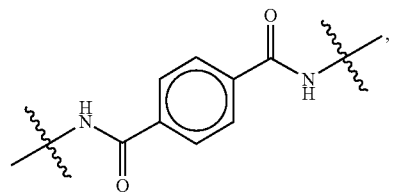

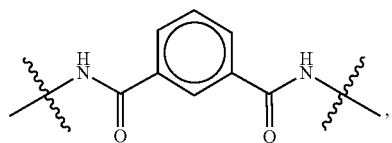

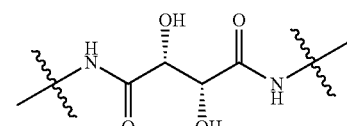

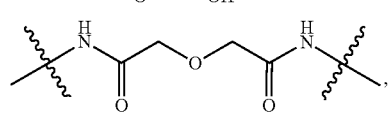

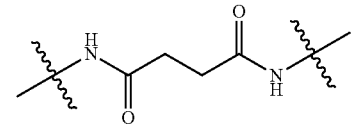

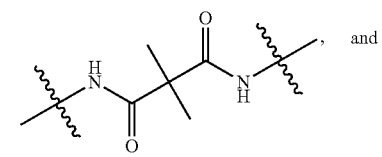

and

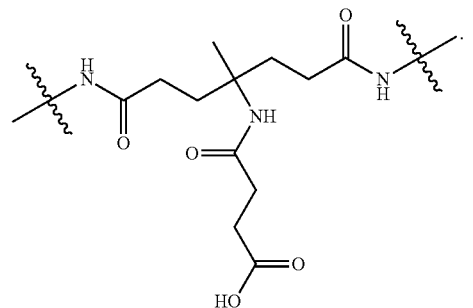

In certain embodiments, the NHE-binding small molecule moiety has the following structure of Formula (XII-H):

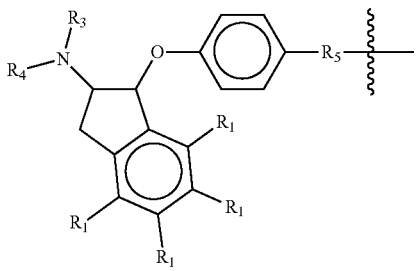

(XII-H)

wherein:
each $R_3$ and $R_4$ are independently selected from the group consisting of hydrogen and optionally substituted $C_{1-4}$alkyl, or $R_3$ and $R_4$, taken together with the nitrogen to which they are bonded, form an optionally substituted 4-8 membered heterocyclyl;
each $R_1$ is independently selected from the group consisting of hydrogen, halogen, $C_{1-6}$alkyl, and $C_{1-6}$haloalkyl; and
$R_5$ is selected from the group consisting of —$SO_2$—$NR_7$— and —NHC(=O)NH—, wherein $R_7$ is hydrogen or $C_{1-4}$alkyl.

In some embodiments, $R_3$ and $R_4$, taken together with the nitrogen to which they are bonded, form an optionally substituted 5 or 6 membered heterocyclyl. In certain embodiments, the optionally substituted 5 or 6 membered heterocyclyl is pyrrolidinyl or piperidinyl. In certain embodiments, the optionally substituted 5 or 6 membered heterocyclyl is pyrrolidinyl or piperidinyl, each substituted with at least one amino or hydroxyl. In some embodiments, $R_3$ and $R_4$ are independently $C_{1-4}$alkyl. In certain embodiments, $R_3$ and $R_4$ are methyl. In some embodiments, each $R_1$ is independently selected from the group consisting of hydrogen or halogen. In certain embodiments, each $R_1$ is independently selected from the group consisting of hydrogen, F and Cl.

In certain embodiments, the compound has the following structure of Formula (I-I):

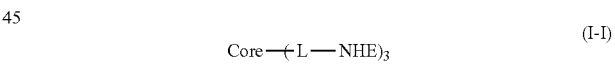

(I-I)

or a stereoisomer, prodrug or pharmaceutically acceptable salt thereof, wherein:
(a) NHE is a NHE-binding small molecule moiety having the following structure of Formula (A-I):

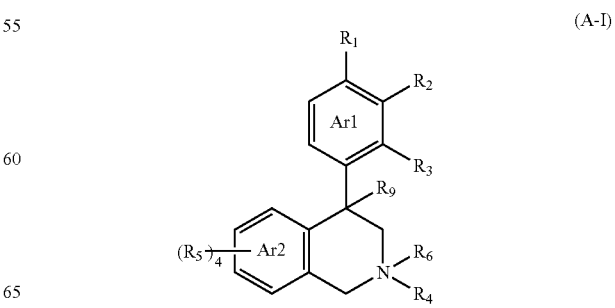

(A-I)

wherein:

each $R_1$, $R_2$, $R_3$, $R_5$ and $R_9$ are independently selected from H, halogen, —$NR_7(CO)R_8$, —$(CO)NR_7R_8$, —$SO_2$—$NR_7R_8$, —$NR_7SO_2R_8$, —$NR_7R_8$, —$OR_7$, —$SR_7$, —$O(CO)NR_7R_8$, —$NR_7(CO)OR_8$, and —$NR_7SO_2NR_8$, where $R_7$ and $R_x$ are independently selected from H, $C_{1-6}$alkyl, —$C_{1-6}$alkyl-OH or a bond linking the NHE-binding small molecule to L, provided at least one is a bond linking the NHE-binding small molecule to L;

$R_4$ is selected from H, $C_1$-$C_7$ alkyl, or a bond linking the NHE-binding small molecule to L;

$R_6$ is absent or selected from H and $C_1$-$C_7$ alkyl; and

Ar1 and Ar2 independently represent an aromatic ring or a heteroaromatic ring;

(b) Core is a Core moiety having the following structure of Formula (B-I):

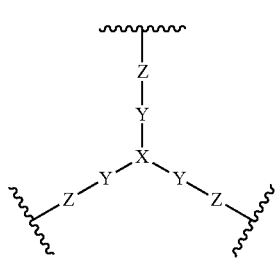

(B-I)

wherein:

X is selected from C(Xi), N and N($C_{1-6}$alkyl);

$X_1$ is selected from hydrogen, optionally substituted alkyl, —$NX_aX_b$, —$NO_2$, —$NX_c$—C(=O)—$NX_c$—$X_a$, —C(=O)$NX_c$—$X_a$, —$NX_c$—C(=O)—$X_a$, —$NX_c$—$SO_2$—$X_a$, —C(=O)—$X_a$ and —$OX_a$, each $X_a$ and $X_b$ are independently selected from hydrogen, optionally substituted alkyl, optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl and optionally substituted heteroarylalkyl;

Y is $C_{1-6}$alkylene;

Z is selected from —$NZ_a$—C(=O)—$NZ_a$—, —C(=O) $NZ_a$—, —$NZ_a$—C(=O)— and heteroaryl when X is $CX_1$;

Z is selected from —$NZ_a$—C(=O)—$NZ_a$—, —$NZ_a$—C (=O)— and heteroaryl when X is N or N($C_{1-6}$alkyl); and each $X_c$ and $Z_a$ is independently selected from hydrogen and $C_{1-6}$alkyl; and (c) L is a bond or linker connecting the Core moiety to the NHE-binding small molecule moieties.

In some embodiments, the NHE-binding small molecule moiety has the following structure:

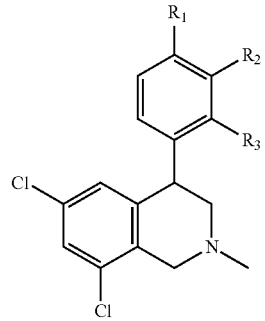

wherein:

each $R_1$, $R_2$ and $R_3$ are independently selected from H, halogen, —$NR_7(CO)R_8$, —$(CO)NR_7R_8$, —$SO_2$—$NR_7R_8$, —$NR_7SO_2R_8$, —$NR_7R_8$, —$OR_7$, —$SR_7$, —$O(CO)NR_7R_8$, —$NR_7(CO)OR_8$, and —$NR_7SO_2NR_8$, where $R_7$ and $R_8$ are independently selected from H, $C_{1-6}$alkyl, —$C_{1-6}$alkyl-OH or a bond linking the NHE-binding small molecule to L, provided at least one is a bond linking the NHE-binding small molecule to L.

In some embodiments, the NHE-binding small molecule moiety has one of the following structures:

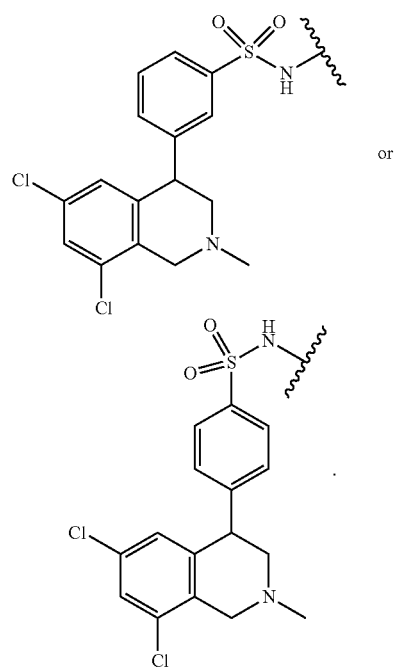

or

In some embodiments, L is a polyalkylene glycol linker. In certain embodiments, L is a polyethylene glycol linker. In some embodiments, X is C($X_1$). In some embodiments, each $X_c$ is hydrogen. In certain embodiments, X is N. In certain embodiments, each $Z_a$ is hydrogen. In some embodiments, the compound has the structure of Formula (II):

(II-I)

or a stereoisomer, prodrug or pharmaceutically acceptable salt thereof,
wherein:
(a) NHE is a NHE-binding small molecule moiety having the structure of Formula (A-I):

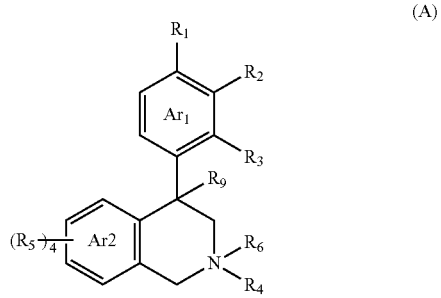

wherein:
each $R_1$, $R_2$, $R_3$, $R_5$ and $R_9$ are independently selected from H, halogen, —$NR_7(CO)R_8$, —$(CO)NR_7R_8$, —$SO_2$—$NR_7R_8$, —$NR_7SO_2R_8$, —$NR_7R_8$, —$OR_7$, —$SR_7$, —$O(CO)NR_7R_8$, —$NR_7(CO)OR_8$, and —$NR_7SO_2NR_8$, where $R_7$ and $R_8$ are independently selected from H, $C_{1-6}$alkyl, —$C_{1-6}$alkyl-OH or a bond linking the NHE-binding small molecule to L, provided at least one is a bond linking the NHE-binding small molecule to L;
$R_4$ is selected from H, $C_1$-$C_7$ alkyl, or a bond linking the NHE-binding small molecule to L;
$R_6$ is absent or selected from H and $C_1$-$C_7$ alkyl; and
Ar1 and Ar2 independently represent an aromatic ring or a heteroaromatic ring;
(b) Core is a Core moiety having the following structure of Formula (C-I):

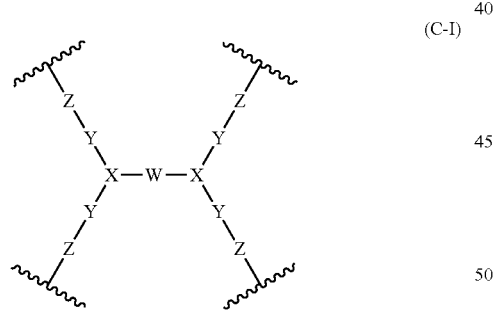

wherein:
W is selected from alkylene, polyalkylene glycol, —C(=O)—NH-(alkylene)-NH—C(=O)—, —C(=O)—NH-(polyalkylene glycol)-NH—C(=O)—, —C(=O)-(alkylene)-C(=O)—, —C(=O)-(polyalkylene glycol)-C(=O)— and cycloalkyl,
X is N;
Y is $C_{1-6}$alkylene;
Z is selected from —$NZ_a$—C(=O)—$NZ_a$—, —C(=O) $NZ_a$—, —$NZ_a$—C(=O)— and heteroaryl;
each $Z_a$ is independently selected from hydrogen and $C_{1-6}$alkyl; and
(c) L is a bond or linker connecting the Core moiety to the NHE-binding small molecules.

In certain embodiments, the NHE-binding small molecule moiety has the following structure:

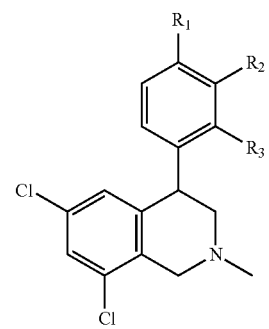

wherein:
each $R_1$, $R_2$ and $R_3$ are independently selected from H, halogen, —$NR_7(CO)R_8$, —$(CO)NR_7R_8$, —$SO_2$—$NR_7R_8$, —$NR_7SO_2R_8$, —$NR_7R_8$, —$OR_7$, —$SR_7$, —$O(CO)NR_7R_8$, —$NR_7(CO)OR_8$, and —$NR_7SO_2NR_8$, where $R_7$ and $R_8$ are independently selected from H, $C_{1-6}$alkyl, —$C_{1-6}$alkyl-OH or a bond linking the NHE-binding small molecule to L, provided at least one is a bond linking the NHE-binding small molecule to L.

In certain embodiments, the NHE-binding small molecule moiety has one of the following structures:

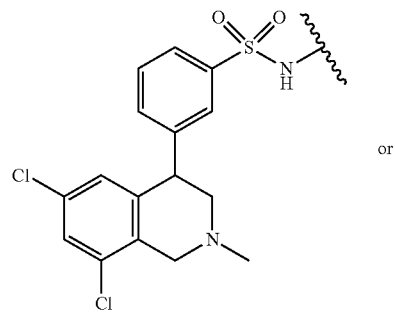

or

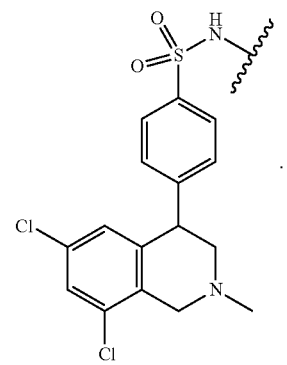

In another embodiment, the NHE inhibitor is:

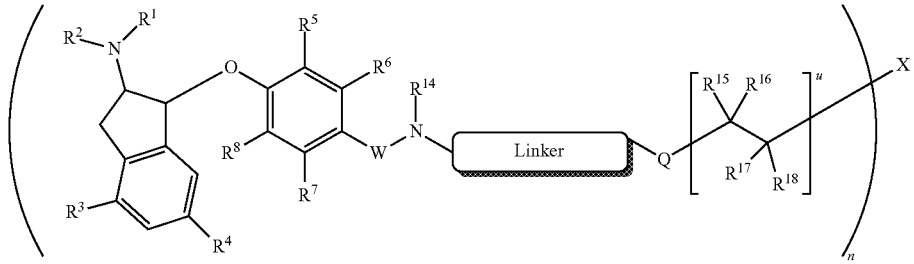

and pharmaceutically acceptable salts, prodrugs, solvates, hydrates, isomers, and tautomers thereof,
wherein:
Linker is —(CHR$^{13}$)$_p$—[Y—(CH$_2$)$_r$]$_s$—Z—R$^{13}$—(CH$_2$)$_t$—Z—;
W is independently, at each occurrence, S(O)$_2$, C(O), or —(CH$_2$)$_m$—;
Z is independently, at each occurrence, a bond, C(O), or —C(O)NH—;
Y is independently, at each occurrence, O, S, NH, N(C$_1$-C$_3$alkyl), or —C(O)NH—;
Q is a bond, NH, —C(O)NH—, —NHC(O)NH—, —NHC(O)N(CH$_3$)—, or —NHC(O)NH—(CHR$^{13}$); m is an integer from 1 to 2; n is an integer from 1 to 4;
r and p are independently, at each occurrence, integers from 0 to 8;
s is an integer from 0 to 4;
t is an integer from 0 to 4;
u is an integer from 0 to 2;
R$^1$ and R$^2$ are independently H, C$_1$-C$_6$alkyl, C$_2$-C$_6$alkenyl, C$_4$-C$_8$cycloalkenyl, C$_2$-C$_6$alkynyl, C$_3$-C$_8$cycloalkyl, heterocyclyl, aryl, heteroaryl containing 1-5 heteroatoms selected from the group consisting of N, S, P and O, wherein each alkyl, alkenyl, cycloalkenyl, alkynyl, cycloalkyl, heterocyclyl, aryl, or heteroaryl is optionally substituted with one or more halogen, OH, CN, —NO$_2$, OXO, —SR$^9$, —OR$^9$, —NHR$^9$, —NR$^9$R$^{10}$, —S(O)$_2$N(R$^9$)$_2$—, —S(O)$_2$R$^9$, —C(O)R$^9$, —C(O)OR$^9$, —C(O)NR$^9$R$^{10}$, —NR$^9$S(O)$_2$R$^{10}$, —S(O)R$^9$, —S(O)NR$^9$R$^{10}$, —NR$^8$S(O)R$^9$, C$_1$-C$_6$alkyl, C$_2$-C$_6$alkenyl, C$_4$-C$_8$cycloalkenyl, C$_2$-C$_6$alkynyl, C$_3$-C$_8$cycloalkyl, heterocyclyl, heterocycle, aryl, or heteroaryl; or
R$^1$ and R$^2$ together with the nitrogen to which they are attached can form a heterocyclyl or heteroaryl containing 1-5 heteroatoms selected from the group consisting of N, S, P and O, wherein the heterocyclyl or heteroaryl group is optionally substituted with one or more halogen, OH, CN, —NO$_2$, OXO, —SR$^9$, —OR$^9$, —NHR$^9$, —NR$^9$R$^{10}$, —S(O)$_2$N(R$^9$)$_2$—, —S(O)$_2$R$^9$, —C(O)R$^9$, —C(O)OR$^9$, —C(O)NR$^9$R$^{10}$, —NR$^9$S(O)$_2$R$^{10}$, —S(O)R$^9$, —S(O)NR$^9$R$^{10}$, —NR$^9$S(O)R$^{10}$, C$_1$-C$_6$alkyl, C$_2$-C$_6$alkenyl, C$_4$-C$_8$cycloalkenyl, C$_2$-C$_6$alkynyl, C$_3$-C$_8$cycloalkyl, heterocyclyl, heterocycle, aryl, or heteroaryl;
R$^3$ and R$^4$ are independently halogen, OH, CN, C$_1$-C$_6$alkyl, C$_1$-C$_6$alkoxy, C$_1$-C$_6$haloalkyl, C$_1$-C$_6$haloalkoxy, or —C(O)NR$^9$R$^{10}$;
R$^5$, R$^6$, R$^7$, and R$^8$ are independently H, halogen, OH. CN, —NO$_2$, C$_1$-C$_6$alkyl, C$_2$-C$_6$alkenyl, C$_4$-C$_8$cycloalkenyl, C$_2$-C$_6$alkynyl, C$_3$-C$_8$cycloalkyl, heterocyclyl, aryl, heteroaryl containing 1-5 heteroatoms selected from the group consisting of N, S, P and O, —SR$^9$, —OR$^9$, —NHR$^9$, —NR$^9$R$^{10}$, —S(O)$_2$N(R$^9$)$_2$—, —S(O)$_2$R$^9$, —C(O)R$^9$, —C(O)OR$^9$, —NR$^9$S(O)$_2$R$^{10}$, —S(O)R$^9$, —S(O)NR$^9$R$^{10}$, —NR$^8$S(O)R$^9$;

R$^9$ and R$^{10}$ are independently H, C$_1$-C$_6$alkyl, C$_2$-C$_6$alkenyl, C$_4$-C$_8$cycloalkenyl, C$_2$-C$_6$alkynyl, C$_3$-C$_8$cycloalkyl, heterocyclyl, aryl, or heteroaryl containing 1-5 heteroatoms selected from the group consisting of N, S, P and O X is a bond, H, N, O, CR$^{11}$R$^{12}$, CR$^{11}$, C, —NHC(O)NH—, or C$_3$-C$_6$cyclolakyl;

R$^{11}$ and R$^{12}$ are independently H, C$_1$-C$_6$alkyl, OH, NH$_2$, CN, or NO$_2$;

R$^{13}$ is independently, at each occurrence, a bond, H, C$_1$-C$_6$alkyl, C$_4$-C$_8$cycloalkenyl, C$_3$-C$_8$cycloalkyl, heterocyclyl, aryl, or heteroaryl, wherein each cycloalkenyl, cycloalkyl, heterocyclyl, aryl, or heteroaryl is optionally substituted with one or more R$^{19}$;

R$^{14}$ is independently, at each occurrence, H, C$_1$-C$_6$alkyl, or C$_1$-C$_6$haloalkyl; or R$^6$ and R$^{14}$ together with the atoms to which they are attached may combine to form, independently, at each occurrence, 5- to 6- membered heterocyclyl, wherein each C$_3$-C$_5$ cycloalkyl, or heterocyclyl is optionally substituted with one or more R$^{19}$; or R$^{13}$ and R$^{14}$ together with the atoms to which they are attached may combine to form independently, at each occurrence, C$_3$-C$_5$ cycloalkyl, heterocyclyl, aryl, or heteroaryl containing 1-5 heteroatoms selected from the group consisting of N, S, P and O, wherein each heterocyclyl or heteroaryl is optionally substituted with one or more R$^{19}$;

R$^{15}$, R$^{16}$, R$^{17}$, and R$^{18}$ are independently, at each occurrence, H, OH, NH$_2$, or C$_1$-C$_3$ alkyl, wherein the alkyl is optionally substituted with one or more R$^{19}$; and R$^{19}$ are independently, at each occurrence, H, OH, NH$_2$, oxo, C$_1$-C$_6$alkyl, C$_1$-C$_6$Hhaloalkyl, C$_1$-C$_6$alkoxy.

In an embodiment, the NHE3 inhibitor is a compound according to the foregoing formula provided that:

(1) when X is H, n is 1;

(2) when X is a bond, O, or CR$^{11}$R$^{12}$, n is 2;

(3) when n is 3, X is CR$^{11}$ or N;

(4) when n is 4 X is C;

(5) only one of Q or X is —NHC(O)NH— at the time, (6) R$^1$ and R$^2$ together with the nitrogen to which they are attached, cannot form a pyrrolidinyl;

(7) when R$^1$ and R$^2$ are methyl, R$^3$ and R$^4$ are halogen, and R$^5$ and R$^8$ are H, Linker is not (8) when $R^1$ and $R^2$ together with the nitrogen to which they are attached form a piperidinyl, $R^3$ and $R^4$ are halogen, and $R^5$ and $R^8$ are H, Linker is not

[structure]

or (9) when $R^1$ and $R^2$, together with the nitrogen to which they are attached, form 3-aminopiperidin-1-yl, $R^3$ and $R^4$ are halogen, and $R^5$, $R^6$, $R^7$, and $R^8$ are H, Linker is not

[structure]

In an embodiment, the NHE3 compound has a structure according to the following formula:

[structure]

and pharmaceutically acceptable salts, prodrugs, solvates, hydrates, isomers, and tautomers thereof, wherein:
Linker is —$(CHR^8)_p$—$[Y—(CH_2)_r]_s$—$Z$—$R^8$—$(CH_2)_t$—$Z$—;
Q is a bond or —NHC(O)NH—;
Z is independently, at each occurrence, a bond, C(O), or —C(O)NH—;
Y is independently, at each occurrence, O, S, NH, N($C_1$-$C_3$alkyl), or —C(O)NH—;
X is a bond, N, O, $CR^{11}R^{12}$, $CR^{11}$, C, or —NHC(O)NH—;
n is an integer from 2 to 4;
r and p are independently, at each occurrence, integers from 0 to 8;
s is an integer from 0 to 4;
t is an integer from 0 to 4;
u is an integer from 0 to 2;
$R^1$ and $R^2$ are independently halogen, OH, CN, $C_1$-$C_6$alkyl, $C_1$-$C_6$alkoxy, $C_1$-$C_6$haloalkyl, $C_1$-$C_6$haloalkoxy, or —C(O)$NR^9R^{10}$;
$R^3$, $R^4$, $R^5$, and $R^6$ are independently H, halogen, OH. CN, —$NO_2$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl containing 1-5 heteroatoms selected from the group consisting of N, S, P and O, —$SR^9$, —$OR^9$, —$NHR^9$, —$NR^9R^{10}$, —$S(O)_2N(R^9)_2$—, —$S(O)_2R^9$, —$C(O)R^9$, —$C(O)OR^9$, —$NR^9S(O)_2R^{10}$, —$S(O)R^9$, —$S(O)NR^9R^{10}$, —$NR^8S(O)R^9$;

$R^7$ is independently, at each occurrence, H, $C_1$-$C_6$alkyl, or $C_1$-$C_6$haloalkyl;
$R^8$ is independently, at each occurrence, a bond, H, $C_1$-$C_6$alkyl, $C_4$-$C_8$cycloalkenyl, $C_3$-$C_8$cycloalkyl, heterocyclyl, aryl, or heteroaryl, wherein each cycloalkenyl, cycloalkyl, heterocyclyl, aryl, or heteroaryl is optionally substituted with one or more $R^{17}$; or
$R^7$ and $R^8$ together with the atoms to which they are attached may combine to form independently, at each occurrence, heterocyclyl or heteroaryl containing 1-5 heteroatoms selected from the group consisting of N, S, P and O, wherein each heterocyclyl or heteroaryl is optionally substituted with one or more $R^{17}$;
$R^9$ and $R^{10}$ are independently H, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, or heteroaryl containing 1-5 heteroatoms selected from the group consisting of N, S, P and O;
$R^{11}$ and $R^{12}$ are independently H, $C_1$-$C_6$alkyl, OH, $NH_2$, CN, or $NO_2$;
$R^{13}$, $R^{14}$, $R^{15}$, and $R^{16}$ are independently, at each occurrence, H, OH, $NH_2$, or $C_1$-$C_3$ alkyl, wherein the alkyl is optionally substituted with one or more $R^{17}$; and
$R^{17}$ is independently, at each occurrence, H, OH, $NH_2$, oxo, $C_1$-$C_6$alkyl, $C_1$-$C_6$haloalkyl, or $C_1$-$C_6$alkoxy.

In an embodiment, the NHE3 inhibitor compound has a structure according to the foregoing formula provided that:

(1) when X is a bond, O, or $CR^{11}R^{12}$, n is 2;

(2) when n is 3, X is $CR^{11}$ or N;

(3) when n is 4 X is C;

(4) only one of Q or X is —NHC(O)NH— at the time;

(5) when $R^1$ and $R^2$ are chloro, Q is —NHC(O)NH—, and $R^3$, $R^4$, $R^5$, and $R^6$ are H, Linker is not

[structure]

(6) when $R^1$ and $R^2$ are chloro, Q is —NHC(O)NH—, and $R^3$, $R^4$, $R^5$, and $R^6$ are H, Linker is not

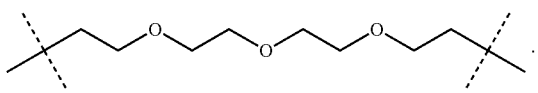

In an embodiment, the NHE3 inhibitor compound has a structure according to the following formula:

N,N'-(10,17-Dioxo-3,6,21,24-tetraoxa-9,11,16,18-tetraazahexacosane-1,26-diyl)bis[3-(6-chloro-2,8-dimethyl-1,2,3,4-tetrahydroisoquinolin-4-yl)benzenesulfonamide];

N,N'-(10,17-Dioxo-3,6,21,24-tetraoxa-9,11,16,18-tetraazahexacosane-1,26-diyl)bis[3-(6-chloro-8-cyano-2-methyl-1,2,3,4-tetrahydroisoquinolin-4-yl)benzenesulfonamide];

N,N'-(10,17-Dioxo-3,6,21,24-tetraoxa-9,11,16,18-tetraazahexacosane-1,26-diyl)bis[3-(6,8-dichloro-2-methyl-1,2,3,4-tetrahydroisoquinolin-4-yl)-4-methylbenzenesulfonamide];

N,N'-(10,17-Dioxo-3,6,21,24-tetraoxa-9,11,16,18-tetraazahexacosane-1,26-diyl)bis[3-(6-chloro-2,8-dimethyl-1,2,3,4-tetrahydroisoquinolin-4-yl)-4-methylbenzenesulfonamide];

N,N'-(10,17-Dioxo-3,6,21,24-tetraoxa-9,11,16,18-tetraazahexacosane-1,26-diyl)bis[3-(6-chloro-8-cyano-2-methyl-1,2,3,4-tetrahydroisoquinolin-4-yl)-4-methylbenzenesulfonamide];

N,N'-(10,17-Dioxo-3,6,21,24-tetraoxa-9,11,16,18-tetraazahexacosane-1,26-diyl)bis[5-(6,8-dichloro-2-methyl-1,2,3,4-tetrahydroisoquinolin-4-yl)-2-methylbenzenesulfonamide];

N,N'-(10,17-Dioxo-3,6,21,24-tetraoxa-9,11,16,18-tetraazahexacosane-1,26-diyl)bis[5-(6-chloro-2,8-dimethyl-1,2,3,4-tetrahydroisoquinolin-4-yl)-2-methylbenzenesulfonamide];

N,N'-(10,17-Dioxo-3,6,21,24-tetraoxa-9,11,16,18-tetraazahexacosane-1,26-diyl)bis(5-(6-chloro-8-cyano-2-methyl-1,2,3,4-tetrahydroisoquinolin-4-yl)-2-methylbenzenesulfonamide);

N,N'-(10,17-Dioxo-3,6,21,24-tetraoxa-9,11,16,18-tetraazahexacosane-1,26-diyl)bis[3-(6,8-dichloro-2-methyl-1,2,3,4-tetrahydroisoquinolin-4-yl)-4-fluorobenzenesulfonamide];

N,N'-(10,17-Dioxo-3,6,21,24-tetraoxa-9,11,16,18-tetraazahexacosane-1,26-diyl)bis[3-(6-chloro-2,8-dimethyl-1,2,3,4-tetrahydroisoquinolin-4-yl)-4-fluorobenzenesulfonamide];

N,N'-(10,17-Dioxo-3,6,21,24-tetraoxa-9,11,16,18-tetraazahexacosane-1,26-diyl)bis[3-(6-chloro-8-cyano-2-methyl-1,2,3,4-tetrahydroisoquinolin-4-yl)-4-fluorobenzenesulfonamide];

N,N'-[(3S,3'S)-(7,14-Dioxo-3,18-dioxa-6,8,13,15-tetraazaicosane-1,20-diyl)bis(pyrrolidine-1,3-diyl)]bis[3-(6,8-dichloro-2-methyl-1,2,3,4-tetrahydroisoquinolin-4-yl)benzenesulfonamide];

N,N'-[(3S,3'S)-(7,14-Dioxo-3,18-dioxa-6,8,13,15-tetraazaicosane-1,20-diyl)bis(pyrrolidine-1,3-diyl)]bis[3-(6-chloro-2,8-dimethyl-1,2,3,4-tetrahydroisoquinolin-4-yl)benzenesulfonamide];

N,N'-[(3S,3'S)-(7,14-Dioxo-3,18-dioxa-6,8,13,15-tetraazaicosane-1,20-diyl)bis(pyrrolidine-1,3-diyl)]bis[3-(6-chloro-8-cyano-2-methyl-1,2,3,4-tetrahydroisoquinolin-4-yl)benzenesulfonamide];

N,N'-[(3S,3'S)-(7,14-Dioxo-3,18-dioxa-6,8,13,15-tetraazaicosane-1,20-diyl)bis(pyrrolidine-1,3-diyl)]bis[3-(6,8-dichloro-2-methyl-1,2,3,4-tetrahydroisoquinolin-4-yl)-4-methylbenzenesulfonamide];

N,N'-[(3S,3'S)-(7,14-Dioxo-3,18-dioxa-6,8,13,15-tetraazaicosane-1,20-diyl)bis(pyrrolidine-1,3-diyl)]bis[3-(6-chloro-2,8-dimethyl-1,2,3,4-tetrahydroisoquinolin-4-yl)-4-methylbenzenesulfonamide];

N,N'-[(3S,3'S)-(7,14-Dioxo-3,18-dioxa-6,8,13,15-tetraazaicosane-1,20-diyl)bis(pyrrolidine-1,3-diyl)]bis[3-(6-chloro-8-cyano-2-methyl-1,2,3,4-tetrahydroisoquinolin-4-yl)-4-methylbenzenesulfonamide];

N,N'-[(3S,3'S)-(7,14-Dioxo-3,18-dioxa-6,8,13,15-tetraazaicosane-1,20-diyl)bis(pyrrolidine-1,3-diyl)]bis[5-(6,8-dichloro-2-methyl-1,2,3,4-tetrahydroisoquinolin-4-yl)-2-methylbenzenesulfonamide];

N,N'-[(3S,3'S)-(7,14-Dioxo-3,18-dioxa-6,8,13,15-tetraazaicosane-1,20-diyl)bis(pyrrolidine-1,3-diyl)]bis[5-(6-chloro-2,8-dimethyl-1,2,3,4-tetrahydroisoquinolin-4-yl)-2-methylbenzenesulfonamide];

N,N'-[(3S,3'S)-(7,14-Dioxo-3,18-dioxa-6,8,13,15-tetraazaicosane-1,20-diyl)bis(pyrrolidine-1,3-diyl)]bis[5-(6-chloro-8-cyano-2-methyl-1,2,3,4-tetrahydroisoquinolin-4-yl)-2-methylbenzenesulfonamide];

N,N'-[(3S,3'S)-(7,14-Dioxo-3,18-dioxa-6,8,13,15-tetraazaicosane-1,20-diyl)bis(pyrrolidine-1,3-diyl)]bis[3-(6,8-dichloro-2-methyl-1,2,3,4-tetrahydroisoquinolin-4-yl)-4-fluorobenzenesulfonamide];

N,N'-[(3S,3'S)-(7,14-Dioxo-3,18-dioxa-6,8,13,15-tetraazaicosane-1,20-diyl)bis(pyrrolidine-1,3-diyl)]bis[3-(6-chloro-2,8-dimethyl-1,2,3,4-tetrahydroisoquinolin-4-yl)-4-fluorobenzenesulfonamide];

N,N'-[(3S,3'S)-(7,14-Dioxo-3,18-dioxa-6,8,13,15-tetraazaicosane-1,20-diyl)bis(pyrrolidine-1,3-diyl)]bis[3-(6-chloro-8-cyano-2-methyl-1,2,3,4-tetrahydroisoquinolin-4-yl)-4-fluorobenzenesulfonamide];

N,N'-[(3R,3'R)-(7,14-Dioxo-3,18-dioxa-6,8,13,15-tetraazaicosane-1,20-diyl)bis(pyrrolidine-1,3-diyl)]bis[3-(6,8-dichloro-2-methyl-1,2,3,4-tetrahydroisoquinolin-4-yl)benzenesulfonamide];

N,N'-[(3R,3'R)-(7,14-Dioxo-3,18-dioxa-6,8,13,15-tetraazaicosane-1,20-diyl)bis(pyrrolidine-1,3-diyl)]bis[3-(6-chloro-2,8-dimethyl-1,2,3,4-tetrahydroisoquinolin-4-yl)benzenesulfonamide];

N,N'-[(3R,3'R)-(7,14-Dioxo-3,18-dioxa-6,8,13,15-tetraazaicosane-1,20-diyl)bis(pyrrolidine-1,3-diyl)]bis[3-(6-chloro-8-cyano-2-methyl-1,2,3,4-tetrahydroisoquinolin-4-yl)benzenesulfonamide];

N,N'-[(3R,3'R)-(7,14-Dioxo-3,18-dioxa-6,8,13,15-tetraazaicosane-1,20-diyl)bis(pyrrolidine-1,3-diyl)]bis[3-(6,8-dichloro-2-methyl-1,2,3,4-tetrahydroisoquinolin-4-yl)-4-methylbenzenesulfonamide];

N,N'-[(3R,3'R)-(7,14-Dioxo-3,18-dioxa-6,8,13,15-tetraazaicosane-1,20-diyl)bis(pyrrolidine-1,3-diyl)]bis[3-(6-chloro-2,8-dimethyl-1,2,3,4-tetrahydroisoquinolin-4-yl)-4-methylbenzenesulfonamide];

N,N'-[(3R,3'R)-(7,14-Dioxo-3,18-dioxa-6,8,13,15-tetraazaicosane-1,20-diyl)bis(pyrrolidine-1,3-diyl)]bis[3-(6-chloro-8-cyano-2-methyl-1,2,3,4-tetrahydroisoquinolin-4-yl)-4-methylbenzenesulfonamide];

N,N'-[(3R,3'R)-(7,14-Dioxo-3,18-dioxa-6,8,13,15-tetraazaicosane-1,20-diyl)bis(pyrrolidine-1,3-diyl)]bis[5-(6,8-dichloro-2-methyl-1,2,3,4-tetrahydroisoquinolin-4-yl)-2-methylbenzenesulfonamide];

N,N'-[(3R,3'R)-(7,14-Dioxo-3,18-dioxa-6,8,13,15-tetraazaicosane-1,20-diyl)bis(pyrrolidine-1,3-diyl)]bis[5-(6-chloro-2,8-dimethyl-1,2,3,4-tetrahydroisoquinolin-4-yl)-2-methylbenzenesulfonamide];

N,N'-[(3R,3'R)-(7,14-Dioxo-3,18-dioxa-6,8,13,15-tetraazaicosane-1,20-diyl)bis(pyrrolidine-1,3-diyl)]bis[5-(6- chloro-8-cyano-2-methyl-1,2,3,4-tetrahydroisoquinolin-4-yl)-2-methylbenzenesulfonamide];

N,N'-[(3R,3'R)-(7,14-Dioxo-3,18-dioxa-6,8,13,15-tetraazaicosane-1,20-diyl)bis(pyrrolidine-1,3-diyl)]bis[3-(6,8-dichloro-2-methyl-1,2,3,4-tetrahydroisoquinolin-4-yl)-4-fluorobenzenesulfonamide];

N,N'-[(3R,3'R)-(7,14-Dioxo-3,18-dioxa-6,8,13,15-tetraazaicosane-1,20-diyl)bis(pyrrolidine-1,3-diyl)]bis[3-(6-chloro-2,8-dimethyl-1,2,3,4-tetrahydroisoquinolin-4-yl)-4-fluorobenzenesulfonamide];

N,N'-[(3R,3'R)-(7,14-Dioxo-3,18-dioxa-6,8,13,15-tetraazaicosane-1,20-diyl)bis(pyrrolidine-1,3-diyl)]bis[3-(6-chloro-8-cyano-2-methyl-1,2,3,4-tetrahydroisoquinolin-4-yl)-4-fluorobenzenesulfonamide];

N,N'-[(7,14-Dioxo-3,18-dioxa-6,8,13,15-tetraazaicosane-1,20-diyl)bis(piperidine-1,4-diyl)]bis[3-(6-chloro-2,8-dimethyl-1,2,3,4-tetrahydroisoquinolin-4-yl)benzenesulfonamide];

N,N'-[(7,14-Dioxo-3,18-dioxa-6,8,13,15-tetraazaicosane-1,20-diyl)bis(piperidine-1,4-diyl)]bis[3-(6-chloro-8-cyano-2-methyl-1,2,3,4-tetrahydroisoquinolin-4-yl)benzenesulfonamide];

1,1'-[(3R,3'R)-(7,14-Dioxo-3,18-dioxa-6,8,13,15-tetraazaicosane-1,20-diyl)bis(pyrrolidine-1,3-diyl)]bis[N-([3-(6-chloro-2,8-dimethyl-1,2,3,4-tetrahydroisoquinolin-4-yl)phenyl]sulfonyl)formamide];

1,1'-[(3R,3'R)-(7,14-Dioxo-3,18-dioxa-6,8,13,15-tetraazaicosane-1,20-diyl)bis(pyrrolidine-1,3-diyl)]bis[N-([3-(6-chloro-8-cyano-2-methyl-1,2,3,4-tetrahydroisoquinolin-4-yl)phenyl]sulfonyl)formamide];

1,1'-(5,12-Dioxo-4,6,11,13-tetraazahexadecane-1,16-diyl)bis[N-([3-(6,8-dichloro-2-methyl-1,2,3,4-tetrahydroisoquinolin-4-yl)phenyl]sulfonyl)piperidine-4-carboxamide];

1,1'-(5,12-Dioxo-4,6,11,13-tetraazahexadecane-1,16-diyl)bis[N-([3-(6,8-dichloro-2-methyl-1,2,3,4-tetrahydroisoquinolin-4-yl)phenyl]sulfonyl)piperidine-3-carboxamide];

$N^1,N^{18}$-Bis([3-(6,8-Dichloro-2-dimethyl-1,2,3,4-tetrahydroisoquinolin-4-yl)phenyl]sulfonyl)-6,13-dioxo-5,7,12,14-tetraazaoctadecanediamide;

N,N'-[(3S,3'S)-(6,13-Dioxo-5,7,12,14-tetraazaoctadecanedioyl)bis(pyrrolidine-1,3-diyl)]bis[3-(6-chloro-2,8-dimethyl-1,2,3,4-tetrahydroisoquinolin-4-yl)benzenesulfonamide];

N,N'-[(3S,3'S)-(6,13-Di oxo-5,7,12,14-tetraazaoctadecanedioyl)bis(pyrrolidine-1,3-diyl)]bis[3-(6-chloro-8-cyano-2-methyl-1,2,3,4-tetrahydroisoquinolin-4-yl)benzenesulfonamide];

1-[2-(2-[(1-[(3-[(S)-6,8-Dichloro-2-methyl-1,2,3,4-tetrahydroisoquinolin-4-yl]phenyl)sulfonyl]piperidin-4-yl)oxy]ethoxy)ethyl]-3-[4-(3-[2-(2-[(1-[(3-[(S)-6,8-dichloro-2-methyl-1,2,3,4-tetrahydroisoquinolin-4-yl]phenyl)sulfonyl]piperidin-4-yl)oxy]ethoxy)ethyl]ureido)butyl]urea;

1-(2-(2-(((R)-1-((3-((S)-6,8-dichloro-2-methyl-1,2,3,4-tetrahydroisoquinolin-4-yl)phenyl)sulfonyl)pyrrolidin-3-yl)oxy)ethoxy)ethyl)-3-(4-(3-(2-(2-(((S)-1-((3-((S)-6,8-dichloro-2-methyl-1,2,3,4-tetrahydroisoquinolin-4-yl)phenyl)sulfonyl)pyrrolidin-3-yl)oxy)ethoxy)ethyl)ureido)butyl)urea;

1-(2-[2-([(S)-1-[(3-[(S)-6,8-dichloro-2-methyl-1,2,3,4-tetrahydroisoquinolin-4-yl]phenyl)sulfonyl]pyrrolidin-3-yl]oxy)ethoxy]ethyl)-3-(4-[3-(2-[2-([(S)-1-[(3-[(S)-6,8-dichloro-2-methyl-1,2,3,4-tetrahydroisoquinolin-4-yl]phenyl)sulfonyl]pyrrolidin-3-yl]oxy)ethoxy]ethyl)ureido]butyl)urea;

3-[(S)-6,8-Dichloro-2-methyl-1,2,3,4-tetrahydroisoquinolin-4-yl]-N-[(3R,2R)-28-[(3-[(S)-6,8-dichloro-2-methyl-1,2,3,4-tetrahydroisoquinolin-4-yl]phenyl)sulfonamido]-2,29-dimethyl-12,19-dioxo-5,8,23,26-tetraoxa-11,13,18,20-tetraazatriacontan-3-yl]benzenesulfonamide;

N,N'-(10-Oxo-3,6,14,17-tetraoxa-9,11-diazanonadecane-1,19-diyl)bis[3-(6,8-dichloro-2-methyl-1,2,3,4-tetrahydroisoquinolin-4-yl)benzenesulfonamide];

N,N'-[(3S,3'S)-(7-Oxo-3,11-dioxa-6,8-diazatridecane-1,13-diyl]bis[pyrrolidine-1,3-diyl))bis(3-(6,8-dichloro-2-methyl-1,2,3,4-tetrahydroisoquinolin-4-yl)benzenesulfonamide];

$N^1,N^{18}$-Bis(1-[(3-[(S)-6,8-dichloro-2-methyl-1,2,3,4-tetrahydroisoquinol in-4-yl]phenyl)sulfonyl]piperidin-4-yl)-6,13-dioxo-5,7,12,14-tetraazaoctadecanediamid;

$N^1,N^{18}$-Bis(1-[(3-[(S)-6-chloro-8-cyano-2-methyl-1,2,3,4-tetrahydroisoquinolin-4-yl]phenyl)sulfonyl]piperidin-4-yl)-6,13-dioxo-5,7,12,14-tetraazaoctadecanediamide; or $N^1,N^{18}$-Bis(1-[(3-[(S)-6-chloro-2,8-dim ethyl-1,2,3,4-tetrahydroisoquinolin-4-yl]phenyl)sulfonyl]piperidin-4-yl)-6,13-dioxo-5,7,12,14-tetraazaoctadecanediamide.

In one embodiment of the invention, the NHE3 inhibitor is a compound according to the formula:

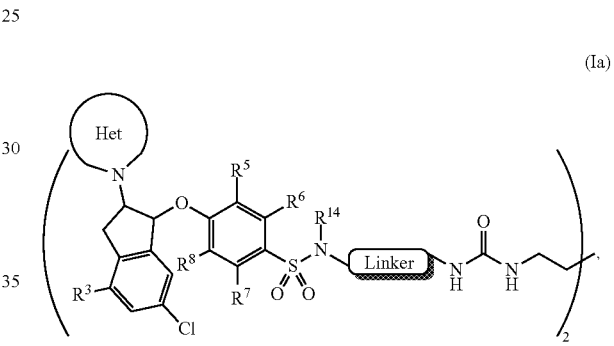

(Ia)

In one embodiment of the invention, the NHE3 inhibitor is a compound according to the formula:

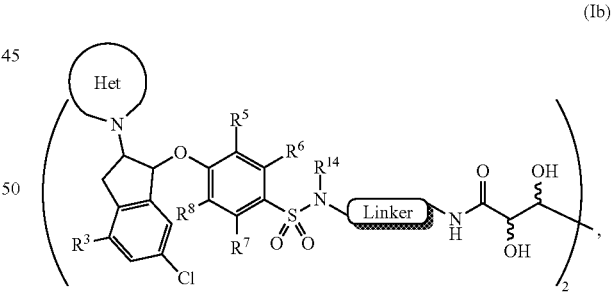

(Ib)

In an embodiment the NHE3 inhibitor is one of the following compounds:

1-[2-(2-[2-[(4-[[(1S,2S)-2-[(3R)-3-Aminopiperidin-1-yl]-4,6-dichloro-2,3-dihydro-1H-inden-1-yl]oxy]-3-methylbenzene)sulfonamido]ethoxy]ethoxy)ethyl]-3-[4-([[2-(2-[2-[(4-[[(1S,2S)-2-[(3R)-3-aminopiperidin-1-yl]-4,6-dichloro-2,3-dihydro-1H-inden-1-yl]oxy]-3-methylbenzene)sulfonamido]ethoxy]ethoxy)ethyl]carbamoyl]amino)butyl]urea;

3-[2-(2-[2-[(4-[[(1S,2S)-2-[(3R)-3-Aminopiperidin-1-yl]-4,6-dichloro-2,3-dihydro-1H-inden-1-yl]oxy]-3-fluorobenzene)sulfonamido]ethoxy]ethoxy)ethyl]-1-[4-([[2-(2-[2-

[(4-[[(1S,2S)-2-[(3R)-3-aminopiperidin-1-yl]-4,6-dichloro-2,3-dihydro-1H-inden-1-yl]oxy]-3-fluorobenzene)sulfonamido]ethoxy]ethoxy]ethyl]carbamoyl]amino)butyl]urea;

3-[2-(2-[2-[(4-[[(1S,2S)-2-[(3R)-3-Aminopiperidin-1-yl]-6-chloro-4-methyl-2,3-dihydro-1H-inden-1-yl]oxy]benzene)sulfonamido]ethoxy]ethoxy)ethyl]-1-[4-([[2-(2-[2-[(4-[[(1S,2S)-2-[(3R)-3-aminopiperidin-1-yl]-6-chloro-4-methyl-2,3-dihydro-1H-inden-1-yl]oxy]benzene)sulfonamido]ethoxy]ethoxy)ethyl]carbamoyl]amino)butyl]urea;

3-[2-(2-[2-[(4-[[(1S,2S)-2-[(3R)-3-Aminopiperidin-1-yl]-6-chloro-4-cyano-2,3-dihydro-1H-inden-1-yl]oxy]benzene)sulfonamido]ethoxy]ethoxy)ethyl]-1-[4-([[2-(2-[2-[(4-[[(1S,2S)-2-[(3R)-3-aminopiperidin-1-yl]-6-chloro-4-cyano-2,3-dihydro-1H-inden-1-yl]oxy]benzene)sulfonamido]ethoxy]ethoxy)ethyl]carbamoyl]amino)butyl]urea;

3-[2-(2-[2-[(4-[[(1S,2S)-2-[(3R)-3-Aminopiperidin-1-yl]-6-chloro-4-m ethoxy-2,3-dihydro-1H-inden-1-yl]oxy]benzene)sulfonamido]ethoxy]ethoxy)ethyl]-1-[4-([[2-(2-[2-[(4-[[(1S,2S)-2-[(3R)-3-aminopiperidin-1-yl]-6-chloro-4-methoxy-2,3-dihydro-1H-inden-1-yl]oxy]benzene)sulfonamido]ethoxy]ethoxy)ethyl]carbamoyl]amino)butyl]urea;

1-[2-(2-[2-[(4-[[(1S,2S)-2-[(3R)-3-Aminopiperidin-1-yl]-6-chloro-4-fluoro-2,3-dihydro-1H-inden-1-yl]oxy]-3-methylbenzene)sulfonamido]ethoxy]ethoxy)ethyl]-3-[4-([[2-(2-[2-[(4-[[(1 S,2S)-2-[(3R)-3-aminopiperidin-1-yl]-6-chloro-4-fluoro-2,3-dihydro-1H-inden-1-yl]oxy]-3-methylbenzene)sulfonamido]ethoxy]ethoxy)ethyl]carbamoyl]amino)butyl]urea;

3-[2-(2-[2-[(4-[[(1S,2S)-2-[(3R)-3-Aminopiperidin-1-yl]-6-chloro-4-methyl-2,3-dihydro-1H-inden-1-yl]oxy]-3-methylbenzene)sulfonamido]ethoxy]ethoxy)ethyl]-1-[4-([[2-(2-[2-[(4-[[(1S,2S)-2-[(3R)-3-aminopiperidin-1-yl]-6-chloro-4-methyl-2,3-dihydro-1H-inden-1-yl]oxy]-3-methylbenzene)sulfonamido]ethoxy]ethoxy)ethyl]carbamoyl]amino)butyl]urea;

3-[2-(2-[2-[(4-[[(1S,2S)-2-[(3R)-3-Aminopiperidin-1-yl]-6-chloro-4-cyano-2,3-dihydro-1H-inden-1-yl]oxy]-3-methylbenzene)sulfonamido]ethoxy]ethoxy)ethyl]-1-[4-([[2-(2-[2-[(4-[[(1 S,2S)-2-[(3R)-3-aminopiperidin-1-yl]-6-chloro-4-cyano-2,3-dihydro-1H-inden-1-yl]oxy]-3-methylbenzene) sulfonamido]ethoxy]ethoxy)ethyl]carbamoyl]amino)butyl]urea;

3-[2-(2-[2-[(4-[[(1S,2S)-2-[(3R)-3-Aminopiperidin-1-yl]-6-chloro-4-methoxy-2,3-dihydro-1H-inden-1-yl]oxy]-3-methylbenzene)sulfonamido]ethoxy]ethoxy)ethyl]-1-[4-([[2-(2-[2-[(4-[[(1S,2S)-2-[(3R)-3-aminopiperidin-1-yl]-6-chloro-4-methoxy-2,3-dihydro-1H-inden-1-yl]oxy]-3-methylbenzene)sulfonamido]ethoxy]ethoxy)ethyl]carbamoyl]amino) butyl]urea;

3-[2-(2-[2-[(4-[[(1S,2S)-2-[(3R)-3-Aminopiperidin-1-yl]-6-chloro-4-methyl-2,3-dihydro-1H-inden-1-yl]oxy]-3-fluoro benzene)sulfonamido]ethoxy]ethoxy)ethyl]-1-[4-([[2-(2-[2-[(4-[[(1S,2S)-2-[(3R)-3-aminopiperidin-1-yl]-6-chloro-4-methyl-2,3-dihydro-1H-inden-1-yl]oxy]-3-fluorobenzene)sulfonamido]ethoxy]ethoxy)ethyl]carbamoyl]amino)butyl]urea;

3-[2-(2-[2-[(4-[[(1S,2S)-6-Chloro-2-(dimethylamino)-4-methyl-2,3-dihydro-1H-inden-1-yl]oxy]benzene)sulfonamido]ethoxy]ethoxy)ethyl]-1-[4-([[2-(2-[2-[(4-[[(1S,2S)-6-chloro-2-(dimethylamino)-4-methyl-2,3-dihydro-1H-inden-1-yl]oxy]benzene)sulfonamido]ethoxy]ethoxy)ethyl]carbamoyl]amino)butyl]urea;

3-[2-(2-[2-[(4-[[(1S,2S)-6-Chloro-4-cyano-2-(dimethylamino)-2,3-dihydro-1H-inden-1-yl]oxy]benzene)sulfonamido]ethoxy]ethoxy)ethyl]-1-[4-([[2-(2-[2-[(4-[[(1S,2S)-6-chloro-4-cyano-2-(dimethylamino)-2,3-dihydro-1H-inden-1-yl]oxy]benzene)sulfonamido]ethoxy]ethoxy)ethyl]carbamoyl]amino)butyl]urea;

3-[2-(2-[2-[(4-[[(1S,2S)-6-Chloro-2-(dimethylamino)-4-(trifluoromethyl)-2,3-dihydro-1H-inden-1-yl]oxy]benzene)sulfonamido]ethoxy]ethoxy)ethyl]-1-[4-([[2-(2-[2-[(4-[[(1S,2S)-6-chloro-2-(dimethylamino)-4-(trifluoromethyl)-2,3-dihydro-1H-inden-1-yl]oxy]benzene)sulfonamido]ethoxy]ethoxy)ethyl]carbamoyl]amino)butyl]urea;

1-[2-(2-[2-[(4-[[(1S,2S)-6-Chloro-2-(dimethylamino)-4-(trifluoromethoxy)-2,3-dihydro-1H-inden-1-yl]oxy]benzene)sulfonamido]ethoxy]ethoxy)ethyl]-3-[4-([[2-(2-[2-[(4-[[(1S,2S)-6-chloro-2-(dimethylamino)-4-(trifluoromethoxy)-2,3-dihydro-1H-inden-1-yl]oxy]benzene)sulfonamido]ethoxy]ethoxy)ethyl]carbamoyl]amino)butyl]urea;

3-[2-(2-[2-[(4-[[(1S,2S)-6-Chloro-2-(dimethylamino)-4-methoxy-2,3-dihydro-1H-inden-1-yl]oxy]benzene)sulfonamido]ethoxy]ethoxy)ethyl]-1 -[4-([[2-(2-[2-[(4-[[(1S,2S)-6-chloro-2-(dimethylamino)-4-m ethoxy-2,3-dihydro-1H-inden-1-yl]oxy]benzene)sulfonamido]ethoxy]ethoxy)ethyl]carbamoyl]amino)butyl]urea;

3-[2-(2-[2-[(4-[[(1S,2S)-6-Chloro-2-(dimethylamino)-4-fluoro-2,3-dihydro-1H-inden-1-yl]oxy]-3-methylbenzene)sulfonamido]ethoxy]ethoxy)ethyl]-1-[4-([[2-(2-[2-[(4-[[(1S,2S)-6-chloro-2-(dimethylamino)-4-fluoro-2,3-dihydro-1H-inden-1-yl]oxy]-3-methylbenzene)sulfonamido]ethoxy]ethoxy)ethyl]carbamoyl]amino)butyl]urea;

3-[2-(2-[2-[(4-[[(1S,2S)-6-Chloro-2-(dimethylamino)-4-methyl-2,3-dihydro-1H-inden-1-yl]oxy]-3-methyl benzene)sulfonamido]ethoxy]ethoxy)ethyl]-1-[4-([[2-(2-[2-[(4-[[(1S,2S)-6-chloro-2-(dimethylamino)-4-methyl-2,3-dihydro-1H-inden-1-yl]oxy]-3-methylbenzene)sulfonamido]ethoxy]ethoxy)ethyl]carbamoyl]amino)butyl]urea;

3-[2-(2-[2-[(4-[[(1S,2S)-6-Chloro-4-cyano-2-(dimethylamino)-2,3-dihydro-1H-inden-1-yl]oxy]-3-methylbenzene)sulfonamido]ethoxy]ethoxy)ethyl]-1-[4-([[2-(2-[2-[(4-[[(1S,2S)-6-chloro-4-cyano-2-(dimethylamino)-2,3-dihydro-1H-inden-1-yl]oxy]-3-methylbenzene)sulfonamido]ethoxy]ethoxy) ethyl]carbamoyl]amino) butyl]urea;

3-[2-(2-[2-[(4-[[(1S,2S)-6-Chloro-2-(dimethylamino)-4-(trifluoromethyl)-2,3-dihydro-1H-inden-1-yl]oxy]-3-methylbenzene)sulfonamido]ethoxy]ethoxy)ethyl]-1-[4-([[2-(2-[2-[(4-[[(1S,2S)-6-chloro-2-(dimethylamino)-4-(trifluoromethyl)-2,3-dihydro-1H-inden-1-yl]oxy]-3-methylbenzene)sulfonamido]ethoxy]ethoxy)ethyl]-carbamoyl]amino)butyl]urea;

1-[2-(2-[2-[(4-[[(1S,2S)-6-Chloro-2-(dimethylamino)-4-(trifluoromethoxy)-2,3-dihydro-1H-inden-1-yl]oxy]-3-methylbenzene)sulfonamido]ethoxy]ethoxy)ethyl]-3-[4-([[2-(2-[2-[(4-[[(1S,2S)-6-chloro-2-(dimethylamino)-4-(trifluoromethoxy)-2,3-dihydro-1H-inden-1-yl]oxy]-3-methylbenzene)sulfonamido]ethoxy]ethoxy)ethyl]carbamoyl]amino)butyl]urea;

3-[2-(2-[2-[(4-[[(1S,2S)-6-Chloro-2-(dimethylamino)-4-methoxy-2,3-dihydro-1H-inden-1-yl]oxy]-3-methylbenzene)sulfonamido]ethoxy]ethoxy)ethyl]-1-[4-([[2-(2-[2-[(4-[[(1S,2S)-6-chloro-2-(dimethylamino)-4-methoxy-2, 3-dihydro-1H-inden-1-yl]oxy]-3-methylbenzene)
sulfonamido]ethoxy]ethoxy)ethyl]carbamoyl]amino)
butyl]urea;

3-[2-(2-[2-[(4-[[(1S,2S)-4,6-Dichloro-2-(dimethylamino)-2,3-dihydro-1H-inden-1-yl]oxy]-3-methylbenzene)sulfonamido]ethoxy]ethoxy)ethyl]-1-[4-([[2-(2-[2-[(4-[[(1S,2S)-4,6-dichloro-2-(dimethylamino)-2,3-dihydro-1H-inden-1-yl]oxy]-3-methyl benzene)sulfonamido]ethoxy]ethoxy)ethyl]carbamoyl]amino)butyl]urea dihydrochloride;

3-[2-(2-[2-[(4-[[(1S,2S)-4,6-Dichloro-2-(dimethylamino)-2,3-dihydro-1H-inden-1-yl]oxy]-3-fluorobenzene)sulfonamido]ethoxy]ethoxy)ethyl]-1-[4-([[2-(2-[2-[(4-[[(1S,2S)-4,6-dichloro-2-(dimethylamino)-2,3-dihydro-1H-inden-1-yl]oxy]-3-fluorobenzene)sulfonamido]ethoxy]ethoxy)ethyl]carbamoyl]amino)butyl]urea;

3-[2-(2-[2-[(4-[[(1S,2S)-6-Chloro-2-(dimethylamino)-4-methyl-2,3-dihydro-1H-inden-1-yl]oxy]-3-fluorobenzene)sulfonamido]ethoxy]ethoxy)ethyl]-1-[4-([[2-(2-[2-[(4-[[(1S,2S)-6-chloro-2-(dimethylamino)-4-methyl-2,3-dihydro-1H-inden-1-yl]oxy]-3-fluorobenzene)sulfonamido]ethoxy]ethoxy)ethyl]carbamoyl]amino)butyl]urea;

3-[2-(2-[2-[(4-[[(1S,2S)-4,6-Dichloro-2-[(3R)-3-(dimethylamino)piperidin-1-yl]-2,3-dihydro-1H-inden-1-yl]oxy]benzene)sulfonamido]ethoxy]ethoxy)ethyl]-1-[4-([[2-(2-[2-[(4-[[(1S,2S)-4,6-dichloro-2-[(3R)-3-(dimethylamino)piperidin-1-yl]-2,3-dihydro-1H-inden-1-yl]oxy]benzene)sulfonamido]ethoxy]ethoxy)ethyl]carbamoyl]amino)butyl]urea;

3-[2-(2-[2-[(4-[[(1S,2S)-4,6-Dichloro-2-[(3R)-3-(dimethylamino)piperidin-1-yl]-2,3-dihydro-1H-inden-1-yl]oxy]-3-methylbenzene)sulfonamido]ethoxy]ethoxy)ethyl]-1-[4-([[2-(2-[2-[(4-[[(1S,2S)-4,6-dichloro-2-[(3R)-3-(dimethylamino)piperidin-1-yl]-2,3-dihydro-1H-inden-1-yl]oxy]-3-methylbenzene)sulfonamido]ethoxy]ethoxy)ethyl]carbamoyl]amino)butyl]urea;

3-[2-(2-[2-[(4-[[(1S,2S)-4,6-Dichloro-2-[(3R)-3-(dimethylamino)piperidin-1-yl]-2,3-dihydro-1H-inden-1-yl]oxy]-3-fluorobenzene)sulfonamido]ethoxy]ethoxy)ethyl]-1-[4-([[2-(2-[2-[(4-[[(1S,2S)-4,6-dichloro-2-[(3R)-3-(dimethylamino)piperidin-1-yl]-2,3-dihydro-1H-inden-1-yl]oxy]-3-fluorobenzene)sulfonamido]ethoxy]ethoxy)ethyl]-carbamoyl]amino)butyl]urea;

3-[2-(2-[2-[(4-[[(1S,2S)-6-Chloro-2-[(3R)-3-(dimethylamino)piperidin-1-yl]-4-methyl-2,3-dihydro-1H-inden-1-yl]oxy]benzene)sulfonamido]ethoxy]ethoxy)ethyl]-1-[4-([[2-(2-[2-[(4-[[(1S,2S)-6-chloro-2-[(3R)-3-(dimethylamino)piperidin-1-yl]-4-methyl-2,3-dihydro-1H-inden-1-yl]oxy]benzene)sulfonamido]ethoxy]ethoxy)ethyl]carbamoyl]amino)butyl]urea;

3-[2-(2-[2-[(4-[[(1S,2S)-6-Chloro-2-[(3R)-3-(dimethylamino)piperidin-1-yl]-4-methyl-2,3-dihydro-1H-inden-1-yl]oxy]-3-methylbenzene)sulfonamido]ethoxy]ethoxy)ethyl]-1-[4-([[2-(2-[2-[(4-[[(1S,2S)-6-chloro-2-[(3R)-3-(dimethylamino)piperidin-1-yl]-4-methyl-2,3-dihydro-1H-inden-1-yl]oxy]-3-methylbenzene)sulfonamido]ethoxy]ethoxy)ethyl]carbamoyl]amino)butyl]urea;

3-[2-(2-[2-[(4-[[(1S,2S)-6-Chloro-2-[(3R)-3-(dimethylamino)piperidin-1-yl]-4-methyl-2,3-dihydro-1H-inden-1-yl]oxy]-3-fluorobenzene)sulfonamido]ethoxy]ethoxy)ethyl]-1-[4-([[2-(2-[2-[(4-[[(1S,2S)-6-chloro-2-[(3R)-3-(dimethylamino)piperidin-1-yl]-4-methyl-2,3-dihydro-1H-inden-1-yl]oxy]-3-fluorobenzene)sulfonamido]ethoxy]ethoxy)ethyl]carbamoyl]amino)butyl]urea;

3-[2-(2-[2-[(4-[[(1S,2S)-4,6-Dichloro-2-(piperazin-1-yl)-2,3-dihydro-1H-inden-1-yl]oxy]benzene)sulfonamido]ethoxy]ethoxy)ethyl]-1-[4-([[2-(2-[2-[(4-[[(1S,2S)-4,6-dichloro-2-(piperazin-1-yl)-2,3-dihydro-1H-inden-1-yl]oxy]benzene)sulfonamido]ethoxy]ethoxy)ethyl]carbamoyl]amino)butyl]urea;

3-[2-(2-[2-[(4-[[(1S,2S)-4,6-Dichloro-2-(piperazin-1-yl)-2,3-dihydro-1H-inden-1-yl]oxy]-3-methylbenzene)sulfonamido]ethoxy]ethoxy)ethyl]-1-[4-([[2-(2-[2-[(4-[[(1S,2S)-4,6-dichloro-2-(piperazin-1-yl)-2,3-dihydro-1H-inden-1-yl]oxy]-3-methylbenzene)sulfonamido]ethoxy]ethoxy)ethyl]carbamoyl]amino)butyl]urea;

3-[2-(2-[2-[(4-[[(1S,2S)-4,6-Dichloro-2-(piperazin-1-yl)-2,3-dihydro-1H-inden-1-yl]oxy]-3-fluorobenzene)sulfonamido]ethoxy]ethoxy)ethyl]-1-[4-([[2-(2-[2-[(4-[[(1S,2S)-4,6-dichloro-2-(piperazin-1-yl)-2,3-dihydro-1H-inden-1-yl]oxy]-3-fluorobenzene)sulfonamido]ethoxy]ethoxy)ethyl]carbamoyl]amino)butyl]urea;

3-[2-(2-[2-[(4-[[(1S,2S)-6-Chloro-4-methyl-2-(piperazin-1-yl)-2,3-dihydro-1H-inden-1-yl]oxy]benzene)sulfonamido]ethoxy]ethoxy)ethyl]-1-[4-([[2-(2-[2-[(4-[[(1S,2S)-6-chloro-4-methyl-2-(piperazin-1-yl)-2,3-dihydro-1H-inden-1-yl]oxy]benzene)sulfonamido]ethoxy]ethoxy)ethyl]carbamoyl]amino)butyl]urea;

3-[2-(2-[2-[(4-[[(1S,2S)-6-Chloro-4-methyl-2-(piperazin-1-yl)-2,3-dihydro-1H-inden-1-yl]oxy]-3-methylbenzene)sulfonamido]ethoxy]ethoxy)ethyl]-1-[4-([[2-(2-[2-[(4-[[(1S,2S)-6-chloro-4-methyl-2-(piperazin-1-yl)-2,3-dihydro-1H-inden-1-yl]oxy]-3-methylbenzene)sulfonamido]ethoxy]ethoxy)ethyl]carbamoyl]amino)butyl]urea;

3-[2-(2-[2-[(4-[[(1S,2S)-6-Chloro-4-methyl-2-(piperazin-1-yl)-2,3-dihydro-1H-inden-1-yl]oxy]-3-fluorobenzene)sulfonamido]ethoxy]ethoxy)ethyl]-1-[4-([[2-(2-[2-[(4-[[(1S,2S)-6-chloro-4-methyl-2-(piperazin-1-yl)-2,3-dihydro-1H-inden-1-yl]oxy]-3-fluorobenzene)sulfonamido]ethoxy]ethoxy)ethyl]carbamoyl]amino)butyl]urea;

3-[2-(2-[2-[(4-[[(1S,2S)-6-Chloro-4-cyano-2-(dimethylamino)-2,3-dihydro-1H-inden-1-yl]oxy]-3-fluorobenzene)sulfonamido]ethoxy]ethoxy)ethyl]-1-[4-([[2-(2-[2-[(4-[[(1S,2S)-6-chloro-4-cyano-2-(dimethylamino)-2,3-dihydro-1H-inden-1-yl]oxy]-3-fluorobenzene)sulfonamido]ethoxy]ethoxy)ethyl]carbamoyl]amino)butyl]urea;

3-[2-(2-[2-[(4-[[(1S,2S)-2-[(3R)-3-Aminopiperidin-1-yl]-6-chloro-4-methyl-2,3-dihydro-1H-inden-1-yl]oxy]-3-fluorobenzene)sulfonamido]ethoxy]ethoxy)ethyl]-1-[4-([[2-(2-[2-[(4-[[(1S,2S)-2-[(3R)-3-aminopiperidin-1-yl]-6-chloro-4-methyl-2,3-dihydro-1H-inden-1-yl]oxy]-3-fluorobenzene)sulfonamido]ethoxy]ethoxy)ethyl]carbamoyl]amino)butyl]urea;

3-[2-(2-[2-[(4-[[(1S,2S)-6-Chloro-4-cyano-2-[(3R)-3-(dimethylamino)piperidin-1-yl]-2,3-dihydro-1H-inden-1-yl]oxy]-3-methylbenzene)sulfonamido]ethoxy]ethoxy)ethyl]-1-[4-([[2-(2-[2-[(4-[[(1S,2S)-6-chloro-4-cyano-2-[(3R)-3-(dimethylamino)piperidin-1-yl]-2,3-dihydro-1H-inden-1-yl]oxy]-3-methylbenzene)sulfonamido]ethoxy]ethoxy)ethyl]carbamoyl]amino)butyl]urea;

3-[2-(2-[2-[(4-[[(1S,2S)-6-Chloro-4-cyano-2-[(3R)-3-(dimethylamino)piperidin-1-yl]-2,3-dihydro-1H-inden-1-yl]oxy]-3-fluorobenzene)sulfonamido]ethoxy]ethoxy)ethyl]-1-[4-([[2-(2-[2-[(4-[[(1S,2S)-6-chloro-4-cyano-2-[(3R)-3-(dimethylamino)piperidin-1-yl]-2,3-dihydro-1H-inden-1-yl]oxy]-3-fluorobenzene)sulfon amido]ethoxy]ethoxy) ethyl]carb amoyl]amino)butyl]urea;

3-[2-(2-[2-[(4-[[(1S,2S)-6-Chloro-4-cyano-2-(piperazin-1-yl)-2,3-dihydro-1H-inden-1-yl]oxy]benzene)sulfonamido]ethoxy]ethoxy)ethyl]-1-[4-([[2-(2-[2-[(4-[[(1S,2S)-6-chloro-4-cyano-2-(piperazin-1-yl)-2,3-dihydro-1H- inden-1-yl]oxy]benzene)sulfonamido]ethoxy]ethoxy)ethyl]carbamoyl]amino)butyl]urea;

3-[2-(2-[2-[(4-[[(1S,2S)-6-Chloro-4-cyano-2-(piperazin-1-yl)-2,3-dihydro-1H-inden-1-yl]oxy]-3-methylbenzene)sulfonamido]ethoxy]ethoxy)ethyl]-1-[4-([[2-(2-[2-[(4-[[(1S,2S)-6-chloro-4-cyano-2-(piperazin-1-yl)-2,3-dihydro-1H-inden-1-yl]oxy]-3-methylbenzene)sulfonamido]ethoxy]ethoxy)ethyl]carbamoyl]amino)butyl]urea;

3-[2-(2-[2-[(4-[[(1S,2S)-6-Chloro-4-cyano-2-(piperazin-1-yl)-2,3-dihydro-1H-inden-1-yl]oxy]-3-fluorobenzene)sulfonamido]ethoxy]ethoxy)ethyl]-1-[4-([[2-(2-[2-[(4-[[(1S,2S)-6-chloro-4-cyano-2-(piperazin-1-yl)-2,3-dihydro-1H-inden-1-yl]oxy]-3-fluorobenzene)sulfonamido]ethoxy]ethoxy)ethyl]carbamoyl]amino)butyl]urea;

3-[2-(2-[[(3S)-1-[(4-[[(1S,2S)-4,6-dichloro-2-(dimethylamino)-2,3-dihydro-1H-inden-1-yl]oxy]-3-methylbenzene)sulfonyl]pyrrolidin-3-yl]methoxy]ethoxy)ethyl]-1-[4-([[2-(2-[[(3S)-1-[(4-[[(1S,2S)-4,6-dichloro-2-(dimethylamino)-2,3-dihydro-1H-inden-1-yl]oxy]-3-methylbenzene)sulfonyl]pyrrolidin-3-yl]methoxy]ethoxy)ethyl]carbamoyl]amino) butyl]urea;

3-[2-(2-[[(3R)-1-[(4-[[(1S,2S)-4,6-Dichloro-2-(dimethylamino)-2,3-dihydro-1H-inden-1-yl]oxy]-3-methylbenzene)sulfonyl]pyrrolidin-3-yl]methoxy]ethoxy)ethyl]-1-[4-([[2-(2-[[(3R)-1-[(4-[[(1S,2S)-4,6-dichloro-2-(dimethylamino)-2,3-dihydro-1H-inden-1-yl]oxy]-3-methylbenzene)sulfonyl]pyrrolidin-3-yl]methoxy]ethoxy)ethyl]carbamoyl]amino)butyl]urea;

3-[2-(2-[[(3S)-1-[(4-[[(1S,2S)-6-Chloro-4-cyano-2-(dimethylamino)-2,3-dihydro-1H-inden-1-yl]oxy]-3-methylbenzene)sulfonyl]pyrrolidin-3-yl]methoxy]ethoxy)ethyl]-1-[4-([[2-(2-[[(3 S)-1-[(4-[[(1S,2S)-6-chloro-4-cyano-2-(dimethylamino)-2,3-dihydro-1H-inden-1-yl]oxy]-3-methylbenzene)sulfonyl]pyrrolidin-3-yl]methoxy]ethoxy)ethyl]carbamoyl]amino)butyl]urea;

3-[2-(2-[[(3R)-1-[(4-[[(1S,2S)-6-Chloro-4-cyano-2-(dimethylamino)-2,3-dihydro-1H-inden-1-yl]oxy]-3-methylbenzene)sulfonyl]pyrrolidin-3-yl]methoxy]ethoxy)ethyl]-1-[4-([[2-(2-[[(3R)-1-[(4-[[(1S,2S)-6-chloro-4-cyano-2-(dimethylamino)-2,3-dihydro-1H-inden-1-yl]oxy]-3-methylbenzene)sulfonyl]pyrrolidin-3-yl]methoxy]ethoxy)ethyl]carbamoyl]amino)butyl]urea;

3-[(4-[[(3S)-1-[(4-[[(1S,2S)-4,6-Dichloro-2-(dimethylamino)-2,3-dihydro-1H-inden-1-yl]oxy]-3-methylbenzene)sulfonyl]pyrrolidin-3-yl]methoxy]pyridin-2-yl)methyl]-1-4-([[(4-[[(3 S)-1-[(4-[[(1S,2S)-4,6-dichloro-2-(dimethylamino)-2,3-dihydro-1H-inden-1-yl]oxy]-3-methylbenzene)sulfonyl]pyrrolidin-3-yl]methoxy]pyridin-2-yl)methyl]carbamoyl]amino)butyl]urea;

3-[(4-[[(3R)-1-[(4-[[(1S,2S)-4,6-Dichloro-2-(dimethylamino)-2,3-dihydro-1H-inden-1-yl]oxy]-3-methylbenzene)sulfonyl]pyrrolidin-3-yl]methoxy]pyridin-2-yl)methyl]-1-4-([[(4-[[(3R)-1-[(4-[[(1S,2S)-4,6-dichloro-2-(dimethylamino)-2,3-dihydro-1H-inden-1-yl]oxy]-3-methylbenzene)sulfonyl]pyrrolidin-3-yl]methoxy]pyridin-2-yl)methyl]carbamoyl]amino)butyl]urea;

3-[(4-[[(3S)-1-[(4-[[(1S,2S)-6-Chloro-4-cyano-2-(dimethylamino)-2,3-dihydro-1H-inden-1-yl]oxy]-3-methylbenzene)sulfonyl]pyrrolidin-3-yl]methoxy]pyridin-2-yl)methyl]-1-4-([[(4-[[(3 S)-1-[(4-[[(1S,2S)-6-chloro-4-cyano-2-(dimethylamino)-2,3-dihydro-1H-inden-1-yl]oxy]-3-methylbenzene)sulfonyl]pyrrolidin-3-yl]methoxy]pyridin-2-yl)methyl]carbamoyl]amino)butyl]urea;

3-[(4-[[(3R)-1-[(4-[[(1S,2S)-6-Chloro-4-cyano-2-(dimethylamino)-2,3-dihydro-1H-inden-1-yl]oxy]-3-methylbenzene)sulfonyl]pyrrolidin-3-yl]methoxy]pyridin-2-yl)methyl]-1-4-([[(4-[[(3R)-1-[(4-[[(1S,2S)-6-chloro-4-cyano-2-(dimethylamino)-2,3-dihydro-1H-inden-1-yl]oxy]-3-methylbenzene)sulfonyl]pyrrolidin-3-yl]methoxy]pyridin-2-yl)methyl]carbamoyl]amino)butyl]urea;

3-(2-[2-[(3S)-3-[(4-[[(1S,2S)-4,6-Dichloro-2-(dimethylamino)-2,3-dihydro-1H-inden-1-yl]oxy]-3-methylbenzene) sulfonamido]pyrrolidin-1-yl]ethoxy]ethyl)-1-(4-[[(2-[2-[(3S)-3-[(4-[[(1S,2S)-4,6-dichloro-2-(dimethylamino)-2,3-dihydro-1H-inden-1-yl]oxy]-3-methylbenzene)sulfonamido]pyrrolidin-1-yl]ethoxy] ethyl) carbamoyl]amino]butyl)urea;

3-(2-[2-[(3R)-3-[(4-[[(1S,2S)-4,6-Dichloro-2-(dimethylamino)-2,3-dihydro-1H-inden-1-yl]oxy]-3-methylbenzene)sulfonamido]pyrrolidin-1-yl]ethoxy]ethyl)-1-(4-[[(2-[2-[(3R)-3-[(4-[[(1S,2S)-4,6-dichloro-2-(dimethylamino)-2,3-dihydro-1H-inden-1-yl]oxy]-3-methylbenzene)sulfonamido]pyrrolidin-1-yl]ethoxy]ethyl)carbamoyl]amino]butyl)urea;

3-(2-[2-[(3 S)-3-[(4-[[(1S,2S)-6-Chloro-4-cyano-2-(dimethylamino)-2,3-dihydro-1H-inden-1-yl]oxy]-3-methylbenzene)sulfonamido]pyrrolidin-1-yl]ethoxy]ethyl)-1-(4-[[(2-[2-[(3S)-3-[(4-[[(1S,2S)-6-chloro-4-cyano-2-(dimethylamino)-2,3-dihydro-1H-inden-1-yl]oxy]-3-methylbenzene)sulfonamido]pyrrolidin-1-yl]ethoxy]ethyl)carbamoyl]amino]butyl)urea;

3-(2-[2-[(3R)-3-[(4-[[(1S,2S)-6-Chloro-4-cyano-2-(dimethylamino)-2,3-dihydro-1H-inden-1-yl]oxy]-3-methylbenzene)sulfonamido]pyrrolidin-1-yl]ethoxy]ethyl)-1-(4-[[(2-[2-[(3R)-3-[(4-[[(1S,2S)-6-chloro-4-cyano-2-(dimethylamino)-2,3-dihydro-1H-inden-1-yl]oxy]-3-methylbenzene)sulfonamido]pyrrolidin-1-yl]ethoxy]ethyl)carbamoyl]amino]butyl)urea;

1-([1-[2-(2-[2-[(4-[[(1S,2S)-2-[(3R)-3-Aminopiperidin-1-yl]-4,6-dichloro-2,3-dihydro-1H-inden-1-yl]oxy]benzene) sulfonamido]ethoxy]ethoxy)ethyl]-1H-1,2,3-triazol-4-yl]methyl)-3-(4-[[([1-[2-(2-[2-[(4-[[(1S,2S)-2-[(3R)-3-aminopiperidin-1-yl]-4,6-dichloro-2,3-dihydro-1H-inden-1-yl]oxy]benzene)sulfonamido]ethoxy]ethoxy)ethyl]-1H-1,2,3-triazol-4-yl]methyl)carbamoyl]amino]butyl)urea;

(2R,3S,4R,5S)—N1,N6-Bis([1-[2-(2-[2-[(4-[[(1S,2S)-2-[(3R)-3-aminopiperidin-1-yl]-4,6-dichloro-2,3-dihydro-1H-inden-1-yl]oxy]benzene)sulfonamido]ethoxy]ethoxy)ethyl]-1H-1,2,3-triazol-4-yl]methyl)-2,3,4,5-tetrahydroxyhexanediamide;

3-[(1-[4-[(4-[[(1S,2S)-2-[(3R)-3-Aminopiperidin-1-yl]-4,6-dichloro-2,3-dihydro-1H-inden-1-yl]oxy]benzene)sulfonamido]butyl]-1H-1,2,3-triazol-4-yl)methyl]-1-[4-([[(1-[4-[(4-[[(1S,2S)-2-[(3R)-3-aminopiperidin-1-yl]-4,6-dichloro-2,3-dihydro-1H-inden-1-yl]oxy]benzene)sulfonamido]butyl]-1H-1,2,3-triazol-4-yl)methyl]carbamoyl]amino)butyl]urea;

3-[(1-[6-[(4-[[(1S,2S)-2-[(3R)-3-Aminopiperidin-1-yl]-4,6-dichloro-2,3-dihydro-1H-inden-1-yl]oxy]benzene)sulfonamido]hexyl]-1H-1,2,3-triazol-4-yl)methyl]-1-[4-([[(1-[6-[(4-[[(1S,2S)-2-[(3R)-3-aminopiperidin-1-yl]-4,6-dichloro-2,3-dihydro-1H-inden-1-yl]oxy]benzene)sulfonamido]hexyl]-1H-1,2,3-triazol-4-yl)methyl]carbamoyl]amino)butyl]urea;

(4R,4aS,8S,8aR)—N4,N8-Bis([1-(4-[4-((1S,2S)-2-[(3R)-3-aminopiperidin-1-yl]-4,6-dichloro-2,3-dihydro-1H-inden-1-yloxy)phenyl sulfonamide]butyl)-1H-1,2,3-triazol- 4-yl]methyl)-2,2,6,6-tetramethyl-tetrahydro-[1,3]dioxino[5,4-d][1,3]dioxine-4,8-dicarboxamide;

(4R,4aS,8S,8aR)—N4,N8-Bis([1-(6-[4-((1S,2S)-2-[(3R)-3-amino piperidin-1-yl]-4,6-dichloro-2,3-dihydro-1H-inden-1-yloxy)phenylsulfonamido]hexyl)-1H-1,2,3-triazol-4-yl]methyl)-2,2,6,6-tetramethyl-tetrahydro-[1,3]dioxino[5,4-d][1,3]dioxine-4,8-dicarboxamide;

3-[8-[(4-[[(1S,2S)-2-[(3R)-3-Aminopiperidin-1-yl]-4,6-dichloro-2,3-dihydro-1H-inden-1-yl]oxy]benzene)sulfonamido]octyl]-1-[4-[([8-[(4-[[(1S,2S)-2-[(3R)-3-aminopiperidin-1-yl]-4,6-dichloro-2,3-dihydro-1H-inden-1-yl]oxy]benzene) sulfonamido]octyl]carbamoyl)amino]butyl]urea;

3-[8-[(4-[[(1S,2S)-2-[(3R)-3-Aminopiperidin-1-yl]-4,6-dichloro-2,3-dihydro-1H-inden-1-yl]oxy]-3-methylbenzene) sulfonamido]octyl]-1-[4-[([8-[(4-[[(1S,2S)-2-[(3R)-3-aminopiperidin-1-yl]-4,6-dichloro-2,3-dihydro-1H-inden-1-yl]oxy]-3-methylbenzene)sulfonamido]octyl]carbamoyl)amino]butyl]urea;

3-[8-[(4-[[(1S,2S)-4,6-Dichloro-2-(dimethylamino)-2,3-dihydro-1H-inden-1-yl]oxy]benzene)sulfonamido]octyl]-1-[4-[([8-[(4-[[(1S,2S)-4,6-dichloro-2-(dimethylamino)-2,3-dihydro-1H-inden-1-yl]oxy]benzene) sulfonamido]octyl]carbamoyl)amino]butyl]urea;

3-[8-[(4-[[(1S,2S)-4,6-Dichloro-2-(dimethylamino)-2,3-dihydro-1H-inden-1-yl]oxy]-3-methylbenzene)sulfonamido]octyl]-1-[4-[([8-[(4-[[(1S,2S)-4,6-dichloro-2-(dimethyl amino)-2,3-dihydro-1H-inden-1-yl]oxy]-3-methylbenzene) sulfonamido]octyl]carbamoyl)amino]butyl]urea;

3-[2-(2-[2-[(4-[[(1S,2S)-4,6-Dichloro-2-[(2R)-2-methylpiperidin-1-yl]-2,3-dihydro-1H-inden-1-yl]oxy]benzene)sulfonamido]ethoxy]ethoxy)ethyl]-1-[4-([[2-(2-[2-[(4-[[(1S,2S)-4,6-dichloro-2-[(2R)-2-methylpiperidin-1-yl]-2,3-dihydro-1H-inden-1-yl]oxy]benzene)sulfonamido]ethoxy]ethoxy)ethyl]carbamoyl]amino)butyl]urea;

3-[2-(2-[2-[(4-[[(1S,2S)-4,6-Dichloro-2-[(2S)-2-methylpiperidin-1-yl]-2,3-dihydro-1H-inden-1-yl]oxy]benzene)sulfonamido]ethoxy]ethoxy)ethyl]-1-[4-([[2-(2-[2-[(4-[[(1S,2S)-4,6-dichloro-2-[(2S)-2-methylpiperidin-1-yl]-2,3-dihydro-1H-inden-1-yl]oxy]benzene)sulfonamido]ethoxy]ethoxy)ethyl]carbamoyl]amino)butyl]urea;

3-[2-(2-[2-[(4-[[(1S,2S)-2-[2-Azabicyclo[2.2.1]heptan-2-yl]-4,6-dichloro-2,3-dihydro-1H-inden-1-yl]oxy]benzene)sulfonamido]ethoxy]ethoxy)ethyl]-1-[4-([[2-(2-[2-[(4-[[(1S,2S)-2-[2-azabicyclo[2.2.1]heptan-2-yl]-4,6-dichloro-2,3-dihydro-1H-inden-1-yl]oxy]benzene)sulfonamido]ethoxy]ethoxy)ethyl]carbamoyl]amino)butyl]urea; 1-[2-(2-[2-[(4-[[(1S,2S)-2-[2-Azabicyclo[2.2.2]octan-2-yl]-4,6-dichloro-2,3-dihydro-1H-inden-1-yl]oxy]benzene)sulfonamido]ethoxy]ethoxy)ethyl]-3-[4-([[2-(2-[2-[(4-[[(1S,2S)-2-[2-azabicyclo[2.2.2]octan-2-yl]-4,6-dichloro-2,3-dihydro-1H-inden-1-yl]oxy]benzene)sulfonamido]ethoxy]ethoxy)ethyl]carbamoyl]amino)butyl]urea;

3-[2-(2-[2-[(4-[[(1S,2S)-2-[8-azabicyclo[3.2.1]octan-8-yl]-4,6-dichloro-2,3-dihydro-1H-inden-1-yl]oxy]benzene)sulfonamido]ethoxy]ethoxy)ethyl]-1-[4-([[2-(2-[2-[(4-[[(1S,2S)-2-[8-azabicyclo[3.2.1]octan-8-yl]-4,6-dichloro-2,3-dihydro-1H-inden-1-yl]oxy]benzene)sulfonamido]ethoxy]ethoxy)ethyl]carbamoyl]amino)butyl]urea;

1-[2-(2-[2-[(4-[[(1S,2S)-2-[9-Azabicyclo[3.3.1]nonan-9-yl]-4,6-dichloro-2,3-dihydro-1H-inden-1-yl]oxy]benzene)sulfonamido]ethoxy]ethoxy)ethyl]-3-[4-([[2-(2-[2-[(4-[[(1S,2S)-2-[9-azabicyclo[3.3.1]nonan-9-yl]-4,6-dichloro-2,3-dihydro-1H-inden-1-yl]oxy]benzene) sulfonamido]ethoxy]ethoxy)ethyl]carbamoyl]amino)butyl]urea;

3-[2-(2-[2-[(4-[[(1S,2S)-4,6-Dichloro-2-(4-methylpiperazin-1-yl)-2,3-dihydro-1H-inden-1-yl]oxy]benzene)sulfonamido]ethoxy]ethoxy)ethyl]-1-[4-([[2-(2-[2-[(4-[[(1S,2S)-4,6-dichloro-2-(4-methylpiperazin-1-yl)-2,3-dihydro-1H-inden-1-yl]oxy]benzene)sulfonamido]ethoxy]ethoxy)ethyl]carbamoyl]amino)butyl]urea;

3-[2-(2-[2-[(4-[[(1S,2S)-4,6-Dichloro-2-(4-methylpiperazin-1-yl)-2,3-dihydro-1H-inden-1-yl]oxy]-3-methylbenzene)sulfonamido]ethoxy]ethoxy)ethyl]-1 -[4-([[2-(2-[2-[(4-[[(1S,2S)-4,6-dichloro-2-(4-methylpiperazin-1-yl)-2,3-dihydro-1H-inden-1-yl]oxy]-3-methylbenzene) sulfonamido]ethoxy]ethoxy)ethyl]carbamoyl]amino)butyl]urea;

3-[2-(2-[2-[(4-[[(1S,2S)-2-(4-Acetylpiperazin-1-yl)-4,6-dichloro-2,3-dihydro-1H-inden-1-yl]oxy]benzene)sulfonamido]ethoxy]ethoxy)ethyl]-1-[4-([[2-(2-[2-[(4-[[(1S,2S)-2-(4-acetylpiperazin-1-yl)-4,6-dichloro-2,3-dihydro-1H-inden-1-yl]oxy]benzene)sulfonamido]ethoxy]ethoxy)ethyl]carbamoyl]amino)butyl]urea;

3-[2-(2-[2-[(4-[[(1S,2S)-2-(4-Acetylpiperazin-1-yl)-4,6-dichloro-2,3-dihydro-1H-inden-1-yl]oxy]-3-methylbenzene)sulfonamido]ethoxy]ethoxy)ethyl]-1 -[4-([[2-(2-[2-[(4-[[(1S,2S)-2-(4-acetylpiperazin-1-yl)-4,6-dichloro-2,3-dihydro-1H-inden-1-yl]oxy]-3-methylbenzene) sulfonamido]ethoxy]ethoxy)ethyl]carbamoyl]amino)butyl]urea;

4-[(1S,2S)-4,6-dichloro-1-[4-[(2-[2-[2-([[4-([[2-(2-[2-[(4-[[(1S,2S)-4,6-dichloro-2-[4-(dimethylcarbamoyl)piperazin-1-yl]-2,3-dihydro-1H-inden-1-yl]oxy]benzene) sulfonamido]ethoxy]ethoxy)ethyl]carbamoyl]amino) butyl]carbamoyl]amino)ethoxy]ethoxy]ethyl]sulfamoyl]phenoxy]-2,3-dihydro-1H-inden-2-yl]-N,N-dimethylpiperazine-1-carboxamide;

4-[(1S,2S)-4,6-dichloro-1-[4-[(2-[2-[2-([[4-([[2-(2-[2-[(4-[[(1S,2S)-4,6-dichloro-2-[4-(dimethylcarbamoyl)piperazin-1-yl]-2,3-dihydro-1H-inden-1-yl]oxy]-3-methylbenzene)sulfonamido]ethoxy]ethoxy)ethyl]carbamoyl]amino)butyl]carbamoyl]amino)ethoxy]ethoxy]ethyl)sulfamoyl]-2-methylphenoxy]-2,3-dihydro-1H-inden-2-yl]-N,N-dimethylpiperazine-1-carboxamide;

3-[2-(2-[2-[(4-[[(1S,2S)-4,6-Dichloro-2-[(3R)-3-[methyl(propan-2-yl)amino]piperidin-1-yl]-2,3-dihydro-1H-inden-1-yl]oxy]benzene) sulfonamido]ethoxy]ethoxy)ethyl]-1-[4-([[2-(2-[2-[(4-[[(1S,2S)-4,6-dichloro-2-[(3R)-3-[methyl(propan-2-yl)amino]piperidin-1-yl]-2,3-dihydro-1H-inden-1-yl]oxy]benzene)sulfonamido]ethoxy]ethoxy)ethyl]carbamoyl]amino)butyl]urea;

3-[2-(2-[2-[(4-[[(1S,2S)-2-[(3R)-3-Aminopiperidin-1-yl]-4,6-dichloro-2,3-dihydro-1H-inden-1-yl]oxy]-3,5-dimethylbenzene)sulfonamido]ethoxy]ethoxy)ethyl]-1-[4-([[2-(2-[2-[(4-[[(1S,2S)-2-[(3R)-3-aminopiperidin-1-yl]-4,6-dichloro-2,3-dihydro-1H-inden-1-yl]oxy]-3,5-dimethylbenzene)sulfonamido]ethoxy]ethoxy)ethyl]carbamoyl]amino)butyl]urea; hydrochloride;

1-[2-(2-[2-[(3-[[(1S,2S)-4,6-dichloro-2-(dimethylamino)-2,3-dihydro-1H-inden-1-yl]oxy]-2,4-dimethylbenzene)sulfonamido]ethoxy]ethoxy) ethyl]-3-[4-([[2-(2-[2-[(4-[[(1S,2S)-4,6-dichloro-2-(dimethylamino)-2,3-dihydro-1H-inden-1-yl]oxy]-3,5-dimethylbenzene) sulfonamido]ethoxy]ethoxy)ethyl]carbamoyl]amino) butyl]urea;

3-[2-(2-[2-[(4-[[(1S,2S)-2-[(3R)-3-Aminopiperidin-1-yl]-4,6-dichloro-2,3-dihydro-1H-inden-1-yl]oxy]-2,5-dimethylbenzene) sulfonamido]ethoxy]ethoxy)ethyl]-1-[4-([[2-

(2-[2-[(4-[[(1S,2S)-2-[(3R)-3-aminopiperidin-1-yl]-4,6-dichloro-2,3-dihydro-1H-inden-1-yl]oxy]-2,5-dimethylbenzene)sulfonamido]ethoxy]ethoxy)ethyl]carbamoyl]amino)butyl]urea;

3-[2-(2-[2-[(4-[[(1S,2S)-4,6-Dichloro-2-(dimethylamino)-2,3-dihydro-1H-inden-1-yl]oxy]-2,5-dimethylbenzene)sulfonamido]ethoxy]ethoxy)ethyl]-1-[4-([[2-(2-[2-[(4-[[(1S,2S)-4,6-dichloro-2-(dimethylamino)-2,3-dihydro-1H-inden-1-yl]oxy]-2,5-dimethylbenzene)sulfonamido]ethoxy]ethoxy)ethyl]carbamoyl]amino)butyl]urea;

1-[2-(2-[2-[(4-[[(1S,2S)-2-[(3R)-3-Aminopiperidin-1-yl]-4,6-dichloro-2,3-dihydro-1H-inden-1-yl]oxy]-3-fluoro-5-methylbenzene)sulfonamido]ethoxy]ethoxy)ethyl]-3-[4-([[2-(2-[2-[(4-[[(1S,2S)-2-[(3R)-3-aminopiperidin-1-yl]-4,6-dichloro-2,3-dihydro-1H-inden-1-yl]oxy]-3-fluoro-5-methylbenzene)sulfonamido]ethoxy]ethoxy)ethyl]-carbamoyl]amino)butyl]urea; hydrochloride;

1-[2-(2-[2-[(4-[[(1S,2S)-4,6-Dichloro-2-(dimethylamino)-2,3-dihydro-1H-inden-1-yl]oxy]-3-fluoro-5-methylbenzene)sulfonamido]ethoxy]ethoxy)ethyl]-3-[4-([[2-(2-[2-[(4-[[(1S,2S)-4,6-dichloro-2-(dimethylamino)-2,3-dihydro-1H-inden-1-yl]oxy]-3-fluoro-5-methylbenzene)sulfonamido]ethoxy]ethoxy)ethyl]carbamoyl]amino)butyl]urea;

3-[2-(2-[2-[(4-[[(1S,2S)-2-[(3R)-3-Aminopiperidin-1-yl]-4,6-dichloro-2,3-dihydro-1H-inden-1-yl]oxy]-3,5-difluorobenzene) sulfonamido]ethoxy]ethoxy)ethyl]-1-[4-([[2-(2-[2-[(4-[[(1S,2S)-2-[(3R)-3-aminopiperidin-1-yl]-4,6-dichloro-2,3-dihydro-1H-inden-1-yl]oxy]-3,5-difluorobenzene)sulfonamido]ethoxy]ethoxy)ethyl]carbamoyl]amino)butyl]urea;

4-([[(1S,2S)-4,6-dichloro-2-(dimethylamino)-2,3-dihydro-1H-inden-1-yl]oxy)-N-[26-([4-([[(1S,2S)-4,6-dichloro-2-(dimethylamino)-2,3-dihydro-1H-inden-1-yl]oxy)-3,5-difluorophenyl]sulfonamido)-10,17-dioxo-3,6,21,24-tetraoxa-9,11,16,18-tetraazahexacosyl]-3,5-difluorobenzenesulfonamide;

3-[2-(2-[2-[(4-[[(1S,2S)-2-[(3R)-3-Aminopiperidin-1-yl]-4,6-dichloro-2,3-dihydro-1H-inden-1-yl]oxy]-5-fluoro-2-methylbenzene)sulfonamido]ethoxy]ethoxy)ethyl]-1-[4-([[2-(2-[2-[(4-[[(1 S,2S)-2-[(3R)-3-aminopiperidin-1-yl]-4,6-dichloro-2,3-dihydro-1H-inden-1-yl]oxy]-5-fluoro-2-methylbenzene)sulfonamido]ethoxy]ethoxy)ethyl]carbamoyl]amino)butyl]urea;

3-[2-(2-[2-[(4-[[(1S,2S)-4,6-Dichloro-2-(dimethylamino)-2,3-dihydro-1H-inden-1-yl]oxy]-5-fluoro-2-methylbenzene)sulfonamido]ethoxy]ethoxy)ethyl]-1-[4-([[2-(2-[2-[(4-[[(1S,2S)-4,6-dichloro-2-(dimethylamino)-2,3-dihydro-1H-inden-1-yl]oxy]-5-fluoro-2-methylbenzene)sulfonamido]ethoxy]ethoxy)ethyl]carbamoyl]amino)butyl]urea;

3-[2-(2-[2-[(4-[[(1S,2S)-2-[(3R)-3-Aminopiperidin-1-yl]-4,6-dichloro-2,3-dihydro-1H-inden-1-yl]oxy]-2-fluoro-5-methylbenzene)sulfonamido]ethoxy]ethoxy)ethyl]-1-[4-([[2-(2-[2-[(4-[[(1 S,2S)-2-[(3R)-3-aminopiperidin-1-yl]-4,6-dichloro-2,3-dihydro-1H-inden-1-yl]oxy]-2-fluoro-5-methylbenzene)sulfonamido]ethoxy]ethoxy)ethyl]carbamoyl]amino)butyl]urea;

3-[2-(2-[2-[(4-[[(1S,2S)-4,6-Dichloro-2-(dimethylamino)-2,3-dihydro-1H-inden-1-yl]oxy]-2-fluoro-5-methylbenzene)sulfonamido]ethoxy]ethoxy)ethyl]-1-[4-([[2-(2-[2-[(4-[[(1S,2S)-4,6-dichloro-2-(dimethylamino)-2,3-dihydro-1H-inden-1-yl]oxy]-2-fluoro-5-methylbenzene)sulfonamido]ethoxy]ethoxy)ethyl]carbamoyl]amino)butyl]urea;

1-(2-[2-[(3S)-3-[(4-[[(1S,2S)-4,6-Dichloro-2-(dimethylamino)-2,3-dihydro-1H-inden-1-yl]oxy]-3-methylbenzene)sulfonamido]-2-oxopyrrolidin-1-yl]ethoxy]ethyl)-3-(4-[[(2-[2-[(3 S)-3-[4-[[(1S,2S)-4,6-dichloro-2-(dimethylamino)-2,3-dihydro-1H-inden-1-yl]oxy]-3-methylbenzene)sulfonamido]-2-oxopyrrolidin-1-yl]ethoxy]ethyl)carbamoyl]amino]butyl)urea;

1-(2-[2-[(3S)-3-[(4-[[(1S,2S)-6-Chloro-4-cyano-2-(dimethylamino)-2,3-dihydro-1H-inden-1-yl]oxy]-3-methylbenzene)sulfonamido]-2-oxopyrrolidin-1-yl]ethoxy]ethyl)-3-(4-[[(2-[2-[(3 S)-3-[4-[[(1S,2S)-6-chloro-4-cyano-2-(dimethylamino)-2,3-dihydro-1H-inden-1-yl]oxy]-3-methylbenzene)sulfonamido]-2-oxopyrrolidin-1-yl]ethoxy]ethyl)carbamoyl]amino]butyl)urea;

3-[2-(2-[[(3R)-1-[(4-[[(1S,2S)-2-[(3R)-3-Aminopiperidin-1-yl]-4,6-dichloro-2,3-dihydro-1H-inden-1-yl]oxy]benzene)sulfonyl]pyrrolidin-3-yl]oxy]ethoxy)ethyl]-1-[4-([[2-(2-[[(3R)-1-[(4-[[(1S,2S)-2-[(3R)-3-aminopiperidin-1-yl]-4,6-dichloro-2,3-dihydro-1H-inden-1-yl]oxy]benzene)sulfonyl]pyrrolidin-3-yl]oxy]ethoxy)ethyl]carbamoyl]amino)butyl]urea;

3-[2-(2-[[(3 S)-1-[(4-[[(1S,2S)-2-[(3R)-3-Aminopiperidin-1-yl]-4,6-dichloro-2,3-dihydro-1H-inden-1-yl]oxy]benzene)sulfonyl]pyrrolidin-3-yl]oxy]ethoxy)ethyl]-1-[4-([[2-(2-[[(3S)-1-[(4-[[(1S,2S)-2-[(3R)-3-aminopiperidin-1-yl]-4,6-dichloro-2,3-dihydro-1H-inden-1-yl]oxy]benzene)sulfonyl]pyrrolidin-3-yl]oxy]ethoxy)ethyl]carbamoyl]amino)butyl]urea;

3-[2-[2-([1-[(4-[[(1S,2S)-2-[(3R)-3-Aminopiperidin-1-yl]-4,6-dichloro-2,3-dihydro-1H-inden-1-yl]oxy]benzene)sulfonyl]piperidin-4-yl]oxy)ethoxy]ethyl]-1-[4-[([2-[2-([1-[(4-[[(1S,2S)-2-[(3R)-3-aminopiperidin-1-yl]-4,6-dichloro-2,3-dihydro-1H-inden-1-yl]oxy]benzene)sulfonyl]piperidin-4-yl]oxy)ethoxy]ethyl]carbamoyl)amino]butyl]urea;

1-(2-[2-[(2S)-2-[(4-[[(1S,2S)-2-[(3R)-3-Aminopiperidin-1-yl]-4,6-dichloro-2,3-dihydro-1H-inden-1-yl]oxy]benzene)sulfonamido]propoxy]ethoxy]ethyl)-3-(4-[[(2-[2-[(2S)-2-[(4-[[(1S,2S)-2-[(3R)-3-aminopiperidin-1-yl]-4,6-dichloro-2,3-dihydro-1H-inden-1-yl]oxy]benzene)sulfonamido]propoxy]ethoxy]ethyl)carbamoyl]amino]butyl)urea; hydrochloride;

3-(2-[2-[(2R)-2-[(4-[[(1S,2S)-2-[(3R)-3-Aminopiperidin-1-yl]-4,6-dichloro-2,3-dihydro-1H-inden-1-yl]oxy]benzene)sulfonamido]propoxy]ethoxy]ethyl)-1-(4-[[(2-[2-[(2R)-2-[(4-[[(1S,2S)-2-[(3R)-3-aminopiperidin-1-yl]-4,6-dichloro-2,3-dihydro-1H-inden-1-yl]oxy]benzene)sulfonamido]propoxy]ethoxy]ethyl)carbamoyl]amino]butyl)urea;

3-(2-[2-[(2S)-2-[(4-[[(1S,2S)-2-[(3R)-3-Aminopiperidin-1-yl]-4,6-dichloro-2,3-dihydro-1H-inden-1-yl]oxy]benzene)sulfonamido]-3-methylbutoxy]ethoxy]ethyl)-1-(4-[[(2-[2-[(2S)-2-[(4-[[(1S,2S)-2-[(3R)-3-aminopiperidin-1-yl]-4,6-dichloro-2,3-dihydro-1H-inden-1-yl]oxy]benzene) sulfonamido]-3-methylbutoxy]ethoxy]ethyl)carbamoyl]amino]butyl)urea dihydrochloride;

3-(2-[2-[(2R)-2-[(4-[[(1S,2S)-2-[(3R)-3-Aminopiperidin-1-yl]-4,6-dichloro-2,3-dihydro-1H-inden-1-yl]oxy]benzene)sulfonamido]-3-methylbutoxy]ethoxy]ethyl)-1-(4-[[(2-[2-[(2R)-2-[(4-[[(1S,2S)-2-[(3R)-3-aminopiperidin-1-yl]-4,6-dichloro-2,3-dihydro-1H-inden-1-yl]oxy]benzene)sulfonamido]-3-methylbutoxy]ethoxy]ethyl)carbamoyl]amino]butyl)urea;

1-[2-(2-[2-[(4-[[(1S,2S)-2-[(3R)-3-Aminopiperidin-1-yl]-4,6-dichloro-2,3-dihydro-1H-inden-1-yl]oxy]benzene)sulfonamido]-2-methylpropoxy]ethoxy)ethyl]-3-[4-([[2-(2-[2-[(4-[[(1S,2S)-2-[(3R)-3-aminopiperidin-1-yl]-4,6-dichloro-2,3-dihydro-1H-inden-1-yl]oxy]benzene)

sulfonamido]-2-methylpropoxy]ethoxy)ethyl]carbamoyl]
amino)butyl]urea; hydrochloride;
1-[2-(2-[2-[(4-[[(1S,2S)-2-[(3R)-3-Aminopiperidin-1-yl]-4,
6-dichloro-2,3-dihydro-1H-inden-1-yl]oxy]-2-methoxy-
benzene)sulfonamido]ethoxy]ethoxy)ethyl]-3-[4-([[2-(2-
[2-[(4-[[(1S,2S)-2-[(3R)-3-aminopiperidin-1-yl]-4,6-
dichloro-2,3-dihydro-1H-inden-1-yl]oxy]-2-
methoxybenzene)sulfonamido]ethoxy]ethoxy)ethyl]
carbamoyl]amino)butyl]urea;
3-[2-(2-[2-[(4-[[(1S,2S)-2-[(3R)-3-Aminopiperidin-1-yl]-4,
6-dichloro-2,3-dihydro-1H-inden-1-yl]oxy]-2-methyl-
benzene)sulfonamido]ethoxy]ethoxy)ethyl]-1-[4-([[2-(2-
[2-[(4-[[(1S,2S)-2-[(3R)-3-aminopiperidin-1-yl]-4,6-
dichloro-2,3-dihydro-1H-inden-1-yl]oxy]-2-
methylbenzene)sulfonamido]ethoxy]ethoxy)ethyl]
carbamoyl]amino)butyl]urea; 1-[2-(2-[2-[(4-[[(1S,2S)-2-
[(3R)-3-Aminopiperidin-1-yl]-4,6-dichloro-2,3-dihydro-
1H-inden-1-yl]oxy]-2-fluorobenzene)sulfonamido]
ethoxy]ethoxy)ethyl]-3-[4-([[2-(2-[2-[(4-[[(1S,2S)-2-
[(3R)-3-aminopiperidin-1-yl]-4,6-dichloro-2,3-dihydro-
1H-inden-1-yl]oxy]-2-fluorobenzene)sulfonamido]
ethoxy]ethoxy)ethyl]carbamoyl]amino)butyl]urea;
4-([(1S,2S)-2-[(R)-3-Aminopiperidin-1-yl]-4,6-dichloro-2,
3-dihydro-1H-inden-1-yl]oxy)-N-[26-([(1S,2S)-2-
[(R)-3-aminopiperidin-1-yl]-4,6-dichloro-2,3-dihydro-
1H-inden-1-yl]oxy)-2-chlorophenyl]sulfonamido)-10,17-
dioxo-3,6,21,24-tetraoxa-9,11,16,18-tetraazahexacosyl]-
2-chlorobenzenesulfonamide;
4-([(1S,2S)-4,6-Dichloro-2-(piperazin-1-yl)-2,3-dihydro-
1H-inden-1-yl]oxy)-N—[(R)-1-(20-[(R)-3-([4-([(1S,2S)-
4,6-dichloro-2-(piperazin-1-yl)-2,3-dihydro-1H-inden-1-
yl]oxy)-3-fluorophenyl]sulfonamido)pyrrolidin-1-yl]-7,
14-dioxo-3,18-dioxa-6,8,13,15-tetraazaicosyl)pyrrolidin-
3-yl]-3-fluorobenzenesulfonamide; tetra(trifluoroacetate);
4-([(1S,2S)-4,6-Dichloro-2-(piperazin-1-yl)-2,3-dihydro-
1H-inden-1-yl]oxy)-N—[(S)-1-(20-[(S)-3-([4-([(1S,2S)-
4,6-dichloro-2-(piperazin-1-yl)-2,3-dihydro-1H-inden-1-
yl]oxy)-3-fluorophenyl]sulfonamido)pyrrolidin-1-yl]-7,
14-dioxo-3,18-dioxa-6,8,13,15-tetraazaicosyl)pyrrolidin-
3-yl]-3-fluorobenzenesulfonamide; tetra(trifluoroacetate);
4-([(1 S,2S)-6-Chloro-4-cyano-2-(piperazin-1-yl)-2,3-di-
hydro-1H-inden-1-yl]oxy)-N—[(S)-1-(20-[(S)-3-([4-
([(1S,2S)-6-chloro-4-cyano-2-(piperazin-1-yl)-2,3-di-
hydro-1H-inden-1-yl]oxy)phenyl]sulfonamido)
pyrrolidin-1-yl]-7,14-dioxo-3,18-dioxa-6,8,13,15-
tetraazaicosyl)pyrrolidin-3-yl]benzenesulfonamide; tetra
(trifluoroacetate);
4-([(1S,2S)-6-Chloro-4-cyano-2-(piperazin-1-yl)-2,3-di-
hydro-1H-inden-1-yl]oxy)-N—[(R)-1-(20-[(R)-3-([4-([(1
S,2S)-6-chloro-4-cyano-2-(piperazin-1-yl)-2,3-dihydro-
1H-inden-1-yl]oxy)phenyl]sulfonamido)pyrrolidin-1-yl]-
7,14-dioxo-3,18-dioxa-6,8,13,15-tetraazaicosyl)pyrroli-
din-3-yl]benzenesulfonamide; tetra(trifluoroacetate);
4-([(1S,2S)-6-Chloro-4-cyano-2-(piperazin-1-yl)-2,3-di-
hydro-1H-inden-1-yl]oxy)-N—[(R)-1-(20-[(R)-3-[(4-
([(1S,2S)-6-chloro-4-cyano-2-(piperazin-1-yl)-2,3-di-
hydro-1H-inden-1-yl]oxy)-3-fluorophenyl)sulfonamide)
pyrrolidin-1-yl]-7,14-dioxo-3,18-dioxa-6,8,13,15-
tetraazaicosyl)pyrrolidin-3-yl]-3-
fluorobenzenesulfonamide; tetra(trifluoroacetate);
4-([(1 S,2S)-6-Chloro-4-cyano-2-(piperazin-1-yl)-2,3-di-
hydro-1H-inden-1-yl]oxy)-N—[(S)-1-(20-[(S)-3-[(4-
([(1S,2S)-6-chloro-4-cyano-2-(piperazin-1-yl)-2,3-di-
hydro-1H-inden-1-yl]oxy)-3-fluorophenyl)sulfonamido)
pyrrolidin-1-yl]-7,14-dioxo-3,18-dioxa-6,8,13,15-
tetraazaicosyl)pyrrolidin-3-yl]-3-
fluorobenzenesulfonamide; tetra(trifluoroacetate);
4-([(1S,2S)-4,6-Dichloro-2-(dimethylamino)-2,3-dihydro-
1H-inden-1-yl]oxy)-N—[(S)-1-(20-[(S)-3-([4-([(1S,2S)-
4,6-dichloro-2-(dimethylamino)-2,3-dihydro-1H-inden-
1-yl]oxy)-3-fluorophenyl]sulfonamido)pyrrolidin-1-yl]-
7,14-dioxo-3,18-dioxa-6,8,13,15-tetraazaicosyl)
pyrrolidin-3-yl]-3-fluorobenzenesulfonamide; tetra
(trifluoroacetate);
4-([(1S,2S)-4,6-Dichloro-2-(dimethylamino)-2,3-dihydro-
1H-inden-1-yl]oxy)-N—[(R)-1-(20-[(R)-3-([4-([(1S,2S)-
4,6-dichloro-2-(dimethylamino)-2,3-dihydro-1H-inden-
1-yl]oxy)-3-fluorophenyl]sulfonamido)pyrrolidin-1-yl]-
7,14-dioxo-3,18-dioxa-6,8,13,15-tetraazaicosyl)
pyrrolidin-3-yl]-3-fluorobenzenesulfonamide; tetra
(trifluoroacetate);
4-([(1S,2S)-6-Chloro-2-[(R)-3-(dimethylamino)piperidin-1-
yl]-4-methyl-2,3-dihydro-1H-inden-1-yl]oxy)-N—[(R)-
1-(20-[(R)-3-([4-([(1 S,2 S)-6-chloro-2-[(R)-3-(dimethyl-
amino)piperidin-1-yl]-4-methyl-2,3-dihydro-1H-inden-1-
yl]oxy)-3-methylphenyl]sulfonamido)pyrrolidin-1-yl]-7,
14-dioxo-3,18-dioxa-6,8,13,15-tetraazaicosyl)pyrrolidin-
3-yl]-3-methylbenzenesulfonamide; tetra
(trifluoroacetate);
4-([(1S,2S)-6-Chloro-2-[(R)-3-(dimethylamino)piperidin-1-
yl]-4-methyl-2,3-dihydro-1H-inden-1-yl]oxy)-N—[(S)-
1-(20-[(S)-3-([4-([(1S,2S)-6-chloro-2-[(R)-3-(dimethyl-
amino)piperidin-1-yl]-4-methyl-2,3-dihydro-1H-inden-1-
yl]oxy)-3-methylphenyl]sulfonamido)pyrrolidin-1-yl]-7,
14-dioxo-3,18-dioxa-6,8,13,15-tetraazaicosyl)pyrrolidin-
3-yl]-3-methylbenzenesulfonamide; tetra
(trifluoroacetate);
4-([(1S,2S)-6-Chloro-4-cyano-2-(piperazin-1-yl)-2,3-di-
hydro-1H-inden-1-yl]oxy)-N-[1-(18-[4-([(1S,2S)-6-
chloro-4-cyano-2-(piperazin-1-yl)-2,3-dihydro-1H-in-
den-1-yl]oxy)phenyl]sulfonamido)piperidin-1-yl]-6,13,
18-trioxo-5,7,12,14-tetraazaoctadecanoyl)piperidin-4-yl]
benzenesulfonamide;
4-([(1S,2S)-6-Chloro-4-cyano-2-(piperazin-1-yl)-2,3-di-
hydro-1H-inden-1-yl]oxy)-N—[(S)-1-(14-[(S)-3-([4-
([(1S,2S)-6-chloro-4-cyano-2-(piperazin-1-yl)-2,3-di-
hydro-1H-inden-1-yl]oxy)phenyl]sulfonamido)
pyrrolidin-1-yl]-4,11,14-trioxo-3,5,10,12-
tetraazatetradecanoyl)pyrrolidin-3-yl]
benzenesulfonamide;
4-([(1 S,2S)-6-Chloro-4-cyano-2-(piperazin-1-yl)-2,3-di-
hydro-1H-inden-1-yl]oxy)-N—[(S)-1-[(2S,13S)-14-[(S)-
3-([4-([(1S,2 S)-6-chloro-4-cyano-2-(piperazin-1-yl)-2,3-
dihydro-1H-inden-1-yl]oxy)phenyl]sulfonamido)
pyrrolidin-1-yl]-2,13-dimethyl-4,11,14-trioxo-3,5,10,12-
tetraazatetradecanoyl]pyrrolidin-3-yl]
benzenesulfonamide;
N1,N14-bis(2-[(S)-3-([4-([(1S,2S)-6-chloro-4-cyano-2-
(piperazin-1-yl)-2,3-dihydro-1H-inden-1-yl]oxy)phenyl]
sulfonamido)pyrrolidin-1-yl]-2-oxoethyl)-4,11-dioxo-3,
5,10,12-tetraazatetradecanedi ami de;
N1,N14-bis(2-[(R)-3-([4-([(1S,2S)-6-chloro-4-cyano-2-
(piperazin-1-yl)-2,3-dihydro-1H-inden-1-yl]oxy)phenyl]
sulfonamido)pyrrolidin-1-yl]-2-oxoethyl)-4,11-dioxo-3,
5,10,12-tetraazatetradecanedi ami de;
N1,N18-Bis(1-([4-([(1S,2S)-6-chloro-4-cyano-2-(piper-
azin-1-yl)-2,3-dihydro-1H-inden-1-yl]oxy)phenyl]sulfo-
nyl)piperidin-4-yl)-6,13-dioxo-5,7,12,14-tetraazaoctade-
canediamide;
4-([(1S,2S)-6-Chloro-4-cyano-2-[(R)-3-(dimethylamino)pi-
peridin-1-yl]-2,3-dihydro-1H-inden-1-yl]oxy)-N-[26-([4-
([(1S,2S)-6-chloro-4-cyano-2-[(R)-3-(dimethylamino)pi-
peridin-1-yl]-2,3-dihydro-1H-inden-1-yl]oxy)phenyl]

sulfonamido)-10,17-dioxo-3,6,21,24-tetraoxa-9,11,16, 18-tetraazahexacosyl]benzenesulfonamide;

4-([(1 S,2S)-6-Chloro-4-cyano-2-[(S)-3-(dimethylamino)piperidin-1-yl]-2,3-dihydro-1H-inden-1-yl]oxy)-N-[26-([4-([[(1S,2S)-6-chloro-4-cyano-2-[(S)-3-(dimethylamino)piperidin-1-yl]-2,3-dihydro-1H-inden-1-yl]oxy)phenyl] sulfonamido)-10,17-dioxo-3,6,21,24-tetraoxa-9,11,16, 18-tetraazahexacosyl]benzenesulfonamide;

4-([(1 S,2S)-6-chloro-4-cyano-2-(piperazin-1-yl)-2,3-dihydro-1H-inden-1-yl]oxy)-N-[1-(20-[4-([(1S,2S)-6-chloro-4-cyano-2-(piperazin-1-yl)-2,3-dihydro-1H-inden-1-yl]oxy)phenyl]sulfonamide]piperidin-1-yl)-7,14-dioxo-3,18-dioxa-6,8,13,15-tetraazaicosyl]piperidin-4-yl)benzenesulfonamide;

N1,N18-Bis([4-([[(1S,2S)-6-chloro-4-cyano-2-(piperazin-1-yl)-2,3-dihydro-1H-inden-1-yl]oxy)phenyl]sulfonyl)-6, 13-dioxo-5,7,12,14-tetraazaoctadecanediamide;

N-([4-([[(1S,2S)-6-chloro-4-cyano-2-(piperazin-1-yl)-2,3-dihydro-1H-inden-1-yl]oxy)phenyl]sulfonyl)-1-[16-(4-[([4-([[(1S,2S)-6-chloro-4-cyano-2-(piperazin-1-yl)-2,3-dihydro-1H-inden-1-yl]oxy)phenyl]sulfonyl)carbamoyl] piperidin-1-yl]-5,12-dioxo-4,6,11,13-tetraazahexadecyl] piperidine-4-carboxamide;

4-([(1S,2S)-6-chloro-4-cyano-2-(1,4-diazepan-1-yl)-2,3-dihydro-1H-inden-1-yl]oxy)-N—[(S)-1-(20-[(S)-3-([4-([[(1S,2S)-6-chloro-4-cyano-2-(1,4-diazepan-1-yl)-2,3-dihydro-1H-inden-1-yl]oxy)phenyl]sulfonamido) pyrrolidin-1-yl]-7,14-dioxo-3,18-dioxa-6,8,13,15-tetraazaicosyl)pyrrolidin-3-yl]benzenesulfonamide;

4-([(1S,2S)-6-chloro-4-cyano-2-(1,4-diazepan-1-yl)-2,3-dihydro-1H-inden-1-yl]oxy)-N—[(R)-1-(20-[(R)-3-([4-([(1 S,2S)-6-chloro-4-cyano-2-(1,4-diazepan-1-yl)-2,3-dihydro-1H-inden-1-yl]oxy)phenyl]sulfonamido)pyrrolidin-1-yl]-7,14-dioxo-3,18-dioxa-6,8,13,15-tetraazaicosyl)pyrrolidin-3-yl]benzenesulfonamide;

4-([(1 S,2 S)-6-chloro-4-cyano-2-(4-methyl -1,4-diazepan-1-yl)-2,3-dihydro-1H-inden-1-yl]oxy)-N—[(S)-1-(20-[(S)-3-([4-([[(1S,2S)-6-chloro-4-cyano-2-(4-methyl-1,4-diazepan-1-yl)-2,3-dihydro-1H-inden-1-yl]oxy)phenyl] sulfonamido)pyrrolidin-1-yl]-7,14-dioxo-3,18-dioxa-6,8, 13,15-tetraazaicosyl)pyrrolidin-3-yl] benzenesulfonamide;

4-([(1 S,2 S)-6-chloro-4-cyano-2-(4-methyl -1,4-diazepan-1-yl)-2,3-dihydro-1H-inden-1-yl]oxy)-N—[(R)-1-(20-[(R)-3-([4-([(1 S,2S)-6-chloro-4-cyano-2-(4-methyl-1,4-diazepan-1-yl)-2,3-dihydro-1H-inden-1-yl]oxy)phenyl] sulfonamido)pyrrolidin-1-yl]-7,14-dioxo-3,18-dioxa-6,8, 13,15-tetraazaicosyl)pyrrolidin-3-yl] benzenesulfonamide;

4-([(1S,2S)-2-[(1S,4S)-2,5-diazabicyclo[2.2.1]heptan-2-yl]-6-chloro-4-cyano-2,3-dihydro-1H-inden-1-yl]oxy)-N—[(S)-1-(20-[(S)-3-([4-([[(1S,2S)-2-[(1S,4S)-2,5-diazabicyclo[2.2.1]heptan-2-yl]-6-chloro-4-cyano-2,3-dihydro-1H-inden-1-yl]oxy)phenyl]sulfonamido)pyrrolidin-1-yl]-7,14-dioxo-3,18-dioxa-6,8,13,15-tetraazaicosyl) pyrrolidin-3-yl]benzenesulfonamide;

4-([(1S,2S)-2-[(1S,4S)-2,5-diazabicyclo[2.2.1]heptan-2-yl]-6-chloro-4-cyano-2,3-dihydro-1H-inden-1-yl]oxy)-N—[(R)-1-(20-[(R)-3-([4-([[(1S,2S)-2-[(1S,4S)-2,5-diazabicyclo[2.2.1]heptan-2-yl]-6-chloro-4-cyano-2,3-dihydro-1H-inden-1-yl]oxy)phenyl]sulfonamido)pyrrolidin-1-yl]-7,14-dioxo-3,18-dioxa-6,8,13,15-tetraazaicosyl) pyrrolidin-3-yl]benzenesulfonamide;

4-([(1S,2S)-6-chloro-4-cyano-2-[(R)-3-methylpiperazin-1-yl]-2,3-dihydro-1H-inden-1-yl]oxy)-N—[(S)-1-(20-[(S)-3-([4-([[(1S,2S)-6-chloro-4-cyano-2-[(R)-3-methylpiperazin-1-yl]-2,3-dihydro-1H-inden-1-yl]oxy)phenyl] sulfonamido)pyrrolidin-1-yl]-7,14-dioxo-3,18-dioxa-6,8, 13,15-tetraazaicosyl)pyrrolidin-3-yl] benzenesulfonamide;

4-([(1S,2S)-6-chloro-4-cyano-2-[(R)-3-methylpiperazin-1-yl]-2,3-dihydro-1H-inden-1-yl]oxy)-N—[(R)-1-(20-[(R)-3-([4-([[(1S,2S)-6-chloro-4-cyano-2-[(R)-3-methylpiperazin-1-yl]-2,3-dihydro-1H-inden-1-yl]oxy)phenyl] sulfonamido)pyrrolidin-1-yl]-7,14-dioxo-3,18-dioxa-6,8, 13,15-tetraazaicosyl)pyrrolidin-3-yl] benzenesulfonamide;

4-([(1S,2S)-6-chloro-4-cyano-2-[(S)-3-methylpiperazin-1-yl]-2,3-dihydro-1H-inden-1-yl]oxy)-N—[(S)-1-(20-[(S)-3-([4-([(1 S,2S)-6-chloro-4-cyano-2-[(S)-3-methylpiperazin-1-yl]-2,3-dihydro-1H-inden-1-yl]oxy)phenyl] sulfonamido)pyrrolidin-1-yl]-7,14-dioxo-3,18-dioxa-6,8, 13,15-tetraazaicosyl)pyrrolidin-3-yl] benzenesulfonamide;

4-([(1S,2S)-6-chloro-4-cyano-2-[(S)-3-methylpiperazin-1-yl]-2,3-dihydro-1H-inden-1-yl]oxy)-N—[(R)-1-(20-[(R)-3-([4-([[(1S,2S)-6-chloro-4-cyano-2-[(S)-3-methylpiperazin-1-yl]-2,3-dihydro-1H-inden-1-yl]oxy)phenyl] sulfonamido)pyrrolidin-1-yl]-7,14-dioxo-3,18-dioxa-6,8, 13,15-tetraazaicosyl)pyrrolidin-3-yl] benzenesulfonamide;

4-([(1S,2S)-6-chloro-4-cyano-2-[(3S,5R)-3,5-dimethylpiperazin-1-yl]-2,3-dihydro-1H-inden-1-yl]oxy)-N—[(S)-1-(20-[(S)-3-([4-([[(1S,2S)-6-chloro-4-cyano-2-[(3S,5R)-3, 5-dimethylpiperazin-1-yl]-2,3-dihydro-1H-inden-1-yl] oxy)phenyl]sulfonamido)pyrrolidin-1-yl]-7,14-dioxo-3, 18-dioxa-6,8,13,15-tetraazaicosyl)pyrrolidin-3-yl] benzenesulfonamide;

4-([(1S,2S)-6-chloro-4-cyano-2-[(3S,5R)-3,5-dimethylpiperazin-1-yl]-2,3-dihydro-1H-inden-1-yl]oxy)-N—[(R)-1-(20-[(R)-3-([4-([[(1S,2S)-6-chloro-4-cyano-2-[(3S,5R)-3, 5-dimethylpiperazin-1-yl]-2,3-dihydro-1H-inden-1-yl] oxy)phenyl]sulfonamido)pyrrolidin-1-yl]-7,14-dioxo-3, 18-dioxa-6,8,13,15-tetraazaicosyl)pyrrolidin-3-yl] benzenesulfonamide;

4-([(1 S,2S)-6-chloro-4-cyano-2-(piperazin-1-yl)-2,3-dihydro-1H-inden-1-yl]oxy)-N—[(S)-1-(20-[(S)-3-([4-([[(1S,2S)-6-chloro-4-cyano-2-(piperazin-1-yl)-2,3-dihydro-1H-inden-1-yl]oxy)phenyl]sulfonamido)-2-oxopiperidin-1-yl]-7,14-dioxo-3,18-dioxa-6,8,13,15-tetraazaicosyl)-2-oxopiperidin-3-yl]benzenesulfonamide;

4-([(1S,2S)-6-Chloro-4-cyano-2-(piperazin-1-yl)-2,3-dihydro-1H-inden-1-yl]oxy)-N-[2-(2-[2-(3-[(1r,4r)-4-(3-[2-(2-[2-([4-([[(1S,2S)-6-chloro-4-cyano-2-(piperazin-1-yl)-2,3-dihydro-1H-inden-1-yl]oxy)phenyl]sulfonamido) ethoxy]ethoxy)ethyl]ureido)cyclohexyl]ureido)ethoxy] ethoxy)ethyl]benzenesulfonamide;

4-([(1S,2S)-6-Chloro-4-cyano-2-(piperazin-1-yl)-2,3-dihydro-1H-inden-1-yl]oxy)-N—[(R)-1-(18-[(R)-3-([4-([(1 S,2S)-6-chloro-4-cyano-2-(piperazin-1-yl)-2,3-dihydro-1H-inden-1-yl]oxy)phenyl]sulfonamido)pyrrolidin-1-yl]-6,13,18-trioxo-5,7,12,14-tetraazaoctadecanoyl)pyrrolidin-3-yl]benzenesulfonamide;

4-([(1S,2S)-6-Chloro-4-cyano-2-(piperazin-1-yl)-2,3-dihydro-1H-inden-1-yl]oxy)benzenesulfonamide;

N-(2-[2-(2-Aminoethoxy)ethoxy]ethyl)-4-([(1S,2S)-6-chloro-4-cyano-2-(piperazin-1-yl)-2,3-dihydro-1H-inden-1-yl]oxy)benzenesulfonamide;

N-[1-(4-Aminobutanoyl)piperidin-4-yl]-4-([(1S,2S)-6-chloro-4-cyano-2-(piperazin-1-yl)-2,3-dihydro-1H-inden-1-yl]oxy)benzenesulfonamide;

4-([(1S,2S)-6-Chloro-4-cyano-2-(piperazin-1-yl)-2,3-dihydro-1H-inden-1-yl]oxy)-N-(3-oxo-7,10-dioxa-2,4-diazadodecan-12-yl)benzenesulfonamide;

4-([(1S,2S)-6-Chloro-4-cyano-2-(piperazin-1-yl)-2,3-dihydro-1H-inden-1-yl]oxy)-N-(1-[4-(3-methylureido)butanoyl]piperidin-4-yl)benzenesulfonamide;

4-([(1S,2S)-6-Chloro-4-cyano-2-(piperazin-1-yl)-2,3-dihydro-1H-inden-1-yl]oxy)-N-[(2S,3R,4S,5R)-1,3,4,5,6-pentahydroxyhexan-2-yl]benzenesulfonamide;

4-([4-([(1S,2S)-6-Chloro-4-cyano-2-(piperazin-1-yl)-2,3-dihydro-1H-inden-1-yl]oxy)phenyl]sulfonamido)-N-[(2S,3R,4S,5R)-1,3,4,5,6-pentahydroxyhexan-2-yl]piperidine-1-carboxamide;

4-(3-[4-([4-([(1S,2S)-6-Chloro-4-cyano-2-(piperazin-1-yl)-2,3-dihydro-1H-inden-1-yl]oxy)phenyl]sulfonamido)-4-oxobutyl]ureido)-N-([4-([(1S,2S)-6-chloro-4-cyano-2-(piperazin-1-yl)-2,3-dihydro-1H-inden-1-yl]oxy)phenyl]sulfonyl)butanamide;

4-([(1S,2S)-6-Chloro-4-cyano-2-(piperazin-1-yl)-2,3-dihydro-1H-inden-1-yl]oxy)-N-[1-(4-[3-(4-[4-([(1S,2S)-6-chloro-4-cyano-2-(piperazin-1-yl)-2,3-dihydro-1H-inden-1-yl]oxy)phenyl]sulfonamido)piperidin-1-yl]-4-oxobutyl)ureido]butanoyl)piperidin-4-yl]benzenesulfonamide;

4-([(1S,2S)-6-Chloro-4-cyano-2-(piperazin-1-yl)-2,3-dihydro-1H-inden-1-yl]oxy)-N-[19-([4-([(1S,2S)-6-chloro-4-cyano-2-(piperazin-1-yl)-2,3-dihydro-1H-inden-1-yl]oxy)phenyl]sulfonamido)-10-oxo-3,6,14,17-tetraoxa-9,11-diazanonadecyl]benzenesulfonamide;

4-([(1S,2S)-6-Chloro-4-amido-2-(piperazin-1-yl)-2,3-dihydro-1H-inden-1-yl]oxy)-N-[26-([4-([(1S,2S)-6-chloro-4-amido-2-(piperazin-1-yl)-2,3-dihydro-1H-inden-1-yl]oxy)phenyl]sulfonamido)-10,17-dioxo-3,6,21,24-tetraoxa-9,11,16,18-tetraazahexacosyl]benzenesulfonamide;

4-([(1S,2S)-4-Cyano-6-methyl-2-(piperazin-1-yl)-2,3-dihydro-1H-inden-1-yl]oxy)-N-[26-([4-([(1S,2S)-4-cyano-6-methyl-2-(piperazin-1-yl)-2,3-dihydro-1H-inden-1-yl]oxy)phenyl]sulfonamido)-10,17-dioxo-3,6,21,24-tetraoxa-9,11,16,18-tetraazahexacosyl]benzenesulfonamide;

1,1'-(Butane-1,4-diyl)bis[3-(4-[6-([(1S,2S)-6-chloro-4-cyano-2-(piperazin-1-yl)-2,3-dihydro-1H-inden-1-yl]oxy)-3,4-dihydroisoquinolin-2(1H)-yl]-4-oxobutyl)urea];

1,1'-(Butane-1,4-diyl)bis[3-(4-[7-([(1S,2S)-6-chloro-4-cyano-2-(piperazin-1-yl)-2,3-dihydro-1H-inden-1-yl]oxy)-3,4-dihydroisoquinolin-2(1H)-yl]-4-oxobutyl)urea];

N,N'-(6,14-Dioxo-10-oxa-5,7,13,15-tetraazanonadecane-1,19-diyl)bis[6-([(1S,2S)-6-chloro-4-cyano-2-(piperazin-1-yl)-2,3-dihydro-1H-inden-1-yl]oxy)-3,4-dihydroisoquinoline-2(1H)-carboxamide];

N,N'-(6,14-Dioxo-10-oxa-5,7,13,15-tetraazanonadecane-1,19-diyl)bis[7-([(1S,2S)-6-chloro-4-cyano-2-(piperazin-1-yl)-2,3-dihydro-1H-inden-1-yl]oxy)-3,4-dihydroisoquinoline-2(1H)-carboxamide];

4-([(1S,2S)-6-Chloro-4-cyano-2-[(R)-3-methylpiperazin-1-yl]-2,3-dihydro-1H-inden-1-yl]oxy)-N—[(S)-1-(18-[(S)-3-([4-([(1S,2S)-6-chloro-4-cyano-2-[(R)-3-methylpiperazin-1-yl]-2,3-dihydro-1H-inden-1-yl]oxy)phenyl]sulfonamido)pyrrolidin-1-yl]-6,13,18-trioxo-5,7,12,14-tetraazaoctadecanoyl)pyrrolidin-3-yl]benzenesulfonamide;

4-([(1S,2S)-6-Chloro-4-cyano-2-[(R)-3-methylpiperazin-1-yl]-2,3-dihydro-1H-inden-1-yl]oxy)-N—[(R)-1-(18-[(R)-3-([4-([(1S,2S)-6-chloro-4-cyano-2-[(R)-3-methylpiperazin-1-yl]-2,3-dihydro-1H-inden-1-yl]oxy)phenyl]sulfonamido)pyrrolidin-1-yl]-6,13,18-trioxo-5,7,12,14-tetraazaoctadecanoyl)pyrrolidin-3-yl]benzenesulfonamide;

4-([(1S,2S)-6-Chloro-4-cyano-2-[(R)-3-methylpiperazin-1-yl]-2,3-dihydro-1H-inden-1-yl]oxy)-N-[1-(18-[4-([(1S,2S)-6-chloro-4-cyano-2-[(R)-3-methylpiperazin-1-yl]-2,3-dihydro-1H-inden-1-yl]oxy)phenyl]sulfonamido)piperidin-1-yl]-6,13,18-trioxo-5,7,12,14-tetraazaoctadecanoyl)piperidin-4-yl]benzenesulfonamide;

N1,N14-Bis(2-[(S)-3-([4-([(1S,2S)-6-chloro-4-cyano-2-[(R)-3-methylpiperazin-1-yl]-2,3-dihydro-1H-inden-1-yl]oxy)phenyl]sulfonamido)pyrrolidin-1-yl]-2-oxoethyl)-4,11-dioxo-3,5,10,12-tetraazatetradecanediamide;

4-([(1S,2S)-6-Chloro-4-cyano-2-[(R)-3-methylpiperazin-1-yl]-2,3-dihydro-1H-inden-1-yl]oxy)-N-[1-(20-[4-([(1S,2S)-6-chloro-4-cyano-2-[(R)-3-methylpiperazin-1-yl]-2,3-dihydro-1H-inden-1-yl]oxy)phenyl]sulfonamido)piperidin-1-yl]-7,14-dioxo-3,18-dioxa-6,8,13,15-tetraazaicosyl)piperidin-4-yl]benzenesulfonamide;

4-([(1S,2S)-4,6-Dichloro-2-[(R)-3-methylpiperazin-1-yl]-2,3-dihydro-1H-inden-1-yl]oxy)-N—[(S)-1-(20-[(S)-3-([4-([(1S,2S)-4,6-dichloro-2-[(R)-3-methylpiperazin-1-yl]-2,3-dihydro-1H-inden-1-yl]oxy)phenyl]sulfonamido)pyrrolidin-1-yl]-7,14-dioxo-3,18-dioxa-6,8,13,15-tetraazaicosyl)pyrrolidin-3-yl]benzenesulfonamide;

N1,N14-Bis(2-[(S)-3-([4-([(1S,2S)-4,6-dichloro-2-[(R)-3-methylpiperazin-1-yl]-2,3-dihydro-1H-inden-1-yl]oxy)phenyl]sulfonamido)pyrrolidin-1-yl]-2-oxoethyl)-4,11-dioxo-3,5,10,12-tetraazatetradecanediamide;

1,1'-(Butane-1,4-diyl)bis(3-[2-(2-[6-([(1S,2S)-6-chloro-4-cyano-2-(piperazin-1-yl)-2,3-dihydro-1H-inden-1-yl]oxy)-1-oxoisoindolin-2-yl]ethoxy)ethyl]urea); and 1,1'-(Butane-1,4-diyl)bis(3-[2-(2-[5-([(1S,2S)-6-chloro-4-cyano-2-(piperazin-1-yl)-2,3-dihydro-1H-inden-1-yl]oxy)-1-oxoisoindolin-2-yl]ethoxy)ethyl]urea).

EXAMPLES

The invention will be more fully understood by reference to the following examples. They should not, however, be construed as limiting the scope of the invention. For example, the synthesis of non-exemplified compounds may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds described herein.

Example 1 (2S,4aS,6aS,6bR,8aS,10S,12aS,12bR,14bR)-10-(Methoxycarbonyl)-2,4a,6a,6b,9,9,12a-heptamethyl-13-oxo-1,2,3,4,4a,5,6,6a,6b,7,8,8a,9,10,1142,12a,12b,13,14b-icosahydropicene-2-carboxylic Acid (1-9)
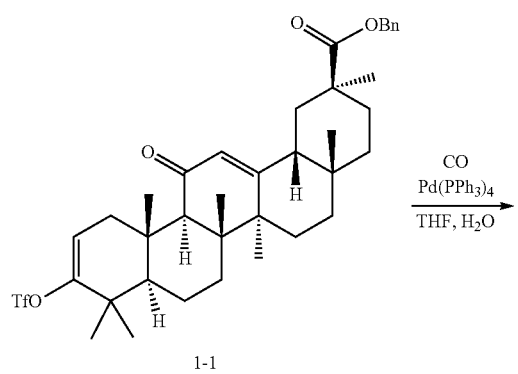
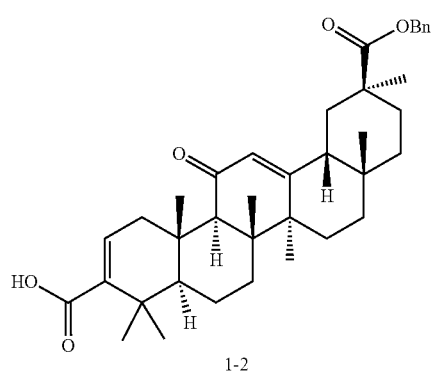
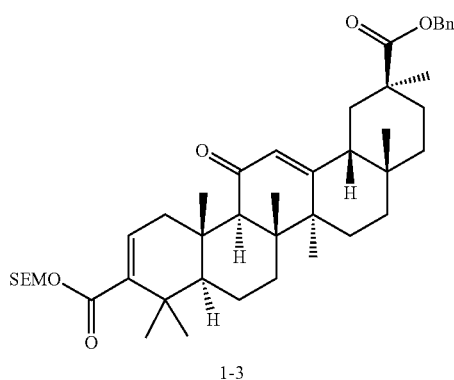
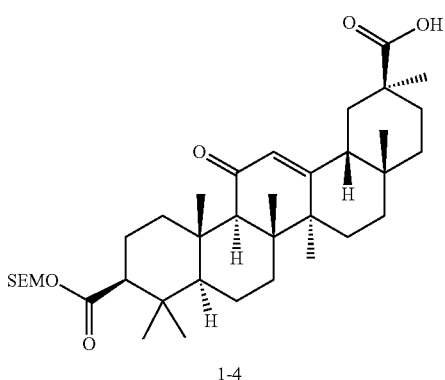
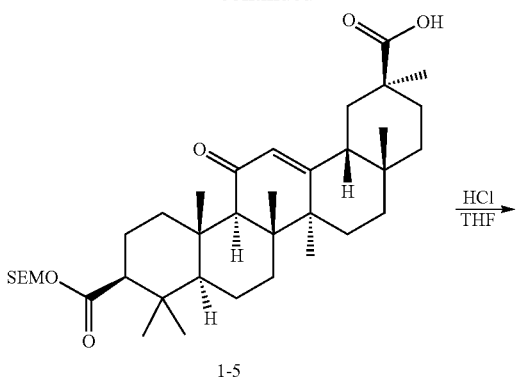
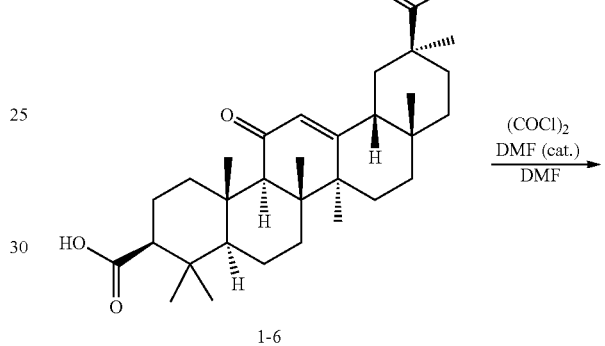
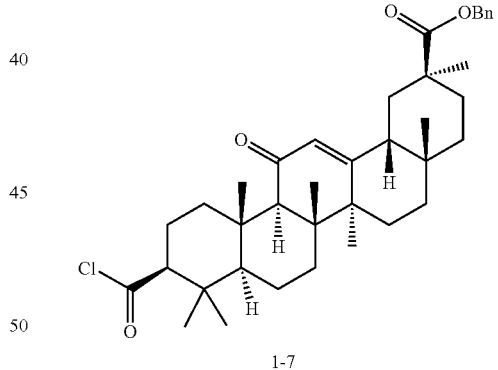
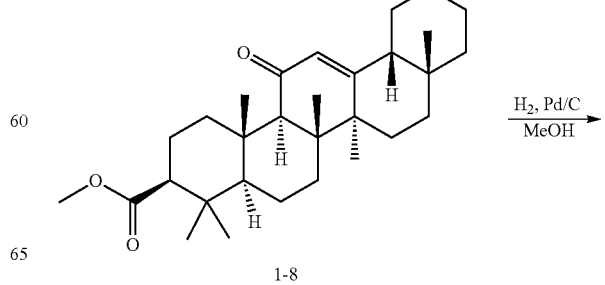

-continued

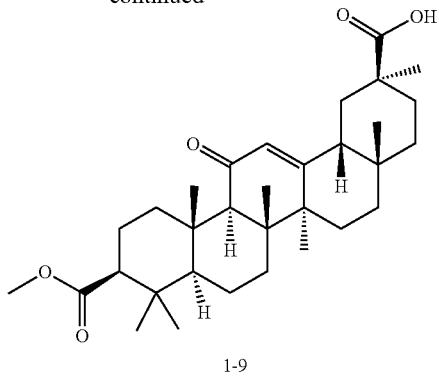

1-9

Synthesis of (4aR,6aR,6bS,8aS,11S,12aR,14aR, 14bS)-11-((Benzyloxy)carbonyl)-4,4,6a,6b,8a,11, 14b-heptamethyl-14-oxo-1,4,4a,5,6,6a,6b,7,8,8a,9, 10,11,12,12a,14,14a,14b-octadecahydropicene-3-carboxylic Acid (1-2)

Into a 1-L pressure tank reactor (10 atm) purged and maintained with an inert atmosphere of CO, was placed benzyl (2S,4aS,6aS,6bR,8aR,12aS,12bR,14bR)-2,4a,6a,6b, 9,9,12a-heptamethyl-13-oxo-10-(((trifluoromethyl)sulfonyl)oxy)-1,2,3,4,4a,5,6,6a,6b,7,8,8a,9,12,12a,12b,13,14b-octadecahydropicene-2-carboxylate 1-1 (prepared according to the method described in US Patent application publication no. 20160151387) (11 g, 15.92 mmol, 1.00 equiv), tetrakis (triphenylphosphine)palladium(0) (4 g, 3.46 mmol, 0.20 equiv), THF (250 mL), and water (150 mL). The resulting solution was stirred for 2 days at 50° C. The resulting solution was extracted with $CH_2Cl_2$ (3×150 mL) and the organic layers combined. The resulting mixture was washed with brine (3×150 mL). The mixture was dried over anhydrous $Na_2SO_4$ and concentrated under vacuum. The residue was applied onto a silica gel column with EtOAc/petroleum ether (1:10) (20 mL). The crude product was purified by flash-prep-HPLC with the following conditions (Combi-Flash-1)—Column: $C_{18}$ silica gel; mobile phase:

MeCN:water=100:0; detector: UV 254 nm. 1 L product was obtained. This resulted in 6.5 g (69.6%) of 1-2 as a light yellow solid.

Synthesis of 2-Benzyl 10-((2-(trimethylsilyl)ethoxy) methyl) (2S,4aS,6aS,6bR,8aR,12aS,12bR,14bR)-2, 4a,6a,6b,9,9,12a-heptamethyl-13-oxo-1,2,3,4,4a,5,6, 6a,6b,7,8,8a,9,12,12a,12b,13,14b-octadecahydropicene-2,10-dicarboxylate (1-3)

TEA (3 mL, 5.80 equiv) was added dropwise with stirring at 0° C. to 1-2 (3 g, 5.11 mmol, 1 equiv) and DMAP (102.4 mg, 0.84 mmol, 0.10 equiv) in DMF (30 mL). This was followed by the addition of 2-(trimethylsilyl)ethoxymethyl chloride (4.2 mL, 4.8 equiv) dropwise with stirring at 0° C. The reaction was stirred for 1.5 h at rt and then quenched by the addition of aq. $K_2CO_3$ (50 mL). The mixture was diluted with $CH_2Cl_2$ (250 mL), washed with brine (3×150 mL), dried ($Na_2SO_4$) and concentrated under vacuum. The residue was purified by silica gel column eluting with EtOAc/petroleum ether (1:10). This resulted in 3.5 g (95.5%) of 1-3 as a light-yellow oil.

Synthesis of (2S,4aS,6aS,6bR,8aS,10S,12aS,12bR, 14bR)-2,4a,6a,6b,9,9,12a-Heptamethyl-13-oxo-10-(((2-(trimethylsilyl)ethoxy)methoxy)carbonyl)-1,2,3, 4,4a,5,6,6a,6b,7,8,8a,9,10,11,12,12a,12b,13,14b-icosahydropicene-2-carboxylic Acid (1-4)

Into a 300-mL pressure tank reactor (40 atm) purged and maintained with an inert atmosphere of hydrogen, was placed 1-3 (6.6 g, 9.20 mmol, 1.00 equiv), Pd/C (1.32 g, 0.20 equiv), acetone (150 mL). The reaction was stirred overnight at 50° C. and then concentrated under vacuum. This resulted in 4.2 g (73%) of 1-4 as a white solid.

Synthesis of 2-Benzyl 10-((2-(trimethylsilyl)ethoxy)methyl) (2S,4aS,6aS,6bR,8aS,10S,12aS,12bR,14bR)-2,4a,6a,6b, 9,9,12a-heptamethyl-13-oxo-1,2,3,4,4a,5,6,6a,6b,7,8,8a,9, 10,11,12,12a,12b,13,14b-icosahydropicene-2,10-dicarboxylate (1-5) 1-4 (5.25 g, 8.35 mmol, 1 equiv), cesium carbonate (4.1 g, 12.58 mmol, 1.5 equiv) and benzyl bromide (2.86 g, 16.72 mmol, 2 equiv) in DMF (70 mL) were stirred for 2 h at 60° C. The reaction was diluted with water (250 mL) and extracted with $CH_2Cl_2$ (2×100 mL). The organic layers were combined, dried ($Na_2SO_4$) and concentrated. The residue was purified by silica gel column eluting with EtOAc/petroleum ether (1:10). This resulted in 6 g (99%) of 1-5 as an off-white solid.

Synthesis of (3S,4aS,6aR,6bS,8aS,11S,12aR,14aR, 14bS)-11-((Benzyloxy)carbonyl)-4,4,6a,6b,8a,11, 14b-heptamethyl-14-oxo-1,2,3,4,4a,5,6,6a,6b,7,8,8a, 9,10,11,12,12a,14,14a,14b-icosahydropicene-3-carboxylic Acid (1-6)

Hydrogen chloride (4M in dioxane, 30 mL) was added to 1-5 (5.6 g, 7.79 mmol, 1 equiv) in THF (40 mL) and the reaction stirred for 2 h at 60° C. The solution was adjusted to pH=3 with aqueous sodium bicarbonate (sat.). The mixture was extracted with $CH_2Cl_2$ (3×100 mL). The organic layers were combined, washed with brine (2×150 mL), dried ($Na_2SO_4$) and concentrated. The residue was purified by Flash-prep-HPLC with the following conditions (Combi-Flash-1) -Column: $C_{18}$ silica gel; mobile phase: MeCN:water=100:0; detector: UV 254 nm. This resulted in 3.1 g (68%, 97% purity) of 1-6 as a white solid. MS (ES, m/z): $[M+H]^+$=589.4; $^1$H-NMR (400 MHz, Chloroform-d): δ 0.76 (s, 4H), 0.91 (s, 5H), 1.01-1.21 (m, 12H), 1.24-1.49 (m, 9H), 1.56-1.75 (m, 4H), 1.83 (td, J=13.6, 4.6 Hz, 1H), 1.91-2.10 (m, 5H), 2.23 (d, J=8.2 Hz, 1H), 2.37 (s, 1H), 2.86 (d, J=13.2 Hz, 1H), 5.11 (d, J=12.0 Hz, 1H), 5.23 (d, J=12.4 Hz, 1H), 5.57 (s, 1H), 7.30-7.45 (m, 5H).

Synthesis of Benzyl (2S,4aS,6aS,6bR,8aS,10S, 12aS,12bR,14bR)-10-(chlorocarbonyl)-2,4a,6a,6b,9, 9,12a-heptamethyl-13-oxo-1,2,3,4,4a,5,6,6a,6b,7,8, 8a,9,10,11,12,12a,12b,13,14b-icosahydropicene-2-carboxylate (1-7)

Oxalyl chloride (0.144 mL, 1.70 mmol) was added dropwise to 1-6 (0.50 g, 0.85 mmol) and DMF (1 drop) in $CH_2Cl_2$ (50 mL) at rt. The mixture was stirred at rt for 1 hour and then evaporated to dryness. The material was used in the following steps without purification.

Synthesis of 2-Benzyl 10-methyl (2S,4aS,6aS,6bR, 8aS,10S,12aS,12bR,14bR)-2,4a,6a,6b,9,9,12a-heptamethyl-13-oxo-1,2,3,4,4a,5,6,6a,6b,7,8,8a,9,10,11, 12,12a,12b,13,14b-icosahydropicene-2,10-dicarboxylate (1-8)

1-7 (200 mg, 0.33 mmol, 1 equiv) and TEA (0.274 mL, 6 equiv) in MeOH (20 mL) were stirred overnight at rt. The reaction was concentrated under vacuum. This resulted in 198 mg (100%) of 1-8 as a light-yellow crude solid.

Synthesis of (2S,4aS,6aS,6bR,8aS,10S,12aS,12bR, 14bR)-10-(Methoxycarbonyl)-2,4a,6a,6b,9,9,12a-heptamethyl-13-oxo-1,2,3,4,4a,5,6,6a,6b,7,8,8a,9,10, 11,12,12a,12b,13,14b-icosahydropicene-2-carboxylic Acid (1-9)

1-8 (198 mg, 0.33 mmol, 1.00 equiv) and Pd/C (20 mg) in MeOH (40 mL) were placed under a hydrogen atmosphere and stirred for 1 h at rt. The reaction was filtered and concentrated under vacuum. The crude product (200 mg) was purified by prep-HPLC with the following conditions—Column: XBridge Prep C18 OBD, 190*150 mm, 5 μm; mobile phase: water (10 mM $NH_4HCO_3$+0.1% $NH_4OH$) and $CH_3CN$ (50.0% $CH_3CN$ up to 62.0% in 7 min); detector: UV 254/220 nm. This resulted in 111.8 mg (66%) of 1-9 as a light yellow solid. MS (ES, m/z): [M+H]+=513.60; $^1H$ NMR (400 MHz, Chloroform-d) δ 0.76 (d, J=11.2 Hz, 1H), 0.84 (s, 3H), 0.88-0.96 (m, 4H), 0.99-1.08 (m, 4H), 1.18 (s, 3H), 1.19-1.28 (m, 7H), 1.31-1.39 (m, 4H), 1.40-1.48 (m, 4H), 1.50-1.59 (m, 1H), 1.60-1.72 (m, 3H), 1.79-1.89 (m, 1H), 1.91-2.09 (m, 4H), 2.15-2.25 (m, 2H), 2.37 (s, 1H), 2.82 (dt, J=10.4, 3.2 Hz, 1H), 3.65 (s, 3H), 5.70 (s, 1H), 9.89 (s, 1H).

Example 2 (2S,4aS,6aS,6bR,8aR,10S,12aS,12bR, 14bR)-10-(Carboxymethoxy)-2,4a,6a,6b,9,9,12a-heptamethyl-13-oxo-1,2,3,4,4a,5,6,6a,6b,7,8,8a,9,10, 1142,12a,12b,13,14b-icosahydropicene-2-carboxylic (78-2)

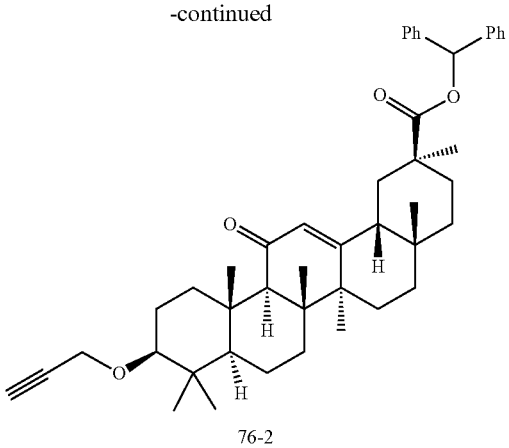

76-2

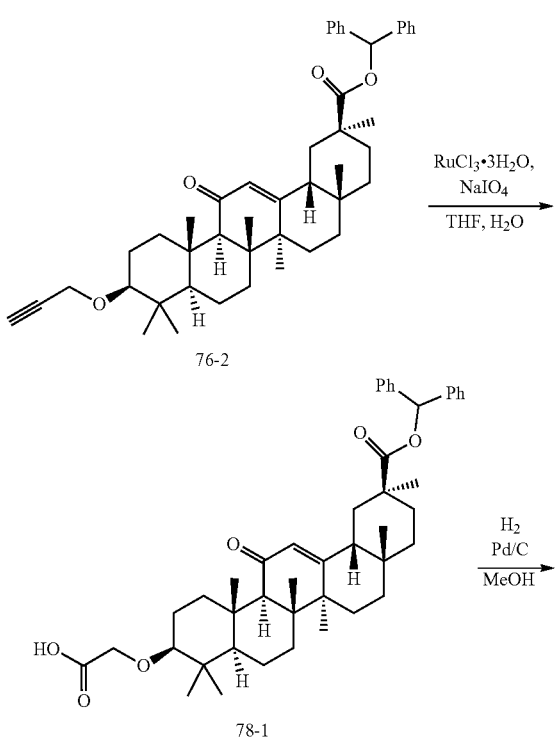

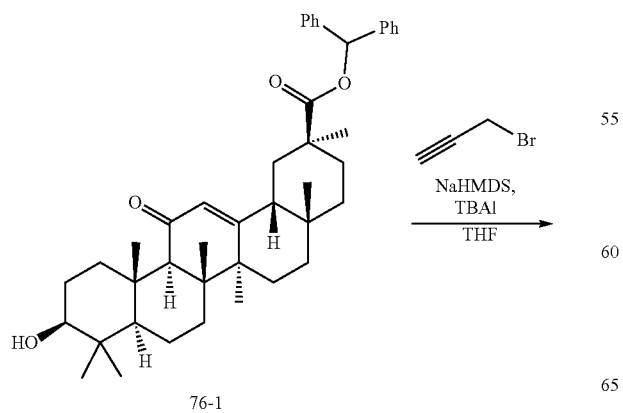

76-1

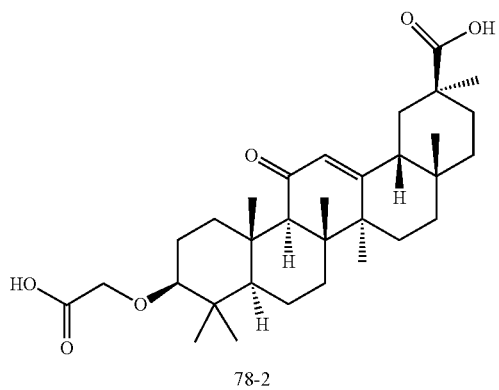

78-2

Synthesis of Benzhydryl (2S,4aS,6aS,6bR,8aR,10S, 12aS,12bR,14bR)-2,4a,6a,6b,9,9,12a-heptamethyl-13-oxo-10-(prop-2-yn-1-yloxy)-1,2,3,4,4a,5,6,6a,6b, 7,8,8a,9,10,11,12,12a,12b,13,14b-icosahydropicene-2-carboxylate (76-2)

76-1 (prepared as described in *Bioorg. Med Chem.* 2010, 18, 433-454) (1.674 g, 2.63 mmol, 1 equiv), NaHMDS (2.63 mL, 2 equiv), 3-bromoprop-1-yne (0.45 mL, 2 equiv), and tetrabutylammonium iodide (486 mg, 1.32 mmol, 0.5 equiv) in THF (2 mL) were stirred overnight at rt. The reaction was diluted with water (30 mL), extracted with DCM (2×50 mL). The extract was dried ($Na_2SO_4$) and concentrated under vacuum. The residue was purified by silica gel column eluting with EtOAc/petroleum ether (1:10). This resulted in 1.395 g (79%) of 76-2 as a light yellow solid.

Synthesis of 2-(((3S,4aR,6aR,6bS,8aS,11S,12aR, 14aR,14bS)-11-((Benzhydryloxy)carbonyl)-4,4,6a, 6b,8a,11,14b-heptamethyl-14-oxo-1,2,3,4,4a,5,6,6a, 6b,7,8,8a,9,10,11,12,12a,14,14a,14b-icosahydropicen-3-yl)oxy)acetic Acid (78-1)

Ruthenium(III) chloride hydrate (20 mg, 0.10 mmol, 6.8 equiv), 76-2 (100 mg, 0.15 mmol, 1 equiv), sodium periodate (150 mg, 0.70 mmol, 5 equiv) in THF (4 mL) and water (1 mL) were stirred for 2h at rt. The reaction was diluted with water (20 mL) and extracted with DCM (2×50 mL). The extract was dried ($Na_2SO_4$) and concentrated under vacuum. The residue was purified by silica gel column eluting with EtOAc/petroleum ether (1:5). This resulted in 80 mg (78%) of 78-1 as a white solid.

Synthesis of (2S,4aS,6aS,6bR,8aR,10S,12aS,12bR, 14bR)-10-(Carboxymethoxy)-2,4a,6a,6b,9,9,12a-heptamethyl-13-oxo-1,2,3,4,4a,5,6,6a,6b,7,8,8a,9,10, 11,12,12a,12b,13,14b-icosahydropicene-2-carboxylic Acid (78-2)

78-1 (148 mg, 0.21 mmol, 1 equiv) and Pd/C (100 mg) in EtOAc (15 mL) were placed under a hydrogen atmosphere (1 atm) and stirred overnight at rt. The reaction was filtered and concentrated under vacuum. The residue was purified by prep-HPLC with the following conditions—Column: XBridge Shield RP18 OBD, 5 μm, 19*150 mm; mobile phase: water (0.05% $NH_4OH$) and $CH_3CN$ (10.0% $CH_3CN$ up to 40.0% in 8 min); detector: UV 254 nm. This resulted in 31.1 mg (28%) of 78-2 as a white solid. MS (ES, m/z) $[M+H]^+$=529.40; $^1H$ NMR (300 MHz, MeOH-$d_4$, ppm) δ 0.78-0.88 (m, 7H), 0.94-1.08 (m, 5H), 1.16-1.18 (m, 9H), 1.27 (d, J=13.5 Hz, 1H), 1.39-1.51 (m, 8H), 1.56-2.12 (m, 8H), 2.13-2.26 (m, 2H), 2.47 (s, 1H), 2.76 (dt, J=13.5, 3.5 Hz, 1H), 2.94 (dd, J=11.7, 4.2 Hz, 1H), 3.93 (d, J=15.6 Hz, 1H), 4.05 (d, J=15.6 Hz, 1H), 5.61 (s, 1H).

Example 3 (2S,4aS,6aS,6bR,8aR,9R,10S,12aS, 12bR,14bR)-10-Hydroxy-9-(hydroxymethyl)-2,4a, 6a,6b,9,12a-hexamethyl-13-oxo-1,2,3,4,4a,5,6,6a,6b, 7,8,8a,9,10,1142,12a,12b,13,14b-icosahydropicene-2-carboxylic Acid (121-2)

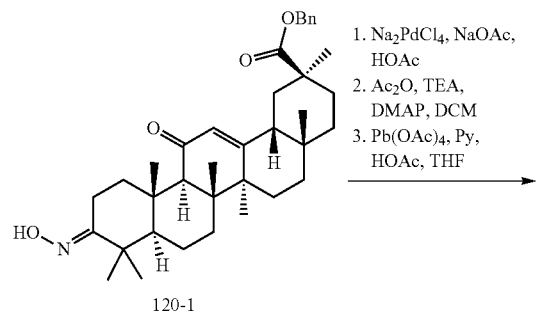

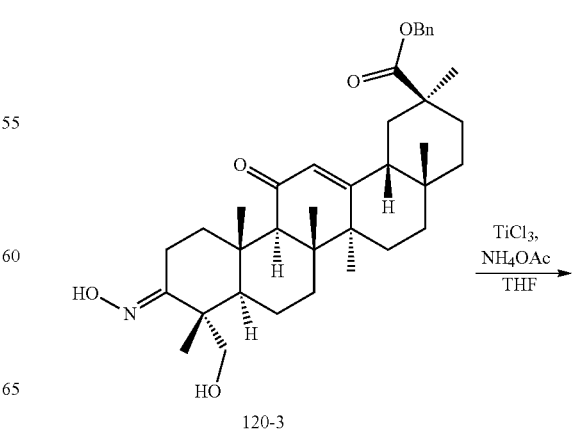

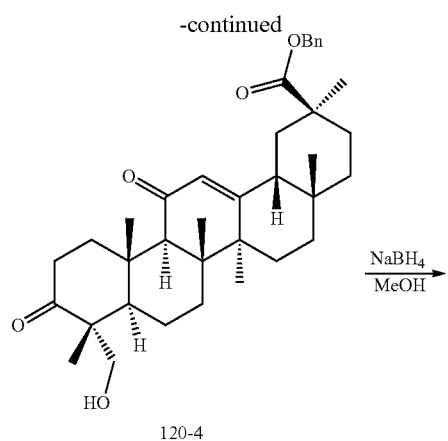

120-4

121-1

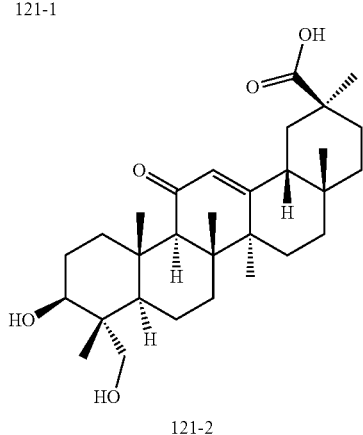

121-2

Synthesis of Benzyl (2S,4aS,6aS,6bR,8aR,9S,12aS, 12bR,14bR,E)-10-(acetoxyimino)-9-(acetoxymethyl)-2,4a,6a,6b,9,12a-hexamethyl-13-oxo-1,2,3,4, 4a,5,6,6a,6b,7,8,8a,9,10,11,12,12a,12b,13,14b-icosahydropicene-2-carboxylate (120-2)

120-1, prepared from (2S,4aS,6aS,6bR,8aR,12aS,12bR, 14bR)-2,4a,6a,6b,9,9,12a-heptamethyl-10,13-dioxo-1,2,3,4, 4a,5,6,6a,6b,7,8,8a,9,10,11,12,12a,12b,13,14b-icosahydropicene-2-carboxylic acid (as described in *Bioorg. Med Chem.* 2010, 18, 433-454) (1.0 g, 1.7 mmol, 1 equiv), sodium tetrachloropalladate(II) (0.76 g, 2.04 mmol, 1.2 equiv) and sodium acetate (0.21 g, 1.36 mmol, 0.8 equiv) in acetic acid (100 mL) were stirred at rt for 72h. The reaction was poured onto ice and the resulting precipitate collected by filtration and dried under vacuum. DCM (120 mL), acetic anhydride (0.435 g, 3.24 mmol, 1.8 equiv), TEA (0.364 g, 2.72 mmol, 1.6 equiv) and DMAP (6 mg, 0.02 equiv) were added and the mixture stirred for 1 h at rt. The reaction was washed with water (1×300 mL), dried (Na$_2$SO$_4$) and concentrated under vacuum. Pyridine (0.6 mL) and THF (100 mL) were added and the mixture stirred at rt for 15 min. The reaction was cooled to −78° C. in a dry ice/acetone bath and lead tetraacetate (4.9 g, 8.5 mmol, 5 equiv) in acetic acid (100 mL) were added slowly. The mixture was allowed to warm to rt and stirred at rt for 16h. A solution of sodium borohydride (60 mg) in 1 N aqueous NaOH solution (50 mL) was added and stirring was continued for 10 min. The reaction was filtered through celite and extracted with DCM (300 mL). The extract was washed with aqueous sat. NaHCO$_3$ (3×300 mL) and brine (2×300 mL), dried (Na$_2$SO$_4$) and concentrated under vacuum. This resulted in 1.03 g (88%, crude) of 120-2 as a light yellow solid.

Synthesis of Benzyl (2S,4aS,6aS,6bR,8aR,9S,12aS, 12bR,14bR,E)-10-(hydroxyimino)-9-(hydroxymethyl)-2,4a,6a,6b,9,12a-hexamethyl-13-oxo-1,2,3,4, 4a,5,6,6a,6b,7,8,8a,9,10,11,12,12a,12b,13,14b-icosahydropicene-2-carboxylate (120-3)

120-2 (1.03 g, 1.53 mmol, 1 equiv) and sodium carbonate (820 mg, 7.74 mmol, 5 equiv) in MeOH (120 mL) were stirred for 16h at rt. The reaction was concentrated under vacuum and the residue dissolved in DCM (200 mL). The mixture was washed with aq. sat. sodium bicarbonate (2×200 mL) and brine (1×200 mL) and concentrated under vacuum. This resulted in 1.1 g (crude) of 120-3 as a yellow solid.

Synthesis of Benzyl (2S,4aS,6aS,6bR,8aR,9R,12aS, 12bR,14bR)-9-(hydroxymethyl)-2,4a,6a, 6b,9,12a-hexamethyl-10,13-dioxo-1,2,3,4,4a,5,6,6a,6b,7,8,8a, 9,10,11,12,12a,12b,13,14b-icosahydropicene-2-carboxylate (120-4)

120-3 (1.1 g, 1.87 mmol, 1 equiv) in THF (70 mL) was added dropwise to ammonium acetate (3.88 g, 27 equiv) and titanium(III) chloride (4 mL) in water (80 mL). The reaction was stirred overnight at rt and then partially concentrated under vacuum. The remaining solution was extracted with DCM (200 mL), washed with aq. sat. sodium bicarbonate (1×200 mL) and brine (1×200 mL), dried (Na$_2$SO$_4$) and concentrated under vacuum. The residue was purified by silica gel column eluting with EtOAc/petroleum ether (1:1). This resulted in 190 mg (18%) of 120-4 as a white solid.

Synthesis of (2S,4aS,6aS,6bR,8aR,9R,12aS,12bR, 14bR)-9-(Hydroxymethyl)-2,4a,6a,6b,9,12a-hexamethyl-10,13-dioxo-1,2,3,4,4a,5,6,6a,6b,7,8,8a,9,10, 11,12,12a,12b,13,14b-icosahydropicene-2-carboxylic Acid (120-5)

120-4 (100 mg, 0.17 mmol) and Pd/C (20 mg) in EtOAc (15 mL) were placed under a hydrogen atmosphere (1 atm) and stirred for 1 h at rt. The reaction was filtered and concentrated under vacuum. The residue was purified by prep-HPLC with the following conditions—Column: XBridge Shield RP18 OBD, 5 mm, 19*150 mm; mobile phase: water (0.05% TFA) and MeCN (20.0% MeCN up to 30.0% in 10 min); detector: UV 254 nm. This resulted in 5.3 mg (6%) of 120-5 as a white solid. MS (ES, m/z): [M+H]$^+$= 485.30; $^1$H NMR (400 MHz, MeOH-d$_4$, ppm): δ 0.86 (s, 3H), 0.96 (s, 3H), 1.01-1.09 (m, 1H), 1.13 (s, 3H), 1.19-1.42

(m, 9H), 1.46-1.73 (m, 8H), 1.80-2.08 (m, 5H), 2.12-2.29 (m, 1H), 2.19-2.48 (m, 2H), 2.48-2.64 (m, 1H), 2.66 (s, 1H), 2.77-2.98 (m, 1H), 3.35-3.42 (m, 2H), 3.65 (d, J=10.8 Hz, 1H), 5.75 (s, 1H).

Synthesis of Benzyl (2S,4aS,6aS,6bR,8aR,9R,10S, 12aS,12bR,14bR)-10-hydroxy-9-(hydroxymethyl)-2, 4a,6a,6b,9,12a-hexamethyl-13-oxo-1,2,3,4,4a,5,6,6a, 6b,7,8,8a,9,10,11,12,12a,12b,13,14b-icosahydropicene-2-carboxylate (121-1)

120-4 (150 mg, 0.26 mmol, 1 equiv) and sodium borohydride (40 mg, 1.06 mmol, 4 equiv) in MeOH (20 mL) were stirred for 1 h at rt. The reaction was quenched by the addition of water (5 mL) and the mixture concentrated under vacuum. The residue was a diluted with DCM, washed with water and brine, dried (Na$_2$SO$_4$) and concentrated. This resulted in 140 mg (93%) of 121-1 as a white solid.

Synthesis of (2S,4aS,6aS,6bR,8aR,9R,10S,12aS, 12bR,14bR)-10-Hydroxy-9-(hydroxymethyl)-2,4a, 6a,6b,9,12a-hexamethyl-13-oxo-1,2,3,4,4a,5,6,6a,6b, 7,8,8a,9,10,11,12,12a,12b,13,14b-icosahydropicene-2-carboxylic Acid (121-2)

121-1 (180 mg, 0.31 mmol) and Pd/C (36 mg) in EtOAc (15 mL) were placed under a hydrogen atmosphere (1 atm) and stirred for 1 h at rt. The reaction was filtered and concentrated under vacuum. The residue was purified by prep-HPLC with the following conditions—Column: XBridge Shield RP18 OBD, 5 μm, 19*150 mm; mobile phase: water (0.05% TFA) and MeCN (42.0% MeCN up to 57.0% in 8 min); detector: UV 254 nm. This resulted in 37.9 mg (25%) of 121-2 as a white solid. MS (ES, m/z): [M+H]$^+$= 487.25; $^1$H NMR (400 MHz, MeOH-d$_4$, ppm) δ 0.72 (s, 3H), 0.86 (s, 3H), 0.97-1.12 (m, 2H), 1.14-1.33 (m, 11H), 1.37-1.65 (m, 10H), 1.67-1.79 (m, 2H), 1.80-2.03 (m, 4H), 2.10-2.27 (m, 2H), 2.51 (s, 1H), 2.73 (dt, J=13.5, 3.6 Hz, 1H), 3.29-3.32 (m, 1H), 3.56 (d, J=11.0 Hz, 1H), 3.64 (dd, J=11.8, 4.7 Hz, 1H), 5.60 (s, 1H).

Example 4 (2S,4aS,6aS,6bR,8aR,9S,10S,12aS, 12bR,14bR)-10-Hydroxy-2,4a,6a,6b,9,12a-hexamethyl-13-oxo-1,2,3,4,4a,5,6,6a,6b,7,8,8a,9,10,1142, 12a,12b,13,14b-icosahydropicene-2,9-dicarboxylic Acid (122-3)

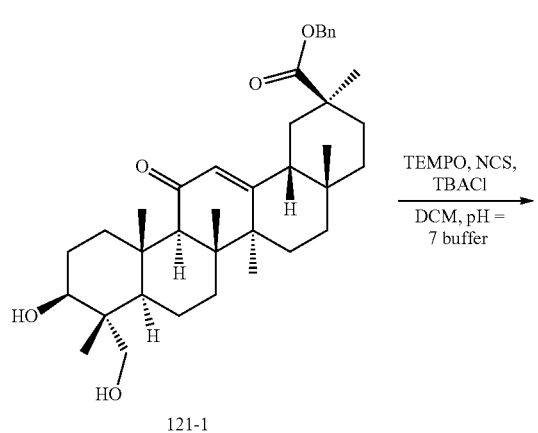

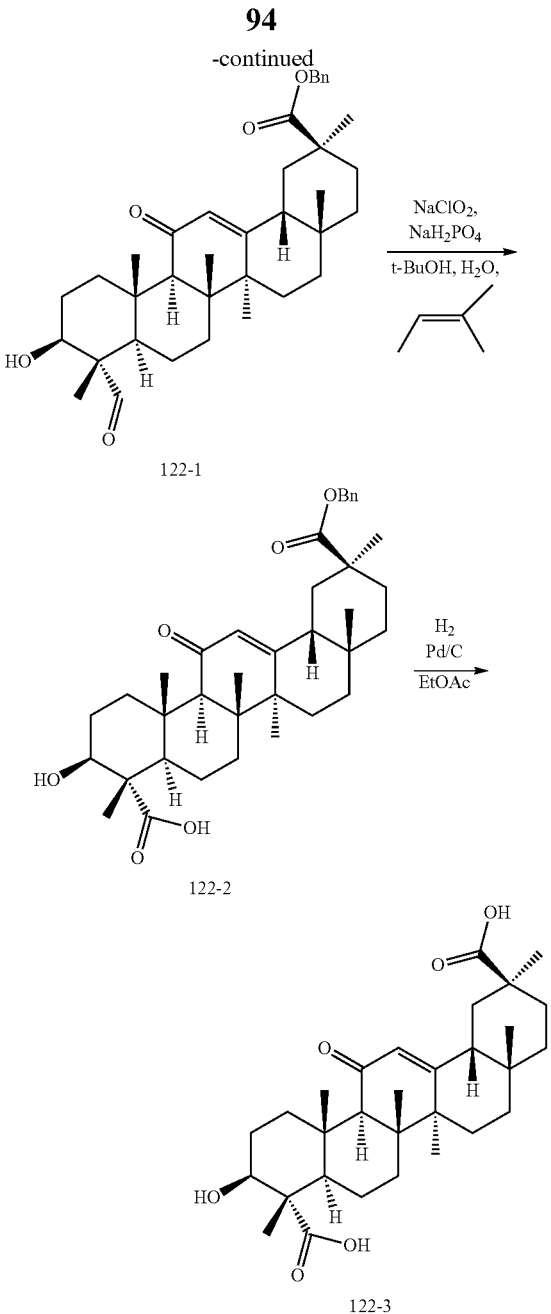

Synthesis of Benzyl (2S,4aS,6aS,6bR,8aR,9S,10S, 12aS,12bR,14bR)-9-formyl-10-hydroxy-2,4a,6a,6b, 9,12a-hexamethyl-13-oxo-1,2,3,4,4a,5,6,6a,6b,7,8, 8a,9,10,11,12,12a,12b,13,14b-icosahydropicene-2-carboxylate (122-1)

121-1 (300 mg, 0.52 mmol, 1 equiv), pH=8.6 phosphate buffer (5 mL), TEMPO (240 mg, 1.54 mmol, 3 equiv), tetrabutylammonium chloride (0.36 g, 2.5 equiv), N-chlorosuccinimide (280 mg, 2.10 mmol, 4 equiv) in DCM (25 mL) were stirred overnight at 40° C. The reaction was extracted with DCM (200 mL). The extract was washed with water (1×200 mL) and brine (1×200 mL), dried (Na$_2$SO$_4$) and concentrated. This resulted in 0.4 g (134%, crude) of 122-1 as a yellow semi-solid.

Synthesis of (3S,4S,4aR,6aR,6bS,8aS,11S,12aR, 14aR,14bS)-11-((Benzyl oxy)carbonyl)-3-hydroxy-4,6a, 6b, 8a, 11,14b-hexamethyl -14-oxo-1,2,3,4,4a, 5,6,6a,6b,7,8,8a,9,10,11,12,12a,14,14a,14b-icosahydropicene-4-carboxylic Acid (122-2)

122-1 (400 mg, 0.70 mmol, 1 equiv), 2-methylbut-2-ene (2 mL), sodium phosphate monobasic (0.5 g, 6.00 equiv) and sodium chlorite (0.38 g, 6.00 equiv) in water (6 mL) and t-butanol (12 mL) were stirred for 30 min at −2° C. The reaction was partially concentrated under vacuum and the residue extracted with DCM (200 mL). The extract was washed with brine (1×200 mL), dried (Na$_2$SO$_4$) and concentrated under vacuum. This resulted in 0.758 g (184%, crud) of 122-2 as a yellow semi-solid.

Synthesis of (2S,4aS,6aS,6bR,8aR,9S,10S, 12aS, 12bR,14bR)-10-Hydroxy-2,4a,6a,6b,9,12a-hexamethyl-13-oxo-1,2,3,4,4a,5,6,6a,6b,7,8,8a,9,10,11,12, 12a,12b,13,14b-icosahydropicene-2,9-dicarboxylic Acid (122-3)

122-2 (225 mg, 0.38 mmol) and Pd/C (45 mg) in EtOAc (16 mL) were placed under a hydrogen atmosphere (1 atm) and stirred overnight at rt. The reaction was filtered and concentrated under vacuum. The residue was purified by prep-HPLC with the following conditions—Column: XBridge Shield RP18 OBD, 5 μm, 19*150 mm; mobile phase: water (0.05% TFA) and MeCN (38.0% MeCN up to 55.0% in 8 min); detector: UV 254 nm. This resulted in 18.5 mg (10%) of 122-3 as a white solid. MS (ES, m/z): [M+H]$^+$= 501.20; $^1$H NMR (400 MHz, MeOH-d$_4$, ppm) δ 0.85 (s, 3H), 1.01-1.31 (m, 16H), 1.44 (d, J=13.4 Hz, 7H), 1.54 (d, J=10.8 Hz, 1H), 1.59-1.81 (m, 5H), 1.81-2.01 (m, 3H), 2.10-2.28 (m, 2H), 2.54 (s, 1H), 2.79 (dt, J=13.7, 3.6 Hz, 1H), 3.99 (dd, J=11.8, 4.7 Hz, 1H), 5.62 (s, 1H).

Example 5 (2S,4aS,6aS,6bR,8aS,10S,12aS,12bR, 14bR)-2,4a,6a,6b,9,9,12a-Heptamethyl-10-(((5-methyl-2-oxo-1,3-dioxol-4-yl)methoxy)carbonyl)-13-oxo-1,2,3,4,4a,5,6,6a,6b,7,8,8a,9,10,1142,12a, 12b,13,14b-icosahydropicene-2-carboxylic Acid (176-2)

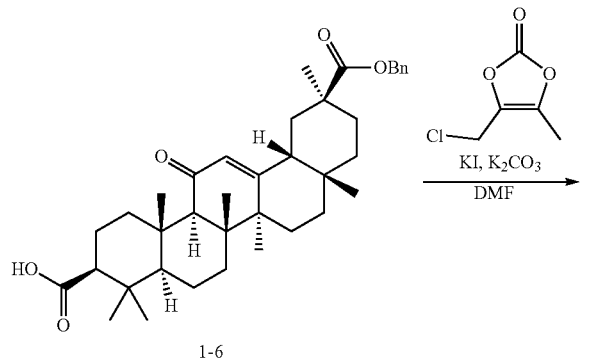

1-6

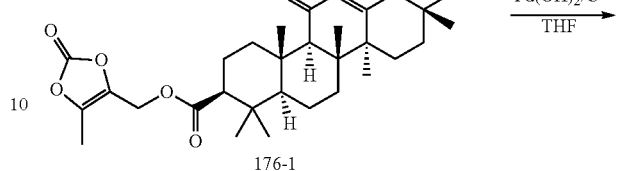

176-1

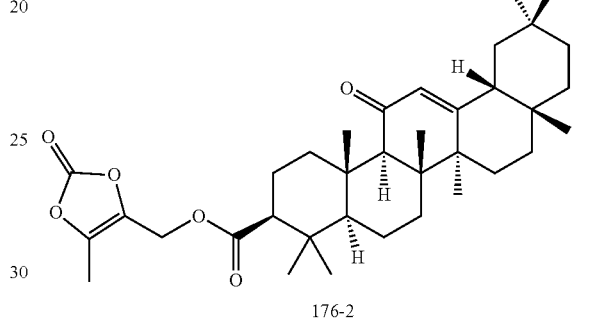

176-2

Synthesis of 2-Benzyl 10-((5-methyl-2-oxo-1,3-dioxol-4-yl)methyl) (2S,4aS,6aS,6bR,8aS,10S,12aS, 12bR,14bR)-2,4a,6a,6b,9,9,12a-heptamethyl-13-oxo-1,2,3,4,4a,5,6,6a,6b,7,8,8a,9,10,11,12,12a,12b, 13,14b-icosahydropicene-2,10-dicarboxylate (176-1)

1-6 (400 mg, 0.68 mmol, 1 equiv), potassium iodide (56 mg, 0.5 equiv), 4-(chloromethyl)-5-methyl-2H-1,3-dioxol-2-one (182 mg, 1.23 mmol, 1.8 equiv), and potassium carbonate (282 mg, 2.04 mmol, 3 equiv) in DMF (2.5 mL) were stirred for 2 h at 60° C. The reaction was diluted with EtOAc, washed with water and brine, dried (Na$_2$SO$_4$) and concentrated under vacuum. The residue was purified by silica gel column eluting with EtOAc/petroleum ether (1:3). This resulted in 460 mg (97%) of 176-1 as a light-yellow solid.

Synthesis of (2S,4aS,6aS,6bR,8aS,10S,12aS,12bR, 14bR)-2,4a,6a,6b,9,9,12a-Heptamethyl-10-(((5-methyl-2-oxo-1,3-dioxol-4-yl)methoxy)carbonyl)-13-oxo-1,2,3,4,4a,5,6,6a,6b,7,8,8a,9,10,11,12,12a, 12b,13,14b-icosahydropicene-2-carboxylic Acid (176-2)

176-1 (70 mg) and Pd(OH)$_2$/C (5.6 mg) in THF (5 mL) were placed under a hydrogen atmosphere (1 atm) and stirred for 13h at rt. The reaction was filtered and concentrated. The residue was purified by prep-HPLC with the following conditions—Column: XBridge Shield RP18 OBD, 5 μm, 19*150 mm; mobile phase: water (0.05% TFA)

and MeCN (68% Phase B up to 77% in 10 min); detector: UV. This resulted in 13.2 mg (21.64%) of 176-2 as a white solid. MS (ES, m/z): [M+H]$^+$=611.45; $^1$H NMR (400 MHz, MeOH-d$_4$) δ 0.88 (d, J=13.9 Hz, 6H), 0.90-0.93 (m, 1H), 0.95-1.09 (m, 5H), 1.10-1.24 (m, 9H), 1.25-1.30 (m, 1H), 1.31-1.55 (m, 9H), 1.63-1.80 (m, 3H), 1.81-2.06 (m, 4H), 2.09-2.22 (m, 5H), 2.29 (dd, J=13.2, 3.2 Hz, 1H), 2.50 (s, 1H), 2.76 (d, J=13.6 Hz, 1H), 4.89-4.99 (m, 2H), 5.57 (s, 1H).

Example 6 (2S,4aS,6aS,6bR,8aS,10S,12aS,12bR, 14bR)-2,4a,6a,6b,9,9,12a-Heptamethyl-10-(((5-methyl-2-oxo-1,3-dioxolan-4-yl)methoxy)carbonyl)-13-oxo-1,2,3,4,4a,5,6,6a,6b,7,8,8a,9,10,1142,12a, 12b,13,14b-icosahydropicene-2-carboxylic (178-1)

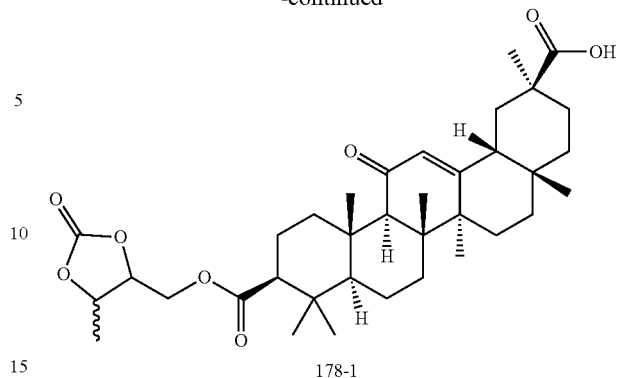

176-1 (110 mg) and Pd(OH)$_2$/C (11 mg) in THF (10 mL) and EtOH (10 mL) were stirred for 1 h at rt. The reaction was filtered and concentrated. The residue was purified by prep-HPLC with the following conditions—Column: XBridge Shield RP18 OBD, 5 μm, 19*150 mm; mobile phase: water (0.05% TFA) and MeCN (5% Phase B up to 84% in 1 min, up to 93% in 7 min); detector: UV. This resulted in 26.4 mg 178-1 as a white solid. MS (ES, m/z): [M+H]$^+$=613.40; NMR (400 MHz, MeOH-d$_4$) δ 0.83 (s, 3H), 0.85-0.91 (m, 4H), 0.97-1.09 (m, 5H), 1.13-1.16 (m, 3H), 1.18-1.19 (m, 5H), 1.21-1.31 (m, 2H), 1.38-1.58 (m, 12H), 1.63-1.78 (m, 3H), 1.79-2.08 (m, 4H), 2.16 (qd, J=12.8, 4.4 Hz, 2H), 2.28 (dt, J=13.2, 4.4 Hz, 1H), 2.51 (s, 1H), 2.77 (d, J=13.2 Hz, 1H), 4.19-4.32 (m, 1H), 4.36-4.50 (m, 1H), 4.91-4.99 (m, 1H), 5.00-5.09 (m, 1H), 5.57 (s, 1H).

Example 7 (2S,4aS,6aS,6bR,8aR,9S,10S,12aS, 12bR,14bR)-10-((2,5,8,11-tetraoxatetradecan-14-oyl)oxy)-2,4a,6a,6b,9,12a-hexamethyl-13-oxo-1,2,3, 4,4a,5,6,6a,6b,7,8,8a,9,10,1142,12a,12b,13,14b-icosahydropicene-2,9-dicarboxylic Acid (190-3)

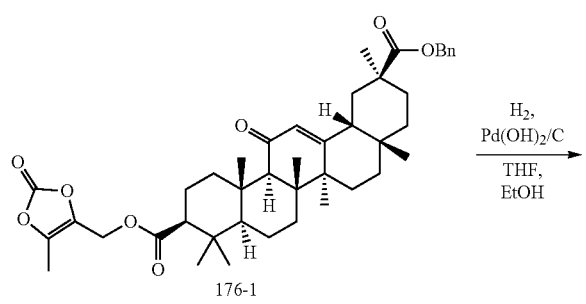

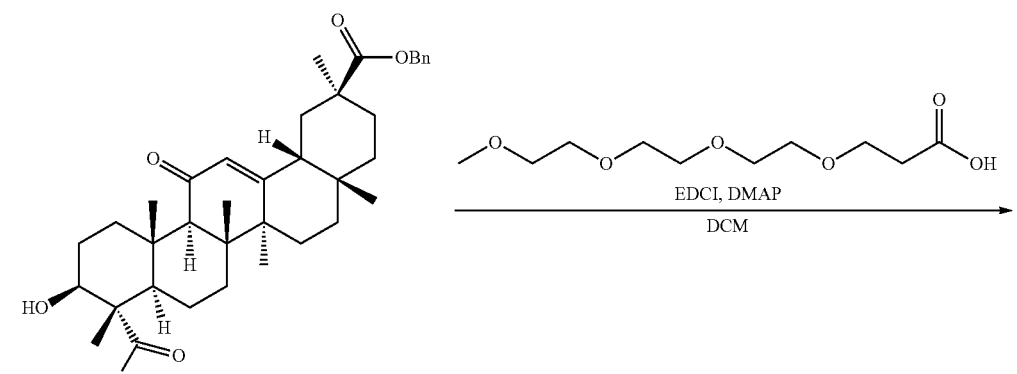

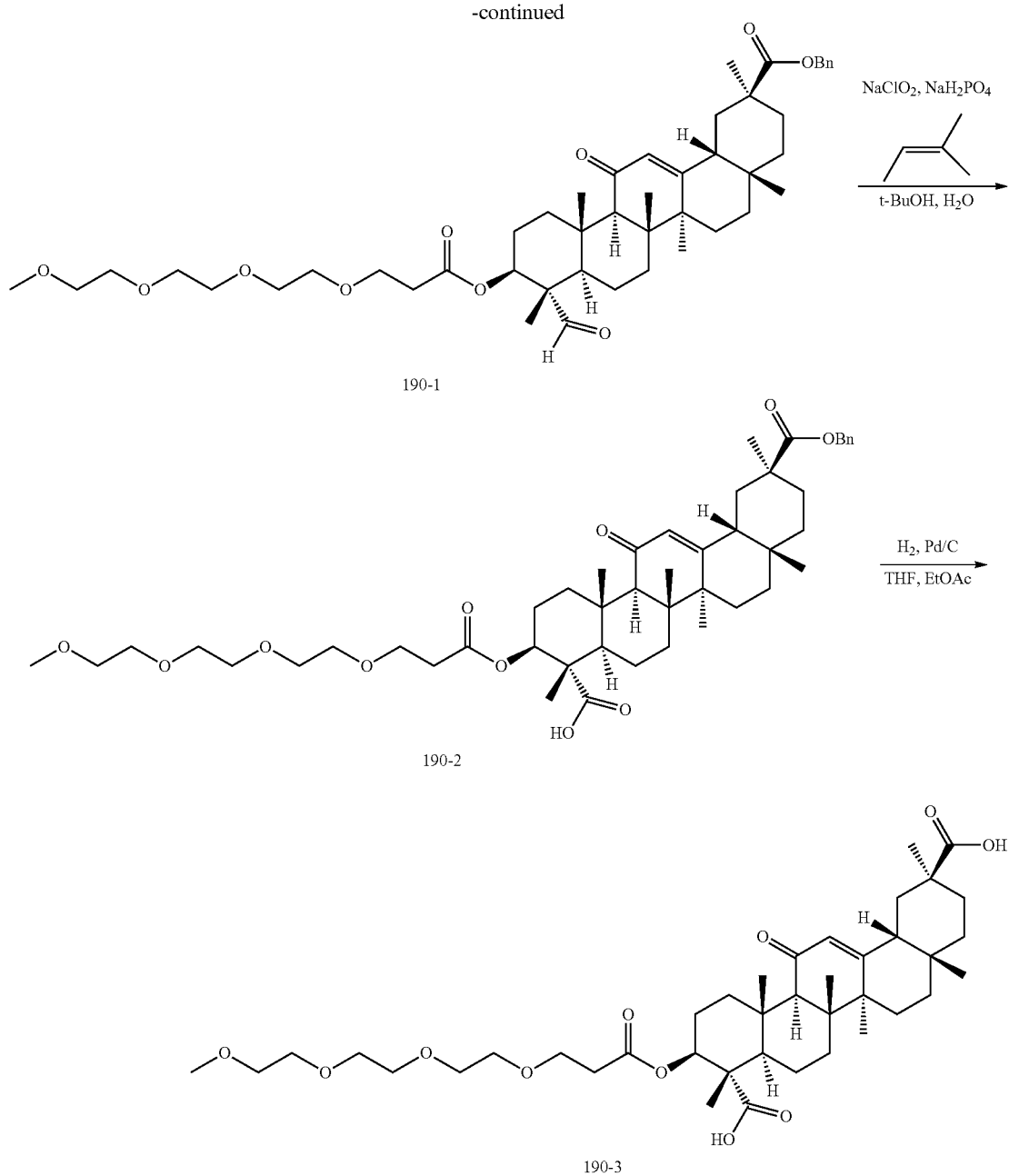

Synthesis of (3S,4S,4aR,6aR,6bS,8aS,11S,12aR, 14aR,14bS)-11-((benzyloxy)carbonyl)-4-formyl-4, 6a,6b,8a,11,14b-hexamethyl-14-oxo-1,2,3,4,4a,5,6, 6a,6b,7,8,8a,9,10,11,12,12a,14,14a,14b-icosahydropicen-3-yl 2,5,8,11-tetraoxatetradecan-14-oate (190-1)

EDCI (250 mg, 1.30 mmol, 2.5 equiv) was added to 122-1 (300 mg, 0.52 mmol, 1 equiv), 2,5,8,11-tetraoxatetradecan-14-oic acid (370 mg, 1.57 mmol, 3 equiv) and DMAP (130 mg, 1.06 mmol, 2 equiv) in DCM (20 mL). The reaction was stirred for 3 h at rt and then concentrated under vacuum. The residue was purified by silica gel column eluting with EtOAc/hexane (2:1). This resulted in 0.2 g (48%) of 190-1 as a yellow semi-solid.

Synthesis of (3S,4S,4aR,6aR,6bS,8aS,11S,12aR, 14aR,14bS)-3-((2,5,8,11-tetraoxatetradecan-14-oyl) oxy)-11-((benzyloxy)carbonyl)-4,6a,6b,8a,11,14b-hexamethyl-14-oxo-1,2,3,4,4a,5,6,6a,6b,7,8,8a,9,10, 11,12,12a,14,14a,14b-icosahydropicene-4-carboxylic Acid (190-2)

190-1 (200 mg, 0.25 mmol, 1 equiv), 2-methylprop-1-ene (2 mL), sodium dihydrogen phosphate (0.18 g, 6.00 equiv) and sodium chlorite (0.14 g, 6.00 equiv) in t-butanol (9 mL) and water (3 mL) were stirred for 2 h at rt. The reaction was concentrated under vacuum, diluted with DCM, washed with brine, dried over anhydrous sodium sulfate and concentrated under vacuum. This resulted in 0.2 g (98%) of 190-2 as a yellow solid.

Example 8 (2S,4aS,6aS,6bR,8aR,9S,10S,12aS, 12bR,14bR)-2,4a,6a,6b,9,12a-Hexamethyl-9-(((5-methyl-2-oxo-1,3-dioxol-4-yl)methoxy)carbonyl)-10-(2-(methylthio)acetoxy)-13-oxo-1,2,3,4,4a,5,6,6a, 6b,7,8,8a,9,10,1142,12a,12b,13,14b-icosahydropicene-2-carboxylic Acid (194-10)
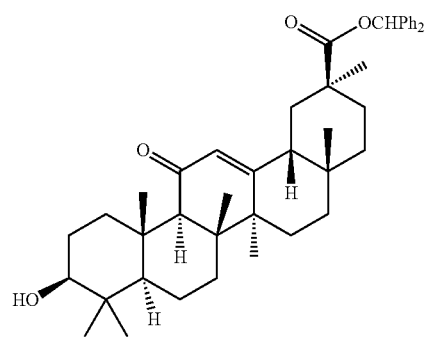
76-1
DMP / CH$_2$Cl$_2$
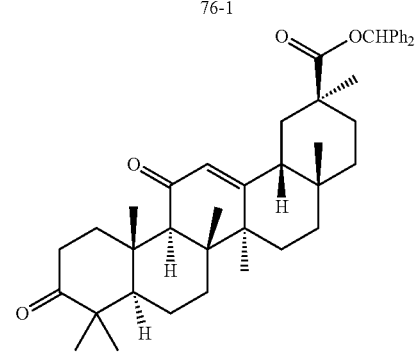
194-1
H$_2$NOH·HCl / Pyridine, 70° C.
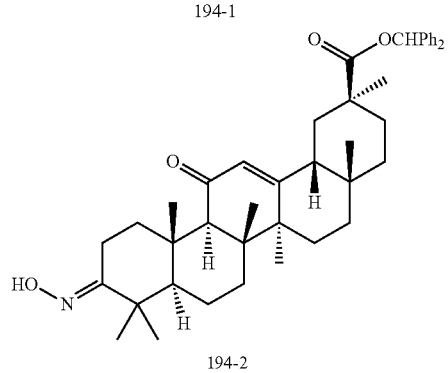
194-2
Pd(OAc)$_2$, PhI(OAc)$_2$ / 1:1 AcOH:Ac$_2$O
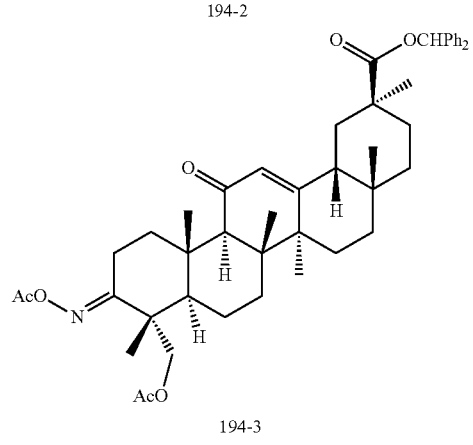
194-3
2M HCl (aq) / MeOH/ THF/ acetone
-continued
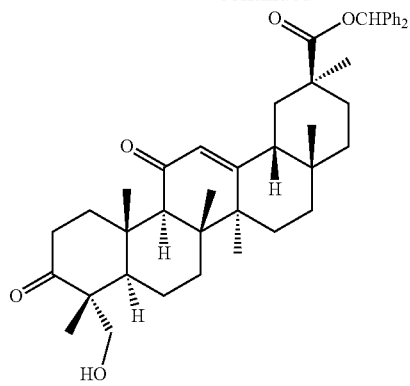
194-4
NaBH$_4$ / MeOH
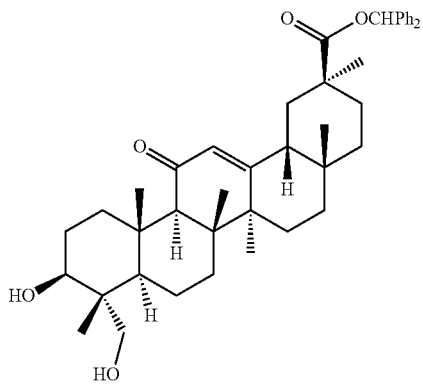
194-5
TEMPO, NCS, TBACl / CH$_2$Cl$_2$, pH 8.6 buffer
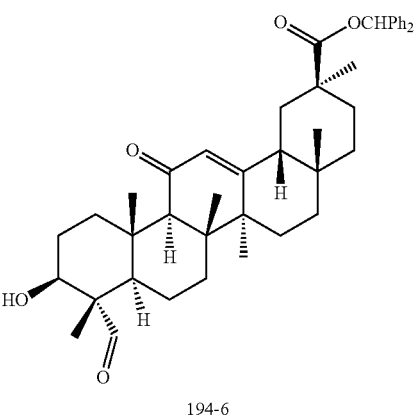
194-6
NaClO$_2$, NaH$_2$PO$_4$ / t-BuOH, H$_2$O
194-7
K$_2$CO$_3$, DMF, KI

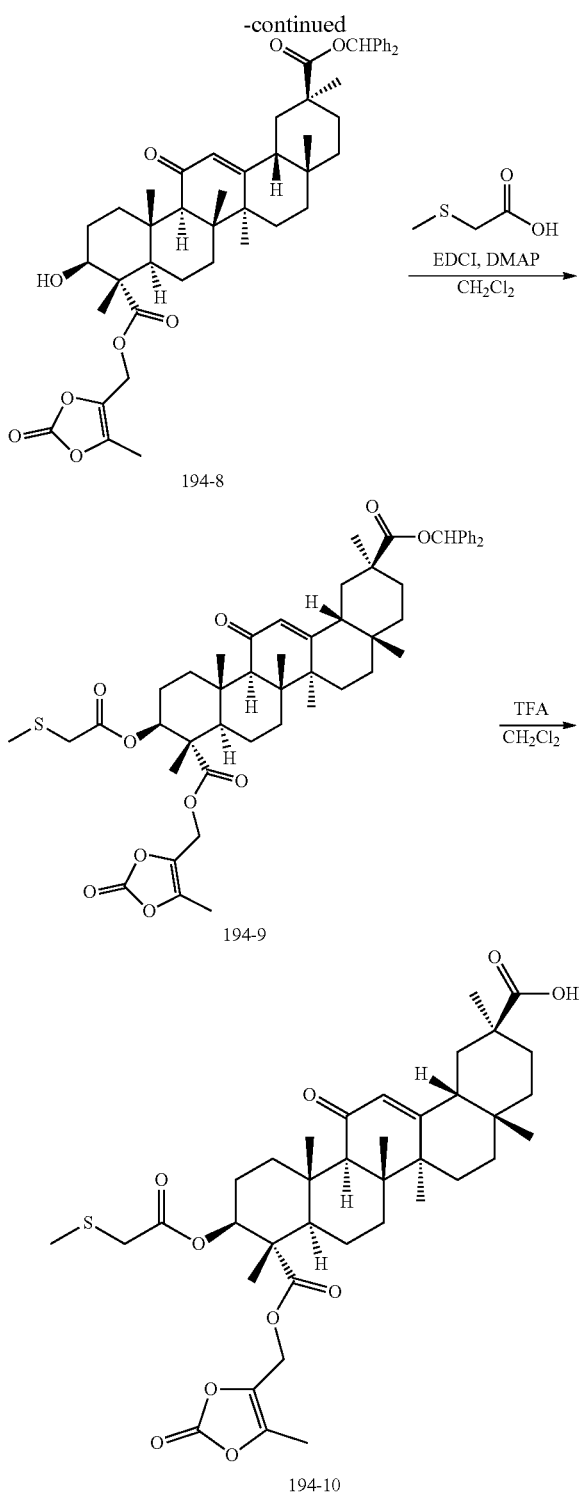

Synthesis of benzhydryl (2S,4aS,6aS,6bR,8aR,12aS, 12bR,14bR)-2,4a,6a,6b,9,9,12a-heptamethyl-10,13-dioxo-1,2,3,4,4a,5,6,6a,6b,7,8,8a,9,10,11,12,12a, 12b,13,14b-icosahydropicene-2-carboxylate (194-1)

Into a 2-L round-bottom flask was placed 76-1 (prepared as described in Bioorg. Med Chem. 2010, 18, 433-454) (105 g, 165 mmol, 1 equiv), $CH_2Cl_2$ (800 mL), and Dess-Martin periodinane (139.8 g, 330 mmol, 2 equiv). The resulting mixture was stirred overnight at room temperature. The reaction was quenched by the addition of 300 mL of sodium bicarbonate. The reaction mixture was washed with 3×1 L of $H_2O$. The organic layer was dried over anhydrous sodium sulfate, filtered, and concentrated under vacuum. The crude product was re-crystallized from petroleum ether and $CH_2Cl_2$ to provide 194-1 (100 g, 96%) as a white solid.

Synthesis of benzhydryl (2S,4aS,6aS,6bR,8aR,12aS, 12bR,14bR,E)-10-(hydroxyimino)-2,4a,6a,6b,9,9, 12a-heptamethyl-13-oxo-1,2,3,4,4a,5,6,6a,6b,7,8,8a, 9,10,11,12,12a,12b,13,14b-icosahydropicene-2-carboxylate (194-2)

Into a 2-L round-bottom flask was placed 194-1 (59.5 g, 93.7 mmol, 1 equiv), pyridine (1 L), and $NH_2OH·HCl$ (23.2 g, 335 mmol, 3.6 equiv). The reaction slurry was stirred for 1 h at 70° C. The reaction mixture was concentrated under vacuum, diluted with 2 L of $CH_2Cl_2$, and washed with 4×1 L of 3 N HCl and 1 L of brine. The combined organic layers were dried over anhydrous $Na_2SO_4$, filtered, and concentrated under reduced pressure. The crude product was re-crystallized from $CH_2Cl_2$/petroleum ether to afford 194-2 (55.1 g, 90%) as a white solid. MS (ES, m/z): $[M+1]^+=$ 650.15; $^1$H NMR (300 MHz, Chloroform-d) δ 7.58-7.21 (m, 10H), 6.96 (s, 1H), 5.55 (s, 1H), 5.32 (s, 1H), 3.09 (ddd, J=15.5, 5.1, 3.6 Hz, 1H), 2.90 (ddd, J=13.3, 5.7, 3.6 Hz, 1H), 2.41-2.21 (m, 2H), 2.12-1.96 (m, 4H), 1.92-1.76 (m, 1H), 1.65 (q, J=18.6, 16.7 Hz, 3H), 1.56-1.25 (m, 11H), 1.24-0.92 (m, 16H), 0.70 (s, 3H).

Synthesis of benzhydryl (2S,4aS,6aS,6bR,8aR,9S, 12aS,12bR,14bR,E)-10-(acetoxyimino)-9-(acetoxymethyl)-2,4a,6a,6b,9,12a-hexamethyl-13-oxo-1,2,3, 4,4a,5,6,6a,6b,7,8,8a,9,10,11,12,12a,12b,13,14b-icosahydropicene-2-carboxylate (194-3)

Into a 2-L round-bottom flask was placed 194-2 (53.4 g, 82.2 mmol, 1 equiv), AcOH (400 mL), $AC_2O$ (400 mL), $Pd(OAc)_2$ (3.3 g, 14.8 mmol, 0.18 equiv), and $PhI(OAc)_2$ (31.8 g, 98.6 mmol, 1.2 equiv). The reaction slurry was stirred overnight at 60° C. The reaction mixture was concentrated, diluted in $CH_2Cl_2$, washed with saturated $NaHCO_{3(aq)}$ and brine, dried over anhydrous $Na_2SO_4$, filtered, and concentrated. The residue was purified by silica gel column chromatography, eluting with 0-40% EtOAc in petroleum ether to afford 194-3 (31.3 g, 51%) as a light yellow solid (mixture of isomers, ~6:1 C-23:C-24 acetates).

Synthesis of benzhydryl (2S,4aS,6aS,6bR,8aR,9R, 12aS,12bR,14bR)-9-(hydroxymethyl)-2,4a,6a, 6b,9, 12a-hexamethyl-10,13-dioxo-1,2,3,4,4a,5,6,6a,6b,7, 8,8a,9,10,11,12,12a,12b,13,14b-icosahydropicene-2-carboxylate (194-4)

Into a 1000-mL round-bottom flask was placed diphenylmethyl 194-3 (15 g, 20 mmol), THF (90 mL), MeOH (90 mL), acetone (90 mL), and 2 N HCl (90 mL). The reaction slurry was stirred overnight at 50° C. The reaction mixture was concentrated, diluted with $CH_2Cl_2$, and washed with 2×300 mL of saturated $NaHCO_3$ and 2×300 mL of brine. The organic layer was dried over anhydrous $Na_2SO_4$, filtered, and concentrated. The solid was dried in an oven under reduced pressure. The residue was applied onto a silica gel column with CH$_2$Cl$_2$/ethyl acetate (4:1) to provide 9 g (69%) of 194-4 as a yellow solid (single C-23 OH isomer).

Synthesis of benzhydryl (2S,4aS,6aS,6bR,8aR,9R, 10S,12aS,12bR,14bR)-10-hydroxy-9-(hydroxymethyl)-2,4a,6a,6b,9,12a-hexamethyl-13-oxo-1,2,3,4, 4a,5,6,6a,6b,7,8,8a,9,10,11,12,12a,12b,13,14b-icosahydropicene-2-carboxylate (194-5)

To a stirred slurry of 194-4 (10 g, 15.4 mmol) in methanol (200 mL) was added NaBH$_4$ (0.6 g, 17 mmol, 1.1 equiv) in portions as −10° C. The reaction slurry was stirred for 1 h at room temperature. Upon completion the reaction was quenched with ice water and extracted with EtOAc. The combined organic layers were washed with brine, dried over anhydrous Na$_2$SO$_4$, filtered, and concentrated. The residue was applied onto a silica gel column with ethyl acetate (0% to 60% in 30 min) in petroleum ether to provide 8.4 g (84%) of 194-5 as a white foam (single C-3-beta isomer).

Synthesis of benzhydryl (2S,4aS,6aS,6bR,8aR,9S, 10S,12aS,12bR,14bR)-9-formyl-10-hydroxy-2,4a,6a, 6b,9,12a-hexamethyl-13-oxo-1,2,3,4,4a,5,6,6a,6b,7, 8,8a,9,10,11,12,12a,12b,13,14b-icosahydropicene-2-carboxylate (194-6)

Into a 250-mL round-bottom flask was placed 194-5 (4 g, 6.13 mmol), CH$_2$Cl$_2$ (40 mL), pH 8.6 buffer (20 mL), TEMPO (2.87 g, 18.4 mmol, 3 equiv), TBACl (4.26 g), and NCS (3.2 g, 24 mmol, 3.9 equiv). The resulting solution was stirred for 1.5 h at 40° C. The reaction mixture was cooled and extracted with 3×50 mL of CH$_2$Cl$_2$. The combined organic layers were washed with 2×100 mL of brine, dried over anhydrous Na$_2$SO$_4$, filtered, and concentrated. The residue was applied onto a silica gel column with ethyl acetate (0-60%) in petroleum ether to provide 3.8 g (95%) of 194-6 as a white solid.

Synthesis of (3S,4S,4aR,6aR,6bS,8aS,11S,12aR, 14aR,14bS)-11-((benzhydryloxy)carbonyl)-3-hydroxy-4,6a, 6b, 8a, 11,14b-hexamethyl -14-oxo-1,2, 3,4,4a,5,6,6a,6b,7,8,8a,9,10,11,12,12a,14,14a,14b-icosahydropicene-4-carboxylic Acid (194-7)

To a stirred solution of 194-6 (4 g, 6.2 mmol) and 2-methylbut-2-ene (6.6 mL) in water (8.9 mL) and t-BuOH (26.6 mL) was added NaH$_2$PO$_4$ (4.4 g, 36.87 mmol, 6 equiv) at 0° C. To the above mixture was added NaClO$_2$ (3.3 g, 37 mmol, 6 equiv) in portions at 0° C. The reaction slurry was stirred for 2 h at room temperature. The reaction mixture was extracted with CH$_2$Cl$_2$ and the combined organic layers were washed with brine, dried over anhydrous Na$_2$SO$_4$, filtered, and concentrated to provide 4 g of crude 194-7 as light yellow solid, which was used in the next step directly without further purification.

Synthesis of (3S,4S,4aR,6aR,6bS,8aS,11S,12aR, 14aR,14bS)-11-((benzhydryloxy)carbonyl)-3-hydroxy-4,6a,6b,8a,11,14b-hexamethyl-14-oxo-1,2,3,4, 4a,5,6,6a,6b,7,8,8a,9,10,11,12,12a,14,14a,14b-icosahydropicene-4-carboxylic Acid (194-8)

A solution of 194-7 (6.0 g, 9 mmol), K$_2$CO$_3$ (3.7 g, 27 mmol, 3 equiv) and KI (0.75 g, 4.5 mmol, 0.5 equiv) in DMF was stirred for 2 h at 60° C. The reaction mixture was extracted with EtOAc. The combined organic layers were washed with brine, dried over anhydrous Na$_2$SO$_4$, filtered, and concentrated under reduced pressure. The residue was purified by silica gel column chromatography, elutin with 2:1 petroleum ether/EtOAc to afford 194-8 (6.0 g, 86%) as a light yellow solid. MS (ES, m/z): [M+1]$^+$=779.00; $^1$H NMR (400 MHz, Chloroform-d) δ 7.50-7.29 (m, 10H), 6.95 (s, 1H), 5.54 (s, 1H), 5.04 (d, J=13.8 Hz, 1H), 4.80 (d, J=13.9 Hz, 1H), 4.44 (s, 2H), 4.03 (dd, J=9.9, 6.5 Hz, 1H), 2.98 (s, 1H), 2.88 (d, J=19.4 Hz, 2H), 2.79 (s, 4H), 2.40 (s, 1H), 2.22 (d, J=6.6 Hz, 6H), 2.14-1.93 (m, 4H), 1.70 (dddd, J=37.5, 31.0, 16.9, 7.4 Hz, 8H), 1.48 (d, J=10.1 Hz, 1H), 1.41-1.32 (m, 6H), 1.27 (dd,7=14.6, 3.4 Hz, 1H), 1.24-1.10 (m, 11H), 1.08 (s, 3H), 1.04-0.94 (m, 1H), 0.88 (d, J=8.8 Hz, 1H), 0.67 (s, 3H).

Synthesis of 2-Benzhydryl 9-((5-methyl-2-oxo-1,3-dioxol-4-yl)methyl) (2S,4aS,6aS,6bR,8aR,9S,10S, 12aS,12bR,14bR)-2,4a,6a,6b,9,12a-hexamethyl-10-(2-(methylthio)acetoxy)-13-oxo-1,2,3,4,4a,5,6,6a,6b, 7,8,8a,9,10,11,12,12a,12b,13,14b-icosahydropicene-2,9-dicarboxylate (194-9)

EDCI (250 mg, 1.30 mmol, 5 equiv) was added to 194-8 (200 mg, 0.26 mmol, 1 equiv), 2-(methylsulfanyl)acetic acid (270 mg, 2.54 mmol, 10 equiv) and DMAP (120 mg, 0.98 mmol, 4 equiv) in CH$_2$Cl$_2$ (4 mL). The reaction was stirred overnight at rt and concentrated under vacuum. The residue was purified by silica gel column with 1:1 EtOAc:petroleum ether to provide 240 mg (quant) of 194-9 as a light yellow solid.

Synthesis of (2S,4aS,6aS,6bR,8aR,9S,10S,12aS, 12bR,14bR)-2,4a,6a,6b,9,12a-Hexamethyl-9-(((5-methyl-2-oxo-1,3-dioxol-4-yl)methoxy)carbonyl)-10-(2-(methylthio)acetoxy)-13-oxo-1,2,3,4,4a,5,6,6a, 6b,7,8,8a,9,10,11,12,12a,12b,13,14b-icosahydropicene-2-carboxylic Acid (194-10)

194-9 (130 mg, 0.15 mmol, 1 equiv) and TFA (0.2 mL) in CH$_2$Cl$_2$ (2 mL) were stirred for 1 h at rt. The reaction was concentrated under vacuum and the residue purified by prep-HPLC with the following conditions—Column: XBridge Shield RP18 OBD, 30*150 mm, 5 μm; mobile phase: water (0.05% TFA) and MeCN (65% Phase B up to 75% in 8 min); detector: UV. This resulted in 24.8 mg (24%) of 194-10 as an off-white solid. MS (ES, m/z) [M+H]$^+$= 701.10; $^1$H-NMR (300 MHz, MeOH-d$_4$) δ 5.62 (s, 1H), 5.22 (dd, J=11.3, 5.3 Hz, 1H), 5.04 (d, J=13.9 Hz, 1H), 4.91 (s, 1H), 3.15 (s, 2H), 2.85 (d, J=13.7 Hz, 1H), 2.59 (s, 1H), 2.19 (d, J=8.2 Hz, 8H), 2.04-1.62 (m, 9H), 1.45 (d, J=13.6 Hz, 7H), 1.35-1.12 (m, 14H), 1.02 (dd,7=29.5, 10.7 Hz, 2H), 0.85 (s, 3H).

Example 9 (2S,4aS,6aS,6bR,8aR,9S,10S,12aS,12bR,14bR)-2,4a,6a,6b,9,12a-Hexamethyl-9-(((5-methyl-2-oxo-1,3-dioxol-4-yl)methoxy)carbonyl)-10-(2-(methylsulfonyl)acetoxy)-13-oxo-1,2,3,4,4a,5,6,6a,6b,7,8,8a,9,10,11,12,12a,12b,13,14b-icosahydropicene-2-carboxylic Acid (195-2)

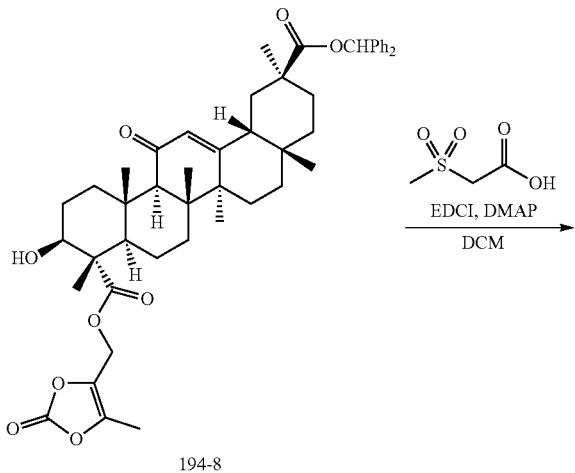

194-8

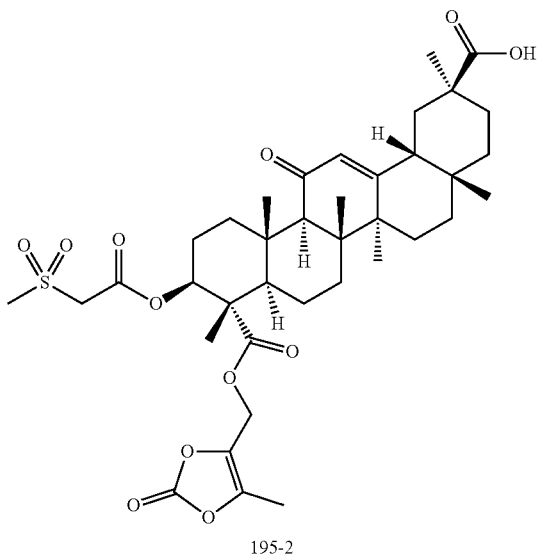

195-2

Synthesis of 2-Benzhydryl 9-((5-methyl-2-oxo-1,3-dioxol-4-yl)methyl) (2S,4aS,6aS,6bR,8aR,9S,10S,12aS,12bR,14bR)-2,4a,6a,6b,9,12a-hexamethyl-10-(2-(methylsulfonyl)acetoxy)-13-oxo-1,2,3,4,4a,5,6,6a,6b,7,8,8a,9,10,11,12,12a,12b,13,14b-icosahydropicene-2,9-dicarboxylate (195-1)

EDCI (175 mg, 0.91 mmol, 5 equiv) was added to 194-8 (140 mg, 0.18 mmol, 1 equiv), 2-methanesulfonylacetic acid (248 mg, 1.80 mmol, 10 equiv) and DMAP (84 mg, 0.69 mmol, 4 equiv) in $CH_2Cl_2$ (2.5 mL) and the reaction stirred overnight at rt. The resulting mixture was concentrated under vacuum and the residue purified by silica gel column with EtOAc/Petroleum ether (1/1). This resulted in 160 mg (99%) of 195-1 as a light yellow solid.

Synthesis of (2S,4aS,6aS,6bR,8aR,9S,10S,12aS,12bR,14bR)-2,4a,6a,6b,9,12a-Hexamethyl-9-(((5-methyl-2-oxo-1,3-dioxol-4-yl)methoxy)carbonyl)-10-(2-(methyl sulfonyl)acetoxy)-13-oxo-1,2,3,4,4a,5,6,6a,6b,7,8,8a,9,10,11,12,12a,12b,13,14b-icosahydropicene-2-carboxylic Acid (195-2)

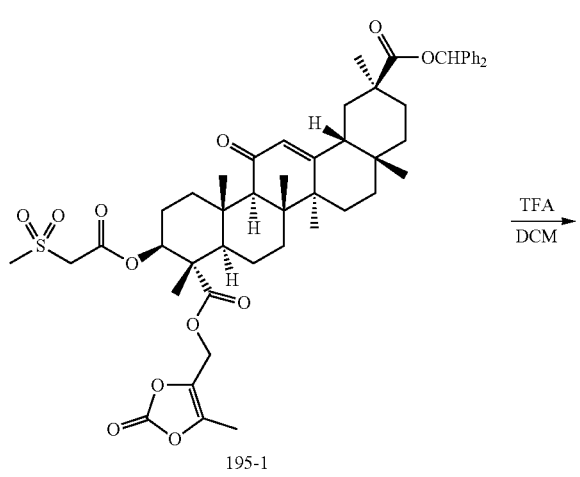

195-1

A mixture of 195-1 (100 mg, 0.11 mmol, 1 equiv) and TFA (0.1 mL, 0.01 equiv) in DCM was stirred for 1 h at rt. The resulting mixture was concentrated under vacuum. The crude product was purified by prep-HPLC with the following conditions—Column: XBridge Shield RP18 OBD, 5 μm, 19*150 mm; mobile phase: water (0.05% TFA) and MeCN (50% Phase B up to 63% in 13 min); detector: UV. This resulted in 195-2 (35.1 mg, 43.06%) as a light yellow solid. MS (ES, m/z): $[M+H]^+$=732.95; $^1H$ NMR (300 MHz, MeOH-d4) δ 5.63 (s, 1H), 5.39-5.26 (m, 1H), 5.05 (d, J=13.9 Hz, 1H), 4.21 (s, 2H), 3.14 (d, J=1.0 Hz, 3H), 2.87 (d, J=14.0 Hz, 1H), 2.60 (s, 1H), 2.21 (s, 5H), 1.85 (s, 6H), 1.77 (d, J=13.2 Hz, 1H), 1.70 (d, J=16.6 Hz, 2H), 1.46 (d, J=13.0 Hz, 7H), 1.30 (s, 4H), 1.25-1.13 (m, 10H), 1.00 (s, 1H), 0.86 (s, 3H).

Example 10 (2S,4aS,6aS,6bR,8aR,9S,10S,12aS, 12bR,14bR)-10-(((L-Valyl)oxy)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic Acid (196-2)
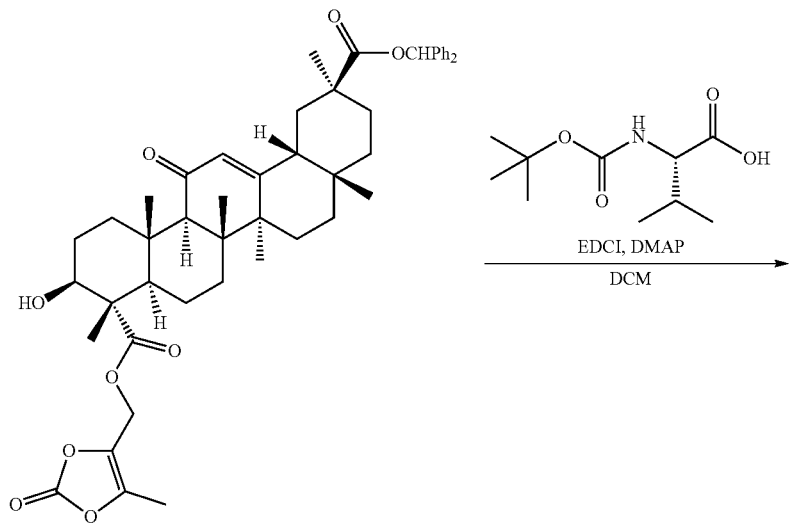
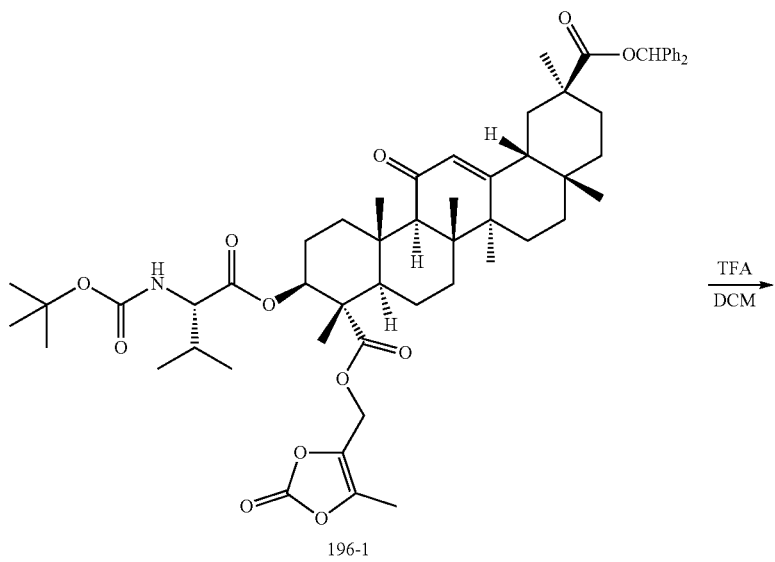

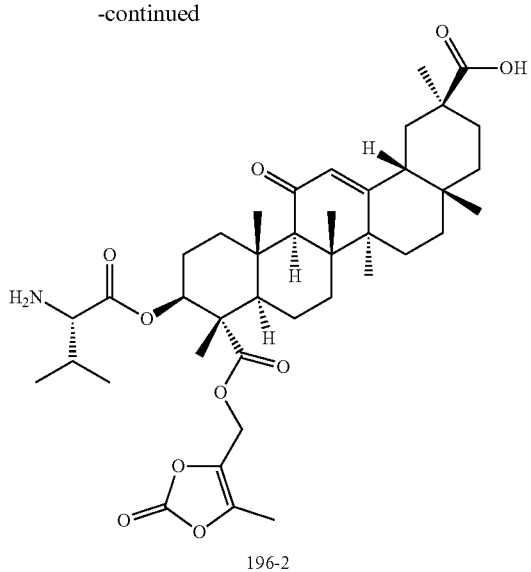

196-2

Synthesis of 2-Benzhydryl 9-((5-methyl-2-oxo-1,3-dioxol-4-yl)methyl) (2S,4aS,6aS,6bR,8aR,9S,10S,12aS,12bR,14bR)-10-(((tert-butoxycarbonyl)-L-valyl)oxy)-2,4a,6a,6b,9,12a-hexamethyl-13-oxo-1,2,3,4,4a,5,6,6a,6b,7,8,8a,9,10,11,12,12a,12b,13,14b-icosahydropicene-2,9-dicarboxylate (196-1)

EDCI (172.3 mg, 0.90 mmol, 5 equiv) was added to 194-8 (140 mg, 0.18 mmol, 1 equiv), (2S)-2-[[(tert-butoxy)carbonyl]amino]-3-methylbutanoic acid (195.2 mg, 0.90 mmol, 5 equiv) and DMAP (87.8 mg, 0.72 mmol, 4 equiv) in DCM. The reaction was stirred overnight at rt and concentrated under reduced pressure. The residue was purified by prep-TLC (Petroleum ether/EtOAc 1:1) to afford 196-1 (170 mg, 96.70%) as a light yellow solid.

Synthesis of (2S,4aS,6aS,6bR,8aR,9S,10S,12aS,12bR,14bR)-10-((L-Valyl)oxy)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic acid (196-2)

196-1 (170 mg, 0.17 mmol, 1 equiv) and TFA (0.15 mL, 2.02 mmol, 12 equiv) in DCM was stirred for 1 h at rt and then concentrated under vacuum. The crude product was purified by prep-HPLC with the following conditions— Column: Xselect CSH OBD, 30*150 mm, 5 μm; mobile phase A: water (0.05% TFA), mobile phase B: MeCN; Flow rate: 60 mL/min; Gradient: 37% B to 65% B in 8 min; detector UV 254 nm to afford 196-2 (51.5 mg, 41.63%) as an off-white solid. MS (ES, m/z): [M+H]$^+$=712.45; $^1$H NMR (400 MHz, MeOH-d$_4$) δ 5.63 (s, 1H), 5.43-5.34 (m, 1H), 5.11 (d, J=14.0 Hz, 1H), 4.84 (d, J=14.0 Hz, 1H), 3.92 (d, J=4.2 Hz, 1H), 2.87 (d, J=13.6 Hz, 1H), 2.59 (s, 1H), 2.27-2.12 (m, 2H), 2.21 (s, 4H), 1.98 (d, J=10.0 Hz, 1H), 1.87 (d, J=9.7 Hz, 4H), 1.80-1.60 (m, 4H), 1.44 (d, J=16.3 Hz, 6H), 1.25 (d, J=31.4 Hz, 7H), 1.20 (s, 3H), 1.16 (s, 3H), 1.09 (s, 1H), 1.03 (dd, J=7.0, 2.9 Hz, 5H), 0.99-0.92 (m, 1H), 0.85 (s, 3H).

Example 12 (2S,4aS,6aS,6bR,8aR,9S,10S,12aS,12bR,14bR)-10-(Benzoyloxy)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic Acid (197-2)

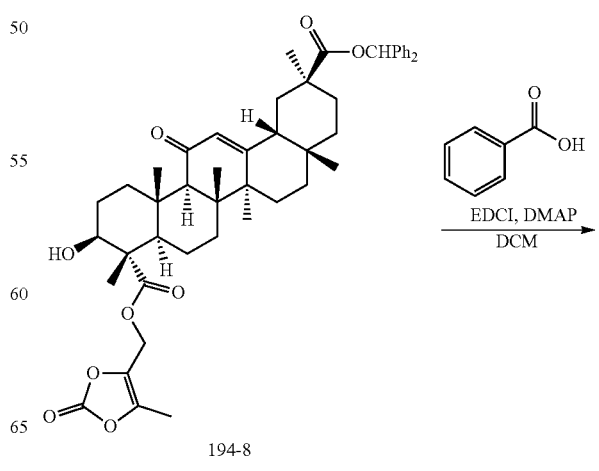

194-8

-continued

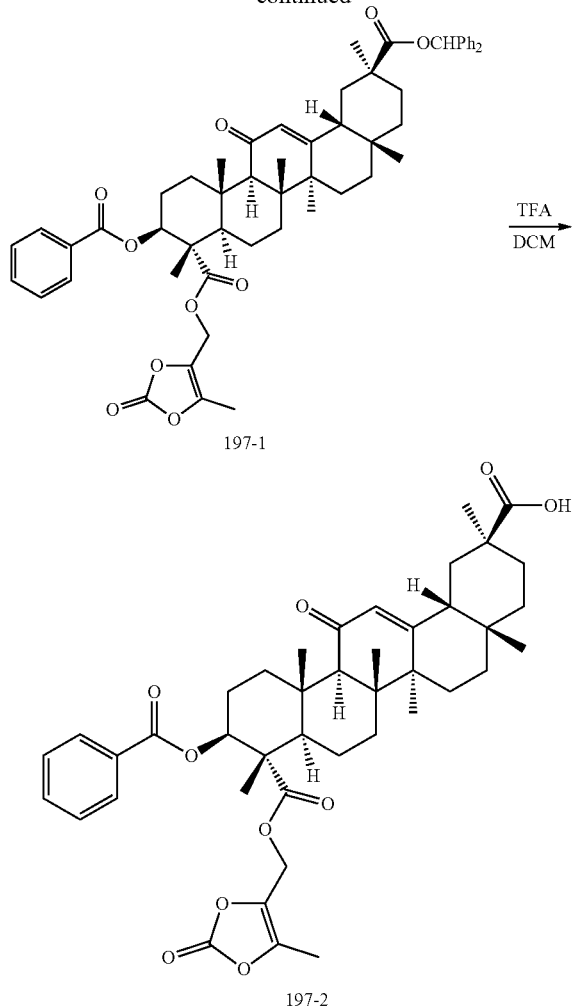

197-1

197-2

Synthesis of 2-Benzhydryl 9-((5-methyl-2-oxo-1,3-dioxol-4-yl)methyl) (2S,4aS,6aS,6bR,8aR,9S,10S,12aS,12bR,14bR)-10-(benzoyloxy)-2,4a,6a,6b,9,12a-hexamethyl-13-oxo-1,2,3,4,4a,5,6,6a,6b,7,8,8a,9,10,11,12,12a,12b,13,14b-icosahydropicene-2,9-dicarboxylate (197-1)

EDCI (175 mg, 0.91 mmol, 5 equiv) was added to 194-8 (140 mg, 0.18 mmol, 1 equiv), benzoic acid (110 mg, 0.90 mmol, 5 equiv) and DMAP (84 mg, 0.69 mmol, 4 equiv) in DCM (2.5 mL). The reaction was stirred overnight at rt and then concentrated under vacuum. The residue was purified by silica gel column eluting with EtOAc/petroleum ether (1/1). This resulted in 160 mg (101%) of 197-1 as a light yellow solid.

Synthesis of (2S,4aS,6aS,6bR,8aR,9S,10S,12aS,12bR,14bR)-10-(Benzoyloxy)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic Acid (197-2)

197-1 (160 mg, 0.18 mmol, 1 equiv) and TFA (0.2 mL, 2.69 mmol, 15 equiv) in DCM was stirred for 1 h at rt. The resulting mixture was concentrated under vacuum and the residue purified by prep-TLC with the following conditions—Column: Xselect CSH OBD, 30*150 mm, 5 μm; mobile phase A: water (0.05% TFA), mobile phase B: MeCN; Flow rate: 60 mL/min; Gradient: 37% B to 65% B in 8 min; detector: UV 254 nm to afford 197-2 (27.8 mg, 21.40%) as an off-white solid. MS (ES, m/z): [M+H]$^+$= 717.00; $^1$H NMR (300 MHz, MeOH-d$_4$) δ 8.02-7.88 (m, 2H), 7.63 (t, J=7.4 Hz, 1H), 7.49 (t, J=7.6 Hz, 2H), 5.65 (s, 1H), 5.41 (dd, J=11.5, 5.1 Hz, 1H), 4.95 (s, 2H), 2.91 (d, J=13.9 Hz, 1H), 2.65 (s, 1H), 2.25 (d, J=14.8 Hz, 2H), 1.97 (s, 8H), 1.85-1.68 (m, 4H), 1.51 (s, 3H), 1.43 (d, J=7.6 Hz, 7H), 1.34 (d, J=12.3 Hz, 2H), 1.27 (s, 3H), 1.20 (d, J=6.8 Hz, 6H), 1.06 (t, J=13.9 Hz, 2H), 0.87 (s, 3H).

Example 13 (2S,4aS,6aS,6bR,8aR,9S,10S,12aS,12bR,14bR)-10-((Cyclopropanecarbonyl)oxy)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic Acid (198-2)

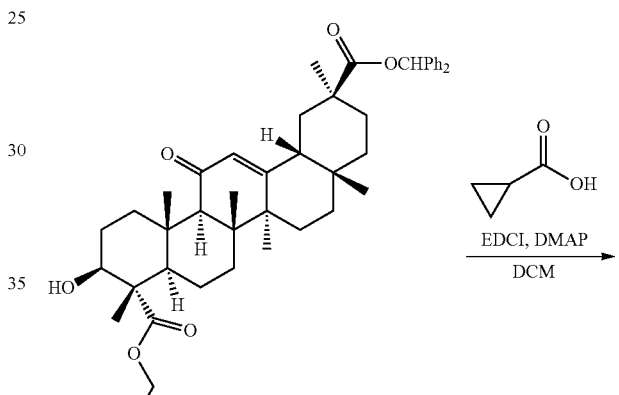

194-8

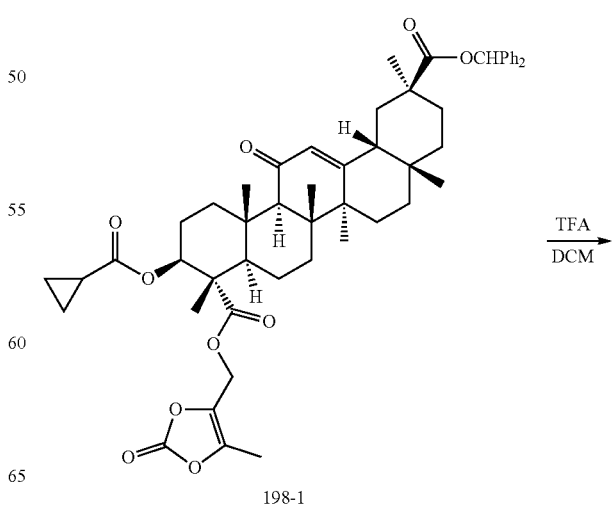

198-1

115
-continued

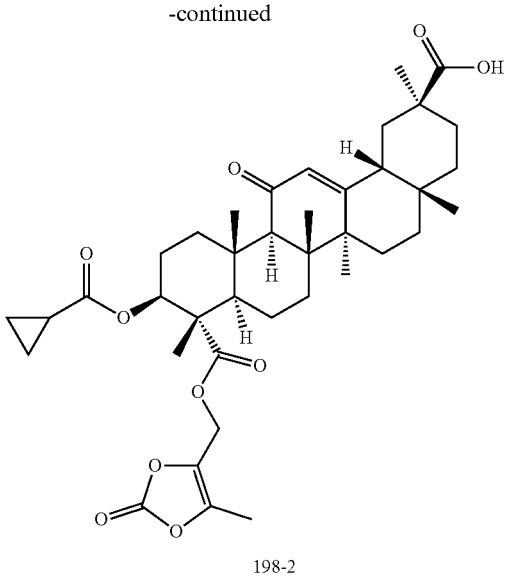

198-2

Synthesis of 2-Benzhydryl 9-((5-methyl-2-oxo-1,3-dioxol-4-yl)methyl) (2S,4aS,6aS,6bR,8aR,9S,10S,12aS,12bR,14bR)-10-((cyclopropanecarbonyl)oxy)-2,4a,6a,6b,9,12a-hexamethyl-13-oxo-1,2,3,4,4a,5,6,6a,6b,7,8,8a,9,10,11,12,12a,12b,13,14b-icosahydropicene-2,9-dicarboxylate (198-1)

EDCI (250 mg, 1.30 mmol, 5 equiv) was added to 194-8 (200 mg, 0.26 mmol, 1 equiv), cyclopropanecarboxylic acid (220 mg, 2.56 mmol, 10 equiv), and DMAP (120 mg, 0.98 mmol, 4 equiv) in DCM (4 mL) and the reaction stirred overnight at rt. The mixture was concentrated under vacuum and the residue purified by silica gel column eluting with EtOAc/petroleum ether (1/1). This resulted in 230 mg (106%) of 198-1 as a light yellow solid.

Synthesis of (2S,4aS,6aS,6bR,8aR,9S,10S,12aS,12bR,14bR)-10-((Cyclopropanecarbonyl)oxy)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic Acid (198-2)

198-1 (115 mg, 0.14 mmol, 1 equiv) and TFA (0.15 mL) in DCM (1.5 mL) were stirred for 1 h at rt. The reaction was concentrated under vacuum and the residue (115 mg) purified by prep-HPLC with the following conditions—Column: Xselect CSH OBD, 30*150 mm, 5 µm; mobile phase A: water (0.05% TFA), mobile phase B: MeCN; Flow rate: 60 mL/min; Gradient: 30% B to 60% B in 8 min; detector: 254 nm. This resulted in 26.9 mg (29%) of 198-2 as an off-white solid. MS (ES, m/z): [M+H]$^+$=681.20; $^1$H NMR (300 MHz, MeOH-d4) δ 5.62 (s, 1H), 5.14 (dd, J=11.5, 5.1 Hz, 1H), 5.02 (d, J=13.9 Hz, 1H), 4.93 (s, 1H), 2.83 (d, J=13.6 Hz, 1H), 2.58 (s, 1H), 2.20 (s, 5H), 2.01-1.58 (m, 8H), 1.57-1.33 (m, 10H), 1.33-1.13 (m, 10H), 1.07 (d, J=12.8 Hz, 3H), 0.95 (s, 2H), 0.87 (d, J=13.2 Hz, 6H).

116

Example 14 (2S,4aS,6aS,6bR,8aR,9S,10S,12aS,12bR,14bR)-10-(((R)-2-Methoxypropanoyl)oxy)-2,4a,6a,6b,9,12a-hexamethyl-9-((((5-methyl-2-oxo-1,3-dioxol-4-yl)methoxy)carbonyl)-13-oxo-1,2,3,4,4a,5,6,6a,6b,7,8,8a,9,10,1142,12a,12b,13,14b-icosahydropicene-2-carboxylic Acid (203-2)

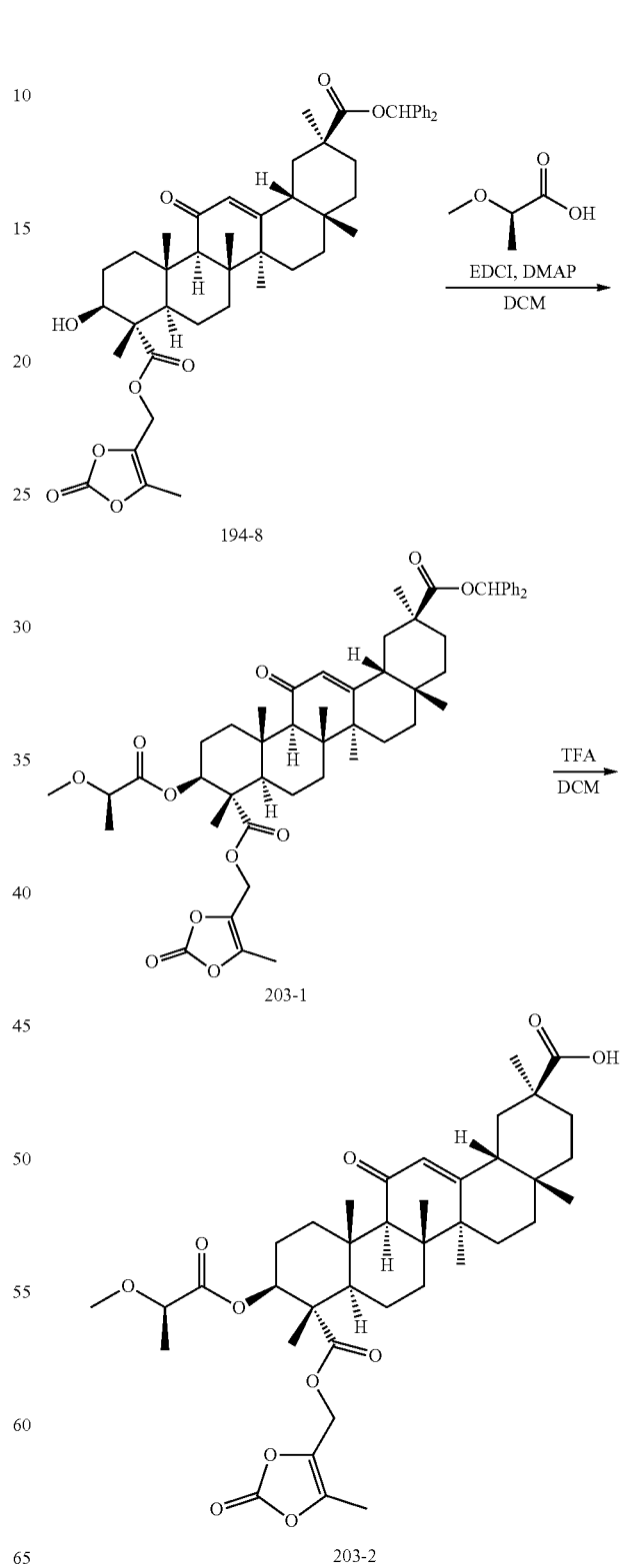

Synthesis of 2-Benzhydryl 9-((5-methyl-2-oxo-1,3-dioxol-4-yl)methyl) (2S,4aS,6aS,6bR,8aR,9S,10S,12aS,12bR,14bR)-10-(((R)-2-methoxypropanoyl)oxy)-2,4a,6a,6b,9,12a-hexamethyl-13-oxo-1,2,3,4,4a,5,6,6a,6b,7,8,8a,9,10,11,12,12a,12b,13,14b-icosahydropicene-2,9-dicarboxylate (203-1)

EDCI (240 mg, 1 mmol, 5 equiv) was added to 194-8 (200 mg, 0.2 mmol, 1 equiv), (2R)-2-methoxypropanoic acid (132 mg, 1 mmol, 5 equiv) and DMAP (132 mg, 0.8 mmol, 4 equiv) in DCM (2 mL) and the reaction stirred for 2 hr at rt. The mixture was concentrated under vacuum and the residue purified by silica gel column with EtOAc/petroleum ether (1/1). This resulted in 150 mg of 203-1 as a light yellow solid.

Synthesis of (2S,4aS,6aS,6bR,8aR,9S,10S,12aS,12bR,14bR)-10-(((R)-2-Methoxypropanoyl)oxy)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic Acid (203-2)

203-1 (150 mg, 0.17 mmol, 1 equiv) and TFA (0.2 mL) in DCM (2 mL) were stirred for 2 hr at rt. The resulting mixture was concentrated and the residue purified by Flash-prep-HPLC resulting in 47.5 mg (39.20%) of 203-1 as a white solid. MS (ES, m/z): [M+H]$^+$=699; $^1$H NMR (300 MHz, Chloroform-7) δ 5.72 (s, 1H), 5.25 (dd, J=11.6, 5.0 Hz, 1H), 4.99 (d, J=13.7 Hz, 1H), 4.69 (d, J=13.8 Hz, 1H), 3.79 (q, J=6.8 Hz, 1H), 3.34 (s, 3H), 2.89 (d, J=13.7 Hz, 1H), 2.44 (s, 1H), 2.19 (s, 4H), 1.99 (s, 7H), 1.79 (s, 10H), 1.42-1.30 (m, 14H), 1.27-1.15 (m, 1H), 0.82 (s, 4H).

Example 15 (2S,4aS,6aS,6bR,8aR,9S,10S,12aS,12bR,14bR)-10-(((S)-2-Methoxypropanoyl)oxy)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,1142,12a,12b,13,14b-icosahydropicene-2-carboxylic Acid (204-2)

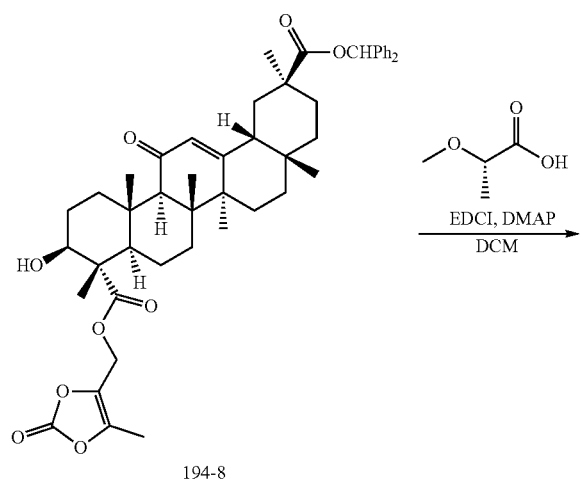

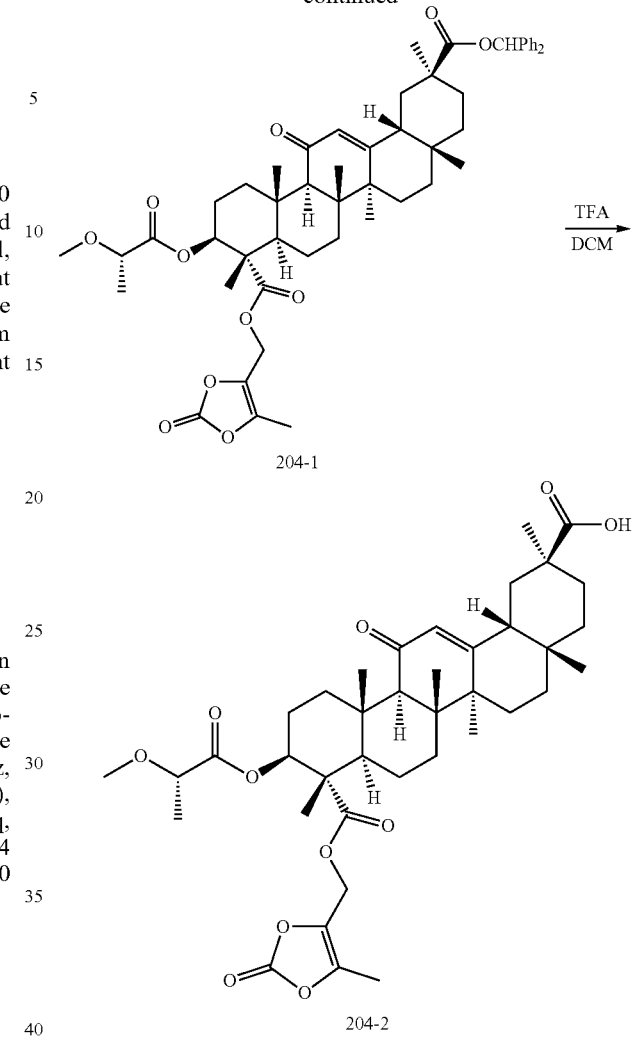

Synthesis of 2-Benzhydryl 9-((5-methyl-2-oxo-1,3-dioxol-4-yl)methyl) (2S,4aS,6aS,6bR,8aR,9S,10S,12aS,12bR,14bR)-10-(((S)-2-methoxypropanoyl)oxy)-2,4a,6a,6b,9,12a-hexamethyl-13-oxo-1,2,3,4,4a,5,6,6a,6b,7,8,8a,9,10,11,12,12a,12b,13,14b-icosahydropicene-2,9-dicarboxylate (204-1)

EDCI (240 mg, 1.2 mmol, 5 equiv) was added to 194-8 (200 mg, 0.2 mmol, 1 equiv), (2S)-2-methoxypropanoic acid (132 mg, 1.2 mmol, 5 equiv) and DMAP (120 mg, 0.8 mmol, 4 equiv) in DCM (2 mL) and the reaction stirred for 3 hr at 25° C. The mixture was concentrated under vacuum and the residue purified by silica gel column with EtOAc/petroleum ether (1/1). This resulted in 150 mg of 204-1 as a light yellow solid.

Synthesis of (2S,4aS,6aS,6bR,8aR,9S,10S,12aS,12bR,14bR)-10-(((S)-2-Methoxypropanoyl)oxy)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic Acid (204-2)

204-1 (150 mg, 0.17 mmol, 1 equiv) and TFA (0.2 mL, 0.01 equiv) in DCM (2 mL) were stirred for 2 hr at 25° C.

The reaction was concentrated and the crude product purified by prep-HPLC with the following conditions—Column: Xselect CSH OBD, 30*150 mm, 5 μm; mobile phase: water (0.05% TFA) and MeCN (57% Phase B up to 85% in 8 min); detector: UV. This resulted in 204-2 as a white solid. MS (ES, m/z): [M+H]$^+$=699; $^1$H NMR (300 MHz, Chloroform-7) δ 5.72 (s, 1H), 5.26 (dd, J=11.6, 4.9 Hz, 1H), 4.98 (d, J=13.7 Hz, 1H), 4.68 (d, J=13.8 Hz, 1H), 3.79 (t, 7=6.9 Hz, 1H), 3.36 (s, 3H), 2.89 (d, J=13.8 Hz, 1H), 2.45 (s, 1H), 2.19 (s, 4H), 2.00 (s, 3H), 1.87-1.71 (m, 7H), 1.39 (s, 6H), 1.33 (d, J=6.9 Hz, 4H), 1.27-1.15 (m, 12H), 1.11 (s, 3H), 1.04 (d, J=12.6 Hz, 1H), 0.82 (s, 4H).

Example 16 (2S,4aS,6aS,6bR,8aR,9S,10S,12aS,12bR,14bR)-10-(Methoxymethoxy)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic Acid (205-2)

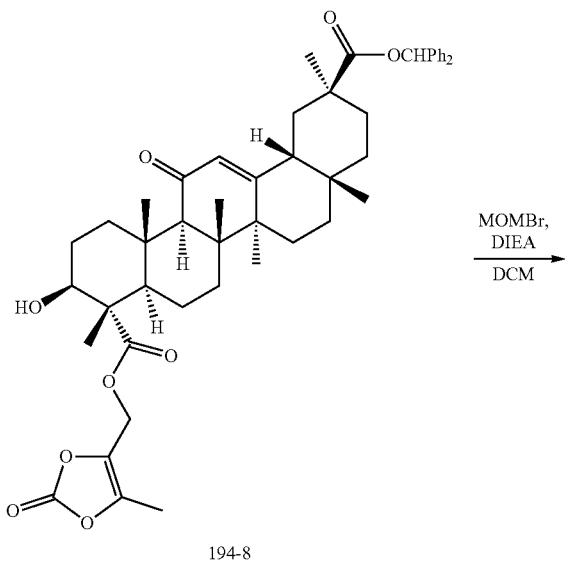

194-8

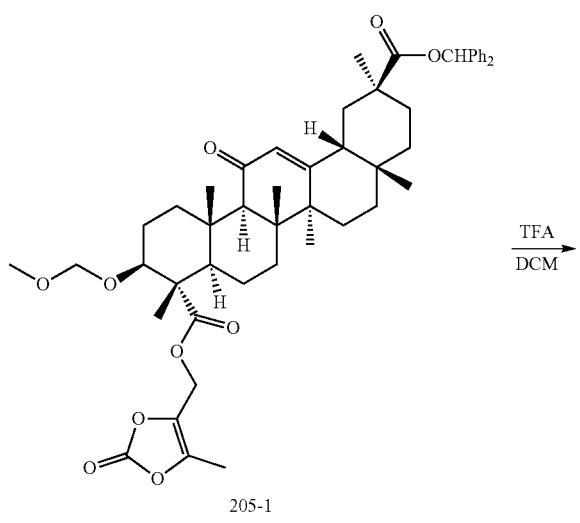

205-1

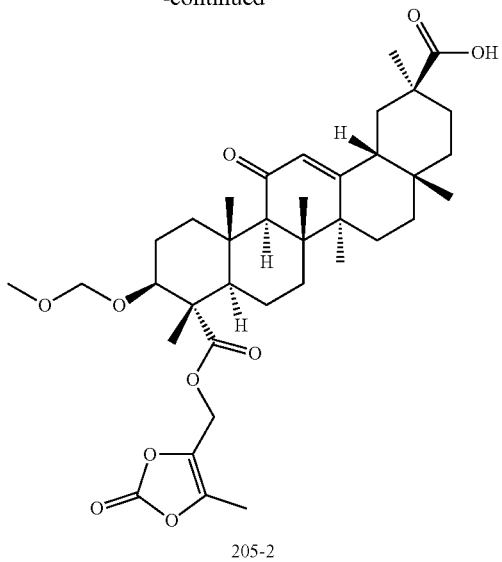

205-2

Synthesis of 2-Benzhydryl 9-((5-methyl-2-oxo-1,3-dioxol-4-yl)methyl) (2S,4aS,6aS,6bR,8aR,9S,10S,12aS,12bR,14bR)-10-(methoxymethoxy)-2,4a,6a,6b,9,12a-hexamethyl-13-oxo-1,2,3,4,4a,5,6,6a,6b,7,8,8a,9,10,11,12,12a,12b,13,14b-icosahydropicene-2,9-dicarboxylate (205-1)

Bromo(methoxy)methane (0.063 mL, 4.0 equiv) was a added dropwise at 0° C. to 194-8 (150 mg, 1 equiv) and DIEA (0.318 mL, 10.0 equiv) in DCM (10 mL) and then heated at 60° C. for 1 hr. The reaction was concentrated and the residue purified by silica gel column with EtOAc/petroleum ether (1:1). This resulted in 178.1 mg (112.38%) of 205-1 as a white crude solid.

Synthesis of (2S,4aS,6aS,6bR,8aR,9S,10S,12aS,12bR,14bR)-10-(Methoxymethoxy)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic Acid (205-2)

205-1 (178.1 mg) and 10% TFA/DCM (10 mL) were stirred for 5 hr at rt. The reaction mixture was washed with brine (3×50 mL), dried over anhydrous sodium sulfate and concentrated under vacuum. The residue was purified by prep-HPLC with the following conditions—Column: Xselect CSH OBD, 30*150 mm, 5 μm; mobile phase: water (0.05% TFA) and CH$_3$CN (58% Phase B up to 76% in 8 min); detector: UV. This resulted in 40.0 mg (28%) of 205-2 as a white solid. MS (ES, m/z): [M+H]$^+$=657.25; $^1$H NMR (400 MHz, Chloroform-7) δ 0.85 (s, 4H), 1.01-1.15 (m, 5H), 1.20 (d, J=12.0 Hz, 6H), 1.26 (s, 4H), 1.33-1.58 (m, 8H), 1.59-1.61 (m, 1H), 1.65-1.70 (m, 2H), 1.72-1.91 (m, 2H), 1.92-2.17 (m, 4H), 2.18-2.20 (m, 1H), 2.22 (s, 3H), 2.43 (s, 1H), 2.87 (d, J=14.0 Hz, 1H), 3.29 (s, 3H), 3.97 (dd, J=11.6, 4.4 Hz, 1H), 4.52 (d, 7=6.8 Hz, 1H), 4.66 (d, J=7.2 Hz, 1H), 4.75 (d, J=13.6 Hz, 1H), 5.06 (d, J=13.6 Hz, 1H), 5.74 (s, 1H).

Example 17 (2S,4aS,6aS,6bR,8aR,9S,10S,12aS,12bR,14bR)-10-((Ethylcarbamoyl)oxy)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic Acid (206-2)

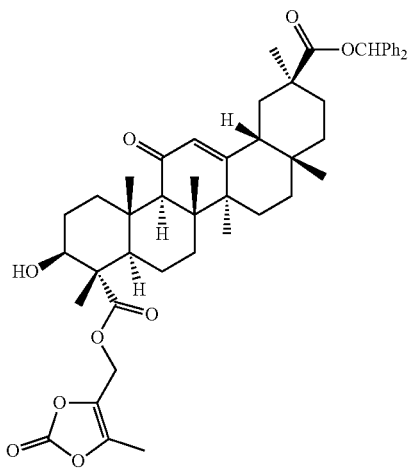

194-8

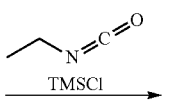

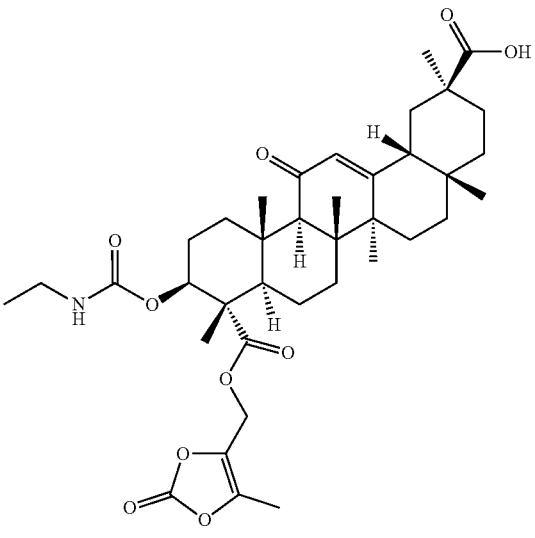

206-2

Synthesis of 2-benzhydryl 9-((5-methyl-2-oxo-1,3-dioxol-4-yl)methyl) (2S,4aS,6aS,6bR,8aR,9S,10S,12aS,12bR,14bR)-10-((ethylcarbamoyl)oxy)-2,4a,6a,6b,9,12a-hexamethyl-13-oxo-1,2,3,4,4a,5,6,6a,6b,7,8,8a,9,10,11,12,12a,12b,13,14b-icosahydropicene-2,9-dicarboxylate (206-1)

Isocyanatoethane (0.061 mL, 3 equiv), chlorotrimethylsilane (0.111 mL, 5 equiv), and 194-8 (200 mg, 0.26 mmol) in CH$_2$Cl$_2$ (10 mL) were stirred overnight at rt. The reaction was concentrated under vacuum and the residue purified by silica gel column with EtOAc/petroleum ether (1:1). This resulted in 239.9 mg (quant) of 206-1 as a white crude solid.

Synthesis of (2S,4aS,6aS,6bR,8aR,9S,10S,12aS,12bR,14bR)-10-((Ethylcarbamoyl)oxy)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic Acid (206-2)

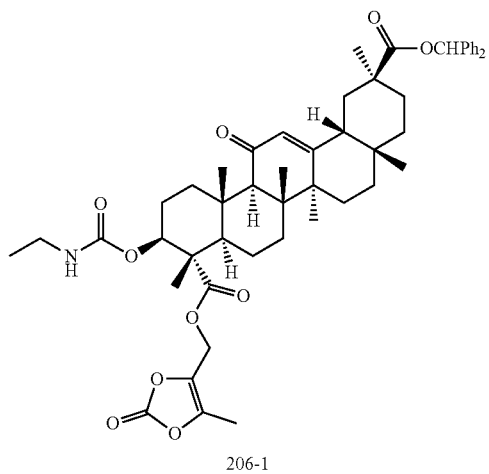

206-1

206-1 (239.9 mg) and 10% TFA/CH$_2$Cl$_2$ (10 mL) were stirred for 1 hr at rt. The reaction was concentrated and the residue purified by prep-HPLC with the following conditions—Column: Xselect CSH OBD, 30*150 mm, 5 μm; mobile phase: water (0.05% TFA) and MeCN (57% Phase B up to 77% in 8 min); detector: UV. This resulted in 65.7 mg (34%) of 206-2 as a white solid. MS (ES, m/z): [M+H]$^+$= 684.05; $^1$H NMR (400 MHz, MeOH-d$_4$) δ 0.82 (s, 3H), 0.89-0.99 (m, 1H), 1.01-1.04 (m, 1H), 1.09 (t, J=7.2 Hz, 3H), 1.13 (s, 3H), 1.17-1.28 (m, 11H), 1.33-1.48 (m, 7H), 1.61-1.79 (m, 6H), 1.81-1.90 (m, 2H), 1.95 (d, J=10.0 Hz, 1H), 2.11-2.28 (m, 5H), 2.55 (s, 1H), 2.79 (d, J=14.0 Hz, 1H), 2.98-3.17 (m, 2H), 4.89 (d, J=14.0 Hz, 1H), 4.95-5.05 (m, 2H), 5.59 (s, 1H).

Example 18 (2S,4aS,6aS,6bR,8aR,9S,10S,12aS, 12bR,14bR)-10-((butylcarbamoyl)oxy)-2,4a,6a,6b,9, 12a-hexamethyl-9-(((5-methyl-2-oxo-1,3-dioxol-4-yl)methoxy)carbonyl)-13-oxo-1,2,3,4,4a,5,6,6a,6b,7, 8,8a,9,10,11,12,12a,12b,13,14b-icosahydropicene-2-carboxylic Acid (207-2)

Synthesis of 2-benzhydryl 9-((5-methyl-2-oxo-1,3-dioxol-4-yl)methyl) (2S,4aS,6aS,6bR,8aR,9S,10S, 12aS,12bR,14bR)-10-((butylcarbamoyl)oxy)-2,4a, 6a,6b,9,12a-hexamethyl-13-oxo-1,2,3,4,4a,5,6,6a,6b, 7,8,8a,9,10,11,12,12a,12b,13,14b-icosahydropicene-2,9-dicarboxylate (207-1)

1-Isocyanatobutane (0.0868 mL, 3 equiv), TMSCl (0.111 mL, 5 equiv), and 194-8 (200 mg, 0.26 mmol, 1 equiv) in $CH_2Cl_2$ (10 mL) were stirred overnight at rt. The reaction was concentrated under vacuum and the residue purified by silica gel column with EtOAc/petroleum ether (1:1). This resulted in 256.9 mg (114%) of 207-1 as a white crude solid.

Synthesis of (2S,4aS,6aS,6bR,8aR,9S,10S,12aS, 12bR,14bR)-10-((butylcarbamoyl)oxy)-2,4a,6a,6b,9, 12a-hexamethyl-9-(((5-methyl-2-oxo-1,3-dioxol-4-yl)methoxy)carbonyl)-13-oxo-1,2,3,4,4a,5,6,6a,6b,7, 8,8a,9,10,11,12,12a,12b,13,14b-icosahydropicene-2-carboxylic Acid (207-2)

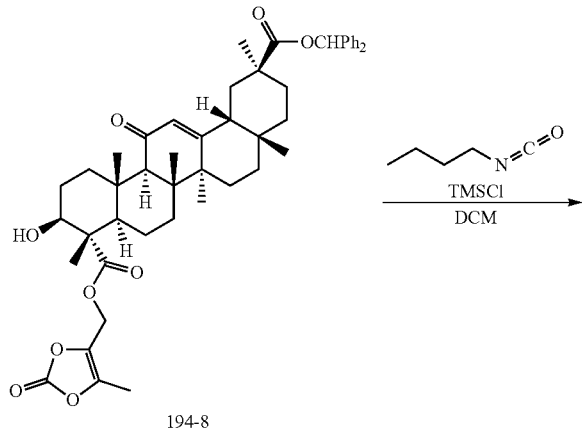

207-1 (256.9 mg) and 10% $TFA/CH_2Cl_2$ (10 mL) were stirred for 1 hr at rt. The reaction was concentrated under vacuum and the crude product purified by prep-HPLC with the following conditions—Column: XBridge Shield RP18 OBD, 5 μm, 19*150 mm; mobile phase: water (0.05% TFA) and MeCN (71% Phase B up to 72% in 8 min); detector: UV. This resulted in 28.8 mg (14%) of 207-2 as an off-white solid. MS (ES, m/z): $[M+H]^+$=712.05; $^1$H NMR (400 MHz, MeOH-$d_4$) δ 0.85 (s, 3H), 0.94 (t, J=7.4 Hz, 4H), 1.07 (d, J=13.6 Hz, 1H), 1.12-1.30 (m, 14H), 1.31-1.59 (m, 11H), 1.63-1.82 (m, 6H), 1.83-1.93 (m, 2H), 1.96-2.08 (m, 1H), 2.09-2.32 (m, 5H), 2.57 (s, 1H), 2.81 (d, J=14.0 Hz, 1H), 2.97-3.14 (m, 2H), 4.90 (d, J=13.6 Hz, 1H), 4.97-5.11 (m, 2H), 5.62 (s, 1H).

Example 19 (2S,4aS,6aS,6bR,8aR,9S,10S,12aS, 12bR,14bR)-2,4a,6a,6b,9,12a-hexamethyl-9-(((5-methyl-2-oxo-1,3-dioxol-4-yl)methoxy)carbonyl)-13-oxo-10-((pyrrolidine-1-carbonyl)oxy)-1,2,3,4,4a, 5,6,6a,6b,7,8,8a,9,10,11,12,12a,12b,13,14b-icosahydropicene-2-carboxylic acid (208-2)

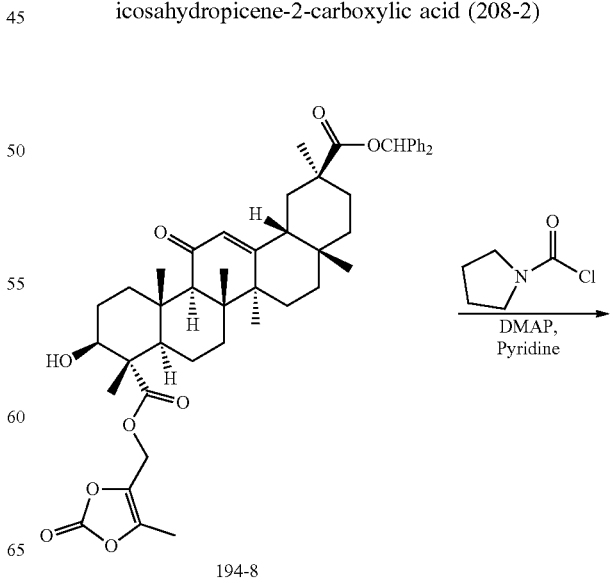

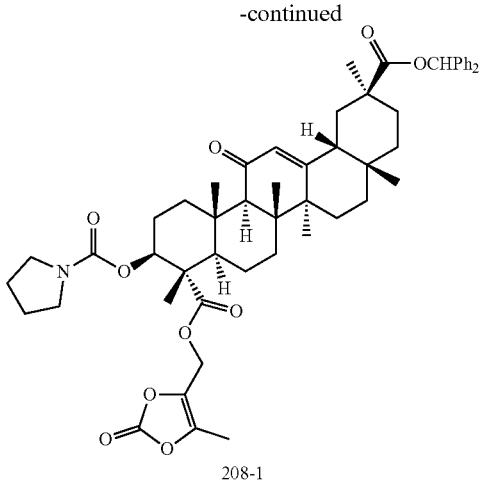

208-1

TFA / DCM →

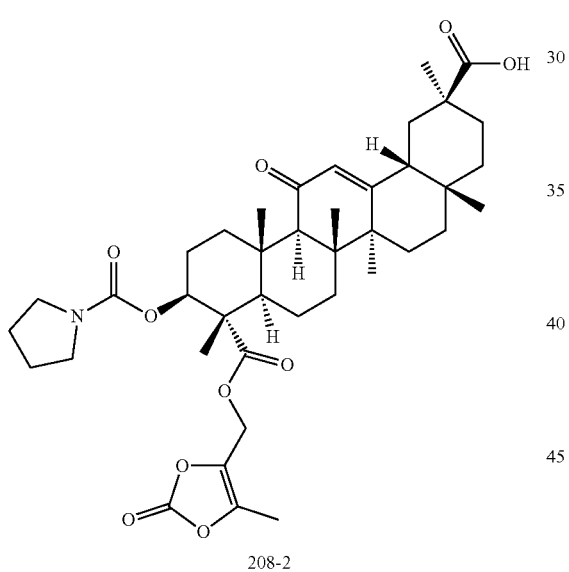

208-2

Synthesis of 2-benzhydryl 9-((5-methyl-2-oxo-1,3-dioxol-4-yl)methyl) (2S,4aS,6aS,6bR,8aR,9S,10S,12aS,12bR,14bR)-2,4a,6a,6b,9,12a-hexamethyl-13-oxo-10-((pyrrolidine-1-carbonyl)oxy)-1,2,3,4,4a,5,6,6a,6b,7,8,8a,9,10,11,12,12a,12b,13,14b-icosahydropicene-2,9-dicarboxylate (208-1)

194-8 (400 mg), pyrrolidine-1-carbonyl chloride (0.17 mL, 3 equiv), and DMAP (62.7 mg, 1 equiv) in pyridine (10 mL) were stirred for 9 days at 90° C. The reaction mixture was concentrated and the residue dissolved in EtOAc. The solution was washed with 1 M HCl (3 × 50 mL) and brine (1×50 mL), dried over anhydrous $Na_2SO_4$, and concentrated to provide 170 mg (38%) of 208-1 as a white solid.

Synthesis of (2S,4aS,6aS,6bR,8aR,9S,10S,12aS,12bR,14bR)-2,4a,6a,6b,9,12a-hexamethyl-9-(((5-methyl-2-oxo-1,3-dioxol-4-yl)methoxy)carbonyl)-13-oxo-10-((pyrrolidine-1-carbonyl)oxy)-1,2,3,4,4a,5,6,6a,6b,7,8,8a,9,10,11,12,12a,12b,13,14b-icosahydropicene-2-carboxylic acid (208-2)

208-1 (170 mg, 1 equiv) and 10% $TFA/CH_2Cl_2$ (10 mL) were stirred for 1 hr at rt. The reaction mixture was concentrated under vacuum and the residue purified by prep-HPLC with the following conditions—Column: Xselect CSH OBD, 30*150 mm, 5 µm; mobile phase: water (0.05% TFA) and $CH_3CN$ (68% Phase B up to 80% in 8 min); detector: UV. This resulted in 9.5 mg (6.5%) of 208-2 as a white solid. MS (ES, m/z): $[M+H]^+=710.20$; $^1H$ NMR (400 MHz, MeOH-$d_4$) δ 0.83 (s, 3H), 0.94-0.99 (m, 1H), 1.04 (d, J=13.6 Hz, 1H), 1.15 (s, 3H), 1.18 (s, 6H), 1.21-1.27 (m, 6H), 1.29-1.36 (m, 2H), 1.38-1.41 (m, 3H), 1.44 (s, 3H), 1.57-1.61 (m, 1H), 1.63-1.79 (m, 6H), 1.87 (s, 6H), 1.95 (d, J=10.0 Hz, 1H), 2.10-2.15 (m, 5H), 2.56 (s, 1H), 2.80 (d, J=14.0 Hz, 1H), 3.13-3.24 (m, 1H), 3.29 (s, 3H), 4.90-5.04 (m, 3H), 5.60 (s, 1H).

Example 20 (2S,4aS,6aS,6bR,8aR,9S,10S,12aS,12bR,14bR)-10-acetoxy-9-(((5-isopropyl-2-oxo-1,3-dioxol-4-yl)methoxy)carbonyl)-2,4a,6a,6b,9,12a-hexamethyl-13-oxo-1,2,3,4,4a,5,6,6a,6b,7,8,8a,9,10,1142,12a,12b,13,14b-icosahydropicene-2-carboxylic Acid (209-3)

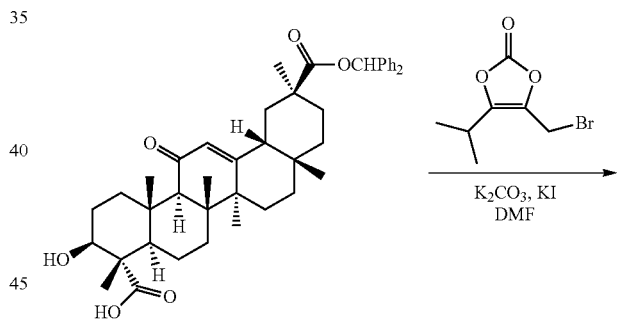

194-7

$K_2CO_3$, KI
DMF

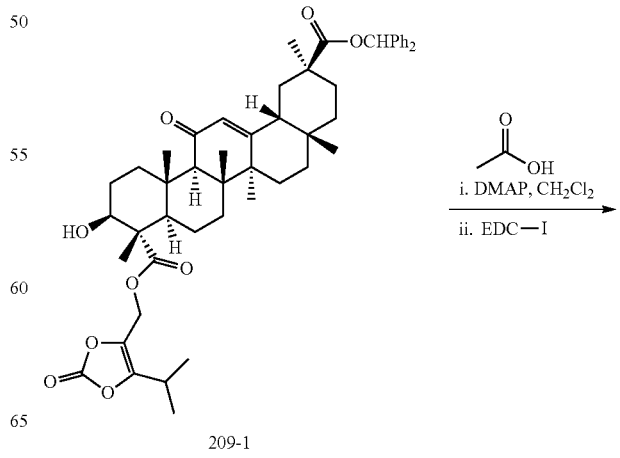

i. DMAP, $CH_2Cl_2$
ii. EDC—I 209-1

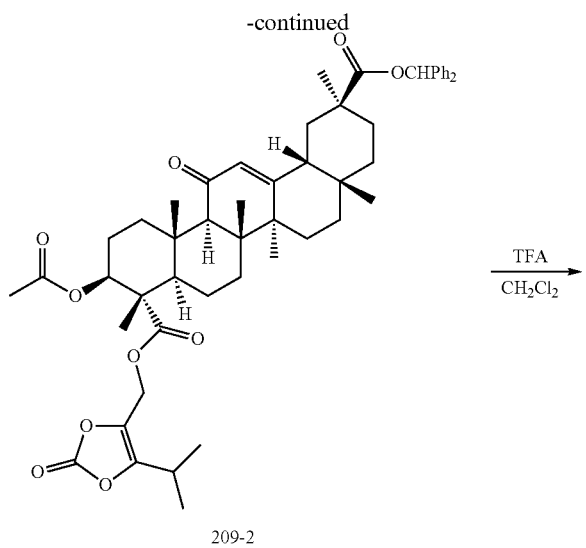

209-2

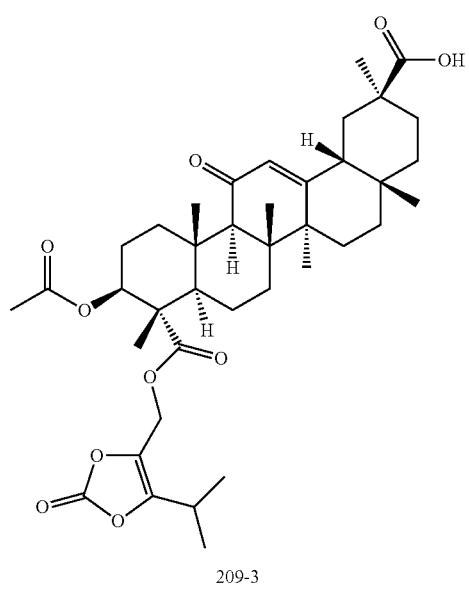

209-3

Synthesis of 2-benzhydryl 9-((5-isopropyl-2-oxo-1,
3-dioxol-4-yl)methyl) (2S,4aS,6aS,6bR,8aR,9S,10S,
12aS,12bR,14bR)-10-hydroxy-2,4a,6a,6b,9,12a-
hexamethyl-13-oxo-1,2,3,4,4a,5,6,6a,6b,7,8,8a,9,10,
11,12,12a,12b,13,14b-icosahydropicene-2,9-
dicarboxylate (209-1)

4-(Bromomethyl)-5-isopropyl-1,3-dioxol-2-one was prepared according to literature procedures (Sun et al, *Tetrahedron Letters*, 2002, 43, 1161-1164). A mixture of 4-(bromomethyl)-5-isopropyl-1,3-dioxol-2-one (2.7 g, 1.5 equiv), $K_2CO_3$ (3.4 g, 3 equiv), KI (0.68 g, 0.5 equiv), and 194-7 (5.5 g, 1 equiv) in DMF (80 mL) was stirred for 1 h at 60° C. The reaction mixture was cooled to room temperature and extracted with EtOAc. The combined organic layers were washed with brine, dried over anhydrous $Na_2SO_4$, filtered, and concentrated. The residue was purified by silica gel column chromatography, eluting with 3:1 petroleum ether: EtOAc to afford 209-1 (5.5 g, 83%) as a light yellow solid. MS (ES, m/z) $[M+1]^+$=806.95; $^1H$ NMR (400 MHz, Chloroform-d) δ 7.48-7.28 (m, 10H), 6.95 (s, 1H), 5.54 (s, 1H), 5.07 (d, J=13.8 Hz, 1H), 4.83 (d, J=13.8 Hz, 1H), 4.10-3.93 (m, 1H), 3.11-2.94 (m, 2H), 2.94-2.82 (m, 2H), 2.40 (s, 1H), 2.17-1.93 (m, 5H), 1.91-1.53 (m, 7H), 1.48 (d, J=10.6 Hz, 2H), 1.43-1.31 (m, 6H), 1.31-1.22 (m, 8H), 1.22-1.11 (m, 12H), 1.08 (s, 3H), 1.00 (d, J=13.7 Hz, 1H), 0.90 (t, J=10.1 Hz, 1H), 0.67 (s, 3H).

Synthesis of 2-benzhydryl 9-((5-isopropyl-2-oxo-1,
3-dioxol-4-yl)methyl) (2S,4aS,6aS,6bR,8aR,9S,10S,
12aS,12bR,14bR)-10-acetoxy-2,4a,6a,6b,9,12a-hex-
amethyl-13-oxo-1,2,3,4,4a,5,6,6a,6b,7,8,8a,9,10,11,
12,12a,12b,13,14b-icosahydropicene-2,9-
dicarboxylate (209-2)

Into an 8-mL round-bottom flask was placed 209-1 (100 mg, 0.12 mmol), $CH_2Cl_2$ (2 mL), DMAP (29 mg, 0.24 mmol, 1.9 equiv), AcOH (21.2 mg, 0.35 mmol, 2.85 equiv), and then EDCI (57 mg, 0.3 mmol, 2.4 equiv). The reaction slurry was stirred overnight at room temperature. The reaction mixture was concentrated and the residue was applied onto a silica gel column with ethyl acetate/petroleum ether (1:1) to provide 60 mg (57%) of 209-2 as a white solid.

Synthesis of (2S,4aS,6aS,6bR,8aR,9S,10S,12aS,
12bR,14bR)-10-acetoxy-9-(((5-isopropyl-2-oxo-1,3-
dioxol-4-yl)methoxy)carbonyl)-2,4a,6a,6b,9,12a-
hexamethyl-13-oxo-1,2,3,4,4a,5,6,6a,6b,7,8,8a,9,10,
11,12,12a,12b,13,14b-icosahydropicene-2-
carboxylic Acid (209-3)

Into a 25-mL round-bottom flask was placed 209-2 (60 mg, 0.07 mmol), $CH_2Cl_2$ (5 mL), and TFA (0.5 mL, 6.7 mmol, 95 equiv). The reaction slurry was stirred for 1 hr at room temperature. The resulting mixture was concentrated and the crude product was purified by prep-HPLC with the following conditions: column, XSelect CSH Prep C18 OBD, 5 μm, 19*150 mm; mobile phase, water (0.05% TFA) and $CH_3CN$ (70% Phase B up to 90% in 8 min); detector, uv. This resulted in 29.6 mg (61%) of 209-3 as a white solid. The product was tested in the assay in described in example 112 demonstrating a pIC50 of 7.2 compared to the corresponding acid metabolite (2S,4aS,6aS,6bR,8aR,9S,10S, 12aS,12bR,14bR)-10-(acetyloxy)-2,4a,6a,6b,9,12a-hexamethyl-13-oxo-1,2,3,4,4a,5,6,6a,6b,7,8,8a,9,10,11,12,12a, 12b,13,14b-icosahydropicene-2,9-dicarboxylic acid having a $pIC_{50}$ of 5.9. MS (ES, m/z): $[M+1]^+$=683; $^1H$ NMR (300 MHz, methanol-$d_4$) δ 0.85 (s, 3H), 0.95 (s, 1H), 1.07 (d, J=13.8 Hz, 1H), 1.18 (d, J=13.4 Hz, 8H), 1.22-1.34 (m, 9H), 1.45 (d, J=12.8 Hz, 6H), 1.65-1.83 (m, 5H), 1.88 (dd, J=12.1, 4.9 Hz, 1H), 1.96 (s, 3H), 2.09-2.29 (m, 2H), 2.58 (s, 1H), 2.83 (d, J=13.7 Hz, 1H), 3.07 (h, J=6.9 Hz, 1H), 4.89 (d, J=13.9 Hz, 1H), 5.07 (d, J=13.9 Hz, 1H), 5.16 (dd, J=11.4, 5.2 Hz, 1H), 5.62 (s, 1H).

Example 21 (2S,4aS,6aS,6bR,8aR,9S,10S,12aS, 12bR,14bR)-2,4a,6a,6b,9,12a-hexamethyl-9-(((5-methyl-2-oxo-1,3-dioxol-4-yl)methoxy)carbonyl)-13-oxo-10-(propionyloxy)-1,2,3,4,4a,5,6,6a,6b,7,8, 8a,9,10,1142,12a,12b,13,14b-icosahydropicene-2-carboxylic Acid (211-1)

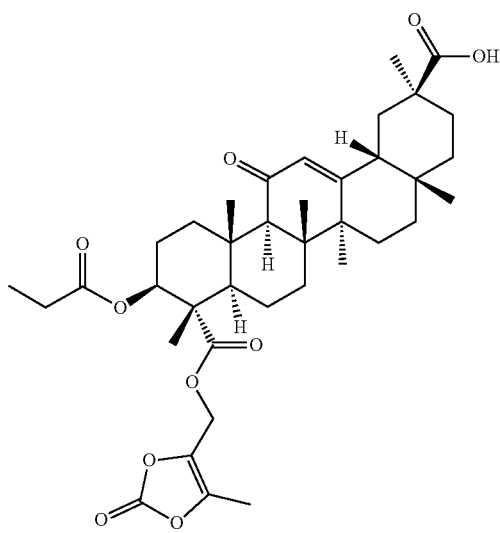

211-1

The title compound was prepared according to the methods for compound 194-10, beginning with 194-8 and propanoic acid. The crude product was purified by prep-HPLC with the following conditions: Column, X Select CSH OBD, 30*150 mm, 5 μm; mobile phase, water (0.05% TFA) and CH$_3$CN (60% Phase B up to 85% in 8 min); detector, UV. 69.7 mg of 211-1 was obtained as white solid. MS (ES, m/z): [M+1]$^+$=669; $^1$H NMR (300 MHz, Chloroform-d) δ 5.72 (s, 1H), 5.22-5.11 (m, 1H), 4.96 (d, J=13.8 Hz, 1H), 4.72 (d, J=13.8 Hz, 1H), 2.86 (d, J=13.9 Hz, 1H), 2.45 (s, 1H), 2.32-2.16 (m, 6H), 1.99 (s, 3H), 1.79 (s, 5H), 1.70 (d, J=9.9 Hz, 2H), 1.39 (s, 4H), 1.24 (s, 3H), 1.19 (d, J=9.0 Hz, 12H), 1.14-1.03 (m, 6H), 0.83 (s, 4H).

Example 22 (2S,4aS,6aS,6bR,8aR,9S,10S,12aS, 12bR,14bR)-10-((cyclopentanecarbonyl)oxy)-2,4a, 6a,6b,9,12a-hexamethyl-9-(((5-methyl-2-oxo-1,3-dioxol-4-yl)methoxy)carbonyl)-13-oxo-1,2,3,4,4a,5, 6,6a,6b,7,8,8a,9,10,11,12,12a,12b,13,14b-icosahydropicene-2-carboxylic Acid (212-1)

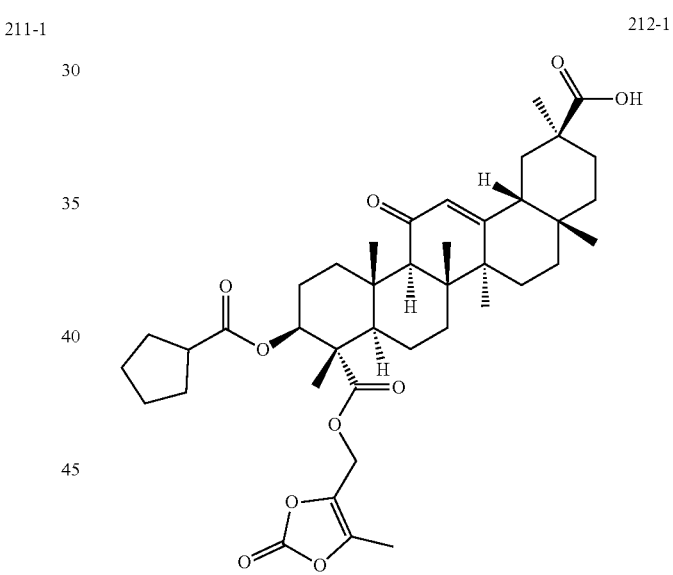

212-1

The title compound was prepared according to the methods for compound 194-10, beginning with 194-8 and cyclopentanoic acid. The crude product was purified by prep-HPLC with the following conditions: Column, Kinetex EVO C18, 21.2*150; 5 μm; mobile phase, water (0.05% TFA) and CH$_3$CN (70% PhaseB up to 88% in 8 min); detector, UV. This resulted in 66.3 mg of 212-1 as a white solid. MS (ES, m/z): [M+1]$^+$=709; $^1$H NMR (300 MHz, Chloroform-d) δ 5.72 (s, 1H), 5.14 (dd, J=10.5, 6.3 Hz, 1H), 4.94 (d, J=13.8 Hz, 1H), 4.71 (d, J=13.8 Hz, 1H), 2.86 (d, J=14.0 Hz, 1H), 2.64 (q, J=8.0, 7.5 Hz, 1H), 2.44 (s, 1H), 2.18 (s, 4H), 1.99 (s, 3H), 1.82 (d, J=8.5 Hz, 14H), 1.39 (s, 7H), 1.27-1.14 (m, 13H), 1.11 (s, 1H), 1.03 (d, J=12.7 Hz, 1H), 0.83 (s, 4H).

Example 23 (2S,4aS,6aS,6bR,8aR,9S,10S,12aS,
12bR,14bR)-2,4a,6a,6b,9,12a-hexamethyl-9-(((5-
methyl-2-oxo-1,3-dioxol-4-yl)methoxy)carbonyl)-
13-oxo-10-((3-(piperidin-1-yl)propanoyl)oxy)-1,2,3,
4,4a,5,6,6a,6b,7,8,8a,9,10,1142,12a,12b,13,14b-
icosahydropicene-2-carboxylic Acid (215-1)

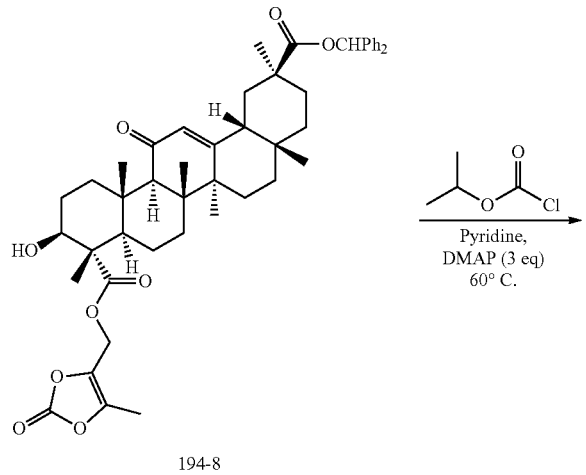

215-1

The title compound was prepared according to the methods for compound 194-10, beginning with 194-8 and 3-(piperidin-1-yl)propanoic acid. The crude product was purified by prep-HPLC with the following conditions: Column, Xselect CSH OBD Column 30*150 mm 5 um, n; mobile phase, water (0.05% TFA) and ACN (40% Phase B up to 53% in 8 min); detector, UV 254 nm. This resulted in 35.2 mg (33%) of 215-1 as a white solid. MS (ES, m/z): [M+1]$^+$= 752.43; $^1$H NMR (300 MHz, Chloroform-d) δ 11.9 (s, 1H), 5.71 (s, 1H), 5.16 (s, 1H), 4.86 (d, J=4.5 Hz, 2H), 3.56 (s, 3H), 3.27 (s, 6H), 2.88 (d, J=17.7 Hz, 3H), 2.66 (s, 2H), 2.20 (s, 5H), 1.98 (s, 4H), 1.88 (d, J=14.0 Hz, 5H), 1.61 (d, J=12.0 Hz, 7H), 1.39 (d, J=6.4 Hz, 9H), 1.26-1.14 (m, 16H), 1.12 (s, 2H), 0.82 (s, 3H).

Example 24 (2S,4aS,6aS,6bR,8aR,9S,10S,12aS,
12bR,14bR)-10-((isopropoxycarbonyl)oxy)-2,4a,6a,
6b,9,12a-hexamethyl-9-(((5-methyl-2-oxo-1,3-di-
oxol-4-yl)methoxy)carbonyl)-13-oxo-1,2,3,4,4a,5,6,
6a,6b,7,8,8a,9,10,1142,12a,12b,13,14b-
icosahydropicene-2-carboxylic Acid (216-2)

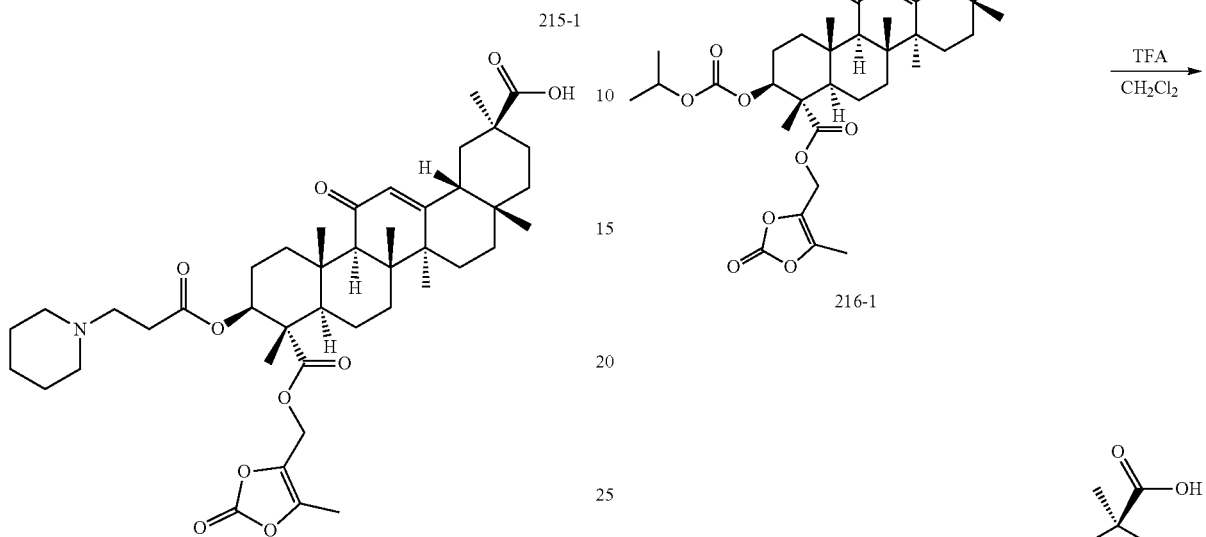

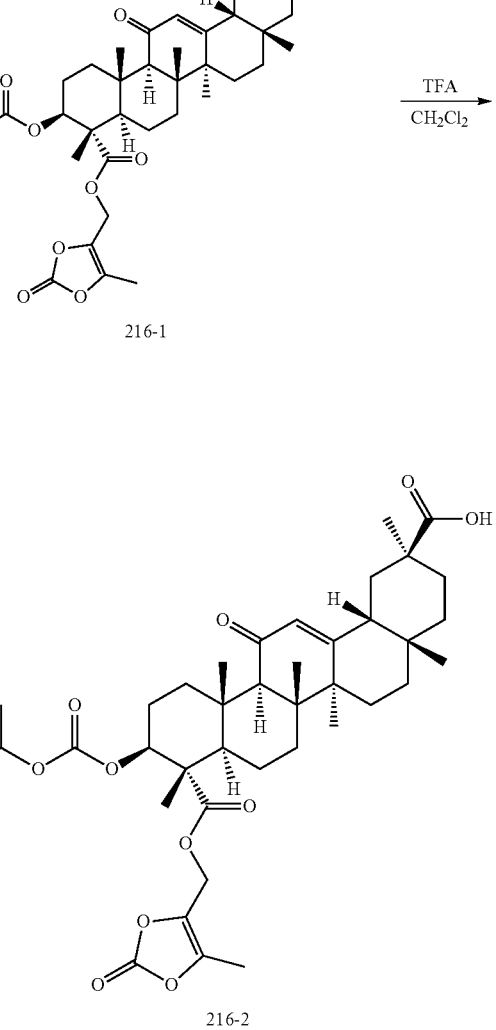

Synthesis of 2-benzhydryl 9-((5-methyl-2-oxo-1,3-
dioxol-4-yl)methyl) (2S,4aS,6aS,6bR,8aR,9S,10S,
12aS,12bR,14bR)-10-((isopropoxycarbonyl)oxy)-2,
4a,6a,6b,9,12a-hexamethyl-13-oxo-1,2,3,4,4a,5,6,6a,
6b,7,8,8a,9,10,11,12,12a,12b,13,14b-
icosahydropicene-2,9-dicarboxylate (216-1)

Into a 8 mL sealed tube were added 194-8 (200 mg, 0.26 mmol), pyridine (3 mL), DMAP (94.1 mg, 0.77 mmol, 3 equiv), and isopropyl chloroformate (315 mg, 2.6 mmol, 10 equiv) at room temperature. The reaction slurry was stirred for 6 h at 60° C. under nitrogen atmosphere. To the above mixture was added an additional portion of isopropyl chloroformate (315 mg, 2.6 mmol, 10 equiv) at 60° C. The reaction slurry was stirred for additional 6 h at 60° C. To the reaction mixture was added a third portion of isopropyl chloroformate (315 mg, 2.6 mmol, 10 equiv) at 60° C. The reaction slurry was stirred for an additional 6 h at 60° C. The reaction mixture was concentrated under vacuum. The residue was purified by prep-TLC (PE/EtOAc 1:1) to afford 216-1 (130 mg, 59%) as a pale yellow foam.

Synthesis of (2S,4aS,6aS,6bR,8aR,9S,10S,12aS, 12bR,14bR)-10-((isopropoxycarbonyl)oxy)-2,4a,6a, 6b,9,12a-hexamethyl-9-(((5-methyl-2-oxo-1,3-dioxol-4-yl)methoxy)carbonyl)-13-oxo-1,2,3,4,4a,5,6, 6a,6b,7,8,8a,9,10,11,12,12a,12b,13,14b-icosahydropicene-2-carboxylic Acid (216-2)

Into a 25-mL round-bottom flask was 216-1 (130 mg, 0.15 mmol, 1 equiv), CH$_2$Cl$_2$ (2 mL), and TFA (0.2 mL). The resulting solution was stirred for 30 min at room temperature. The resulting mixture was concentrated. The crude product was purified by prep-HPLC with the following condition: Column, Xselect CSH OBD 30*150 mm, 5 μm; mobile phase, water (0.05% TFA) and CH$_3$CN (64% Phase B up to 87% in 8 min); detector, UV. This resulted in 40.9 mg (39%) of 216-2 as a white solid. MS (ES, m/z): [M+1]$^+$= 698.37; $^1$H NMR (400 MHz, Chloroform-d) δ 7.38 (dd, J=17.4, 5.5 Hz, 1H), 5.75 (s, 1H), 5.14-4.93 (m, 2H), 4.87-4.75 (m, 2H), 2.90 (d, J=13.8 Hz, 1H), 2.45 (s, 1H), 2.21 (s, 4H), 2.11-1.90 (m, 4H), 1.87-1.76 (m, 3H), 1.65 (dd, J=12.4, 6.5 Hz, 5H), 1.57-1.32 (m, 9H), 1.28 (dd, J=6.3, 3.4 Hz, 7H), 1.25 (d, J=6.9 Hz, 7H), 1.19 (d, J=5.5 Hz, 5H), 1.13 (s, 4H), 1.10-1.00 (m, 2H), 0.85 (s, 5H), 0.09 (s, 3H).

Example 25 (2S,4aS,6aS,6bR,8aR,9S,10S,12aS, 12bR,14bR)-10-(2,2-Difluoroacetoxy)-2,4a,6a,6b,9, 12a-hexamethyl-9-(((5-methyl-2-oxo-1,3-dioxol-4-yl)methoxy)carbonyl)-13-oxo-1,2,3,4,4a,5,6,6a,6b,7, 8,8a,9,10,11,12,12a,12b,13,14b-icosahydropicene-2-carboxylic Acid (223-1)

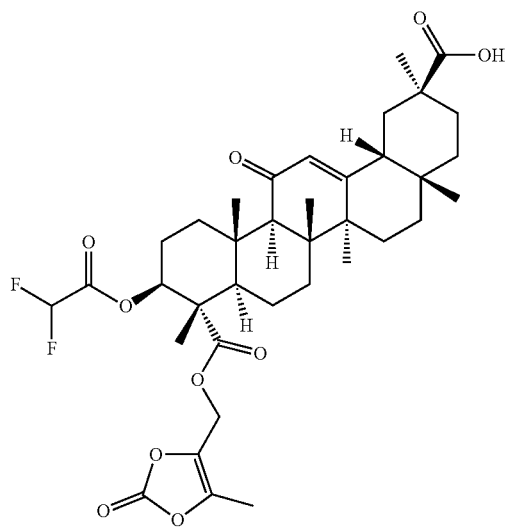

223-1

The title compound was prepared according to the methods for compound 194-10, beginning with 194-8 and 2,2-difluoroacetic acid. The crude product was purified by prep-HPLC with the following conditions—Column: Xselect CSH OBD 30*150 mm, 5 μm; mobile phase: water (0.05% TFA) and CH$_3$CN (68% Phase B up to 80% in 8 min); detector: UV. This resulted in 82.1 mg (46%) of 223-1 as a white solid. MS (ES, m/z): [M+H]$^+$=691.15; $^1$H NMR (400 MHz, MeOH-d$_4$) δ 0.83 (s, 3H), 0.97 (d, J=7.6 Hz, 1H), 1.05 (d, J=13.6 Hz, 1H), 1.14 (s, 3H), 1.18 (d, J=8.4 Hz, 6H), 1.22-1.31 (m, 5H), 1.40 (s, 4H), 1.45 (s, 3H), 1.64-1.80 (m, 5H), 1.82-1.90 (m, 3H), 1.92-2.00 (m, 1H), 2.09-2.29 (m, 5H), 2.57 (s, 1H), 2.88 (d, J=10.4 Hz, 1H), 4.88 (d, J=14.0 Hz, 1H), 5.02 (d, J=14.0 Hz, 1H), 5.33 (dd, J=14.0, 5.2 Hz, 1H), 5.61 (s, 1H), 6.05 (t, J=53.2 Hz, 1H).

Example 26 (2S,4aS,6aS,6bR,8aR,9R,10S,12aS, 12bR,14bR)-10-Hydroxy-2,4a,6a,6b,9,12a-hexamethyl-9-((2-((5-methyl-2-oxo-1,3-dioxol-4-yl) methoxy)-2-oxoethoxy)methyl)-13-oxo-1,2,3,4,4a,5, 6,6a,6b,7,8,8a,9,10,1142,12a,12b,13,14b-icosahydropicene-2-carboxylic Acid (240-8)

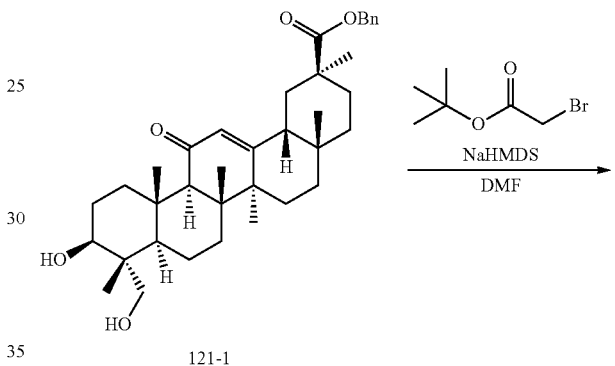

121-1

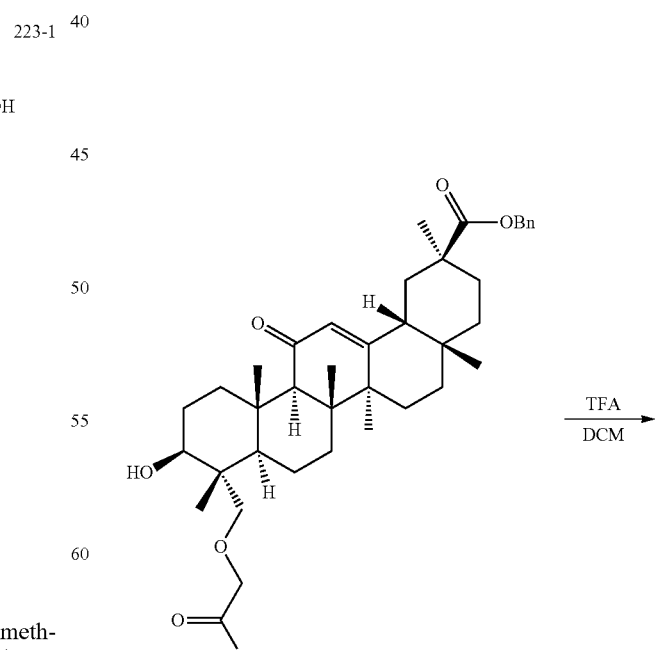

240-1

135
-continued
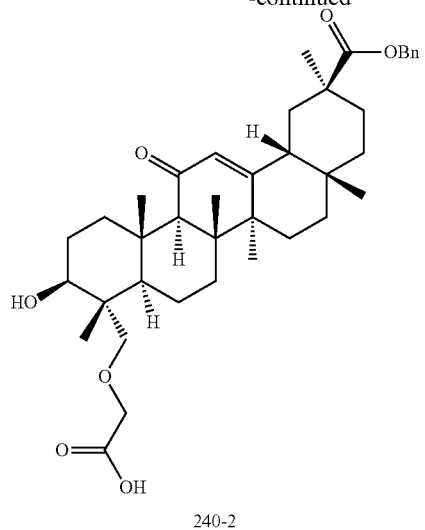
240-2
TMSCH₂N
───────→
DCM, MeOH
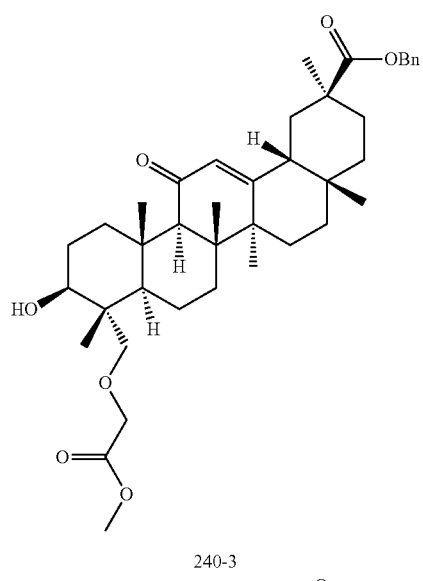
240-3
H₂, Pd/C
─────→
EtOAc
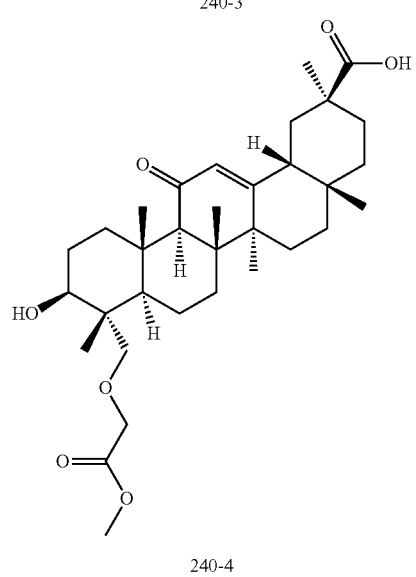
240-4
Ph₂CN₂
──────→
MeOH/ether
136
-continued
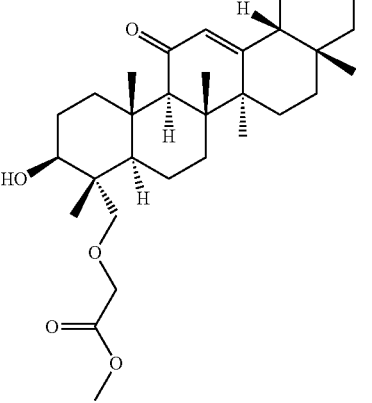
240-5
LiOH
──────→
THF, H₂O
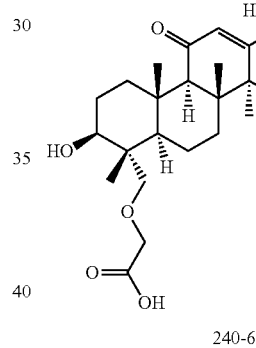
240-6
K₂CO₃, KI
──────────→
DMF, 50° C.
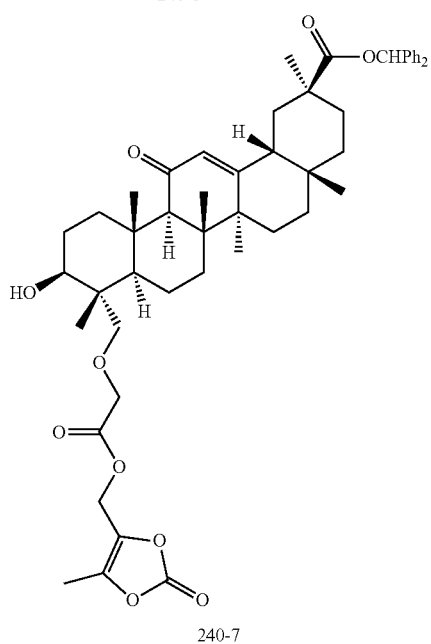
240-7
TFA
─────→
CH₂Cl₂

-continued

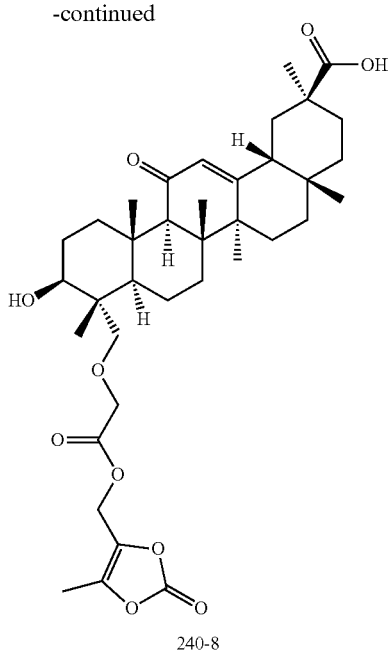
240-8

Synthesis of Benzyl (2S,4aS,6aS,6bR,8aR,9R,10S, 12aS,12bR,14bR)-9-((2-(tert-butoxy)-2-oxoethoxy) methyl)-10-hydroxy-2,4a,6a,6b,9,12a-hexamethyl-13-oxo-1,2,3,4,4a,5,6,6a,6b,7,8,8a,9,10,11,12,12a, 12b,13,14b-icosahydropicene-2-carboxylate (240-1)

Sodium bis(trimethylsilyl)amide (0.5 mL, 2 equiv) was added to 121-1 (355 mg, 0.62 mmol, 1 equiv) and tert-butyl 2-bromoacetate (240.6 mg, 1.24 mmol, 2 equiv) in DMF (5 mL). The reaction slurry was stirred overnight at rt, diluted with $CH_2Cl_2$ (100 mL), washed with brine (2×100 mL), dried over anhydrous $Na_2SO_4$, filtered, and concentrated. The residue was purified by silica gel column eluting with EtOAc/petroleum ether (1:1) to provide 300 mg (71%) of 240-1 as a white solid.

Synthesis of 2-(((3S,4R,4aR,6aR,6bS,8aS,11S,12aR, 14aR,14bS)-11-((Benzyloxy)carbonyl)-3-hydroxy-4, 6a, 6b, 8a, 11,14b-hexamethyl -14-oxo-1,2,3,4,4a,5, 6,6a,6b,7,8,8a,9,10,11,12,12a,14,14a,14b-icosahydropicen-4-yl)methoxy)acetic Acid (240-2)

240-1 (300 mg, 0.43 mmol, 1 equiv) and TFA (1 mL) were combined in $CH_2Cl_2$ (10 mL) for 1 h at rt. The reaction mixture was diluted with $CH_2Cl_2$ (100 mL), washed with brine (3×50 mL), dried over anhydrous $Na_2SO_4$, filtered, and concentrated. This resulted in 270 mg (98%) of 240-2 as a yellow solid.

Synthesis of Benzyl (2S,4aS,6aS,6bR,8aR,9R,10S, 12aS,12bR,14bR)-10-hydroxy-9-((2-methoxy-2-oxoethoxy)methyl)-2,4a,6a,6b,9,12a-hexamethyl-13-oxo-1,2,3,4,4a,5,6,6a,6b,7,8,8a,9,10,11,12,12a,12b, 13,14b-icosahydropicene-2-carboxylate (240-3)

(Trimethylsilyl)diazomethane (1 mL) was added dropwise to 240-2 (270 mg, 0.43 mmol, 1 equiv) in MeOH (5 mL) and $CH_2Cl_2$ (10 mL). The reaction slurry was stirred for 2 h at rt. The reaction mixture was concentrated to provide 260 mg (94%) of 240-3 as a white solid.

Synthesis of (2S,4aS,6aS,6bR,8aR,9R,10S,12aS, 12bR,14bR)-10-Hydroxy-9-((2-methoxy-2-oxoethoxy)methyl)-2,4a,6a,6b,9,12a-hexamethyl-13-oxo-1, 2,3,4,4a,5,6,6a,6b,7,8,8a,9,10,11,12,12a,12b,13,14b-icosahydropicene-2-carboxylic Acid (240-4)

240-3 (270 mg, 0.42 mmol) and Pd/C (20 mg, 10% wt) in EtOAc (30 mL) were stirred for 2 h under $H_2$ (1 atm). The reaction mixture was filtered and concentrated to provide 216 mg (93%) of 240-4 as a white solid.

Synthesis of Benzhydryl (2S,4aS,6aS,6bR,8aR,9R, 10S,12aS,12bR,14bR)-10-hydroxy-9-((2-methoxy-2-oxoethoxy)methyl)-2,4a,6a,6b,9,12a-hexamethyl-13-oxo-1,2,3,4,4a,5,6,6a,6b,7,8,8a,9,10,11,12,12a,12b, 13,14b-icosahydropicene-2-carboxylate (240-5)

(Diazomethylene)dibenzene (180 mg) in MeOH (20 mL) was added to 240-4 (216 mg, 1 equiv) in ether (10 mL). The reaction slurry was stirred for 3 h at rt. The reaction mixture was concentrated and the residue purified by silica gel column eluting with EtOAc/petroleum ether (1:10) to provide 220 mg (79%) of 240-5 as a white solid.

Synthesis of 2-(((3S,4R,4aR,6aR,6bS,8aS,11S,12aR, 14aR,14bS)-11-((Benzhydryloxy)carbonyl)-3-hydroxy-4,6a,6b,8a,11,14b-hexamethyl-14-oxo-1,2,3,4, 4a,5,6,6a,6b,7,8,8a,9,10,11,12,12a,14,14a,14b-icosahydropicen-4-yl)methoxy)acetic Acid (240-6)

240-5 (220 mg, 0.30 mmol, 1 equiv) and lithium hydroxide (73 mg, 3 mmol, 10 equiv) were combined in THF (10 mL), $H_2O$ (1 mL), and MeOH (1 mL), stirring for 2 h at rt. The reaction mixture was adjusted to pH=4 with 1 M HCl and extracted with $CH_2Cl_2$ (2×100 mL). The combined organic layers were dried over anhydrous $Na_2SO_4$, filtered, and concentrated to provide 200 mg (93%) of 240-6 as a white solid.

Synthesis of Benzhydryl (2S,4aS,6aS,6bR,8aR,9R, 10S,12aS,12bR,14bR)-10-hydroxy-2,4a,6a,6b,9,12a-hexamethyl-9-((2-((5-methyl-2-oxo-1,3-dioxol-4-yl) methoxy)-2-oxoethoxy)methyl)-13-oxo-1,2,3,4,4a,5, 6,6a,6b,7,8,8a,9,10,11,12,12a,12b,13,14b-icosahydropicene-2-carboxylate (240-7)

240-6 (200 mg, 0.28 mmol, 1 equiv), 4-(chloromethyl)-5-methyl-2H-1,3-dioxol-2-one (84 mg, 0.57 mmol, 2 equiv), $K_2CO_3$ (194 mg, 1.40 mmol, 5 equiv), and potassium iodide (70 mg, 0.42 mmol, 1.5 equiv) were combined in DMF (10 mL) and stirred for 1 h at 50° C. The reaction mixture was diluted with $CH_2Cl_2$ (100 mL), washed with brine (3×100 mL), dried over anhydrous $Na_2SO_4$, filtered, and concentrated to provide 200 mg (86%) of 240-7 as a white solid.

Synthesis of (2S,4aS,6aS,6bR,8aR,9R,10S,12aS, 12bR,14bR)-10-Hydroxy-2,4a,6a,6b,9,12a-hexamethyl-9-((2-((5-methyl-2-oxo-1,3-dioxol-4-yl)methoxy)-2-oxoethoxy)methyl)-13-oxo-1,2,3,4,4a,5, 6,6a,6b,7,8,8a,9,10,11,12,12a,12b,13,14b-icosahydropicene-2-carboxylic Acid (240-8)

240-7 (200 mg, 0.24 mmol, 1 equiv) and TFA (1 mL) were combined in CH$_2$Cl$_2$ (10 mL) and stirred for 1 h. The solids were collected by filtration. The resulting mixture was concentrated and the residue purified by prep-HPLC with the following conditions—mobile phase: water (0.05% TFA) and CH$_3$CN (hold 5% Phase B in 0 min, up to 63% in 1 min, up to 68% in 8 min); detector: UV. This resulted in 14.5 mg (9%) of 240-8 as a white solid. MS (ES, m/z): [M+H]$^+$=657.25; $^1$H NMR (400 MHz, chloroform-rf) δ 0.72 (s, 3H), 0.86 (s, 3H), 1.03 (t, J=15.2 Hz, 2H), 1.13-1.22 (m, 9H), 1.22-1.37 (m, 2H), 1.43 (d, J=5.6 Hz, 8H), 1.66-1.97 (m, 8H), 2.21 (s, 5H), 2.51 (s, 1H), 2.73 (d, J=13.6 Hz, 1H), 3.39 (s, 2H), 3.72 (dd, J=11.8, 4.8 Hz, 1H), 4.09 (d, J=16.8 Hz, 1H), 4.26 (d, J=16.8 Hz, 1H), 4.92 (s, 1H), 5.03 (s, 2H), 5.60 (s, 1H).

Example 27 (2S,4aS,6aS,6bR,8aR,9S,10S,12aS, 12bR,14bR)-10-Acetoxy-2,4a,6a,6b,9,12a-hexamethyl-9-((((5-methyl-2-oxo-1,3-dioxol-4-yl)methoxy)carbonyl)-13-oxo-1,2,3,4,4a,5,6,6a,6b,7,8,8a,9,10, 1142,12a,12b,13,14b-icosahydropicene-2-carboxylic (243-1)

The title compound was prepared according to the methods for compound 194-10, beginning with 194-8 and acetic acid. The crude product was purified by prep-HPLC with the following conditions—Column: XSelect CSHPrep C18 OBD, 5 μm, 19*150 mm; mobile phase: water (0.05% TFA) and CH$_3$CN (hold 5% Phase B in 0 min, up to 65% in 1 min, up to 85% in 8 min); detector: UV. This resulted in 24.7 mg (20%) of 243-1 as a white solid. MS (ES, m/z): [M+H]$^+$= 655.15; 1HNMR (400 MHz, methanol-d$_4$) δ 0.85 (s, 3H), 0.96 (d, J=5.6 Hz, 1H), 1.06 (d, J=14.1 Hz, 1H), 1.16-1.29 (m, 14H), 1.36-1.49 (m, 7H), 1.63-1.80 (m, 6H), 1.80-1.92 (m, 2H), 1.92-2.01 (m, 4H), 2.08-2.08 (m, 5H), 2.55 (s, 1H), 2.78-2.86 (m, 1H), 4.89 (d, J=13.9 Hz, 1H), 5.03 (d, J=14.0 Hz, 1H), 5.15 (dd, J=11.7, 4.9 Hz, 1H), 5.62 (s, 1H).

Example 28 (2S,4aS,6aS,6bR,8aR,9S,10S,12aS, 12bR,14bR)-10-(2-Hydroxyacetoxy)-2,4a,6a,6b,9, 12a-hexamethyl-9-(((5-methyl-2-oxo-1,3-dioxol-4-yl)methoxy)carbonyl)-13-oxo-1,2,3,4,4a,5,6,6a,6b,7, 8,8a,9,10,11,12,12a,12b,13,14b-icosahydropicene-2-carboxylic Acid (244-1)

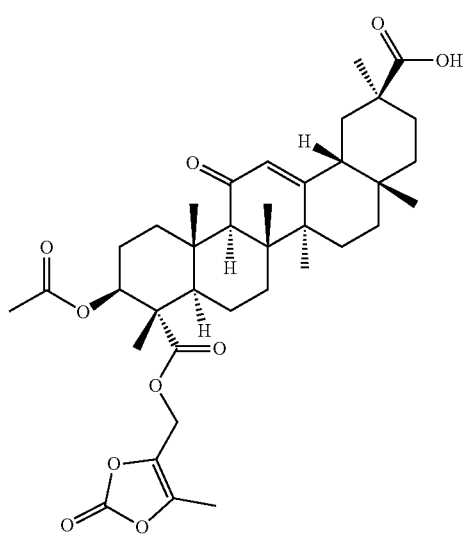

243-1

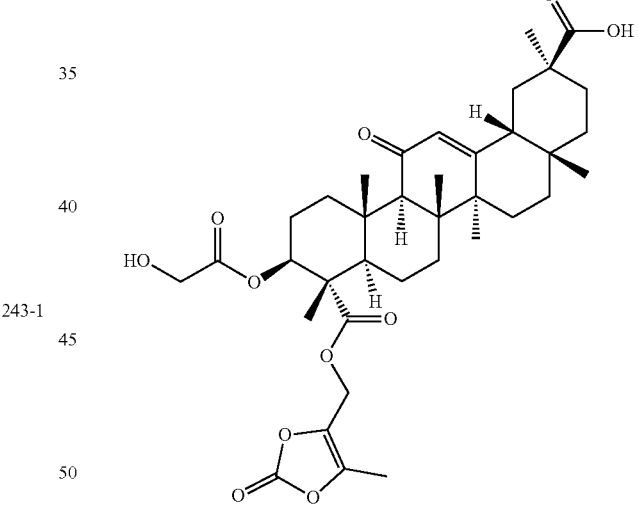

244-1

The title compound was prepared according to the methods for compound 194-10, beginning with 194-8 and 2-[(4-methoxyphenyl)methoxy]acetic acid. The crude product was purified by prep-HPLC with the following conditions— Column: XBridge Prep Cl8 OBD, 19*150 mm, 5 μm; mobile phase: water (0.05% TFA) and CH$_3$CN (35% Phase B up to 90% in 7 min); detector: UV. This resulted in 25.8 mg (28%) of 244-1 as a white solid. MS (ES, m/z): [M+H]$^+$= 671.35; $^1$H NMR (400 MHz, methanol-d$_4$) δ 0.85 (s, 3H), 0.95 (s, 1H), 1.06 (d, J=14.0 Hz, 1H), 1.15 (s, 3H), 1.17-1.27 (m, 10H), 1.27 (d, J=8.0 Hz, 1H), 1.33-1.524 (m, 7H), 1.61-2.00 (m, 9H), 2.20 (s, 5H), 2.58 (s, 1H), 2.80-2.88 (m, 1H), 3.96-4.11 (m, 2H), 4.87 (d, J=13.9 Hz, 1H), 5.06 (d, J=14.0 Hz, 1H), 5.26 (dd, J=11.7, 5.0 Hz, 1H), 5.62 (s, 1H).

Example 29 (2S,4aS,6aS,6bR,8aR,9S,10S,12aS, 12bR,14bR)-10-(2-Methoxyacetoxy)-2,4a,6a,6b,9, 12a-hexamethyl-9-(((5-methyl-2-oxo-1,3-dioxol-4-yl)methoxy)carbonyl)-13-oxo-1,2,3,4,4a,5,6,6a,6b,7, 8,8a,9,10,11,12,12a,12b,13,14b-icosahydropicene-2-carboxylic Acid (245-1)

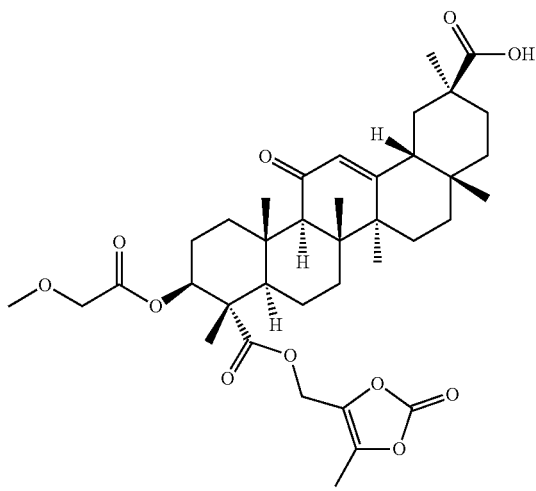

245-1

The title compound was prepared according to the methods for compound 194-10, beginning with 194-8 and 2-methoxyacetic acid. The crude product was purified by prep-HPLC with the following conditions—Column: XSelect CSHPrep C18 OBD, 5 μm, 19*150 mm: mobile phase: water (0.05% TFA) and CH$_3$CN (hold 5% Phase B in 0 min, up to 62% in 1 min, up to 82% in 8 min); detector: UV. This resulted in 25.9 mg (19%) of 245-1 as a white solid. MS (ES, m/z): [M+H]$^+$=685.15; $^1$H NMR (400 MHz, methanol-d$_4$) δ 0.85 (s, 3H), 1.06 (d, J=14.1 Hz, 1H), 1.00-1.10 (m, 1H), 1.10-1.30 (m, 14H), 1.35-1.51 (m, 7H), 1.61-2.08 (m, 9H), 2.09-2.28 (m, 5H), 2.59 (s, 1H), 2.80-2.88 (m, 1H), 3.39 (s, 3H), 3.97 (d, J=1.3 Hz, 2H), 4.88 (d, J=14.0 Hz, 1H), 5.05 (d, J=13.9 Hz, 1H), 5.27 (dd, J=11.8, 5.0 Hz, 1H), 5.62 (s, 1H).

Example 30 (2S,4aS,6aS,6bR,8aR,9S,10S,12aS, 12bR,14bR)-10-((2,5,8,11-Tetraoxadodecanoyl) oxy)-2,4a,6a,6b,9,12a-hexamethyl-9-(((5-methyl-2-oxo-1,3-dioxol-4-yl)methoxy)carbonyl)-13-oxo-1,2, 3,4,4a,5,6,6a,6b,7,8,8a,9,10,1142,12a,12b,13,14b-icosahydropicene-2-carboxylic Acid (246-3)

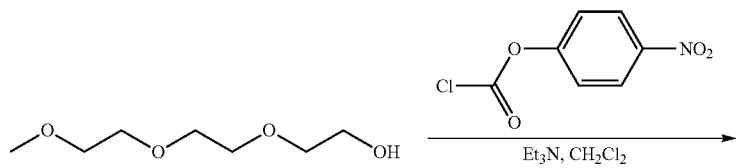

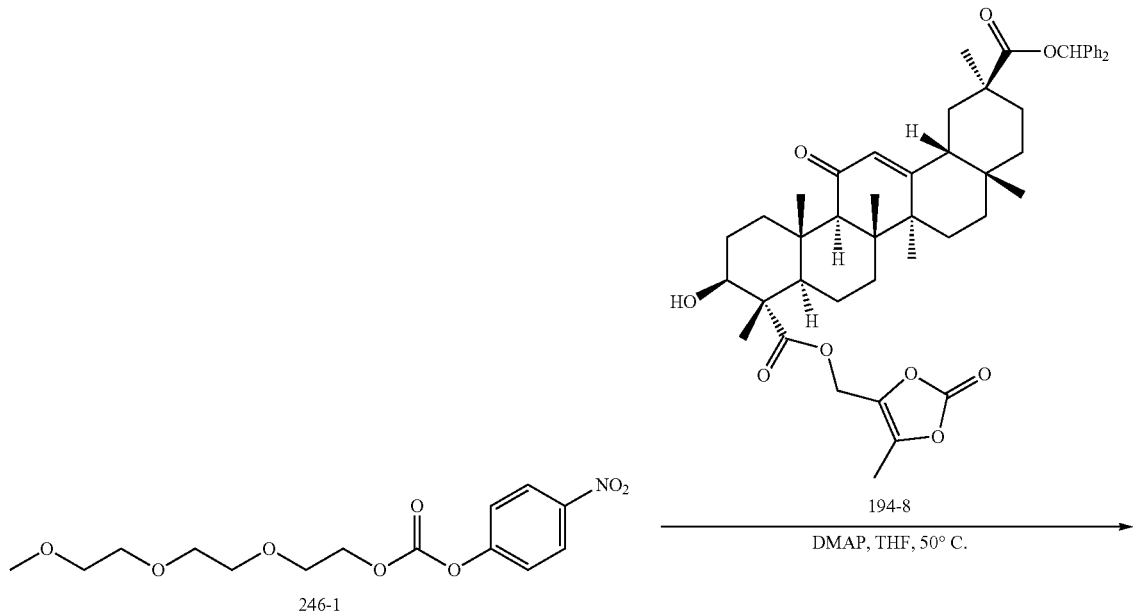

246-1

-continued

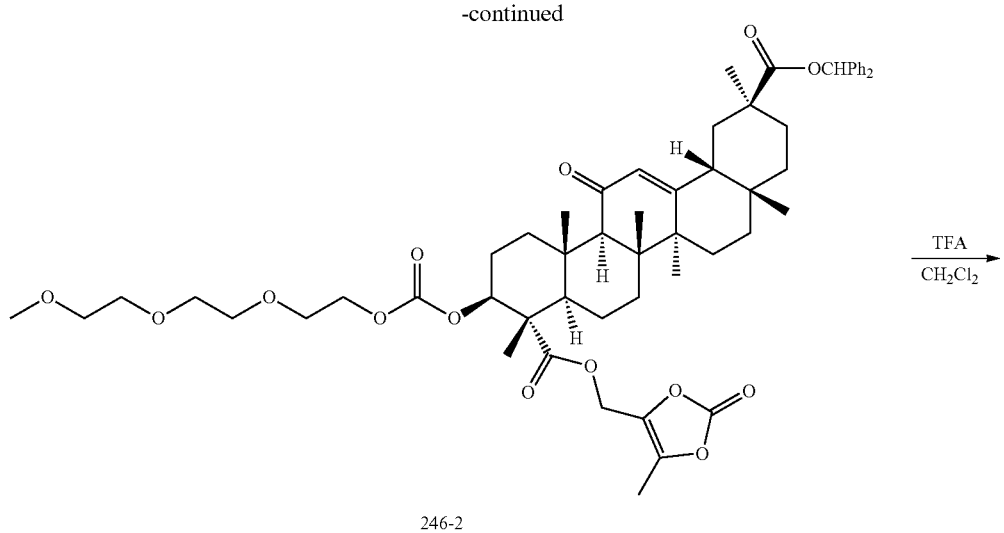

246-2

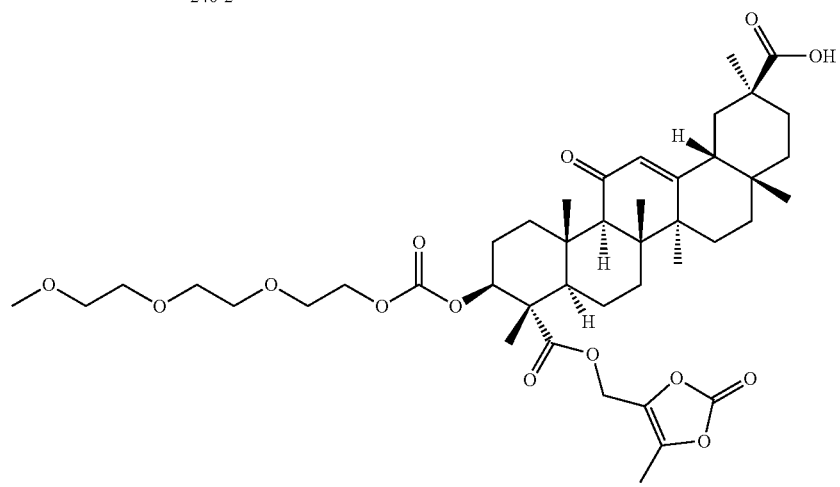

246-3

Synthesis of 2-(2-(2-Methoxyethoxy)ethoxy)ethyl (4-nitrophenyl) carbonate (246-1) 2-[2-(2-Methoxyethoxy)ethoxy]ethan-1-ol (3.0 g, 18.3 mmol, 1 equiv), p-nitrophenyl chloroformate (4.4 g, 20.4 mmol, 1.1 equiv) and Et$_3$N (5 mL, 36 mmol, 2 equiv) in CH$_2$Cl$_2$ (20 mL) were stirred for 1 h at rt. The reaction was concentrated and the residue purified by silica gel column eluting with EtOAc/petroleum ether (1:1) to provide 4.2 g (67%) of 246-1 as a clear liquid.

Synthesis of 2-Benzhydryl 9-((5-methyl-2-oxo-1,3-dioxol-4-yl)methyl) (2S,4aS,6aS,6bR,8aR,9S,10S,12aS,12bR,14bR)-10-((2,5,8,11-tetraoxadodecanoyl)oxy)-2,4a,6a,6b,9,12a-hexamethyl-13-oxo-1,2,3,4,4a,5,6,6a,6b,7,8,8a,9,10,11,12,12a,12b,13,14b-icosahydropicene-2,9-dicarboxylate (246-2)

194-8 (150 mg, 0.19 mmol, 1 equiv), 246-1 (640 mg, 1.9 mmol, 10 equiv), and DMAP (94 mg, 0.77 mmol, 4 equiv) in THF (8 mL) were stirred for 24 h at 50° C. The reaction mixture was diluted with CH$_2$Cl$_2$ (300 mL), washed with brine (3×100 mL), dried over anhydrous Na$_2$SO$_4$, filtered, and concentrated. The residue was purified by silica gel column eluting with EtOAc/petroleum ether (1:1) to provide 156 mg (84%) of 246-2 as a yellow oil.

Synthesis of (2S,4aS,6aS,6bR,8aR,9S,10S,12aS,12bR,14bR)-10-((2,5,8,11-Tetraoxadodecanoyl)oxy)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic Acid (246-3)

246-2 (156 mg, 0.16 mmol, 1 equiv), and TFA (1 mL) in CH$_2$Cl$_2$ (10 mL) were stirred for 1 h at rt. The reaction mixture was concentrated and the residue purified by prep-HPLC with the following conditions—Column, XBridge Prep C18 OBD, 19*150 mm, 5 μm; mobile phase: water (0.05% TFA) and CH$_3$CN (35% Phase B up to 90% in 7 min); detector: UV. This resulted in 21.5 mg (16%) of 246-3 as a white solid. MS (ES, m/z): [M+H]$^+$=803.20; $^1$H NMR (400 MHz, methanol-d$_4$) δ 0.85 (s, 3H), 0.98 (d, J=9.2 Hz, 1H), 1.06 (d, J=14.1 Hz, 1H), 1.13-1.25 (m, 14H), 1.44 (d, J=18.2 Hz, 7H), 1.61-1.93 (m, 8H), 1.97 (d, J=9.6 Hz, 1H), 2.11-2.37 (m, 5H), 2.58 (s, 1H), 2.81-2.89 (m, 1H), 3.38 (s, 3H), 3.52-3.61 (m, 2H), 3.61-3.73 (m, 8H), 4.12-4.30 (m, 2H), 4.91-5.07 (m, 3H), 5.62 (s, 1H).

Example 31 (2S,4aS,6aS,6bR,8aR,9S,10S,12aS,12bR,14bR)-10-Methoxy-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,1142,12a,12b,13,14b-icosahydropicene-2-carboxylic acid (249-5)

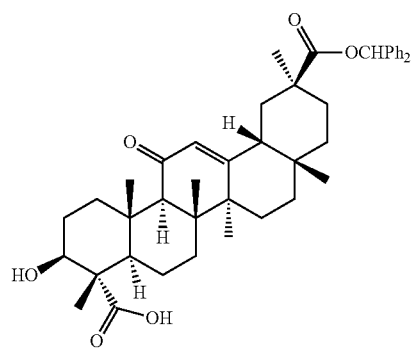

194-7

TMSCHN₂
CH₂Cl₂, MeOH

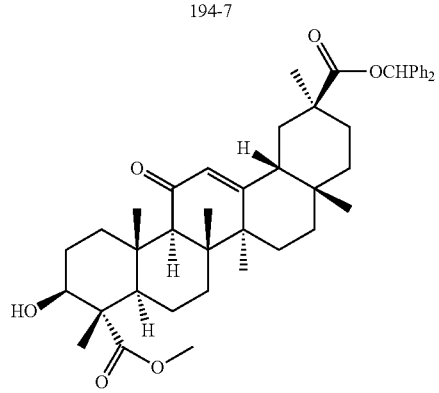

249-1

MeI, NaH
THF, 50° C.

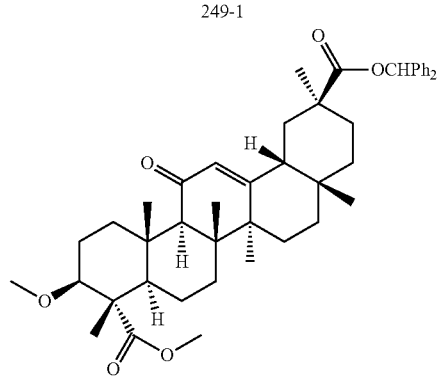

249-2

LiI, pyridine
125° C.

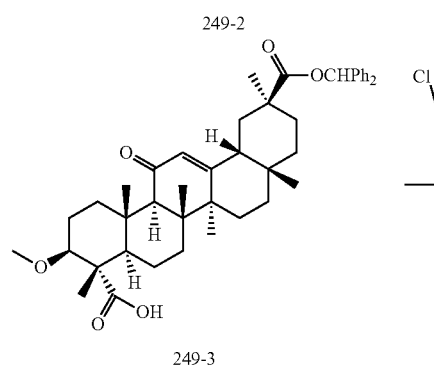

249-3

<br>Cl—[chloromethyl methyl dioxolone]<br>
K₂CO₃, KI
DMF, 50° C.

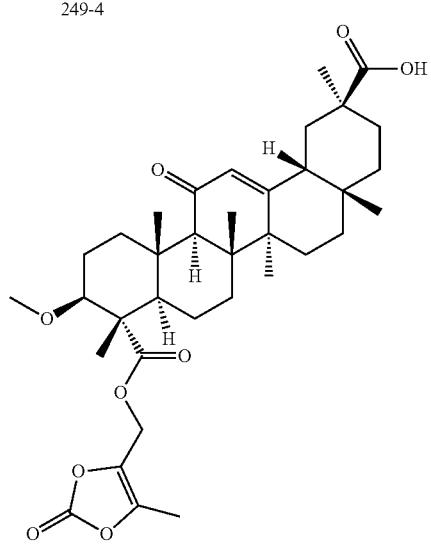

249-4

TFA
CH₂Cl₂

249-5

Synthesis of 2-benzhydryl 9-methyl (2S,4aS,6aS,6bR,8aR,9S,10S,12aS,12bR,14bR)-10-hydroxy-2,4a,6a,6b,9,12a-hexamethyl-13-oxo-1,2,3,4,4a,5,6,6a,6b,7,8,8a,9,10,11,12,12a,12b,13,14b-icosahydropicene-2,9-dicarboxylate (249-1) (Trimethylsilyl)diazomethane (1 mL) was added to 194-7 (200 mg, 0.30 mmol, 1 equiv) in CH₂Cl₂ (5 mL) and MeOH (2.5 mL), The resulting solution was stirred for 1 h at rt. The reaction mixture was concentrated to provide 200 mg (98%) of 249-1 as a white solid.

Synthesis of 2-benzhydryl 9-methyl (2S,4aS,6aS,6bR,8aR,9S,10S,12aS,12bR,14bR)-10-methoxy-2,4a,6a,6b,9,12a-hexamethyl-13-oxo-1,2,3,4,4a,5,6,6a,6b,7,8,8a,9,10,11,12,12a,12b,13,14b-icosahydropicene-2,9-dicarboxylate (249-2)

Sodium hydride (100 mg, 4.17 mmol, 14 equiv) was added portionwise at rt to 249-1 (200 mg, 0.29 mmol, 1 equiv) and iodomethane (0.5 mL, 8.03 mmol) in THF (10 mL). The reaction slurry was stirred overnight at 50° C. and then quenched by the addition of water. The reaction mixture was extracted with EtOAc (3×50 mL), dried over anhydrous Na$_2$SO$_4$, filtered, and concentrated. The residue was purified by silica gel column eluting with EtOAc/petroleum ether (1:1) to provide 180 mg (88%) of 249-2 as a white solid.

Synthesis of (3S,4S,4aR,6aR,6bS,8aS,11S,12aR, 14aR,14bS)-11-((benzhydryloxy)carbonyl)-3-methoxy-4,6a,6b,8a,11,14b-hexamethyl-14-oxo-1,2, 3,4,4a,5,6,6a,6b,7,8,8a,9,10,11,12,12a,14,14a,14b-icosahydropicene-4-carboxylic Acid (249-3)

A slurry of 249-2 (180 mg, 0.26 mmol, 1 equiv) and lithium iodide (100 mg, 0.75 mmol, 2.9 equiv) in pyridine (5 mL) was stirred for 2 days at 125° C. The reaction mixture was diluted with CH$_2$Cl$_2$, washed with brine, dried over anhydrous Na$_2$SO$_4$, filtered, and concentrated. The residue was purified by silica gel column eluting with EtOAc/petroleum ether (1:1) to provide 110 mg (62%) of 249-3 as a yellow solid.

Synthesis of 2-benzhydryl 9-((5-methyl-2-oxo-1,3-dioxol-4-yl)methyl) (2S,4aS,6aS,6bR,8aR,9S,10S, 12aS,12bR,14bR)-10-methoxy-2,4a,6a,6b,9,12a-hexamethyl-13-oxo-1,2,3,4,4a,5,6,6a,6b,7,8,8a,9,10, 11,12,12a,12b,13,14b-icosahydropicene-2,9-dicarboxylate (249-4)

249-3 (110 mg, 0.16 mmol, 1 equiv), 4-(chloromethyl)-5-methyl-2H-1,3-dioxol-2-one (150 mg, 1.0 mmol, 6.3 equiv), K$_2$CO$_3$ (150 mg, 1.1 mmol, 6.7 equiv), and potassium iodide (50 mg, 0.30 mmol, 1.9 equiv) in DMF (10 mL) were stirred for 1 h at 50° C. The reaction mixture was diluted with CH$_2$Cl$_2$ (100 mL), washed with brine, dried over anhydrous Na$_2$SO$_4$, filtered, and concentrated. The residue was purified by silica gel column eluting with EtOAc/petroleum ether (1:1) to provide 100 mg (78%) of 249-4 as a white solid.

Synthesis of (2S,4aS,6aS,6bR,8aR,9S,10S,12aS, 12bR,14bR)-10-methoxy-2,4a,6a,6b,9,12a-hexamethyl-9-(((5-methyl-2-oxo-1,3-dioxol-4-yl)methoxy) carbonyl)-13-oxo-1,2,3,4,4a,5,6,6a,6b,7,8,8a,9,10, 11,12,12a,12b,13,14b-icosahydropicene-2-carboxylic acid (249-5)

249-4 (150 mg, 0.19 mmol, 1 equiv) and TFA (1 mL) in CH$_2$Cl$_2$ (10 mL) were stirred for 1 h at rt. The reaction mixture was concentrated and the residue purified by prep-HPLC with the following conditions—mobile phase: water (0.05% TFA) and CH$_3$CN (66% Phase B up to 74% in 8 min); detector: UV. This resulted in 38.3 mg (32%) of 249-5 as a white solid. MS (ES, m/z) [M+H]$^+$=627.55; $^1$H NMR (400 MHz, methanol-d$_4$) δ 0.85 (s, 3H), 0.90 (d, J=9.8 Hz, 1H), 0.96-1.29 (m, 15H), 1.44 (d, J=8.1 Hz, 5H), 1.54 (t, J=13.0 Hz, 2H), 1.60-1.99 (m, 6H), 2.22 (s, 5H), 2.54 (s, 1H), 2.83 (d, J=13.8 Hz, 1H), 3.26 (s, 3H), 3.64 (dd, J=11.8, 4.2 Hz, 1H), 4.92 (s, 1H), 5.13 (d, J=14.0 Hz, 1H), 5.61 (s, 1H).

Example 32 (2S,4aS,6aS,6bR,8aR,9S,10S,12aS, 12bR,14bR)-9-(((5-Isopropyl-2-oxo-1,3-dioxol-4-yl) methoxy)carbonyl)-10-methoxy-2,4a,6a,6b,9,12a-hexamethyl-13-oxo-1,2,3,4,4a,5,6,6a,6b,7,8,8a,9,10, 1142,12a,12b,13,14b-icosahydropicene-2-carboxylic Acid (252-2)

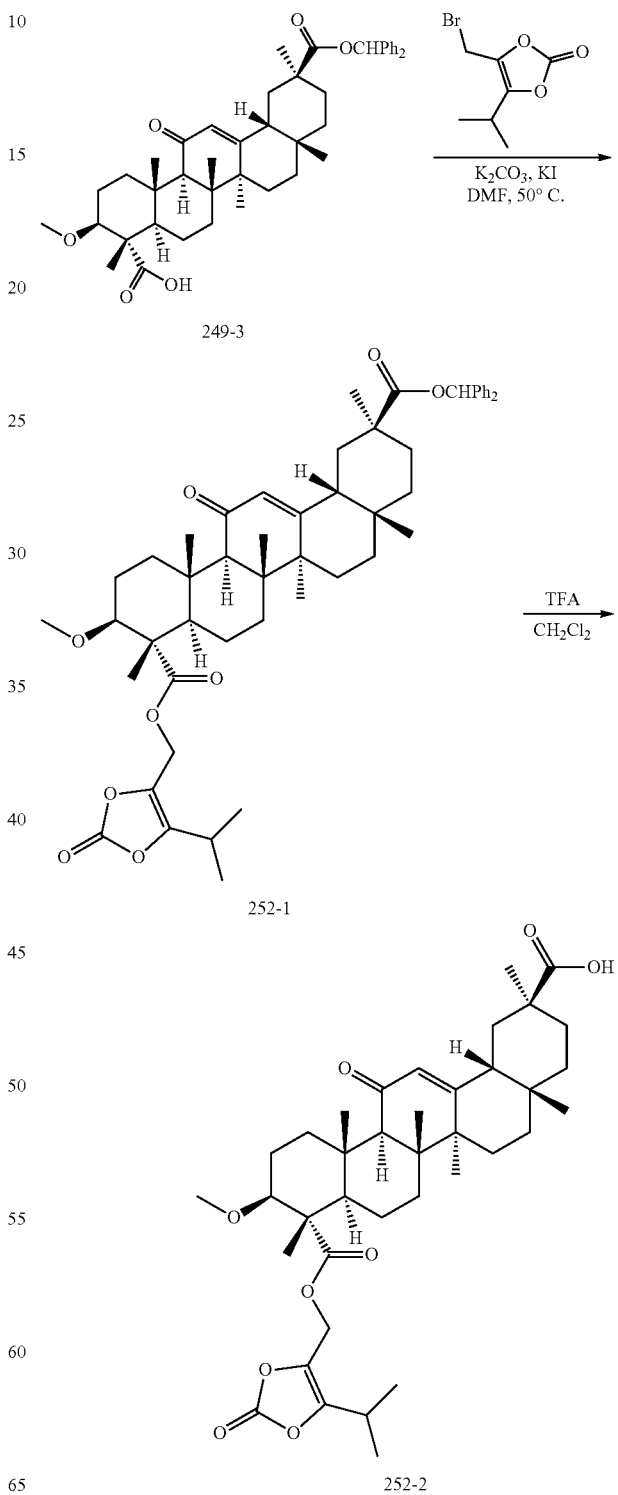

Synthesis of 2-Benzhydryl 9-((5-isopropyl-2-oxo-1,3-dioxol-4-yl)methyl) (2S,4aS,6aS,6bR,8aR,9S,10S,12aS,12bR,14bR)-10-methoxy-2,4a,6a,6b,9,12a-hexamethyl-13-oxo-1,2,3,4,4a,5,6,6a,6b,7,8,8a,9,10,11,12,12a,12b,13,14b-icosahydropicene-2,9-dicarboxylate (252-1)

249-3 (300 mg, 0.44 mmol, 1 equiv), 4-(bromomethyl)-5-(propan-2-yl)-2H-1,3-dioxol-2-one (100 mg, 0.45 mmol, 1.03 equiv), $K_2CO_3$ (200 mg, 1.45 mmol, 3.3 equiv), and potassium iodide (50 mg, 0.30 mmol, 0.68 equiv) in DMF (30 mg, 0.41 mmol, 0.93 equiv) were stirred for 1 h at 50° C. The reaction mixture was diluted with $CH_2Cl_2$ (100 mL), washed with brine, dried over anhydrous $Na_2SO_4$, filtered, and concentrated. The residue was purified by silica gel column eluting with EtOAc/petroleum ether (1:1) to provide 190 mg (52%) of 252-1 as a white solid.

Synthesis of (2S,4aS,6aS,6bR,8aR,9S,10S,12aS,12bR,14bR)-9-(((5-Isopropyl-2-oxo-1,3-dioxol-4-yl)methoxy)carbonyl)-10-methoxy-2,4a,6a,6b,9,12a-hexamethyl-13-oxo-1,2,3,4,4a,5,6,6a,6b,7,8,8a,9,10,11,12,12a,12b,13,14b-icosahydropicene-2-carboxylic Acid (252-2)

252-1 (190 mg, 0.23 mmol, 1 equiv) and TFA (1 mL) in $CH_2Cl_2$ (10 mL) were stirred for 1 h at rt. The reaction was concentrated and purified by prep-TLC (PE/EtOAc; 1:1). This resulted in 68.6 mg (45%) of 252-2 as a white solid. MS (ES, m/z): [M+H]$^+$=657.25; $^1$H NMR (400 MHz, chloroform-tf) δ 0.85 (s, 4H), 1.00 (d, J=12.8 Hz, 1H), 1.07 (s, 1H), 1.10-1.41 (m, 20H), 1.36-1.57 (m, 8H), 1.65-1.92 (m, 6H), 2.01 (s, 3H), 2.21 (d, J=10.9 Hz, 1H), 2.43 (s, 1H), 2.90 (d, J=13.8 Hz, 1H), 3.03 (p, J=7.2 Hz, 1H), 3.27 (s, 3H), 3.60 (dd, J=11.8, 4.4 Hz, 1H), 4.88 (d, J=13.8 Hz, 1H), 5.02 (d, J=13.8 Hz, 1H), 5.74 (s, 1H).

Example 33 (2S,4aS,6aS,6bR,8aR,9R,12aS,12bR,14bR)-2,4a,6a,6b,9,12a-Hexamethyl-9-(((5-methyl-2-oxo-1,3-dioxol-4-yl)methoxy)carbonyl)-13-oxo-1,2,3,4,4a,5,6,6a,6b,7,8,8a,9,10,1142,12a,12b,13,14b-icosahydropicene-2-carboxylic (253-4)

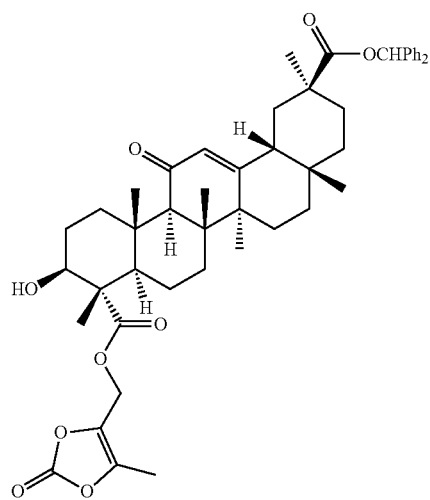

194-8

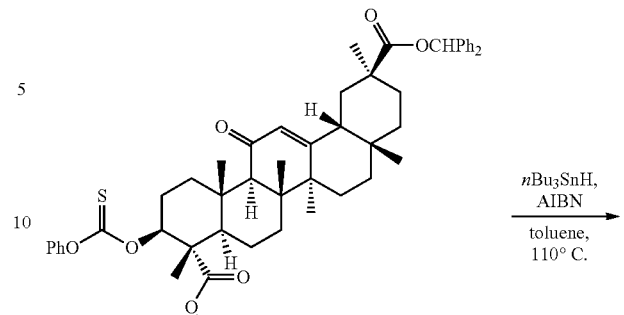

253-1

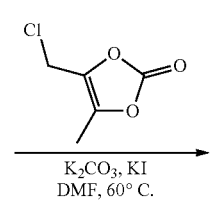

253-2

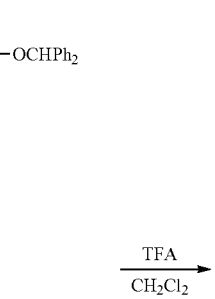

253-3

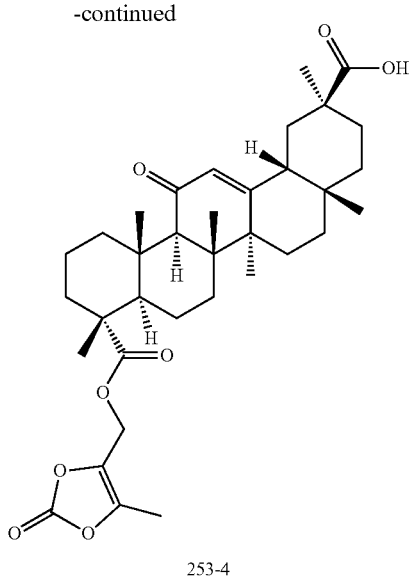

253-4

Synthesis of 2-Benzhydryl 9-((5-methyl-2-oxo-1,3-dioxol-4-yl)methyl) (2S,4aS,6aS,6bR,8aR,9S,10S,12aS,12bR,14bR)-2,4a,6a,6b,9,12a-hexamethyl-13-oxo-10-((phenoxycarbonothioyl)oxy)-1,2,3,4,4a,5,6,6a,6b,7,8,8a,9,10,11,12,12a,12b,13,14b-icosahydropicene-2,9-dicarboxylate (253-1)

194-8 (120 mg, 0.15 mmol, 1 equiv), phenyl chloromethanethioate (133.0 mg, 0.77 mmol, 5 equiv), and DMAP (37.6 mg, 0.31 mmol, 2 equiv) in $CH_2Cl_2$ (5 mL) were stirred for 2 days at 40° C. The reaction mixture was concentrated and the residue purified by prep-TLC (petroleum ether/EtOAc; 5:1) to afford 253-1 (100 mg, 71%) as a light-yellow solid.

Synthesis of (4R,4aR,6aR,6bS,8aS,11S,12aR,14aR,14bS)-11-((Benzhydryloxy)carbonyl)-4,6a,6b,8a,11,14b-hexamethyl-14-oxo-1,2,3,4,4a,5,6,6a,6b,7,8,8a,9,10,11,12,12a,14,14a,14b-icosahydropicene-4-carboxylic Acid (253-2)

253-1 (100 mg, 0.11 mmol, 1 equiv), azobisisobutyronitrile (43.1 mg, 0.26 mmol, 2.4 equiv), and tributyltin hydride (139.4 mg, 0.48 mmol, 4.4 equiv) in toluene (3 mL) were stirred overnight at 110° C. The reaction mixture was concentrated, diluted with EtOAc, washed with brine, dried over anhydrous $Na_2SO_4$, and concentrated. The crude 253-2 was used in the next step directly without further purification.

Synthesis of 2-Benzhydryl 9-((5-methyl-2-oxo-1,3-dioxol-4-yl)methyl) (2S,4aS,6aS,6bR,8aR,9R,12aS,12bR,14bR)-2,4a,6a,6b,9,12a-hexamethyl-13-oxo-1,2,3,4,4a,5,6,6a,6b,7,8,8a,9,10,11,12,12a,12b,13,14b-icosahydropicene-2,9-dicarboxylate (253-3)

253-2 (100 mg, 0.15 mmol, 1 equiv), 4-(chloromethyl)-5-methyl-2H-1,3-dioxol-2-one (45.6 mg, 0.31 mmol, 2 equiv), $K_2CO_3$ (63.7 mg, 0.46 mmol, 3 equiv), and potassium iodide (12.8 mg, 0.08 mmol, 0.5 equiv) in DMF (3 mL) were stirred for 2 h at 60° C. The reaction was diluted with EtOAc, washed with brine, dried over anhydrous $Na_2SO_4$, and concentrated. The crude 253-3 was used in the next step directly without further purification.

Synthesis of (2S,4aS,6aS,6bR,8aR,9R,12aS,12bR,14bR)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic Acid (253-4)

253-3 (100 mg, 0.13 mmol, 1 equiv) and TFA (0.1 mL, 1.35 mmol, 10 equiv) in $CH_2Cl_2$ (5 mL) were stirred for 1 h at rt. The reaction mixture was concentrated and the residue purified by prep-HPLC with the following conditions—Column: Xselect CSH OBD, 30*150 mm, 5 μm; mobile phase: water (0.05% TFA) and $CH_3CN$ (68% Phase B up to 80% in 8 min); detector: UV. This resulted in 253-4 (8.1 mg, 10%) as a colorless oil. MS (ES, m/z) $[M+H]^+$= 597.15; $^1H$ NMR (400 MHz, chloroform-7) δ 6.89 (d, J=102.7 Hz, 2H), 5.74 (s, 1H), 5.00 (d, J=13.8 Hz, 1H), 4.75 (d, J=13.8 Hz, 1H), 2.78 (d, J=13.1 Hz, 1H), 2.52 (s, 1H), 2.22 (s, 4H), 2.11-1.89 (m, 3H), 1.88-1.47 (m, 9H), 1.47-1.31 (m, 8H), 1.26 (s, 4H), 1.20 (d, J=7.8 Hz, 6H), 1.14 (s, 3H), 1.10-0.88 (m, 4H), 0.85 (s, 3H).

Example 34 (2S,4aS,6aS,6bR,8aR,9S,10S,12aS,12bR,14bR)-10-Acetoxy-2,4a,6a,6b,9,12a-hexamethyl-9-((((5-methyl-2-oxo-1,3-dioxol-4-yl)methoxy)carbonyl)amino)-13-oxo-1,2,3,4,4a,5,6,6a,6b,7,8,8a,9,10,1142,12a,12b,13,14b-icosahydropicene-2-carboxylic (254-3)

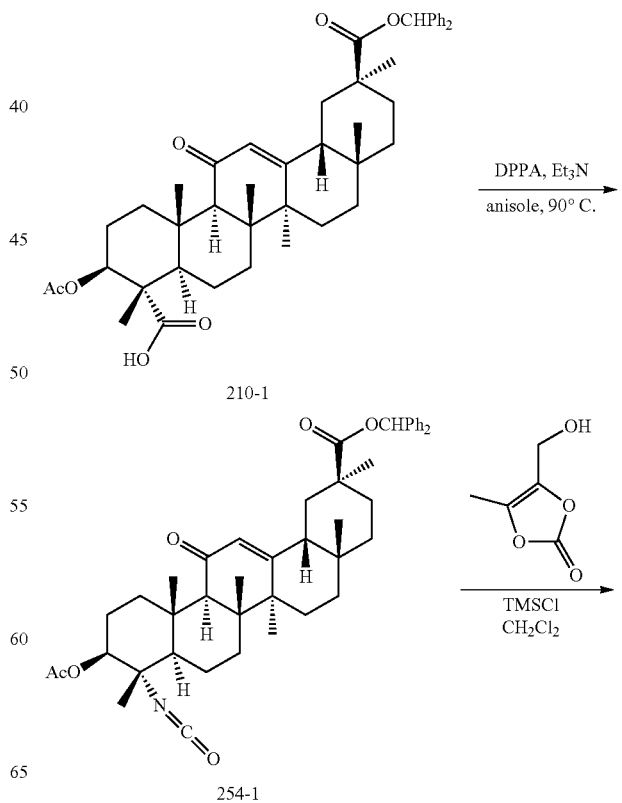

153

-continued

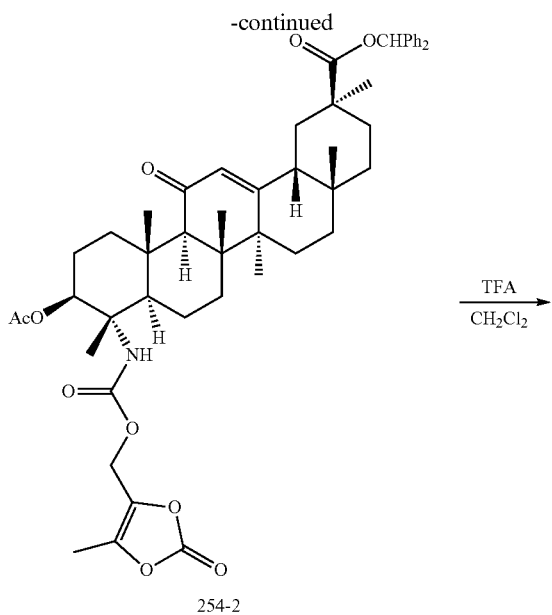

254-2

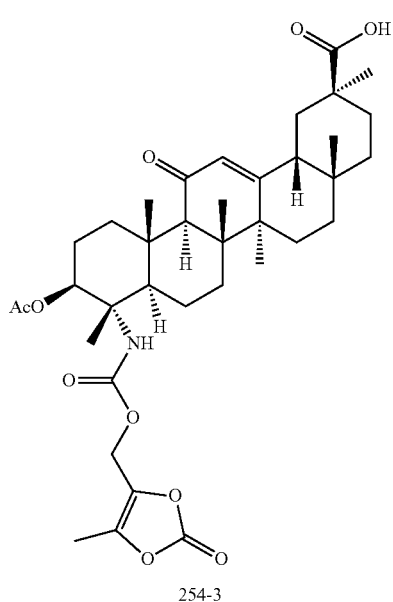

254-3

Synthesis of Benzhydryl (2S,4aS,6aS,6bR,8aR,9S,
10S,12aS,12bR,14bR)-10-acetoxy-9-isocyanato-2,
4a,6a,6b,9,12a-hexamethyl-13-oxo-1,2,3,4,4a,5,6,6a,
6b,7,8,8a,9,10,11,12,12a,12b,13,14b-
icosahydropicene-2-carboxylate (254-1)

Triethylamine (0.135 mL, 0.97 mmol, 1.5 equiv) was added at rt to 210-1 (450 mg, 0.63 mmol, 1 equiv) and DPPA (0.225 mL, 1.04 mmol, 1.6 equiv) in anisole (5 mL). The reaction was stirred for 1.5 h at 90° C. The reaction mixture was concentrated under vacuum and the residue purified by prep-TLC (CH$_2$Cl$_2$/MeOH; 5:1) to afford 254-1 (400 mg, 89%) as a light-yellow solid.

154

Synthesis of benzhydryl (2S,4aS,6aS,6bR,8aR,9S,
10S,12aS,12bR,14bR)-10-acetoxy-2,4a,6a,6b,9,12a-
hexamethyl-9-((((5-methyl-2-oxo-1,3-dioxol-4-yl)
methoxy)carbonyl)amino)-13-oxo-1,2,3,4,4a,5,6,6a,
6b,7,8,8a,9,10,11,12,12a,12b,13,14b-
icosahydropicene-2-carboxylate (254-2)

4-(Hydroxymethyl)-5-methyl-2H-1,3-dioxol-2-one (66.3 mg, 0.51 mmol, 3 equiv) in CH$_2$Cl$_2$ was added dropwise at rt to 254-1 (120 mg, 0.17 mmol, 1 equiv) and chlorotrimethylsilane (92.3 mg, 0.85 mmol, 5 equiv) in CH$_2$Cl$_2$ (5 mL). The reaction slurry was stirred overnight at rt and then concentrated. The residue was purified by prep-TLC (petroleum ether/EtOAc 2:1) to afford 254-2 (120 mg, 84%) as a light yellow solid.

Synthesis of (2S,4aS,6aS,6bR,8aR,9S,10S, 12aS,
12bR,14bR)-10-acetoxy-2,4a,6a,6b,9,12a-hexam-
ethyl-9-((((5-methyl-2-oxo-1,3-dioxol-4-yl)
methoxy)carbonyl)amino)-13-oxo-1,2,3,4,4a,5,6,6a,
6b,7,8,8a,9,10,11,12,12a,12b,13,14b-
icosahydropicene-2-carboxylic Acid (254-3)

254-2 (120 mg, 0.14 mmol, 1 equiv) and TFA (0.1 mL, 1.35 mmol, 9.4 equiv) in CH$_2$Cl$_2$ were stirred for 1 h at rt. The reaction mixture was concentrated under vacuum and the residue purified by prep-TLC to afford 254-3 (21.2 mg, 22%) as an off-white solid. MS (ES, m z): [M+H]$^+$=670.25; $^1$H NMR (400 MHz, chloroform-d) δ 6.94 (d, J=67.6 Hz, 2H), 5.75 (s, 1H), 5.47 (t, J=5.7 Hz, 1H), 4.77 (s, 2H), 4.44 (s, 1H), 2.81 (d, J=13.5 Hz, 1H), 2.50 (s, 1H), 2.21 (s, 2H), 2.05 (s, 3H), 1.91-1.53 (m, 8H), 1.42 (d, J=19.1 Hz, 8H), 1.26 (s, 5H), 1.19-0.97 (m, 11H), 0.86 (s, 3H).

Example 35 (2S,4aS,6aS,6bR,8aR,9S,10S,12aS,
12bR,14bR)-10-Acetoxy-9-((((5-isopropyl-2-oxo-1,
3-dioxol-4-yl)methoxy)carbonyl)amino)-2,4a,6a,6b,
9,12a-hexamethyl-13-oxo-1,2,3,4,4a,5,6,6a,6b,7,8,
8a,9,10,1142,12a,12b,13,14b-icosahydropicene-2-
carboxylic (255-2)

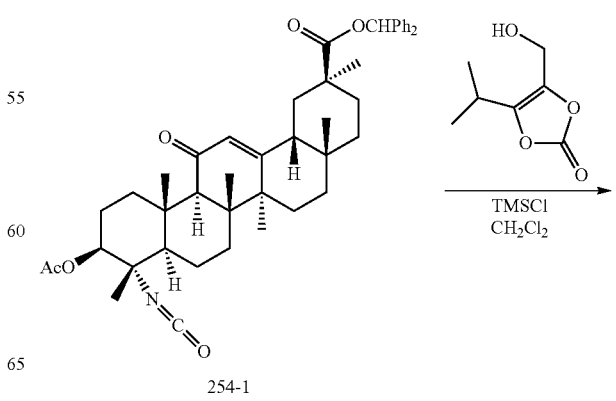

254-1

-continued

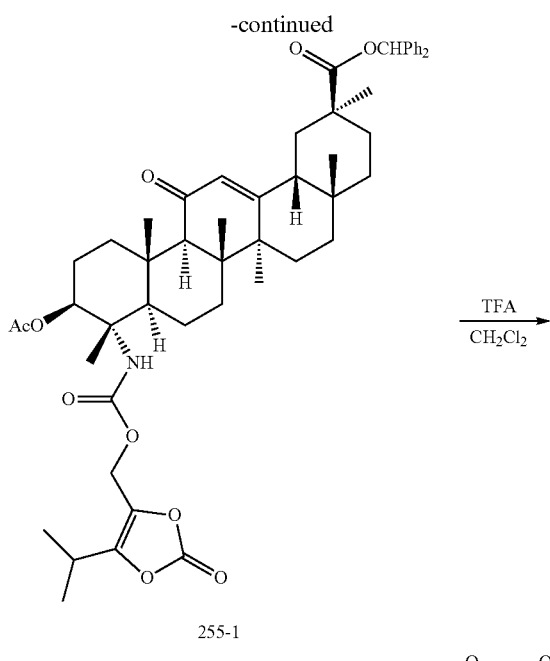

255-1

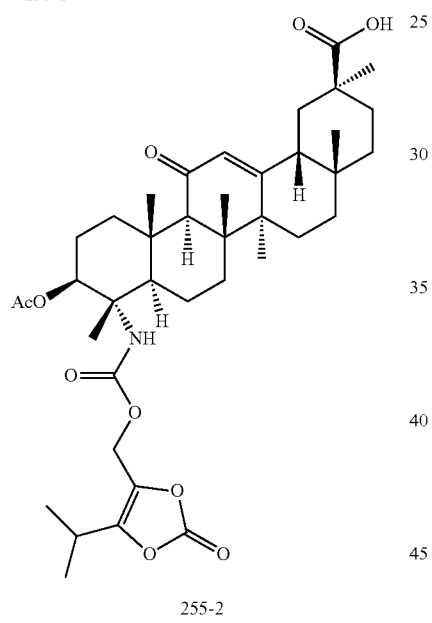

255-2

Synthesis of Benzhydryl (2S,4aS,6aS,6bR,8aR,9S,10S,12aS,12bR,14bR)-10-acetoxy-9-((((5-isopropyl-2-oxo-1,3-dioxol-4-yl)methoxy)carbonyl)amino)-2,4a,6a,6b,9,12a-hexamethyl-13-oxo-1,2,3,4,4a,5,6,6a,6b,7,8,8a,9,10,11,12,12a,12b,13,14b-icosahydropicene-2-carboxylate (255-1)

4-(Hydroxymethyl)-5-(propan-2-yl)-2H-1,3-dioxol-2-one (67.2 mg, 0.42 mmol, 3 equiv) in CH$_2$Cl$_2$ was added dropwise at rt to 254-1 (100 mg, 0.14 mmol, 1 equiv) and chlorotrimethylsilane (76.9 mg, 0.71 mmol, 5 equiv) in CH$_2$Cl$_2$. The reaction slurry was stirred overnight at rt and concentrated. The residue was purified by prep-TLC (petroleum ether/EtOAc 2:1) to afford 255-1 (100 mg, 82%) as a light yellow solid.

Synthesis of (2S,4aS,6aS,6bR,8aR,9S,10S,12aS,12bR,14bR)-10-Acetoxy-9-((((5-isopropyl-2-oxo-1,3-dioxol-4-yl)methoxy)carbonyl)amino)-2,4a,6a,6b,9,12a-hexamethyl-13-oxo-1,2,3,4,4a,5,6,6a,6b,7,8,8a,9,10,11,12,12a,12b,13,14b-icosahydropicene-2-carboxylic Acid (255-2)

255-1 (100 mg, 0.12 mmol, 1 equiv) and TFA (0.1 mL) in CH$_2$Cl$_2$ (10 mL) were stirred for 1 h at rt. The mixture was concentrated under vacuum and the residue purified by prep-HPLC with the following conditions—Column: XSelect CSHPrep C18 OBD, 5 μm, 19*150 mm; mobile phase: water (0.05% TFA) and CH$_3$CN (70% Phase B up to 85% in 7 min); detector: UV. This resulted in 255-2 (11.7 mg, 14%) as an off-white solid. MS (ES, m/z): [M+H]$^+$=698.25; $^1$H NMR (400 MHz, chloroform-7) δ 7.20-6.72 (m, 2H), 5.75 (s, 1H), 5.46 (dd, J=11.1, 5.0 Hz, 1H), 4.87 (d, J=13.8 Hz, 1H), 4.72 (d, J=14.0 Hz, 1H), 4.43 (s, 1H), 3.03 (p, J=6.9 Hz, 1H), 2.82 (d, J=13.5 Hz, 1H), 2.50 (s, 1H), 2.22 (d, J=12.2 Hz, 2H), 2.13-1.91 (m, 6H), 1.90-1.53 (m, 6H), 1.42 (d, J=24.7 Hz, 8H), 1.31-1.21 (m, 10H), 1.21-0.99 (m, 12H), 0.86 (s, 3H).

Example 36 (2S,4aS,6aS,6bR,8aR,9S,10S,12aS,12bR,14bR)-10-(2,2-Difluoroacetoxy)-9-(((5-isopropyl-2-oxo-1,3-dioxol-4-yl)methoxy)carbonyl)-2,4a,6a,6b,9,12a-hexamethyl-13-oxo-1,2,3,4,4a,5,6,6a,6b,7,8,8a,9,10,11,12,12a,12b,13,14b-icosahydropicene-2-carboxylic Acid (256-2)

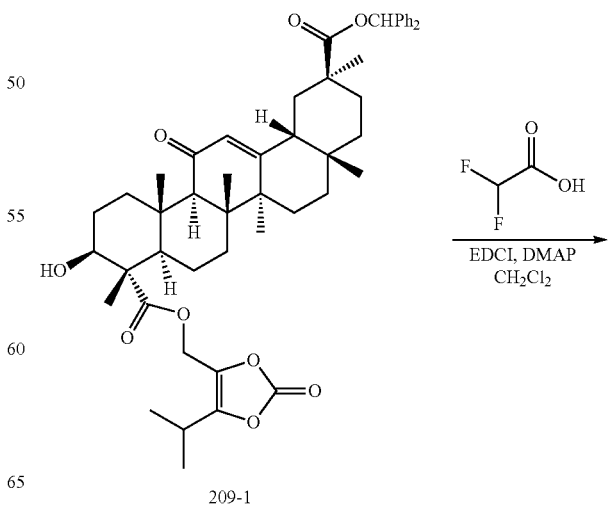

209-1

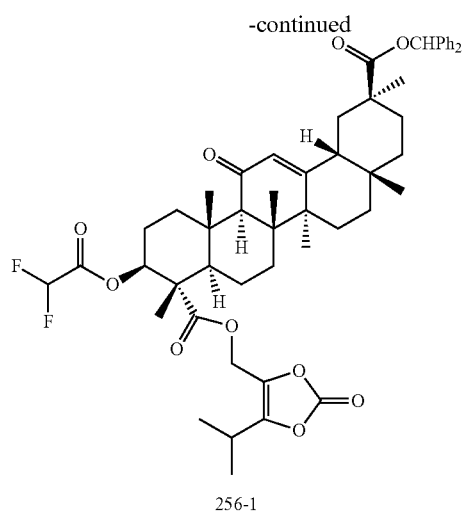

256-1

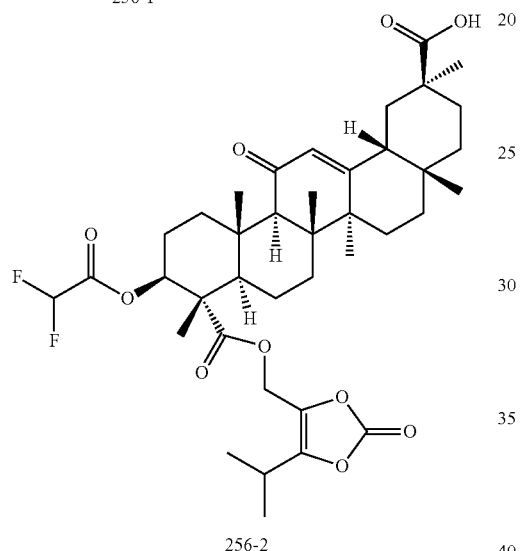

256-2

Synthesis of 2-Benzhydryl 9-((5-isopropyl-2-oxo-1,3-dioxol-4-yl)methyl) (2S,4aS,6aS,6bR,8aR,9S,10S,12aS,12bR,14bR)-10-(2,2-difluoroacetoxy)-2,4a,6a,6b,9,12a-hexamethyl-13-oxo-1,2,3,4,4a,5,6,6a,6b,7,8,8a,9,10,11,12,12a,12b,13,14b-icosahydropicene-2,9-dicarboxylate (256-1)

EDCI (178.1 mg, 5 equiv) was added to 209-1 (150 mg, 1 equiv), 2,2-difluoroacetic acid (0.0234 mL, 2 equiv), and DMAP (11.4 mg, 0.5 equiv) in CH$_2$Cl$_2$ (10 mL) and the reaction slurry stirred for 1 h at rt. The reaction mixture was concentrated and the residue purified by silica gel column with EtOAc/petroleum ether (1:3) to provide 234.2 mg (100%) of 256-1 as an off-white semi-solid.

Synthesis of (2S,4aS,6aS,6bR,8aR,9S,10S,12aS,12bR,14bR)-10-(2,2-Difluoroacetoxy)-9-(((5-isopropyl-2-oxo-1,3-dioxol-4-yl)methoxy)carbonyl)-2,4a,6a,6b,9,12a-hexamethyl-13-oxo-1,2,3,4,4a,5,6,6a,6b,7,8,8a,9,10,11,12,12a,12b,13,14b-icosahydropicene-2-carboxylic Acid (256-2)

256-1 (164 mg, 1 equiv) and TFA (1 mL) in CH$_2$Cl$_2$ (10 mL) were stirred for 1 h at rt. The reaction mixture was concentrated and the residue purified by prep-HPLC with the following conditions—Column: Xselect CSH OBD, 30*150 mm, 5 μm; mobile phase: water (0.05% TFA) and CH$_3$CN (65% Phase B up to 85% in 8 min); detector: UV. This resulted in 74.8 mg (56%) of 256-2 as a white solid. MS (ES, m/z): [M+H]$^+$=719.20; $^1$H NMR (400 MHz, methanol-d$_4$) δ 0.83 (s, 3H), 0.96 (d, J=9.6 Hz, 1H), 1.05 (d, J=14.4 Hz, 1H), 1.17 (s, 3H), 1.18-1.32 (m, 17H), 1.38-1.49 (m, 7H), 1.63-1.91 (m, 8H), 1.94 (d, J=9.5 Hz, 1H), 2.09-2.29 (m, 2H), 2.57 (s, 1H), 2.86 (d, J=14.0 Hz, 1H), 3.05 (h, J=13.6 Hz, 1H), 4.88 (d, J=14.0 Hz, 1H), 5.06 (d, J=14.0 Hz, 1H), 5.34 (dd, J=12.0, 5.2 Hz, 1H), 5.60 (s, 1H), 6.04 (t, J=53.0 Hz, 1H).

Example 37 (2S,4aS,6aS,6bR,8aR,9S,10S,12aS,12bR,14bR)-9-(((5-Isopropyl-2-oxo-1,3-dioxol-4-yl)methoxy)carbonyl)-10-(methoxymethoxy)-2,4a,6a,6b,9,12a-hexamethyl-13-oxo-1,2,3,4,4a,5,6,6a,6b,7,8,8a,9,10,1142,12a,12b,13,14b-icosahydropicene-2-carboxylic (258-2)

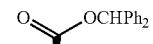

209-1

258-1

159

-continued

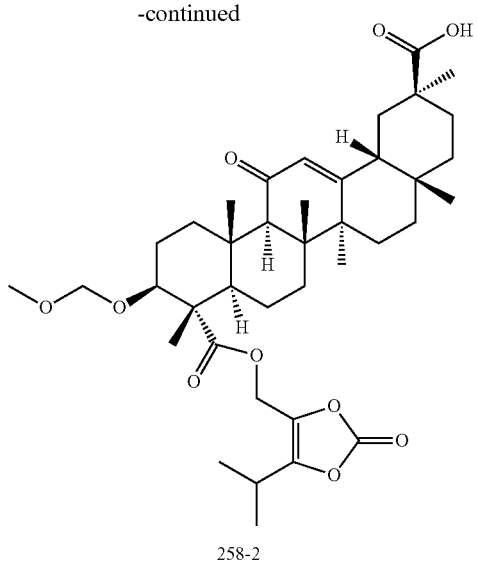

258-2

Synthesis of 2-Benzhydryl 9-((5-isopropyl-2-oxo-1,3-dioxol-4-yl)methyl) (2S,4aS,6aS,6bR,8aR,9S,10S,12aS,12bR,14bR)-10-(methoxymethoxy)-2,4a,6a,6b,9,12a-hexamethyl-13-oxo-1,2,3,4,4a,5,6,6a,6b,7,8,8a,9,10,11,12,12a,12b,13,14b-icosahydropicene-2,9-dicarboxylate (258-1)

Bromomethyl methyl ether (0.0687 mL, 4.0 equiv) was added dropwise with stirring at 0° C. to 209-1 (150 mg, 0.19 mmol, 1 equiv) and iPr$_2$EtN (0.307 mL, 10 equiv) in CH$_2$Cl$_2$ (10 mL) and then stirred for 2 h at 60° C. The reaction mixture was concentrated and the residue purified by silica gel column eluting with EtOAc/petroleum ether (1:2) to provide 158 mg (100%) of 258-1 as a white solid.

160

Synthesis of (2S,4aS,6aS,6bR,8aR,9S,10S,12aS,12bR,14bR)-9-(((5-Isopropyl-2-oxo-1,3-dioxol-4-yl)methoxy)carbonyl)-10-(methoxymethoxy)-2,4a,6a,6b,9,12a-hexamethyl-13-oxo-1,2,3,4,4a,5,6,6a,6b,7,8,8a,9,10,11,12,12a,12b,13,14b-icosahydropicene-2-carboxylic Acid (258-2)

258-1 (158 mg, 1 equiv) and TFA (0.2068 mL, 15.0 equiv) in CH$_2$Cl$_2$ (15 mL) were stirred for 6 h at rt. The reaction mixture was washed with brine (3×20 mL), dried over anhydrous Na$_2$SO$_4$, filtered, and concentrated. The residue was purified by prep-HPLC with the following conditions—Column: XBridge Shield RP18 OBD, 5 μm, 19*150 mm; mobile phase: water (0.05% TFA) and CH$_3$CN (65-85% Phase B in 7 min); detector: UV. This resulted in 55.8 mg (44%) of 258-2 as a white solid. MS (ES, m/z): [M+H]$^+$= 685.15; $^1$H NMR (400 MHz, methanol-d$_4$) δ 0.82 (s, 3H), 0.87 (d, J=10.0 Hz, 1H), 1.04 (d, J=13.6 Hz, 1H), 1.10-1.20 (m, 13H), 1.24 (d, J=6.8 Hz, 7H), 1.34 (d, J=8.4 Hz, 2H), 1.38 (d, J=14.8 Hz, 6H), 1.54 (d, J=10.4 Hz, 1H), 1.61-1.71 (m, 3H), 1.73-1.90 (m, 3H), 1.95 (d, J=10.0 Hz, 1H), 2.16 (ddd, J=30.3, 16.8, 4.8 Hz, 2H), 2.51 (s, 1H), 2.78 (d, J=13.6 Hz, 1H), 3.10 (p, 7=6.9 Hz, 1H), 3.25 (s, 3H), 3.95 (dd, J=12.0, 4.4 Hz, 1H), 4.48 (d, J=7.2 Hz, 1H), 4.63 (d, J=6.8 Hz, 1H), 4.83 (d, J=14.0 Hz, 1H), 5.15 (d, J=14.0 Hz, 1H), 5.59 (s, 1H).

Example 38 (2S,4aS,6aS,6bR,8aR,9S,10S,12aS,12bR,14bR)-10-((2,5,8,11-tetraoxatetradecan-14-oyl)oxy)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,1142,12a,12b,13,14b-icosahydropicene-2-carboxylic Acid (264-1)

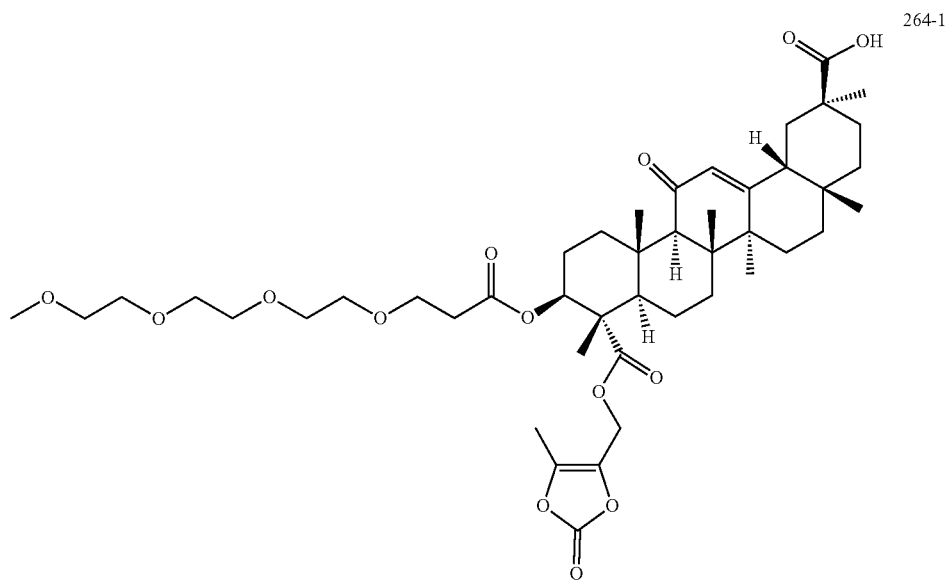

264-1

The title compound was prepared according to the methods for compound 194-10, beginning with 194-8 and 2,5,8,11-tetraoxatetradecan-14-oic acid. The crude product was purified by prep-HPLC with the following conditions: Column, XBridge Prep OBD Cl8, 30*150 mm, 5 μm; mobile phase, water (0.05% TFA) and CH₃CN (55.0% CH₃CN up to 69.0% in 8 min); detector, UV 220 nm. This resulted in 103.0 mg (55%) of 264-1 as a white solid. MS (ES, m/z): [M+H]⁺=848.25. ¹H NMR (400 MHz, methanol-$d_4$) δ 0.86 (s, 3H), 0.96 (s, 1H), 1.07 (d, J=13.9 Hz, 1H), 1.10-1.29 (m, 14H), 1.35-1.50 (m, 7H), 1.65-1.80 (m, 6H), 1.81-1.91 (m, 2H), 1.95 (d, J=9.6 Hz, 1H), 2.22 (s, 5H), 2.49 (t, J=10.8 Hz, 2H), 2.56 (s, 1H), 2.81 (d, J=13.6 Hz, 1H), 3.35 (s, 3H), 3.51-3.71 (m, 14H), 4.88 (s, 1H), 5.01 (d, J=14.0 Hz, 1H), 5.18 (dd, J=11.6, 4.8 Hz, 1H), 5.60 (s, 1H).

Example 39 (2S,4aS,6aS,6bR,8aR,9S,10S,12aS,12bR,14bR)-10-((2,5,8,11-tetraoxatetradecan-14-oyl)oxy)-2,4a,6a,6b,9,12a-hexamethyl-9-(((5-methyl-2-oxo-1,3-dioxolan-4-yl)methoxy)carbonyl)-13-oxo-1,2,3,4,4a,5,6,6a,6b,7,8,8a,9,10,1142,12a,12b,13,14b-icosahydropicene-2-carboxylic Acid (265-2)

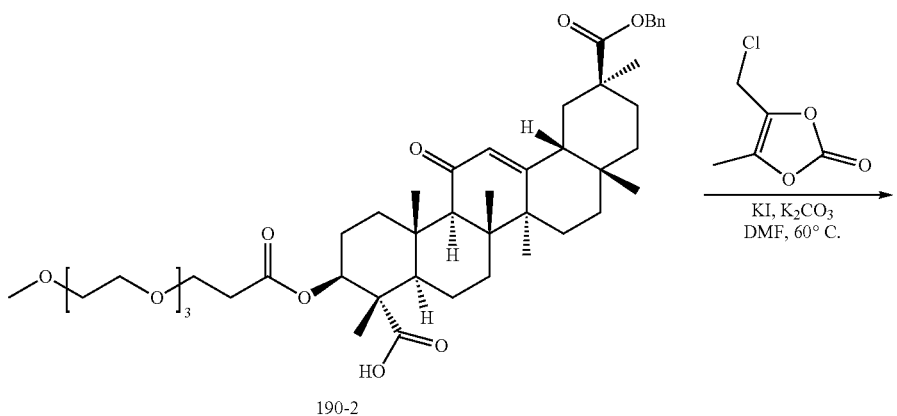

190-2

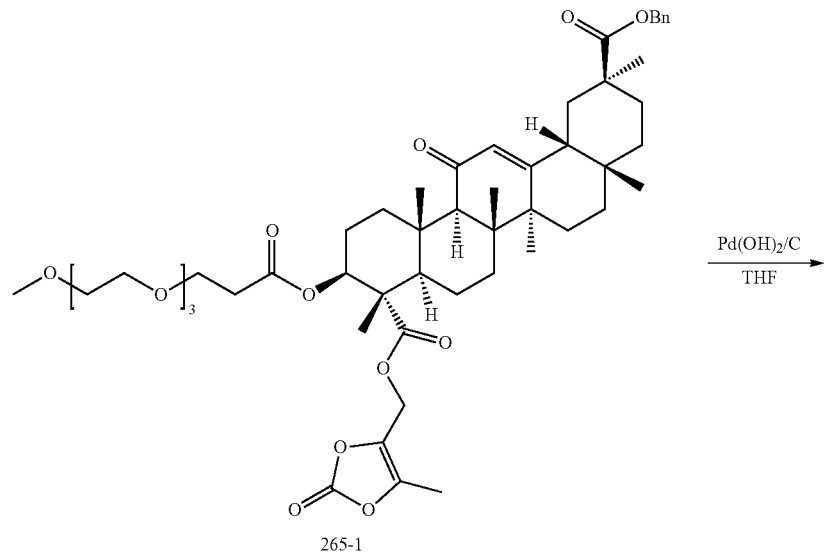

265-1

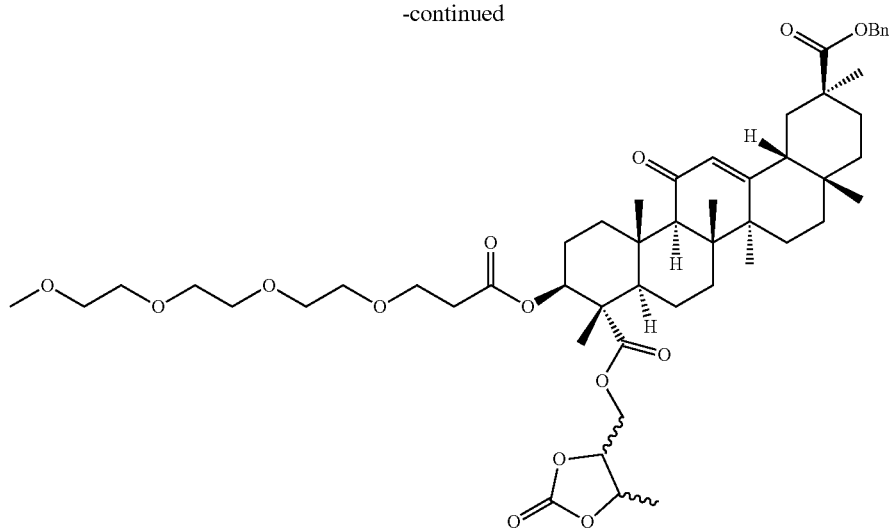

265-2

Synthesis of 2-benzyl 9-((5-methyl-2-oxo-1,3-dioxol-4-yl)methyl) (2S,4aS,6aS,6bR,8aR,9S,10S, 12aS,12bR,14bR)-10-((2,5,8,11-tetraoxatetradecan-14-oyl)oxy)-2,4a,6a,6b,9,12a-hexamethyl-13-oxo-1, 2,3,4,4a,5,6,6a,6b,7,8,8a,9,10,11,12,12a,12b,13,14b-icosahydropicene-2,9-dicarboxylate (265-1)

Into a 50-mL round-bottom flask was placed 190-2 (220 mg, 1 equiv), KI (22.5 mg, 0.5 equiv), DMF (1 mL), $K_2CO_3$ (112.7 mg, 3 equiv), and 4-(chloromethyl)-5-methyl-2H-1, 3-dioxol-2-one (72.7 mg, 7.2 equiv). The reaction slurry was stirred for 2 days at 60° C. The reaction mixture was extracted with ethyl acetate and the organic layer washed with 3×100 ml of $H_2O$ and 1×100 ml of brine. The organic layer was dried over anhydrous $Na_2SO_4$, filtered, and concentrated. The residue was applied onto a silica gel column with $CH_2Cl_2$/methanol (30:1) to provide 248.6 mg (99%) of 265-1 as pale yellow oil.

Synthesis of (2S,4aS,6aS,6bR,8aR,9S,10S,12aS, 12bR,14bR)-10-((2,5,8,11-tetraoxatetradecan-14-oyl)oxy)-2,4a,6a,6b,9,12a-hexamethyl-9-(((5-methyl-2-oxo-1,3-dioxolan-4-yl)methoxy)carbonyl)-13-oxo-1,2,3,4,4a,5,6,6a,6b,7,8,8a,9,10,11,12,12a, 12b,13,14b-icosahydropicene-2-carboxylic Acid (265-2)

Into a 25-mL round-bottom flask purged and maintained with an inert atmosphere of $H_2$ (1 atm) was placed 265-1 (124 mg, 1 equiv), THF (5 mL), and $Pd(OH)_2/C$ (49.6 mg). The reaction slurry was stirred for 1.5 hr at room temperature. The solids were filtered off and the filtrate concentrated. The residue was purified by prep-HPLC with the following conditions: Column, XBridge Shield RP18 OBD, 5 μm, 19*150 mm; mobile phase, water (0.05% TFA) and $CH_3CN$ (hold 5% Phase B in 0 min, up to 55% in 1 min, up to 71% in 8 min); detector, UV. This resulted in 19.9 mg (18%) of 265-2 as an off-white semi-solid. MS (ES, m/z): $[M+H]^+=$ 833.25; $^1H$ NMR (400 MHz, methanol-$d_4$) δ 0.85 (s, 3H), 1.06 (d, J=10.4 Hz, 2H), 1.16 (s, 3H), 1.20 (s, 6H), 1.24-1.30 (m, 5H), 1.39-1.46 (m, 4H), 1.47-1.53 (m, 6H), 1.62-1.82 (m, 5H), 1.83-2.01 (m, 4H), 2.13-2.28 (m, 2H), 2.54 (q, J=6.4 Hz, 2H), 2.60 (s, 1H), 2.79-2.90 (m, 1H), 3.38 (s, 3H), 3.55-3.59 (m, 2H), 3.59-3.61 (m, 2H), 3.62-3.69 (m, 8H), 3.69-3.73 (m, 2H), 4.18-4.30 (m, 1H), 4.38-4.50 (m, 1H), 4.95-5.11 (m, 2H), 5.15-5.25 (m, 1H), 5.62 (s, 1H).

Example 40 (2S,4aS,6aS,6bR,8aR,10S,12aS,12bR, 14bR)-2,4a,6a,6b,9,9,12a-heptamethyl-10-(2-((5-methyl-2-oxo-1,3-dioxol-4-yl)methoxy)-2-oxoethoxy)-13-oxo-1,2,3,4,4a,5,6,6a,6b,7,8,8a,9,10,1142, 12a,12b,13,14b-icosahydropicene-2-carboxylic Acid (279-2)

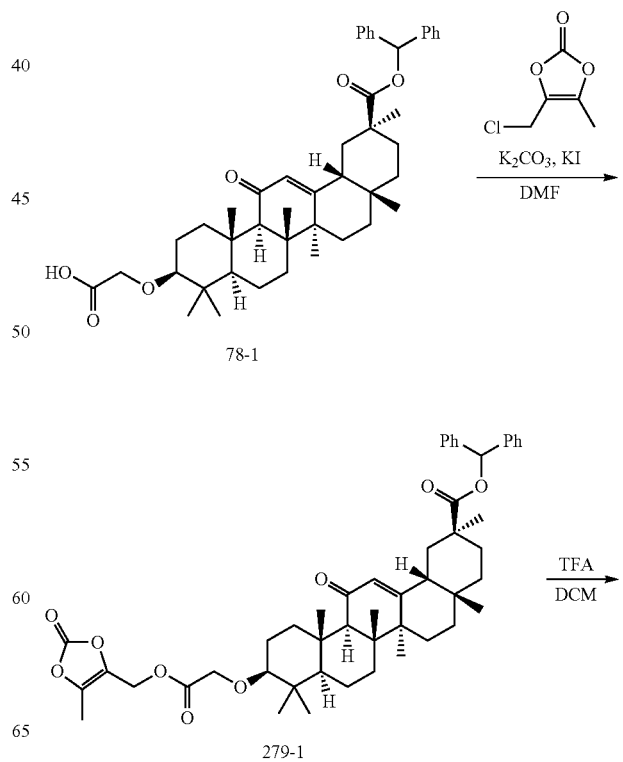

78-1

279-1

165
-continued

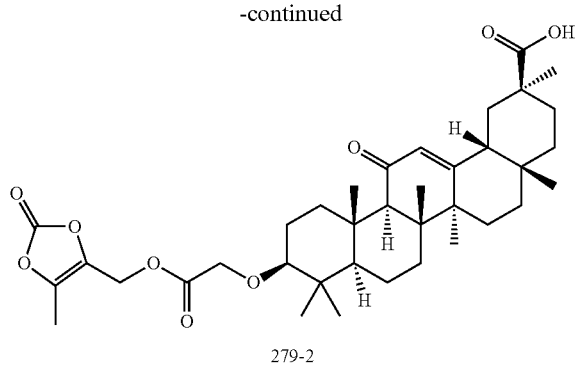

279-2

Synthesis of benzhydryl (2S,4aS,6aS,6bR,8aR,10S, 12aS,12bR,14bR)-2,4a,6a,6b,9,9,12a-heptamethyl-10-(2-((5-methyl-2-oxo-1,3-dioxol-4-yl)methoxy)-2-oxoethoxy)-13-oxo-1,2,3,4,4a,5,6,6a,6b,7,8,8a,9,10, 11,12,12a,12b,13,14b-icosahydropicene-2-carboxylate (279-1)

Into a 50-mL round-bottom flask was placed 78-1 (100 mg, 1 equiv), DMF (1 mL), 4-(chloromethyl)-5-methyl-2H-1,3-dioxol-2-one (38.5 mg, 1.8 equiv), KI (11.9 mg, 0.5 equiv), and $K_2CO_3$ (59.6 mg, 3 equiv). The reaction slurry was stirred overnight at room temperature. The reaction mixture was diluted with ethyl acetate, washed with 3×20 ml of $H_2O$ and 1×20 ml of brine, dried over anhydrous $Na_2SO_4$, filtered, and concentrated. The residue was applied onto a silica gel column with ethyl acetate/petroleum ether (1:3) to provide 107.5 mg (93%) of 279-1 as a white solid.

Synthesis of (2S,4aS,6aS,6bR,8aR,10S,12aS,12bR, 14bR)-2,4a,6a,6b,9,9,12a-heptamethyl-10-(2-((5-methyl-2-oxo-1,3-dioxol-4-yl)methoxy)-2-oxoethoxy)-13-oxo-1,2,3,4,4a,5,6,6a,6b,7,8,8a,9,10,11,12, 12a,12b,13,14b-icosahydropicene-2-carboxylic Acid (279-2)

Into a 50-mL round-bottom flask was placed 279-1 (107.5 mg, 1 equiv), $CH_2Cl_2$ (10 mL), and TFA (1 mL). The reaction slurry was stirred for 1 h at room temperature. The reaction mixture was concentrated. The crude product was purified by prep-HPLC with the following conditions: Column, XSelect CSH Prep C18 OBD, 5 μm, 19*150 mm; mobile phase, water (0.05% TFA) and $CH_3CN$ (hold 5% Phase B in 0 min, up to 68% in 1 min, up to 85% in 8 min); detector, UV. This resulted in 34.9 mg (41%) of 279-2 as a white solid. MS (ES, m/z) $[M+H]^+=641.25$; $^1H$ NMR (400 MHz, chloroform-7) δ 0.70 (d, J=11.2 Hz, 1H), 0.84 (s, 7H), 1.01 (s, 1H), 1.05 (s, 3H), 1.14 (d, J=12 Hz, 6H), 1.22 (s, 4H), 1.36 (s, 4H), 1.39-1.49 (m, 4H), 1.57-1.76 (m, 5H), 1.79-2.09 (m, 4H), 2.19 (s, 4H), 2.33 (s, 1H), 2.83 (d, J=13.2 Hz, 1H), 2.94 (dd, 7=11.6, 4.4 Hz, 1H), 4.16 (t, 7=18.8 Hz, 2H), 4.89 (d, J=10.6 Hz, 2H), 5.71 (s, 1H).

166

Example 41 (2S,4aS,6aS,6bR,8aR,9S,10S,12aS, 12bR,14bR)-10-amino-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12, 12a,12b,13,14b-icosahydropicene-2-carboxylic Acid (280-7)

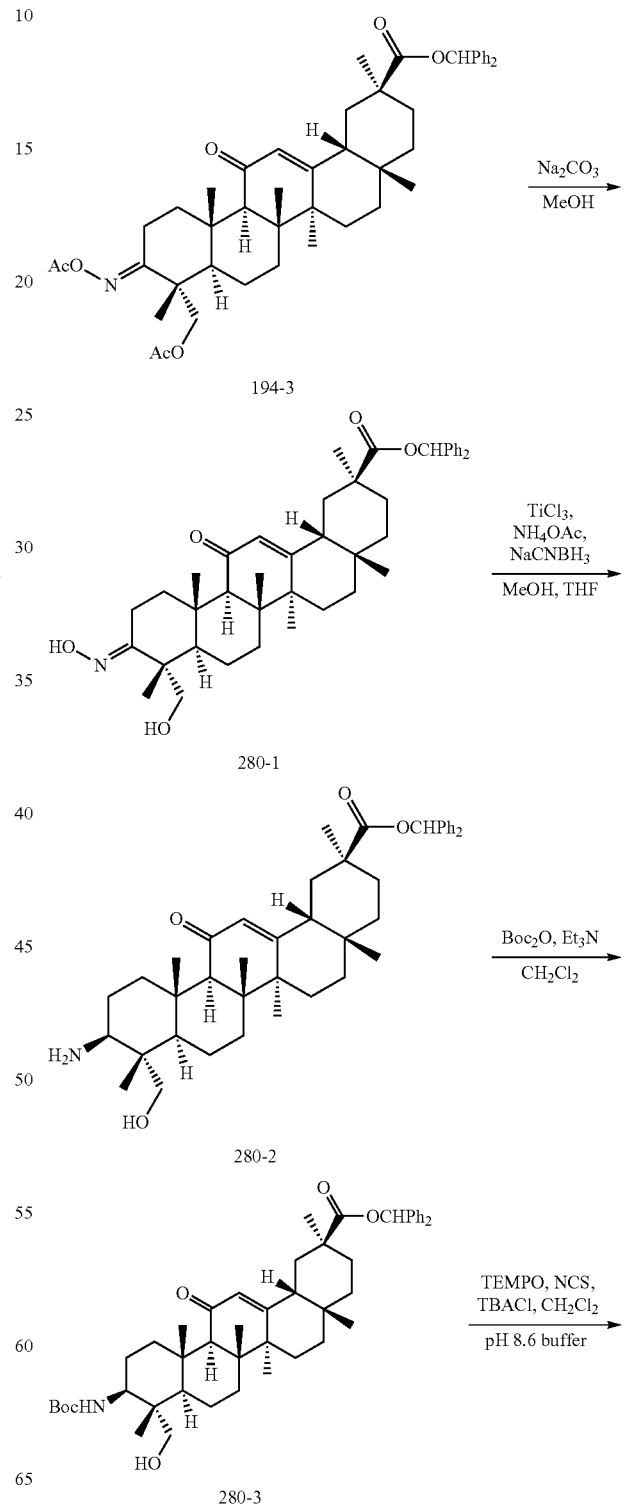

167
-continued

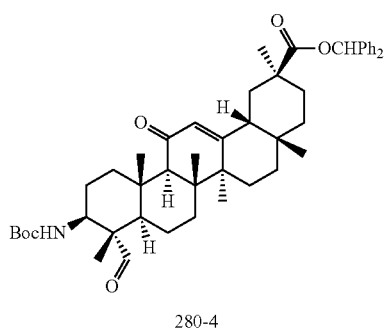 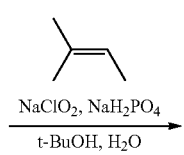

280-4

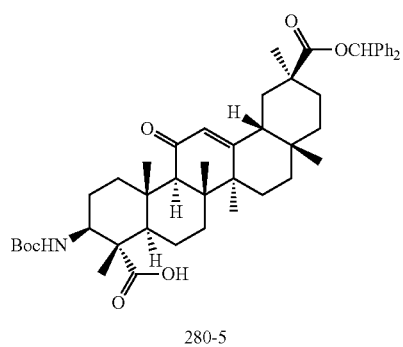 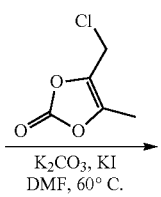

280-5

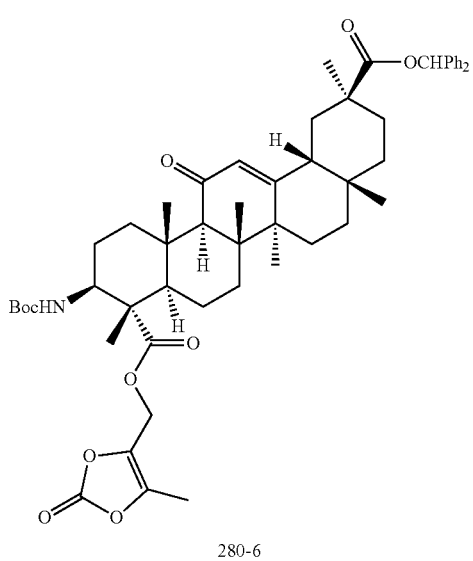

280-6

168
-continued

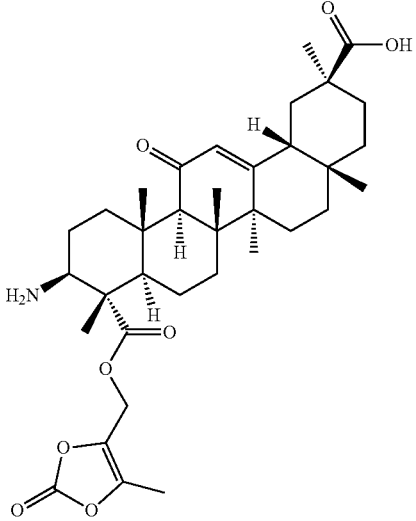

280-7

Synthesis of benzhydryl (2S,4aS,6aS,6bR,8aR,9S, 12aS,12bR,14bR,E)-10-(hydroxyimino)-9-(hydroxymethyl)-2,4a,6a,6b,9,12a-hexamethyl-13-oxo-1,2,3,4,4a,5,6,6a,6b,7,8,8a,9,10,11,12,12a,12b,13, 14b-icosahydropicene-2-carboxylate (280-1)

Into a 250-mL round-bottom flask was placed 194-3 (3.0 g, 4.45 mmol, 1 equiv), MeOH (50 mL), and Na$_2$CO$_3$ (2.4 g, 22.6 mmol, 5.1 equiv). The reaction slurry was stirred for 48 hr at room temperature. The reaction mixture was concentrated, diluted in 500 mL of CH$_2$Cl$_2$, and the pH adjusted to 4 with 2 M HCl$_{(aq)}$. The organic layer was washed with 2×500 ml of brine, dried over anhydrous Na$_2$SO$_4$, filtered, and concentrated. The residue was applied onto a silica gel column with ethyl acetate/petroleum ether (1:1) to provide 2.46 g (94%) of 280-1 as a yellow solid.

Synthesis of benzhydryl (2S,4aS,6aS,6bR,8aR,9S, 10S,12aS,12bR,14bR)-10-amino-9-(hydroxymethyl)-2,4a,6a,6b,9,12a-hexamethyl-13-oxo-1,2,3,4, 4a,5,6,6a,6b,7,8,8a,9,10,11,12,12a,12b,13,14b-icosahydropicene-2-carboxylate (280-2)

Into a 500-mL round-bottom flask was placed 280-1 (2.48 g, 4.20 mmol, 1 equiv), MeOH (250 mL), NH$_4$OAC (4.9 g, 63.6 mmol, 15 equiv), NaBH$_3$CN (3.2 g, 51 mmol, 12 equiv), TiCl$_3$ (18 mL) at 0° C. The reaction slurry was stirred overnight at room temperature. The reaction mixture was diluted with 500 mL of ethyl acetate and the pH adjusted to 12 with 4 M NaOH$_{(aq)}$. The organic layer was washed with 3×500 ml of brine, dried over anhydrous Na$_2$SO$_4$, filtered, and concentrated to provide 1.77 g (73%) of crude 280-2 as a yellow solid.

Synthesis of benzhydryl (2S,4aS,6aS,6bR,8aR,9S, 10S,12aS,12bR,14bR)-10-((tert-butoxycarbonyl) amino)-9-(hydroxymethyl)-2,4a,6a,6b,9,12a-hexamethyl-13-oxo-1,2,3,4,4a,5,6,6a,6b,7,8,8a,9,10,11,12, 12a,12b,13,14b-icosahydropicene-2-carboxylate (280-3)

Into a 3000-mL round-bottom flask was placed 280-2 (34.6 g, 53 mmol), CH$_2$Cl$_2$ (100 mL), BoC$_2$O (23.2 g, 106 mmol, 2 equiv), and Et₃N (36.9 mL, 265 mmol, 5 equiv). The reaction slurry was stirred for 1 hr at room temperature. The reaction mixture was extracted with 1000 mL of CH₂Cl₂ and washed with 3×1000 ml of brine. The organic layer was dried over anhydrous Na₂SO₄, filtered, and concentrated. The residue was applied onto a silica gel column with ethyl acetate/petroleum ether (1:5) to provide 18.3 g (46%) of 280-3 as a yellow solid.

Synthesis of benzhydryl (2S,4aS,6aS,6bR,8aR,9S, 10S,12aS,12bR,14bR)-10-((tert-butoxycarbonyl) amino)-9-formyl-2,4a,6a,6b,9,12a-hexamethyl-13-oxo-1,2,3,4,4a,5,6,6a,6b,7,8,8a,9,10,11,12,12a,12b, 13,14b-icosahydropicene-2-carboxylate (280-4)

Into a 1000-mL round-bottom flask was placed 280-3 (27.0 g, 35.9 mmol), CH₂Cl₂ (150 mL), pH 8.6 buffer (150 mL), TEMPO (28.0 g, 179 mmol, 5 equiv), TBACl (39.9 g, 144 mmol, 4 equiv), and NCS (33.6 g, 251 mmol, 7 equiv). The reaction slurry was stirred for 2 hr at 40° C. The reaction mixture was washed with 3×500 ml of brine, dried over anhydrous Na₂SO₄, filtered, and concentrated. The residue was applied onto a silica gel column with ethyl acetate/petroleum ether (1:3) to provide 19.3 g (72%) of 280-4 as a white solid.

Synthesis of (3S,4S,4aR,6aR,6bS,8aS,11S,12aR, 14aR,14bS)-11-((benzhydryloxy)carbonyl)-3-((tert-butoxycarbonyl)amino)-4,6a,6b,8a,11,14b-hexamethyl-14-oxo-1,2,3,4,4a,5,6,6a,6b,7,8,8a,9,10,11,12, 12a,14,14a,14b-icosahydropicene-4-carboxylic Acid (280-5)

Into a 100-mL round-bottom flask was placed 280-4 (1.57 g, 2.1 mmol), t-BuOH (10 mL), H₂O (5 mL), and 2-methylbut-2-ene (1 mL). To this slurry was added NaH₂PO₄ (2.01 g, 16.8 mmol, 8 equiv) at 0° C. followed by NaClO₂ (1.51 g, 16.7 mmol, 8 equiv) at 0° C. The reaction slurry was stirred for 1 hr at room temperature. The reaction mixture was extracted with 500 mL of CH₂Cl₂. The solution pH was adjusted to 4 with 2 M HCl$_{(aq)}$ and then washed with 3×500 ml of brine. The organic layer was dried over anhydrous Na₂SO₄, filtered, and concentrated to provide 1.67 g (quant) of crude 280-5 as a yellow solid.

Synthesis of 2-benzhydryl 9-((5-methyl-2-oxo-1,3-dioxol-4-yl)methyl) (2S,4aS,6aS,6bR,8aR,9S,10S, 12aS,12bR,14bR)-10-((tert-butoxycarbonyl)amino)-2,4a,6a,6b,9,12a-hexamethyl-13-oxo-1,2,3,4,4a,5,6, 6a,6b,7,8,8a,9,10,11,12,12a,12b,13,14b-icosahydropicene-2,9-dicarboxylate (280-6)

Into a 100-mL round-bottom flask was placed 280-5 (1.67 g, 2.18 mmol), DMF (10 mL), 4-(chloromethyl)-5-methyl-2H-1,3-dioxol-2-one (1.62 g, 11 mmol, 5 equiv), KI (0.36 g, 2.2 mmol, 1 equiv), and K₂CO₃ (1.50 g, 11 mmol, 5 equiv). The reaction slurry was stirred for 1 hr at 60° C. The reaction mixture was diluted with 500 mL of CH₂Cl₂, washed with 5×500 ml of brine, dried over anhydrous Na₂SO₄, filtered, and concentrated. The residue was applied onto a silica gel column with ethyl acetate/petroleum ether (1:4) to provide 1.07 g (56%) of 280-6 as a white solid.

Synthesis of (2S,4aS,6aS,6bR,8aR,9S,10S,12aS, 12bR,14bR)-10-amino-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12, 12a,12b,13,14b-icosahydropicene-2-carboxylic Acid (280-7)

Into a 100-mL round-bottom flask was placed 280-6 (100 mg, 0.11 mmol), CH₂Cl₂ (10 mL), and TFA (1 mL). The reaction slurry was stirred for 1 hr at room temperature. The reaction mixture was concentrated, and the crude product was purified by prep-HPLC with the following conditions: Column, XBridge Prep C18 OBD, 19*150 mm, 5 μm; mobile phase, water (0.05% TFA) and CH₃CN (40% Phase B up to 73% in 7 min); detector, UV. This resulted in 8.5 mg (12%) of 280-7 as a white solid. MS (ES, m/z): [M+H]⁺= 612.25; ¹H NMR (400 MHz, methanol-d₄) δ 0.85 (s, 3H), 0.99-1.11 (m, 2H), 1.13-1.32 (m, 14H), 1.44 (d, J=18.2 Hz, 7H), 1.49-1.58 (m, 1H), 1.60-1.92 (m, 7H), 1.97 (d, J=9.6 Hz, 1H), 2.11-2.37 (m, 5H), 2.58 (s, 1H), 2.81-2.99 (m, 1H), 3.65-3.80 (m, 1H), 4.90-4.99 (m, 1H), 5.12-5.28 (m, 1H), 5.62 (s, 1H).

Example 42 (2S,4aS,6aS,6bR,8aR,9S,10S,12aS, 12bR,14bR)-10-((methoxycarbonyl)amino)-2,4a,6a, 6b,9,12a-hexamethyl-9-(((5-methyl-2-oxo-1,3-dioxol-4-yl)methoxy)carbonyl)-13-oxo-1,2,3,4,4a,5,6, 6a,6b,7,8,8a,9,10,1142,12a,12b,13,14b-icosahydropicene-2-carboxylic Acid (281-3)

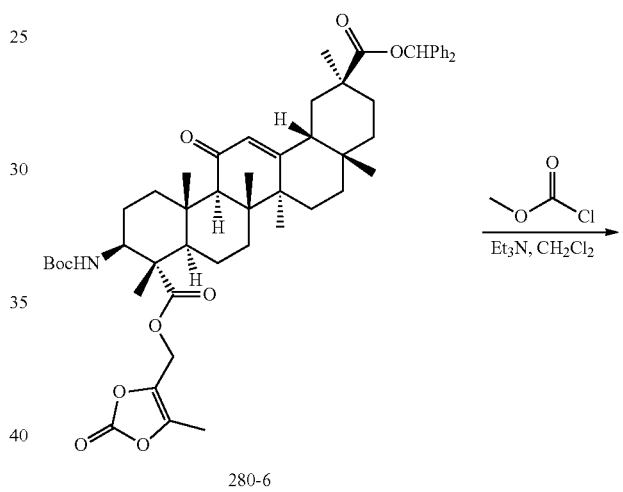

280-6

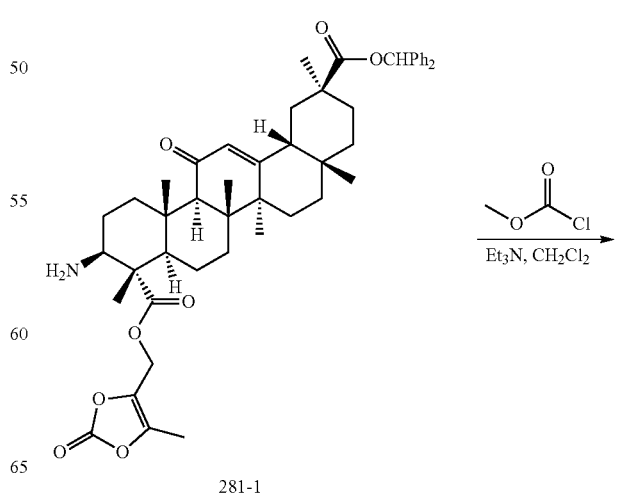

281-1

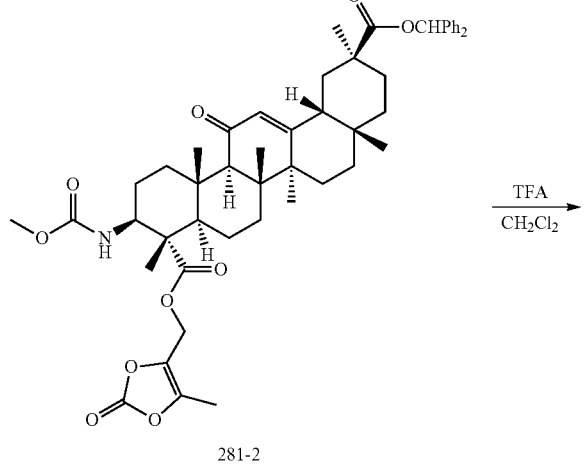

281-2

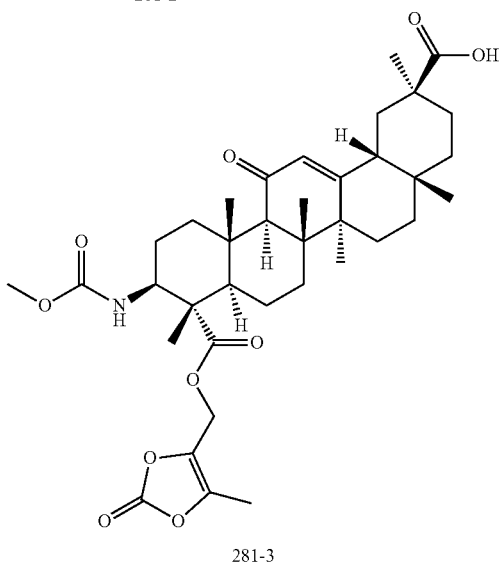

281-3

Synthesis of 2-benzhydryl 9-((5-methyl-2-oxo-1,3-dioxol-4-yl)methyl) (2S,4aS,6aS,6bR,8aR,9S,10S,12aS,12bR,14bR)-10-((tert-butoxycarbonyl)amino)-2,4a,6a,6b,9,12a-hexamethyl-13-oxo-1,2,3,4,4a,5,6,6a,6b,7,8,8a,9,10,11,12,12a,12b,13,14b-icosahydropicene-2,9-dicarboxylate (281-1)

Into a 500-mL round-bottom flask, was placed PH-RDX-013-869-8 (10.1 g, 11.50 mmol, 1 equiv), DCM (150 mL), 2,6-dimethylpyridine (6.6 mL, 5.0 equiv). This was followed by the addition of (10.2 g, 46.01 mmol, 4.0 equiv) at 0° C. The resulting solution was stirred for 1.5 hr at room temperature. The resulting solution was extracted with 3×200 mL of dichloromethane. The resulting mixture was washed with 3 ×500 ml of 2M HCl. The mixture was dried over anhydrous sodium sulfate. The solids were filtered out. The resulting mixture was concentrated. This resulted in 10.0728 g (112.56%) of 281-1 as a yellow solid. MS (ES, m/z): [M+H]$^+$=778.30; $^1$H NMR (400 MHz, DMSO-d$_6$) δ 0.62 (s, 3H), 0.83-0.90 (m, 1H), 1.00 (d, J=18.4 Hz, 7H), 1.12 (s, 4H), 1.13-1.18 (m, 4H), 1.20-1.58 (m, 10H), 1.60-1.73 (m, 3H), 1.75-1.96 (m, 4H), 2.00-2.20 (m, 5H), 2.42 (s, 1H), 2.65 (d, J=13.7 Hz, 1H), 3.39 (dd, J=11.4, 5.1 Hz, 1H), 4.93 (d, J=14.0 Hz, 1H), 5.02-5.14 (m, 1H), 5.28 (s, 1H), 6.86 (s, 1H), 7.24-7.44 (m, 10H), 8.31 (d, J=9.2 Hz, 1H).

Synthesis of 2-benzhydryl 9-((5-methyl-2-oxo-1,3-dioxol-4-yl)methyl) (2S,4aS,6aS,6bR,8aR,9S,10S,12aS,12bR,14bR)-10-((methoxycarbonyl)amino)-2,4a,6a,6b,9,12a-hexamethyl-13-oxo-1,2,3,4,4a,5,6,6a,6b,7,8,8a,9,10,11,12,12a,12b,13,14b-icosahydropicene-2,9-dicarboxylate (281-2)

Into a 100-mL round-bottom flask was placed 281-1 (230 mg, 0.30 mmol), CH$_2$Cl$_2$ (5 mL), methyl chloroformate (280 mg, 3 mmol, 10 equiv), and Et$_3$N (0.33 mL, 2.4 mmol, 8 equiv). The reaction slurry was stirred for 2 hr at room temperature. The reaction mixture was diluted with 300 mL of CH$_2$Cl$_2$ and washed with 3×300 ml of brine. The organic layer was dried over anhydrous Na$_2$SO$_4$, filtered, and concentrated to provide 130 mg (53%) of crude 281-2 as a white solid.

Synthesis of (2S,4aS,6aS,6bR,8aR,9S,10S,12aS,12bR,14bR)-10-((methoxycarbonyl)amino)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic Acid (281-3)

Into a 100-mL round-bottom flask was placed 281-2 (100 mg, 0.12 mmol), CH$_2$Cl$_2$ (10 mL), and TFA (1 mL). The reaction slurry was stirred for 1 hr at room temperature then concentrated. The crude product was purified by prep-HPLC with the following conditions: Column, XBridge Prep C18 OBD, 5 μm, 19*150 mm; mobile phase, water (0.05% TFA) and CH$_3$CN (43% Phase B up to 73% in 8 min); detector, UV. This resulted in 24.8 mg (29%) of 281-3 as a white solid. MS (ES, m/z): [M+H]$^+$=670.15; $^1$H NMR (400 MHz, methanol-d$_4$) δ 0.85 (s, 3H), 0.91 (d, J=12.7 Hz, 1H), 1.05-1.34 (m, 16H), 1.33-1.57 (m, 8H), 1.59-1.82 (m, 5H), 1.87 (dd, J=12.6, 6.2 Hz, 2H), 1.97 (d, J=9.7 Hz, 1H), 2.11-2.29 (m, 5H), 2.58 (s, 1H), 2.75-2.84 (m, 1H), 3.58 (s, 3H), 3.98 (dd, J=12.5, 4.3 Hz, 1H), 4.87 (s, 1H), 5.01 (d, J=14.0 Hz, 1H), 5.61 (s, 1H).

Example 43 (2S,4aS,6aS,6bR,8aR,9S,10S,12aS,12bR,14bR)-2,4a,6a,6b,9,12a-hexamethyl-9-(((5-methyl-2-oxo-1,3-dioxol-4-yl)methoxy)carbonyl)-13-oxo-10-(pentanoyloxy)-1,2,3,4,4a,5,6,6a,6b,7,8,8a,9,10,1142,12a,12b,13,14b-icosahydropicene-2-carboxylic (282-2)

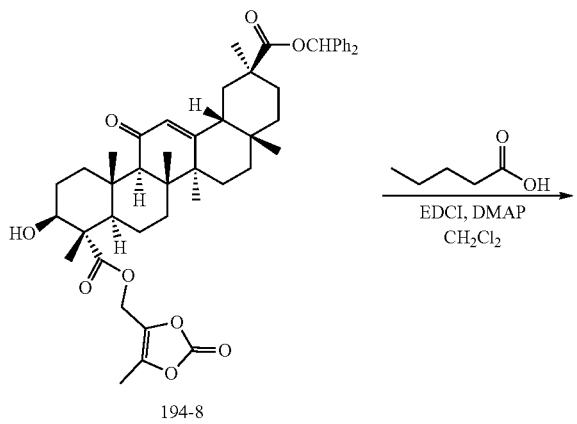

194-8

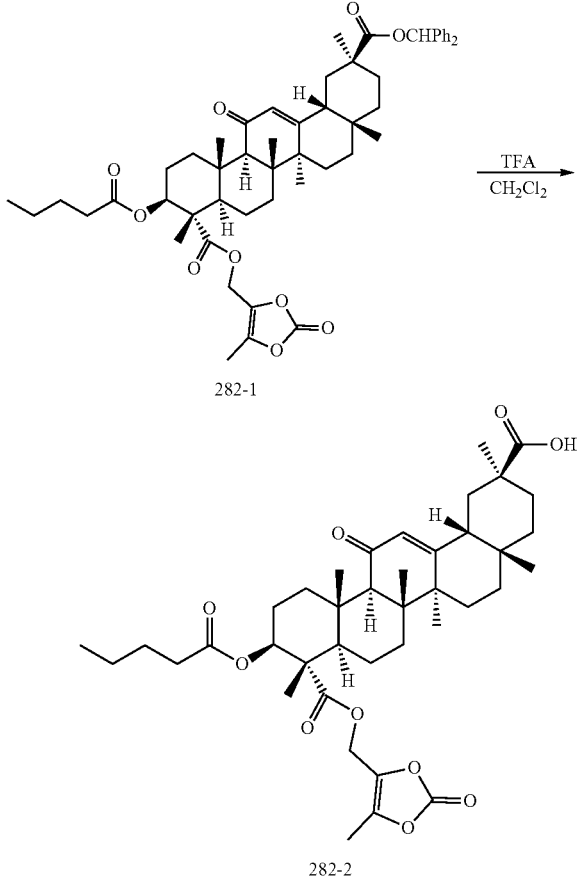

282-1

282-2

Synthesis of 2-benzhydryl 9-((5-methyl-2-oxo-1,3-dioxol-4-yl)methyl) (2S,4aS,6aS,6bR,8aR,9S,10S,12aS,12bR,14bR)-2,4a,6a,6b,9,12a-hexamethyl-13-oxo-10-(pentanoyloxy)-1,2,3,4,4a,5,6,6a,6b,7,8,8a,9,10,11,12,12a,12b,13,14b-icosahydropicene-2,9-dicarboxylate (282-1)

Into a 100-mL round-bottom flask was placed 194-8 (120 mg, 0.15 mmol), CH$_2$Cl$_2$ (8 mL), pentanoic acid (0.17 mL), DMAP (75 mg, 0.61 mmol, 4 equiv), and EDCI (150 mg, 0.78 mmol, 5.2 equiv). The reaction slurry was stirred overnight at room temperature. The reaction mixture was diluted with 300 mL of CH$_2$Cl$_2$ and the pH of the solution adjusted to 4 with 2 M HCl$_{(aq)}$. The resulting mixture was washed with 3×500 ml of brine. The organic layer was dried over anhydrous Na$_2$SO$_4$, filtered, and concentrated to provide 115 mg (86%) of crude 282-1 as a white solid.

Synthesis of (2S,4aS,6aS,6bR,8aR,9S,10S,12aS,12bR,14bR)-2,4a,6a,6b,9,12a-hexamethyl-9-(((5-methyl-2-oxo-1,3-dioxol-4-yl)methoxy)carbonyl)-13-oxo-10-(pentanoyloxy)-1,2,3,4,4a,5,6,6a,6b,7,8,8a,9,10,11,12,12a,12b,13,14b-icosahydropicene-2-carboxylic Acid (282-2)

Into a 100-mL round-bottom flask was placed 282-1 (120 mg, 0.14 mmol), CH$_2$Cl$_2$ (10 mL), and TFA (1 mL). The reaction slurry was stirred for 1 hr at room temperature and concentrated. The crude product was purified by prep-HPLC with the following conditions: Column, XBridge Prep C18 OBD, 19*150 mm, 5 μm; mobile phase, water (0.05% TFA) and CH$_3$CN (65% Phase B up to 95% in 7 min); detector, UV. This resulted in 54.1 mg (53%) of 282-2 as a white solid. MS (ES, m/z): [M+H]$^+$=697.20; $^1$H NMR (400 MHz, methanol-d$_4$) δ 0.85 (s, 3H), 0.93 (t, J=7.3 Hz, 4H), 1.06 (d, J=14.5 Hz, 1H), 1.19 (dd, J=16.9, 15.8 Hz, 14H), 1.27-1.39 (m, 2H), 1.35-1.49 (m, 6H), 1.48-1.60 (m, 2H), 1.61-1.81 (m, 6H), 1.81-2.01 (m, 3H), 2.05 (s, 1H), 2.11-2.29 (m, 7H), 2.58 (s, 1H), 2.77-2.87 (m, 1H), 4.89 (s, 1H), 5.02 (d, J=13.9 Hz, 1H), 5.17 (dd, J=11.7, 5.0 Hz, 1H), 5.62 (s, 1H).

Example 44 (2S,4aS,6aS,6bR,8aR,9S,10S,12aS,12bR,14bR)-2,4a,6a,6b,9,12a-hexamethyl-9-(((5-methyl-2-oxo-1,3-dioxol-4-yl)methoxy)carbonyl)-10-(2-(4-methylpiperazin-1-yl)acetoxy)-13-oxo-1,2,3,4,4a,5,6,6a,6b,7,8,8a,9,10,1142,12a,12b,13,14b-icosahydropicene-2-carboxylic Acid (283-2)

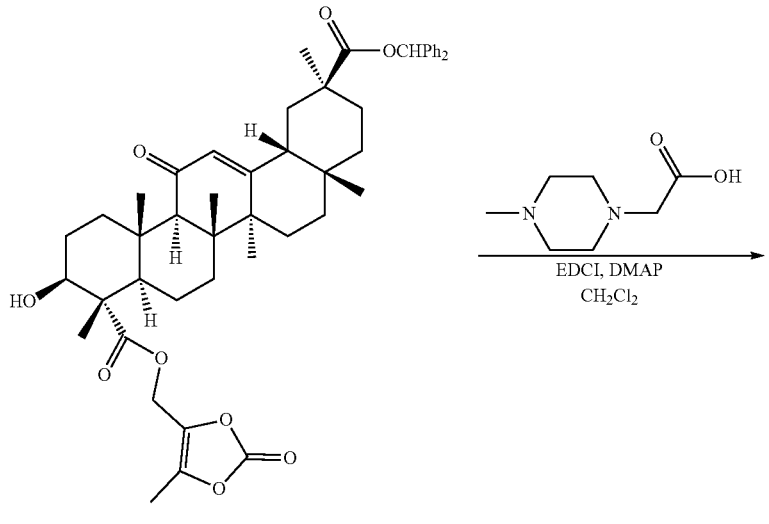

194-8

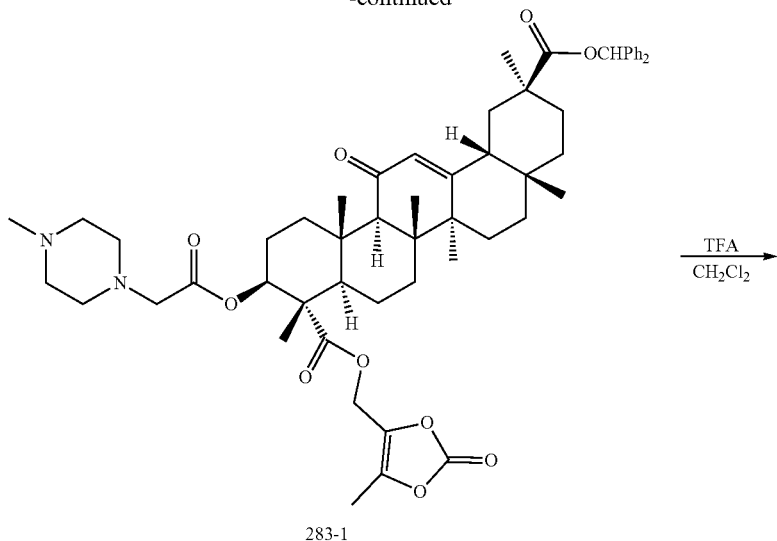

283-1

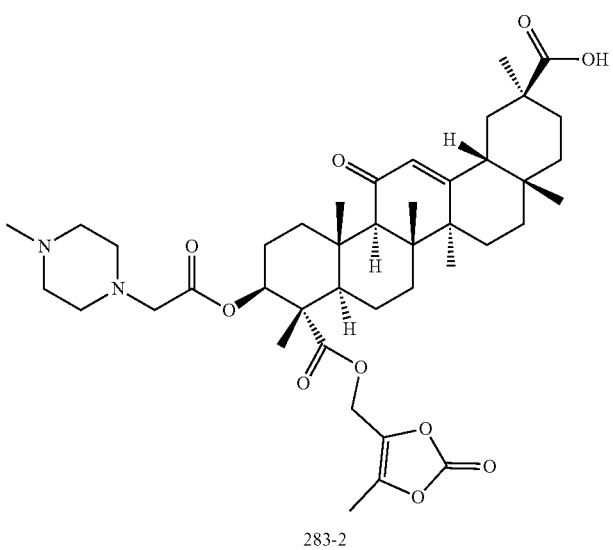

283-2

Synthesis of 2-benzhydryl 9-((5-methyl-2-oxo-1,3-dioxol-4-yl)methyl) (2S,4aS,6aS,6bR,8aR,9S,10S,12aS,12bR,14bR)-2,4a,6a,6b,9,12a-hexamethyl-10-(2-(4-methylpiperazin-1-yl)acetoxy)-13-oxo-1,2,3,4,4a,5,6,6a,6b,7,8,8a,9,10,11,12,12a,12b,13,14b-icosahydropicene-2,9-dicarboxylate (283-1)

Into a 100-mL round-bottom flask was placed 194-8 (120 mg, 0.15 mmol, 1 equiv), CH₂Cl₂ (6 mL), 2-(4-methylpiperazin-1-yl)acetic acid (240 mg, 1.52 mmol, 10 equiv), DMAP (94 mg, 0.77 mmol, 5.1 equiv), and EDCI (300 mg, 1.56 mmol, 10 equiv). The reaction slurry was stirred overnight at room temperature. The reaction mixture was diluted with 300 mL of CH₂Cl₂ and the pH of the solution adjusted to 4 with 2 M HCl$_{(aq)}$. The resulting mixture was washed with 3 x 300 ml of brine, dried over anhydrous Na₂SO₄, filtered, and concentrated to provide 125 mg (88%) of 283-1 as a white solid.

Synthesis of (2S,4aS,6aS,6bR,8aR,9S,10S,12aS,12bR,14bR)-2,4a,6a,6b,9,12a-hexamethyl-9-(((5-methyl-2-oxo-1,3-dioxol-4-yl)methoxy)carbonyl)-10-(2-(4-methylpiperazin-1-yl)acetoxy)-13-oxo-1,2,3,4,4a,5,6,6a,6b,7,8,8a,9,10,11,12,12a,12b,13,14b-icosahydropicene-2-carboxylic acid (283-2)

Into a 100-mL round-bottom flask was placed 283-1 (125 mg, 0.14 mmol), CH₂Cl₂ (10 mL), and TFA (1 mL). The reaction slurry was stirred for 1 hr at room temperature then concentrated. The crude product was purified by prep-HPLC with the following conditions: Column, XBridge Prep C18 OBD, 19*150 mm, 5 μm; mobile phase, water (0.05% TFA) and CH₃CN (30% Phase B up to 68% in 7 min); detector, UV. This resulted in 59.5 mg (58%) of 283-2 as a white solid. MS (ES, m/z): [M+H]⁺=753.25; ¹H NMR (400 MHz, methanol-d₄) δ 0.85 (s, 3H), 0.98-1.30 (m, 17H), 1.30-1.53 (m, 8H), 1.54-2.09 (m, 10H), 2.12-2.28 (m, 5H), 2.58 (s, 1H), 2.63-3.03 (m, 8H), 3.34 (s, 3H), 4.94 (d, J=14.0 Hz, 1H), 5.01 (d, J=13.9 Hz, 1H), 5.24 (dd, J=11.7, 4.9 Hz, 1H), 5.62 (s, 1H).

Example 45 (2S,4aS,6aS,6bR,8aR,9S,10S,12aS,12bR,14bR)-2,4a,6a,6b,9,12a-hexamethyl-9-(((5-methyl-2-oxo-1,3-dioxol-4-yl)methoxy)carbonyl)-10-((3-morpholinopropanoyl)oxy)-13-oxo-1,2,3,4,4a,5,6,6a,6b,7,8,8a,9,10,1142,12a,12b,13,14b-icosahydropicene-2-carboxylic Acid (284-2)
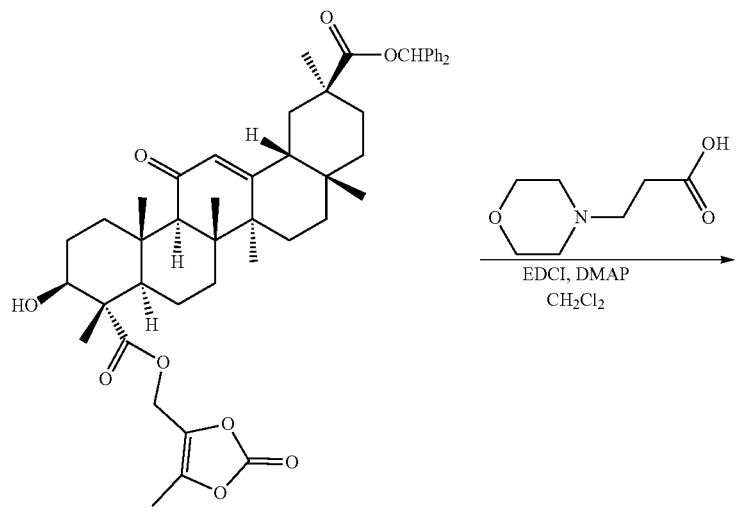
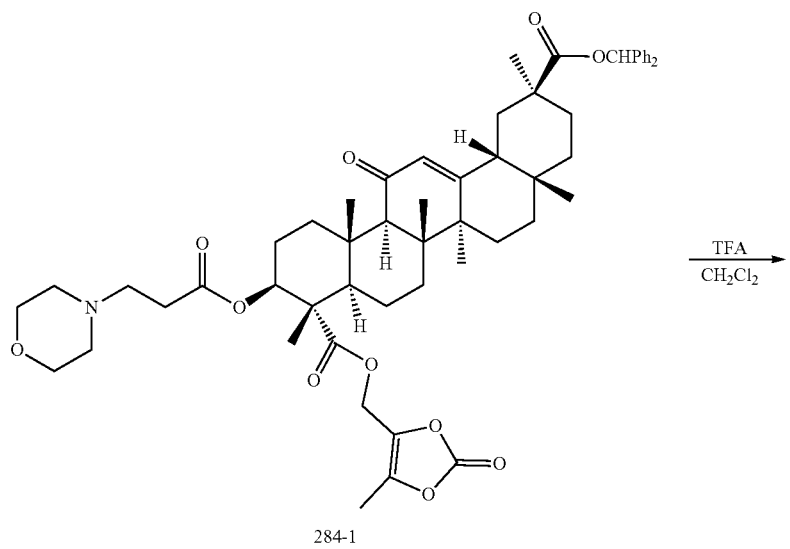

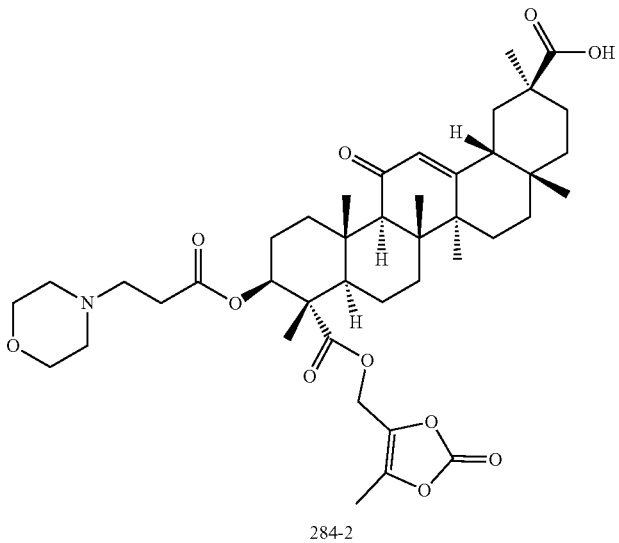

284-2

Synthesis of 2-benzhydryl 9-((5-methyl-2-oxo-1,3-dioxol-4-yl)methyl) (2S,4aS,6aS,6bR,8aR,9S,10S,12aS,12bR,14bR)-2,4a,6a,6b,9,12a-hexamethyl-10-((3-morpholinopropanoyl)oxy)-13-oxo-1,2,3,4,4a,5,6,6a,6b,7,8,8a,9,10,11,12,12a,12b,13,14b-icosahydropicene-2,9-dicarboxylate (284-1)

Into a 100-mL round-bottom flask was placed 194-8 (150 mg, 0.19 mmol), CH$_2$Cl$_2$ (8 mL), 3-(morpholin-4-yl)propanoic acid (310 mg, 1.95 mmol, 10 equiv), DMAP (75 mg, 0.61 mmol, 3.2 equiv), and EDCI (200 mg, 1.04 mmol, 5.4 equiv). The reaction slurry was stirred overnight at room temperature. The reaction mixture was diluted with 300 mL of CH$_2$Cl$_2$ and the pH of the solution was adjusted to 4 with 2 M HCl$_{(aq)}$. The resulting mixture was washed with 3×300 ml of brine. The organic layer was dried over anhydrous Na$_2$SO$_4$, filtered, and concentrated to provide 143 mg (81%) of crude 284-1 as a white solid.

Synthesis of (2S,4aS,6aS,6bR,8aR,9S,10S,12aS,12bR,14bR)-2,4a,6a,6b,9,12a-hexamethyl-9-(((5-methyl-2-oxo-1,3-dioxol-4-yl)methoxy)carbonyl)-10-((3-morpholinopropanoyl)oxy)-13-oxo-1,2,3,4,4a,5,6,6a,6b,7,8,8a,9,10,11,12,12a,12b,13,14b-icosahydropicene-2-carboxylic Acid (284-2)

Into a 100-mL round-bottom flask was placed 284-1 (143 mg, 0.16 mmol), CH$_2$Cl$_2$ (139 mL), TFA (13.9 mL). The reaction slurry was stirred for 1 hr at room temperature then concentrated. The crude product was purified by prep-HPLC with the following conditions: column, XBridge Prep C18 OBD, 19*150 mm, 5 μm; mobile phase, water (0.05% TFA) and CH$_3$CN (35% Phase B up to 75% in 7 min); detector, UV. This resulted in 10.3 mg (8%) of 284-2 as a white solid. MS (ES, m/z): [M+H]$^+$=754.45; $^1$H NMR (400 MHz, methanol-d$_4$) δ 0.85 (s, 3H), 0.94-1.30 (m, 16H), 1.44 (d, J=18.7 Hz, 7H), 1.67-2.08 (m, 9H), 2.14-2.30 (m, 5H), 2.58 (s, 1H), 2.72-2.98 (m, 3H), 3.15-2.30 (m, 2H), 3.45 (s, 1H), 3.40-3.50 (m, 3H), 3.65-4.28 (m, 4H), 4.99 (d, J=1.9 Hz, 2H), 5.23 (dd, J=11.6, 5.1 Hz, 1H), 5.62 (s, 1H).

Example 46 (2S,4aS,6aS,6bR,8aR,9S,10S,12aS,12bR,14bR)-2,4a,6a,6b,9,12a-hexamethyl-9-(((5-methyl-2-oxo-1,3-dioxol-4-yl)methoxy)carbonyl)-10-(methylsulfonamido)-13-oxo-1,2,3,4,4a,5,6,6a,6b,7,8,8a,9,10,1142,12a,12b,13,14b-icosahydropicene-2-carboxylic (285-2)

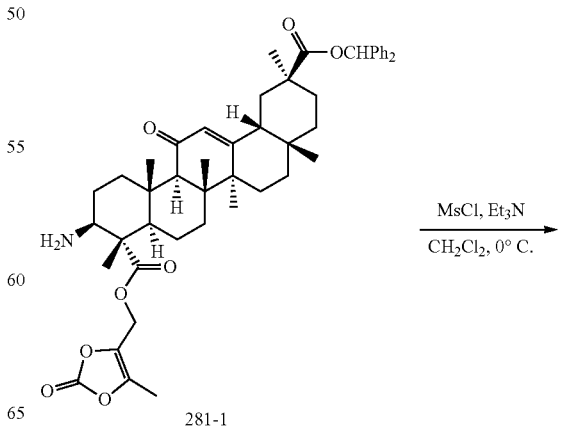

281-1

181
-continued

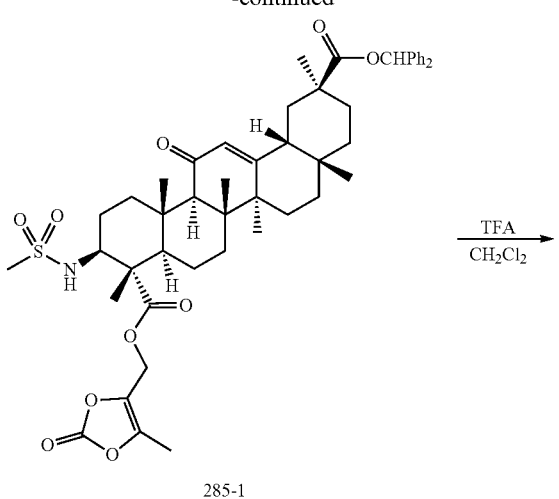

285-1

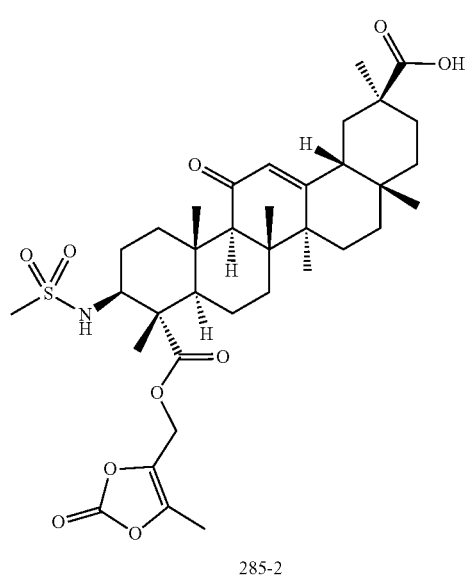

285-2

182

Synthesis of 2-benzhydryl 9-((5-methyl-2-oxo-1,3-dioxol-4-yl)methyl) (2S,4aS,6aS,6bR,8aR,9S,10S,12aS,12bR,14bR)-2,4a,6a,6b,9,12a-hexamethyl-10-(methylsulfonamido)-13-oxo-1,2,3,4,4a,5,6,6a,6b,7,8,8a,9,10,11,12,12a,12b,13,14b-icosahydropicene-2,9-dicarboxylate (285-1)

Into a 100-mL round-bottom flask was placed 281-1 (230 mg, 0.30 mmol) and CH$_2$Cl$_2$ (6 mL) followed by methanesulfonyl chloride (0.5 mL) then Et$_3$N (0.3 mL, 2.2 mmol, 7.3 equiv) at 0° C. The reaction slurry was stirred for 2 hr at room temperature. The reaction mixture was diluted with 300 mL of CH$_2$Cl$_2$ and washed with 3×300 ml of brine. The organic layer was dried over anhydrous Na$_2$SO$_4$, filtered, and concentrated to provide 201 mg (79%) of crude 285-1 as a yellow solid.

Synthesis of (2S,4aS,6aS,6bR,8aR,9S,10S,12aS,12bR,14bR)-2,4a,6a,6b,9,12a-hexamethyl-9-(((5-methyl-2-oxo-1,3-dioxol-4-yl)methoxy)carbonyl)-10-(methylsulfonamido)-13-oxo-1,2,3,4,4a,5,6,6a,6b,7,8,8a,9,10,11,12,12a,12b,13,14b-icosahydropicene-2-carboxylic Acid (285-2)

Into a 100-mL round-bottom flask was placed 285-1 (200 mg, 0.23 mmol), CH$_2$Cl$_2$ (10 mL), and TFA (1 mL). The reaction slurry was stirred for 1 hr at room temperature then concentrated. The crude product was purified by prep-HPLC with the following conditions: column, XBridge Prep C18 OBD, 19*150 mm, 5 μm; mobile phase, water (0.05% TFA) and CH$_3$CN (5% Phase B up to 45% in 5 min, up to 61% in 10 min); detector, UV. This resulted in 16.2 mg (10%) of 285-2 as a white solid. MS (ES, m/z): [M+H]$^+$=690.05; $^1$H NMR (400 MHz, methanol-d$_4$) δ 0.85 (s, 3H), 0.92 (d, J=11.7 Hz, 1H), 1.00-1.31 (m, 16H), 1.31-1.49 (m, 7H), 1.56-1.81 (m, 6H), 1.81-2.01 (m, 3H), 2.08-2.30 (m, 5H), 2.58 (s, 1H), 2.82 (dt, J=13.6, 3.5 Hz, 1H), 2.91 (s, 3H), 3.76 (dd, J=11.9, 4.9 Hz, 1H), 4.82 (d, J=13.9 Hz, 1H), 5.09 (d, J=14.0 Hz, 1H), 5.62 (s, 1H).

Example 47 (2S,4aS,6aS,6bR,8aR,9S,10S,12aS,12bR,14bR)-2,4a,6a,6b,9,12a-hexamethyl-9-(((5-methyl-2-oxo-1,3-dioxol-4-yl)methoxy)carbonyl)-10-(((2-morpholinoethyl)carbamoyl)oxy)-13-oxo-1,2,3,4,4a,5,6,6a,6b,7,8,8a,9,10,1142,12a,12b,13,14b-icosahydropicene-2-carboxylic (286-4)

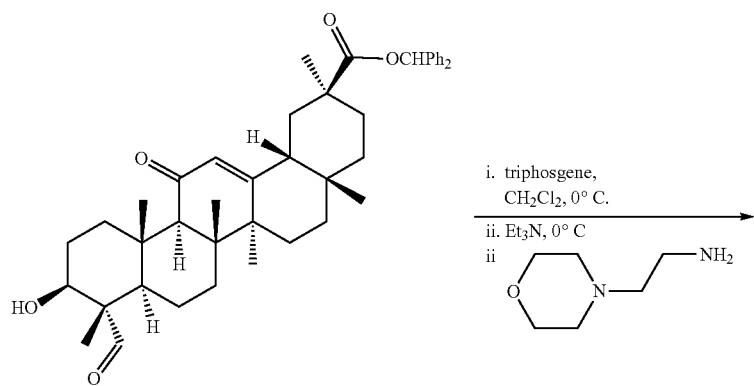

194-6

-continued
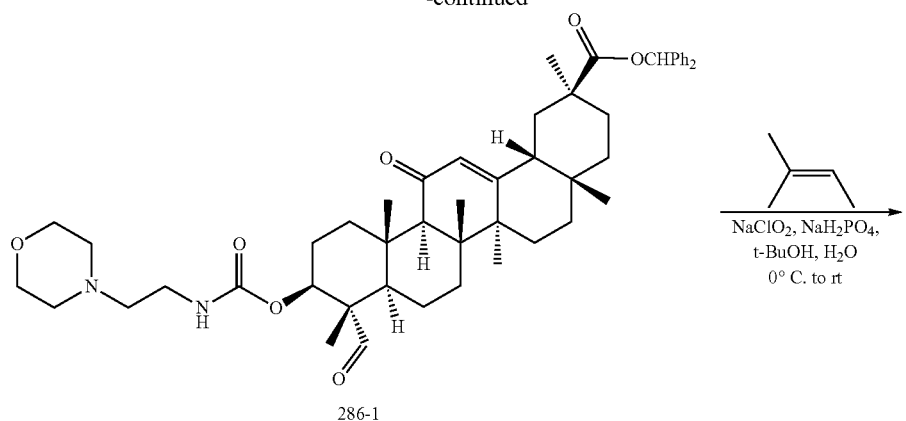
286-1
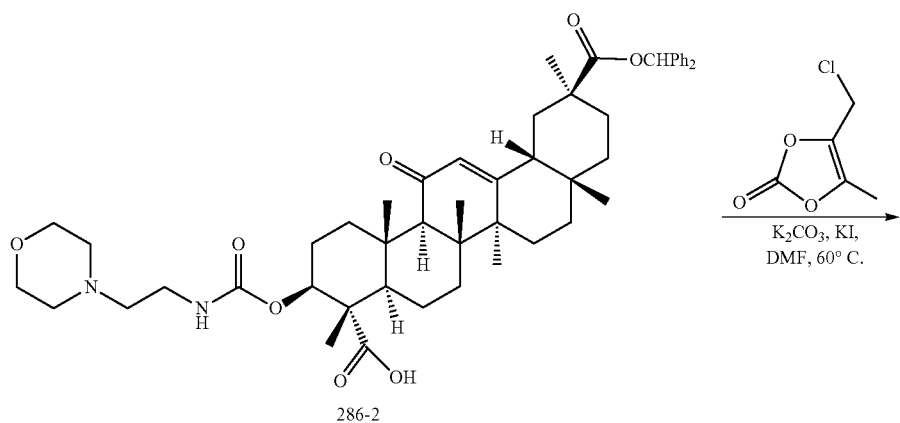
286-2
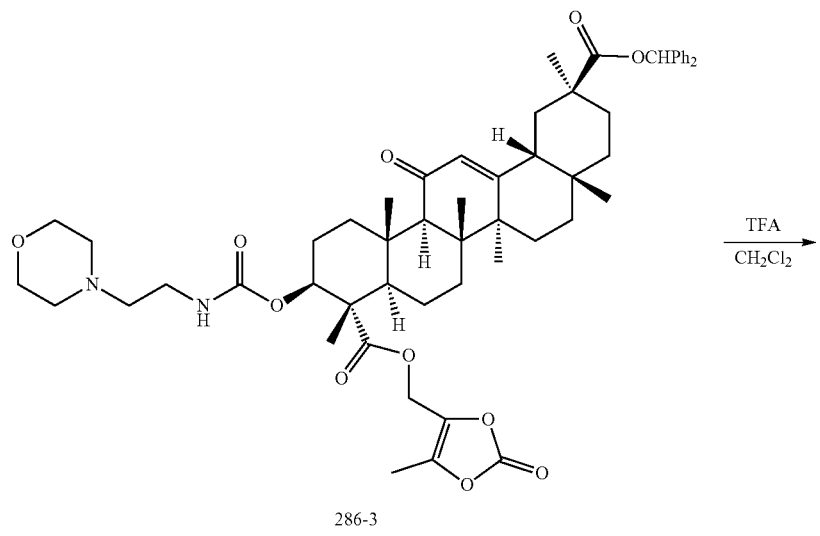
286-3

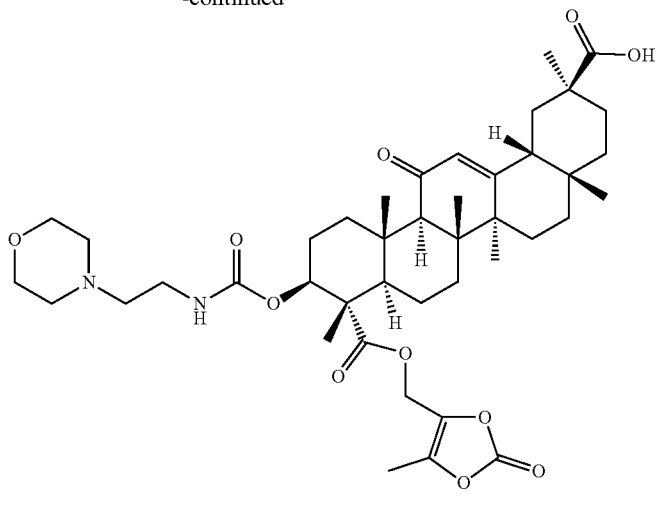

286-4

Synthesis of benzhydryl (2S,4aS,6aS,6bR,8aR,9S,10S,12aS,12bR,14bR)-9-formyl-2,4a,6a,6b,9,12a-hexamethyl-10-(((2-morpholinoethyl)carbamoyl)oxy)-13-oxo-1,2,3,4,4a,5,6,6a,6b,7,8,8a,9,10,11,12,12a,12b,13,14b-icosahydropicene-2-carboxylate (286-1)

Into a 100-mL round-bottom flask was placed 194-6 (190 mg, 0.29 mmol) and $CH_2Cl_2$ (5 mL) followed by triphosgene (69 mg, 0.23 mmol, 0.8 equiv) at 0° C. To this slurry was added $Et_3N$ (0.081 mL, 0.58 mmol, 2 equiv) dropwise. After 1 hour, 2-(morpholin-4-yl)ethan-1-amine (380 mg, 2.9 mmol, 10 equiv) was added at 0° C. The reaction slurry was stirred for 1 hr at 0° C. The reaction mixture was diluted with 300 mL of $CH_2Cl_2$ and washed with 3×300 ml of brine. The organic layer was dried over anhydrous $Na_2SO_4$, filtered, and concentrated. The residue was applied onto a silica gel column with ethyl acetate/petroleum ether (1:1) to provide 170 mg (72%) of 286-1 as a white solid.

Synthesis of (3S,4S,4aR,6aR,6bS,8aS,11S,12aR,14aR,14bS)-11-((benzhydryloxy)carbonyl)-4,6a,6b,8a,11,14b-hexamethyl-3-(((2-morpholinoethyl)carbamoyl)oxy)-14-oxo-1,2,3,4,4a,5,6,6a,6b,7,8,8a,9,10,11,12,12a,14,14a,14b-icosahydropicene-4-carboxylic Acid (286-2)

Into a 100-mL round-bottom flask was placed 286-1 (170 mg, 0.21 mmol), t-BuOH (6 mL), $H_2O$ (2 mL), and 2-methylbut-2-ene (0.5 mL) followed by the addition of $NaH_2PO_4$ (250 mg, 2.1 mmol, 10 equiv) at 0° C. To this slurry was added $NaClO_2$ (190 mg, 2.1 mmol, 10 equiv) at 0° C. The reaction slurry was stirred for 2 hr at room temperature. The reaction mixture was diluted with 300 mL of $CH_2Cl_2$ and washed with 3×300 ml of brine. The organic layer was dried over anhydrous $Na_2SO_4$, filtered, and concentrated to provide 168 mg (97%) of 286-2 as a white solid.

Synthesis of 2-benzhydryl 9-((5-methyl-2-oxo-1,3-dioxol-4-yl)methyl) (2S,4aS,6aS,6bR,8aR,9S,10S,12aS,12bR,14bR)-2,4a,6a,6b,9,12a-hexamethyl-10-(((2-morpholinoethyl)carbamoyl)oxy)-13-oxo-1,2,3,4,4a,5,6,6a,6b,7,8,8a,9,10,11,12,12a,12b,13,14b-icosahydropicene-2,9-dicarboxylate (286-3)

Into a 100-mL round-bottom flask was placed 286-2 (210 mg, 0.26 mmol), DMF (8 mL), 4-(chloromethyl)-5-methyl-2H-1,3-dioxol-2-one (200 mg, 1.35 mmol, 5.3 equiv), KI (43 mg, 0.26 mmol, 1 equiv), and $K_2CO_3$ (180 mg, 1.3 mmol, 5.1 equiv). The reaction slurry was stirred for 1 hr at 60° C. The reaction slurry was cooled to room temperature, diluted with 300 mL of $CH_2Cl_2$, and washed with 5×300 ml of brine. The organic layer was dried over anhydrous $Na_2SO_4$, filtered, and concentrated. The residue was applied onto a silica gel column with ethyl acetate/petroleum ether (1:1) to provide 108 mg (45%) of 286-3 as a white solid.

Synthesis of (2S,4aS,6aS,6bR,8aR,9S,10S,12aS,12bR,14bR)-2,4a,6a,6b,9,12a-hexamethyl-9-(((5-methyl-2-oxo-1,3-dioxol-4-yl)methoxy)carbonyl)-10-(((2-morpholinoethyl)carbamoyl)oxy)-13-oxo-1,2,3,4,4a,5,6,6a,6b,7,8,8a,9,10,11,12,12a,12b,13,14b-icosahydropicene-2-carboxylic Acid (286-4)

Into a 100-mL round-bottom flask was placed 286-3 (108 mg, 0.12 mmol), $CH_2Cl_2$ (10 mL), and TFA (1 mL). The reaction slurry was stirred for 1 hr at room temperature then concentrated. The crude product was purified by prep-HPLC with the following conditions: Column, XSelect CSH Prep C18 OBD, 5 μm, 19*150 mm; mobile phase, water (0.05% TFA) and $CH_3CN$ (32% Phase B up to 49% in 8 min); detector, UV. This resulted in 4.0 mg (4%) of 286-4 as a white solid. MS (ES, m/z): $[M+H]^+$=769.25; $^1H$ NMR (400 MHz, methanol-$d_4$) δ 0.85 (s, 3H), 0.99 (s, 1H), 1.07 (d, J=13.7 Hz, 1H), 1.11-1.37 (m, 15H), 1.38-1.40 (m, 7H), 1.62-1.83 (m, 6H), 1.83-1.94 (m, 3H), 2.12-2.28 (m, 5H), 2.57 (s, 1H), 2.79-2.90 (m, 1H), 3.20-3.30 (m, 3H), 3.35-1.42 (m, 2H), 3.51-3.61 (m, 2H), 3.69-3.84 (m, 2H), 3.97-4.21 (m, 2H), 4.92-5.10 (m, 3H), 5.50 (s, 1H), 5.62 (s, 1H).

Example 48 (2S,4aS,6aS,6bR,8aR,9S,10S,12aS,
12bR,14bR)-2,4a,6a,6b,9,12a-hexamethyl-9-(((5-
methyl-2-oxo-1,3-dioxol-4-yl)methoxy)carbonyl)-
10-(2-(methylsulfinyl)acetoxy)-13-oxo-1,2,3,4,4a,5,
6,6a,6b,7,8,8a,9,10,11,12,12a,12b,13,14b-
icosahydropicene-2-carboxylic Acid (289-2)

Synthesis of 2-benzhydryl 9-((5-methyl-2-oxo-1,3-
dioxol-4-yl)methyl) (2S,4aS,6aS,6bR,8aR,9S,10S,
12aS,12bR,14bR)-2,4a,6a,6b,9,12a-hexamethyl-10-
(2-(methylsulfinyl)acetoxy)-13-oxo-1,2,3,4,4a,5,6,
6a,6b,7,8,8a,9,10,11,12,12a,12b,13,14b-
icosahydropicene-2,9-dicarboxylate (289-1)

A mixture of 194-9 (100 mg, 0.12 mmol) and NaIO$_4$ (27.1 mg, 0.13 mmol, 1.1 equiv) in MeOH and H$_2$O (0.11 mL) was stirred overnight at room temperature. The reaction mixture was extracted with EtOAc. The combined organic layers were washed with brine, dried over anhydrous Na$_2$SO$_4$, filtered, and concentrated under reduced pressure. The residue was purified by prep-TLC (petroleum ether/ EtOAc 5:1) to afford 289-1 (110 mg, quant) as a light yellow solid.

Synthesis of (2S,4aS,6aS,6bR,8aR,9S,10S,12aS,
12bR,14bR)-2,4a,6a,6b,9,12a-hexamethyl-9-(((5-
methyl-2-oxo-1,3-dioxol-4-yl)methoxy)carbonyl)-
10-(2-(methyl sulfinyl)acetoxy)-13-oxo-1,2,3,4,4a,5,
6,6a,6b,7,8,8a,9,10,11,12,12a,12b,13,14b-
icosahydropicene-2-carboxylic Acid (289-2)

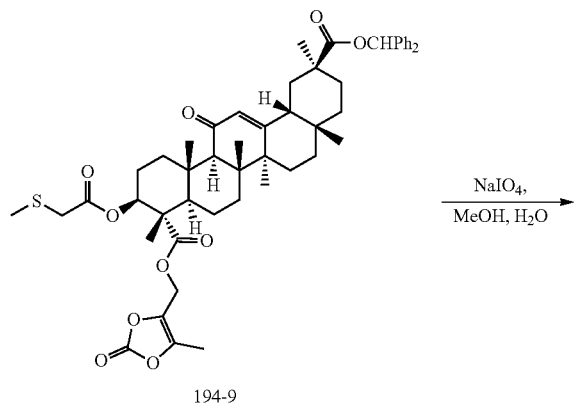

194-9

A mixture of 289-1 (110 mg, 0.12 mmol) and TFA (0.1 mL, 1.35 mmol, 11 equiv) in CH$_2$Cl$_2$ was stirred for 1 h at room temperature. The resulting mixture was concentrated under vacuum. The crude product was purified by prep-HPLC with the following conditions: Column, XSelect CSH Prep C18 OBD, 19*250 mm, 5 μm; mobile phase, water (0.05% TFA) and CH$_3$CN (51% Phase B up to 62% in 8 min); detector, UV. This resulted in 289-2 (27.7 mg, 31%) as an off-white solid. MS (ES, m/z): [M+H]$^+$=717; $^1$H NMR (400 MHz, methanol-d$_4$) δ 5.62 (s, 1H), 5.31 (dd, J=11.4, 5.4 Hz, 1H), 5.06 (d, J=14.0 Hz, 1H), 4.91 (d, J=4.2 Hz, 1H), 3.93 (d, 7=14.3 Hz, 1H), 3.73 (dd, J=14.3, 5.3 Hz, 1H), 2.85 (d, J=13.5 Hz, 1H), 2.75 (d, J=2.8 Hz, 3H), 2.59 (s, 1H), 2.30-2.10 (m, 5H), 1.97 (d, J=9.8 Hz, 1H), 1.94-1.62 (m, 8H), 1.53-1.36 (m, 7H), 1.34-1.12 (m, 14H), 1.07 (d, J=14.0 Hz, 1H), 0.99 (d, J=9.8 Hz, 1H), 0.85 (s, 3H).

289-1

Example 49 (2S,4aS,6aS,6bR,8aR,9S,10S,12aS,
12bR,14bR)-10-((dimethylglycyl)oxy)-2,4a,6a,6b,9,
12a-hexamethyl-9-(((5-methyl-2-oxo-1,3-dioxol-4-
yl)methoxy)carbonyl)-13-oxo-1,2,3,4,4a,5,6,6a,6b,7,
8,8a,9,10,11,12,12a,12b,13,14b-icosahydropicene-2-
carboxylic Acid (290-2)

289-2

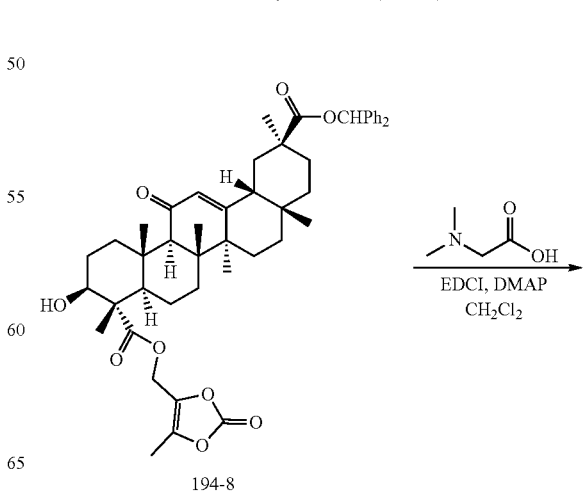

194-8

189

-continued

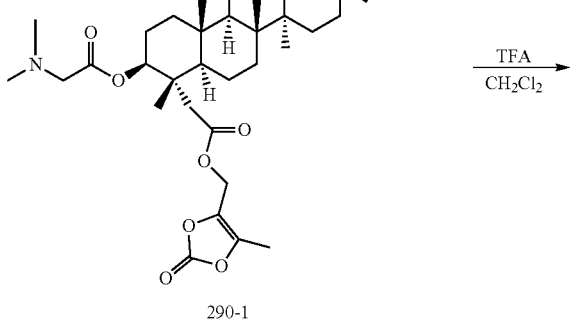

290-1

↓ TFA / CH₂Cl₂

290-2

Synthesis of 2-benzhydryl 9-((5-methyl-2-oxo-1,3-dioxol-4-yl)methyl) (2S,4aS,6aS,6bR,8aR,9S,10S,12aS,12bR,14bR)-10-((dimethylglycyl)oxy)-2,4a,6a,6b,9,12a-hexamethyl-13-oxo-1,2,3,4,4a,5,6,6a,6b,7,8,8a,9,10,11,12,12a,12b,13,14b-icosahydropicene-2,9-dicarboxylate (290-1)

Into a 25-mL round-bottom flask was placed 194-8 (140 mg, 0.18 mmol), 2-(dimethylamino)acetic acid (185 mg, 1.8 mmol, 10 equiv), 4-dimethylaminopyridine (84 mg, 0.69 mmol, 4 equiv), CH₂Cl₂ (2.5 mL), EDCI (175 mg, 0.91 mmol, 5 equiv). The reaction slurry was stirred overnight at room temperature. The reaction mixture was concentrated under vacuum. The residue was applied onto a silica gel column with CH₂Cl₂/methanol (12/1) to provide 100 mg (64%) of 290-1 as a light yellow solid.

190

Synthesis of (2S,4aS,6aS,6bR,8aR,9S,10S,12aS,12bR,14bR)-10-((dimethylglycyl)oxy)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic Acid (290-2)

A mixture 290-1 (100 mg, 0.12 mmol) and TFA (0.1 mL, 1.35 mmol, 12 equiv) in CH₂Cl₂ was stirred for 1 h at room temperature. The reaction mixture was concentrated under reduced pressure. The crude product was purified by prep-HPLC with the following conditions; column: Xselect CSH OBD 30*150 mm, 5 μm; mobile phase: water (0.05% TFA) and CH₃CN (60 mL/min; gradient: 30% B to 60% B in 8 min; 254 nm; Rt: 6.27 min). The residue was repurified by prep-TLC to afford 290-2 (26.6 mg, 33%) as an off-white solid. MS (ES, m/z) [M+H]⁺=698.05; ¹H NMR (300 MHz, methanol-d₄) δ 5.64 (s, 1H), 5.45-5.31 (m, 1H), 5.10 (d, J=13.9 Hz, 1H), 4.95 (d, J=14.1 Hz, 1H), 4.16 (d, J=2.4 Hz, 2H), 2.98 (s, 6H), 2.89 (d, J=14.1 Hz, 1H), 2.60 (s, 1H), 2.22 (s, 5H), 1.92 (d, J=32.7 Hz, 5H), 1.82-1.66 (m, 4H), 1.46 (d, J=12.1 Hz, 7H), 1.28 (s, 5H), 1.25-1.14 (m, 9H), 1.14-0.95 (m, 2H), 0.86 (s, 3H).

Example 50 (2S,4aS,6aS,6bR,8aR,9S,10S,12aS,12bR,14bR)-10-((acetylglycyl)oxy)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic Acid (291-2)

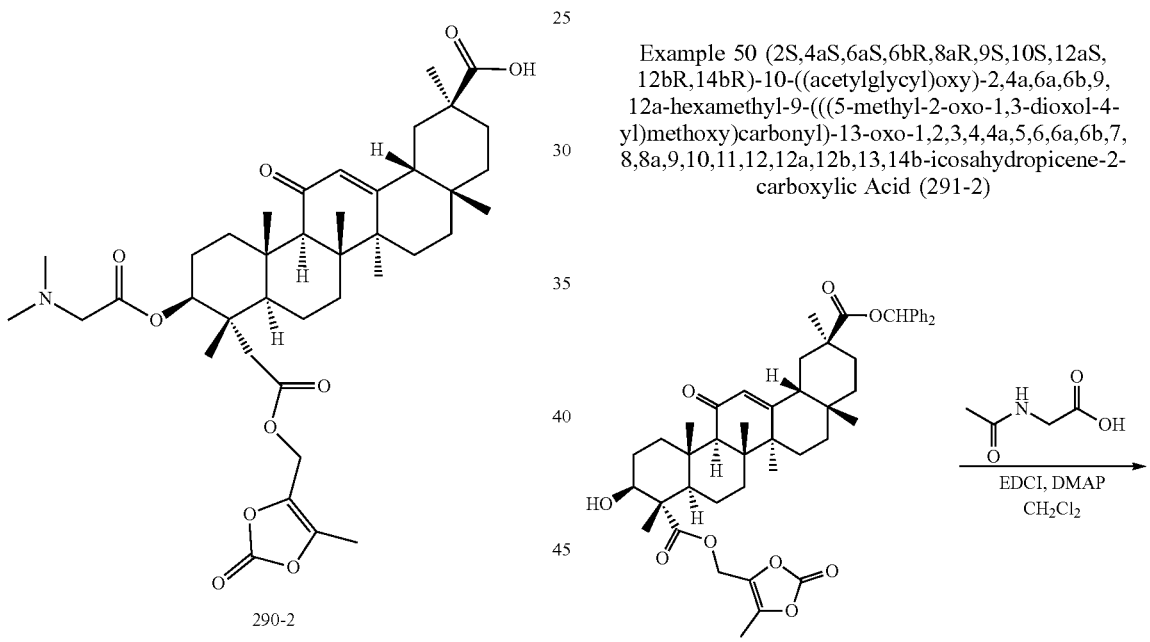

-continued

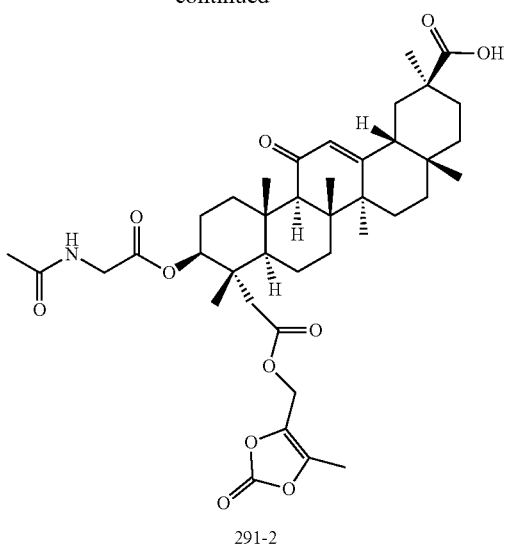

291-2

Synthesis of 2-benzhydryl 9-((5-methyl-2-oxo-1,3-dioxol-4-yl)methyl) (2S,4aS,6aS,6bR,8aR,9S,10S,12aS,12bR,14bR)-10-((acetylglycyl)oxy)-2,4a,6a,6b,9,12a-hexamethyl-13-oxo-1,2,3,4,4a,5,6,6a,6b,7,8,8a,9,10,11,12,12a,12b,13,14b-icosahydropicene-2,9-dicarboxylate (291-1)

Into a 25-mL round-bottom flask was placed 194-8 (140 mg, 0.18 mmol), 2-acetamidoacetic acid (110 mg, 0.94 mmol, 5 equiv), 4-dimethylaminopyridine (84 mg, 0.69 mmol, 4 equiv), $CH_2Cl_2$ (2.5 mL), and EDCI (175 mg, 0.91 mmol, 5 equiv). The reaction mixture was stirred overnight at room temperature and concentrated under vacuum. The residue was applied onto a silica gel column with CThCk/methanol (13/1) to provide 170 mg (quant) of 291-1 as a light yellow solid.

Synthesis of (2S,4aS,6aS,6bR,8aR,9S,10S,12aS,12bR,14bR)-10-((acetylglycyl)oxy)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic Acid (291-2)

A mixture of 291-1 (170 mg, 0.19 mmol) and TFA (0.15 mL, 2 mmol, 10 equiv) in $CH_2Cl_2$ was stirred for 1 h at room temperature. The reaction mixture was concentrated under vacuum. The crude product was purified by prep-HPLC with the following conditions: column, Xselect CSH OBD, 30*150 mm, 5 μm; mobile phase A: water (0.05% TFA), mobile phase B: $CH_3CN$; Flow rate: 60 mL/min; Gradient: 30% B to 65% B in 8 min; 254 nm; Rt: 5.54 min. The residue was repurified by prep-TLC to afford 291-2 (27.1 mg, 20%) as an off-white solid. MS (ES, m z): $[M+H]^+=712$; $^1H$ NMR (300 MHz, methanol-$d_4$) δ 5.63 (s, 1H), 5.23 (dd, J=10.9, 5.7 Hz, 1H), 5.05 (d, J=14.0 Hz, 1H), 4.92 (s, 1H), 3.86 (d, J=2.4 Hz, 2H), 2.85 (d, J=13.8 Hz, 1H), 2.59 (s, 1H), 2.21 (s, 5H), 2.04 (d, J=16.2 Hz, 5H), 1.88 (d, J=10.3 Hz, 2H), 1.74 (dd, J=21.5, 11.7 Hz, 6H), 1.45 (d, J=12.5 Hz, 7H), 1.21 (t, J=13.0 Hz, 15H), 1.08 (d, J=13.9 Hz, 1H), 0.96 (s, 1H), 0.86 (s, 3H).

Example 51 (2S,4aS,6aS,6bR,8aR,9S,10S,12aS,12bR,14bR)-10-acetamido-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic Acid

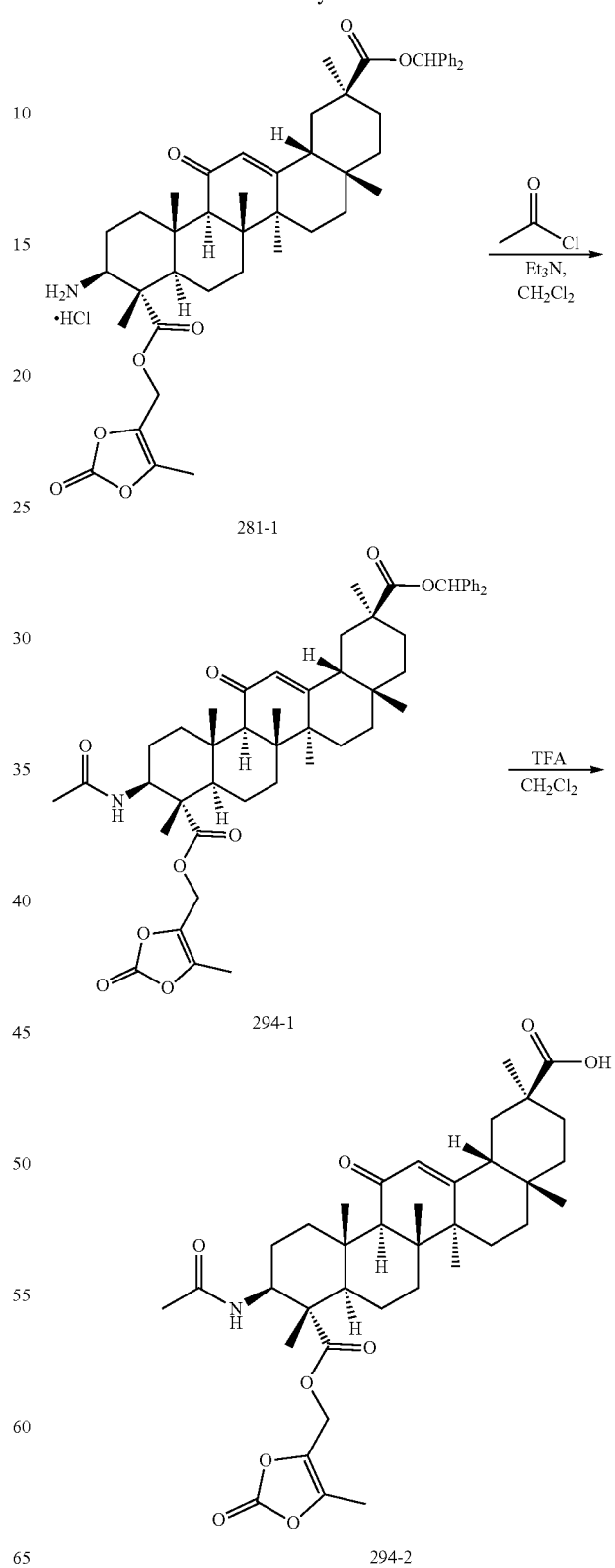

Synthesis of 2-benzhydryl 9-((5-methyl-2-oxo-1,3-dioxol-4-yl)methyl) (2S,4aS,6aS,6bR,8aR,9S,10S,12aS,12bR,14bR)-10-acetamido-2,4a,6a,6b,9,12a-hexamethyl-13-oxo-1,2,3,4,4a,5,6,6a,6b,7,8,8a,9,10,11,12,12a,12b,13,14b-icosahydropicene-2,9-dicarboxylate (294-1)

Into a 100-mL round-bottom flask was placed the HCl salt of 281-1 (200 mg, 0.26 mmol), CH$_2$Cl$_2$ (5 mL), Et$_3$N (0.29 mL, 2.1 mmol, 8 equiv), and acetyl chloride (0.18 mL, 10 equiv). The reaction slurry was stirred for 2 hr at room temperature. The reaction mixture was diluted with 300 mL of CH$_2$Cl$_2$ and was washed with 3×300 ml of brine. The organic layer was dried over anhydrous Na$_2$SO$_4$, filtered, and concentrated. The residue was applied onto a silica gel column with ethyl acetate/petroleum ether (1:1) to provide 150 mg (71%) of 294-1 as a white solid.

Synthesis of (2S,4aS,6aS,6bR,8aR,9S,10S,12aS,12bR,14bR)-10-acetamido-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic Acid (294-2)

Into a 100-mL round-bottom flask was placed 294-1 (100 mg, 0.12 mmol), CH$_2$Cl$_2$ (10 mL), and TFA (1 mL). The reaction slurry was stirred for 1 hr at room temperature then concentrated. The crude product was purified by prep-HPLC with the following conditions: column, XBridge Prep C18 OBD, 19-150 mm, 5 µm; mobile phase, water (0.05% TFA) and CH$_3$CN (40% Phase B up to 73% in 7 min); detector, uv. This resulted in 14.1 mg (17%) of 294-2 as a white solid. MS (ES, m/z): [M+1]$^+$=654.15; $^1$H NMR (400 MHz, methanol-d$_4$) δ 5.61 (s, 1H), 5.04 (d, J=13.9 Hz, 1H), 4.74 (d, J=13.9 Hz, 1H), 4.24 (dd, J=12.6, 4.3 Hz, 1H), 2.84-2.75 (m, 1H), 2.58 (s, 1H), 2.27-2.11 (m, 5H), 2.05 (s, 1H), 1.97 (d, J=9.9 Hz, 1H), 1.89 (s, 4H), 1.87-1.72 (m, 5H), 1.72-1.60 (m, 2H), 1.47 (s, 4H), 1.42 (d, J=3.0 Hz, 3H), 1.40-1.36 (m, 1H), 1.30-1.21 (m, 2H), 1.21-1.13 (m, 12H), 1.06 (d, J=13.9 Hz, 1H), 0.90 (d, J=13.1 Hz, 1H), 0.85 (s, 3H).

Example 52 (2S,4aS,6aS,6bR,8aR,9S,10S,12aS,12bR,14bR)-10-(allyloxy)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic Acid (297-5)

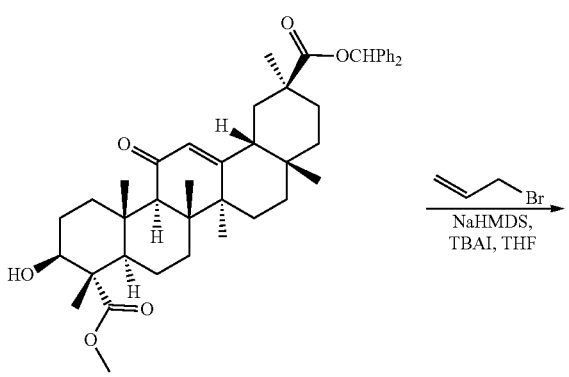

297-1

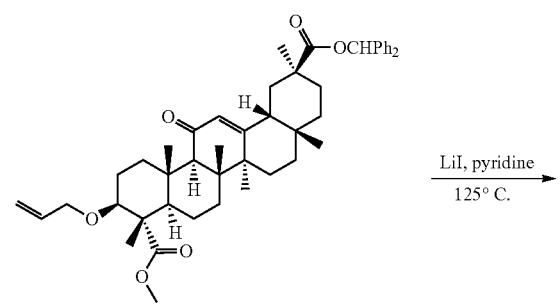

297-2

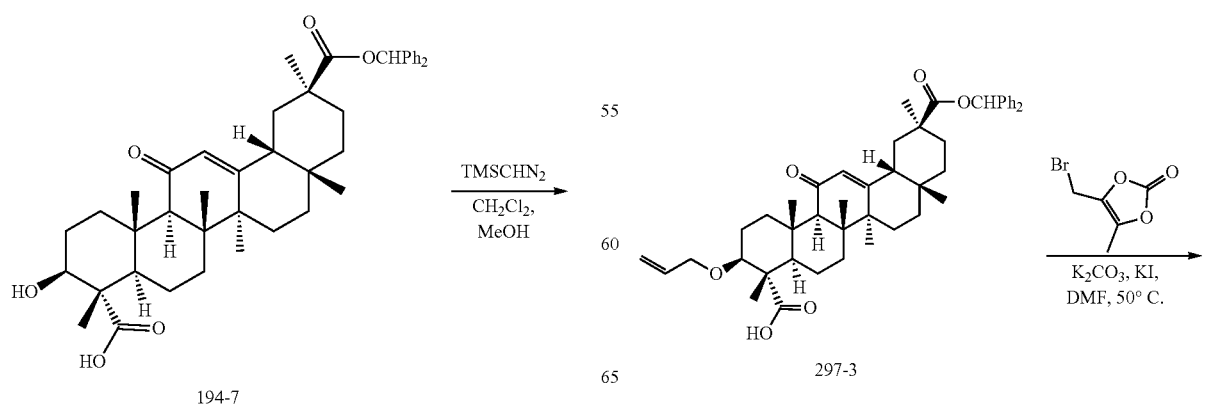

195

-continued

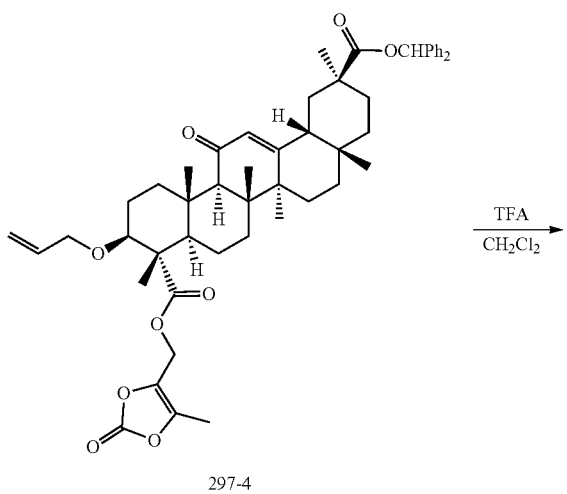

297-4

Synthesis of (3S,4S,4aR,6aR,6bS,8aS,11S,12aR, 14aR,14bS)-11-((benzhydryloxy)carbonyl)-3-hydroxy-4,6a, 6b, 8a, 11,14b-hexamethyl -14-oxo-1,2, 3,4,4a,5,6,6a,6b,7,8,8a,9,10,11,12,12a,14,14a,14b-icosahydropicene-4-carboxylic Acid (297-1)

Into a 100-mL round-bottom flask was placed 194-7 (200 mg, 0.30 mmol), CH$_2$Cl$_2$ (5 mL, 0.06 mmol, 0.2 equiv), MeOH (2.5 mL, 0.08 mmol, 0.26 equiv), and TMSCHN$_2$ (1 mL, 0.01 mmol, 0.03 equiv). The reaction slurry was stirred for 1 hr at room temperature. The reaction mixture was concentrated to provide 200 mg (98%) of 297-1 as a colorless solid.

196

Synthesis of 2-benzhydryl 9-methyl (2S,4aS,6aS, 6bR,8aR,9S,10S,12aS,12bR,14bR)-10-(allyloxy)-2, 4a,6a,6b,9,12a-hexamethyl-13-oxo-1,2,3,4,4a,5,6,6a, 6b,7,8,8a,9,10,11,12,12a,12b,13,14b-icosahydropicene-2,9-dicarboxylate (297-2)

Into a 100-mL round-bottom flask was placed 297-1 (292 mg, 0.43 mmol), allyl bromide (103 mg, 0.85 mmol, 2 equiv), TBAI (79.3 mg, 0.21 mmol, 0.5 equiv), THF (0.4 mL), and NaHMDS (0.429 mL, 0.85 mmol, 2 M in THF, 2 equiv). The reaction slurry was stirred for 2 hr at room temperature. The reaction mixture was diluted with 100 mL of CH$_2$Cl$_2$ and washed with 2×150 ml of brine. The organic layer was dried over anhydrous Na$_2$SO$_4$, filtered, and concentrated. The residue was applied onto a silica gel column with ethyl acetate/petroleum ether (1:1) to provide 190 mg (61%) of 297-2 as a colorless solid.

Synthesis of (3S,4S,4aR,6aR,6bS,8aS,11S,12aR, 14aR,14bS)-3-(allyloxy)-11-((benzhydryloxy)carbonyl)-4,6a,6b,8a,11,14b-hexamethyl-14-oxo-1,2,3,4, 4a,5,6,6a,6b,7,8,8a,9,10,11,12,12a,14,14a,14b-icosahydropicene-4-carboxylic Acid (297-3)

Into a 100-mL round-bottom flask was placed 297-2 (220 mg, 0.31 mmol), lithium iodide (426 mg, 3.18 mmol, 10.4 equiv), and pyridine (5 mL). The reaction slurry was stirred for 2 days at 125° C. The reaction mixture was cooled to room temperature and the pH of the solution was adjusted to 5 with 1 M HCl$_{(aq)}$. The mixture was diluted with 100 mL of CH$_2$Cl$_2$ and washed with 3×50 ml of brine. The organic layer was dried over anhydrous Na$_2$SO$_4$, filtered, and concentrated. The residue was applied onto a silica gel column with CH$_2$Cl$_2$/methanol (10:1) to provide 110 mg (51%) of 297-3 as a white solid.

Synthesis of 2-benzhydryl 9-((5-methyl-2-oxo-1,3-dioxol-4-yl)methyl) (2S,4aS,6aS,6bR,8aR,9S,10S, 12aS,12bR,14bR)-10-(allyloxy)-2,4a,6a,6b,9,12a-hexamethyl-13-oxo-1,2,3,4,4a,5,6,6a,6b,7,8,8a,9,10, 11,12,12a,12b,13,14b-icosahydropicene-2,9-dicarboxylate (297-4)

Into a 100-mL round-bottom flask was placed 297-3 (110 mg, 0.16 mmol), 4-(bromomethyl)-5-methyl-2H-1,3-dioxol-2-one (68.8 mg, 0.36 mmol, 2.3 equiv), K$_2$CO$_3$ (64.5 mg, 0.47 mmol, 3 equiv), KI (12.9 mg, 0.08 mmol, 0.5 equiv), and DMF (5 mL). The reaction slurry was stirred for 1 hr at 50° C. The reaction mixture was diluted with 100 mL of CH$_2$Cl$_2$ and washed with 2 x 50 ml of brine. The organic layer was dried over anhydrous Na$_2$SO$_4$, filtered, and concentrated. The residue was applied onto a silica gel column with ethyl acetate/petroleum ether (1:1) to provide 80 mg (63%) of 297-4 as a white solid.

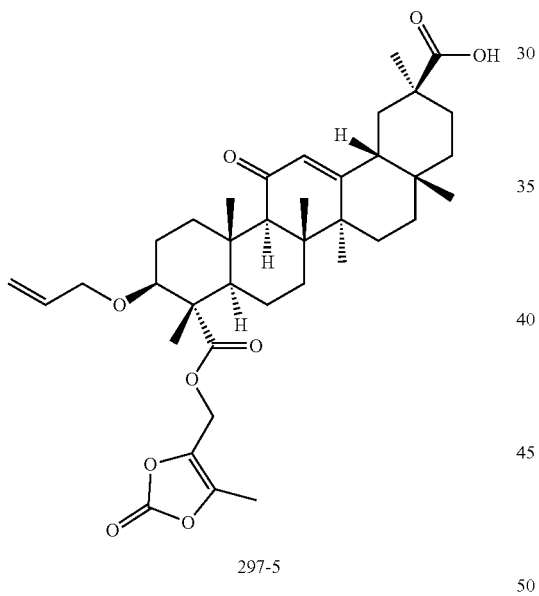

297-5

Synthesis of (2S,4aS,6aS,6bR,8aR,9S,10S,12aS, 12bR,14bR)-10-(allyloxy)-2,4a,6a,6b,9,12a-hexamethyl-9-(((5-methyl-2-oxo-1,3-dioxol-4-yl)methoxy) carbonyl)-13-oxo-1,2,3,4,4a,5,6,6a,6b,7,8,8a,9,10, 11,12,12a,12b,13,14b-icosahydropicene-2-carboxylic Acid (297-5)

Into a 100-mL round-bottom flask was placed 297-4 (190 mg), TFA (1 mL), and CH$_2$Cl$_2$ (10 mL). The resulting solution was stirred for 1 hr at room temperature then concentrated. The crude product was purified by prep-HPLC with the following conditions: column, mobile phase, water (0.05% TFA) and CH$_3$CN (70% Phase B up to 84% in 8 min); detector, UV. This resulted in 33.6 mg (22%) of 297-5 as a white solid. MS (ES, m/z): [M+H]$^+$=653; $^1$H NMR (400 MHz, methanol-d$_4$) δ 0.85 (s, 4H), 1.08-1.28 (m, 15H), 1.28-1.51 (m, 7H), 1.51-1.80 (m, 5H), 1.85-2.02 (m, 4H), 2.05 (s, 1H), 2.09-2.38 (m, 4H), 2.54 (s, 1H), 2.81 (dd, J=13.6, 3.6 Hz, 1H), 3.72-3.88 (m, 2H), 4.05 (ddt, J=13.2, 5.4, 1.6 Hz, 1H), 4.88 (d, J=14.0 Hz, 1H), 5.02-5.26 (m, 3H), 5.61 (s, 1H), 5.70-5.90 (m, 1H).

Example 53 (2S,4aS,6aS,6bR,8aR,9S,10S,12aS, 12bR,14bR)-10-(3-methoxy-3-oxopropanamido)-2, 4a,6a,6b,9,12a-hexamethyl-9-(((5-methyl-2-oxo-1,3-dioxol-4-yl)methyl)carbonyl)-13-oxo-1,2,3,4,4a,5, 6,6a,6b,7,8,8a,9,10,1142,12a,12b,13,14b-icosahydropicene-2-carboxylic Acid (298-2)

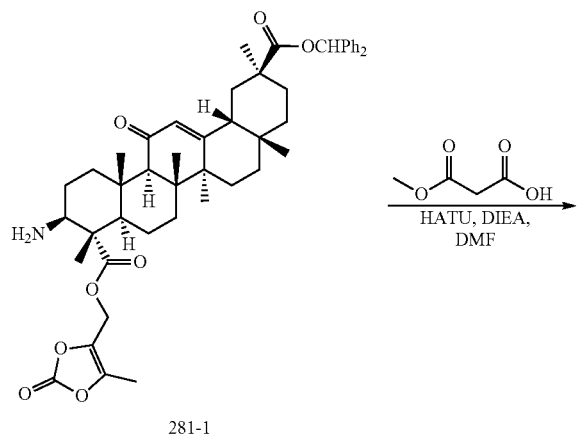

281-1

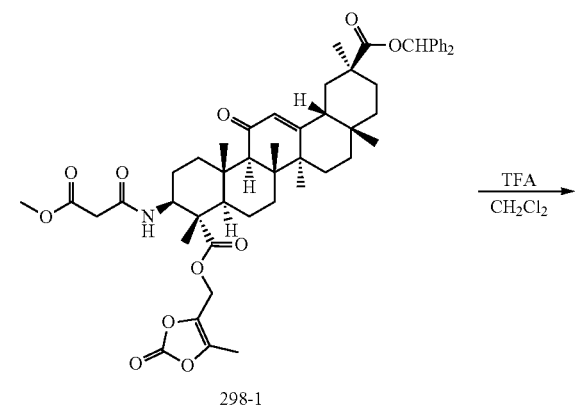

298-1

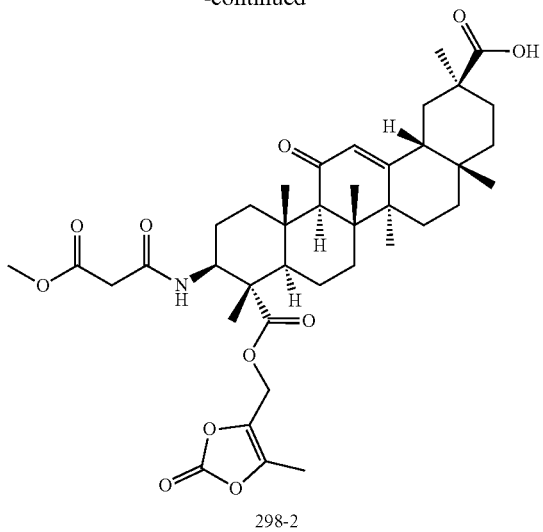

298-2

Synthesis of 2-benzhydryl 9-((5-methyl-2-oxo-1,3-dioxol-4-yl)methyl) (2S,4aS,6aS,6bR,8aR,9S,10S, 12aS,12bR,14bR)-10-(3-methoxy-3-oxopropanamido)-2,4a,6a,6b,9,12a-hexamethyl-13-oxo-1,2,3,4, 4a,5,6,6a,6b,7,8,8a,9,10,11,12,12a,12b,13,14b-icosahydropicene-2,9-dicarboxylate (298-1)

Into a 100-mL round-bottom flask was placed 281-1 (200 mg, 0.26 mmol), DMF (5 mL), 3-methoxy-3-oxopropanoic acid (150 mg, 1.27 mmol, 5 equiv), iPr$_2$EtN (0.17 mL, 1.03 mmol, 4 equiv), and HATU (390 mg, 1.03 mmol, 4 equiv). The reaction slurry was stirred for 2 hr at room temperature. The reaction mixture was diluted with 100 mL of CH$_2$Cl$_2$ and washed with 4×50 ml of brine. The organic layer was dried over anhydrous Na$_2$SO$_4$, filtered, and concentrated to provide 230 mg (quant) of crude 298-1 as a yellow oil.

Synthesis of (2S,4aS,6aS,6bR,8aR,9S,10S,12aS, 12bR,14bR)-10-(3-methoxy-3-oxopropanamido)-2, 4a,6a,6b,9,12a-hexamethyl-9-(((5-methyl-2-oxo-1,3-dioxol-4-yl)methoxy)carbonyl)-13-oxo-1,2,3,4,4a,5, 6,6a,6b,7,8,8a,9,10,11,12,12a,12b,13,14b-icosahydropicene-2-carboxylic Acid (298-2)

Into a 100-mL round-bottom flask was placed 298-1 (230 mg, 0.26 mmol), CH$_2$Cl$_2$ (10 mL), and TFA (1 mL). The reaction slurry was stirred for 1 hr at room temperature and concentrated. The crude product was purified by prep-HPLC with the following conditions: column, XSelect CSH OBD, 30*150 mm, 5 μm; mobile phase, water (0.05% TFA) and CH$_3$CN (52% Phase B up to 63% in 8 min); detector, UV. This resulted in 40.3 mg (20.53%) of 298-2 as a white solid. MS (ES, m/z): [M+H]$^+$=712.25; $^1$H NMR (400 MHz, methanol-d$_4$) δ 0.85 (s, 3H), 0.91 (d, J=12.8 Hz, 1H), 1.06 (d, J=13.9 Hz, 1H), 1.14-1.22 (m, 12H), 1.22-1.30 (m, 2H), 1.35-1.46 (m, 7H), 1.48-1.58 (m, 1H), 1.59-2.03 (m, 8H), 2.09-2.30 (m, 5H), 2.59 (s, 1H), 2.81 (d, J=13.6 Hz, 1H), 3.25 (d, J=1.4 Hz, 2H), 3.72 (s, 3H), 4.29 (dd, J=12.5, 4.4 Hz, 1H), 4.77 (d, J=13.9 Hz, 1H), 5.02 (d, J=14.0 Hz, 1H), 5.62 (s, 1H).

Example 54 (2S,4aS,6aS,6bR,8aR,9S,10S,12aS, 12bR,14bR)-10-(4-methoxy-4-oxobutanamido)-2,4a, 6a,6b,9,12a-hexamethyl-9-(((5-methyl-2-oxo-1,3-dioxol-4-yl)methoxy)carbonyl)-13-oxo-1,2,3,4,4a,5, 6,6a,6b,7,8,8a,9,10,1142,12a,12b,13,14b-icosahydropicene-2-carboxylic Acid (299-2)
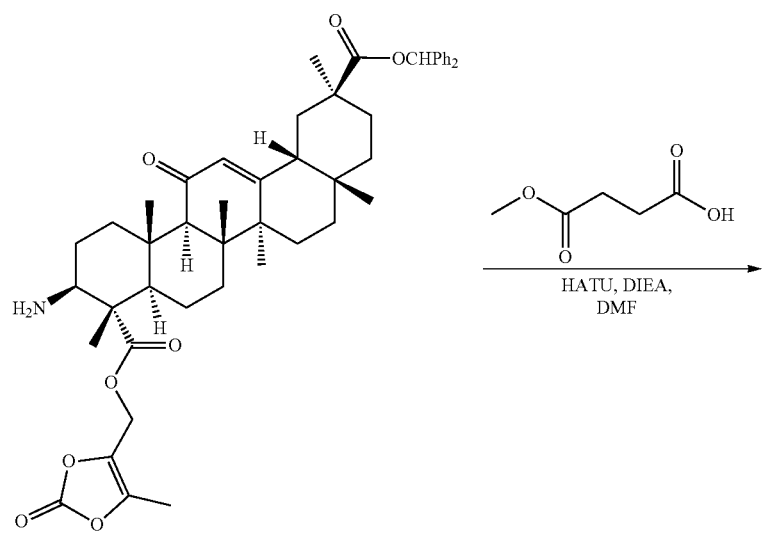
281-1

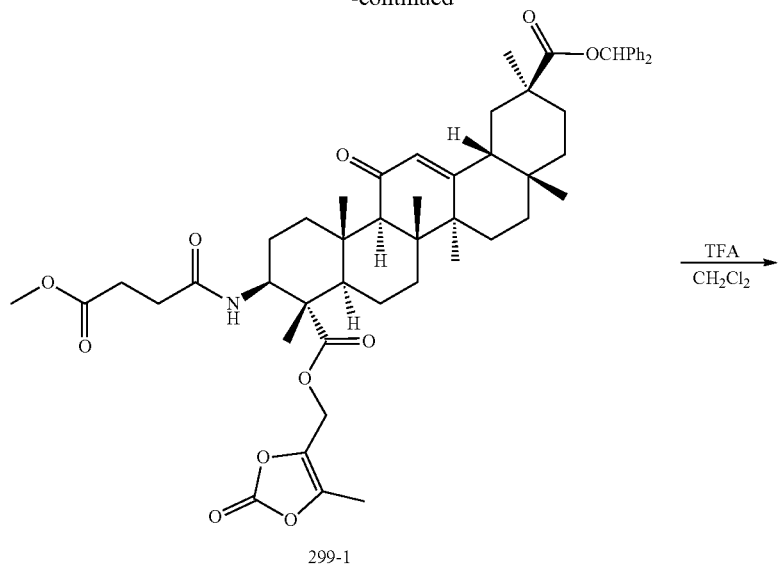

299-1

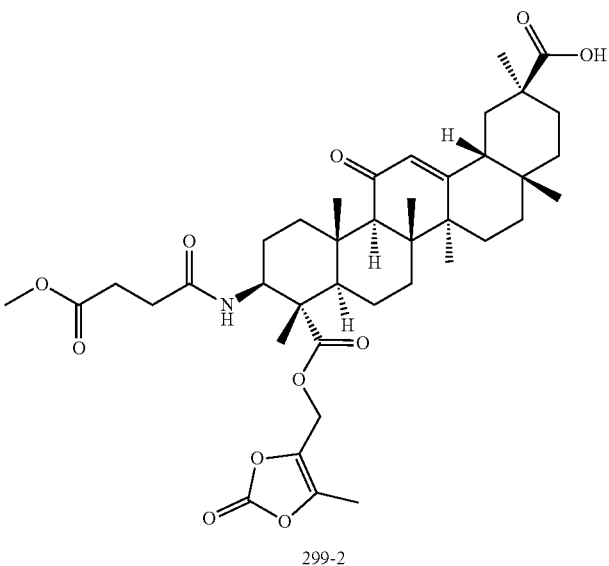

299-2

Synthesis of 2-benzhydryl 9-((5-methyl-2-oxo-1,3-dioxol-4-yl)methyl) (2S,4aS,6aS,6bR,8aR,9S,10S,12aS,12bR,14bR)-10-(4-methoxy-4-oxobutanamido)-2,4a,6a,6b,9,12a-hexamethyl-13-oxo-1,2,3,4,4a,5,6,6a,6b,7,8,8a,9,10,11,12,12a,12b,13,14b-icosahydropicene-2,9-dicarboxylate (299-1)

Into a 100-mL round-bottom flask was placed 281-1 (200 mg, 0.26 mmol), DMF (5 mL), 4-methoxy-4-oxobutanoic acid (170 mg, 1.3 mmol, 5 equiv), iPr$_2$EtN (0.17 mL, 1.03 mmol, 4 equiv), and HATU (390 mg, 1.03 mmol, 4 equiv). The reaction slurry was stirred for 2 hr at room temperature. The reaction mixture was diluted with 100 mL of CH$_2$Cl$_2$, washed with 3×50 ml of brine, dried over anhydrous Na$_2$SO$_4$, filtered, and concentrated to provide 238 mg (quant) of crude 299-1 as a yellow oil.

Synthesis of (2S,4aS,6aS,6bR,8aR,9S,10S,12aS,12bR,14bR)-10-(4-methoxy-4-oxobutanamido)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic Acid (299-2)

Into a 100-mL round-bottom flask was placed 299-1 (238 mg, 0.27 mmol), CH$_2$Cl$_2$ (10 mL), and TFA (1 mL). The reaction slurry was stirred for 1 hr at room temperature then concentrated. The crude product was purified by prep-HPLC with the following conditions: Column, XSelect CSH OBD, 30*150 mm, 5 μm; mobile phase, water (0.05% TFA) and CH$_3$CN (55% Phase B up to 66% in 8 min); detector, UV. This resulted in 52.5 mg (26%) of 299-2 as a white solid. MS (ES, m/z): [M+H]$^+$=726.25; $^1$H NMR (400 MHz, methanol-d$_4$) δ 0.85 (s, 4H), 1.06 (d, J=14.0 Hz, 1H), 1.12-1.32 (m, 14H), 1.33-1.56 (m, 8H), 1.59-1.99 (m, 8H), 2.11-2.27 (m, 5H), 2.34-2.49 (m, 2H), 2.48-2.66 (m, 3H), 2.76-2.84 (m, 1H), 3.68 (s, 3H), 4.25 (dd, J=12.6, 4.3 Hz, 1H), 4.76 (d, J=14.0 Hz, 1H), 5.01 (d, J=13.9 Hz, 1H), 5.61 (s, 1H).

Example 55 (2S,4aS,6aS,6bR,8aR,9S,10S,12aS,12bR,14bR)-10-((butoxycarbonyl)amino)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic Acid (300-1)
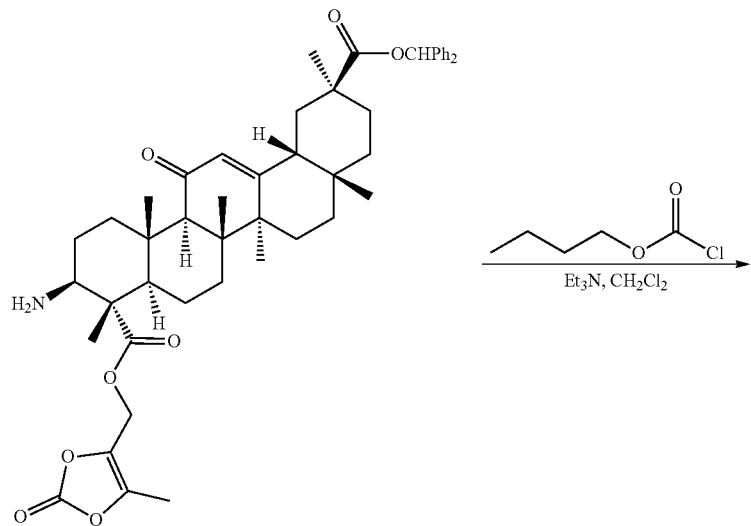
281-1
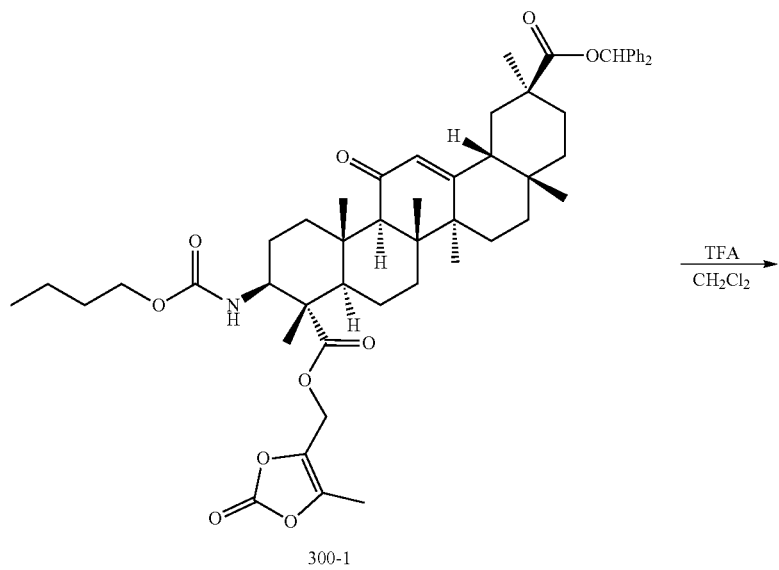
300-1

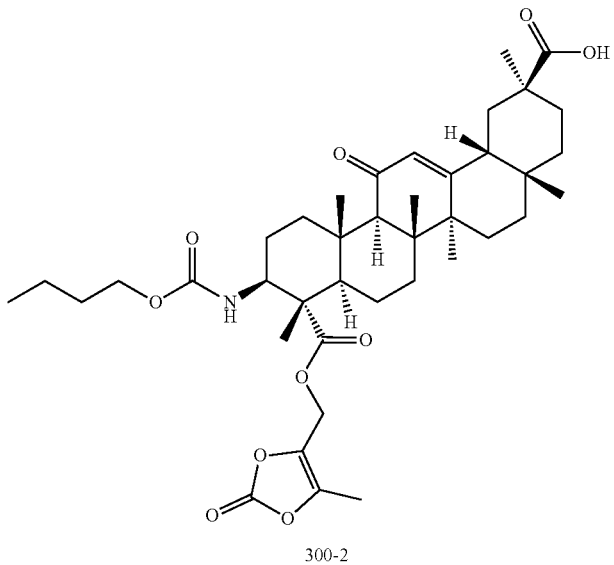

300-2

Synthesis of 2-benzhydryl 9-((5-methyl-2-oxo-1,3-dioxol-4-yl)methyl) (2S,4aS,6aS,6bR,8aR,9S,10S,12aS,12bR,14bR)-10-((butoxycarbonyl)amino)-2,4a,6a,6b,9,12a-hexamethyl-13-oxo-1,2,3,4,4a,5,6,6a,6b,7,8,8a,9,10,11,12,12a,12b,13,14b-icosahydropicene-2,9-dicarboxylate (300-1)

Into a 100-mL round-bottom flask was placed 281-1 (200 mg, 0.26 mmol), $CH_2Cl_2$ (5 mL), n-butyl chloroformate (180 mg, 1.32 mmol, 5 equiv), and $Et_3N$ (0.054 mL, 0.39 mmol, 1.5 equiv). The reaction slurry was stirred for 2 hr at room temperature. The reaction mixture was diluted with 100 mL of $CH_2Cl_2$ and washed with 3×50 ml of brine. The organic layer was dried over anhydrous $Na_2SO_4$, filtered, and concentrated to provide 215 mg (90%) of 300-1 as a yellow semi-solid.

Synthesis of (2S,4aS,6aS,6bR,8aR,9S,10S,12aS,12bR,14bR)-10-((butoxycarbonyl)amino)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic Acid (300-2)

Into a 100-mL round-bottom flask was placed 300-1 (215 mg, 0.24 mmol), $CH_2Cl_2$ (10 mL), and TFA (1 mL). The reaction slurry was stirred for 1 hr at room temperature then concentrated. The crude product was purified by prep-HPLC with the following conditions: Column, XSelect CSH OBD, 30*150 mm, 5 μm; mobile phase, water (0.05% TFA) and $CH_3CN$ (73% Phase B up to 85% in 8 min); detector, UV. This resulted in 41.0 mg (22%) of 300-2 as a white solid. MS (ES, m/z): $[M+H]^+$=712.25; $^1H$ NMR (400 MHz, methanol-$d_4$) δ 0.85 (s, 3H), 0.86-1.02 (m, 4H), 1.03-1.09 (m, 1H), 1.10-1.18 (m, 9H), 1.19-1.31 (m, 5H), 1.33-1.50 (m, 9H), 1.52-1.82 (m, 8H), 1.83-1.94 (m, 2H), 1.94-2.00 (m, 1H), 2.05-2.27 (m, 5H), 2.58 (s, 1H), 2.75-2.84 (m, 1H), 3.91-4.05 (m, 3H), 4.86 (s, 1H), 5.01 (d, J=13.9 Hz, 1H), 5.61 (s, 1H).

Example 56 (2S,4aS,6aS,6bR,8aR,9S,10S,12aS,12bR,14bR)-9-(((5-isopropyl-2-oxo-1,3-dioxol-4-yl)methoxy)carbonyl)-10-((methoxycarbonyl)oxy)-2,4a,6a,6b,9,12a-hexamethyl-13-oxo-1,2,3,4,4a,5,6,6a,6b,7,8,8a,9,10,11,12,12a,12b,13,14b-icosahydropicene-2-carboxylic Acid (301-2)

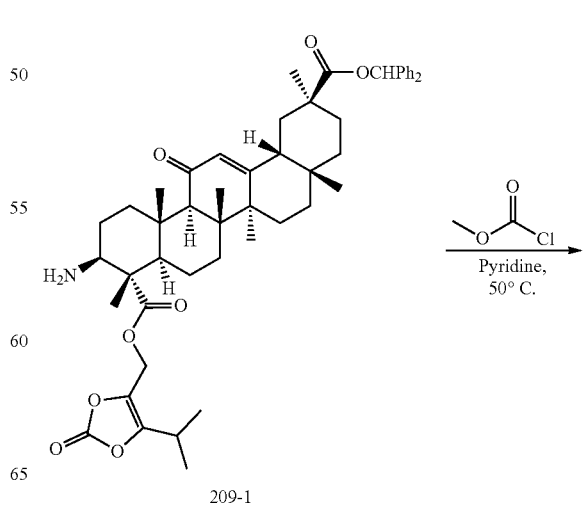

209-1

-continued

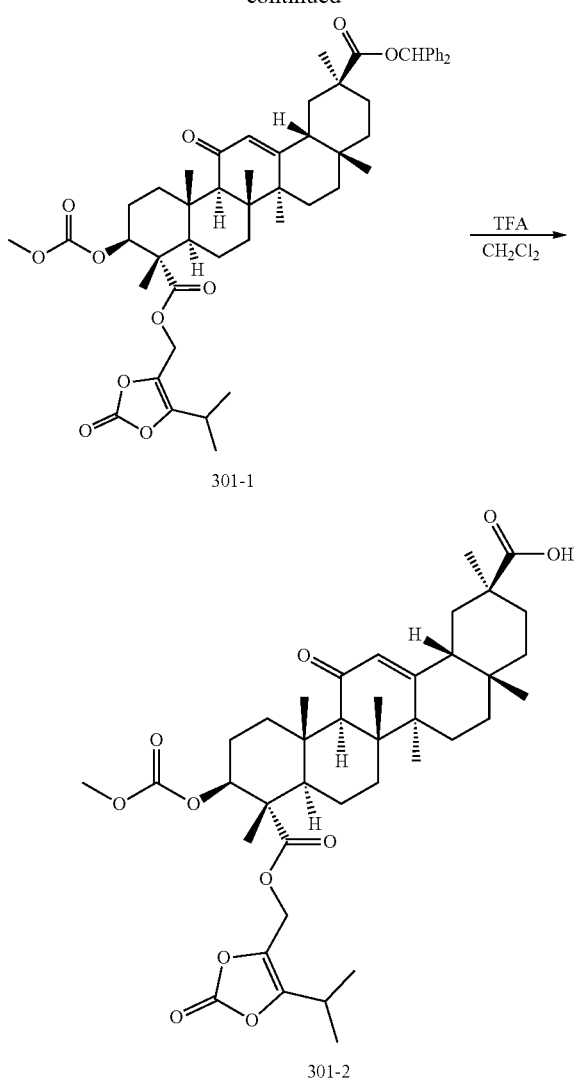

301-1

301-2

Synthesis of 2-benzhydryl 9-((5-isopropyl-2-oxo-1,3-dioxol-4-yl)methyl) (2S,4aS,6aS,6bR,8aR,9S,10S,12aS,12bR,14bR)-10-((methoxycarbonyl)oxy)-2,4a,6a,6b,9,12a-hexamethyl-13-oxo-1,2,3,4,4a,5,6,6a,6b,7,8,8a,9,10,11,12,12a,12b,13,14b-icosahydropicene-2,9-dicarboxylate (300-1)

Into a 100-mL round-bottom flask was placed 209-1 (190 mg, 0.24 mmol), pyridine (5 mL), and methyl chloroformate (0.109 g, 1.2 mmol, 5 equiv). The reaction slurry was stirred for 3 days at 50° C. The reaction mixture was diluted with 100 mL of $CH_2Cl_2$ and washed with 3×100 ml of brine. The organic layer was dried over anhydrous $Na_2SO_4$, filtered, and concentrated to provide 95 mg (48%) of 301-1 as a white solid.

Synthesis of (2S,4aS,6aS,6bR,8aR,9S,10S,12aS,12bR,14bR)-9-(((5-isopropyl-2-oxo-1,3-dioxol-4-yl)methoxy)carbonyl)-10-((methoxycarbonyl)oxy)-2,4a,6a,6b,9,12a-hexamethyl-13-oxo-1,2,3,4,4a,5,6,6a,6b,7,8,8a,9,10,11,12,12a,12b,13,14b-icosahydropicene-2-carboxylic Acid (301-2)

Into a 100-mL round-bottom flask was placed 301-1 (180 mg, 0.22 mmol), TFA (1 mL), and $CH_2Cl_2$ (10 mL). The reaction slurry was stirred for 1 hr at room temperature then concentrated. The crude product was purified by prep-HPLC with the following conditions: mobile phase, water (0.05% TFA) and $CH_3CN$ (70% Phase B up to 90% in 8 min); This resulted in 49.8 mg (35%) of 301-2 as a white solid. MS (ES, m/z): $[M+H]^+=671$; $^1H$ NMR (400 MHz, methanol-df) δ 0.85 (s, 3H), 0.92 (d, J=7.2 Hz, 1H), 1.06 (d, J=13.1 Hz, 1H), 1.13-1.30 (m, 21H), 1.41-1.57 (m, 7H), 1.58-1.73 (m, 4H), 1.78-1.88 (m, 3H), 2.00 (dd, J=21.8, 13.0 Hz, 3H), 2.22 (d, J=12.4 Hz, 1H), 2.46 (s, 1H), 2.91 (d, J=14.0 Hz, 1H), 3.02 (p, J=7.0 Hz, 1H), 3.75 (s, 3H), 4.85 (d, J=13.6 Hz, 1H), 4.95-5.10 (m, 2H), 5.75 (s, 1H).

Example 57 (2S,4aS,6aS,6bR,8aR,9S,10S,12aS,12bR,14bR)-2,4a,6a,6b,9,12a-hexamethyl-9-(((5-methyl-2-oxo-1,3-dioxol-4-yl)methoxy)carbonyl)-10-((((5-methyl-2-oxo-1,3-dioxol-4-yl)methoxy)carbonyl)oxy)-13-oxo-1,2,3,4,4a,5,6,6a,6b,7,8,8a,9,10,11,12,12a,12b,13,14b-icosahydropicene-2-carboxylic Acid (302-3)

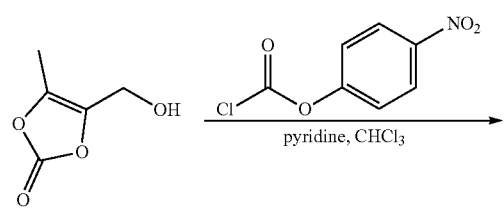

-continued
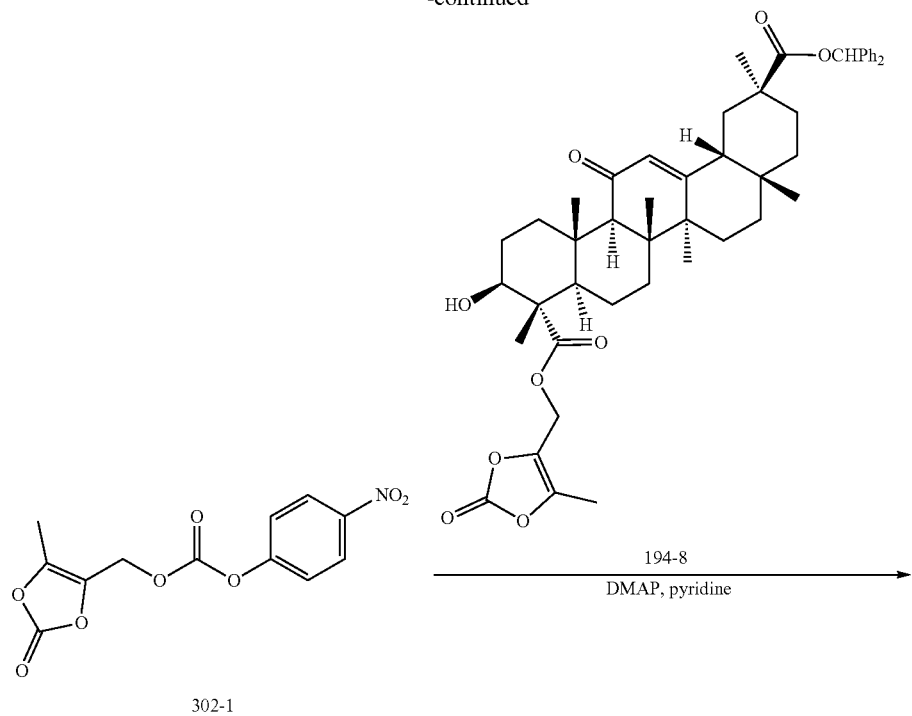
302-1
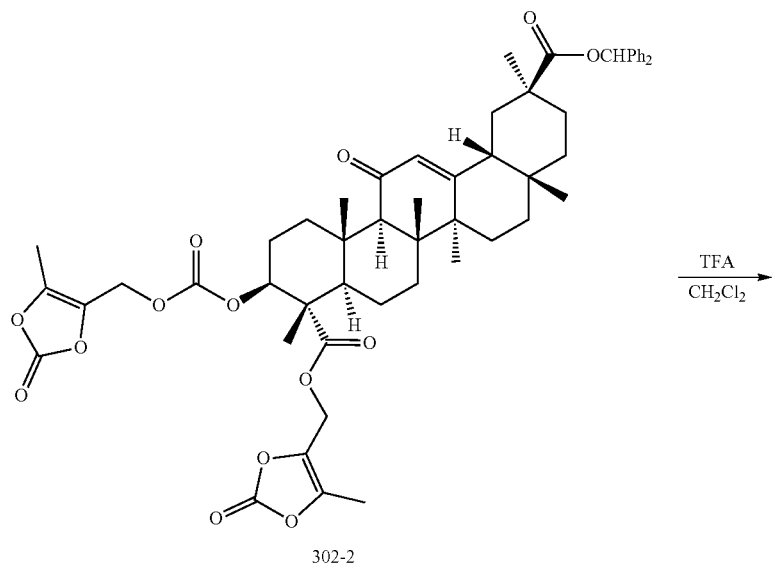
302-2

-continued

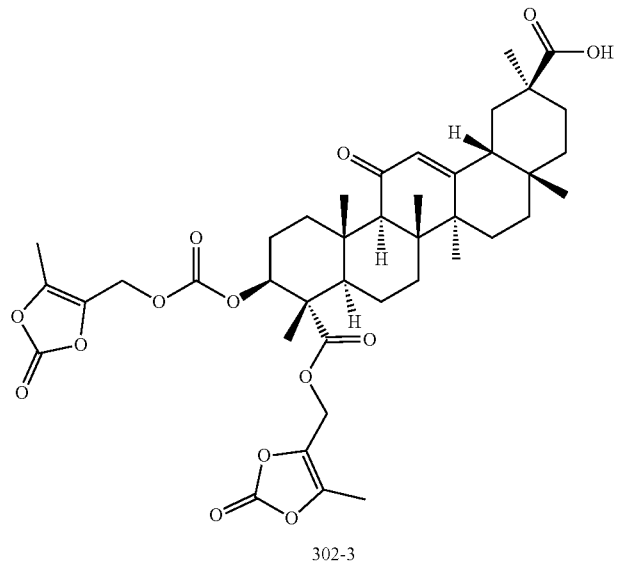

302-3

Synthesis of (5-methyl-2-oxo-1,3-dioxol-4-yl)methyl (4-nitrophenyl) carbonate (302-1)

Into a 100-mL round-bottom flask was placed 4-(hydroxymethyl)-5-methyl-2H-1,3-dioxol-2-one (3 g, 23 mmol), 4-nitrophenyl chloroformate (5 g, 24.8 mmol, 1.08 equiv), chloroform (100 mL), and pyridine (2 g, 25.3 mmol, 1.1 equiv). The reaction slurry was stirred for 12 hr at room temperature. The reaction mixture was diluted with 100 mL of $CH_2Cl_2$ and washed with 2×100 ml of brine. The organic layer was dried over anhydrous $Na_2SO_4$, filtered, and concentrated. The residue was applied onto a silica gel column with ethyl acetate/petroleum ether (1:1) to provide 1.8 g (26%) of 302-1 as a yellow solid.

Synthesis of 2-benzhydryl 9-((5-methyl-2-oxo-1,3-dioxol-4-yl)methyl) (2S,4aS,6aS,6bR,8aR,9S,10S,12aS,12bR,14bR)-2,4a,6a,6b,9,12a-hexamethyl-10-(((((5-methyl-2-oxo-1,3-dioxol-4-yl)methoxy)carbonyl)oxy)-13-oxo-1,2,3,4,4a,5,6,6a,6b,7,8,8a,9,10,11,12,12a,12b,13,14b-icosahydropicene-2,9-dicarboxylate (302-2)

Into a 100-mL round-bottom flask was placed 194-8 (150 mg, 0.19 mmol), 302-1 (113 mg, 0.38 mmol, 2 equiv), pyridine (5 mL), and DMAP (164 mg, 0.38 mmol, 2 equiv). The reaction slurry was stirred for 12 hr at room temperature. The reaction mixture was diluted with 100 mL of $CH_2Cl_2$ and washed with 3×100 of brine. The organic layer was dried over anhydrous $Na_2SO_4$, filtered, and concentrated. The residue was applied onto a silica gel column with ethyl acetate/petroleum ether (1:1) to provide 90 mg (50%) of 302-2 as a white solid.

Synthesis of (2S,4aS,6aS,6bR,8aR,9S,10S,12aS,12bR,14bR)-2,4a,6a,6b,9,12a-hexamethyl-9-(((5-methyl-2-oxo-1,3-dioxol-4-yl)methoxy)carbonyl)-10-((((5-methyl-2-oxo-1,3-dioxol-4-yl)methoxy)carbonyl)oxy)-13-oxo-1,2,3,4,4a,5,6,6a,6b,7,8,8a,9,10,11,12,12a,12b,13,14b-icosahydropicene-2-carboxylic Acid (302-3)

Into a 100-mL round-bottom flask was placed 302-2 (180 mg, 0.19 mmol), $CH_2Cl_2$ (10 mL), and TFA (1 mL). The reaction slurry was stirred for 1 hr at room temperature then concentrated. The crude product was purified by prep-HPLC with the following conditions: mobile phase, water (0.05% TFA) and $CH_3CN$ (73% Phase B up to 77% in 5 min); detector, UV. This resulted in 31.8 mg (21%) of 302-3 as a white solid. MS (ES, m/z): $[M+H]^+=770$; $^1H$ NMR (400 MHz, methanol-$d_4$) δ 0.85 (s, 3H), 1.01-1.33 (m, 16H), 1.41 (d, J=5.6 Hz, 7H), 1.56-1.73 (m, 4H), 1.75-1.89 (m, 3H), 2.03 (d, J=10.4 Hz, 3H), 2.21 (d, J=4.8 Hz, 7H), 2.45 (s, 1H), 2.93 (d, J=13.9 HZ, 1H), 4.78-5.11 (m, 5H), 5.75 (s, 3H).

Example 58 (2S,4aS,6aS,6bR,8aR,9S,10S,12aS, 12bR,14bR)-2,4a,6a,6b,9,12a-hexamethyl-10-((((5-methyl-2-oxo-1,3-dioxol-4-yl)methoxy)carbonyl) oxy)-13-oxo-1,2,3,4,4a,5,6,6a,6b,7,8,8a,9,10,1142, 12a,12b,13,14b-icosahydropicene-2,9-dicarboxylic Acid (307-2)
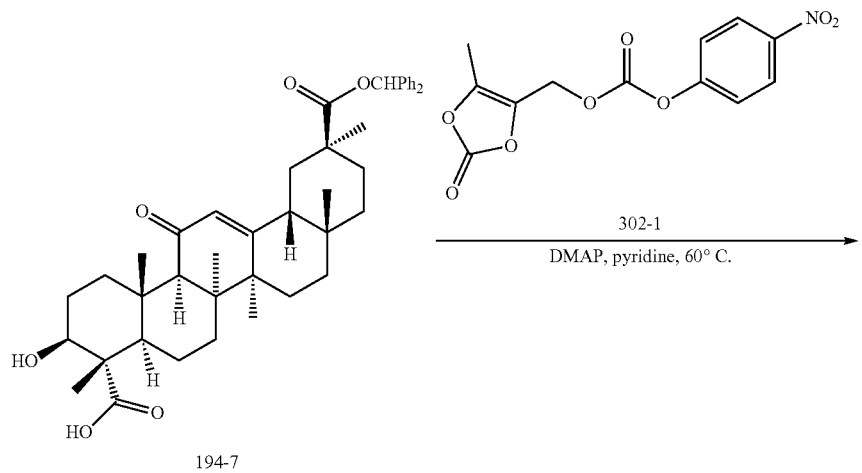
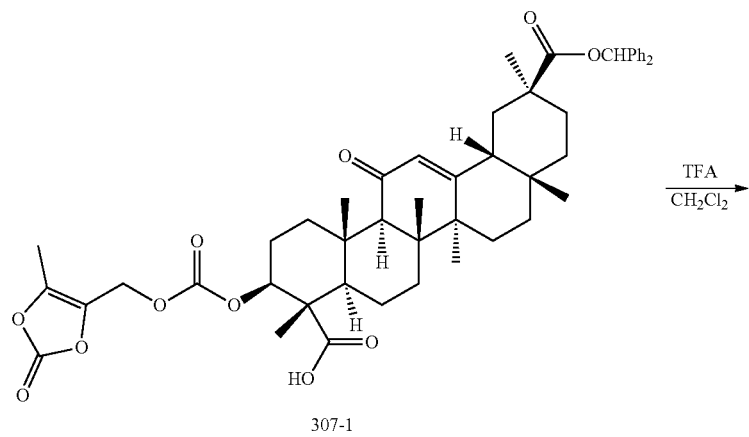
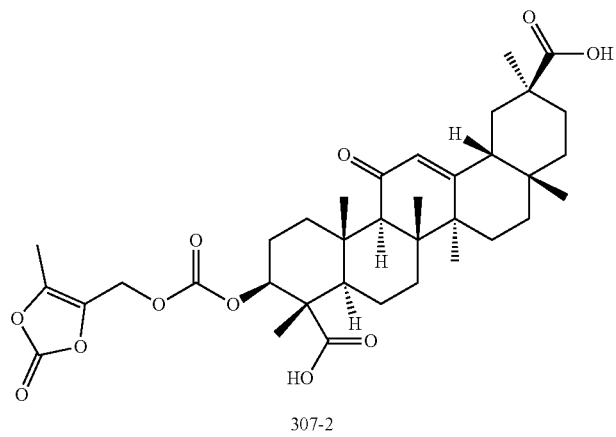

Synthesis of (3S,4S,4aR,6aR,6bS,8aS,11S,12aR, 14aR,14bS)-11-((benzhydryloxy)carbonyl)-4,6a,6b, 8a,11,14b-hexamethyl-3-((((5-methyl-2-oxo-1,3-dioxol-4-yl)methoxy)carbonyl)oxy)-14-oxo-1,2,3,4, 4a,5,6,6a,6b,7,8,8a,9,10,11,12,12a,14,14a,14b-icosahydropicene-4-carboxylic Acid (307-1)

Into a 100-mL round-bottom flask was placed 302-1 (66 mg, 0.22 mmol), 194-7 (60 mg, 0.09 mmol, 0.4 equiv), pyridine (5 mL), and DMAP (76 mg, 0.44 mmol, 2 equiv). The reaction slurry was stirred for 12 min at 60° C. The reaction mixture was diluted with 50 mL of CH$_2$Cl$_2$, washed with 2×100 ml of brine, dried over anhydrous Na$_2$SO$_4$, filtered, and concentrated. The residue was applied onto a silica gel column with ethyl acetate/petroleum ether (1:1) to provide 30 mg (17%) of 307-1 as a white solid.

Synthesis of (2S,4aS,6aS,6bR,8aR,9S,10S,12aS, 12bR,14bR)-2,4a,6a,6b,9,12a-hexamethyl-10-((((5-methyl-2-oxo-1,3-dioxol-4-yl)methoxy)carbonyl) oxy)-13-oxo-1,2,3,4,4a,5,6,6a,6b,7,8,8a,9,10,11,12, 12a,12b,13,14b-icosahydropicene-2,9-dicarboxylic Acid (307-2)

Into a 100-mL round-bottom flask was placed 307-1 (170 mg, 0.21 mmol), TFA (1 mL), and CH$_2$Cl$_2$ (10 mL). The reaction slurry was stirred for 1 hr at room temperature then concentrated. The crude product was purified by prep-HPLC with the following conditions: mobile phase, water (0.05% TFA) and CH$_3$CN (50% Phase B up to 55% in 8 min); detector, UV. This resulted in 6.7 mg (4.9%) of 307-2 as a white solid. MS (ES, m/z): [M+H]$^+$=657.06; $^1$H NMR (400 MHz, methanol-d$_4$) δ 0.86 (s, 3H), 1.07-1.29 (m, 17H), 1.45 (d, J=11.6 Hz, 8H), 1.59-2.02 (m, 10H), 2.01-2.29 (m, 6H), 2.57 (s, 1H), 2.87 (d, J=13.6 Hz, 1H), 4.92 (m, 2H), 5.07 (dd, J=11.2, 5.6 Hz, 1H), 5.63 (s, 1H).

Example 59 (2S,4aS,6aS,6bR,8aR,9S,10S,12aS, 12bR,14bR)-9-(((5-Isopropyl-2-oxo-1,3-dioxol-4-yl) methoxy)carbonyl)-10-(2-methoxyacetoxy)-2,4a,6a, 6b,9,12a-hexamethyl-13-oxo-1,2,3,4,4a,5,6,6a,6b,7, 8,8a,9,10,11,12,12a,12b,13,14b-icosahydropicene-2-carboxylic Acid (308-2)

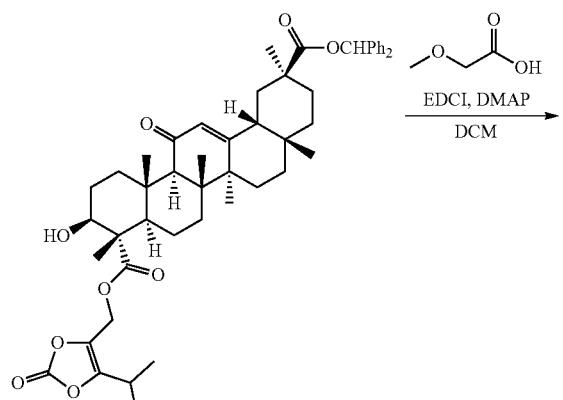

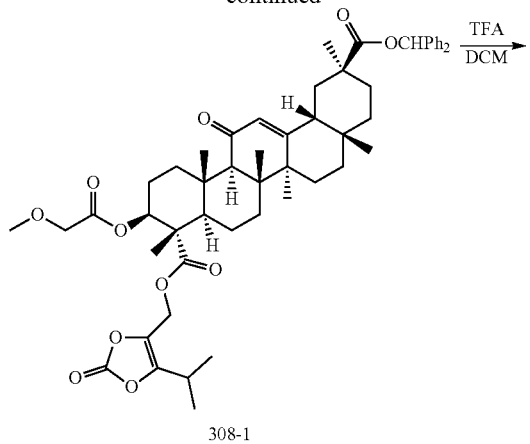

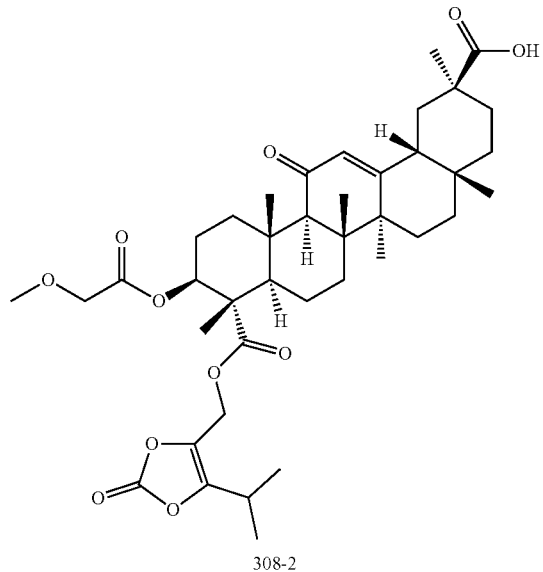

Synthesis of 2-Benzhydryl 9-((5-isopropyl-2-oxo-1, 3-dioxol-4-yl)methyl) (2S,4aS,6aS,6bR,8aR,9S,10S, 12aS,12bR,14bR)-10-(2-methoxyacetoxy)-2,4a,6a, 6b,9,12a-hexamethyl-13-oxo-1,2,3,4,4a,5,6,6a,6b,7, 8,8a,9,10,11,12,12a,12b,13,14b-icosahydropicene-2, 9-dicarboxylate (308-1)

2-Methoxyacetic acid (667 mg, 7.4 mmol, 20 equiv), DMAP (908.3 mg, 7.4 mmol, 20 equiv), and EDCI (1.07 mg, 5.6 mmol, 15 equiv) in CH$_2$Cl$_2$ were stirred for 1 h at rt. 209-1 (300 mg, 0.37 mmol, 1 equiv) in CH$_2$Cl$_2$ was added and the reaction stirred for additional 1 h. The mixture was diluted with CH$_2$Cl$_2$, washed with 1 M HCl(aq), and concentrated under vacuum. The residue was purified by prep-TLC (7:1 CH$_2$Cl$_2$:MeOH) to afford 308-1 (200 mg, 61%) as a light yellow solid.

Synthesis of (2S,4aS,6aS,6bR,8aR,9S,10S,12aS, 12bR,14bR)-9-(((5-Isopropyl-2-oxo-1,3-dioxol-4-yl) methoxy)carbonyl)-10-(2-methoxyacetoxy)-2,4a,6a, 6b,9,12a-hexamethyl-13-oxo-1,2,3,4,4a,5,6,6a,6b,7, 8,8a,9,10,11,12,12a,12b,13,14b-icosahydropicene-2-carboxylic Acid (308-2)

308-1 (300 mg, 0.34 mmol) and TFA (0.3 mL, 4.04 mmol, 12 equiv) in CH$_2$Cl$_2$ (3 mL) were stirred for 1 h at rt. The reaction was concentrated and the residue purified by prep-HPLC under the following conditions—Column: Xselect CSH OBD, 30*150 mm, 5 µm; mobile phase: water (0.05% TFA) and CH₃CN (70% Phase B up to 90% in 8 min); detector: UV. This resulted in 308-2 (104.9 mg, 43%) as an off-white solid. MS (ES, m/z): [M+H]$^+$=713.05; $^1$H NMR (400 MHz, methanol-d₄) δ 5.62 (s, 1H), 5.28 (dd, J=11.6, 5.1 Hz, 1H), 5.10 (d, J=13.9 Hz, 1H), 4.87 (s, 1H), 3.97 (d, J=3.1 Hz, 2H), 3.39 (s, 3H), 3.09 (p, J=7.0 Hz, 1H), 2.85 (d, J=13.8 Hz, 1H), 2.59 (s, 1H), 2.27-2.10 (m, 2H), 1.97 (d, J=10.2 Hz, 1H), 1.85 (t, 7=14.9 Hz, 3H), 1.80-1.66 (m, 5H), 1.47 (s, 3H), 1.41 (d, J=14.2 Hz, 4H), 1.32-1.22 (m, 6H), 1.20 (d, J=2.3 Hz, 6H), 1.16 (s, 3H), 1.07 (d, J=14.0 Hz, 1H), 0.96 (s, 1H), 0.85 (s, 3H).

Example 60 (2S,4aS,6aS,6bR,8aR,9S,10S,12aS, 12bR,14bR)-10-(2,2-Difluoroacetamido)-2,4a,6a,6b, 9,12a-hexamethyl-9-(((5-methyl-2-oxo-1,3-dioxol-4-yl)methoxy)carbonyl)-13-oxo-1,2,3,4,4a,5,6,6a,6b,7, 8,8a,9,10,11,12,12a,12b,13,14b-icosahydropicene-2-carboxylic Acid (309-2)

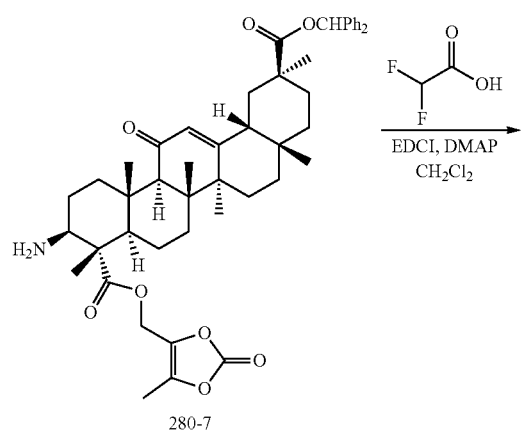

280-7

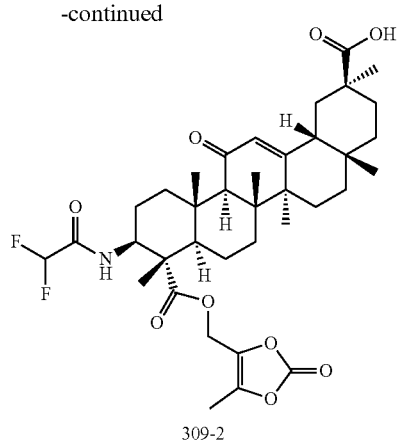

309-2

Synthesis of 2-Benzhydryl 9-((5-methyl-2-oxo-1,3-dioxol-4-yl)methyl) (2S,4aS,6aS,6bR,8aR,9S,10S, 12aS,12bR,14bR)-10-(2,2-difluoroacetamido)-2,4a, 6a,6b,9,12a-hexamethyl-13-oxo-1,2,3,4,4a,5,6,6a,6b, 7,8,8a,9,10,11,12,12a,12b,13,14b-icosahydropicene-2,9-dicarboxylate (309-1)

EDCI (246.4 mg, 10 equiv) was added to 280-7 (100 mg, 1 equiv), 2,2-difluoroacetic acid (0.0323 mL, 4 equiv) and DMAP (15.6 mg, 1 equiv) in CH₂Cl₂ (10 mL) and the reaction slurry stirred overnight at rt. The reaction mixture was concentrated under vacuum and the residue purified by silica gel column eluting with EtOAc/petroleum ether (1:1). This resulted in 113 mg (100%) of 309-1 as a white solid.

Synthesis of (2S,4aS,6aS,6bR,8aR,9S,10S,12aS, 12bR,14bR)-10-(2,2-Difluoroacetamido)-2,4a,6a,6b, 9,12a-hexamethyl-9-(((5-methyl-2-oxo-1,3-dioxol-4-yl)methoxy)carbonyl)-13-oxo-1,2,3,4,4a,5,6,6a,6b,7, 8,8a,9,10,11,12,12a,12b,13,14b-icosahydropicene-2-carboxylic Acid (309-2)

309-1 (186 mg, 1 equiv) and TFA (1 mL) in CH₂Cl₂ (10 mL) were stirred for 1 h at rt. The reaction was concentrated and the residue purified by prep-HPLC with the following conditions—column, Xselect CSH OBD, 30*150 mm, 5 µm; mobile phase: water (0.05% TFA) and CH₃CN (58% Phase B up to 62% in 8 min); detector: UV. This resulted in 63.8 mg (43%) of 309-2 as a white solid. MS (ES, m/z): [M+H]$^+$= 690.15; $^1$H NMR (400 MHz, methanol-d₄) δ 0.83 (s, 3H), 0.90 (d, J=14.0 Hz, 1H), 1.05 (d, J=13.6 Hz, 1H), 1.13-1.20 (m, 12H), 1.25 (d, J=13.6 Hz, 2H), 1.38-1.57 (m, 8H), 1.59-2.00 (m, 8H), 2.10-2.27 (m, 5H), 2.58 (s, 1H), 2.82 (d, J=13.6 Hz, 1H), 4.29 (dd, J=12.4, 4.4 Hz, 1H), 4.77 (d, J=14.0 Hz, 1H), 4.99 (d, J=13.6 Hz, 1H), 5.60 (s, 1H), 5.93 (t, J=27.0 Hz, 1H).

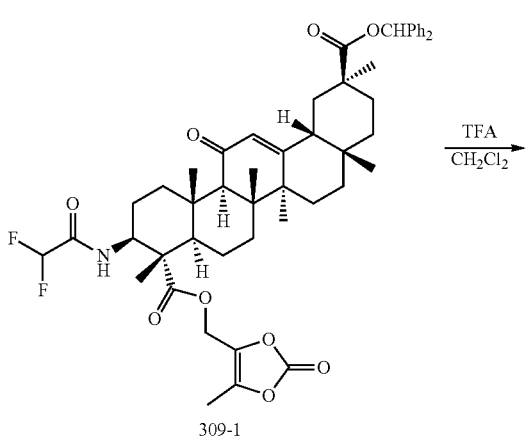

309-1

Example 61 (2S,4aS,6aS,6bR,8aR,9S,10S,12aS, 12bR,14bR)-10-((cyclopropanecarbonyl)oxy)-2,4a, 6a,6b,9,12a-hexamethyl-9-((((5-methyl-2-oxo-1,3-dioxol-4-yl)methoxy)carbonyl)amino)-13-oxo-1,2,3, 4,4a,5,6,6a,6b,7,8,8a,9,10,11,12,12a,12b,13,14b-icosahydropicene-2-carboxylic Acid (314-4)
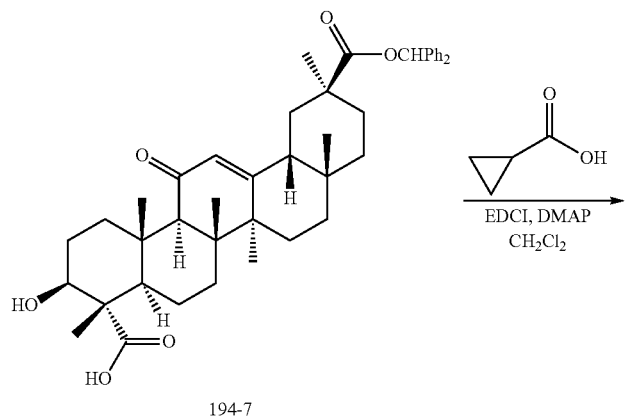
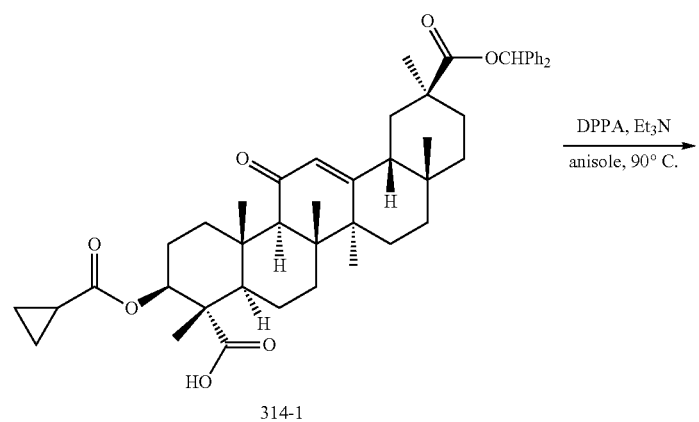
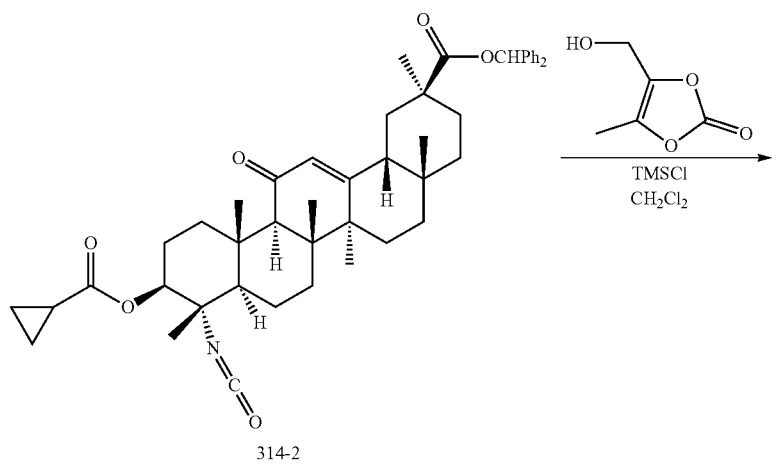

-continued

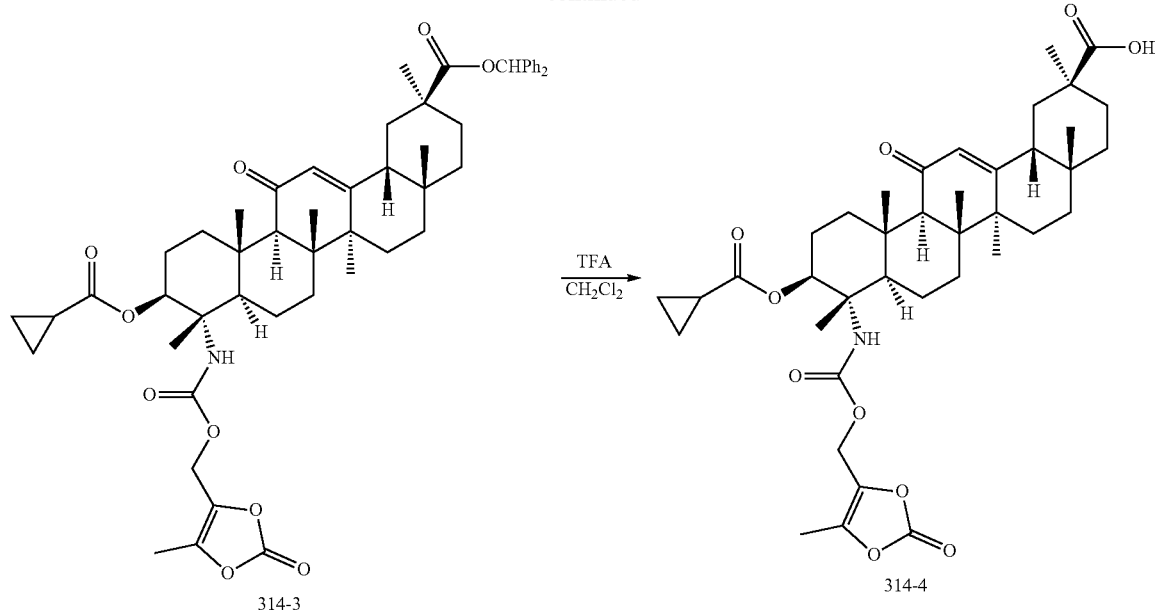

314-3

314-4

Synthesis of (3S,4S,4aR,6aR,6bS,8aS,11S,12aR, 14aR,14bS)-11-((benzhydryloxy)carbonyl)-3-((cyclopropanecarbonyl)oxy)-4,6a,6b,8a,11,14b-hexamethyl-14-oxo-1,2,3,4,4a,5,6,6a,6b,7,8,8a,9,10,11,12, 12a,14,14a,14b-icosahydropicene-4-carboxylic Acid (314-1)

Into a 25-mL round-bottom flask was placed 194-7 (600 mg, 0.9 mmol), CH$_2$Cl$_2$ (6 mL), DMAP (220 mg, 1.8 mmol, 2 equiv), EDCI (432 mg, 2.25 mmol, 2.50 equiv), and cyclopropanecarboxylic acid (232 mg, 2.7 mmol, 3 equiv). The reaction slurry was stirred for 2 hr at room temperature before quenching by the addition of HCl. The reaction mixture was extracted with 3×50 mL of ethyl acetate. The organic layers were combined, washed with 3 x50 ml of brine, dried over anhydrous Na$_2$SO$_4$, filtered, and concentrated. The residue was applied onto a silica gel column with CH$_2$Cl$_2$:methanol (10:1) to provide 170 mg (26%) of 314-1 as a yellow solid.

Synthesis of benzhydryl (2S,4aS,6aS,6bR,8aR,9S, 10S,12aS,12bR,14bR)-10-((cyclopropanecarbonyl) oxy)-9-isocyanato-2,4a,6a,6b,9,12a-hexamethyl-13-oxo-1,2,3,4,4a,5,6,6a,6b,7,8,8a,9,10,11,12,12a,12b, 13,14b-icosahydropicene-2-carboxylate (314-2)

Into a 8-mL round-bottom flask was placed 314-1 (170 mg, 0.23 mmol), anisole (1.9 mL), Et$_3$N (0.05 mL, 0.35 mmol, 1.5 equiv), and DPPA (0.075 mL, 0.35 mmol, 1.5 equiv). The reaction slurry was stirred for 1.5 hr at 90° C. in an oil bath. The reaction mixture was concentrated and applied onto a silica gel column with ethyl acetate:petroleum ether (5:1) to provide 140 mg (83%) of 314-2 as a yellow solid.

Synthesis of benzhydryl (2S,4aS,6aS,6bR,8aR,9S, 10S,12aS,12bR,14bR)-10-((cyclopropanecarbonyl) oxy)-2,4a,6a,6b,9,12a-hexamethyl-9-((((5-methyl-2-oxo-1,3-dioxol-4-yl)methoxy)carbonyl)amino)-13-oxo-1,2,3,4,4a,5,6,6a,6b,7,8,8a,9,10,11,12,12a,12b, 13,14b-icosahydropicene-2-carboxylate (314-3)

Into a 8-mL round-bottom flask was placed 314-2 (120 mg, 0.16 mmol), CH$_2$Cl$_2$ (3 mL, 0.04 mmol, 0.22 equiv), TMSCl (0.071 mL), and 4-(hydroxymethyl)-5-methyl-1,3-dioxolan-2-one (63.6 mg, 0.48 mmol, 3 equiv). The reaction slurry was stirred overnight at room temperature then concentrated to provide 100 mg (71%) of crude 314-3 as a yellow oil.

Synthesis of (2S,4aS,6aS,6bR,8aR,9S,10S,12aS, 12bR,14bR)-10-((cyclopropanecarbonyl)oxy)-2,4a, 6a,6b,9,12a-hexamethyl-9-((((5-methyl-2-oxo-1,3-dioxol-4-yl)methoxy)carbonyl)amino)-13-oxo-1,2,3, 4,4a,5,6,6a,6b,7,8,8a,9,10,11,12,12a,12b,13,14b-icosahydropicene-2-carboxylic Acid (314-4)

Into a 8-mL round-bottom flask was placed 314-3 (30 mg, 0.04 mmol), CH$_2$Cl$_2$ (1 mL), and TFA (0.1 mL). The resulting solution was stirred for 2 hr at room temperature. The crude product was purified by prep-HPLC with the following conditions: column, SunFire C18 OBD column, 5 μm, 19 mm*250 mm; flow rate: 20 mL/min; mobile phase, water (0.05% TFA) and CH$_3$CN (60% Phase B to 69% 16 min); detector, 254 nm. This resulted in 6.5 mg (22%) of 314-4 as a white solid. MS (ES, m/z): [M+1]$^+$=696; $^1$H NMR (400 MHz, chloroform-tf) δ 0.87 (d, J=8.8 Hz, 5H), 0.96 (dt, J=8.1, 4.3 Hz, 2H), 1.06 (d, J=13.8 Hz, 1H), 1.12-1.22 (m, 10H), 1.25 (d, J=6.3 Hz, 4H), 1.31-1.53 (m, 8H), 1.59 (tt, J=8.1, 3.6 Hz, 2H), 1.64-1.79 (m, 4H), 1.80-2.12 (m, 4H), 2.20 (s, 5H), 2.50 (s, 1H), 2.82 (d, J=13.9 Hz, 1H), 4.43 (s, 1H), 4.70 (d, J=13.9 Hz, 1H), 4.84 (d, J=13.9 Hz, 1H), 5.46 (dd, J=11.2, 5.5 Hz, 1H), 5.74 (s, 1H).

Example 62 (2S,4aS,6aS,6bR,8aR,9S,10S,12aS, 12bR,14bR)-10-((cyclopropanecarbonyl)oxy)-9-((((5-ethyl-2-oxo-1,3-dioxol-4-yl)methoxy)carbonyl) amino)-2,4a,6a,6b,9,12a-hexamethyl-13-oxo-1,2,3,4, 4a,5,6,6a,6b,7,8,8a,9,10,1142,12a,12b,13,14b-icosahydropicene-2-carboxylic Acid (315-2)
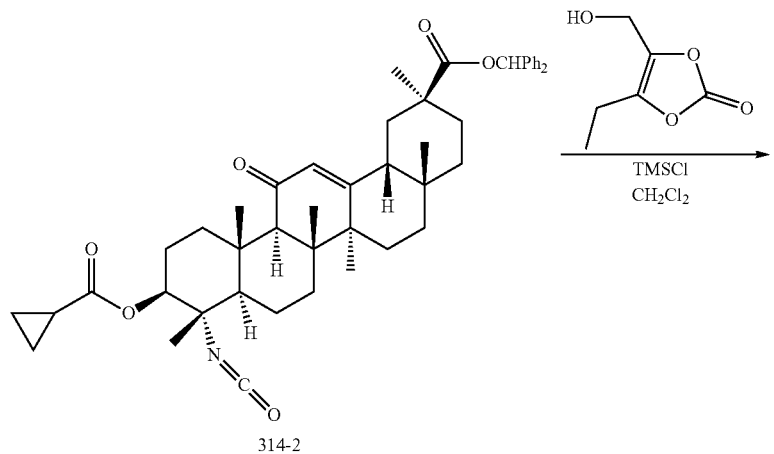
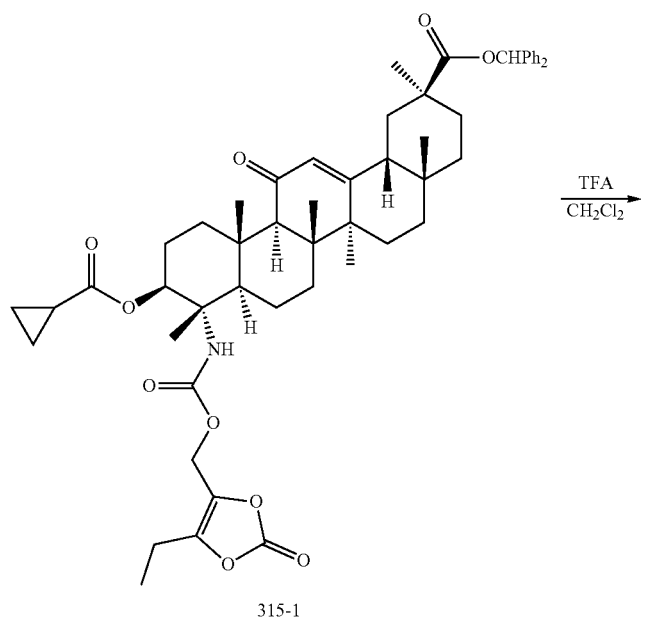

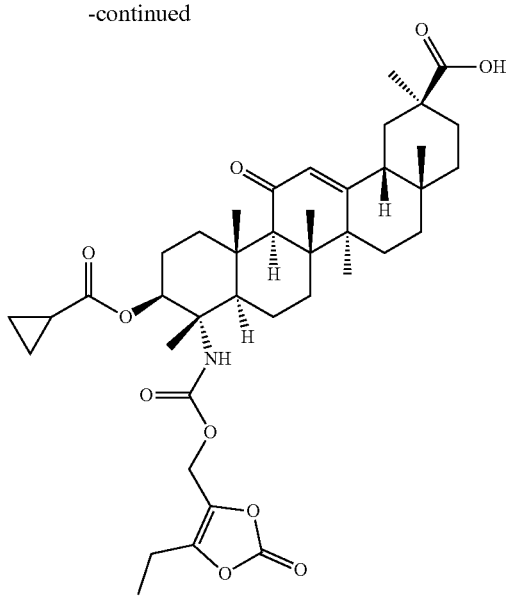

315-2

Synthesis of benzhydryl (2S,4aS,6aS,6bR,8aR,9S, 10S,12aS,12bR,14bR)-10-((cyclopropanecarbonyl) oxy)-9-((((5-ethyl-2-oxo-1,3-dioxol-4-yl)methoxy) carbonyl)amino)-2,4a,6a,6b,9,12a-hexamethyl-13-oxo-1,2,3,4,4a,5,6,6a,6b,7,8,8a,9,10,11,12,12a,12b, 13,14b-icosahydropicene-2-carboxylate (315-1)

Into a 100-mL round-bottom flask was placed 314-2 (0.76 g, 1 mmol), $CH_2Cl_2$ (12 mL), TMSCl (0.68 mg, 0.006 mmol, 6 equiv), and 4-ethyl-5-(hydroxymethyl)-2H-1,3-dioxol-2-one (0.60 mg, 0.004 mmol, 4 equiv). The reaction slurry was stirred for 2 hr at room temperature then concentrated to provide 0.6 g of crude 315-1 as a tan oil.

Synthesis of (2S,4aS,6aS,6bR,8aR,9S,10S,12aS, 12bR,14bR)-10-((cyclopropanecarbonyl)oxy)-9-((((5-ethyl-2-oxo-1,3-dioxol-4-yl)methoxy)carbonyl) amino)-2,4a,6a,6b,9,12a-hexamethyl-13-oxo-1,2,3,4, 4a,5,6,6a,6b,7,8,8a,9,10,11,12,12a,12b,13,14b-icosahydropicene-2-carboxylic Acid (315-2)

Into a 250-mL round-bottom flask was placed 315-1 (0.6 g, 0.685 mmol), $CH_2Cl_2$ (15 mL), and TFA (2 mL). The reaction slurry was stirred for 30 min at room temperature then concentrated. The crude product was purified by prep-HPLC with the following conditions: column, XSelect CSH Prep C18 OBD, 5 μm, 19*150 mm; mobile phase, water (0.05% TFA) and $CH_3CN$ (65% Phase B up to 70% in 10 min); detector, UV. This resulted in 306 mg of 315-2 as a white solid. MS (ES, m/z): $[M+1]^+=710$; $^1H$ NMR (300 MHz, methanol-$d_4$) δ 0.86 (d, J=9.7 Hz, 7H), 1.04-1.31 (m, 17H), 1.43 (d, J=9.1 Hz, 8H), 1.57 (s, 3H), 1.65-1.81 (m, 4H), 1.81-1.98 (m, 3H), 2.20 (s, 2H), 2.30 (d, J=10.3 Hz, 1H), 2.59 (q, J=7.3 Hz, 3H), 2.75 (d, J=13.3 Hz, 1H), 4.72 (d, J=14.2 Hz, 2H), 5.59 (d, J=14.6 Hz, 2H).

Example 63 (2S,4aS,6aS,6bR,8aR,9S,10S,12aS, 12bR,14bR)-10-acetoxy-9-(((5-ethyl-2-oxo-1,3-dioxol-4-yl)methoxy)carbonyl)-2,4a,6a,6b,9,12a-hexamethyl-13-oxo-1,2,3,4,4a,5,6,6a,6b,7,8,8a,9,10, 1142,12a,12b,13,14b-icosahydropicene-2-carboxylic Acid (316-1)

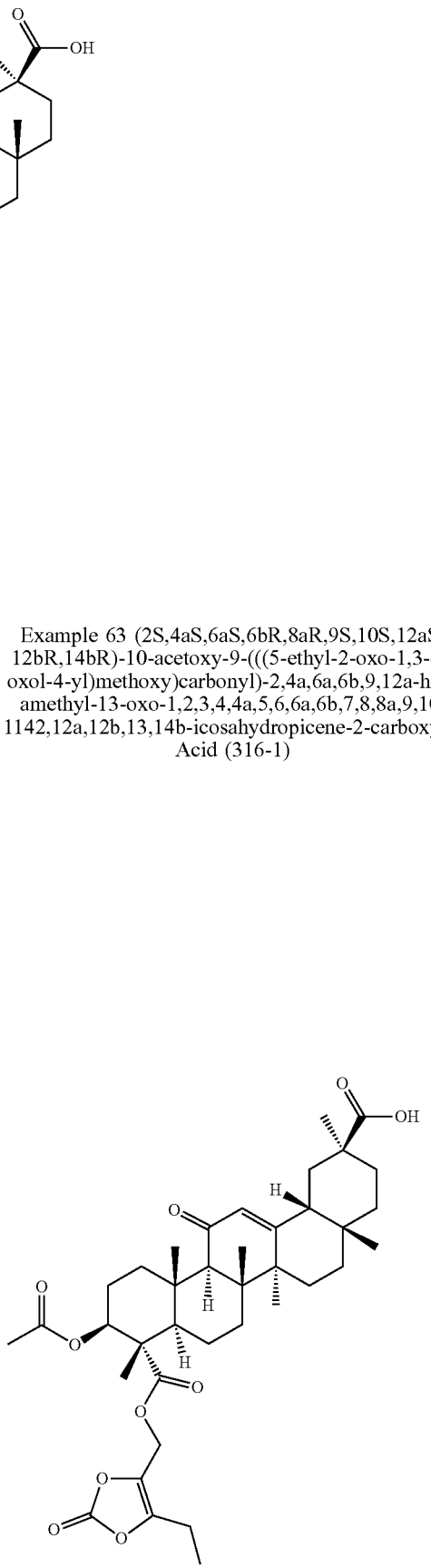

316-1

Synthesis of (2S,4aS,6aS,6bR,8aR,9S,10S,12aS, 12bR,14bR)-10-acetoxy-9-(((5-ethyl-2-oxo-1,3-dioxol-4-yl)methoxy)carbonyl)-2,4a,6a,6b,9,12a-hexamethyl-13-oxo-1,2,3,4,4a,5,6,6a,6b,7,8,8a,9,10,11, 12,12a,12b,13,14b-icosahydropicene-2-carboxylic Acid (316-1)

The title compound was prepared with 4-(bromomethyl)-5-ethyl-1,3-dioxol-2-one (prepared according to literature procedures from Sun et al, Tetrahedron Letters, 2002, 43, 1161-1164) according to the methods to synthesize 209-3. The crude product was purified by Prep-HPLC with the following conditions: column, XBridge Prep OBD C18 Column, 30*150 mm, 5 μm; mobile phase, water (0.05% TFA) and CH$_3$CN (65% phase B up to 70% in 8 min); detector, UV. This resulted in 99.9 mg (62%) of 316-1 as a white solid. MS (ES, m/z) [M+1]$^+$=669; $^1$H NMR (400 MHz, methanol-d$_4$) δ 0.85 (s, 3H), 0.96 (d, J=5.9 Hz, 1H), 1.07 (d, J=13.6 Hz, 1H), 1.16 (s, 3H), 1.18-1.25 (m, 12H), 1.27 (d, J=3.8 Hz, 1H), 1.33-1.49 (m, 6H), 1.66-1.83 (m, 6H), 1.86 (s, 1H), 1.96 (s, 3H), 1.98 (s, 1H), 2.12-2.28 (m, 2H), 2.56-2.66 (m, 3H), 2.79-2.88 (m, 1H), 4.89 (d, J=14.0 Hz, 1H), 5.05 (d, J=13.9 Hz, 1H), 5.16 (dd, J=11.7, 5.0 Hz, 1H), 5.62 (s, 1H).

Example 64 (2S,4aS,6aS,6bR,8aR,9S,10S,12aS, 12bR,14bR)-2,4a,6a,6b,9,12a-hexamethyl-9-((((5-methyl-2-oxo-1,3-dioxol-4-yl)methoxy)carbonyl) amino)-13-oxo-10-(propionyloxy)-1,2,3,4,4a,5,6,6a, 6b,7,8,8a,9,10,11,12,12a,12b,13,14b-icosahydropicene-2-carboxylic (317-6)

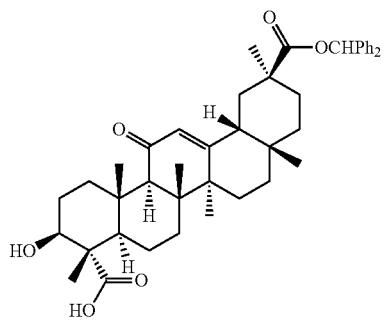
194-7

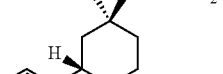
CH$_2$Cl$_2$, MeOH

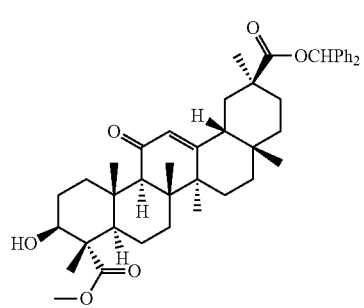
317-1

1. DMAP, CH$_2$Cl$_2$
ii. EDC—I

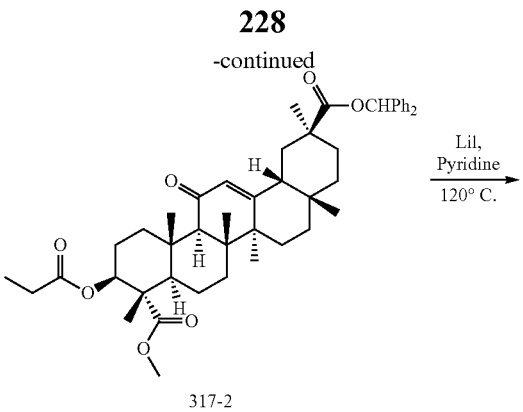
317-2

LiI, Pyridine
120° C.

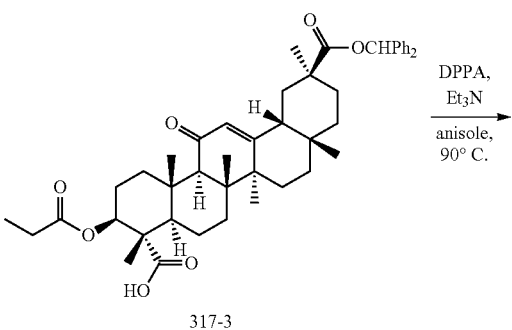
317-3

DPPA, Et$_3$N
anisole, 90° C.

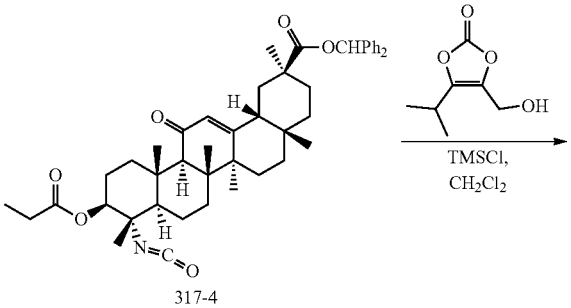
317-4

TMSCl, CH$_2$Cl$_2$

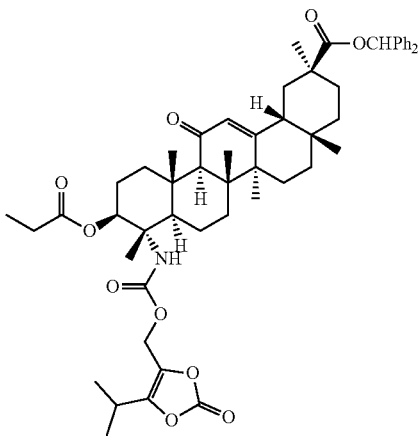
317-5

TFA
CH$_2$Cl$_2$

-continued

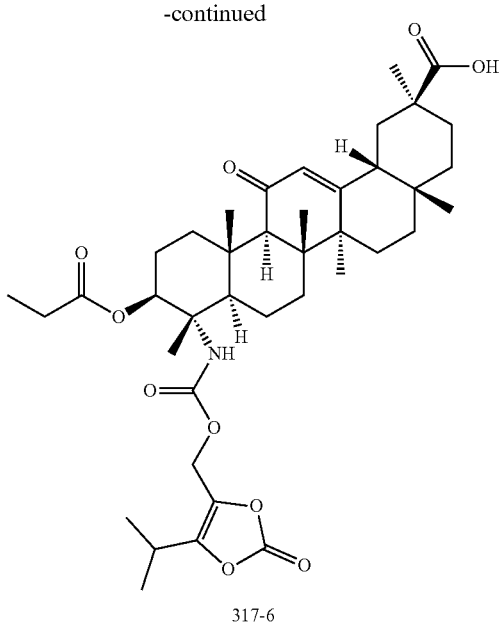

317-6

Synthesis of 2-benzhydryl 9-methyl (2S,4aS,6aS, 6bR,8aR,9S,10S,12aS,12bR,14bR)-10-hydroxy-2,4a, 6a,6b,9,12a-hexamethyl-13-oxo-1,2,3,4,4a,5,6,6a,6b, 7,8,8a,9,10,11,12,12a,12b,13,14b-icosahydropicene-2,9-dicarboxylate (317-1)

(Trimethylsilyl)diazomethane (1 mL) was added to 194-7 (200 mg, 0.30 mmol, 1 equiv) in $CH_2Cl_2$ (5 mL) and MeOH (2.5 mL), The resulting solution was stirred for 1 h at rt. The reaction mixture was concentrated to provide 200 mg (98%) of 317-1 as a white solid, used directly in the next step.

Synthesis of 2-benzhydryl 9-methyl (2S,4aS,6aS, 6bR,8aR,9S,10S,12aS,12bR,14bR)-2,4a,6a,6b,9,12a-hexamethyl-13-oxo-10-(propionyloxy)-1,2,3,4,4a,5, 6,6a,6b,7,8,8a,9,10,11,12,12a,12b,13,14b-icosahydropicene-2,9-dicarboxylate (317-2)

Into a 100-mL round-bottom flask was placed 317-1 (500 mg, 1 equiv), $CH_2Cl_2$ (4 mL), propanoic acid (0.164 mL, 3 equiv), DMAP (180 mg, 2 equiv), and EDCI (211 mg, 1.5 equiv). The resulting solution was stirred for 2 hr at room temperature. The residue was applied onto a silica gel column with 1:5 ethyl acetate:petroleum ether to provide 480 mg of 317-2 as a white solid.

Synthesis of (3S,4S,4aR,6aR,6bS,8aS,11S,12aR, 14aR,14bS)-11-((benzhydryloxy)carbonyl)-4,6a,6b, 8a,11,14b-hexamethyl-14-oxo-3-(propionyloxy)-1,2, 3,4,4a,5,6,6a,6b,7,8,8a,9,10,11,12,12a,14,14a,14b-icosahydropicene-4-carboxylic Acid (317-3)

Into a 100-mL round-bottom flask was placed 317-2 (540 mg, 1 equiv), pyridine (7 mL), and LiI (98 mg, 10 equiv). The reaction mixture was stirred for 2 days at 120° C. The reaction slurry was concentrated, washed with 3×100 ml of 0.5 M HCl and 3×100 mL of brine. The organic layers were combined, dried over anhydrous $Na_2SO_4$, filtered, and concentrated to provide 480 mg of crude 317-3 as a yellow solid.

Synthesis of benzhydryl (2S,4aS,6aS,6bR,8aR,9S, 10S,12aS,12bR,14bR)-9-isocyanato-2,4a,6a,6b,9, 12a-hexamethyl-13-oxo-10-(propionyloxy)-1,2,3,4, 4a,5,6,6a,6b,7,8,8a,9,10,11,12,12a,12b,13,14b-icosahydropicene-2-carboxylate (317-4)

Into a 100-mL round-bottom flask was placed 317-3 (340 mg, 1 equiv), anisole (4 mL), $Et_3N$ (0.1 mL, 1.5 equiv), and DPPA (0.152 mL, 1.5 equiv). The reaction mixture was stirred at 90° C. for 1.5 hr. The reaction slurry was concentrated and the residue applied onto a silica gel column with 1:7 ethyl acetate:petroleum ether to provide 300 mg of 317-4 as a yellow solid.

Synthesis of benzhydryl (2S,4aS,6aS,6bR,8aR,9S, 10S,12aS,12bR,14bR)-9-((((5-isopropyl-2-oxo-1,3-dioxol-4-yl)methoxy)carbonyl)amino)-2,4a,6a,6b,9, 12a-hexamethyl-13-oxo-10-(propionyloxy)-1,2,3,4, 4a,5,6,6a,6b,7,8,8a,9,10,11,12,12a,12b,13,14b-icosahydropicene-2-carboxylate (317-5)

Into a 25-mL round-bottom flask was placed 317-4 (130 mg, 1 equiv), $CH_2Cl_2$ (2 mL), chlorotrimethylsilane (0.094 mL, 6 equiv), and 4-(hydroxymethyl)-5-(propan-2-yl)-2H-1,3-dioxol-2-one (115 mg, 4 equiv). The reaction mixture was stirred overnight at room temperature. The reaction slurry was concentrated to provide 160 mg of crude 317-5 as a yellow oil.

Synthesis of (2S,4aS,6aS,6bR,8aR,9S,10S,12aS, 12bR,14bR)-9-((((5-isopropyl-2-oxo-1,3-dioxol-4-yl)methoxy)carbonyl)amino)-2,4a,6a,6b,9,12a-hexamethyl-13-oxo-10-(propionyloxy)-1,2,3,4,4a,5,6,6a, 6b,7,8,8a,9,10,11,12,12a,12b,13,14b-icosahydropicene-2-carboxylic Acid (317-6)

Into a 100-mL round-bottom flask was placed 317-5 (120 mg, 1 equiv), $CH_2Cl_2$ (5 mL), and TFA (0.5 mL). The reaction mixture was stirred for 1 hr at room temperature. The reaction slurry was concentrated and purified by Prep-HPLC with the following conditions: column, Xselect CSH OBD, 30*150 mm, 5 μm; mobile phase, water (0.05% TFA) and $CH_3CN$ (74% Phase B up to 78% in 8 min); detector, UV. This resulted in 66.1 mg of 317-6 as a white solid. MS (ES, m/z): $[M+1]^+$=712; $^1H$ NMR (300 MHz, methanol-$d_4$) δ 5.60 (d, J=11.9 Hz, 2H), 4.80 (t, J=13.5 Hz, 1H), 3.08 (p, J=7.0 Hz, 1H), 2.76 (d, J=13.5 Hz, 1H), 2.59 (s, 1H), 2.38-2.27 (m, 2H), 2.31-2.19 (m, 1H), 1.99-1.82 (m, 3H), 1.81-1.67 (m, 4H), 1.58 (s, 1H), 1.44 (d, J=9.6 Hz, 7H), 1.31-1.17 (m, 9H), 1.21-1.06 (m, 12H), 1.05 (s, 1H), 0.85 (s, 3H).

Example 65 (2S,4aS,6aS,6bR,8aR,9S,10S,12aS,
12bR,14bR)-9-((((5-ethyl-2-oxo-1,3-dioxol-4-yl)
methoxy)carbonyl)amino)-2,4a,6a,6b,9,12a-hexam-
ethyl-13-oxo-10-(propionyloxy)-1,2,3,4,4a,5,6,6a,
6b,7,8,8a,9,10,1142,12a,12b,13,14b-
icosahydropicene-2-carboxylic (318-1)

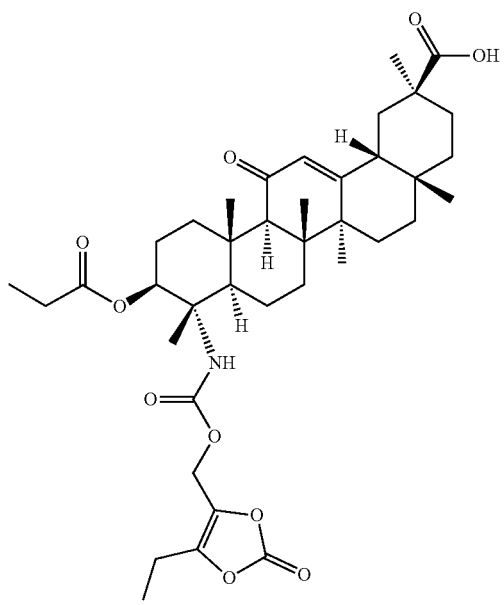

318-1

Synthesis of (2S,4aS,6aS,6bR,8aR,9S,10S,12aS,
12bR,14bR)-9-((((5-ethyl-2-oxo-1,3-dioxol-4-yl)
methoxy)carbonyl)amino)-2,4a,6a,6b,9,12a-hexam-
ethyl-13-oxo-10-(propionyloxy)-1,2,3,4,4a,5,6,6a,
6b,7,8,8a,9,10,11,12,12a,12b,13,14b-
icosahydropicene-2-carboxylic Acid (318-1)

The title compound was prepared with 317-4 and 4-ethyl-5-(hydroxymethyl)-1,3-dioxol-2-one (prepared according to literature procedures from Sun et al, Tetrahedron Letters, 2002, 43, 1161-1164) according to the methods to synthesize 317-6. The crude product was purified by Prep-HPLC with the following conditions: XSelect CSH Prep C18 OBD column, 5 μm, 19*150 mm; mobile phase, water (0.05% TFA) and $CH_3CN$ (60% phase B up to 79% in 8 min); detector, UV to provide 37.2 mg of 318-1 as a white solid. The product was tested in the assay in described in example 112 demonstrating a $pIC_{50}$ of 7.45 compared to the corresponding acid metabolite (2S,4aS,6aS,6bR,8aR,9S,10S,12aS,12bR,14bR)-9-amino-2,4a,6a,6b,9,12a-hexamethyl-13-oxo-10-(propanoyloxy)-1,2,3,4,4a,5,6,6a,6b,7,8,8a,9,10,11,12,12a,12b,13,14b-icosahydropicene-2-carboxylic acid having a $pIC_{50}$ of 6.4 and the subsequent amine metabolite (2S,4aS,6aS,6bR,8aR,9S,10S,12aS,12bR,14bR)-9-amino-10-hydroxy-2,4a,6a,6b,9,12a-hexamethyl-13-oxo-1,2,3,4,4a,5,6,6a,6b,7,8,8a,9,10,11,12,12a,12b,13,14b-icosahydropicene-2-carboxylic acid having a $pIC_{50}$ less than 5. MS (ES, m/z): $[M+1]^+=698$; $^1H$ NMR (400 MHz, methanol-$d_4$) δ 5.62 (s, 2H), 4.86 (slH), 4.74 (d, J=14.1 Hz, 1H), 2.76 (d, J=13.1 Hz, 2H), 2.61 (q, J=7.4 Hz, 2H), 2.31 (q, J=7.9 Hz, 3H), 2.22 (s, 2H), 1.93 (d, J=16.9 Hz, 3H), 1.77 (d, J=13.3 Hz, 2H), 1.70 (s, 2H), 1.57 (s, 2H), 1.44 (d, J=10.7 Hz, 6H), 1.29-1.05 (m, 22H), 0.86 (s, 5H).

Example 66 (2S,4aS,6aS,6bR,8aR,9S,10S,12aS,
12bR,14bR)-2,4a,6a,6b,9,12a-hexamethyl-9-((((5-
methyl-2-oxo-1,3-dioxol-4-yl)methoxy)carbonyl)
amino)-13-oxo-10-(propionyloxy)-1,2,3,4,4a,5,6,6a,
6b,7,8,8a,9,10,1142,12a,12b,13,14b-
icosahydropicene-2-carboxylic (319-1)

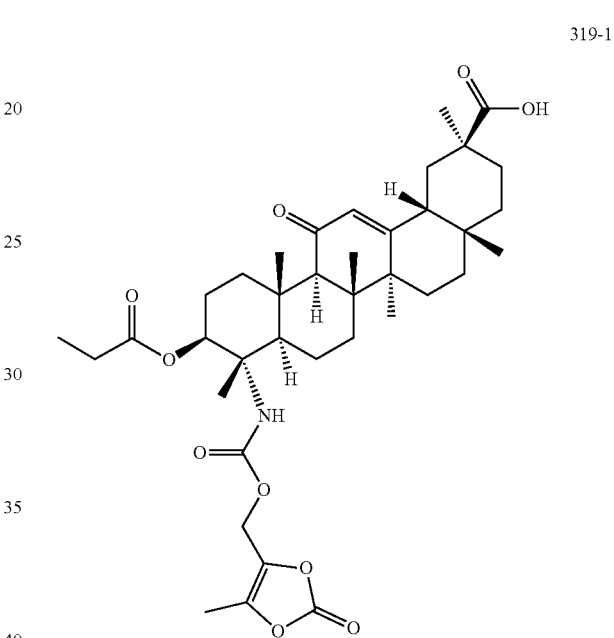

319-1

Synthesis of (2S,4aS,6aS,6bR,8aR,9S,10S,12aS,
12bR,14bR)-2,4a,6a,6b,9,12a-hexamethyl-9-((((5-
methyl-2-oxo-1,3-dioxol-4-yl)methoxy)carbonyl)
amino)-13-oxo-10-(propionyloxy)-1,2,3,4,4a,5,6,6a,
6b,7,8,8a,9,10,11,12,12a,12b,13,14b-
icosahydropicene-2-carboxylic Acid (319-1)

The title compound was prepared with 317-4 and 4-methyl-5-(hydroxymethyl)-1,3-dioxol-2-one (prepared according to literature procedures from Sun et al, Tetrahedron Letters, 2002, 43, 1161-1164) according to the methods to synthesize 317-6. The crude product was purified by Prep-HPLC with the following conditions: XSelect CSH Prep C18 OBD column, 5 μm, 30*150 mm; mobile phase, water (0.05% TFA) and $CH_3CN$ (68% phase B up to 71% in 8 min); detector, UV to provide 56.4 mg of 319-1 as a white solid. MS (ES, m/z): $[M+1]^+=684$; $^1H$ NMR (400 MHz, methanol-$d_4$) δ 5.61 (d, J=11.2 Hz, 2H), 4.89 (s, 1H), 4.70 (d, J=14.1 Hz, 1H), 2.76 (d, J=13.6 Hz, 1H), 2.60 (s, 1H), 2.36-2.23 (m, 3H), 2.20 (s, 3H), 1.96 (s, 1H), 1.88 (d, J=13.4 Hz, 1H), 1.74 (dd, J=19.2, 12.8 Hz, 4H), 1.59 (d, J=13.4 Hz, 1H), 1.45 (d, J=14.4 Hz, 7H), 1.31 (d, J=31.1 Hz, 1H), 1.27-1.03 (m, 17H), 0.86 (s, 3H).

Example 67 (3S,4S,4aR,6aR,6bS,8aS,11S,12aR, 14aR,14bS)-4-(((((5-ethyl-2-oxo-1,3-dioxol-4-yl) methoxy)carbonyl)amino)-4,6a,6b,8a,11,14b-hexamethyl-11-(methylcarbamoyl)-14-oxo-1,2,3,4,4a,5,6, 6a,6b,7,8,8a,9,10,11,12,12a,14,14a,14b-icosahydropicen-3-yl propionate (320-1)

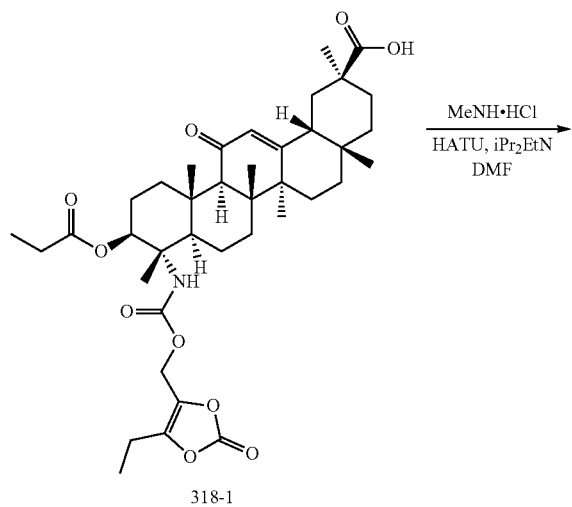

318-1

Example 68 (2S,4aS,6aS,6bR,8aR,9S,10S,12aS, 12bR,14bR)-10-((cyclopropanecarbonyl)oxy)-9-(((((5-isopropyl-2-oxo-1,3-dioxol-4-yl)methoxy)carbonyl)amino)-2,4a,6a,6b,9,12a-hexamethyl-13-oxo-1,2,3,4,4a,5,6,6a,6b,7,8,8a,9,10,1142,12a,12b,13, 14b-icosahydropicene-2-carboxylic Acid (321-1)

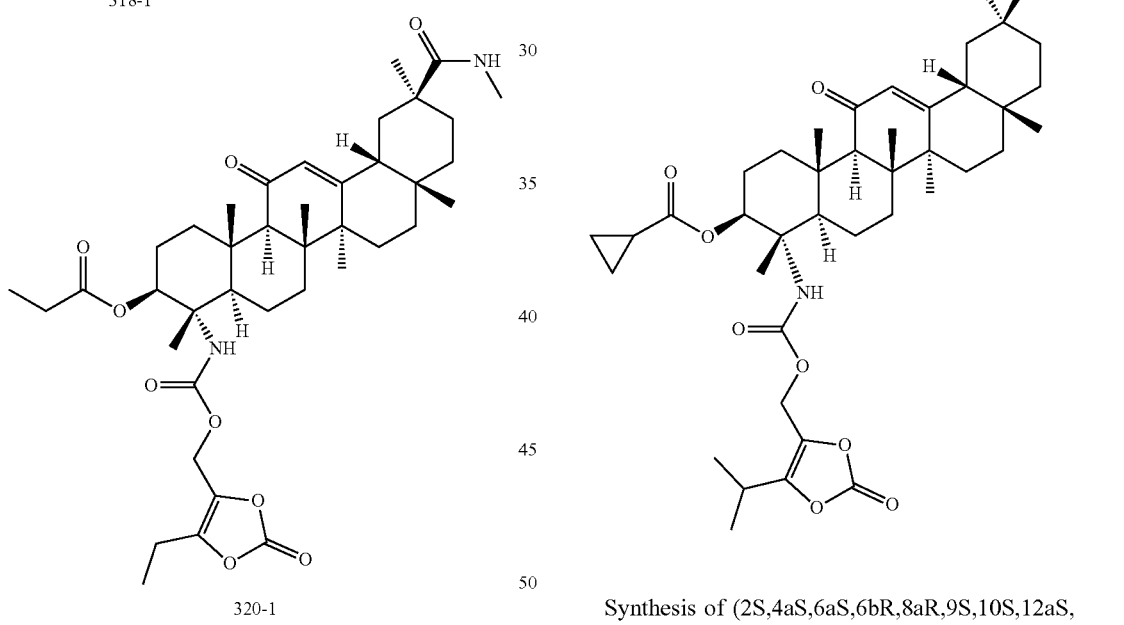

321-1

320-1

Synthesis of (3S,4S,4aR,6aR,6bS,8aS,11S,12aR, 14aR,14bS)-4-(((((5-ethyl-2-oxo-1,3-dioxol-4-yl) methoxy)carbonyl)amino)-4,6a,6b,8a,11,14b-hexamethyl-11-(methylcarbamoyl)-14-oxo-1,2,3,4,4a,5,6, 6a,6b,7,8,8a,9,10,11,12,12a,14,14a,14b-icosahydropicen-3-yl propionate (320-1)

Into a 25-mL round-bottom flask was placed 318-1 (60 mg, 0.086 mmol), DMF (2 mL), methylamine hydrochloride (5.8 mg, 0.086 mmol, 1 equiv), iPr$_2$EtN (0.07 mL, 0.58 mmol, 5 equiv), and HATU (49.0 mg, 0.13 mmol, 1.5 equiv). The reaction slurry was stirred for 2 hr at room temperature. The reaction mixture was extracted with 3×50 mL of ethyl acetate. The combined organic layers were washed with 50 mL of brine, dried over anhydrous Na$_2$SO$_4$, filtered, and concentrated. The crude product was purified by prep-HPLC with the following conditions: column, XBridge Prep OBD C18, mobile phase, water (0.05% TFA) and CH$_3$CN (55% phase B up to 70% in 8 min); detector, UV. This resulted in 38.9 mg of 320-1 as a white solid. MS (ES, m/z): [M+1]$^+$= 711; $^1$H NMR (300 MHz, methanol-d$_4$) δ 5.68 (s, 1H), 5.64-5.54 (m, 1H), 4.74 (d, J=14.1 Hz, 1H), 2.76 (s, 4H), 2.68-2.54 (m, 3H), 2.31 (q, J=7.7 Hz, 3H), 2.17 (d, J=13.8 Hz, 2H), 1.93 (t, J=12.4 Hz, 3H), 1.74 (dd, J=17.5, 11.0 Hz, 4H), 1.43 (d, J=16.4 Hz, 9H), 1.29-1.01 (m, 22H), 0.84 (s, 3H).

Synthesis of (2S,4aS,6aS,6bR,8aR,9S,10S,12aS, 12bR,14bR)-10-((cyclopropanecarbonyl)oxy)-9-(((((5-isopropyl-2-oxo-1,3-dioxol-4-yl)methoxy)carbonyl)amino)-2,4a,6a,6b,9,12a-hexamethyl-13-oxo-1,2,3,4,4a,5,6,6a,6b,7,8,8a,9,10,11,12,12a,12b,13, 14b-icosahydropicene-2-carboxylic Acid (321-1)

The title compound was prepared with 314-2 and 4-(hydroxymethyl)-5-(propan-2-yl)-2H-1,3-dioxol-2-one (prepared according to literature procedures from Sun et al, Tetrahedron Letters, 2002, 43, 1161-1164) according to the methods to synthesize 315-2. The crude product was purified by prep-HPLC with the following conditions: XSelect CSH Prep C18 OBD column, 5 μm, 19*150 mm; mobile phase, water (0.05% TFA) and CH$_3$CN (75% phase B up to 86% in 7 min); detector, 254 nm, to provide 42.3 mg of 321-1 as a white solid. MS (ES, m/z) [M+1]$^+$=724; $^1$H NMR (400

MHz, chloroform-d) δ 5.74 (s, 1H), 5.43 (dd, J=11.8, 5.3 Hz, 1H), 4.83 (d, J=13.9 Hz, 1H), 4.75 (d, J=14.1 Hz, 1H), 4.44 (s, 1H), 3.02 (p, J=7.0 Hz, 1H), 2.82 (d, J=13.4 Hz, 1H), 2.49 (s, 1H), 2.21 (d, J=12.6 Hz, 2H), 2.04-1.91 (m, 1H), 1.73 (d, J=15.5 Hz, 1H), 1.70-1.53 (m, 3H), 1.44 (s, 4H), 1.39 (s, 3H), 1.29-1.23 (m, 8H), 1.22 (s, 1H), 1.20-1.12 (m, 9H), 1.06 (d, J=14.2 Hz, 1H), 0.97 (s, 2H), 0.88 (d, J=3.5 Hz, 1H), 0.86 (s, 4H).
Example 69 (2S,4aS,6aS,6bR,8aR,9S,10S,12aS, 12bR,14bR)-2,4a,6a,6b,9,12a-hexamethyl-9-((((5-methyl-2-oxo-1,3-dioxol-4-yl)methoxy)carbonyl) amino)-13-oxo-10-propoxy-1,2,3,4,4a,5,6,6a,6b,7,8, 8a,9,10,1142,12a,12b,13,14b-icosahydropicene-2-carboxylic (322-6)
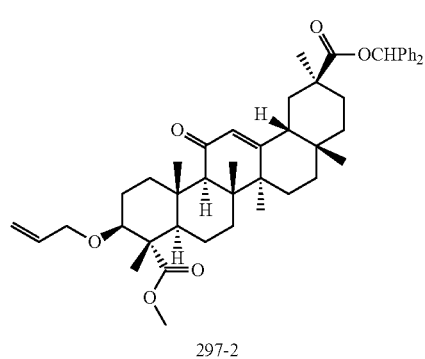
297-2
Pd/C, H₂
MeOH
acetone
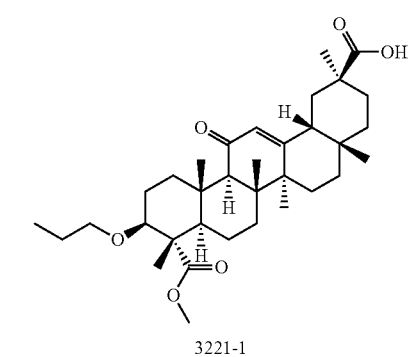
3221-1
Ph₂CN₂, 45° C.
MeOH, Et₂O
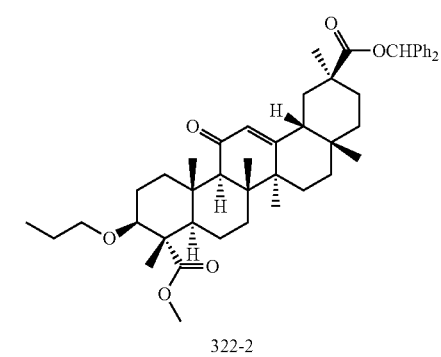
322-2
LiI, pyridine
125° C.
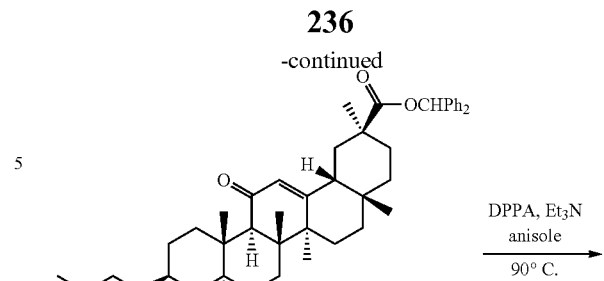
322-3
DPPA, Et₃N
anisole
90° C.
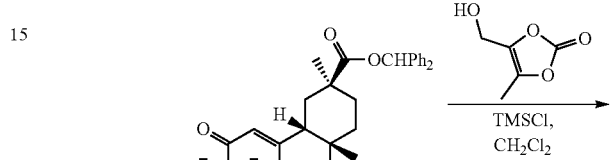
TMSCl,
CH₂Cl₂
322-4
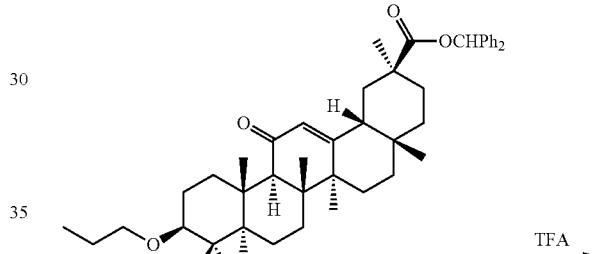
322-5
TFA
CH₂Cl₂
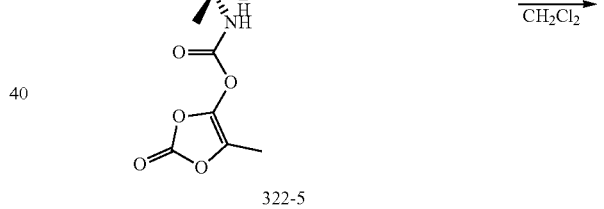
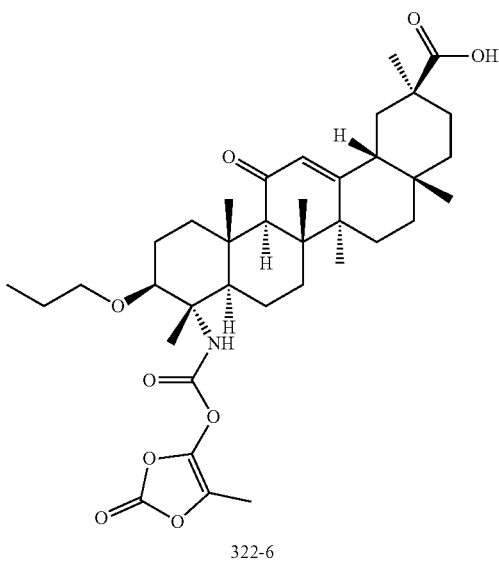
322-6

Synthesis of (2S,4aS,6aS,6bR,8aR,9S,10S,12aS, 12bR,14bR)-9-(methoxycarbonyl)-2,4a,6a,6b,9,12a-hexamethyl-13-oxo-10-propoxy-1,2,3,4,4a,5,6,6a,6b, 7,8,8a,9,10,11,12,12a,12b,13,14b-icosahydropicene-2-carboxylic Acid (322-1)

Into a 100-mL round-bottom flask was placed methanol (5 mg), 297-2 (315 mg, 0.44 mmol, 1 equiv), Pd/C (10%, 152 mg, 1.4 mmol, 3.3 equiv), and acetone (5 mL). The vessel was charged with $H_2(g)$ and the reaction slurry stirred for 4 hr at room temperature. The solids were filtered off and the filtrate was concentrated under vacuum to provide 287 mg of crude 322-1 as a white solid.

Synthesis of 2-benzhydryl 9-methyl (2S,4aS, 6bR,8aR,9S,10S,12aS,12bR,14bR)-2,4a,6a,6b,9,12a-hexamethyl-13-oxo-10-propoxy-1,2,3,4,4a,5,6,6a,6b, 7,8,8a,9,10,11,12,12a,12b,13,14b-icosahydropicene-2,9-dicarboxylate (322-2)

Into a 100-mL round-bottom flask, was placed methanol (4 mL), 322-1 (287 mg, 0.52 mmol, 1 equiv), ether (2 mL), and $Ph_2CN_2$ (300 mg, 1.5 mmol, 3 equiv). The reaction slurry was stirred for 2 hr at 45° C. The reaction mixture was concentrated under vacuum. The residue was applied onto a silica gel column with ethyl acetate:petroleum ether (10:1) to provide 284 mg (76%) of 322-2 as a white solid.

Synthesis of (3S,4S,4aR,6aR,6bS,8aS,11S,12aR, 14aR,14bS)-11-((benzhydryloxy)carbonyl)-4,6a,6b, 8a,11,14b-hexamethyl-14-oxo-3-propoxy-1,2,3,4,4a, 5,6,6a,6b,7,8,8a,9,10,11,12,12a,14,14a,14b-icosahydropicene-4-carboxylic Acid (322-3)

Into a 100-mL round-bottom flask was placed pyridine (5 mL), 322-2 (284 mg, 0.39 mmol, 1 equiv), and LiI (526 mg, 3.9 mmol, 10 equiv). The reaction slurry was stirred for 2 days at 125° C. The reaction mixture was concentrated under vacuum. The residue was diluted with 90 mL of ethyl acetate and washed with 30 mL of brine. The organic layer was dried over anhydrous $Na_2SO_4$, filtered, and concentrated. The residue was applied onto a silica gel column with ethyl acetate:petroleum ether (1:1) to provide 280 mg of 322-3 as a yellow solid.

Synthesis of benzhydryl (2S,4aS,6aS,6bR,8aR,9S, 10S,12aS,12bR,14bR)-9-isocyanato-2,4a,6a,6b,9, 12a-hexamethyl-13-oxo-10-propoxy-1,2,3,4,4a,5,6, 6a,6b,7,8,8a,9,10,11,12,12a,12b,13,14b-icosahydropicene-2-carboxylate (322-4)

Into a 100-mL round-bottom flask was placed anisole (5 mL), 322-3 (287 mg, 0.4 mmol, 1 equiv), $Et_3N$ (102.4 mg, 1 mmol, 2.5 equiv), and DPPA (189.4 mg, 0.69 mmol, 1.7 equiv). The reaction slurry was stirred for 1 hr at 90° C. then concentrated. The residue was applied onto a silica gel column with ethyl acetate:petroleum ether (1:5) to provide 158 mg (55%) of 322-4 as a white solid.

Synthesis of benzhydryl (2S,4aS,6aS,6bR,8aR,9S, 10S,12aS,12bR,14bR)-2,4a,6a,6b,9,12a-hexamethyl-9-((((5-methyl-2-oxo-1,3-dioxol-4-yl)methoxy)carbonyl)amino)-13-oxo-10-propoxy-1,2,3,4,4a,5,6,6a, 6b,7,8,8a,9,10,11,12,12a,12b,13,14b-icosahydropicene-2-carboxylate (322-5)

Into a 50-mL round-bottom flask was placed $CH_2Cl_2$ (3 mL), 322-4 (135 mg, 0.19 mmol, 1 equiv), TMSCl (104 mg, 1 mmol, 5 equiv), and 4-(hydroxymethyl)-5-methyl-2H-1, 3-dioxol-2-one (74.6 mg, 0.57 mmol, 3 equiv). The reaction slurry was stirred overnight at room temperature. The reaction mixture was diluted with brine and extracted with 3×30 mL of ethyl acetate. The combined organic layers were washed with 2×20 mL of brine, dried over anhydrous $Na_2SO_4$, filtered, and concentrated. The residue was applied onto a silica gel column with ethyl acetate:petroleum ether (1:1) to provide 100 mg (64%) of 322-5 as a yellow solid.

Synthesis of (2S,4aS,6aS,6bR,8aR,9S,10S,12aS, 12bR,14bR)-2,4a,6a,6b,9,12a-hexamethyl-9-((((5-methyl-2-oxo-1,3-dioxol-4-yl)methoxy)carbonyl) amino)-13-oxo-10-propoxy-1,2,3,4,4a,5,6,6a,6b,7,8, 8a,9,10,11,12,12a,12b,13,14b-icosahydropicene-2-carboxylic Acid (322-6)

Into a 100-mL round-bottom flask was placed 322-5 (80 mg, 1 equiv), $CH_2Cl_2$ (10 mL), and TFA (1 mL). The resulting solution was stirred for 1 hr at room temperature then concentrated. The crude product was purified by prep-HPLC with the following conditions: column, Xselect CSH OBD 30*150 mm, 5 µm; mobile phase, water (0.05% TFA) and $CH_3CN$ (70% Phase B up to 75% in 8 min); detector, UV. This resulted in 13.9 mg of 322-6 as a white solid. MS (ES, m/z): [M+1]$^+$=670.4; $^1$H NMR (400 MHz, methanol-d$_4$) δ 5.61 (s, 1H), 4.91 (d, J=14.2 Hz, 1H), 4.77 (d, J=14.1 Hz, 1H), 4.02 (d, J=10.0 Hz, 1H), 3.52 (dt, J=9.5, 6.4 Hz, 1H), 2.72 (d, J=13.2 Hz, 1H), 2.55 (s, 1H), 2.24 (s, 1H), 2.19 (s, 3H), 2.21-2.10 (m, 2H), 1.97 (d, J=9.0 Hz, 1H), 1.87 (d, J=12.9 Hz, 1H), 1.83-1.64 (m, 2H), 1.56 (dd, J=18.8, 10.8 Hz, 2H), 1.49 (t, J=7.0 Hz, 2H), 1.43 (d, J=10.4 Hz, 7H), 1.36-1.19 (m, 2H), 1.19 (s, 3H), 1.14 (d, J=2.0 Hz, 6H), 1.04 (s, 6H), 0.93-0.83 (m, 6H).

Example 70 (2S,4aS,6aS,6bR,8aR,9S,10S,12aS, 12bR,14bR)-9-(((((5-isopropyl-2-oxo-1,3-dioxol-4-yl)methoxy)carbonyl)amino)-2,4a,6a,6b,9,12a-hexamethyl-13-oxo-10-propoxy-1,2,3,4,4a,5,6,6a,6b,7, 8,8a,9,10,1142,12a,12b,13,14b-icosahydropicene-2-carboxylic Acid (323-1)

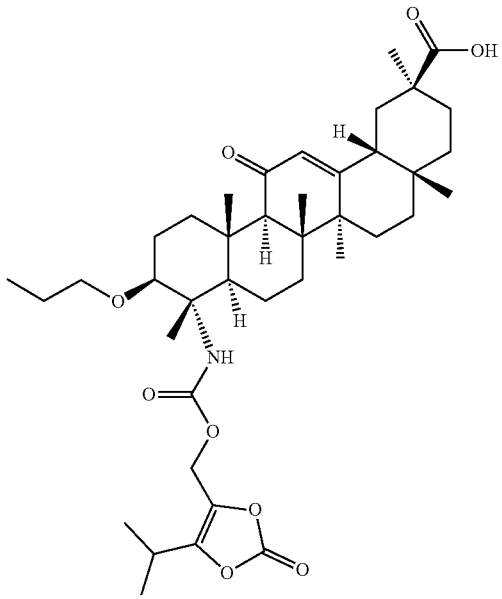

323-1

Synthesis of (2S,4aS,6aS,6bR,8aR,9S,10S,12aS,12bR,14bR)-9-((((5-isopropyl-2-oxo-1,3-dioxol-4-yl)methoxy)carbonyl)amino)-2,4a,6a,6b,9,12a-hexamethyl-13-oxo-10-propoxy-1,2,3,4,4a,5,6,6a,6b,7,8,8a,9,10,11,12,12a,12b,13,14b-icosahydropicene-2-carboxylic Acid (323-1)

The title compound was prepared with 322-4 and 4-(hydroxymethyl)-5-(propan-2-yl)-2H-1,3-dioxol-2-one (prepared according to literature procedures from Sun et al, Tetrahedron Letters, 2002, 43, 1161-1164) according to the methods to synthesize 322-6. The crude product was purified by prep-HPLC with the following conditions: XSelect CSH Prep C18 OBD column, 5 μm, 30*150 mm; mobile phase, water (0.05% TFA) and $CH_3CN$ (78% phase B up to 84% in 8 min); detector, 254 nm, to provide 49.9 mg (41%) of 321-1 as a white solid. MS (ES, m/z) [M+1]$^+$=698; $^1$H NMR (400 MHz, methanol-$d_4$) δ 0.88 (dd, J=13.5, 6.0 Hz, 6H), 1.02 (d, J=15.2 Hz, 3H), 1.11-1.31 (m, 17H), 1.48 (dt, J=20.1, 6.7 Hz, 8H), 1.58 (s, 3H), 1.76 (d, J=13.2 Hz, 1H), 1.82-1.99 (m, 1H), 2.13 (s, 1H), 2.55 (s, 1H), 2.73 (d, J=13.8 Hz, 1H), 3.03-3.14 (m, 1H), 3.35 (d, J=2.8 Hz, 3H), 3.52 (dt, J=12.4, 6.2 Hz, 1H), 4.02 (d, J=10.9 Hz, 1H), 4.92 (d, J=14.9 Hz, 2H), 5.62 (d, J=5.1 Hz, 1H).

Example 71 (2S,4aS,6aS,6bR,8aR,9S,10S,12aS,12bR,14bR)-10-methoxy-2,4a,6a,6b,9,12a-hexamethyl-9-((((5-methyl-2-oxo-1,3-dioxol-4-yl)methoxy)carbonyl)amino)-13-oxo-1,2,3,4,4a,5,6,6a,6b,7,8,8a,9,10,1142,12a,12b,13,14b-icosahydropicene-2-carboxylic Acid (324-3)

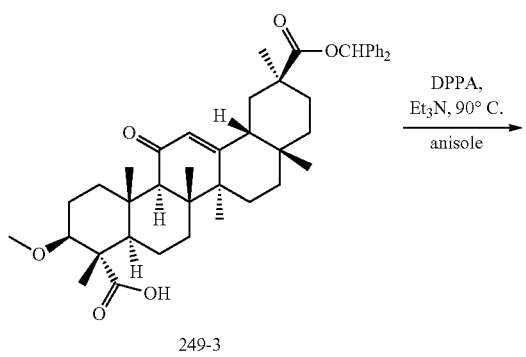

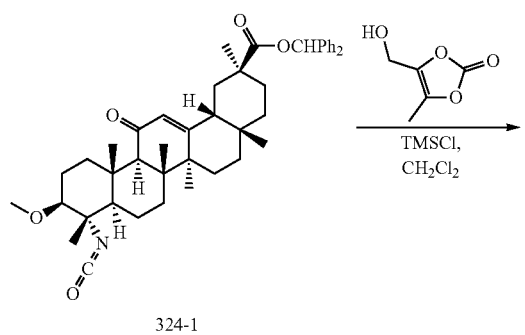

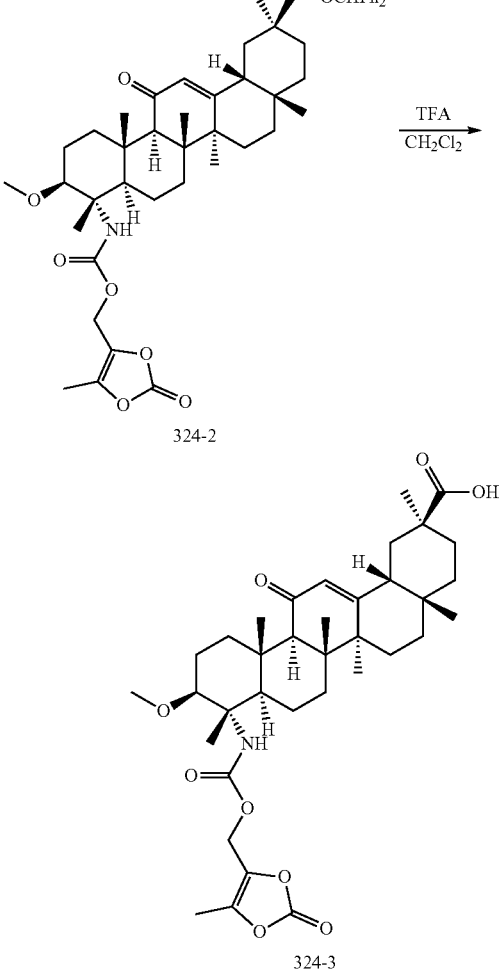

Synthesis of benzhydryl (2S,4aS,6aS,6bR,8aR,9S,10S,12aS,12bR,14bR)-9-isocyanato-10-methoxy-2,4a,6a,6b,9,12a-hexamethyl-13-oxo-1,2,3,4,4a,5,6,6a,6b,7,8,8a,9,10,11,12,12a,12b,13,14b-icosahydropicene-2-carboxylate (324-1)

Into a 8-mL round-bottom flask was placed 249-3 (160 mg, 0.24 mmol), anisole (1.6 mL), Et$_3$N (50 uL, 0.35 mmol, 1.5 equiv), and DPPA (76 uL, 0.35 mmol, 1.5 equiv). The reaction slurry was stirred for 1 hr at 90° C. in an oil bath. The reaction mixture was concentrated. The residue was applied onto a silica gel column with ethyl acetate:petroleum ether (1:5) to provide 140 mg (88%) of 324-1 as a white solid.

Synthesis of benzhydryl (2S,4aS,6aS,6bR,8aR,9S,10S,12aS,12bR,14bR)-10-methoxy-2,4a,6a,6b,9,12a-hexamethyl-9-((((5-methyl-2-oxo-1,3-dioxol-4-yl)methoxy)carbonyl)amino)-13-oxo-1,2,3,4,4a,5,6,6a,6b,7,8,8a,9,10,11,12,12a,12b,13,14b-icosahydropicene-2-carboxylate (324-2)

Into an 8-mL round-bottom flask was placed 324-1 (140 mg, 0.21 mmol), CH$_2$Cl$_2$ (2 mL), TMSCl (89 uL, 5 equiv), amd 4-(hydroxym ethyl)-5-methyl-2H-1,3-dioxol-2-one (81 mg, 0.62 mmol, 3 equiv). The reaction slurry was stirred overnight at room temperature. The resulting mixture was concentrated. The residue was applied onto a silica gel column with ethyl acetate:petroleum ether (1:3) to provide 150 mg (90%) of 324-2 as a white solid.

Synthesis of (2S,4aS,6aS,6bR,8aR,9S,10S,12aS, 12bR,14bR)-10-methoxy-2,4a,6a,6b,9,12a-hexamethyl-9-((((5-methyl-2-oxo-1,3-di oxol-4-yl) methoxy)carbonyl)amino)-13-oxo-1,2,3,4,4a,5,6,6a, 6b,7,8,8a,9,10,11,12,12a,12b,13,14b-icosahydropicene-2-carboxylic Acid (324-3)

Into a 50-mL round-bottom flask was placed 324-2 (150 mg, 0.19 mmol), $CH_2Cl_2$ (10 mL), and TFA (1 mL). The reaction slurry was stirred for 30 minutes at room temperature. The reaction mixture was concentrated. The crude product was purified by prep-HPLC with the following conditions: column, Xselect CSH OBD 30*150 mm, 5 μm; mobile phase, water (0.05% TFA) and $CH_3CN$ (61% Phase B up to 66% in 8 min); detector, UV. This resulted in 47.8 mg (40%) of 324-3 as a white solid. MS (ES, m/z): $[M+1]^+$= 642; $^1$H NMR (300 MHz, methanol-$d_4$) δ 0.85 (s, 3H), 1.03 (s, 3H), 1.09 (s, 1H), 1.12-1.23 (m, 9H), 1.23-1.37 (m, 1H), 1.44 (d, J=7.4 Hz, 13H), 1.53-1.81 (m, 2H), 1.85 (s, 2H), 1.89 (s, OH), 1.96 (s, 1H), 2.12 (d, J=11.1 Hz, 1H), 2.20 (s, 3H), 2.24 (s, 1H), 2.55 (s, 1H), 2.74 (d, J=13.5 Hz, 1H), 3.36 (s, 3H), 3.97 (d, J=9.1 Hz, 1H), 5.61 (s, 1H), 7.34 (dt, J=14.9, 7.5 Hz, 1H).

Example 72 (2S,4aS,6aS,6bR,8aR,9S,10S,12aS, 12bR,14bR)-9-((((5-isopropyl-2-oxo-1,3-dioxol-4-yl)methoxy)carbonyl)amino)-10-methoxy-2,4a,6a, 6b,9,12a-hexamethyl-13-oxo-1,2,3,4,4a,5,6,6a,6b,7, 8,8a,9,10,1142,12a,12b,13,14b-icosahydropicene-2-carboxylic (325-1)

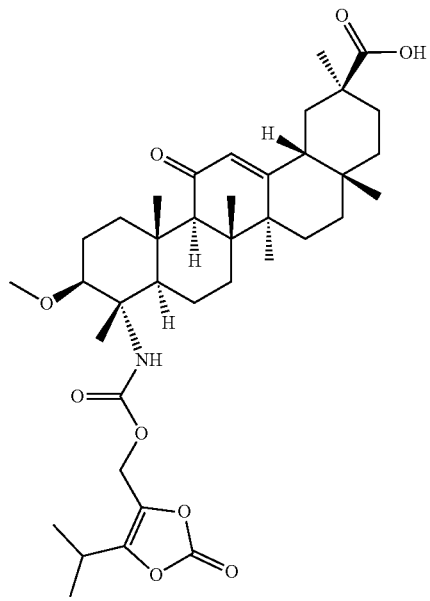

325-1

Synthesis of (2S,4aS,6aS,6bR,8aR,9S,10S,12aS, 12bR,14bR)-9-((((5-isopropyl-2-oxo-1,3-dioxol-4-yl)methoxy)carbonyl)amino)-10-methoxy-2,4a,6a, 6b,9,12a-hexamethyl-13-oxo-1,2,3,4,4a,5,6,6a,6b,7, 8,8a,9,10,11,12,12a,12b,13,14b-icosahydropicene-2-carboxylic Acid (325-1)

The title compound was prepared with 324-1 and 4-(hydroxymethyl)-5-(propan-2-yl)-2H-1,3-dioxol-2-one (prepared according to literature procedures from Sun et al, Tetrahedron Letters, 2002, 43, 1161-1164) according to the methods to synthesize 324-3. The crude product was purified by prep-HPLC with the following conditions: column, Xselect CSH OBD 30*150 mm, 5 μm; mobile phase, water (0.05% TFA) and $CH_3CN$ (70% Phase B up to 75% in 8 min); detector, UV. This resulted in 66.5 mg (52%) of 325-1 as a white solid. MS (ES, m/z): $[M+1]^+$=670; $^1$H NMR (300 MHz, methanol-$d_4$) δ 0.85 (s, 3H), 1.03 (s, 4H), 1.09 (s, 1H), 1.12-1.22 (m, 9H), 1.22-1.37 (m, 8H), 1.43 (d, J=5.2 Hz, 8H), 1.57 (s, 3H), 1.69 (s, 1H), 1.76 (d, J=13.3 Hz, 1H), 1.87 (d, J=13.1 Hz, 3H), 1.97 (d, J=9.7 Hz, 1H), 2.14 (dd, J=18.4, 7.5 Hz, 2H), 2.23 (d, J=10.7 Hz, 1H), 2.55 (s, 1H), 2.74 (d, J=13.7 Hz, 1H), 3.08 (p, J=6.9 Hz, 1H), 3.36 (s, 3H), 3.96 (d, J=12.0 Hz, 1H), 4.89 (s, 1H), 5.61 (s, 1H).

Example 73 (2S,4aS,6aS,6bR,8aR,9S,10S,12aS, 12bR,14bR)-10-acetoxy-9-((((5-ethyl-2-oxo-1,3-dioxol-4-yl)methoxy)carbonyl)amino)-2,4a,6a,6b,9, 12a-hexamethyl-13-oxo-1,2,3,4,4a,5,6,6a,6b,7,8,8a, 9,10,1142,12a,12b,13,14b-icosahydropicene-2-carboxylic (326-1)

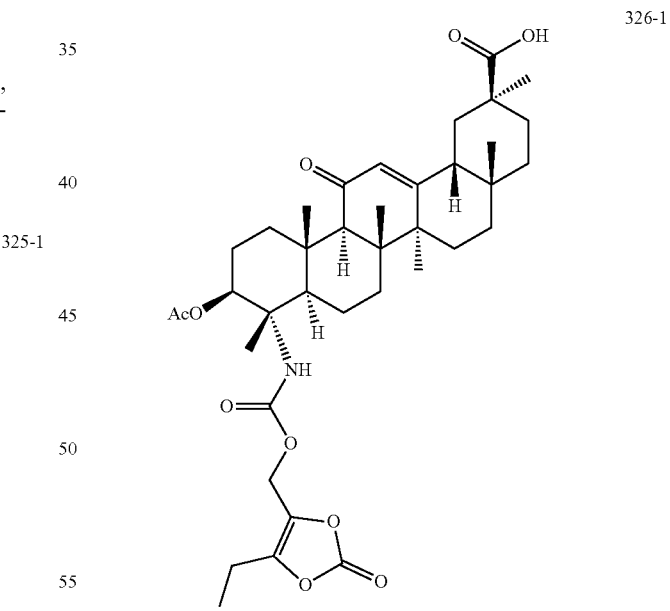

326-1

Synthesis of (2S,4aS,6aS,6bR,8aR,9S,10S,12aS, 12bR,14bR)-10-acetoxy-9-((((5-ethyl-2-oxo-1,3-dioxol-4-yl)methoxy)carbonyl)amino)-2,4a,6a,6b,9, 12a-hexamethyl-13-oxo-1,2,3,4,4a,5,6,6a,6b,7,8,8a, 9,10,11,12,12a,12b,13,14b-icosahydropicene-2-carboxylic acid (326-1)

The title compound was prepared with 254-1 and 4-(hydroxymethyl)-5-ethyl-2H-1,3-dioxol-2-one (prepared according to literature procedures from Sun et al, Tetrahedron Letters, 2002, 43, 1161-1164) according to the methods to synthesize 255-2. The mixture was concentrated under vacuum and the residue purified by prep-HPLC with the following conditions—Column: XSelect CSH Prep C18 OBD, 5 μm, 19*150 mm; mobile phase: water (0.05% TFA) and CH$_3$CN (63% Phase B up to 65% in 8 min); detector: UV. This resulted in 39.3 mg of 326-1 as a white solid. MS (ES, m/z): [M+H]$^+$=684; $^1$H NMR (300 MHz, methanol-d$_4$) δ 0.83-0.89 (s, 3H), 1.08-1.34 (m, 18H), 1.40-1.60 (d, J=10.0 Hz, 7H), 1.67-1.82 (dd, J=11.3, 15.7 Hz, 2H), 1.83-1.98 (m, 4H), 1.98-2.04 (s, 6H), 2.18-2.24 (s, 2H), 2.29-2.39 (d, J=10.8 Hz, 1H), 2.54-2.67 (q, J=7.5 Hz, 3H), 2.71-2.81 (d, J=12.9 Hz, 1H), 4.70-4.86 (t, J=14.8 Hz, 2H), 5.51-5.65 (m, 2H).

Example 74 (2S,4aS,6aS,6bR,8aR,9S,10S,12aS, 12bR,14bR)-10-(4,4-difluoropiperidin-1-yl)-9-((((5-isopropyl-2-oxo-1,3-dioxol-4-yl)methoxy)carbonyl) amino)-2,4a,6a,6b,9,12a-hexamethyl-13-oxo-1,2,3,4, 4a,5,6,6a,6b,7,8,8a,9,10,11,12,12a,12b,13,14b-icosahydropicene-2-carboxylic Acid (327-8)

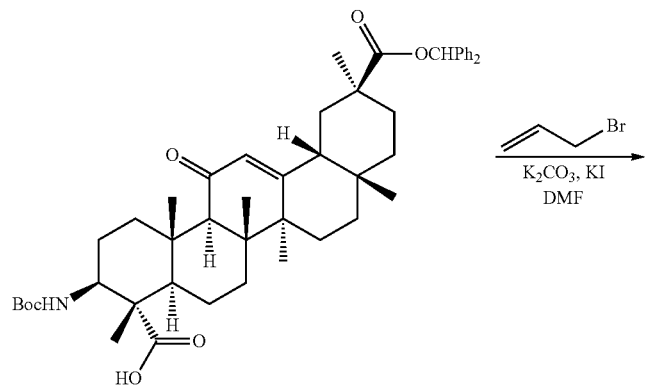

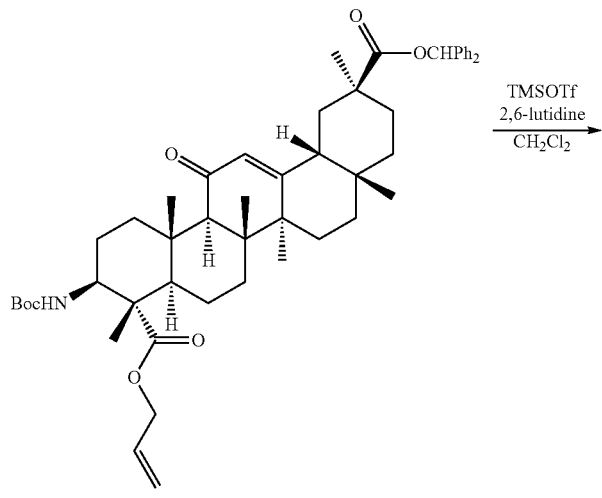

-continued
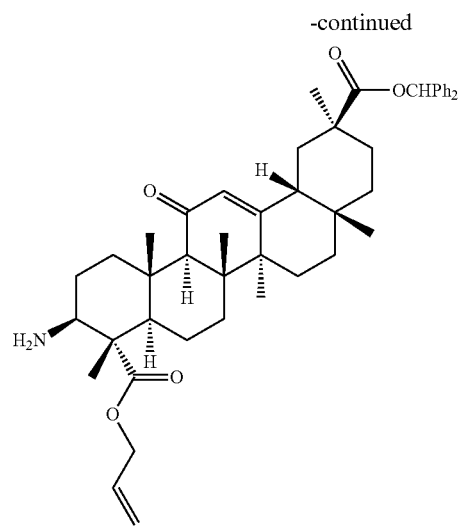
327-2
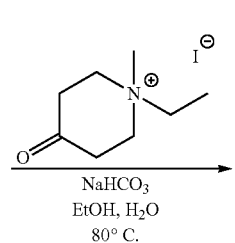
NaHCO₃
EtOH, H₂O
80° C.
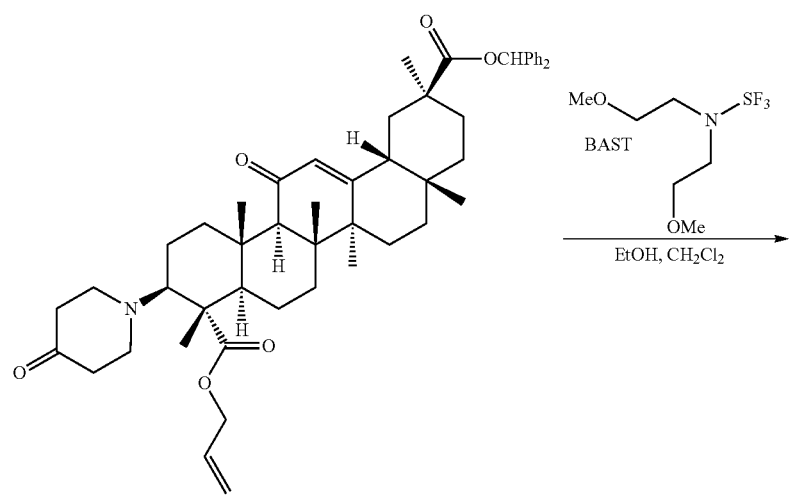
327-2
BAST
EtOH, CH₂Cl₂
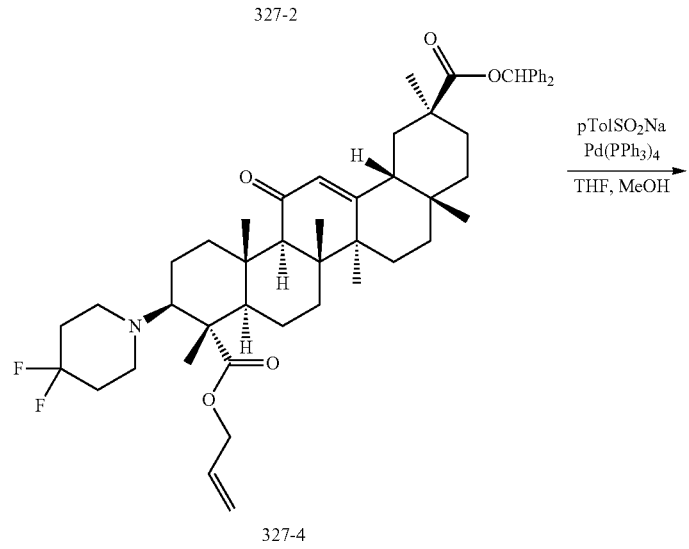
327-4
pTolSO₂Na
Pd(PPh₃)₄
THF, MeOH

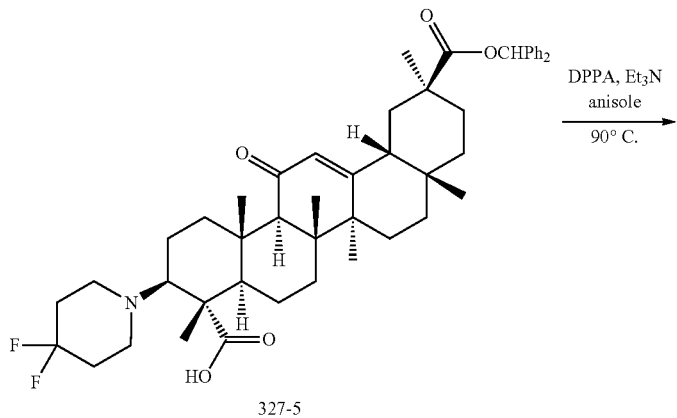
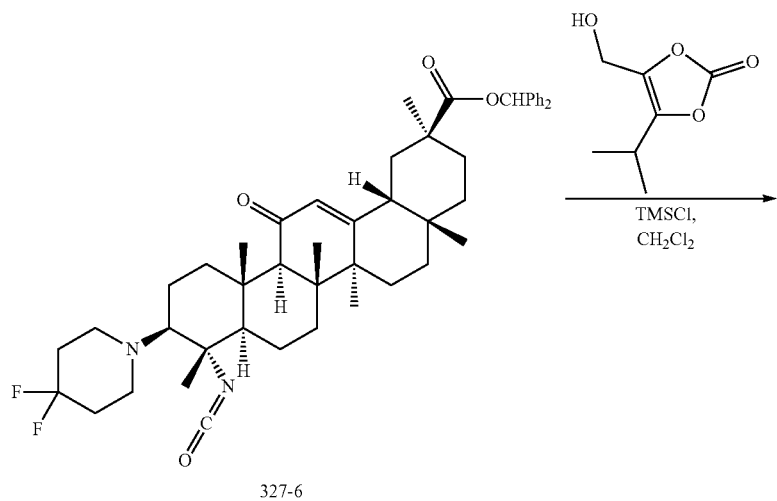
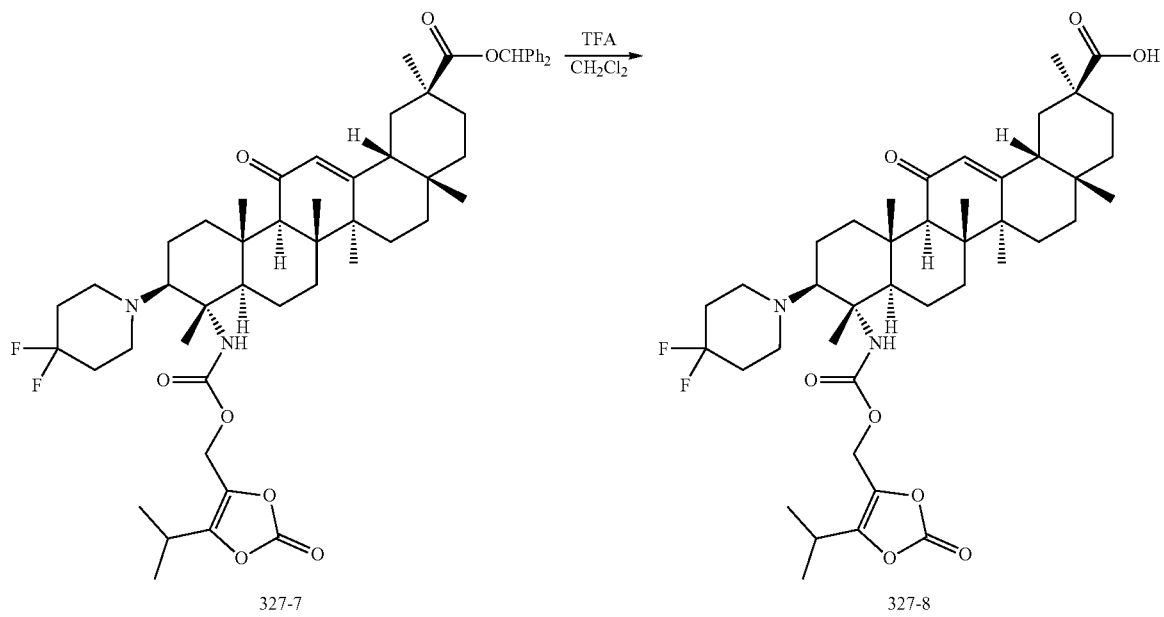

Synthesis of 9-allyl 2-benzhydryl (2S,4aS,6aS,6bR, 8aR,9S,10S,12aS,12bR,14bR)-10-((tert-butoxycarbonyl)amino)-2,4a,6a,6b,9,12a-hexamethyl-13-oxo-1,2,3,4,4a,5,6,6a,6b,7,8,8a,9,10,11,12,12a,12b,13, 14b-icosahydropicene-2,9-dicarboxylate (327-1)

Into a 50-mL round-bottom flask was placed 280-5 (600 mg, 0.78 mmol), DMF (6 mL), 3-bromoprop-1-ene (0.27 mL, 4 equiv), KI (66 mg, 0.4 mmol, 0.5 equiv), and $K_2CO_3$ (540 mg, 4 mmol, 5 equiv). The reaction slurry was stirred for 1 hr at room temperature. The reaction mixture was extracted with 300 mL of $CH_2Cl_2$, washed with 3×300 ml of brine, dried over anhydrous $Na_2SO_4$, filtered, and concentrated. The residue was applied onto a silica gel column with ethyl acetate:petroleum ether (1:5) to provide 616 mg (98%) of 327-1 as a white solid.

Synthesis of 9-allyl 2-benzhydryl (2S,4aS,6aS,6bR, 8aR,9S,10S,12aS,12bR,14bR)-10-amino-2,4a,6a,6b, 9,12a-hexamethyl-13-oxo-1,2,3,4,4a,5,6,6a,6b,7,8, 8a,9,10,11,12,12a,12b,13,14b-icosahydropicene-2,9-dicarboxylate (327-2)

Into a 100-mL round-bottom flask was placed 327-1 (616 mg, 0.76 mmol), $CH_2Cl_2$ (50 mL), and 2,6-lutidine (0.44 mL, 5 equiv). To this slurry was added TMSOTf (679 mg, 3.1 mmol, 4 equiv) at 0° C. The reaction slurry was stirred for 1 hr at room temperature. The reaction mixture was washed with 3×300 ml of brine, dried over anhydrous $Na_2SO_4$, filtered, and concentrated to provide 600 mg (quant) of 327-2 as a yellow solid.

Synthesis of 9-allyl 2-benzhydryl (2S,4aS,6aS,6bR, 8aR,9S,10S,12aS,12bR,14bR)-2,4a,6a,6b,9,12a-hexamethyl-13-oxo-10-(4-oxopiperidin-1-yl)-1,2,3, 4,4a,5,6,6a,6b,7,8,8a,9,10,11,12,12a,12b,13,14b-icosahydropicene-2,9-dicarboxylate (327-3)

Into a 100-mL round-bottom flask was placed 327-2 (3 g), 1-ethyl-1-methyl-4-oxopiperidin-1-ium iodide (2.18 g, 2 equiv), EtOH (3 mL), $H_2O$ (6 mL), and $NaHCO_3$ (850 mg, 2.5 equiv). The reaction slurry was stirred for 1 hr at 80° C. then concentrated. The residue was applied onto a silica gel column with ethyl acetate:petroleum ether (1:1) to provide 2.5 g of 327-3 as a light yellow solid.

Synthesis of 9-allyl 2-benzhydryl (2S,4aS,6aS,6bR, 8aR,9S,10S,12aS,12bR,14bR)-10-(4,4-difluoropiperidin-1-yl)-2,4a,6a,6b,9,12a-hexamethyl-13-oxo-1, 2,3,4,4a,5,6,6a,6b,7,8,8a,9,10,11,12,12a,12b,13,14b-icosahydropicene-2,9-dicarboxylate (327-4)

Into a 25-mL round-bottom plastic flask was placed 327-3 (300 mg), BAST (170 mg, 2 equiv), EtOH (5 mg, 0.3 equiv), and $CH_2Cl_2$ (3 mL). The reaction slurry was stirred for 12 hr at room temperature and concentrated. The residue was applied onto a silica gel column with ethyl acetate:petroleum ether (1:2) to provide 210 mg (68%) of 327-4 as a yellow solid.

Synthesis of (3S,4S,4aR,6aR,6bS,8aS,11S,12aR, 14aR,14bS)-11-((benzhydryloxy)carbonyl)-3-(4,4-difluoropiperidin-1-yl)-4,6a,6b,8a,11,14b-hexamethyl-14-oxo-1,2,3,4,4a,5,6,6a,6b,7,8,8a,9,10,11,12, 12a,14,14a,14b-icosahydropicene-4-carboxylic Acid (327-5)

Into a 100-mL round-bottom flask was placed 327-4 (810 mg), $Pd(PPh_3)_4$ (700 mg, 0.6 equiv), $pTolSO_2Na$ (360 mg, 1.4 equiv), THF (10 mL), and MeOH (30 mL). The reaction slurry was stirred for 1 hr at room temperature at $N_2$ atmosphere then concentrated. The residue was applied onto a silica gel column with $CH_2Cl_2$:methanol (10:1) to provide 660 mg (86%) of 327-5 as a yellow solid.

Synthesis of benzhydryl (2S,4aS,6aS,6bR,8aR,9S, 10S,12aS,12bR,14bR)-10-(4,4-difluoropiperidin-1-yl)-9-isocyanato-2,4a,6a,6b,9,12a-hexamethyl-13-oxo-1,2,3,4,4a,5,6,6a,6b,7,8,8a,9,10,11,12,12a,12b, 13,14b-icosahydropicene-2-carboxylate (327-6)

Into a 100-mL round-bottom flask was placed 327-5 (200 mg), DPPA (107 mg, 1.5 equiv), $Et_3N$ (40 mg, 1.5 equiv), and anisole (2 mL). The reaction slurry was stirred for 1 hr at 90° C. The reaction mixture was concentrated and the residue applied onto a silica gel column with ethyl acetate: petroleum ether (1:1) to provide 130 mg (65%) of 327-6 as a white solid.

Synthesis of benzhydryl (2S,4aS,6aS,6bR,8aR,9S, 10S,12aS,12bR,14bR)-10-(4,4-difluoropiperidin-1-yl)-9-((((5-isopropyl-2-oxo-1,3-dioxol-4-yl) methoxy)carbonyl)amino)-2,4a,6a,6b,9,12a-hexamethyl-13-oxo-1,2,3,4,4a,5,6,6a,6b,7,8,8a,9,10, 11,12,12a,12b,13,14b-icosahydropicene-2-carboxylate (327-7)

Into a 100-mL round-bottom flask was placed 327-6 (70 mg), $CH_2Cl_2$ (3 mL), TMSCl (50 mg, 5 equiv), and 4-(hydroxymethyl)-5-isopropyl-1,3-dioxol-2-one (50 mg, 4.2 equiv). The reaction slurry was stirred for 12 hr at room temperature then concentrated. The residue was applied onto a silica gel column with ethyl acetate:petroleum ether (1:1) to provide 100 mg of 327-7 as colorless oil.

Synthesis of (2S,4aS,6aS,6bR,8aR,9S,10S,12aS, 12bR,14bR)-10-(4,4-difluoropiperidin-1-yl)-9-((((5-isopropyl-2-oxo-1,3-dioxol-4-yl)methoxy)carbonyl) amino)-2,4a,6a,6b,9,12a-hexamethyl-13-oxo-1,2,3,4, 4a,5,6,6a,6b,7,8,8a,9,10,11,12,12a,12b,13,14b-icosahydropicene-2-carboxylic acid (327-8)

Into a 25-mL round-bottom flask, was placed 327-7 (90 mg), TFA (1 ml), and $CH_2Cl_2$ (5 ml). The resulting solution was stirred for 1 hr at room temperature then concentrated. The crude product was purified by prep-HPLC with the following conditions: Column: XSelect CSH Prep $C_{18}$; mobile phase, water (0.05% TFA) and $CH_3CN$ (38% Phase B up to 45% in 8 min); detector: UV. This resulted in 4.6 mg (3%) of 327-8 as a colorless oil. MS (ES, m/z) $[M+H]^+$ =759.5; $^1H$ NMR (300 MHz, methanol-$d_4$) δ 0.85 (s, 3H), 1.07 (d, J=14.8 Hz, 2H), 1.14-1.22 (m, 11H), 1.20-1.33 (m, 11H), 1.43 (s, 7H), 1.48 (d, J=12.8 Hz, 2H), 1.58 (s, 2H), 1.71 (q,7=12.8, 12.4 Hz, 3H), 1.87 (d, J=14.6 Hz, 3H), 2.12 (s, 2H), 2.36 (d, J=11.2 Hz, 3H), 2.99 (s, 1H),3.10 (s, 1H), 3.30 (s, 1H), 3.50 (d, J=12.0 Hz, 2H), 3.55-3.60 (m, 1H), 4.95 (d, J=14.2 Hz, 1H), 5.05 (d, J=14.2 Hz, 1H), 5.63 (s, 1H).

Example 75 (2S,4aS,6aS,6bR,8aR,9S,10S,12aS, 12bR,14bR)-2,4a,6a,6b,9,12a-hexamethyl-9-(((5-methyl-2-oxo-1,3-dioxol-4-yl)methoxy)carbonyl)-13-oxo-10-(1H-pyrrol-1-yl)-1,2,3,4,4a,5,6,6a,6b,7,8, 8a,9,10,1142,12a,12b,13,14b-icosahydropicene-2-carboxylic (328-2)

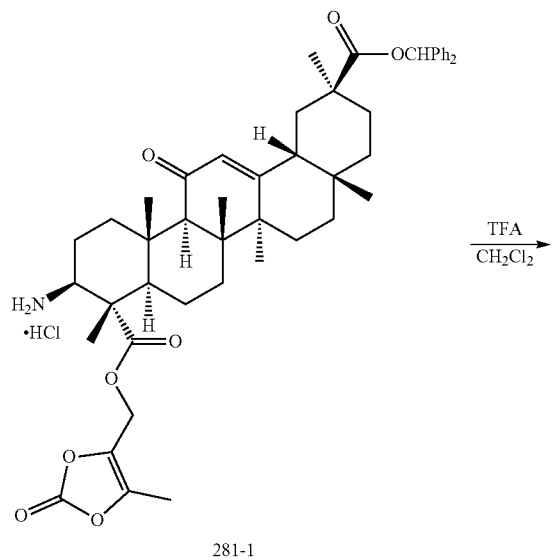

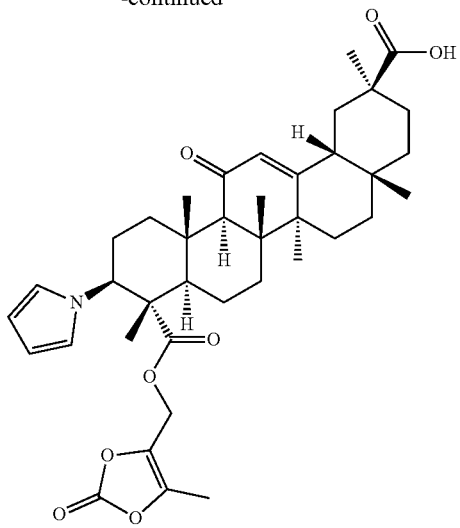

Synthesis of (2S,4aS,6aS,6bR,8aR,9S,10S,12aS, 12bR,14bR)-10-amino-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12, 12a,12b,13,14b-icosahydropicene-2-carboxylic Acid trifluoroacetate (328-1)

Into a 100-mL round-bottom flask was placed 281-1 (300 mg, 0.37 mmol), CH$_2$Cl$_2$ (10 mL), and TFA (1 mL). The resulting solution was stirred for 1 hr at room temperature. The resulting mixture was concentrated to provide 270 mg of 328-1 as a yellow solid.

Synthesis of (2S,4aS,6aS,6bR,8aR,9S,10S,12aS, 12bR,14bR)-2,4a,6a,6b,9,12a-hexamethyl-9-(((5-methyl-2-oxo-1,3-dioxol-4-yl)methoxy)carbonyl)-13-oxo-10-(1H-pyrrol-1-yl)-1,2,3,4,4a,5,6,6a,6b,7,8, 8a,9,10,11,12,12a,12b,13,14b-icosahydropicene-2-carboxylic Acid (328-2)

Into a 25-mL round-bottom flask was placed NaOAc (20 mg, 0.3 mmol, 1 equiv), H$_2$O (2 mL), 328-1 (200 mg, 0.31 mmol, 1 equiv), AcOH (0.5 mL), and 2,5-dimethoxyoxolane (0.032 mL, 0.31 mmol, 1 equiv). The reaction slurry was stirred for 2 hr at 75° C. The reaction mixture was extracted with 3×100 mL of ethyl acetate, washed with 2×150 ml of brine, dried over anhydrous Na$_2$SO$_4$, filtered, and concentrated. The crude product was purified by prep-HPLC with the following conditions: column, XSelect CSH OBD 30*150 mm, 5 μm; mobile phase, water (0.05% TFA) and CH$_3$CN (50% Phase B up to 55% in 8 min); detector, UV. This resulted in 44.2 mg of 328-2 as a white solid. MS (ES, m/z): [M+1]$^+$=662; $^1$H NMR (300 MHz, methanol-d$_4$) δ 6.61 (t, J=2.1 Hz, 2H), 5.98 (t, J=2.1 Hz, 2H), 5.64 (s, 1H), 5.15 (d, J=14.0 Hz, 1H), 4.84 (d, J=13.8 Hz, 1H), 4.52 (dd, J=13.0, 3.7 Hz, 1H), 2.97 (d, J=13.6 Hz, 1H), 2.63 (s, 1H), 2.39 (d, J=13.5 Hz, 1H), 2.25 (d, J=11.8 Hz, 1H), 2.20 (s, 3H), 1.97 (s, 1H), 1.89 (d, J=8.8 Hz, 1H), 1.83-1.70 (m, 2H), 1.52-1.24 (m, 12H), 1.19 (d, J=9.6 Hz, 6H), 1.06 (s, 4H), 0.93 (d, J=11.4 Hz, 1H), 0.86 (s, 3H).

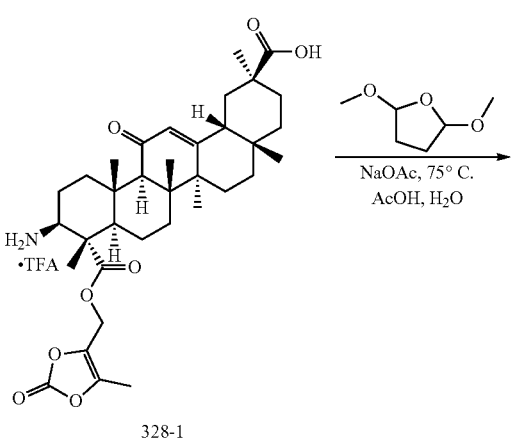

Example 76 (2S,4aS,6aS,6bR,8aR,9S,10S,12aS,12bR,14bR)-2,4a,6a,6b,9,12a-hexamethyl-9-(((5-methyl-2-oxo-1,3-dioxol-4-yl)methoxy)carbonyl)-13-oxo-10-(1H-pyrazol-1-yl)-1,2,3,4,4a,5,6,6a,6b,7,8,8a,9,10,1142,12a,12b,13,14b-icosahydropicene-2-carboxylic Acid
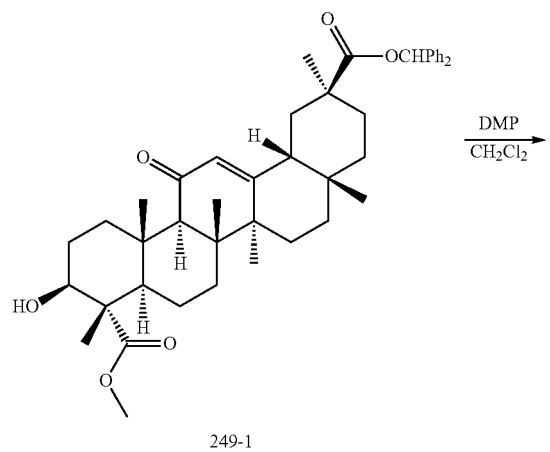
249-1
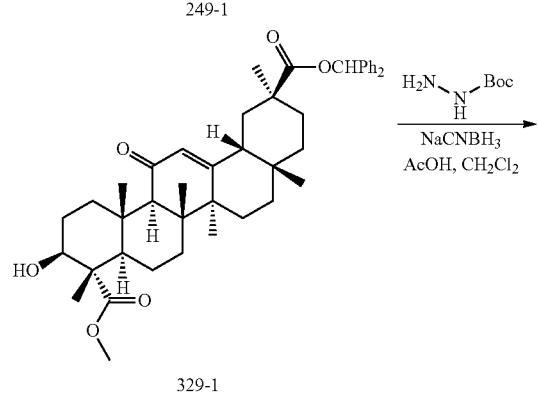
329-1
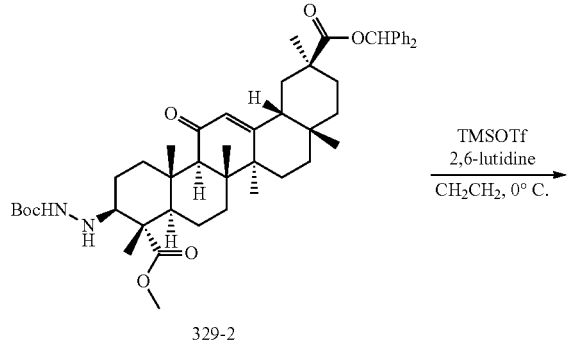
329-2
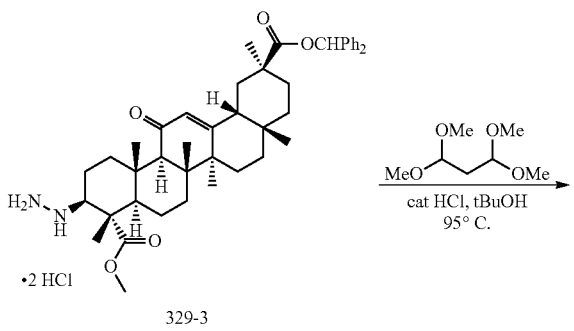
329-3
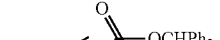
-continued
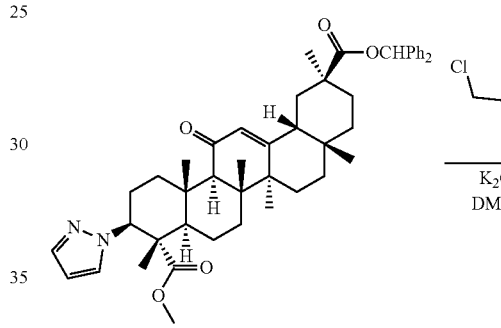
329-4
329-4
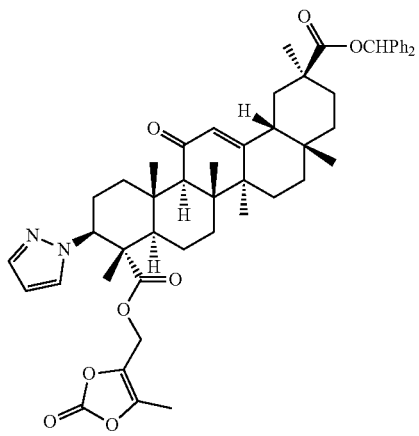
329-6

-continued

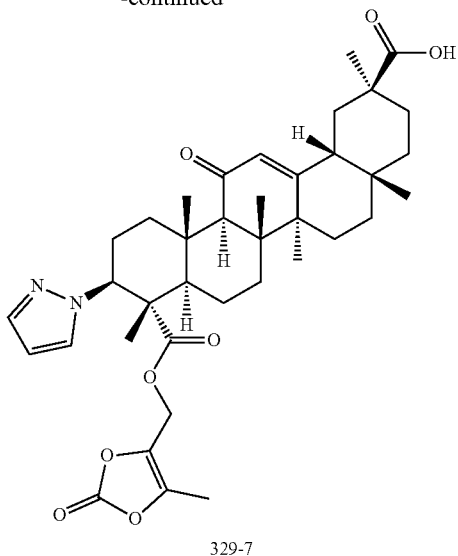

329-7

Synthesis of 2-benzhydryl 9-methyl (2S,4aS,6aS, 6bR,8aR,9S,12aS,12bR,14bR)-2,4a,6a, 6b,9,12a-hexamethyl-10,13-dioxo-1,2,3,4,4a,5,6,6a,6b,7,8,8a, 9,10,11,12,12a,12b,13,14b-icosahydropicene-2,9-dicarboxylate (329-1)

Into a 25-mL round-bottom flask was 249-1 (3.06 g, 4.5 mmol), CH$_2$Cl$_2$ (30 mL), and DMP (3.8 g, 9 mmol, 2 equiv). The reaction slurry was stirred for 3 hr at room temperature, adjusting the pH value of the solution to 8 with saturated NaHCO$_{3(aq)}$. The reaction mixture was extracted with 2×20 mL of CH$_2$Cl$_2$. The organic layer was washed with 3×100 mL of brine, dried over anhydrous Na$_2$SO$_4$, filtered, and concentrated. The residue was applied onto a silica gel column with ethyl acetate:petroleum ether (1:5) to provide 2.5 g (82%) of 329-1 as a light yellow solid.

Synthesis of 2-benzhydryl 9-methyl (2S,4aS,6aS, 6bR,8aR,9S,10S,12aS,12bR,14bR)-10-(2-(tert-butoxycarbonyl)hydrazinyl)-2,4a,6a,6b,9,12a-hexamethyl-13-oxo-1,2,3,4,4a,5,6,6a,6b,7,8,8a,9,10,11,12, 12a,12b,13,14b-icosahydropicene-2,9-dicarboxylate (329-2)

Into a 25-mL round-bottom flask was placed 329-1 (1.0 g, 1.5 mmol), (tert-butoxy)carbohydrazide (211 mg, 1.6 mmol, 1.1 equiv), CH$_2$Cl$_2$ (2 ml), and AcOH (2 ml). The reaction slurry was stirred for 2 h at room temperature, then treated with NaBH$_3$CN (111 mg, 1.76 mmol, 1.2 equiv). The reaction slurry was stirred overnight at room temperature. The reaction mixture was diluted with CH$_2$Cl$_2$ (100 ml) and the reaction quenched by the addition of 100 mL of water. The pH of the solution was adjusted to 9 with saturated NaHCO$_3$ (aq) and extracted with 2×100 ml of CH$_2$Cl$_2$. The combined organic layers were washed with 2×200 ml of brine, dried over anhydrous Na$_2$SO$_4$, filtered, and concentrated. The residue was applied onto a silica gel column with 1:5 ethyl acetate:petroleum ether to provide 880 mg (78%) of 329-2 as a white solid.

Synthesis of 2-benzhydryl 9-methyl (2S,4aS,6aS, 6bR,8aR,9S,10S,12aS,12bR,14bR)-10-hydrazinyl-2, 4a,6a,6b,9,12a-hexamethyl-13-oxo-1,2,3,4,4a,5,6,6a, 6b,7,8,8a,9,10,11,12,12a,12b,13,14b-icosahydropicene-2,9-dicarboxylate dihydrochloride (329-3)

Into a 100-mL round-bottom flask was placed 329-2 (850 mg, 1.1 mmol), CH$_2$Cl$_2$ (50 ml), and 2,6-lutidine (0.63 mL, 6.4 mmol, 5 equiv), followed by the addition of TMSOTf (0.77 mL, 4.3 mmol, 4 equiv) dropwise with stirring at rt. The reaction slurry was stirred for 1 h at room temperature. The reaction mixture was diluted with CH$_2$Cl$_2$ (450 ml) and washed with 200 ml of 0.07 M HCl in brine then 1×300 mL of brine. The organic layer was dried over anhydrous Na$_2$SO$_4$, filtered, and concentrated to provide 650 mg (83%) of crude 329-3 as a light yellow solid.

Synthesis of 2-benzhydryl 9-methyl (2S,4aS,6aS, 6bR,8aR,9S,10S,12aS,12bR,14bR)-2,4a,6a,6b,9,12a-hexamethyl-13-oxo-10-(1H-pyrazol-1-yl)-1,2,3,4,4a, 5,6,6a,6b,7,8,8a,9,10,11,12,12a,12b,13,14b-icosahydropicene-2,9-dicarboxylate (329-4

Into a 25-mL round-bottom flask was placed 329-3 (800 mg, 1.04 mmol) and t-BuOH (3 ml), 1,1,3,3-tetramethoxypropane (171 mg, 1.04 mmol, 1.0 equiv) followed by the addition of cone HCl (0.33 mL, v/v: 1/0.11) dropwise with stirring at rt. The reaction slurry was stirred for 1 h at 95° C. The reaction mixture was cooled and diluted with 100 mL of CH$_2$Cl$_2$, washed with 2×100 ml of brine, dried over anhydrous Na$_2$SO$_4$, filtered, and concentrated. The solid was dried in an oven under reduced pressure and applied onto a silica gel column with 1:5 ethyl acetate:petroleum ether to provide 631 mg (79%) of 329-4 as a white solid.

Synthesis of (3S,4S,4aR,6aR,6bS,8aS,11S,12aR, 14aR,14bS)-11-((benzhydryloxy)carbonyl)-4,6a,6b, 8a,11,14b-hexamethyl-14-oxo-3-(1H-pyrazol-1-yl)-1,2,3,4,4a,5,6,6a,6b,7,8,8a,9,10,11,12,12a,14,14a, 14b-icosahydropicene-4-carboxylic Acid (329-5)

Into a 25-mL sealed tube was placed 329-4 (400 mg, 0.55 mmol), pyridine (4 ml), and LiI (1.11 g, 1.62 mmol, 3 equiv). The reaction slurry was stirred overnight at 125° C. The reaction mixture was cooled and diluted with 100 mL of CH$_2$Cl$_2$ and washed with 2×100 ml of 0.5 M HCl. The organic layer was washed with 2×100 mL of brine, dried over anhydrous Na$_2$SO$_4$, filtered, and concentrated to provide 350 mg (89%) of 329-5 as a yellow solid.

Synthesis of 2-benzhydryl 9-((5-methyl-2-oxo-1,3-dioxol-4-yl)methyl) (2S,4aS,6aS,6bR,8aR,9S,10S, 12aS,12bR,14bR)-2,4a,6a,6b,9,12a-hexamethyl-13-oxo-10-(1H-pyrazol-1-yl)-1,2,3,4,4a,5,6,6a,6b,7,8, 8a,9,10,11,12,12a,12b,13,14b-icosahydropicene-2,9-dicarboxylate (329-6)

Into a 8-mL vial was 329-5 (140 mg, 0.195 mmol), 4-(chloromethyl)-5-methyl-2H-1,3-dioxol-2-one (44 mg, 0.293 mmol, 1.5 equiv), DMF (3 ml), KI (16 mg, 0.098 mmol, 0.5 equiv), and K$_2$CO$_3$ (80 mg, 0.59 mmol, 3 equiv). The reaction slurry was stirred overnight at room temperature. The reaction mixture was diluted with 30 mL of ethyl acetate and the reaction quenched by the addition of 20 ml of water. The layers were separated and the aqueous was extracted with 2×30 ml of ethyl acetate. The combined organic layers were washed with 3×80 ml of brine, dried over anhydrous Na$_2$SO$_4$, filtered, and concentrated. The residue was applied onto a silica gel column with 1:1 ethyl acetate:petroleum ether to provide 131 mg (81%) of 329-6 as a light yellow oil.

Synthesis of (2S,4aS,6aS,6bR,8aR,9S,10S,12aS, 12bR,14bR)-2,4a,6a,6b,9,12a-hexamethyl-9-(((5-methyl-2-oxo-1,3-dioxol-4-yl)methoxy)carbonyl)-13-oxo-10-(1H-pyrazol-1-yl)-1,2,3,4,4a,5,6,6a,6b,7, 8,8a,9,10,11,12,12a,12b,13,14b-icosahydropicene-2-carboxylic Acid (329-7)

Into a 8-mL vial was placed 329-6 (131 mg, 0.16 mmol), CH$_2$Cl$_2$ (3 ml), and TFA (0.3 ml). The reaction slurry was stirred for 30 min at room temperature then concentrated. The crude product was purified by prep-HPLC with the following conditions: column, X-Select CSH OBD 30*150 mm, 5 μm; mobile phase, water (0.05% TFA) and CH$_3$CN (68% Phase B up to 70% in 8 min); detector, UV. This resulted in 53.3 mg (51%) of 329-7 as a white solid. MS (ES, m/z): [M+1]$^+$=663; $^1$H NMR (400 MHz, methanol-d$_4$) δ 0.86 (s, 3H), 0.93 (s, 3H), 1.08 (d, J=14.0 Hz, 1H), 1.19 (d, J=13.4 Hz, 6H), 1.26 (s, 3H), 1.28-1.37 (m, 1H), 1.46 (d, J=24.2 Hz, 6H), 1.60-1.90 (m, 5H), 1.89 (s, 1H), 1.98 (d, J=9.9 Hz, 1H), 2.20 (s, 3H), 2.26 (s, 1H), 2.39-2.53 (m, 1H), 2.64 (s, 1H), 4.82 (dd, J=13.1, 3.9 Hz, 1H), 4.89 (d, J=14.0 Hz, 1H), 5.15 (d, J=13.9 Hz, 1H), 5.64 (s, 1H), 6.25 (t, J=2.1 Hz, 1H), 7.40 (d, J=1.9 Hz, 1H), 7.62 (d, J=2.4 Hz, 1H).

Example 77 (2S,4aS,6aS,6bR,8aR,9S,10S,12aS, 12bR,14bR)-9-(((5-isopropyl-2-oxo-1,3-dioxol-4-yl) methoxy)carbonyl)-2,4a,6a,6b,9,12a-hexamethyl-13-oxo-10-(1H-pyrazol-1-yl)-1,2,3,4,4a,5,6,6a,6b,7,8, 8a,9,10,1142,12a,12b,13,14b-icosahydropicene-2-carboxylic (330-1)

Synthesis of (2S,4aS,6aS,6bR,8aR,9S,10S,12aS, 12bR,14bR)-9-(((5-isopropyl-2-oxo-1,3-dioxol-4-yl) methoxy)carbonyl)-2,4a,6a,6b,9,12a-hexamethyl-13-oxo-10-(1H-pyrazol-1-yl)-1,2,3,4,4a,5,6,6a,6b,7,8, 8a,9,10,11,12,12a,12b,13,14b-icosahydropicene-2-carboxylic Acid (329-7)

The title compound was prepared with 249-1 and 4-(bromomethyl)-5-isopropyl-1,3-dioxol-2-one according to the methods to synthesize 329-7. The crude product was purified by prep-HPLC with the following conditions: column, X-Select CSH OBD 30*150 mm, 5 μm; mobile phase, water (0.05% TFA) and CH$_3$CN (73% Phase B up to 77% in 8 min); detector, UV. This resulted in 46.3 mg of 330-1 as a white solid. MS (ES, m/z): [M+1]$^+$=692; $^1$H NMR (400 MHz, methanol-d$_4$) δ 0.86 (s, 3H), 0.93 (s, 3H), 1.08 (d, J=13.7 Hz, 1H), 1.17 (s, 3H), 1.19-1.33 (m, 12H), 1.31-1.49 (m, 5H), 1.49 (s, 3H), 1.70 (dd, J=29.2, 13.2 Hz, 2H), 1.77-1.88 (m, 1H), 1.85-1.92 (m, 1H), 1.98 (d, J=10.1 Hz, 1H), 2.21 (ddd, J=27.9, 13.4, 4.2 Hz, 2H), 2.39-2.54 (m, 1H), 2.64 (s, 1H), 2.96-3.04 (m, 1H), 3.09 (p, J=7.0 Hz, 1H), 4.83 (dd, J=13.1, 3.9 Hz, 1H), 4.93 (d, J=13.9 Hz, 1H), 5.16 (d, J=13.9 Hz, 1H), 5.64 (s, 1H), 6.25 (t, J=2.2 Hz, 1H), 7.40 (d, J=1.9 Hz, 1H), 7.62 (d, J=2.4 Hz, 1H).

Example 78 (2S,4aS,6aS,6bR,8aR,9S,10S,12aS, 12bR,14bR)-2,4a,6a,6b,9,12a-hexamethyl-10-(5-methyl-1H-pyrazol-1-yl)-9-(((5-methyl-2-oxo-1,3-dioxol-4-yl)methoxy)carbonyl)-13-oxo-1,2,3,4,4a,5, 6,6a,6b,7,8,8a,9,10,11,12,12a,12b,13,14b-icosahydropicene-2-carboxylic Acid (331-2)

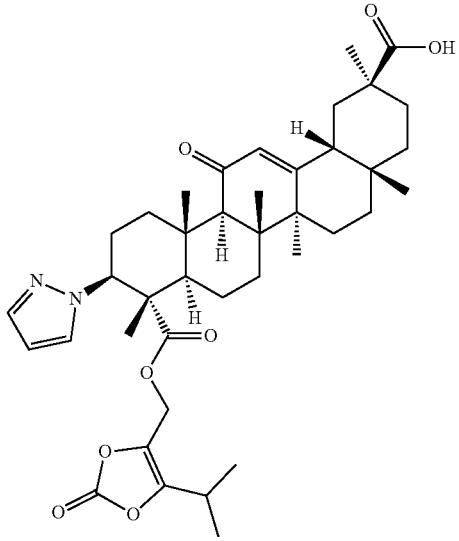

330-1

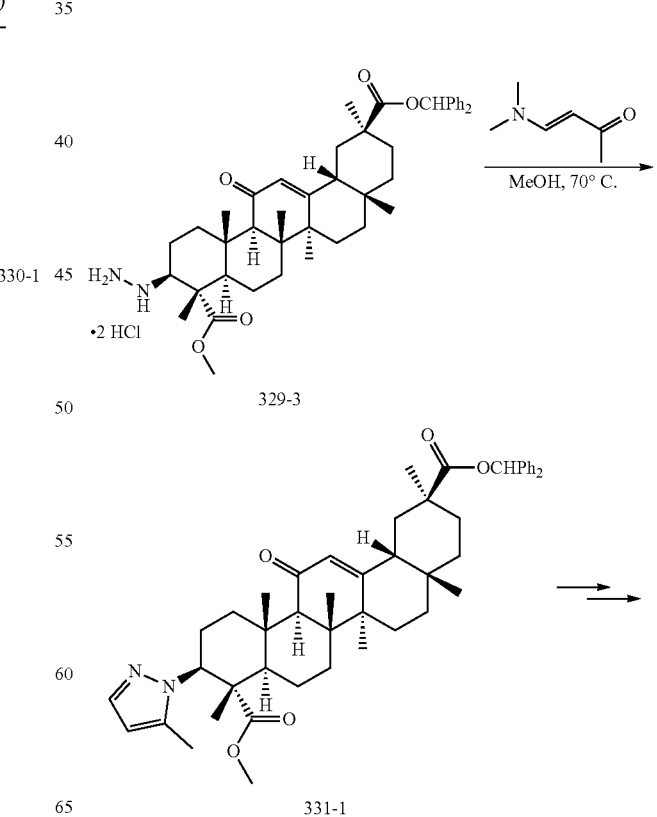

-continued

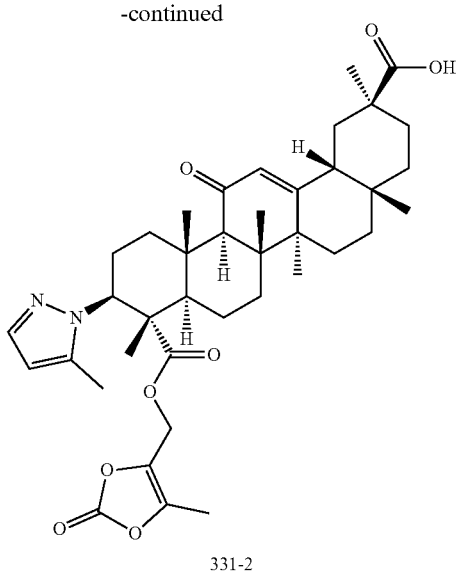

331-2

Synthesis of 2-benzhydryl 9-methyl (2S,4aS,6aS, 6bR,8aR,9S,10S,12aS,12bR,14bR)-2,4a,6a,6b,9,12a-hexamethyl-10-(5-methyl-1H-pyrazol-1-yl)-13-oxo-1,2,3,4,4a,5,6,6a,6b,7,8,8a,9,10,11,12,12a,12b,13,14b-icosahydropicene-2,9-dicarboxylate (331-1)

Into a 25-mL round-bottom flask was placed 329-3 (800 mg, 1.15 mmol), MeOH (6.8 mL), and (3H)-4-(di methyl amino) but-3-en-2-one (156 mg, 1.4 mmol, 1.2 equiv). The reaction slurry was stirred overnight at 70° C. The reaction mixture was cooled, diluted with 100 mL of $CH_2Cl_2$, and washed with 2×100 ml of brine. The organic layer was dried over anhydrous $Na_2SO_4$, filtered, and concentrated. The residue was applied onto a silica gel column with ethyl acetate:petroleum ether (1:5) to provide 640 mg of 331-1 as a white solid.

Synthesis of (2S,4aS,6aS,6bR,8aR,9S,10S,12aS, 12bR,14bR)-2,4a,6a,6b,9,12a-hexamethyl-10-(5-methyl-1H-pyrazol-1-yl)-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic Acid (331-2)

The title compound was prepared with 331-1 according to the methods to synthesize 329-7. The crude product was purified by prep-HPLC with the following conditions: column, X-Select CSH OBD 30*150 mm, 5 μm; mobile phase, water (0.05% TFA) and $CH_3CN$ (hold 68% Phase B for 8 min); detector, UV. This resulted in 49.0 mg of 331-2 as a white solid. MS (ES, m/z) [M+1]$^+$=677; $^1$H NMR (400 MHz, DMSO-d$_6$) δ 0.77 (s, 3H), 0.98 (d, J=13.8 Hz, 1H), 1.06 (s, 3H), 1.12 (s, 3H), 1.17 (d, J=12.5 Hz, 5H), 1.18 (s, 2H), 1.27 (d, J=13.5 Hz, 2H), 1.36 (s, 2H), 1.40 (s, 3H), 1.46 (d, J=14.1 Hz, 1H), 1.62 (d, J=9.1 Hz, 1H), 1.72 (d, J=6.5 Hz, 3H), 1.74-1.84 (m, 1H), 2.06-2.16 (m, 7H), 2.34-2.45 (m, 1H), 2.76 (d, J=13.6 Hz, 1H), 4.54 (d, J=11.8 Hz, 1H), 4.84 (d, J=14.0 Hz, 1H), 5.15 (d, J=14.0 Hz, 1H), 5.45 (s, 1H), 5.90 (s, 1H), 7.28 (d, J=1.7 Hz, 1H).

Example 79 (2S,4aS,6aS,6bR,8aR,9S,10S,12aS, 12bR,14bR)-2,4a,6a,6b,9,12a-hexamethyl-10-(3-methyl-1H-pyrazol-1-yl)-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic Acid (332-2)

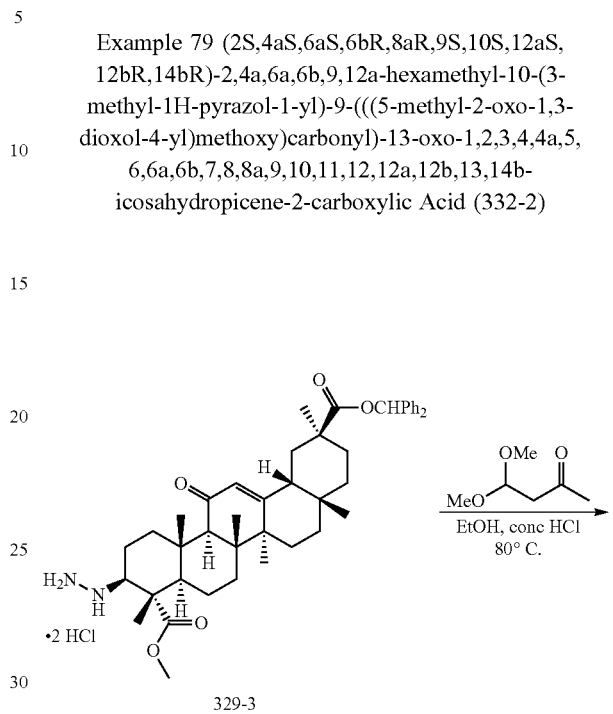

329-3

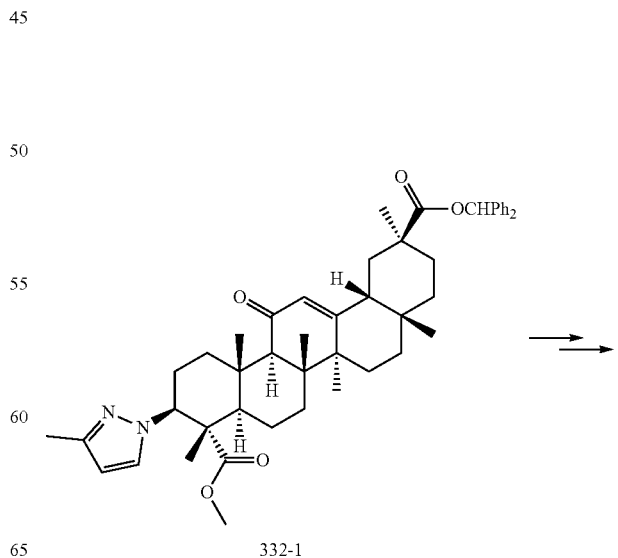

332-1

-continued

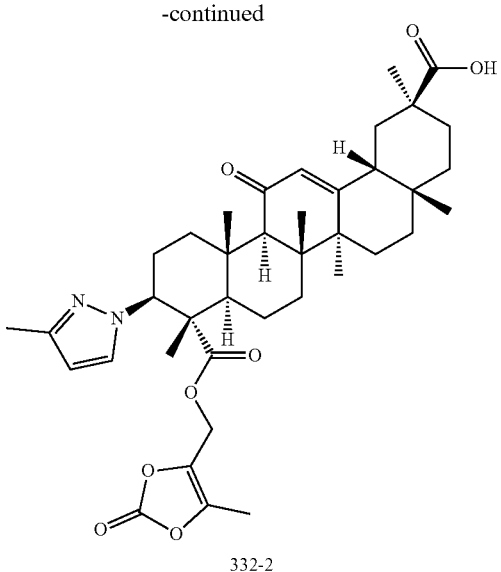

332-2

Synthesis of 2-benzhydryl 9-methyl (2S,4aS,6aS, 6bR,8aR,9S,10S,12aS,12bR,14bR)-2,4a,6a,6b,9,12a-hexamethyl-10-(3-methyl-1H-pyrazol-1-yl)-13-oxo-1,2,3,4,4a,5,6,6a,6b,7,8,8a,9,10,11,12,12a,12b,13,14b-icosahydropicene-2,9-dicarboxylate (332-1)

Into a 100-mL round-bottom flask was placed 329-3 (800 mg, 1.15 mmol), 4,4-dimethoxybutan-2-one (0.25 mL, 1.4 mmol, 1.2 equiv), and EtOH (25 mL). The reaction slurry was stirred for 2 h at reflux. Concentrated HCl (0.025 mL) was added dropwise and the slurry stirred for 2 h at reflux. The reaction mixture was cooled, diluted with 200 mL of CH$_2$Cl$_2$, and washed with 2×200 mL of brine. The organic layer was dried over anhydrous Na$_2$SO$_4$, filtered, and concentrated. The residue was applied onto a silica gel column with ethyl acetate:petroleum ether (1:5) to provide 430 mg of 332-1 as a white solid.

Synthesis of (2S,4aS,6aS,6bR,8aR,9S,10S,12aS, 12bR,14bR)-2,4a,6a,6b,9,12a-hexamethyl-10-(3-methyl-1H-pyrazol-1-yl)-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic Acid (331-2)

The title compound was prepared with 332-1 according to the methods to synthesize 329-7. The crude product was purified by prep-HPLC with the following conditions: column, X-Select CSH OBD 30*150 mm, 5 μm; mobile phase, water (0.05% TFA) and CH$_3$CN (57% Phase B up to 77% over 9 min); detector, UV. This resulted in 46.7 mg of 332-2 as a white solid. MS (ES, m/z): [M+1]$^+$=677; $^1$H NMR (300 MHz, DMSO-7$_6$) δ 0.77 (d, J=3.6 Hz, 7H), 0.87-1.02 (m, 1H), 1.05 (s, 3H), 1.09-1.15 (m, 6H), 1.35 (d, J=24.6 Hz, 7H), 1.54-1.66 (m, 2H), 1.71 (s, 1H), 1.81 (d, J=13.3 Hz, 1H), 2.12 (d, J=31.2 Hz, 6H), 2.33 (s, 1H), 2.81 (d, J=12.7 Hz, 1H), 4.57 (d, J=11.9 Hz, 1H), 4.96 (d, J=14.0 Hz, 1H), 5.07 (d, J=14.0 Hz, 1H), 5.45 (s, 1H), 5.93 (d, J=2.2 Hz, 1H), 7.52 (d, J=2.3 Hz, 1H).

Example 80 (2S,4aS,6aS,6bR,8aR,9S,10S,12aS, 12bR,14bR)-9-((((5-ethyl-2-oxo-1,3-dioxol-4-yl) methoxy)carbonyl)amino)-2,4a,6a,6b,9,12a-hexamethyl-13-oxo-10-(propionyloxy)-1,2,3,4,4a,5,6,6a, 6b,7,8,8a,9,10,1142,12a,12b,13,14b-icosahydropicene-2-carboxylic Acid (333-1)

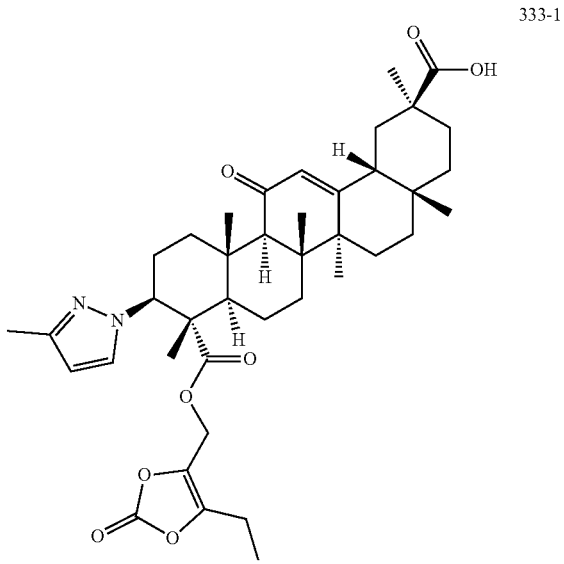

333-1

Synthesis of (2S,4aS,6aS,6bR,8aR,9S,10S,12aS, 12bR,14bR)-9-((((5-ethyl-2-oxo-1,3-dioxol-4-yl) methoxy)carbonyl)-2,4a,6a,6b,9,12a-hexamethyl-10-(3-methyl-1H-pyrazol-1-yl)-13-oxo-1,2,3,4,4a,5,6, 6a,6b,7,8,8a,9,10,11,12,12a,12b,13,14b-icosahydropicene-2-carboxylic Acid (333-1)

The title compound was prepared from 329-3 according to the methods to synthesize 332-2. The crude product was purified by Prep-HPLC with the following conditions: Column, X select CSH OBD, 30*150 mm, 5 μm; mobile phase, water (0.05% TFA) and CH$_3$CN (68% phase B up to 70% in 8 min); detector, UV to provide 41.4 mg (34%) of 333-1 as a white solid. MS (ES, m/z): [M+1]$^+$=691; $^1$H NMR (400 MHz, methanol-d$_4$) δ 7.45 (d, J=2.3 Hz, 1H), 6.01 (d, J=2.3 Hz, 1H), 5.63 (s, 1H), 5.14 (d, J=13.9 Hz, 1H), 4.88 (d, J=14.0 Hz, 1H), 4.71 (dd, J=13.1, 3.9 Hz, 1H), 2.98 (d, J=13.4 Hz, 1H), 2.66-2.54 (m, 3H), 2.50-2.36 (m, 1H), 2.23 (d, J=12.7 Hz, 1H), 2.19 (s, 3H), 1.97 (d, J=9.9 Hz, 1H), 1.91-1.73 (m, 2H), 1.73-1.58 (m, 1H), 1.48 (s, 3H), 1.42 (s, 2H), 1.40-1.33 (m, 1H), 1.33-1.14 (m, 12H), 1.07 (d, J=14.1 Hz, 1H), 1.04-0.94 (m, 1H), 0.95 (s, 3H), 0.94-0.87 (m, 1H), 0.85 (s, 3H).

Example 81 (2S,4aS,6aS,6bR,8aR,9S,10S,12aS,12bR,14bR)-10-(4-(ethoxycarbonyl)-1H-pyrazol-1-yl)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic Acid (334-8)
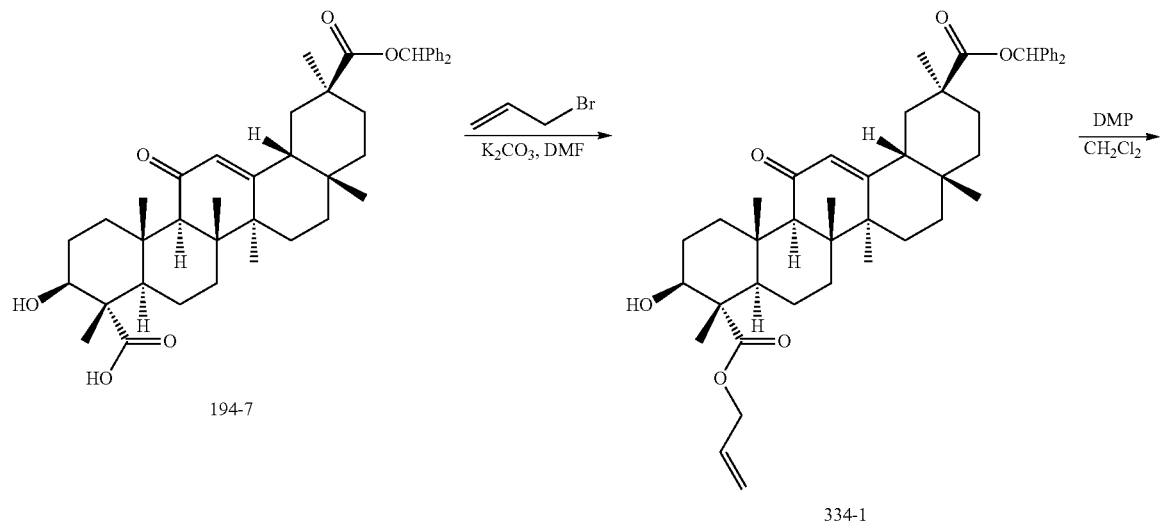
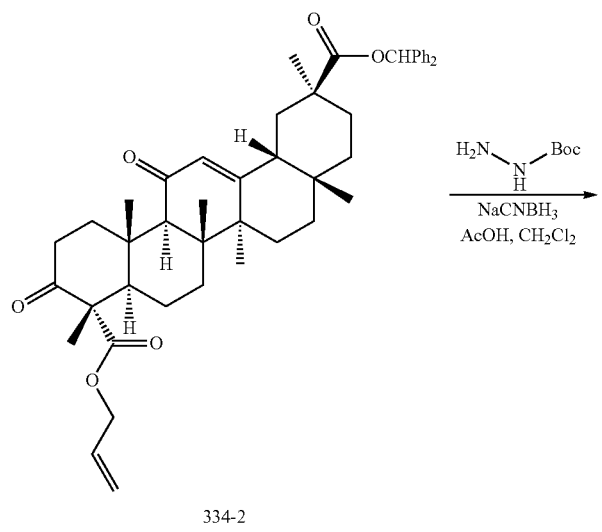

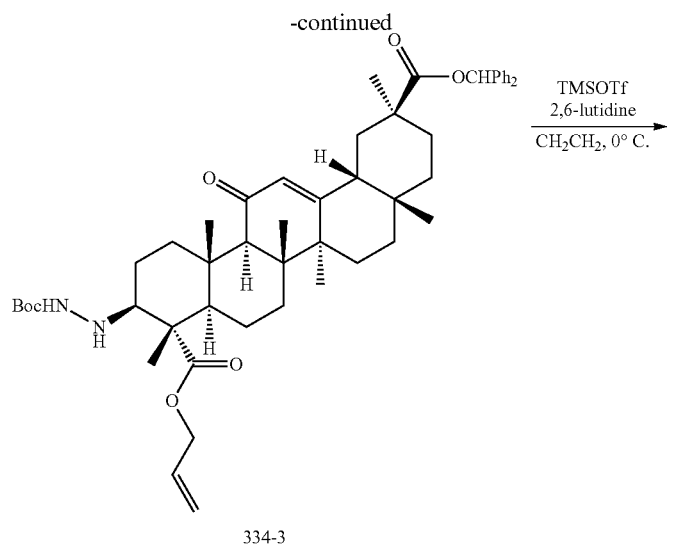
334-3
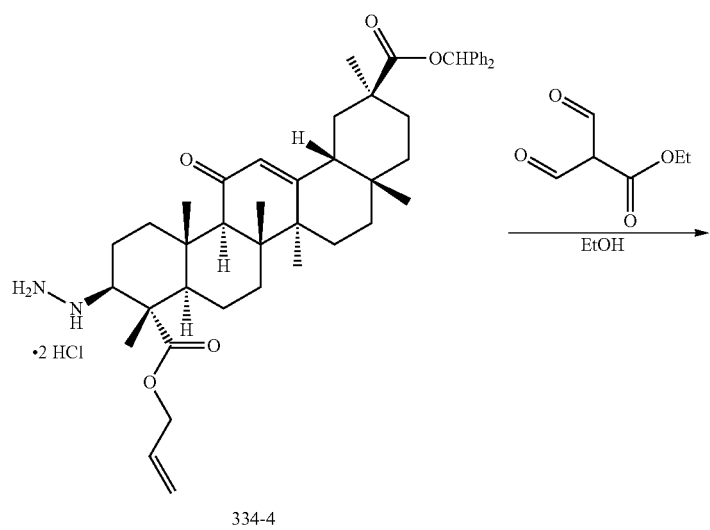
334-4
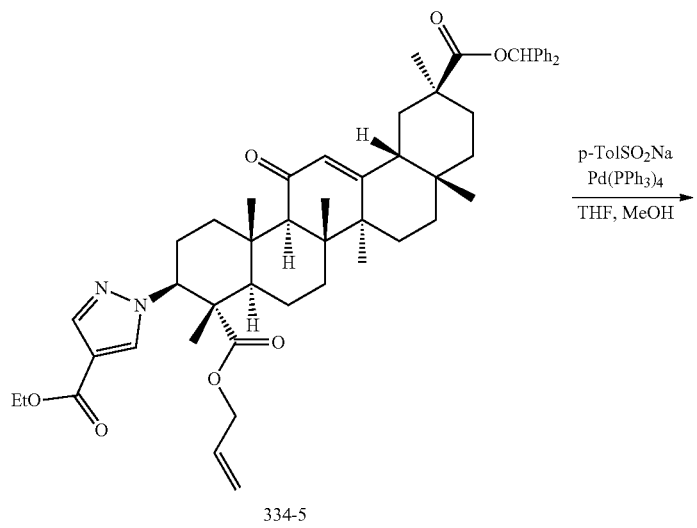
334-5

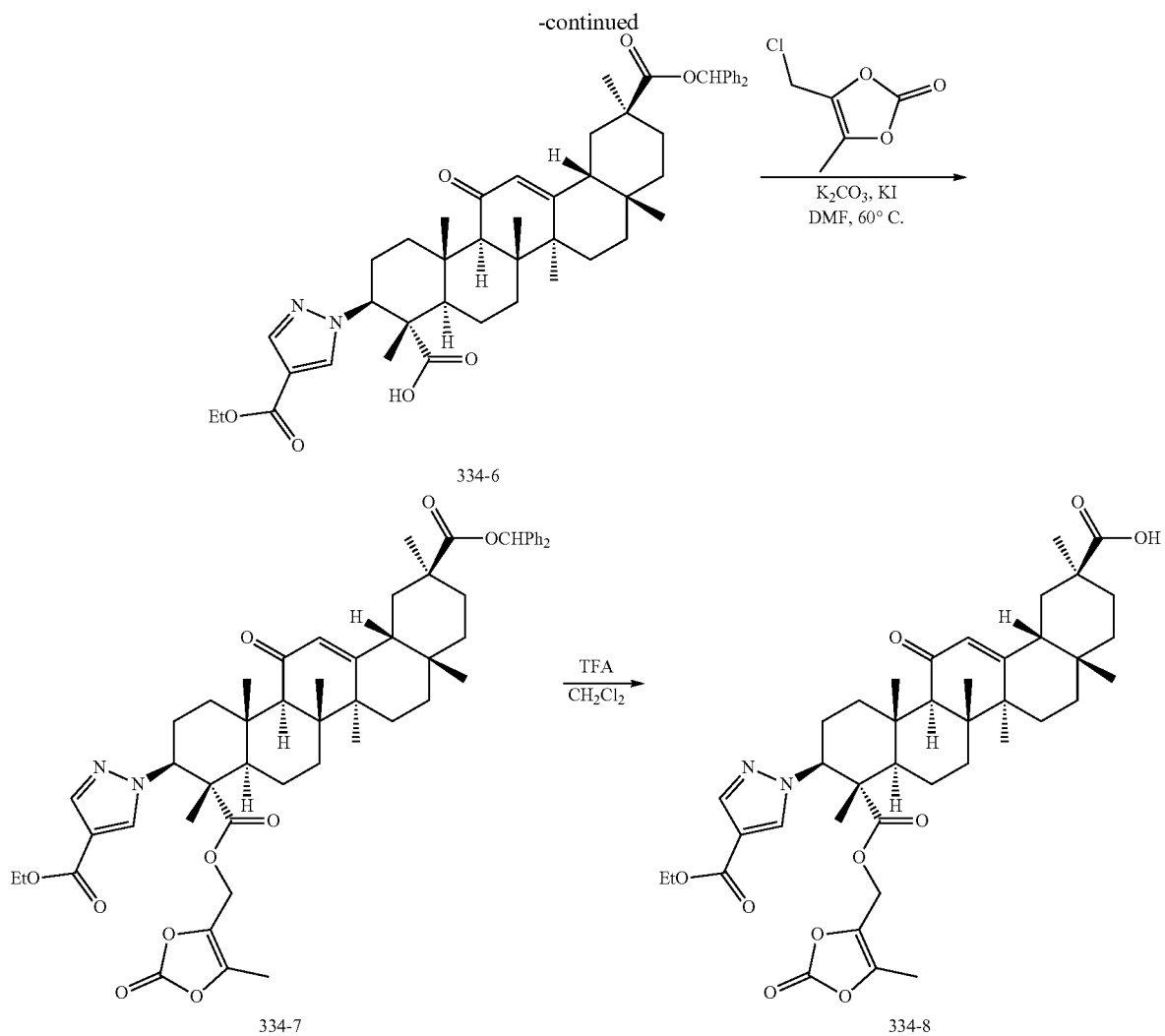

Synthesis of 9-allyl 2-benzhydryl (2S,4aS,6aS,6bR, 8aR,9S,10S,12aS,12bR,14bR)-10-hydroxy-2,4a,6a, 6b,9,12a-hexamethyl-13-oxo-1,2,3,4,4a,5,6,6a,6b,7, 8,8a,9,10,11,12,12a,12b,13,14b-icosahydropicene-2, 9-dicarboxylate (334-1)

Into a 250-mL round-bottom flask was placed 194-7 (3.0 g), DMF (20 mL), KI (0.37 g, 0.5 equiv), 3-bromoprop-1-ene (1.557 mL, 4 equiv), and K₂CO₃ (3.1 g, 5 equiv). The reaction slurry was stirred for 1 h at room temperature. The reaction mixture was diluted with H₂O and extracted with ethyl acetate. The combined organic layers were washed with 2×150 ml of H₂O and 2×150 mL of brine, dried over anhydrous Na₂SO₄, filtered, and concentrated. The residue was applied onto a silica gel column with ethyl acetate: petroleum ether (3:1) to provide 2.69 g (85%) of 334-1 as a light yellow solid.

Synthesis of 9-allyl 2-benzhydryl (2S,4aS,6aS,6bR, 8aR,9S,12aS,12bR,14bR)-2,4a,6a,6b,9,12a-hexamethyl-10,13-dioxo-1,2,3,4,4a,5,6,6a,6b,7,8,8a,9,10, 11,12,12a,12b,13,14b-icosahydropicene-2,9-dicarboxylate (334-2)

Into a 250-mL round-bottom flask was placed 334-1 (2.70 g), CH₂Cl₂ (40 mL), then DMP (4.86 g, 3 equiv) in several batches at 0° C. The reaction slurry was stirred for 3 h then quenched by the addition of saturated NaHCO₃(aq) and extracted with CH₂Cl₂. The organic layer was washed with 2×150 ml of H₂O and 2×150 mL of brine, dried over anhydrous Na₂SO₄, filtered, and concentrated. The residue was applied onto a silica gel column with ethyl acetate: petroleum ether (15:85) to provide 2.61 g (97%) of 334-2 as a white solid.

Synthesis of 9-allyl 2-benzhydryl (2S,4aS,6aS,6bR, 8aR,9S,10S,12aS,12bR,14bR)-10-(2-(tert-butoxycarbonyl)hydrazinyl)-2,4a,6a,6b,9,12a-hexamethyl-13-oxo-1,2,3,4,4a,5,6,6a,6b,7,8,8a,9,10,11,12,12a,12b, 13,14b-icosahydropicene-2,9-dicarboxylate (334-3)

Into a 250-mL round-bottom flask was placed 334-2 (2.61 g), CH₂Cl₂ (10 mL), AcOH (10 mL), and (tert-butoxy) carbohydrazide (538 mg, 1.1 equiv). The reaction slurry was stirred for 2 h at room temperature. The reaction slurry was cooled to 0° C. before portionwise addition of NaBH₃CN (279 mg, 1.2 equiv). After 30 min, the pH of the solution was adjusted to 7 with saturated NaHCO₃(aq) and the slurry was extracted with CH₂Cl₂. The organic layer was washed with 2×200 of H₂O and 2×200 mL of brine. The mixture was dried over anhydrous Na₂SO₄, filtered, and concentrated.

The residue was applied onto a silica gel column with ethyl acetate:petroleum ether (1:5) to provide 2.25 g (74%) of 334-3 as a white solid.

Synthesis of 9-allyl 2-benzhydryl (2S,4aS,6aS,6bR, 8aR,9S,10S,12aS,12bR,14bR)-10-hydrazinyl-2,4a, 6a,6b,9,12a-hexamethyl-13-oxo-1,2,3,4,4a,5,6,6a,6b, 7,8,8a,9,10,11,12,12a,12b,13,14b-icosahydropicene-2,9-dicarboxylate dihydrochloride (334-4)

Into a 100-mL round-bottom flask was placed 334-3 (700 mg, 0.85 mmol), CH$_2$Cl$_2$ (6 mL), 2,6-lutidine (0.5 mL, 4 equiv) followed by TMSOTf (756 mg, 3.4 mmol, 4 equiv) at 0° C. The reaction slurry was stirred for 1 h at room temperature. The reaction mixture was washed with 3×200 ml of brine, dried over anhydrous Na$_2$SO$_4$, filtered, and concentrated to provide 683 mg (quant) of crude 334-4 as a yellow solid.

Synthesis of 9-allyl 2-benzhydryl (2S,4aS,6aS,6bR, 8aR,9S,10S,12aS,12bR,14bR)-10-(4-(ethoxycarbonyl)-1H-pyrazol-1-yl)-2,4a,6a,6b,9,12a-hexamethyl-13-oxo-1,2,3,4,4a,5,6,6a,6b,7,8,8a,9,10,11,12,12a, 12b,13,14b-icosahydropicene-2,9-dicarboxylate (334-4)

Into a 50-mL round-bottom flask was placed 334-4 (684 mg, 0.95 mmol), EtOH (6 mL), and ethyl 2-formyl-3-oxopropanoate (144 mg, 1 mmol, 1.05 equiv). The reaction slurry was stirred for 2 h at room temperature then concentrated. The residue was applied onto a silica gel column with ethyl acetate:petroleum ether (3:7) to provide 567 mg (72%) of 334-5 as a white solid.

Synthesis of (3S,4S,4aR,6aR,6bS,8aS,11S,12aR, 14aR,14bS)-11-((benzhydryloxy)carbonyl)-3-(4-(ethoxycarbonyl)-1H-pyrazol-1-yl)-4,6a,6b,8a,11, 14b-hexamethyl-14-oxo-1,2,3,4,4a,5,6,6a,6b,7,8,8a, 9,10,11,12,12a,14,14a,14b-icosahydropicene-4-carboxylic Acid (334-6)

Into a 50-mL round-bottom flask purged and maintained with an inert atmosphere of nitrogen was placed 334-5 (573 mg, 0.69 mmol), THF (2 mL), MeOH (6 mL), p-TolSO$_2$Na (500 mg, 2.8 mmol, 4 equiv), and Pd(PPh$_3$)$_4$ (400 mg, 0.35 mmol, 0.5 equiv). The reaction slurry was stirred for 1 h at room temperature. The reaction mixture was extracted with 200 mL of CH$_2$Cl$_2$ and the solution pH adjusted to 3 with 1 M HCl$_{(aq)}$. The mixture was concentrated and residue was applied onto a silica gel column with CH$_2$Cl$_2$:methanol (10:1) to provide 508 mg (93%) of 334-6 as a yellow solid.

Synthesis of 2-benzhydryl 9-((5-methyl-2-oxo-1,3-dioxol-4-yl)methyl) (2S,4aS,6aS,6bR,8aR,9S,10S, 12aS,12bR,14bR)-10-(4-(ethoxycarbonyl)-1H-pyrazol-1-yl)-2,4a,6a,6b,9,12a-hexamethyl-13-oxo-1,2,3, 4,4a,5,6,6a,6b,7,8,8a,9,10,11,12,12a,12b,13,14b-icosahydropicene-2,9-dicarboxylate (334-7)

Into a 100-mL round-bottom flask was placed 334-6 (288 mg, 0.37 mmol), DMF (5 mL), 4-(chloromethyl)-5-methyl-2H-1,3-dioxol-2-one (220 mg, 1.5 mmol, 4 equiv), KI (30 mg, 0.18 mmol, 0.5 equiv), and K$_2$CO$_3$ (250 mg, 1.8 mmol, 5 equiv). The reaction slurry was stirred for 1 h at 60° C. The reaction mixture was cooled and extracted with 200 mL of CH$_2$Cl$_2$. The combined organic layers were washed with 3×200 ml of brine, dried over anhydrous Na$_2$SO$_4$, filtered, and concentrated to provide 248 mg (75%) of 334-7 as a yellow oil.

Synthesis of (2S,4aS,6aS,6bR,8aR,9S,10S,12aS, 12bR,14bR)-10-(4-(ethoxycarbonyl)-1H-pyrazol-1-yl)-2,4a,6a,6b,9,12a-hexamethyl-9-(((5-methyl-2-oxo-1,3-dioxol-4-yl)methoxy)carbonyl)-13-oxo-1,2, 3,4,4a,5,6,6a,6b,7,8,8a,9,10,11,12,12a,12b,13,14b-icosahydropicene-2-carboxylic Acid (334-8)

Into a 100-mL round-bottom flask was placed 334-7 (248 mg, 0.28 mmol), CH$_2$Cl$_2$ (10 mL), and TFA (1 mL). The reaction slurry was stirred for 1 h at room temperature then concentrated. The crude product was purified by prep-HPLC with the following conditions: column, XBridge Shield RP18 OBD Column, 30*150 mm, 5 μm; mobile phase, water (0.05% TFA) and CH$_3$CN (60% Phase B up to 75% in 8 min); detector, UV. This resulted in 67.0 mg (33%) of 334-8 as a white solid. MS (ES, m/z): [M+1]$^+$=735.3; $^1$H NMR (400 MHz, chloroform-d) δ 0.87 (d, J=10.7 Hz, 6H), 0.96 (d, J=12.3 Hz, 1H), 1.06 (d, J=13.9 Hz, 1H), 1.15 (s, 3H), 1.24 (d, J=11.2 Hz, 7H), 1.27-1.40 (m, 9H), 1.40-1.50 (m, 3H), 1.52-1.73 (m, 4H), 1.73-90 (m, 1H), 1.90-2.12 (m, 4H), 2.12-2.31 (m, 5H), 2.51 (s, 1H), 3.09 (d, J=14.0 Hz, 1H), 4.30 (q, J=7.1 Hz, 2H), 4.79 (dd, J=13.0, 3.9 Hz, 1H), 4.91 (d, J=13.8 Hz, 1H), 4.99 (d, J=13.8 Hz, 1H), 5.76 (s, 1H), 7.80 (s, 1H), 7.89 (s, 1H).

Example 82 (2S,4aS,6aS,6bR,8aR,9S,10S,12aS, 12bR,14bR)-10-(4-(ethoxycarbonyl)-1H-pyrazol-1-yl)-2,4a,6a,6b,9,12a-hexamethyl-9-(((5-methyl-2-oxo-1,3-dioxol-4-yl)methoxy)carbonyl)-13-oxo-1,2, 3,4,4a,5,6,6a,6b,7,8,8a,9,10,1142,12a,12b,13,14b-icosahydropicene-2-carboxylic Acid (335-1)

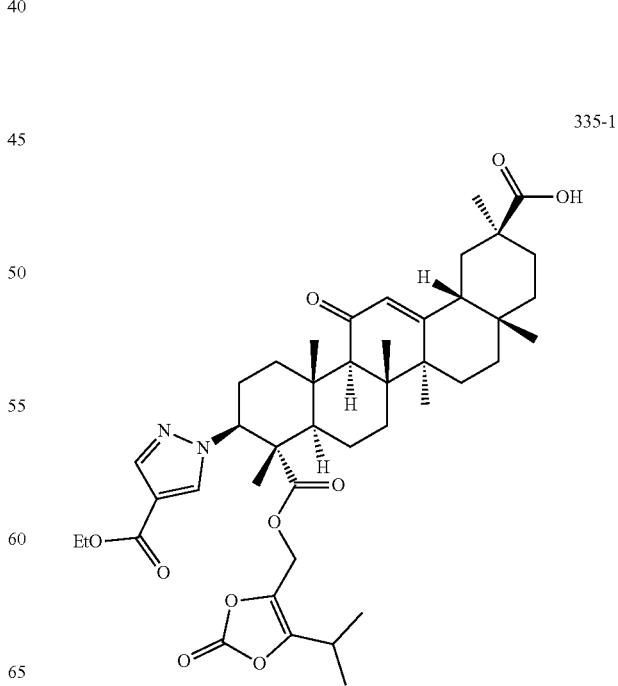

335-1

Synthesis of (2S,4aS,6aS,6bR,8aR,9S,10S,12aS, 12bR,14bR)-10-(4-(ethoxycarbonyl)-1H-pyrazol-1-yl)-9-(((5-isopropyl-2-oxo-1,3-dioxol-4-yl)methoxy) carbonyl)-2,4a,6a,6b,9,12a-hexamethyl-13-oxo-1,2, 3,4,4a,5,6,6a,6b,7,8,8a,9,10,11,12,12a,12b,13,14b-icosahydropicene-2-carboxylic Acid (335-1)

The title compound was prepared from 194-7 according to the methods to synthesize 334-8. The crude product was purified by prep-HPLC with the following conditions: column, XBridge Shield RP18 OBD Column, 30*150 mm, 5 μm; mobile phase, water (0.05% TFA) and CH$_3$CN (65% Phase B up to 80% in 8 min); detector, UV. This resulted in 86.7 mg (37%) of 335-1 as a white solid. MS (ES, m/z): [M+1]$^+$=763.3; $^1$H NMR (400 MHz, chloroform-d) δ 0.87 (d, J=11.0 Hz, 6H), 0.95 (d, J=11.9 Hz, 1H), 1.06 (d, J=14.4 Hz, 2H), 1.15 (s, 3H), 1.19-1.28 (m, 13H), 1.28-1.49 (m, 11H), 1.56-1.77 (m, 4H), 1.77-1.88 (m, 1H), 1.92-2.12 (m, 4H), 2.19-2.33 (m, 2H), 2.51 (s, 1H), 3.01 (h, J=6.9 Hz, 1H), 3.09 (d, J=13.7 Hz, 1H), 4.30 (q, J=7.1 Hz, 3H), 4.40 (m, 2H), 4.80 (dd, J=13.0, 4.0 Hz, 1H), 4.93 (d, J=13.7 Hz, 1H), 5.00 (d, J=13.8 Hz, 1H), 5.76 (s, 1H), 7.81 (s, 1H), 7.90 (s, 1H).

Example 83 (2S,4aS,6aS,6bR,8aR,9S,10S,12aS, 12bR,14bR)-10-(5-(ethoxycarbonyl)-3-methyl-1H-pyrazol-1-yl)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,1142,12a, 12b,13,14b-icosahydropicene-2-carboxylic Acid (336-2)

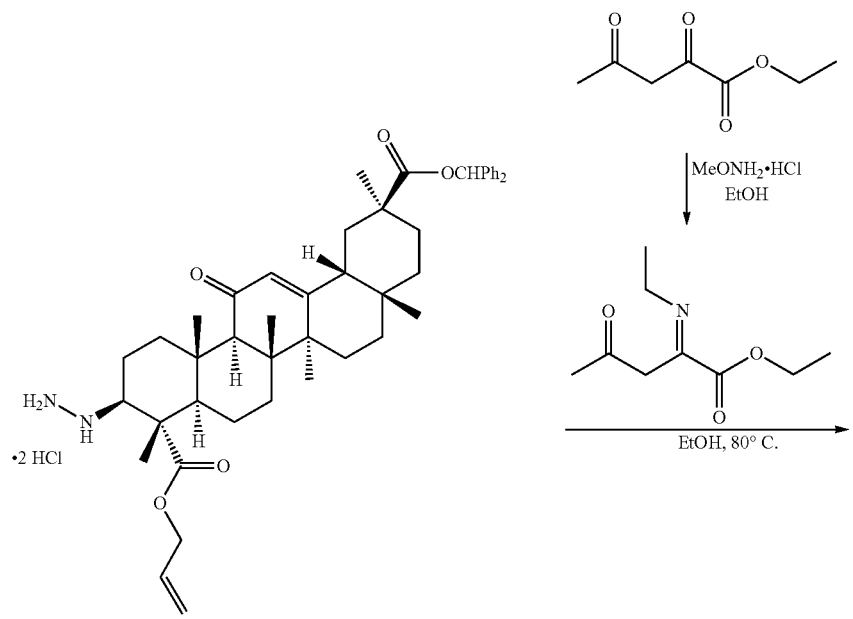

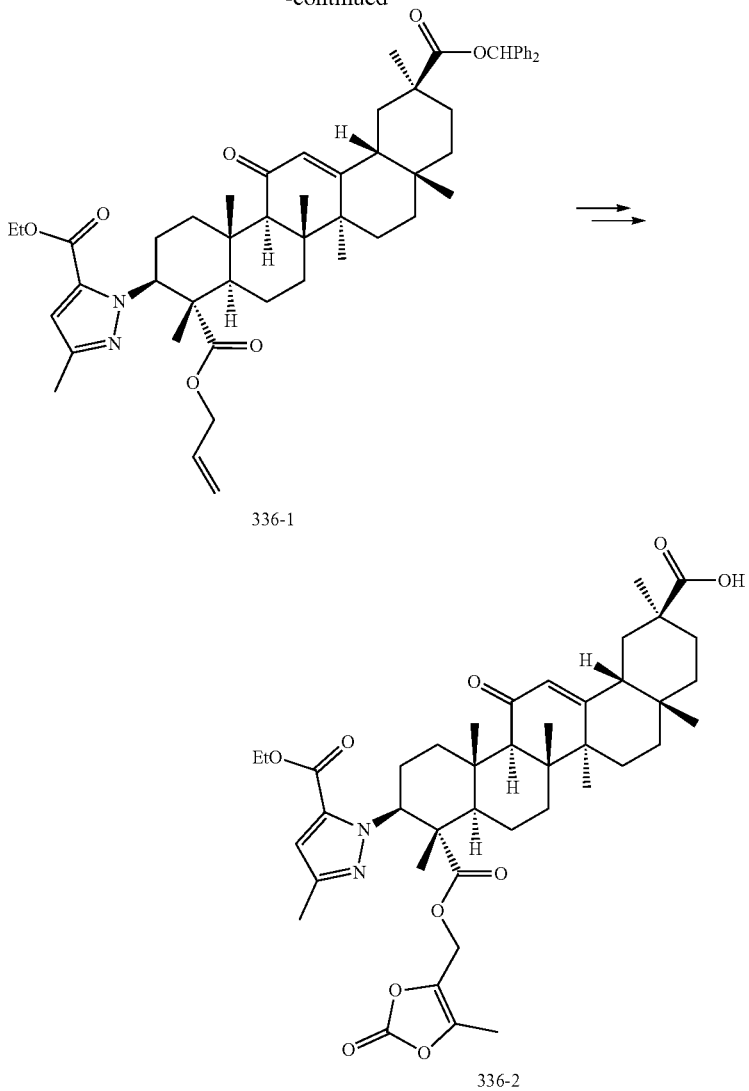

Synthesis of ethyl (E)-2-(methoxyimino)-4-oxopentanoate

Into a 100-mL round-bottom flask purged and maintained with an inert atmosphere of nitrogen was placed ethyl 2,4-dioxopentanoate (2 g), ethanol (13.3 mL), and H-methyl hydroxyl amine hydrochloride (1.11 g, 1.05 equiv). The reaction slurry was stirred for 2 days at room temperature. The reaction mixture was concentrated under vacuum. The residue was applied onto a silica gel column with ethyl acetate:petroleum ether (1:10) to provide 1.24 g (52%) of ethyl (E)-2-(methoxyimino)-4-oxopentanoate as a light yellow oil.

Synthesis of 9-allyl 2-benzhydryl (2S,4aS,6aS,6bR,8aR,9S,10S,12aS,12bR,14bR)-10-(5-(ethoxycarbonyl)-3-methyl-1H-pyrazol-1-yl)-2,4a,6a,6b,9,12a-hexamethyl-13-oxo-1,2,3,4,4a,5,6,6a,6b,7,8,8a,9,10,11,12,12a,12b,13,14b-icosahydropicene-2,9-dicarboxylate (336-1)

Into a 50-mL round-bottom flask, was placed 334-4 (375 mg), ethanol (10 mL), and ethyl (E)-2-(methoxyimino)-4-oxopentanoate (195 mg, 2 equiv). The reaction slurry was stirred for 2 h at 80° C. The reaction mixture was concentrated under vacuum. The residue was applied onto a silica gel column with ethyl acetate:petroleum ether (1:3) to provide 318 mg (72%) of 336-1 as a light yellow solid.

Synthesis of (2S,4aS,6aS,6bR,8aR,9S,10S,12aS,12bR,14bR)-10-(5-(ethoxycarbonyl)-3-methyl-1H-pyrazol-1-yl)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic Acid (336-2)

The title compound was prepared with 336-1 according to the methods to synthesize 334-8. The crude product was purified by prep-HPLC with the following conditions: column, XBridge Prep OBD C18 Column, 30*150 mm, 5 μm; mobile phase, water (0.05% TFA) and $CH_3CN$ (67% phase B up to 69% in 8 min); detector, UV. This resulted in 55.6 mg (51%) of 336-2 as a white solid. MS (ES, m/z): $[M+1]^+=$ 749.35; $^1H$ NMR (400 MHz, methanol-$d_4$) δ 0.86 (s, 3H), 0.94 (d, J=13.6 Hz, 1H), 1.08 (d, J=13.6 Hz, 1H), 1.20 (d, J=10.4 Hz, 6H), 1.28 (d, J=10.4 Hz, 7H), 1.33-1.48 (m, 8H), 1.51 (s, 3H), 1.62-1.82 (m, 4H), 1.85-2.09 (m, 4H), 2.15 (s, 3H), 2.19-2.30 (m, 5H), 2.52-2.68 (m, 2H), 2.95 (d, J=13.6 Hz, 1H), 4.25-4.44 (m, 2H), 4.61 (d, J=14.0 Hz, 1H), 4.96 (d, J=14.0 Hz, 1H), 5.64 (s, 1H), 5.67 (d, J=3.6 Hz, 1H), 6.57 (s, 1H).
Example 84 (2S,4aS,6aS,6bR,8aR,9S,10S,12aS, 12bR,14bR)-10-(3-(ethoxycarbonyl)-5-methyl-1H-pyrazol-1-yl)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,1142,12a, 12b,13,14b-icosahydropicene-2-carboxylic Acid (337-2)
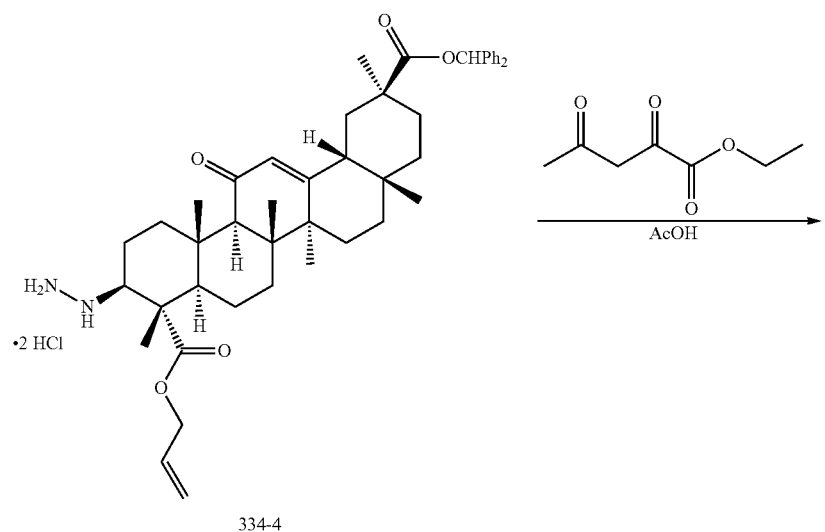
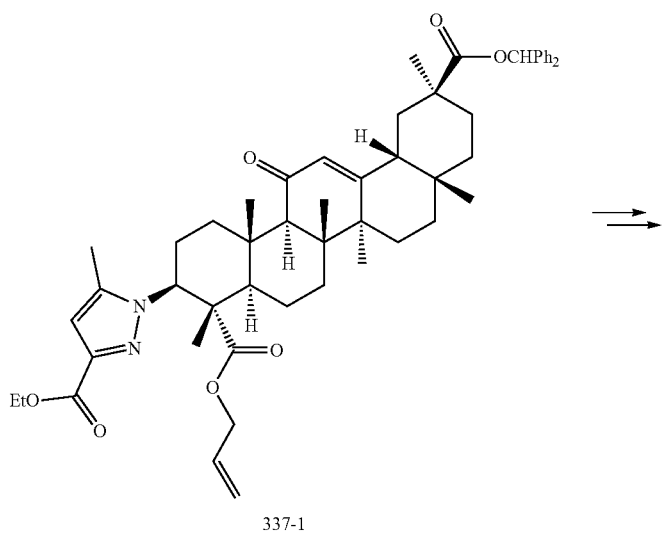

-continued

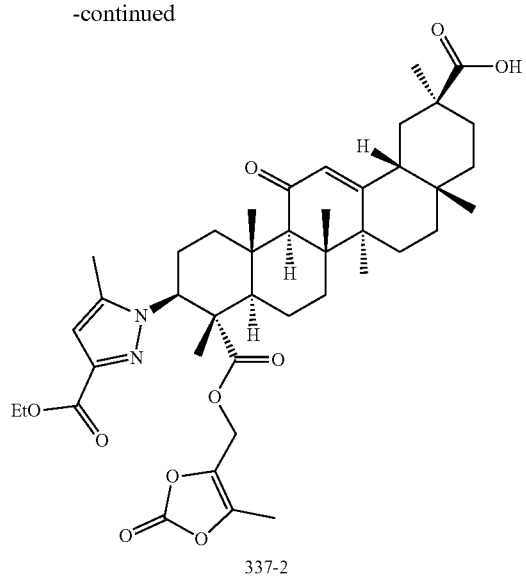

337-2

Synthesis of 9-allyl 2-benzhydryl (2S,4aS,6aS,6bR, 8aR,9S,10S,12aS,12bR,14bR)-10-(3-(ethoxycarbonyl)-5-methyl-1H-pyrazol-1-yl)-2,4a,6a,6b,9,12a-hexamethyl-13-oxo-1,2,3,4,4a,5,6,6a,6b,7,8,8a,9,10, 11,12,12a,12b,13,14b-icosahydropicene-2,9-dicarboxylate (337-1)

Into a 100-mL round-bottom flask was placed 334-4 (392 mg), acetic acid (4 mL), and ethyl 2,4-dioxopentanoate (0.076 mL, 1 equiv). The reaction slurry was stirred for 1 h at room temperature. The solution pH was adjusted to 8 with saturated NaHCO$_{3(aq)}$ and the mixture was extracted with ethyl acetate. The organic layer was washed with 2×100 ml of brine, dried over anhydrous Na$_2$SO$_4$, filtered, and concentrated. The residue was applied onto a silica gel column with ethyl acetate:petroleum ether (1:3) to provide 352 mg (77%) of 337-1 as a light yellow solid.

Synthesis of (2S,4aS,6aS,6bR,8aR,9S,10S,12aS, 12bR,14bR)-10-(3-(ethoxycarbonyl)-5-methyl-1H-pyrazol-1-yl)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a, 12b,13,14b-icosahydropicene-2-carboxylic Acid (337-2)

The title compound was prepared with 337-1 according to the methods to synthesize 334-8. The crude product was purified by prep-HPLC with the following conditions: column, XSelect CSH Prep OBD C18 column, 19*150 mm, 5 μm; mobile phase, water (0.05% TFA) and CH$_3$CN (65% phase B up to 85% in 8 min); detector, UV. This resulted in 80.6 mg (52%) of 337-2 as a white solid. MS (ES, m/z): [M+1]$^+$=749.30; $^1$H NMR (300 MHz, methanol-d$_4$) δ 0.84 (s, 3H), 0.90 (d, J=10.5 Hz, 1H), 1.06 (d, J=12.0 Hz, 1H), 1.12-1.50 (m, 24H), 1.52-2.00 (m, 8H), 2.03 (s, 1H), 2.08-2.38 (m, 8H), 2.50-2.78 (m, 2H), 2.94 (d, J=13.5 Hz, 1H), 4.32 (q, J=7.1 Hz, 2H), 4.62-4.79 (m, 2H), 5.10 (d, J=13.8 Hz, 1H), 5.62 (s, 1H), 6.46 (s, 1H).

Example 85 (2S,4aS,6aS,6bR,8aR,9S,10S,12aS, 12bR,14bR)-2,4a,6a,6b,9,12a-hexamethyl-10-(4-methyl-1H-pyrazol-1-yl)-9-(((5-methyl-2-oxo-1,3-dioxol-4-yl)methoxy)carbonyl)-13-oxo-1,2,3,4,4a,5, 6,6a,6b,7,8,8a,9,10,11,12,12a,12b,13,14b-icosahydropicene-2-carboxylic Acid (338-4)

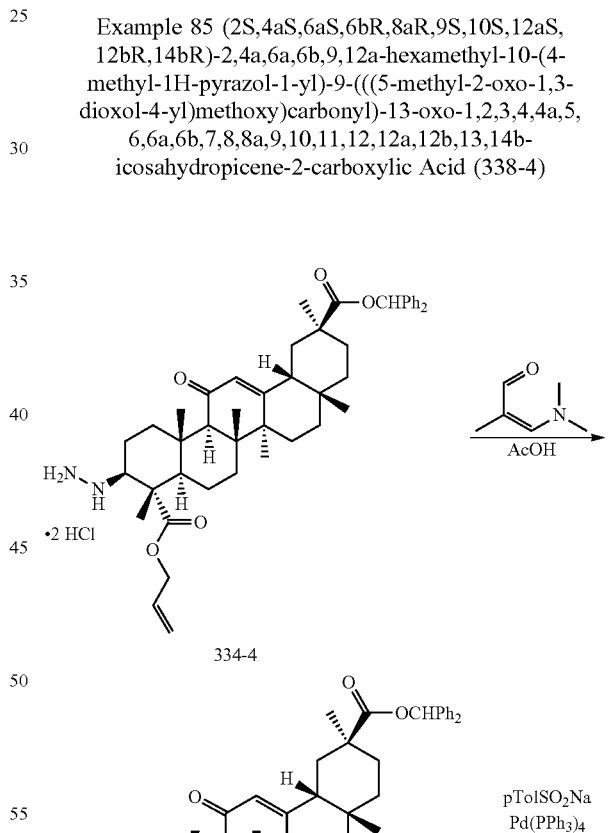

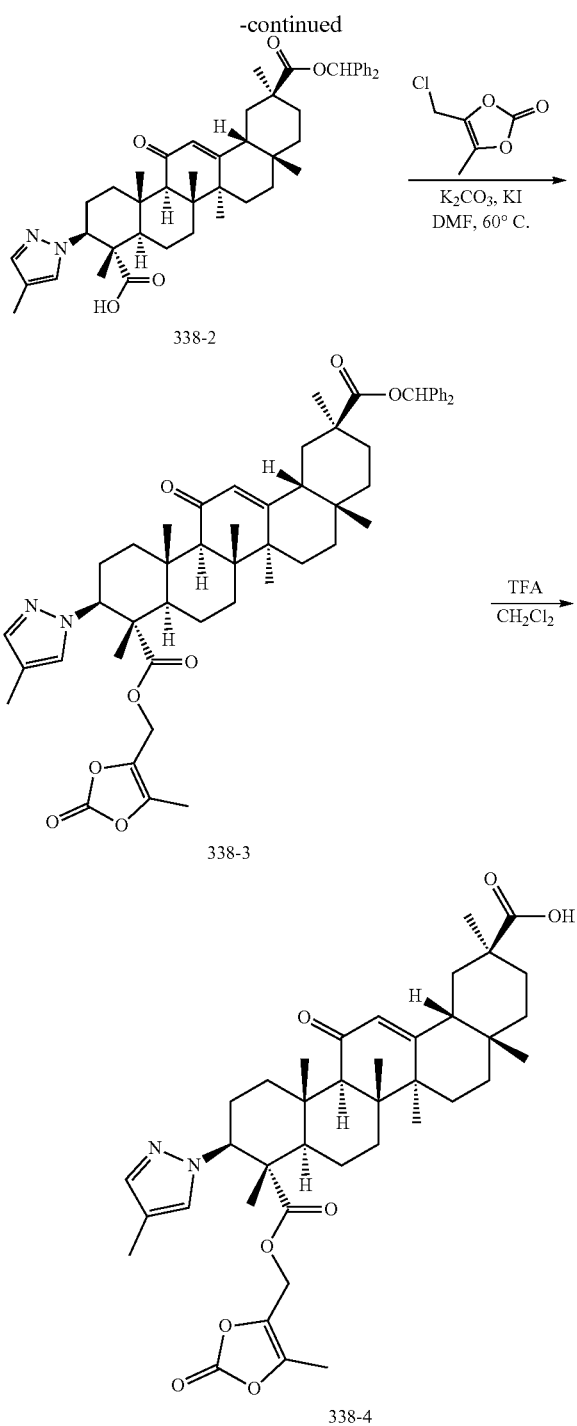

338-2

338-3

338-4

Synthesis of 9-allyl 2-benzhydryl (2S,4aS,6aS,6bR, 8aR,9S,10S,12aS,12bR,14bR)-2,4a,6a,6b,9,12a-hexamethyl-10-(4-methyl-1H-pyrazol-1-yl)-13-oxo-1,2,3,4,4a,5,6,6a,6b,7,8,8a,9,10,11,12,12a,12b,13, 14b-icosahydropicene-2,9-dicarboxylate (338-1)

Into a 50-mL round-bottom flask was placed 334-4 (378 mg, 0.53 mmol), acetic acid (5 mL), and (2Z)-3-(dimethylamino)-2-methylprop-2-enal (0.12 mL, 2 equiv). The reaction slurry was stirred for 1.5 h at room temperature. The solution pH was adjusted to 8 with saturated NaHCO$_3$$_{(aq)}$ and the mixture was extracted with ethyl acetate. The organic layer was washed with 2×100 ml of brine, dried over anhydrous Na$_2$SO$_4$, filtered, and concentrated. The residue was applied onto a silica gel column with ethyl acetate: petroleum ether (1:3) to provide 284 mg (70%) of 338-1 as a light yellow solid.

Synthesis of (3S,4S,4aR,6aR,6bS,8aS,11S,12aR, 14aR,14bS)-11-((benzhydryloxy)carbonyl)-4,6a,6b, 8a, 11,14b-h exam ethyl-3-(4-methyl-1H-pyrazol-1-yl)-14-oxo-1,2,3,4,4a,5,6,6a,6b,7,8,8a,9,10,11,12, 12a,14,14a,14b-icosahydropicene-4-carboxylic Acid (338-2)

Into a 50-mL round-bottom flask purged and maintained with an inert atmosphere of nitrogen was placed 338-1 (284 mg), THF (2 mL), MeOH (6 mL), and sodium toluene-4-sulphinate (263 mg, 4 equiv), and Pd(PPh$_3$)$_4$ (213 mg, 0.5 equiv). The reaction slurry was stirred for 1 h at room temperature then concentrated. The residue was applied onto a silica gel column with CH$_2$Cl$_2$:methanol (10:1) to provide 420 mg (quant) of 338-2 as a yellow solid.

Synthesis of 2-benzhydryl 9-((5-methyl-2-oxo-1,3-dioxol-4-yl)methyl) (2S,4aS,6aS,6bR,8aR,9S,10S, 12aS,12bR,14bR)-2,4a,6a,6b,9,12a-hexamethyl-10-(4-methyl-1H-pyrazol-1-yl)-13-oxo-1,2,3,4,4a,5,6, 6a,6b,7,8,8a,9,10,11,12,12a,12b,13,14b-icosahydropicene-2,9-dicarboxylate (338-3)

Into a 50-mL round-bottom flask was placed 338-2 (170 mg), DMF (5 mL), KI (19.3 mg, 0.5 equiv), 4-(chloromethyl)-5-methyl-2H-1,3-dioxol-2-one (69 mg, 2 equiv), and K$_2$CO$_3$ (96.4 mg, 3 equiv). The reaction slurry was stirred for 30 min at 60° C. The reaction mixture was diluted with H$_2$O and extracted with ethyl acetate. The organic layer was washed with 2×100 ml of brine, dried over anhydrous Na$_2$SO$_4$, filtered, and concentrated. The residue was applied onto a silica gel column with ethyl acetate:petroleum ether (1:3) to provide 112 mg (57%) of 338-3 as a light yellow solid.

Synthesis of (2S,4aS,6aS,6bR,8aR,9S,10S,12aS, 12bR,14bR)-2,4a,6a,6b,9,12a-hexamethyl-10-(4-methyl-1H-pyrazol-1-yl)-9-(((5-methyl-2-oxo-1,3-dioxol-4-yl)methoxy)carbonyl)-13-oxo-1,2,3,4,4a,5, 6,6a,6b,7,8,8a,9,10,11,12,12a,12b,13,14b-icosahydropicene-2-carboxylic Acid (338-4)

Into a 50-mL round-bottom flask was placed 338-3 (112 mg), CH$_2$Cl$_2$ (5 mL), and TFA (0.5 mL). The resulting solution was stirred for 30 min at room temperature. The resulting mixture was concentrated under vacuum. The crude product was purified by prep-HPLC with the following conditions: column, XSelect CSHPrep OBD C18 column, 19*150 mm, 5 μm; mobile phase, water (0.05% TFA) and CH$_3$CN (65% phase B up to 72% in 8 min); detector, UV. This resulted in 80.5 mg (89%) of 338-4 as a white solid. MS (ES, m/z): [M+1]$^+$=677.35; $^1$H NMR (400 MHz, methanol-d$_4$) δ 0.83 (s, 3H), 0.89 (s, 1H), 0.92 (s, 3H), 1.05 (d, J=13.6 Hz, 1H), 1.16 (d, J=14.8 Hz, 6H), 1.23 (s, 3H), 1.25-1.50 (m, 9H), 1.59-1.99 (m, 8H), 2.03 (s, 3H), 2.10-2.17 (m, 1H), 2.18 (s, 3H), 2.20-2.29 (m, 1H), 2.32-2.50 (m, 1H), 2.61 (s, 1H), 2.96 (d, J=14.0 Hz, 1H), 4.71 (dd,7=12.8, 3.6 Hz, 1H), 4.84 (s, 1H), 5.12 (d, J=14.0 Hz, 1H), 5.61 (s, 1H), 7.19 (s, 1H), 7.37 (s, 1H).

281

Example 86 (2S,4aS,6aS,6bR,8aR,9S,10S,12aS, 12bR,14bR)-9-(((5-ethyl-2-oxo-1,3-dioxol-4-yl) methoxy)carbonyl)-2,4a,6a,6b,9,12a-hexamethyl-10- (4-methyl-1H-pyrazol-1-yl)-13-oxo-1,2,3,4,4a,5,6, 6a,6b,7,8,8a,9,10,11,12,12a,12b,13,14b- icosahydropicene-2-carboxylic Acid (339-1)

282

Example 87 (2S,4aS,6aS,6bR,8aR,9S,10S,12aS, 12bR,14bR)-10-((2-methoxy-2-oxoethyl)amino)-2, 4a,6a,6b,9,12a-hexamethyl-9-(((5-methyl-2-oxo-1,3- dioxol-4-yl)methoxy)carbonyl)-13-oxo-1,2,3,4,4a,5, 6,6a,6b,7,8,8a,9,10,1142,12a,12b,13,14b- icosahydropicene-2-carboxylic Acid (341-2)

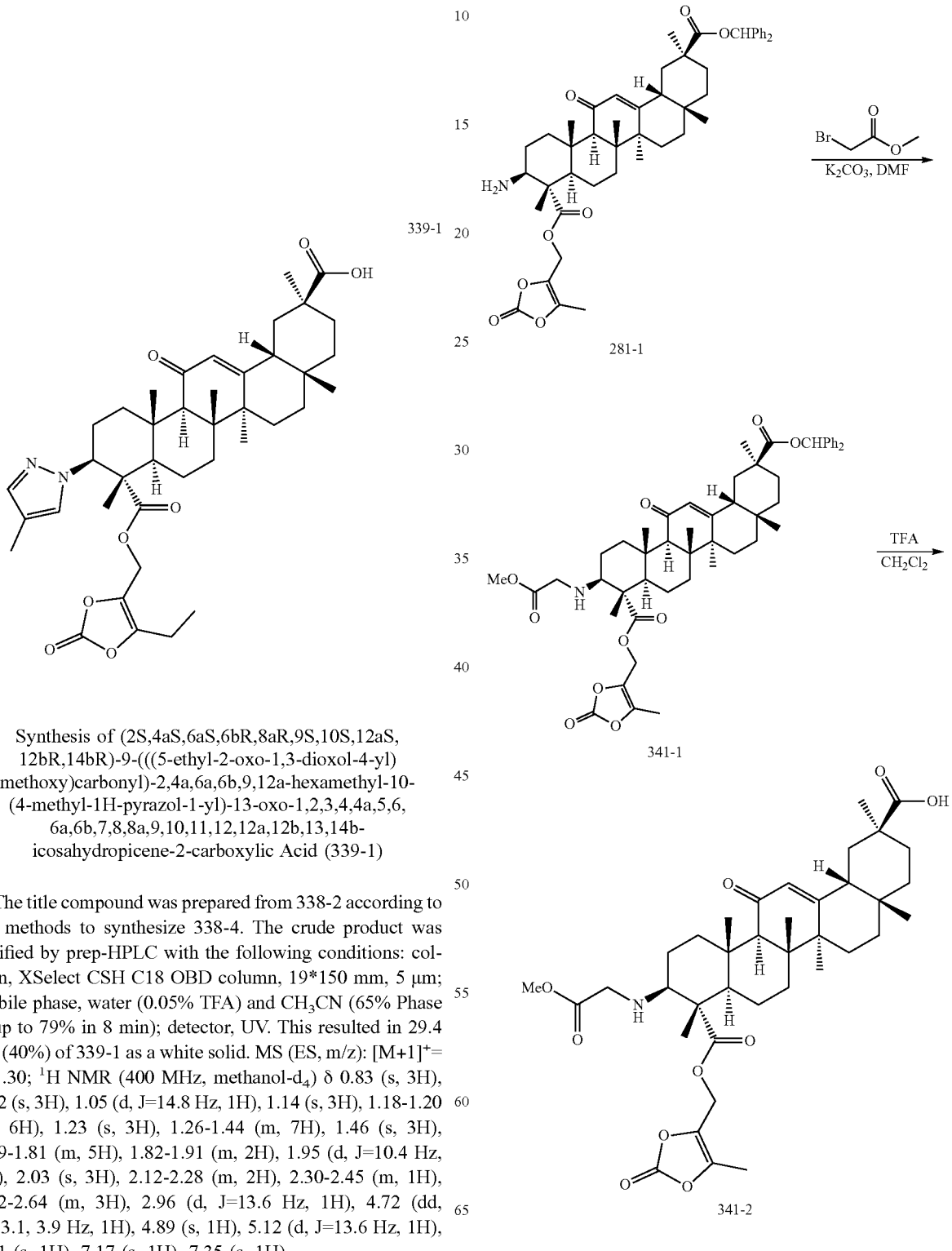

Synthesis of (2S,4aS,6aS,6bR,8aR,9S,10S,12aS, 12bR,14bR)-9-(((5-ethyl-2-oxo-1,3-dioxol-4-yl) methoxy)carbonyl)-2,4a,6a,6b,9,12a-hexamethyl-10- (4-methyl-1H-pyrazol-1-yl)-13-oxo-1,2,3,4,4a,5,6, 6a,6b,7,8,8a,9,10,11,12,12a,12b,13,14b- icosahydropicene-2-carboxylic Acid (339-1)

The title compound was prepared from 338-2 according to the methods to synthesize 338-4. The crude product was purified by prep-HPLC with the following conditions: column, XSelect CSH C18 OBD column, 19*150 mm, 5 µm; mobile phase, water (0.05% TFA) and CH$_3$CN (65% Phase B up to 79% in 8 min); detector, UV. This resulted in 29.4 mg (40%) of 339-1 as a white solid. MS (ES, m/z): [M+1]$^+$= 691.30; $^1$H NMR (400 MHz, methanol-d$_4$) δ 0.83 (s, 3H), 0.92 (s, 3H), 1.05 (d, J=14.8 Hz, 1H), 1.14 (s, 3H), 1.18-1.20 (m, 6H), 1.23 (s, 3H), 1.26-1.44 (m, 7H), 1.46 (s, 3H), 1.59-1.81 (m, 5H), 1.82-1.91 (m, 2H), 1.95 (d, J=10.4 Hz, 1H), 2.03 (s, 3H), 2.12-2.28 (m, 2H), 2.30-2.45 (m, 1H), 2.52-2.64 (m, 3H), 2.96 (d, J=13.6 Hz, 1H), 4.72 (dd, J=13.1, 3.9 Hz, 1H), 4.89 (s, 1H), 5.12 (d, J=13.6 Hz, 1H), 5.61 (s, 1H), 7.17 (s, 1H), 7.35 (s, 1H).

Synthesis of 2-benzhydryl 9-((5-methyl-2-oxo-1,3-dioxol-4-yl)methyl) (2S,4aS,6aS,6bR,8aR,9S,10S,12aS,12bR,14bR)-10-((2-methoxy-2-oxoethyl)amino)-2,4a,6a,6b,9,12a-hexamethyl-13-oxo-1,2,3,4,4a,5,6,6a,6b,7,8,8a,9,10,11,12,12a,12b,13,14b-icosahydropicene-2,9-dicarboxylate (341-1)

Methyl bromoacetate (33 μL, 0.36 mmol) was added to a slurry of 281-1 (150 mg, 0.18 mmol) and K₂CO₃ (124 mg, 0.90 mmol) in DMF (1.5 mL) and stirred at RT. After 90 minutes, EtOAc (50 mL) was added. The mixture was washed with water (3×10 mL), dried (Na₂SO₄) and concentrated onto SiO₂ (3 g). Purification by flash chromatography (4 g SiO₂, 30-70% EtOAc/DCM) gave 341-1 (69 mg).

Synthesis of (2S,4aS,6aS,6bR,8aR,9S,10S,12aS,12bR,14bR)-10-((2-methoxy-2-oxoethyl)amino)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic Acid (341-2)

Trifluoroacetic acid (0.30 mL) was added to a solution of 341-1 (19 mg, 0.022 mmol) in CH₂Cl₂ (0.30 mL). After stirring for 30 minutes, the solution was concentrated under vacuum and purified by preparative HPLC to give a TFA salt of the title compound (14 mg). MS (ES, m/z): [M+H]⁺=684.3; ¹H NMR (400 MHz, methanol-d₄) δ 5.60 (s, 1H), 5.61 (s, 1H), 5.20 (d, J=14.1, 1H), 4.98 (d, J=14.0 Hz, 1H), 4.02 (dd, J=17.1, J=27.4 Hz, 2H), 3.84 (s, 3H), 3.69 (dd, J=4.3 Hz, J=12.5 Hz, 1H), 2.90 (dt, J=14.1 Hz, J=2.5 Hz, 1H), 2.54 (s, 1H), 2.22 (s, 3H), 1.42 (s, 3H), 1.28 (s, 3H), 1.22 (s, 3H), 1.17 (s, 3H), 1.14 (s, 3H), 0.83 (s, 3H).

Example 88 (2S,4aS,6aS,6bR,8aR,9S,10S,12aS,12bR,14bR)-10-((2-amino-2-oxoethyl)amino)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,1142,12a,12b,13,14b-icosahydropicene-2-carboxylic Acid (342-1)

Synthesis of (2S,4aS,6aS,6bR,8aR,9S,10S,12aS,12bR,14bR)-10-((2-methoxy-2-oxoethyl)amino)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic Acid (342-1)

The title compound was prepared through the same route as for 341-2 but using 2-bromoacetamide. The crude product was purified by preparative HPLC to give a TFA salt of 342-1 (13 mg). MS (ES, m/z): [M+H]⁺=724.3; ¹H NMR (400 MHz, methanol-d₄) δ 5.61 (s, 1H), 5.22 (d, J=14.1 Hz, 1H), 4.94 (d, J=14.1 Hz, 1H), 3.80 (dd, J=27.2 Hz, J=16.0 Hz, 2H), 3.59 (dd, J=12.6 Hz, J=4.5 Hz, 1H), 2.90 (dt, J=13.5 Hz, J=3.0 Hz, 1H), 2.55 (s, 1H), 2.22 (s, 3H), 1.43 (s, 3H), 1.29 (s, 3H), 1.19 (s, 3H), 1.17 (s, 3H), 1.14 (s, 3H), 0.83 (s, 3H).

Example 89 (2S,4aS,6aS,6bR,8aR,9S,10S,12aS,12bR,14bR)-10-((2-methoxy-2-oxoethyl)amino)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,1142,12a,12b,13,14b-icosahydropicene-2-carboxylic Acid (343-3)

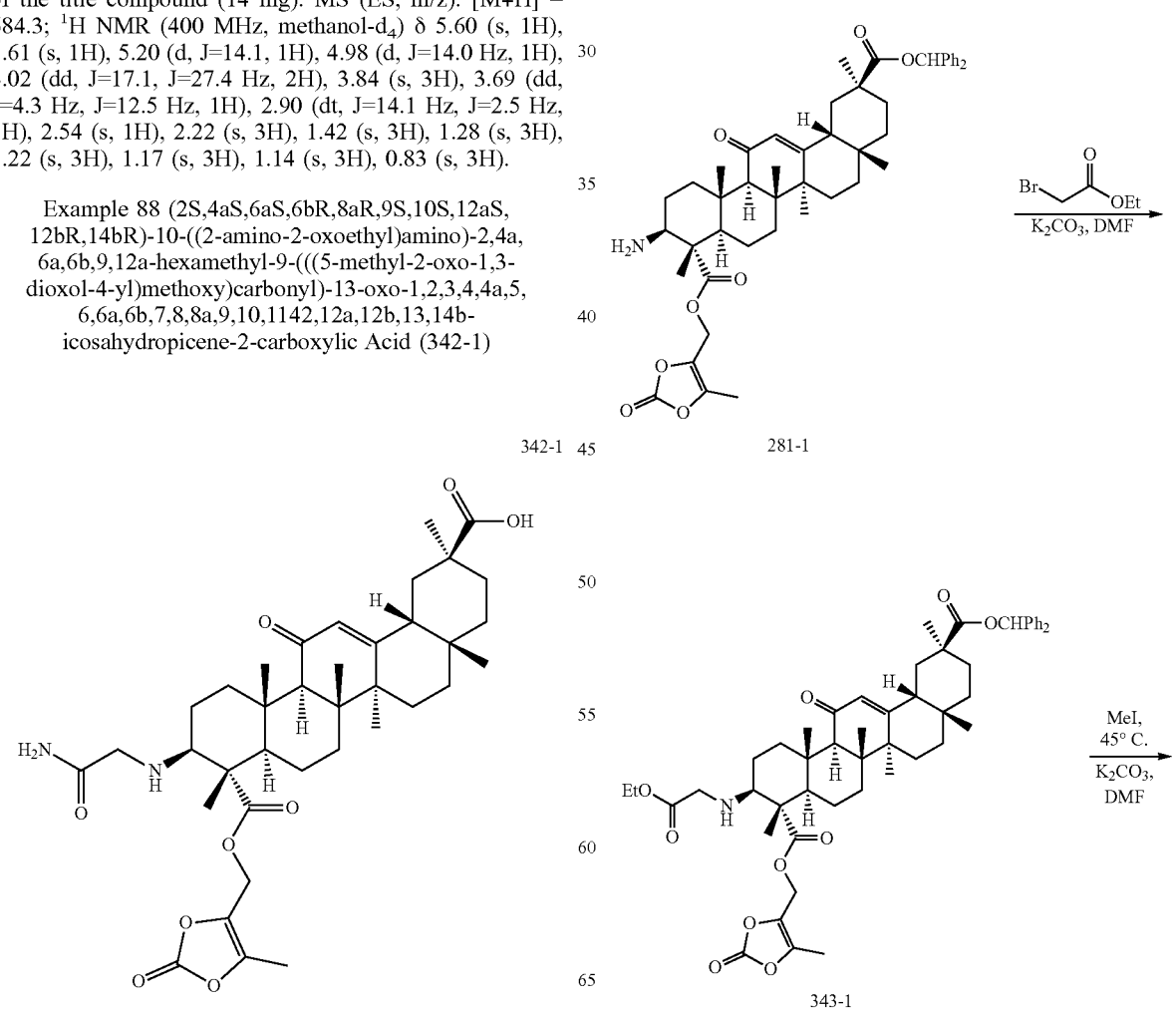

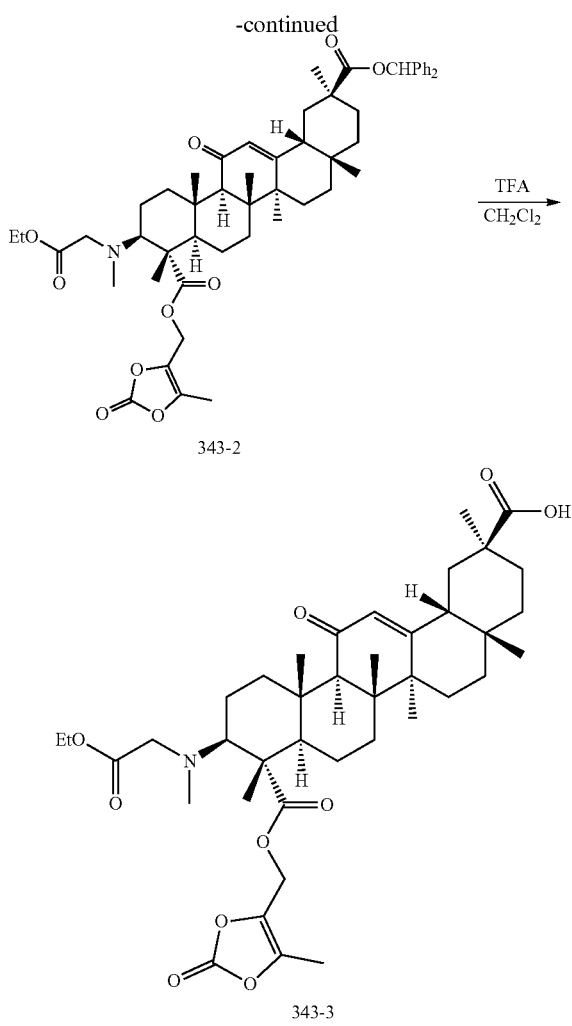

washed with water (3×20 mL), dried (Na$_2$SO$_4$) and concentrated. Purification by flash chromatography (12 g SiO$_2$, 10-60% EtOAc/hexane) gave 343-2 (80 mg).

Synthesis of (2S,4aS,6aS,6bR,8aR,9S,10S,12aS, 12bR,14bR)-10-((2-ethoxy-2-oxoethyl)(methyl) amino)-2,4a,6a,6b,9,12a-hexamethyl-9-(((5-methyl-2-oxo-1,3-dioxol-4-yl)methoxy)carbonyl)-13-oxo-1, 2,3,4,4a,5,6,6a,6b,7,8,8a,9,10,11,12,12a,12b,13,14b-icosahydropicene-2-carboxylic Acid (343-3)

Trifluoroacetic acid (0.30 mL) was added to a solution of 343-2 (80 mg, 0.091 mmol) in CH$_2$Cl$_2$ (0.30 mL). After stirring for 30 minutes, the solution was concentrated under vacuum and purified by preparative HPLC to give a TFA salt of 343-3 (58 mg). MS (ES, m/z): [M+H]$^+$=712.3; $^1$H NMR (400 MHz, methanol-d$_4$) δ 5.60 (s, 1H), 5.22 (d, J=13.8 Hz, 1H), 4.93 (d, J=13.7 Hz, 1H), 4.27 (quar, J=7.2 Hz, 2H), 4.00 (m, 1H), 3.88 (m, 1H), 3.72 (m, 1H), 3.92 (dt, J=13.3 Hz, J=3.0 Hz, 1H), 2.80 (s, 3H), 2.53 (s, 1H), 2.22 (s, 3H), 1.42 (s, 3H), 1.33 (s, 3H), 1.31 (t, J=7.2 Hz), 1.19 (s, 3H), 1.17 (s, 3H), 1.13 (s, 3H), 0.83 (s, 3H).

Example 90 (2S,4aS,6aS,6bR,8aR,9S,10S,12aS, 12bR,14bR)-10-(allyl(2-methoxy-2-oxoethyl) amino)-2,4a,6a,6b,9,12a-hexamethyl-9-(((5-methyl-2-oxo-1,3-dioxol-4-yl)methoxy)carbonyl)-13-oxo-1, 2,3,4,4a,5,6,6a,6b,7,8,8a,9,10,1142,12a,12b,13,14b-icosahydropicene-2-carboxylic Acid (344-1)

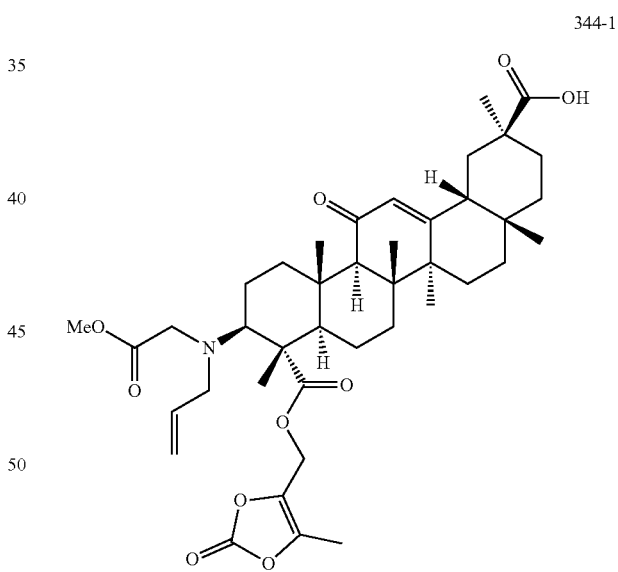

344-1

Synthesis of 2-benzhydryl 9-((5-methyl-2-oxo-1,3-dioxol-4-yl)methyl) (2S,4aS,6aS,6bR,8aR,9S,10S, 12aS,12bR,14bR)-10-((2-ethoxy-2-oxoethyl)amino)-2,4a,6a,6b,9,12a-hexamethyl-13-oxo-1,2,3,4,4a,5,6, 6a,6b,7,8,8a,9,10,11,12,12a,12b,13,14b-icosahydropicene-2,9-dicarboxylate (343-1)

Ethyl bromoacetate (68 µL, 0.61 mmol) was added to a slurry 281-1 (250 mg, 0.31 mmol) and K$_2$CO$_3$ (212 mg, 1.53 mmol) in DMF (2.5 mL) and stirred at RT. After 75 minutes, EtOAc (65 mL) was added. The mixture was washed with water (3×20 mL), dried (Na$_2$SO$_4$) and concentrated onto SiO$_2$ (3 g). Purification by flash chromatography (12 g SiO$_2$, 30-70% EtOAc/DCM) gave 343-1 (117 mg).

Synthesis of 2-benzhydryl 9-((5-methyl-2-oxo-1,3-dioxol-4-yl)methyl) (2S,4aS,6aS,6bR,8aR,9S,10S, 12aS,12bR,14bR)-10-((2-ethoxy-2-oxoethyl) (methyl)amino)-2,4a,6a,6b,9,12a-hexamethyl-13-oxo-1,2,3,4,4a,5,6,6a,6b,7,8,8a,9,10,11,12,12a,12b, 13,14b-icosahydropicene-2,9-dicarboxylate (343-2)

Iodomethane (59 µL, 0.95 mmol) was added to a slurry of 343-1 (117 mg, 0.14 mmol) and K$_2$CO$_3$ (131 mg, 0.95 mmol) in DMF (1.3 mL) and heated at 45° C. After 75 minutes, EtOAc (50 mL) was added. The mixture was Synthesis of (2S,4aS,6aS,6bR,8aR,9S,10S,12aS, 12bR,14bR)-10-(allyl(2-methoxy-2-oxoethyl) amino)-2,4a,6a,6b,9,12a-hexamethyl-9-(((5-methyl-2-oxo-1,3-dioxol-4-yl)methoxy)carbonyl)-13-oxo-1, 2,3,4,4a,5,6,6a,6b,7,8,8a,9,10,11,12,12a,12b,13,14b-icosahydropicene-2-carboxylic Acid (344-1)

The title compound was prepared from 341-1 through the same route as for 343-3 but using allylbromide. The crude product was purified by preparative HPLC to give a TFA salt of 344-1 (13 mg). MS (ES, m/z): [M+H]$^+$=724.3; $^1$H NMR (400 MHz, methanol-$d_4$) δ 5.78 (m, 1H), 5.59 (s, 1H), 5.25 (m, 2H), 5.18 (d, J=13.8 Hz), 4.87 (d, 1H), 3.71 (s, 3H), 3.59-3.36 (m, 5H), 2.86 (dt, J=13.7 Hz, J=2.5 Hz, 1H), 2.53 (s, 1H), 2.21 (s, 3H), 1.43 (s, 3H), 1.23 (s, 3H), 1.17 (s, 3H), 1.16 (s, 3H), 1.12 (s, 3H), 0.83 (s, 3H).

Example 91 (2S,4aS,6aS,6bR,8aR,9S,10S,12aS,12bR,14bR)-10-(((S)-1-methoxy-1-oxopropan-2-yl)amino)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,1142,12a,12b,13,14b-icosahydropicene-2-carboxylic Acid (345-2)

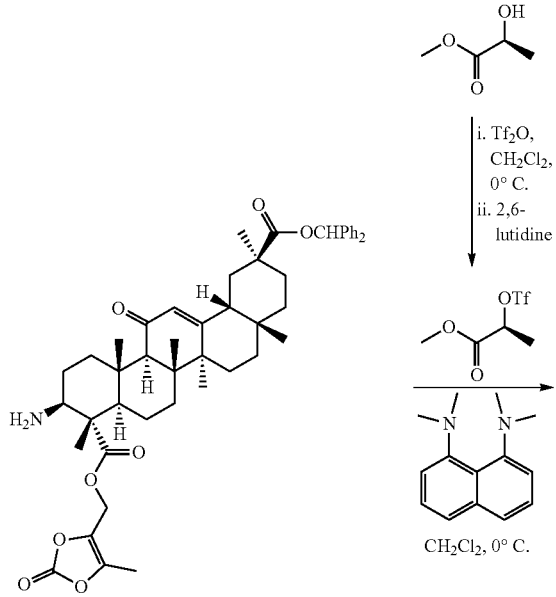

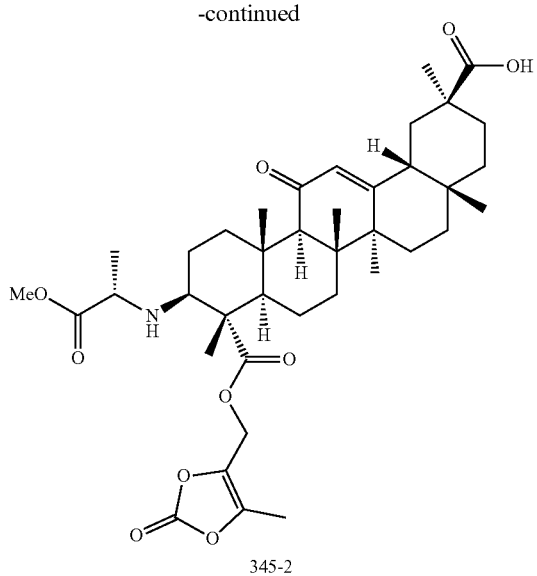

345-2

Synthesis of methyl (2,V)-2-(trifluoromethyl sulfonyloxy)propanoate

Into a 250-mL round-bottom flask purged and maintained with an inert atmosphere of nitrogen was placed methyl (2S)-2-hydroxypropanoate (1.00 g, 9.6 mmol) and $CH_2Cl_2$ (40 mL) followed by $Tf_2O$ (1.77 mL, 6.3 mmol, 1.1 equiv) dropwise with stirring at 0° C. To this was added 2,6-lutidine (1.53 mL, 14.3 mmol, 1.4 equiv) at 0° C. The reaction slurry was stirred for 2 hr at room temperature. The reaction mixture was concentrated and the residue applied onto a silica gel column with ethyl acetate:petroleum ether (1:5) to provide 1.2 g (53%) of methyl (2S)-2-(trifluoromethanesulfonyloxy)propanoate as a yellow oil.

Synthesis of 2-benzhydryl 9-((5-methyl-2-oxo-1,3-dioxol-4-yl)methyl) (2S,4aS,6aS,6bR,8aR,9S,10S,12aS,12bR,14bR)-10-(((S)-1-methoxy-1-oxopropan-2-yl)amino)-2,4a,6a,6b,9,12a-hexamethyl-13-oxo-1,2,3,4,4a,5,6,6a,6b,7,8,8a,9,10,11,12,12a,12b,13,14b-icosahydropicene-2,9-dicarboxylate (345-1)

Into a 8-mL vial was placed methyl (2S)-2-(trifluoromethanesulfonyloxy)propanoate (16 mg, 2.5 equiv) and $CH_2Cl_2$ (0.8 mL). The slurry was cooled to 0° C. and 1,8-bis(dimethylamino)naphthalene (14 mg, 2.5 equiv) in $CH_2Cl_2$ (0.2 mL) was added dropwise followed by a solution of 281-1 (20 mg, 1.0 equiv) in $CH_2Cl_2$ (0.2 mL) dropwise with stirring at 0° C. The reaction slurry was stirred for 1 h at room temperature. The reaction mixture was concentrated and the residue applied onto a silica gel column with ethyl acetate:petroleum ether (1:2) to provide 15 mg (68%) of 345-1 as a yellow solid.

Synthesis of (2S,4aS,6aS,6bR,8aR,9S,10S,12aS,12bR,14bR)-10-(((S)-1-methoxy-1-oxopropan-2-yl)amino)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic Acid (345-2)

Into a 25-mL round-bottom flask was placed 345-1 (200 mg), $CH_2Cl_2$ (5 mL), and TFA (0.5 mL). The reaction slurry

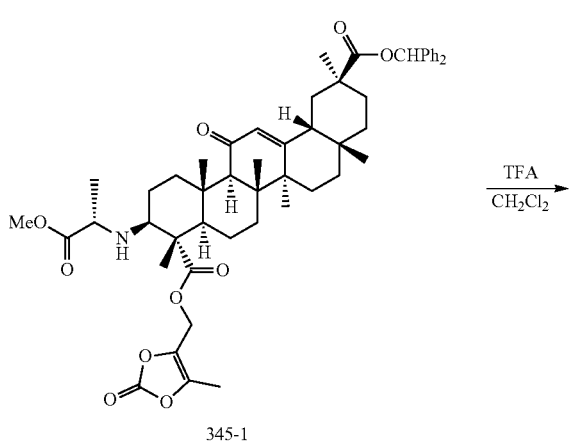

345-1 was stirred for 30 min at room temperature then concentrated. The crude product was purified by prep-HPLC with the following conditions: column, XSelect CSH OBD, 30*150 mm, 5 μm; mobile phase, water (0.1% TFA) and CH₃CN (30% phase B up to 55% in 9 min); detector, UV. This resulted in 119 mg (72%) of 345-2 as a white solid MS (ES, m/z): [M+H]⁺=698; ¹H NMR (300 MHz, methanol-$d_4$) δ 0.82-0.88 (s, 3H), 0.92-0.98 (s, 1H), 1.02-1.13 (d, J=13.1 Hz, 1H), 1.13-1.24 (m, 9H), 1.28-1.34 (s, 3H), 1.41-1.47 (s, 6H), 1.56-1.65 (d, J=7.2 Hz, 3H), 1.65-1.71 (s, 4H), 1.71-1.80 (d, J=13.2 Hz, 1H), 1.81-1.91 (d, J=12.0 Hz, 2H), 1.95-2.01 (s, 2H), 2.19-2.23 (s, 2H), 2.23-2.28 (s, 3H), 2.53-2.59 (s, 1H), 2.85-2.95 (d, J=13.7 Hz, 1H), 3.33-3.39 (s, 2H), 3.54-3.63 (d, J=8.4 Hz, 1H), 3.85-3.91 (s, 3H), 4.30-4.38 (d, J=7.3 Hz, 1H), 5.24-5.35 (d, J=14.0 Hz, 1H), 5.60-5.66 (s, 1H), 7.26-7.42 (dt, J=7.5, 15.1 Hz, 1H).

Example 92 (2S,4aS,6aS,6bR,8aR,9S,10S,12aS, 12bR,14bR)-2,4a,6a,6b,9,12a-hexamethyl-9-(((5-methyl-2-oxo-1,3-dioxol-4-yl)methoxy)carbonyl)-10-(1-methylcyclopropane-1-carboxamido)-13-oxo-1,2,3,4,4a,5,6,6a,6b,7,8,8a,9,10,1142,12a,12b,13, 14b-icosahydropicene-2-carboxylic Acid (346-2)

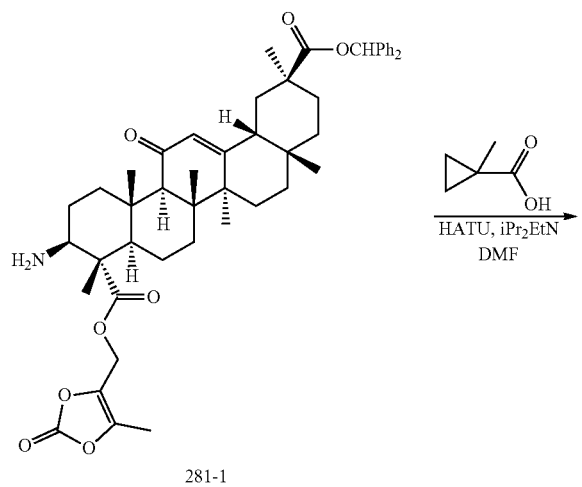

281-1

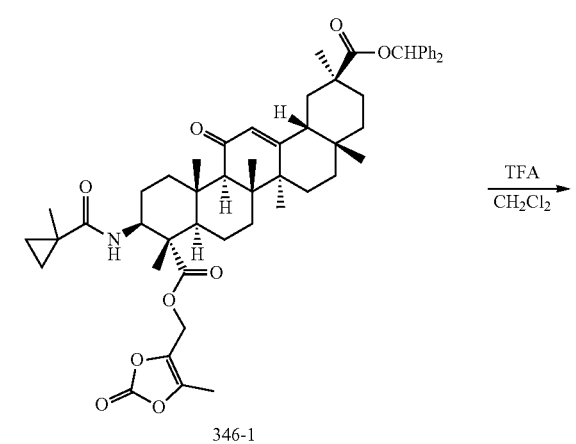

346-1

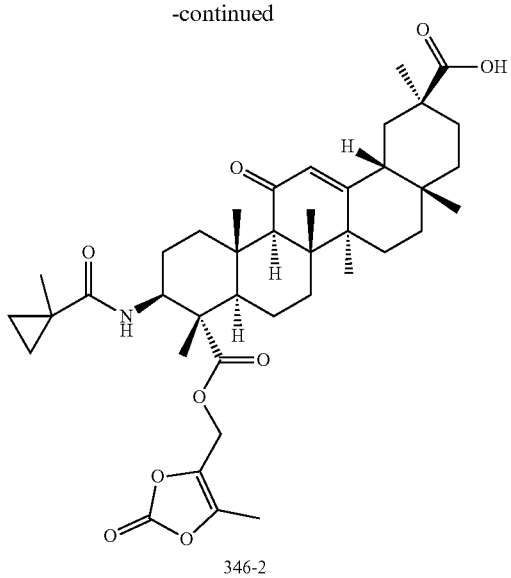

346-2

Synthesis of 2-benzhydryl 9-((5-methyl-2-oxo-1,3-dioxol-4-yl)methyl) (2S,4aS,6aS,6bR,8aR,9S,10S, 12aS,12bR,14bR)-2,4a,6a,6b,9,12a-hexamethyl-10-(1-methyl cyclopropane-1-carboxamido)-13-oxo-1, 2,3,4,4a,5,6,6a,6b,7,8,8a,9,10,11,12,12a,12b,13,14b-icosahydropicene-2,9-dicarboxylate (346-1)

To a mixture of 281-1·HCl (50.2 mg, 0.0616 mmol) and 1-methylcyclopropane-1-carboxylic acid (9 mg, 0.09 mmol, 1.5 equiv) in DMF (0.4 mL) were added iPr₂EtN (32.2 μL, 0.19 mmol, 3 equiv) and HATU (28 mg, 0.074 mmol, 1.2 equiv). The reaction slurry was stirred at rt overnight. Upon completion, the reaction mixture was diluted with water, washed with 2×H₂O and 1×brine, dried over anhydrous Na₂SO₄, filtered, and concentrated. The residue was purified by column chromatography (0-20% EtOAc in CH₂Cl₂) to provide 346-1 as a white solid (32 mg, 61%).

Synthesis of (2S,4aS,6aS,6bR,8aR,9S,10S,12aS, 12bR,14bR)-2,4a,6a,6b,9,12a-hexamethyl-9-(((5-methyl-2-oxo-1,3-dioxol-4-yl)methoxy)carbonyl)-10-(1 -methyl cyclopropane-1-carboxamido)-13-oxo-1,2,3,4,4a,5,6,6a,6b,7,8,8a,9,10,11,12,12a,12b,13, 14b-icosahydropicene-2-carboxylic acid (346-2)

To a mixture of 346-1 (32 mg, 0.038 mmol) in CH₂Cl₂ (0.5 mL) was added TFA (0.5 mL). The mixture was stirred at room temperature for 1 hour, concentrated, and purified by column (0-30% EtOAc/CH₂Cl₂) to give 346-2 as a white solid (20 mg, 76%). LCMS (ES, m/z) [M+H]⁺=694.1; ¹H-NMR (400 MHz, chloroform-7) δ 5.70 (s, 1H), 5.53 (d, J=9.4 Hz, 1H), 4.92 (d, J=13.8 Hz, 1H), 4.68 (d, J=13.9 Hz, 1H), 4.36-4.23 (m, 1H), 2.83 (d, J=13.7 Hz, 1H), 2.45 (s, 1H), 2.25-2.19 (m, 1H), 2.18 (s, 3H), 2.12-1.49 (m, 12H), 1.46-1.41 (m, 1H), 1.39 (s, 3H), 1.34 (d, J=15.4 Hz, 2H), 1.26 (s, 3H), 1.23 (s, 3H), 1.20-1.16 (m, 1H), 1.14 (d, J=1.8 Hz, 6H), 1.09 (s, 3H), 1.07 (dd, J=6.3, 3.6 Hz, 2H), 1.02 (d, J=13.6 Hz, 1H), 0.86 (d, J=12.8 Hz, 1H), 0.81 (s, 3H), 0.53 (dd, J=6.4, 3.7 Hz, 2H).

Example 93 (2S,4aS,6aS,6bR,8aR,9S,10S,12aS,12bR,14bR)-2,4a,6a,6b,9,12a-hexamethyl-9-(((5-methyl-2-oxo-1,3-dioxol-4-yl)methoxy)carbonyl)-13-oxo-10-(2-oxopyrrolidin-1-yl)-1,2,3,4,4a,5,6,6a,6b,7,8,8a,9,10,11,12,12a,12b,13,14b-icosahydropicene-2-carboxylic (347-4)
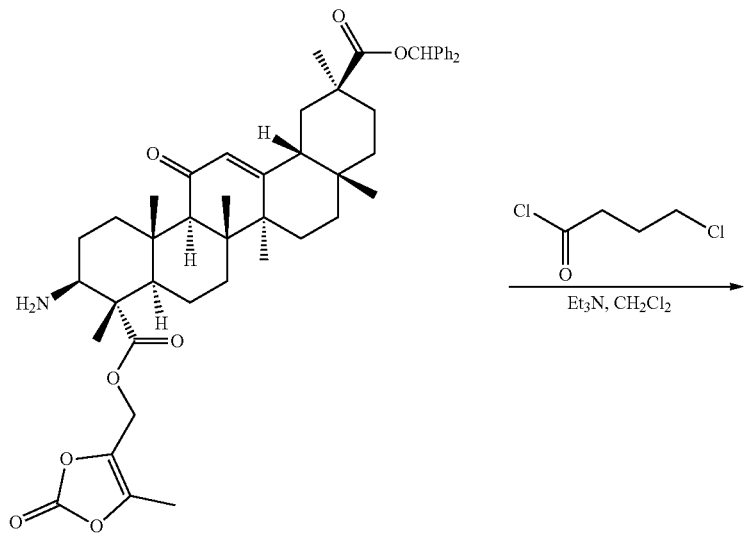
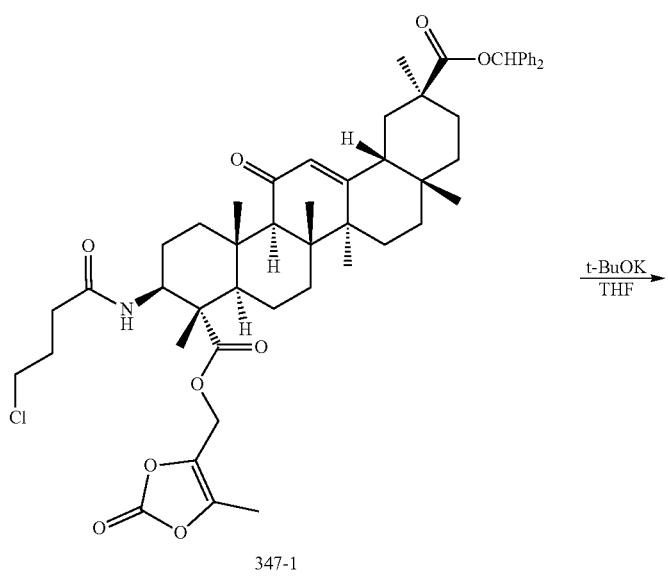

-continued
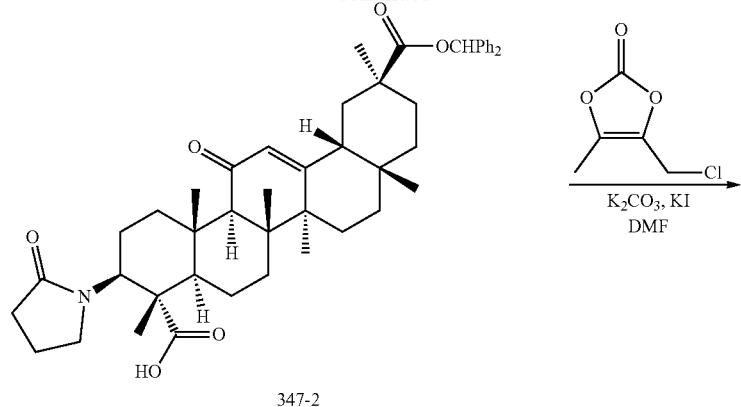
347-2
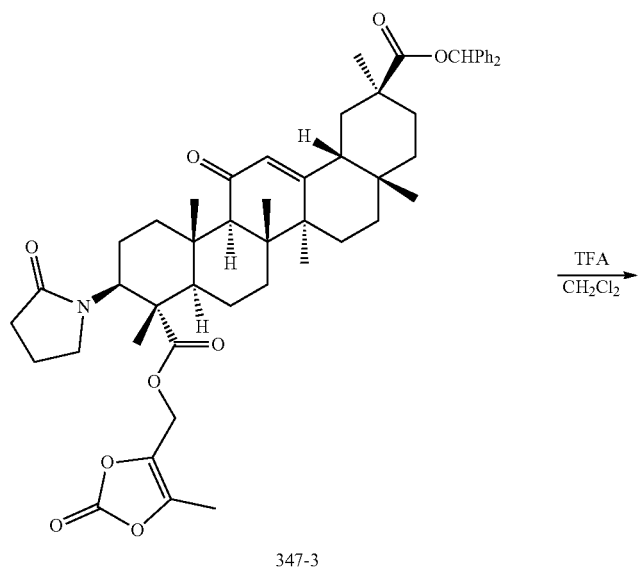
347-3
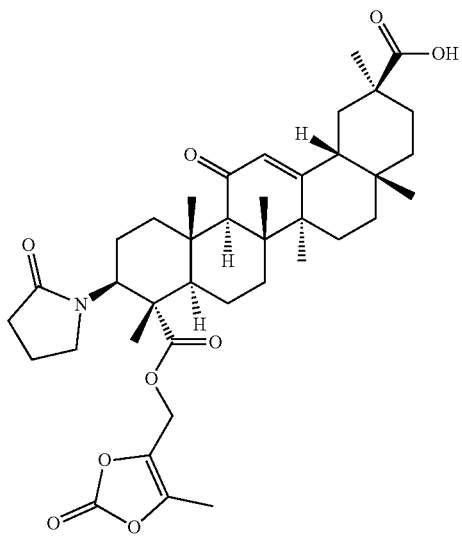
347-4

Synthesis of 2-benzhydryl 9-((5-methyl-2-oxo-1,3-dioxol-4-yl)methyl) (2S,4aS,6aS,6bR,8aR,9S,10S,12aS,12bR,14bR)-10-(4-chlorobutanamido)-2,4a,6a,6b,9,12a-hexamethyl-13-oxo-1,2,3,4,4a,5,6,6a,6b,7,8,8a,9,10,11,12,12a,12b,13,14b-icosahydropicene-2,9-dicarboxylate (347-1)

Into a 100-mL round-bottom flask was placed 281-1 (150 mg), $CH_2Cl_2$ (2 mL), and $Et_3N$ (0.077 mL, 3 equiv). To this slurry was added 4-chlorobutanoyl chloride (0.022 mL, 1.05 equiv) dropwise at room temperature. The reaction slurry was stirred for 2 h at room temperature. The reaction mixture was diluted with 100 mL of $CH_2Cl_2$ and washed with 100 ml of brine. The organic layer was dried over anhydrous $Na_2SO_4$, filtered, and concentrated to provide 140 mg of crude 347-1 as a yellow solid.

Synthesis of (3S,4S,4aR,6aR,6bS,8aS,11S,12aR,14aR,14bS)-11-((benzhydryloxy)carbonyl)-4,6a,6b,8a,11,14b-hexamethyl-14-oxo-3-(2-oxopyrrolidin-1-yl)-1,2,3,4,4a,5,6,6a,6b,7,8,8a,9,10,11,12,12a,14,14a,14b-icosahydropicene-4-carboxylic Acid (347-2)

Into a 100-mL round-bottom flask was placed 347-1 (140 mg), THF (3 mL), and t-BuOK (54 mg, 3 equiv). The reaction slurry was stirred for 48 h at room temperature. The reaction mixture was diluted with neutralized with 0.1 M HCl(aq) and extracted with 3×100 mL of $CH_2Cl_2$. The combined organic layers were washed with 3×100 ml of brine, dried over anhydrous $Na_2SO_4$, filtered, and concentrated to provide 120 mg of crude 347-2 as a yellow solid.

Synthesis of 2-benzhydryl 9-((5-methyl-2-oxo-1,3-dioxol-4-yl)methyl) (2S,4aS,6aS,6bR,8aR,9S,10S,12aS,12bR,14bR)-2,4a,6a,6b,9,12a-hexamethyl-13-oxo-10-(2-oxopyrrolidin-1-yl)-1,2,3,4,4a,5,6,6a,6b,7,8,8a,9,10,11,12,12a,12b,13,14b-icosahydropicene-2,9-dicarboxylate (347-3)

Into a 100-mL round-bottom flask was placed 347-2 (102 mg), DMF (0.5 mL), 4-(chloromethyl)-5-methyl-2H-1,3-dioxol-2-one (41 mg, 2 equiv), $K_2CO_3$ (58 mg, 3 equiv), and KI (12 mg, 0.5 equiv). The reaction slurry was stirred overnight at room temperature. The reaction mixture was diluted with water and extracted with 3×100 mL of ethyl acetate. The combined organic layers were washed with 3×150 ml of brine, dried over anhydrous $Na_2SO_4$, filtered, and concentrated. The residue was applied onto a silica gel column with ethyl acetate:petroleum ether (1:5) to provide 100 mg of 347-3 as a yellow solid.

Synthesis of (2S,4aS,6aS,6bR,8aR,9S,10S,12aS,12bR,14bR)-2,4a,6a,6b,9,12a-hexamethyl-9-(((5-methyl-2-oxo-1,3-dioxol-4-yl)methoxy)carbonyl)-13-oxo-10-(2-oxopyrrolidin-1-yl)-1,2,3,4,4a,5,6,6a,6b,7,8,8a,9,10,11,12,12a,12b,13,14b-icosahydropicene-2-carboxylic Acid (347-4)

Into a 50-mL round-bottom flask was placed 347-3 (100 mg), $CH_2Cl_2$ (10 mL), and TFA (1 mL). The reaction slurry was stirred for 1 h at room temperature. The reaction mixture was dried over anhydrous $Na_2SO_4$, filtered, and concentrated. The crude product was purified by Prep-HPLC with the following conditions: column, XSelect CSH OBD, 30*150 mm, 5 µm; mobile phase, water (0.05% TFA) and $CH_3CN$ (50% phase B up to 55% in 8 min); detector, UV. This resulted in 28.2 mg of 347-4 as a white solid. MS (ES, m/z): $[M+1]^+$=670; $^1H$ NMR (300 MHz, methanol-$d_4$) δ 5.63 (s, 1H), 5.06 (d, J=13.9 Hz, 1H), 4.71 (d, J=13.9 Hz, 1H), 4.30 (dd, J=12.8, 3.9 Hz, 1H), 3.55 (q, J=8.3, 7.4 Hz, 2H), 2.89 (d, J=13.5 Hz, 1H), 2.61 (s, 1H), 2.33 (d, J=7.8 Hz, 1H), 2.27 (d, J=13.4 Hz, 1H), 2.21 (s, 3H), 2.11-1.96 (m, 2H), 1.92 (d, J=11.4 Hz, 1H), 1.86 (s, 1H), 1.71 (dt, J=24.0, 12.9 Hz, 1H), 1.48 (s, 3H), 1.41 (d, J=13.5 Hz, 4H), 1.30 (s, 1H), 1.27-1.14 (m, 13H), 1.08 (d, J=13.1 Hz, 1H), 0.86 (s, 4H).

Example 94 (2S,4aS,6aS,6bR,8aR,9S,10S,12aS,12bR,14bR)-9-(((5-ethyl-2-oxo-1,3-dioxol-4-yl)methoxy)carbonyl)-10-((S)-2-(methoxycarbonyl)pyrrolidin-1-yl)-2,4a,6a,6b,9,12a-hexamethyl-13-oxo-1,2,3,4,4a,5,6,6a,6b,7,8,8a,9,10,11,12,12a,12b,13,14b-icosahydropicene-2-carboxylic Acid (348-11)

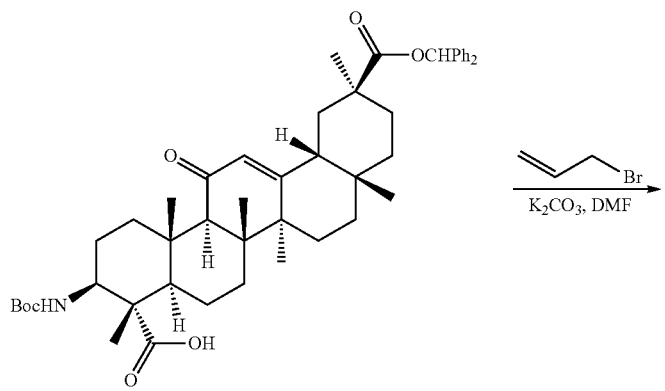

280-5

-continued
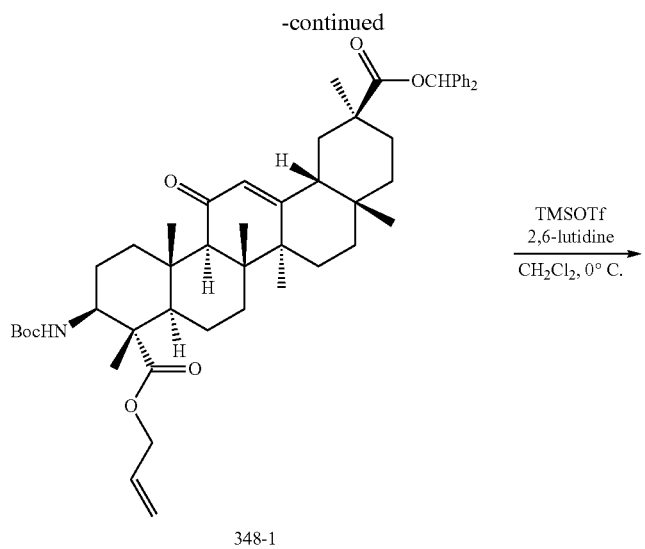
348-1
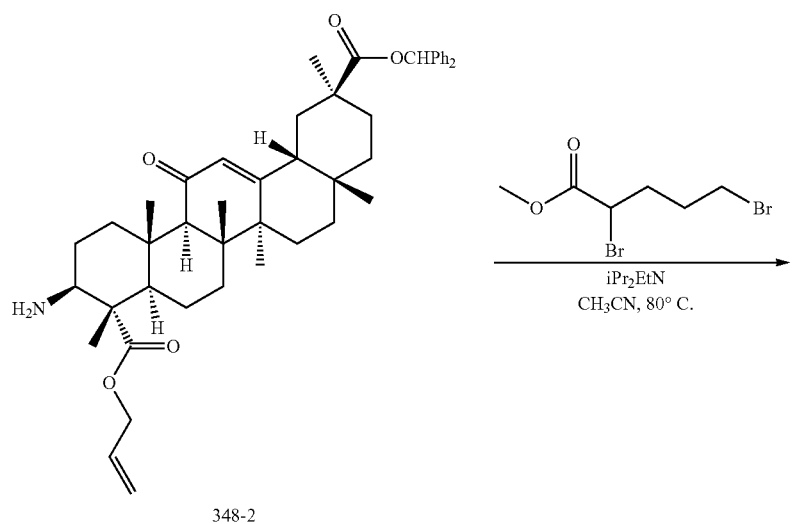
348-2
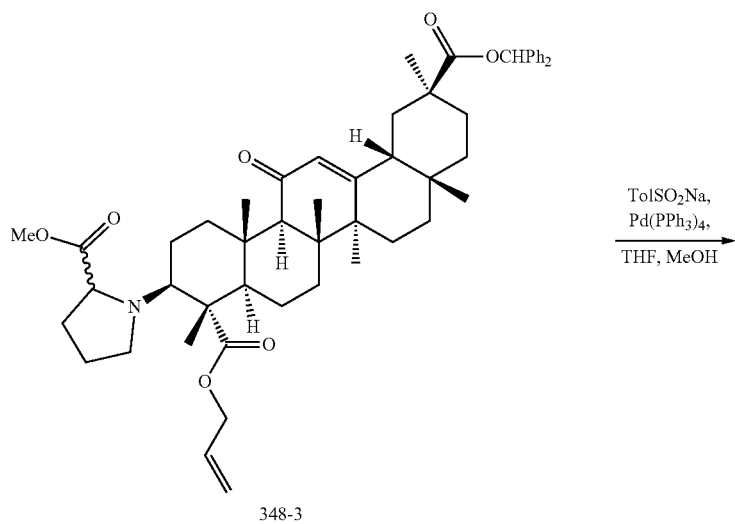
348-3

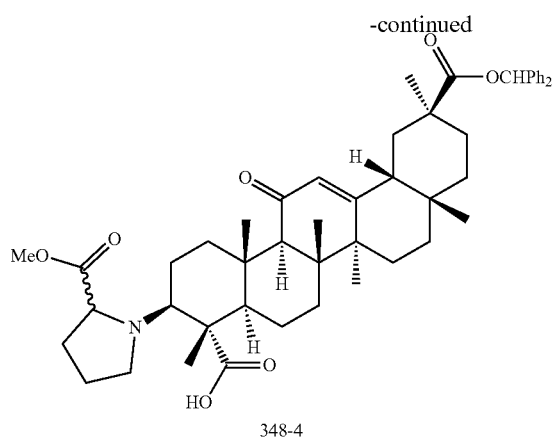
348-4
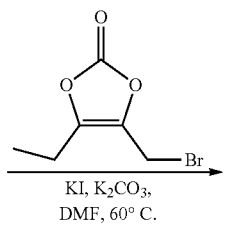
KI, K₂CO₃,
DMF, 60° C.
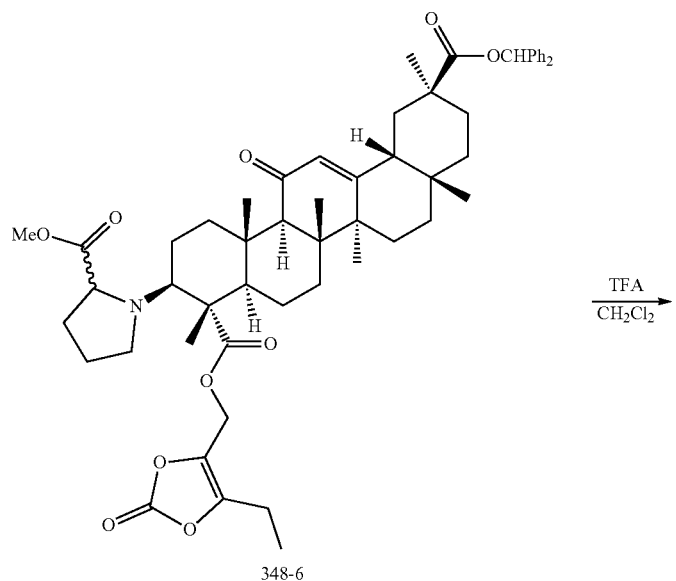
348-6
TFA
CH₂Cl₂
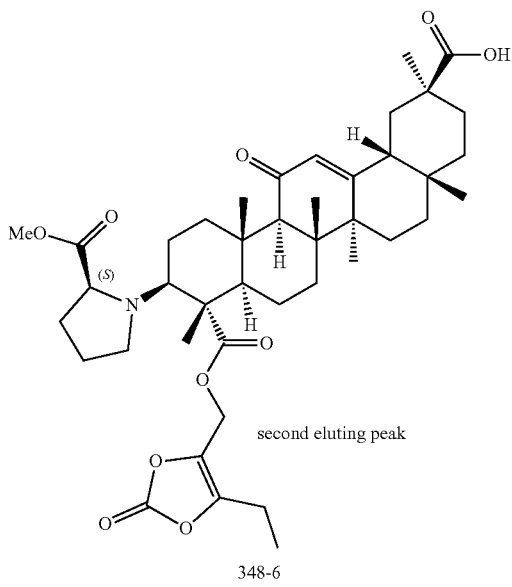
second eluting peak
348-6

Synthesis of 9-allyl 2-benzhydryl (2S,4aS,6aS,6bR, 8aR,9S,10S,12aS,12bR,14bR)-10-((tert-butoxycarbonyl)amino)-2,4a,6a,6b,9,12a-hexamethyl-13-oxo-1,2,3,4,4a,5,6,6a,6b,7,8,8a,9,10,11,12,12a,12b,13, 14b-icosahydropicene-2,9-dicarboxylate (348-1)

Into a 50-mL round-bottom flask was placed 280-5 (600 mg, 0.78 mmol, 1 equiv), DMF (6 mL), allyl bromide (0.27 mL, 4 equiv), KI (66 mg, 0.4 mmol, 0.5 equiv), and $K_2CO_3$ (540 mg, 3.9 mmol, 5 equiv). The reaction mixture was stirred for 1 hr at room temperature then diluted with 300 mL of $CH_2Cl_2$. The resulting mixture was washed with 3×300 ml of brine and the organic layer dried over anhydrous $Na_2SO_4$, filtered, and concentrated. The residue was applied onto a silica gel column with 1:5 ethyl acetate: petroleum ether to provide 616 mg (98%) of 348-1 as a white solid.

Synthesis of 9-allyl 2-benzhydryl (2S,4aS,6aS,6bR, 8aR,9S,10S,12aS,12bR,14bR)-10-amino-2,4a,6a,6b, 9,12a-hexamethyl-13-oxo-1,2,3,4,4a,5,6,6a,6b,7,8, 8a,9,10,11,12,12a,12b,13,14b-icosahydropicene-2,9-dicarboxylate (348-2)

Into a 100-mL round-bottom flask was placed 348-1 (616 mg, 1 equiv), $CH_2Cl_2$ (50 mL), and 2,6-lutidine (0.44 mL, 5 equiv) followed by the addition of TMSOTf (679 mg, 4 equiv) at 0° C. The reaction mixture was stirred for 1 hr at room temperature. The reaction slurry was washed with 2×2 M HCl and 2 x brine. The organic layer was dried over anhydrous $Na_2SO_4$, filtered, and concentrated to provide 600 mg (quant) of crude 348-2 as a yellow solid (HCl salt).

Synthesis of 9-allyl 2-benzhydryl (2S,4aS,6aS,6bR, 8aR,9S,10S,12aS,12bR,14bR)-10-(2-(methoxycarbonyl)pyrrolidin-1-yl)-2,4a,6a,6b,9,12a-hexamethyl-13-oxo-1,2,3,4,4a,5,6,6a,6b,7,8,8a,9,10,11,12,12a, 12b,13,14b-icosahydropicene-2,9-dicarboxylate (348-3)

Into a 25-mL sealed tube was placed 348-2 (600 mg, 0.85 mmol, 1 equiv), $CH_3CN$ (1 mL), methyl 2,5-dibromopentanoate (0.133 mL, 0.85 mmol, 1 equiv), and $iPr_2EtN$ (0.70 mL, 4.0 mmol, 4.7 equiv). The reaction mixture was stirred for 48 hr at 82° C. Upon completion, the reaction slurry was concentrated. The residue was applied onto a silica gel column with 1:5 ethyl acetate:petroleum ether to provide 363 mg (52%) of 348-3 as a white solid.

Synthesis of (3S,4S,4aR,6aR,6bS,8aS,11S,12aR, 14aR,14bS)-11-((benzhydryloxy)carbonyl)-3-(2-(methoxycarbonyl)pyrrolidin-1-yl)-4,6a,6b,8a,11, 14b-hexamethyl-14-oxo-1,2,3,4,4a,5,6,6a,6b,7,8,8a, 9,10,11,12,12a,14,14a,14b-icosahydropicene-4-carboxylic Acid (348-4)

Into a 50-mL round-bottom flask purged and maintained with an inert atmosphere of nitrogen was placed 348-3 (363 mg, 0.44 mmol, 1 equiv), THF (1 mL), MeOH (3 mL), $TolSO_2Na$ (316 mg, 1.78 mmol, 4 equiv), and $Pd(PPh_3)_4$ (256 mg, 0.22 mmol, 0.5 equiv). The reaction mixture was stirred for 1 hr at room temperature. Upon completion the reaction slurry was concentrated and the residue applied onto a silica gel column with 10:1 $CH_2Cl_2$:methanol to provide 300 mg (87%) of 348-4 as a yellow solid.

Synthesis of 2-benzhydryl 9-((5-ethyl-2-oxo-1,3-dioxol-4-yl)methyl) (2S,4aS,6aS,6bR,8aR,9S,10S, 12aS,12bR,14bR)-10-(2-(methoxycarbonyl)pyrrolidin-1-yl)-2,4a,6a,6b,9,12a-hexamethyl-13-oxo-1,2,3, 4,4a,5,6,6a,6b,7,8,8a,9,10,11,12,12a,12b,13,14b-icosahydropicene-2,9-dicarboxylate (348-5)

Into a 100-mL round-bottom flask was placed 348-4 (940 mg, 1.2 mmol, 1 equiv), DMF (10 mL), 4-(bromomethyl)-5-ethyl-1,3-dioxol-2-one (800 mg, 3.9 mmol, 3.2 equiv), KI (100 mg, 0.6 mmol, 0.5 equiv), and $K_2CO_3$ (830 mg, 6 mmol, 5 equiv). The reaction slurry was stirred for 1 hr at 60° C. The reaction mixture was extracted with 300 mL of $CH_2Cl_2$ and the organic layer washed with 3×300 ml of brine, dried over anhydrous $Na_2SO_4$, filtered, and concentrated. The residue was applied onto a silica gel column with ethyl acetate:petroleum ether (1:1) to provide 780 mg (71%) of 348-5 as a brown solid.

Synthesis of (2S,4aS,6aS,6bR,8aR,9S,10S,12aS, 12bR,14bR)-9-(((5-ethyl-2-oxo-1,3-dioxol-4-yl) methoxy)carbonyl)-10-((S)-2-(methoxycarbonyl) pyrrolidin-1-yl)-2,4a,6a,6b,9,12a-hexamethyl-13-oxo-1,2,3,4,4a,5,6,6a,6b,7,8,8a,9,10,11,12,12a,12b, 13,14b-icosahydropicene-2-carboxylic Acid (348-6)

Into a 50-mL round-bottom flask was placed 348-5 (350 mg, 0.38 mmol, 1 equiv), $CH_2Cl_2$ (5 mL), and TFA (0.5 mL). The reaction mixture was stirred for 1 hr at room temperature then concentrated. The crude product was purified by Prep-HPLC with the following conditions: column, XBridge Prep OBD C18, 30*150 mm, 5 µm; mobile phase, water (0.05% TFA) and $CH_3CN$ (30% phase B up to 60% in 8 min); detector, UV to provide 40.2 mg (14%) of 348-6 as a white solid. MS (ES, m/z): $[M+1]^+$=738.3; $^1H$ NMR (400 MHz, methanol-$d_4$) δ 0.84 (s, 3H), 0.92 (d, J=9.7 Hz, 1H), 1.07 (d, J=14.5 Hz, 1H), 1.15 (s, 3H), 1.17 (d, J=6.9 Hz, 6H), 1.20-1.28 (m, 5H), 1.33 (s, 3H), 1.35-1.46 (m, 7H), 1.51-1.78 (m, 4H), 1.81-2.01 (m, 6H), 2.01-2.26 (m, 4H), 2.38 (s, 1H), 2.53 (s, 1H), 2.64 (q, J=7.5 Hz, 2H), 2.91 (d, J=13.8 Hz, 1H), 3.20 (d, J=8.8 Hz, 1H), 3.60 (s, 1H), 3.88 (s, 4H), 4.50 (s, 1H), 4.96 (d, J=14.0 Hz, 1H), 5.29 (d, J=13.9 Hz, 1H), 5.62 (s, 1H).

Example 95 (2S,4aS,6aS,6bR,8aR,9S,10S,12aS, 12bR,14bR)-10-((S)-2-(methoxycarbonyl)pyrrolidin-1-yl)-2,4a,6a,6b,9,12a-hexamethyl-9-(((5-methyl-2-oxo-1,3-dioxol-4-yl)methoxy)carbonyl)-13-oxo-1,2, 3,4,4a,5,6,6a,6b,7,8,8a,9,10,1142,12a,12b,13,14b-icosahydropicene-2-carboxylic Acid (349-1)

Example 96 (2S,4aS,6aS,6bR,8aR,9S,10S,12aS, 12bR,14bR)-9-(((5-isopropyl-2-oxo-1,3-dioxol-4-yl) methoxy)carbonyl)-10-((S)-2-(methoxycarbonyl) pyrrolidin-1-yl)-2,4a,6a,6b,9,12a-hexamethyl-13-oxo-1,2,3,4,4a,5,6,6a,6b,7,8,8a,9,10,1142,12a,12b, 13,14b-icosahydropicene-2-carboxylic Acid (350-1)

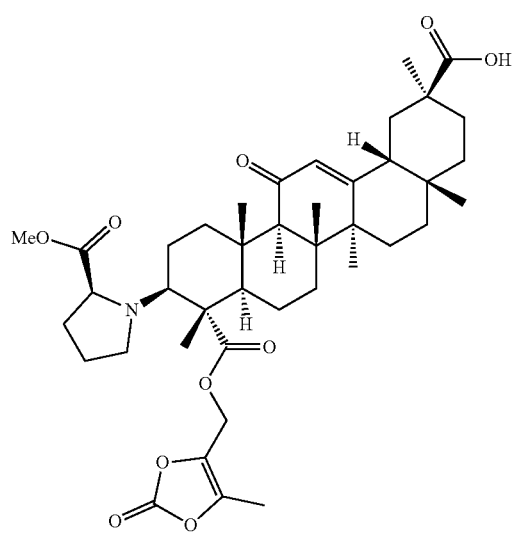

349-1

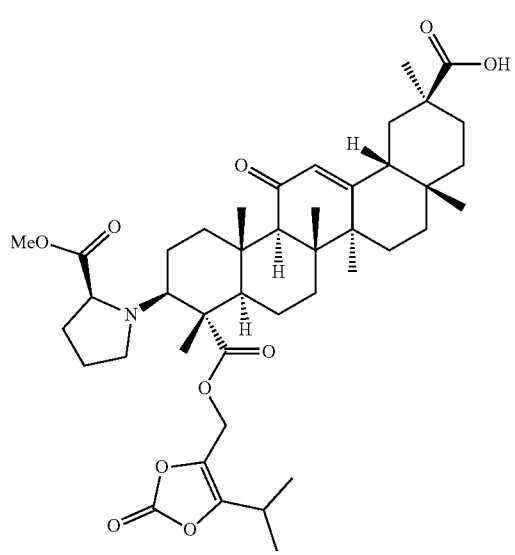

350-1

Synthesis of (2S,4aS,6aS,6bR,8aR,9S,10S,12aS, 12bR,14bR)-10-((S)-2-(methoxycarbonyl)pyrrolidin-1-yl)-2,4a,6a,6b,9,12a-hexamethyl-9-(((5-methyl-2-oxo-1,3-dioxol-4-yl)methoxy)carbonyl)-13-oxo-1,2, 3,4,4a,5,6,6a,6b,7,8,8a,9,10,11,12,12a,12b,13,14b-icosahydropicene-2-carboxylic Acid (349-1)

The title compound was prepared from 348-2 through the same route as for 348-6. The crude product was purified by prep-HPLC with the following conditions: column, XBridge Prep C18 OBD, 5 μm, 19*150 mm; mobile phase, water (0.1% TFA) and CH$_3$CN (45% phase B up to 75% in 11 min); detector, UV. This resulted in 58.0 mg of 349-1 as a white solid. MS (ES, m/z): [M+H]$^+$=724.3; $^1$H NMR (400 MHz, methanol-d$_4$) δ 0.84 (s, 3H), 0.93 (d, J=11.2 Hz, 1H), 1.07 (d, J=13.9 Hz, 1H), 1.11-1.21 (m, 9H), 1.21-1.31 (m, 2H), 1.32 (s, 3H), 1.36-1.51 (m, 7H), 1.57 (d, J=10.9 Hz, 1H), 1.60-1.78 (m, 3H), 1.78-2.02 (m, 6H), 2.02-2.30 (m, 7H), 2.40-2.47 (m, 1H), 2.53 (s, 1H), 2.80-3.02 (m, 1H), 3.24 (q, J=9.3 Hz, 1H), 3.65 (s, 1H), 3.90 (s, 3H), 3.96 (d, J=11.1 Hz, 1H), 4.61 (s, 1H), 4.96 (d, J=14.1 Hz, 1H), 5.31 (d, J=14.0 Hz, 1H), 5.62 (s, 1H).

Synthesis of (2S,4aS,6aS,6bR,8aR,9S,10S,12aS, 12bR,14bR)-9-(((5-isopropyl-2-oxo-1,3-dioxol-4-yl) methoxy)carbonyl)-10-((S)-2-(methoxycarbonyl) pyrrolidin-1-yl)-2,4a,6a,6b,9,12a-hexamethyl-13-oxo-1,2,3,4,4a,5,6,6a,6b,7,8,8a,9,10,11,12,12a,12b, 13,14b-icosahydropicene-2-carboxylic Acid (350-1)

The title compound was prepared from 348-2 through the same route as for 348-6. The crude product was purified by prep-HPLC with the following conditions: column, Sunfire Prep C18 OBD, 10 μm, 19*250 mm; mobile phase, water (0.05% TFA) and CH$_3$CN (50% phase B up to 56% in 8 min); detector, UV. This resulted in 23 mg of 350-1 as a white solid. MS (ES, m/z) [M+H]$^+$=752.35; $^1$H NMR (400 MHz, methanol-d$_4$) δ 0.84 (s, 3H), 0.90 (d, J=5.7 Hz, 1H), 1.00-1.10 (m, 1H), 1.12-1.21 (m, 9H), 1.21-1.40 (m, 15H), 1.40-1.50 (m, 6H), 1.60-1.78 (m, 4H), 1.78-2.01 (m, 7H), 2.10-2.27 (m, 3H), 2.40 (s, 1H), 2.55 (s, 1H), 2.91-3.00 (m, 1H), 3.04-3.16 (m, 2H), 3.54 (s, 1H), 3.87 (s, 3H), 4.96 (d, J=13.9 Hz, 1H), 5.04 (d, J=0.8 Hz, 1H), 5.27 (d, J=13.9 Hz, 1H), 5.62 (s, 1H).

Example 97 (2S,4aS,6aS,6bR,8aR,9S,10S,12aS, 12bR,14bR)-9-(((5-isopropyl-2-oxo-1,3-dioxol-4-yl) methoxy)carbonyl)-10-((R)-2-(methoxycarbonyl) pyrrolidin-1-yl)-2,4a,6a,6b,9,12a-hexamethyl-13-oxo-1,2,3,4,4a,5,6,6a,6b,7,8,8a,9,10,1142,12a,12b, 13,14b-icosahydropicene-2-carboxylic Acid (351-1)

Example 98 (2S,4aS,6aS,6bR,8aR,9S,10S,12aS, 12bR,14bR)-10-((S)-2-(ethoxycarbonyl)pyrrolidin-1-yl)-2,4a,6a,6b,9,12a-hexamethyl-9-(((5-methyl-2-oxo-1,3-dioxol-4-yl)methoxy)carbonyl)-13-oxo-1,2, 3,4,4a,5,6,6a,6b,7,8,8a,9,10,1142,12a,12b,13,14b-icosahydropicene-2-carboxylic Acid (352-1)

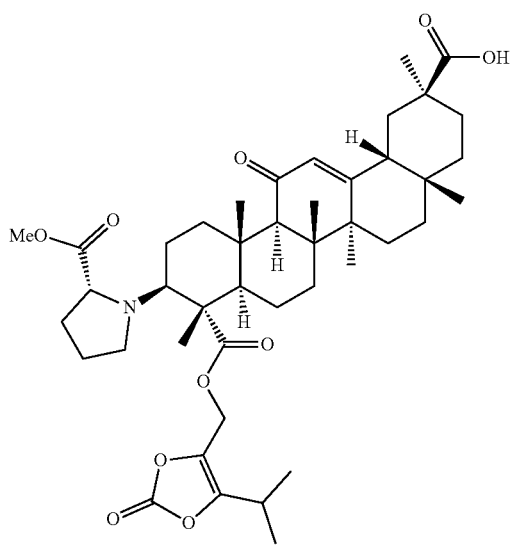

351-1

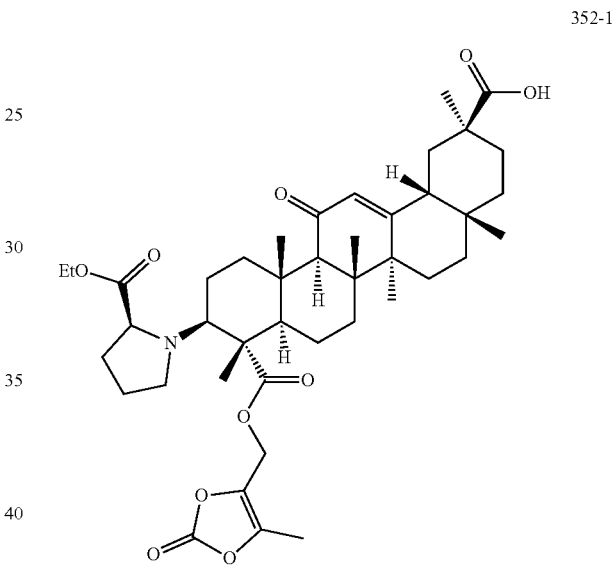

352-1

Synthesis of (2S,4aS,6aS,6bR,8aR,9S,10S,12aS, 12bR,14bR)-9-(((5-isopropyl-2-oxo-1,3-dioxol-4-yl) methoxy)carbonyl)-10-((R)-2-(methoxycarbonyl) pyrrolidin-1-yl)-2,4a,6a,6b,9,12a-hexamethyl-13-oxo-1,2,3,4,4a,5,6,6a,6b,7,8,8a,9,10,11,12,12a,12b, 13,14b-icosahydropicene-2-carboxylic Acid (351-1)

The title compound was prepared from 348-2 through the same route as for 348-6. The crude product was purified by prep-HPLC with the following conditions: column, Sunfire Prep C18 OBD, 10 μm, 19*250 mm; mobile phase, water (0.05% TFA) and CH$_3$CN (50% phase B up to 56% in 8 min); detector, UV. This resulted in 29 mg of 351-1 as a white solid. MS (ES, m/z) [M+H]$^+$=752.35; $^1$H NMR (400 MHz, methanol-d$_4$) δ 0.84 (s, 3H), 0.90 (d, J=5.7 Hz, 1H), 1.00-1.10 (m, 1H), 1.10-1.16 (m, 4H), 1.16-1.22 (m, 6H), 1.22-1.33 (m, 11H), 1.36-1.50 (m, 6H), 1.60-1.78 (m, 4H), 1.79-1.91 (m, 3H), 1.91-2.10 (m, 5H), 2.10-2.27 (m, 2H), 2.40 (s, 1H), 2.55 (s, 1H), 2.91-3.00 (m, 1H), 3.04-3.16 (m, 2H), 3.45 (s, 1H), 3.54 (s, 1H), 3.87 (s, 4H), 4.44 (s, 1H), 5.36 (d, J=14.0 Hz, 1H), 5.62 (s, 1H).

Synthesis of (2S,4aS,6aS,6bR,8aR,9S,10S,12aS, 12bR,14bR)-10-((S)-2-(ethoxycarbonyl)pyrrolidin-1-yl)-2,4a,6a,6b,9,12a-hexamethyl-9-(((5-methyl-2-oxo-1,3-dioxol-4-yl)methoxy)carbonyl)-13-oxo-1,2, 3,4,4a,5,6,6a,6b,7,8,8a,9,10,11,12,12a,12b,13,14b-icosahydropicene-2-carboxylic Acid (352-1)

The title compound was prepared from 348-2 through the same route as for 348-6. The crude product was purified by prep-HPLC with the following conditions: column, Sunfire Prep C18 OBD, 10 μm, 19*250 mm; mobile phase, water (0.1% TFA) and CH$_3$CN (37% phase B up to 40% in 8 min); detector, UV. This resulted in 32.9 mg of 352-1 as a white solid. MS (ES, m/z) [M+H]$^+$=738.35; $^1$H NMR (400 MHz, methanol-d$_4$) δ 0.84 (s, 3H), 0.92 (d, J=7.7 Hz, 1H), 1.06 (d, J=14.0 Hz, 1H), 1.10-1.20 (m, 11H), 1.20-1.36 (m, 9H), 1.36-1.47 (m, 8H), 1.50-1.61 (m, 1H), 1.61-2.00 (m, 11H), 2.10-2.26 (m, 7H), 2.53 (s, 1H), 2.90 (d, J=13.7 Hz, 1H), 4.33 (d, J=14.6 Hz, 2H), 5.26 (s, 1H), 5.62 (s, 1H).

Example 99 (2S,4aS,6aS,6bR,8aR,9S,10S,12aS, 12bR,14bR)-10-((R)-2-(ethoxycarbonyl)pyrrolidin-1-yl)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,1142,12a,12b,13,14b-icosahydropicene-2-carboxylic Acid (353-1)

Example 100 (2S,4aS,6aS,6bR,8aR,9S,10S,12aS, 12bR,14bR)-2,4a,6a,6b,9,12a-hexamethyl-9-(((5-methyl-2-oxo-1,3-dioxol-4-yl)methoxy)carbonyl)-13-oxo-10-(piperidin-1-yl)-1,2,3,4,4a,5,6,6a,6b,7,8, 8a,9,10,1142,12a,12b,13,14b-icosahydropicene-2-carboxylic Acid (356-2)

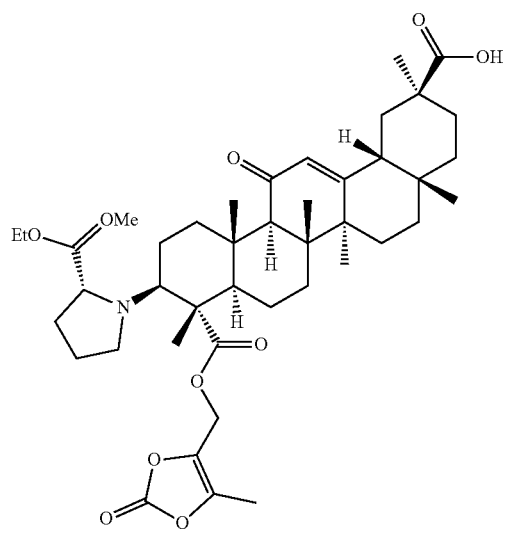

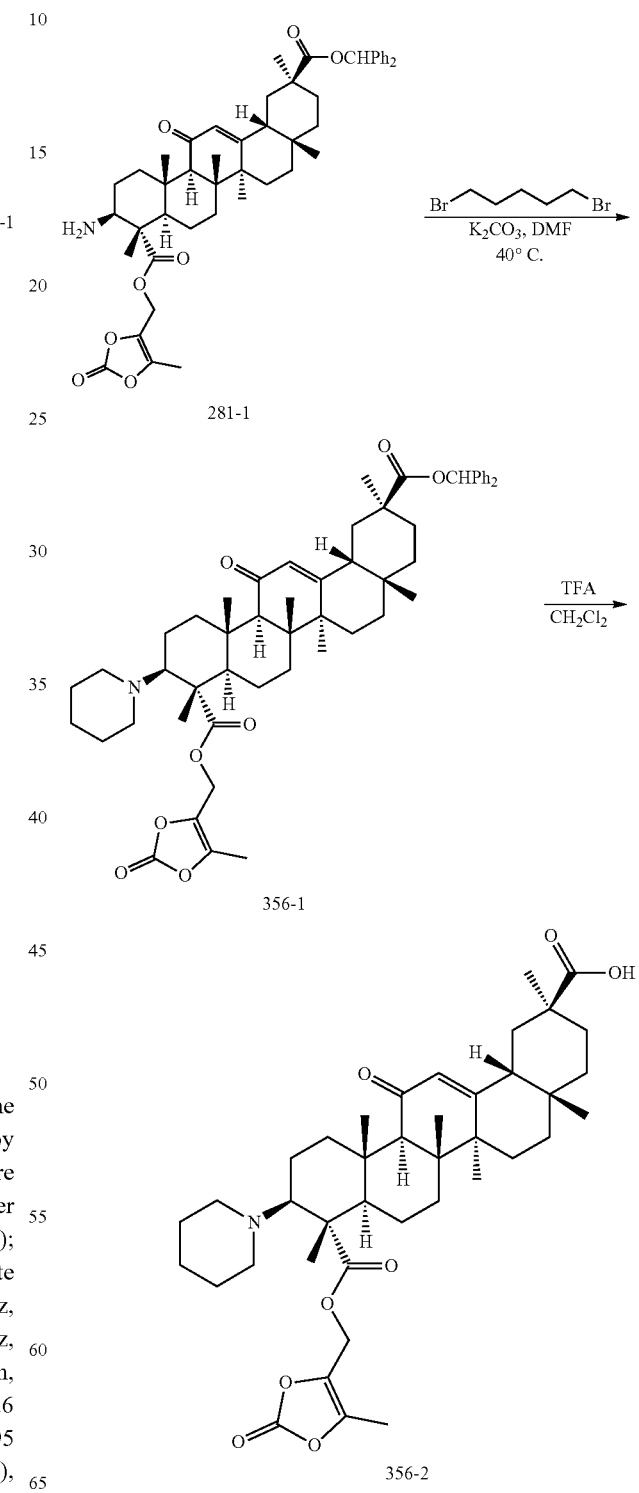

Synthesis of (2S,4aS,6aS,6bR,8aR,9S,10S,12aS, 12bR,14bR)-10-((R)-2-(ethoxycarbonyl)pyrrolidin-1-yl)-2,4a,6a,6b,9,12a-hexamethyl-9-(((5-methyl-2-oxo-1,3-dioxol-4-yl)methoxy)carbonyl)-13-oxo-1,2, 3,4,4a,5,6,6a,6b,7,8,8a,9,10,11,12,12a,12b,13,14b-icosahydropicene-2-carboxylic Acid (353-1)

The title compound was prepared from 348-2 through the same route as for 348-6. The crude product was purified by prep-HPLC with the following conditions: column, Sunfire Prep C18 OBD, 10 μm, 19*250 mm; mobile phase, water (0.1% TFA) and $CH_3CN$ (37% phase B up to 40% in 8 min); detector, UV. This resulted in 36.1 mg of 353-1 as a white solid. MS (ES, m/z) $[M+H]^+$=738.35; $^1H$ NMR (400 MHz, methanol-$d_4$) δ 0.84 (s, 3H), 0.91 (s, 1H), 1.07 (d, J=13.7 Hz, 1H), 1.12-1.23 (m, 9H), 1.25-1.37 (m, 8H), 1.38-1.51 (m, 6H), 1.60-1.77 (m, 4H), 1.81-1.89 (m, 3H), 2.07 (d, J=12.6 Hz, 5H), 2.10-2.26 (m, 5H), 2.40 (s, 1H), 2.55 (s, 1H), 2.95 (d, J=13.8 Hz, 1H), 3.46 (s, 1H), 3.55 (s, 1H), 3.88 (s, 1H), 4.33 (qq, J=7.1, 3.5 Hz, 2H), 4.44 (s, 1H), 5.31 (d, J=14.0 Hz, 1H), 5.62 (s, 1H).

Synthesis of 2-benzhydryl 9-((5-methyl-2-oxo-1,3-dioxol-4-yl)methyl) (2S,4aS,6aS,6bR,8aR,9S,10S,12aS,12bR,14bR)-2,4a,6a,6b,9,12a-hexamethyl-13-oxo-10-(piperidin-1-yl)-1,2,3,4,4a,5,6,6a,6b,7,8,8a,9,10,11,12,12a,12b,13,14b-icosahydropicene-2,9-dicarboxylate (356-1)

Into a 100-mL round-bottom flask, was placed 281-1 (300 mg, 0.39 mmol), DMF (5 mL), $K_2CO_3$ (267 mg, 1.9 mmol, 5 equiv), and 1,5-dibromopentane (176 mg, 0.77 mmol, 2 equiv). The reaction slurry was stirred for 2 d at 40° C. The reaction mixture was diluted with water and extracted with 300 mL of $CH_2Cl_2$. The organic layer was washed with 3×300 ml of brine, dried over anhydrous $Na_2SO_4$, filtered, and concentrated. The residue was applied onto a silica gel column with ethyl acetate:petroleum ether (1:1) to provide 167 mg (51%) of 356-1 as a yellow solid.

Synthesis of (2S,4aS,6aS,6bR,8aR,9S,10S,12aS,12bR,14bR)-2,4a,6a,6b,9,12a-hexamethyl-9-(((5-methyl-2-oxo-1,3-dioxol-4-yl)methoxy)carbonyl)-13-oxo-10-(piperidin-1-yl)-1,2,3,4,4a,5,6,6a,6b,7,8,8a,9,10,11,12,12a,12b,13,14b-icosahydropicene-2-carboxylic Acid (356-2)

Into a 100-mL round-bottom flask, was placed 356-1 (167 mg, 0.2 mmol), $CH_2Cl_2$ (10 mL), and TFA (1 mL). The reaction slurry was stirred for 1 h at room temperature then concentrated. The crude product was purified by prep-HPLC with the following conditions: Column, XSelect CSH OBD, 30*150 mm, 5 μm; mobile phase, water (0.05% TFA) and $CH_3CN$ (35% phase B up to 41% in 8 min); detector, UV. This resulted in 27.8 mg (21%) of 356-2 as a white solid. MS (ES, m/z): $[M+1]^+$=680.30; $^1$H NMR (400 MHz, methanol-$d_4$) δ 0.84 (s, 3H), 1.07 (d, J=14.0 Hz, 1H), 1.13-1.33 (m, 13H), 1.35-1.47 (m, 11H), 1.51-1.78 (m, 4H), 1.79-1.88 (m, 4H), 1.90-2.00 (m, 4H), 2.01-2.16 (m, 2H), 2.17-1.31 (m, 4H), 2.54 (s, 1H), 2.96-3.09 (m, 1H), 2.90-3.17 (m, 3H), 3.36-3.78 (m, 1H), 3.63 (d, J=12.3 Hz, 1H), 3.87 (dd, J=12.5, 4.0 Hz, 1H), 5.07 (d, J=13.9 Hz, 1H), 5.20 (d, J=14.0 Hz, 1H), 5.62 (s, 1H).

Example 101 (2S,4aS,6aS,6bR,8aR,9S,10S,12aS,12bR,14bR)-10-(4,4-difluoropiperidin-1-yl)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic Acid (357-7)

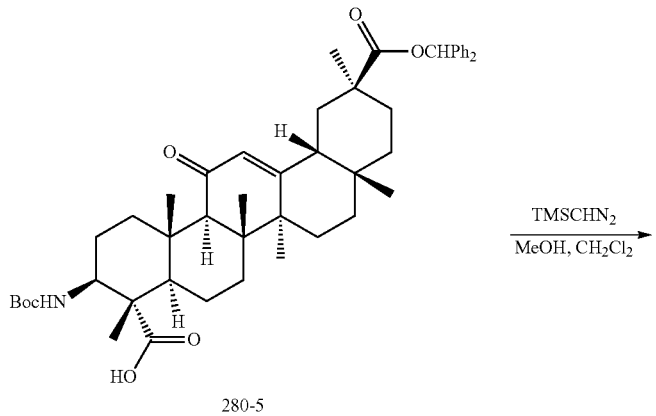

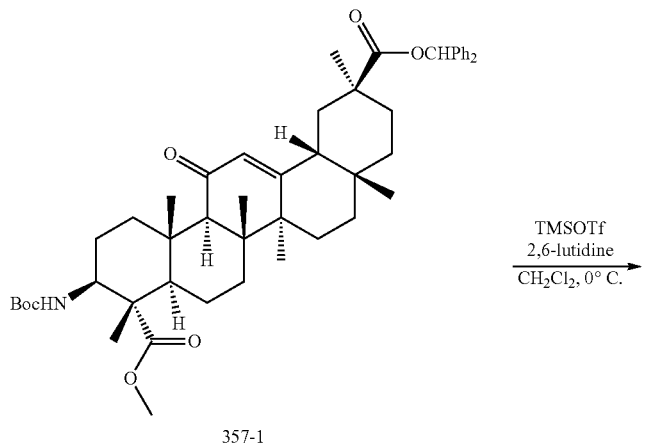

-continued
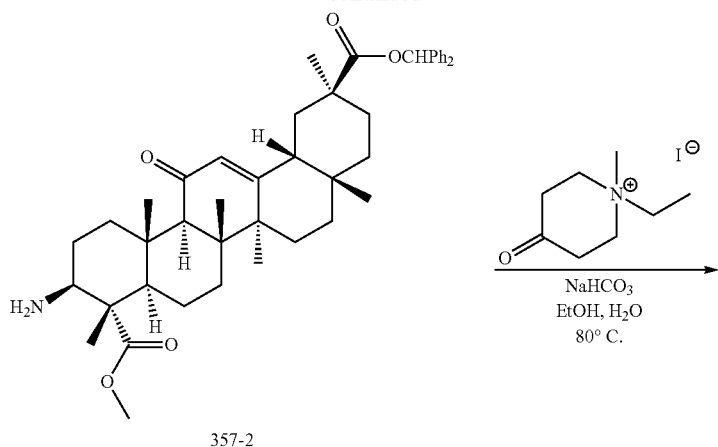
357-2
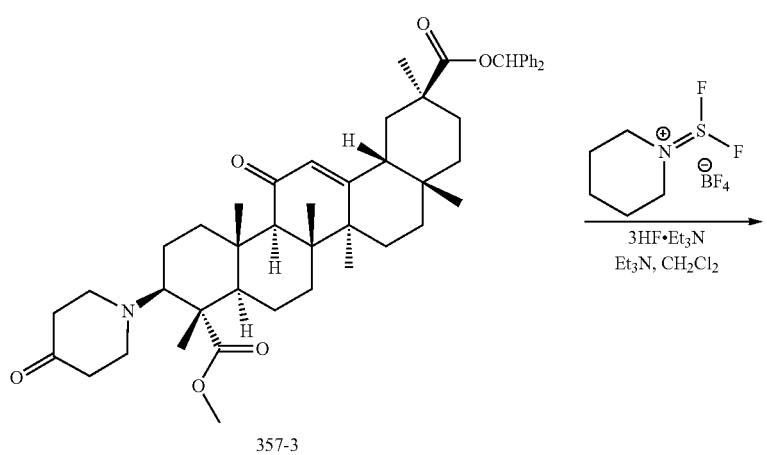
357-3
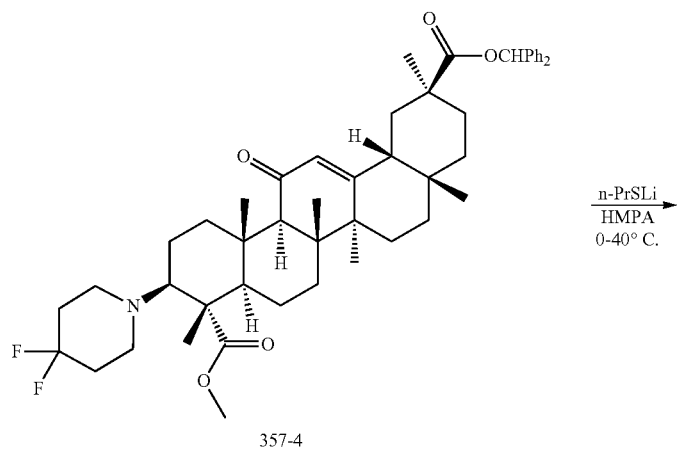
357-4

-continued
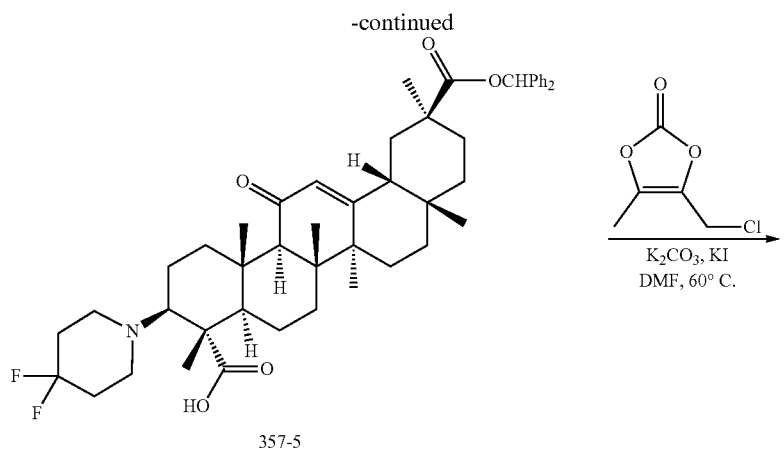
357-5
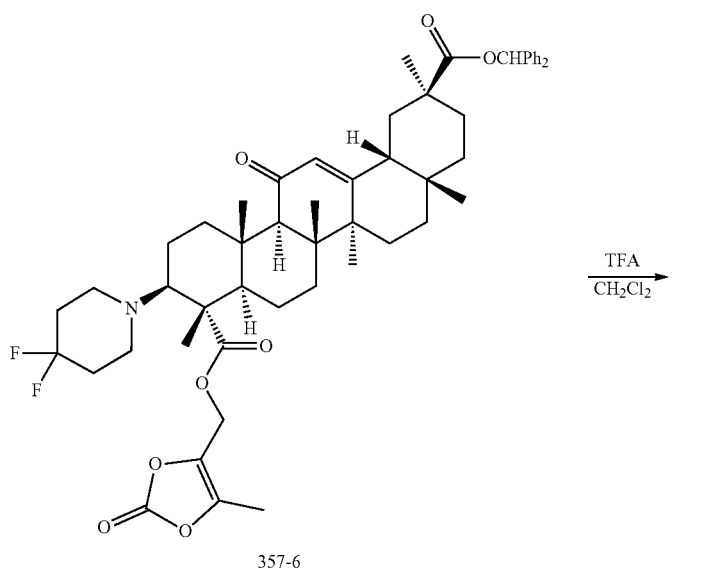
357-6
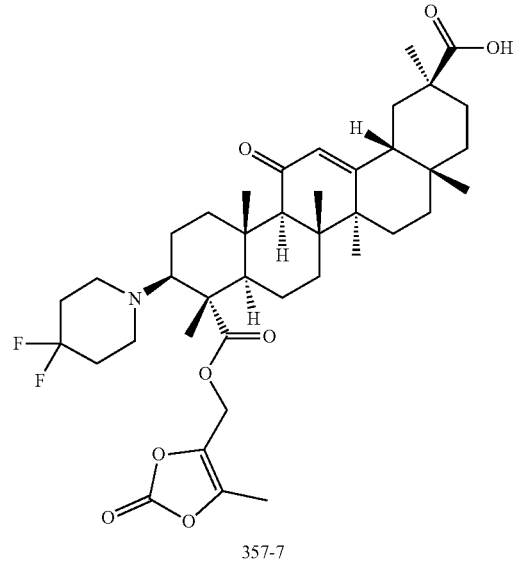
357-7

Synthesis of 2-benzhydryl 9-methyl (2S,4aS,6aS, 6bR,8aR,9S,10S,12aS,12bR,14bR)-10-((tert-butoxycarbonyl)amino)-2,4a,6a,6b,9,12a-hexamethyl-13-oxo-1,2,3,4,4a,5,6,6a,6b,7,8,8a,9,10,11,12,12a,12b, 13,14b-icosahydropicene-2,9-dicarboxylate (357-1)

Into a 250-mL round-bottom flask was placed 280-5 (6.0 g, 7.8 mmol), CH$_2$Cl$_2$ (30 mL), MeOH (30 mL), and TMSCHN$_2$ (4.47 g, 39 mmol, 5 equiv). The reaction slurry was stirred for 1 h at room temperature. The reaction mixture was diluted with water and extracted with 300 mL of CH$_2$Cl$_2$. The organic layer was washed with 3×300 ml of brine, dried over anhydrous Na$_2$SO$_4$, filtered, and concentrated to provide 6.12 g (100%) of crude 357-1 as a yellow solid.

Synthesis of 2-benzhydryl 9-methyl (2S,4aS,6aS, 6bR,8aR,9S,10S,12aS,12bR,14bR)-10-amino-2,4a, 6a,6b,9,12a-hexamethyl-13-oxo-1,2,3,4,4a,5,6,6a,6b, 7,8,8a,9,10,11,12,12a,12b,13,14b-icosahydropicene-2,9-dicarboxylate (357-2)

Into a 250-mL round-bottom flask was placed 357-1 (6.12 g, 7.85 mmol), CH$_2$Cl$_2$ (66 mL), and 2, 6-lutidine (4.15 g, 39 mmol, 5 equiv) followed by TMSOTf (6.99 g, 31.5 mmol, 4 equiv) at 0° C. The reaction slurry was stirred overnight at room temperature. The reaction was quenched with water and the mixture was extracted with 500 mL of CH$_2$Cl$_2$. The organic layer was washed with 3×500 ml of 1 M HCl$_{(aq)}$, dried over anhydrous Na$_2$SO$_4$, filtered, and concentrated to provide 5.05 g (95%) of 357-2 as a white solid.

Synthesis of 2-benzhydryl 9-methyl (2S,4aS,6aS, 6bR,8aR,9S,10S,12aS,12bR,14bR)-2,4a,6a,6b,9,12a-hexamethyl-13-oxo-10-(4-oxopiperidin-1-yl)-1,2,3, 4,4a,5,6,6a,6b,7,8,8a,9,10,11,12,12a,12b,13,14b-icosahydropicene-2,9-dicarboxylate (357-3)

Into a 100-mL round-bottom flask was placed 357-2 hydrochloride (500 mg), 1-ethyl-1-methyl-4-oxop-iperidin-1-ium iodide (396 mg), NaHCO$_3$ (154 mg), EtOH (10 mL), and H$_2$O (2 mL). The reaction slurry was stirred for 1 hr at 80° C. The reaction mixture was diluted with 100 mL of CH$_2$Cl$_2$ and washed with 3×150 ml of brine. The organic layer was dried over anhydrous Na$_2$SO$_4$, filtered, and concentrated to provide 420 mg of 357-3 as a light yellow solid.

Synthesis of 2-benzhydryl 9-methyl (2S,4aS,6aS, 6bR,8aR,9S,10S,12aS,12bR,14bR)-10-(4,4-difluoropiperidin-1-yl)-2,4a,6a,6b,9,12a-hexamethyl-13-oxo-1,2,3,4,4a,5,6,6a,6b,7,8,8a,9,10,11,12,12a,12b, 13,14b-icosahydropicene-2,9-dicarboxylate (357-4)

Into a 100-mL round-bottom flask was placed XtalFluor-M (CAS: 63517-33-9, 151 mg), Et$_3$N (1 mg), CH$_2$Cl$_2$ (10 mL), 3HF.Et$_3$N (149 mg), and 357-3 (300 mg). The reaction slurry was stirred for 2 seconds at room temperature. The reaction mixture was applied directly onto a silica gel column with ethyl acetate:petroleum ether (1:1) to provide 270 mg of 357-4 as a white solid.

Synthesis of (3S,4S,4aR,6aR,6bS,8aS,11S,12aR, 14aR,14bS)-11-((benzhydryloxy)carbonyl)-3-(4,4-difluoropiperidin-1-yl)-4,6a,6b,8a,11,14b-hexamethyl-14-oxo-1,2,3,4,4a,5,6,6a,6b,7,8,8a,9,10,11,12, 12a,14,14a,14b-icosahydropicene-4-carboxylic Acid (357-5)

Into a 100-mL round-bottom flask was placed 357-4 (210 mg, 0.27 mmol) followed by n-PrSLi (5 mL, 1 M in HMPA) at 0° C. The reaction slurry was stirred for 3 h at 40° C. The reaction mixture was cooled and diluted with 100 mL of CH$_2$Cl$_2$. The resulting mixture was washed with 3×150 ml of 1 M HCl$_{(aq)}$, dried over anhydrous Na$_2$SO$_4$, filtered, and concentrated to provide 180 mg of crude 357-5 as a white solid.

Synthesis of 2-benzhydryl 9-(((5-methyl-2-oxo-1,3-dioxol-4-yl)methyl) (2S,4aS,6aS,6bR,8aR,9S,10S, 12aS,12bR,14bR)-10-(4,4-difluoropiperidin-1-yl)-2, 4a,6a,6b,9,12a-hexamethyl-13-oxo-1,2,3,4,4a,5,6,6a, 6b,7,8,8a,9,10,11,12,12a,12b,13,14b-icosahydropicene-2,9-dicarboxylate (357-6)

Into a 100-mL round-bottom flask was placed 357-5 (660 mg, 0.86 mmol), 4-(chloromethyl)-5-methyl-2H-1,3-dioxol-2-one (690 mg, 4.6 mmol, 5.4 equiv), DMF (45 mL), KI (390 mg, 2.3 mmol, 2.7 equiv), and K$_2$CO$_3$ (1.09 g, 0.008 mmol, 0.01 equiv). The reaction slurry was stirred for 1 h at 60° C. The reaction mixture was extracted with 100 mL of CH$_2$Cl$_2$ and the organic layer washed with 3×100 ml of brine, dried over anhydrous Na$_2$SO$_4$, filtered, and concentrated. The residue was applied onto a silica gel column with ethyl acetate/petroleum ether (1:10) to provide 660 mg (87%) of 357-6 as a yellow solid.

Synthesis of (2S,4aS,6aS,6bR,8aR,9S,10S,12aS, 12bR,14bR)-10-(4,4-difluoropiperidin-1-yl)-2,4a,6a, 6b,9,12a-hexamethyl-9-(((5-methyl-2-oxo-1,3-dioxol-4-yl)methoxy)carbonyl)-13-oxo-1,2,3,4,4a,5,6, 6a,6b,7,8,8a,9,10,11,12,12a,12b,13,14b-icosahydropicene-2-carboxylic Acid (357-7)

Into a 100-mL round-bottom flask was placed 357-6 (110 mg), TFA (1 mL), and CH$_2$Cl$_2$ (10 mL). The reaction slurry was stirred for 1 hr at room temperature then concentrated. The crude product was purified by Chiral-Prep-HPLC with the following conditions: mobile phase, hexane (0.1% formic acid) and EtOH (hold 50% EtOH in 10 min); detector, UV 254 nm. This resulted in 15.1 mg of 357-7 as a light yellow solid. MS (ES, m/z): [M+1]$^+$=716.39; $^1$HNMR (300 MHz, methanol-d$_4$) δ 5.61 (s, 1H), 5.10 (d, J=14.0 Hz, 1H), 4.92 (s, 1H), 3.12 (dd, J=12.5, 3.9 Hz, 1H), 2.97-2.72 (m, 3H), 2.56 (d, J=9.3 Hz, 3H), 2.23 (s, 5H), 2.00-1.49 (m, 14H), 1.47-1.28 (m, 8H), 1.28-1.01 (m, 16H), 0.84 (s, 4H).

Example 102 (2S,4aS,6aS,6bR,8aR,9S,10S,12aS, 12bR,14bR)-10-((R)-3-(ethoxycarbonyl)pyrrolidin-1-yl)-2,4a,6a,6b,9,12a-hexamethyl-9-(((5-methyl-2-oxo-1,3-dioxol-4-yl)methoxy)carbonyl)-13-oxo-1,2, 3,4,4a,5,6,6a,6b,7,8,8a,9,10,11,12,12a,12b,13,14b-icosahydropicene-2-carboxylic Acid (358-7)
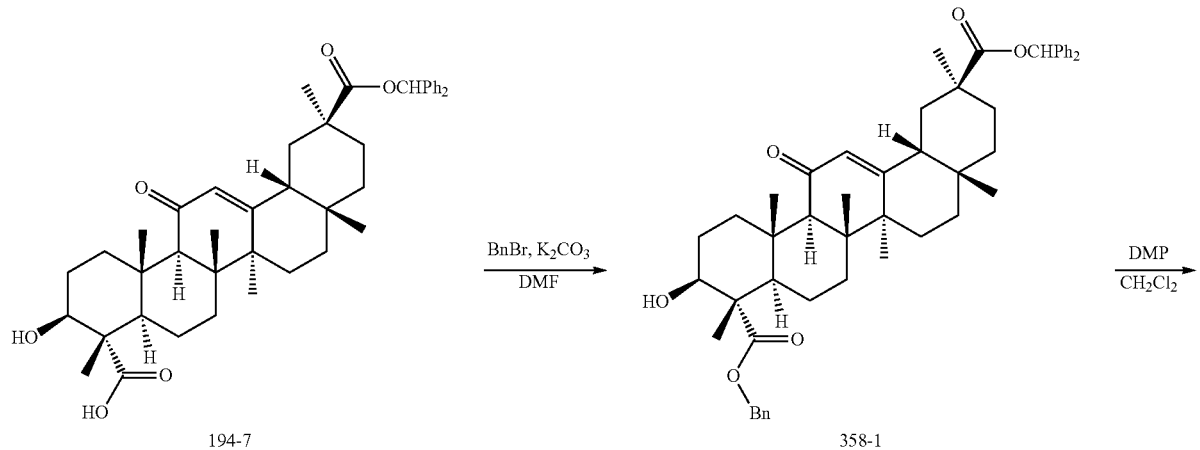
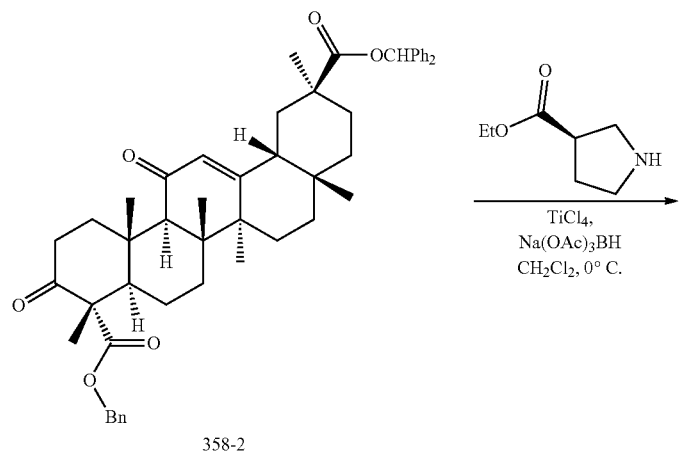
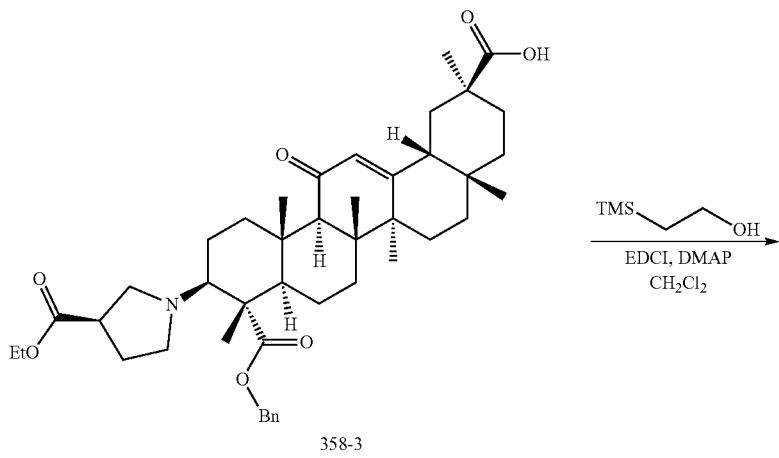

-continued
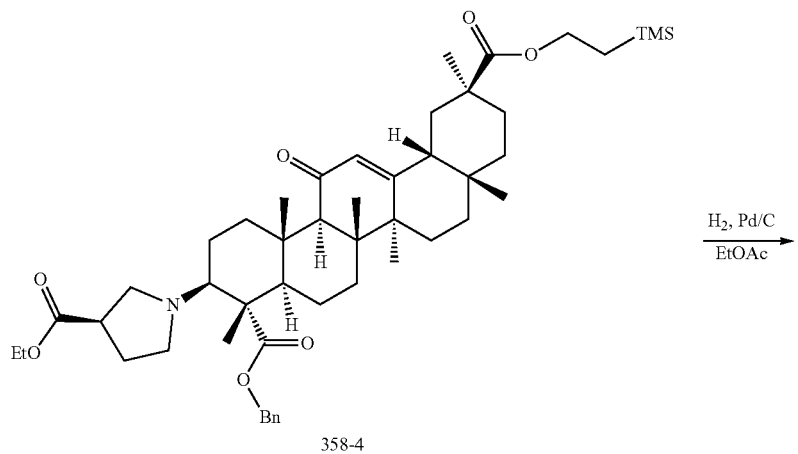
358-4
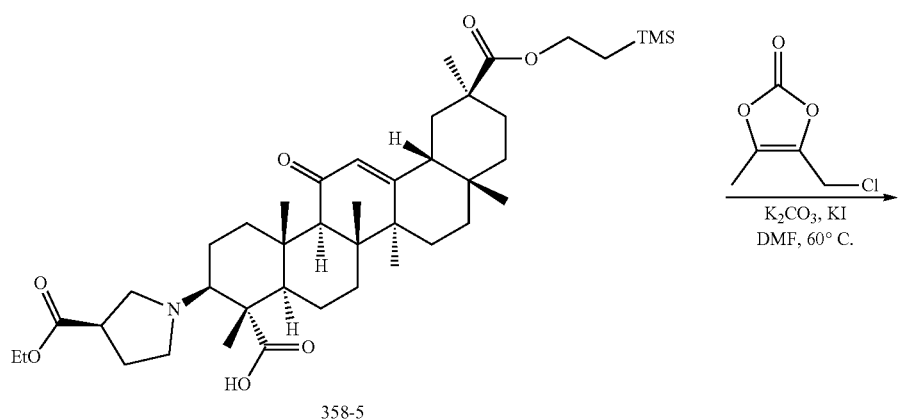
358-5
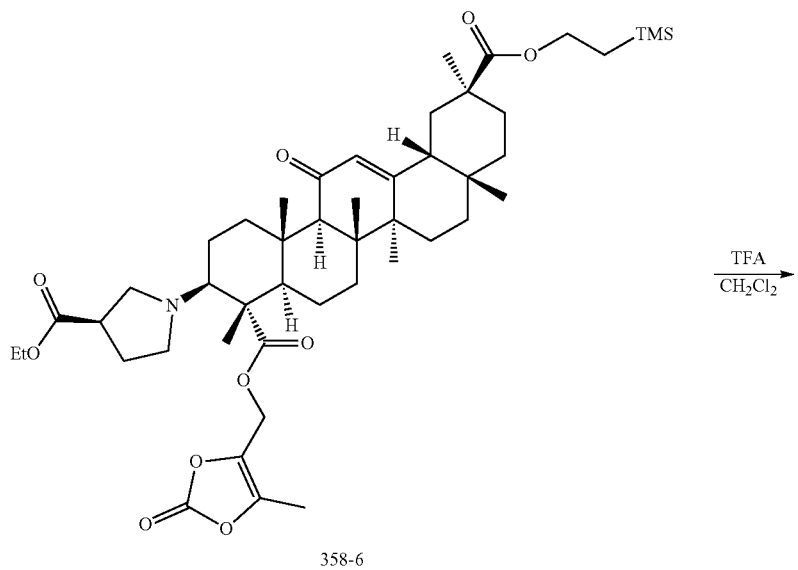
358-6

-continued

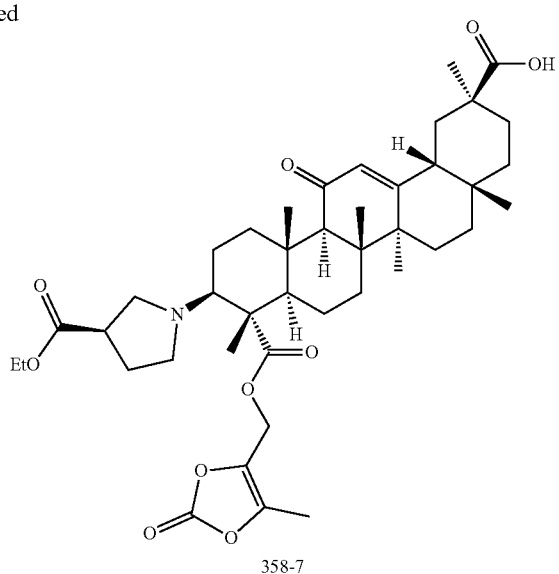

358-7

Synthesis of 2-benzhydryl 9-benzyl (2S,4aS,6aS, 6bR,8aR,9S,10S,12aS,12bR,14bR)-10-hydroxy-2,4a, 6a,6b,9,12a-hexamethyl-13-oxo-1,2,3,4,4a,5,6,6a,6b, 7,8,8a,9,10,11,12,12a,12b,13,14b-icosahydropicene-2,9-dicarboxylate (358-1)

Into a 100-mL round-bottom flask was placed 194-7 (1 g, 1.24 mmol), DMF (10 mL), $K_2CO_3$ (1.0 g, 7.2 mmol, 5 equiv), and BnBr (636 mg, 3.7 mmol, 3 equiv). The reaction slurry was stirred for 1 h at room temperature. The reaction mixture was diluted with 100 mL of ethyl acetate and quenched by the addition of 100 mL of water. The layers were separated, and the aqueous layer was extracted with 2×100 mL of ethyl acetate. The combined organic layers were washed with 3×200 ml of brine, dried over anhydrous $Na_2SO_4$, filtered, and concentrated. The residue was applied onto a silica gel column with ethyl acetate:petroleum ether (eluting 0-20%) to provide 1.0 g of 358-1 as a white solid.

Synthesis of 2-benzhydryl 9-benzyl (2S,4aS,6aS, 6bR,8aR,9S,12aS,12bR,14bR)-2,4a,6a, 6b,9,12a-hexamethyl-10,13-dioxo-1,2,3,4,4a,5,6,6a,6b,7,8,8a, 9,10,11,12,12a,12b,13,14b-icosahydropicene-2,9-dicarboxylate (358-2)

Into a 100-mL round-bottom flask was placed 358-1 (1.0 g, 1.32 mmol), $CH_2Cl_2$ (20 mL), and Dess-Martin periodinane (1.12 g, 2.64 mmol, 2 equiv). The reaction slurry was stirred for 1 h at room temperature. The reaction mixture was diluted with 150 mL of $CH_2Cl_2$. The pH of the solution was adjusted to 8-9 with saturated $NaHCO_{3(aq)}$ and extracted with 2×100 mL of $CH_2Cl_2$. The combined organic layers were washed with 1×200 ml of brine, dried over anhydrous $Na_2SO_4$, filtered, and concentrated. The residue was applied onto a silica gel column with ethyl acetate/petroleum ether (eluting 0-20%) to provide 900 mg (90%) of 358-2 as a white solid.

Synthesis of (2S,4aS,6aS,6bR,8aR,9S,10S,12aS, 12bR,14bR)-9-((benzyloxy)carbonyl)-10-((R)-3-(ethoxycarbonyl)pyrrolidin-1-yl)-2,4a,6a,6b,9,12a-hexamethyl-13-oxo-1,2,3,4,4a,5,6,6a,6b,7,8,8a,9,10, 11,12,12a,12b,13,14b-icosahydropicene-2-carboxylic Acid (358-3)

To a slurry of 358-2 (160 mg, 0.21 mmol) and ethyl (3R)-pyrrolidine-3-carboxylate (60.7 mg, 0.42 mmol, 2 equiv) in $CH_2Cl_2$ at 0° C. was added $TiCl_4$ (161 mg, 0.85 mmol, 4 equiv) dropwise. The reaction slurry was stirred for 3 h at room temperature under nitrogen atmosphere. To the above mixture was added sodium triacetoxyborohydride (449 mg, 2.1 mmol, 10 equiv) dropwise in portions over 1 min at room temperature. The reaction slurry was stirred for additional 1 min at room temperature. The reaction was quenched with water at room temperature and extracted with EtOAc. The combined organic layers were washed with brine, dried over anhydrous $Na_2SO_4$, filtered, and concentrated. The residue was purified by prep-TLC ($CH_2Ch$:MeOH 12:1) to afford 358-3 (90 mg, 59%)

Synthesis of 9-benzyl 2-(2-(trimethylsilyl)ethyl) (2S,4aS,6aS,6bR,8aR,9S,10S,12aS,12bR,14bR)-10-((R)-3-(ethoxycarbonyl)pyrrolidin-1-yl)-2,4a,6a,6b, 9,12a-hexamethyl-13-oxo-1,2,3,4,4a,5,6,6a,6b,7,8, 8a,9,10,11,12,12a,12b,13,14b-icosahydropicene-2,9-dicarboxylate (358-4)

A solution of 358-3 (65 mg, 0.091 mmol) and TMSE (53.6 mg, 0.45 mmol, 5 equiv), and DMAP (44 mg, 0.36 mmol, 4 equiv) in $CH_2Cl_2$ was stirred for 3 h at room temperature. To the above mixture was added EDCI (87.0 mg, 0.45 mmol, 5 equiv) at room temperature. The reaction slurry was stirred overnight at room temperature. The reaction was quenched with water at room temperature and extracted with EtOAc. The combined organic layers were washed with brine, dried over anhydrous $Na_2SO_4$, filtered, and concentrated. The residue was purified by prep-TLC (petroleum ether:EtOAc 3:1) to afford 358-4 (45 mg, 61%).

Synthesis of (3S,4S,4aR,6aR,6bS,8aS,11S,12aR,14aR,14bS)-3-((R)-3-(ethoxycarbonyl)pyrrolidin-1-yl)-4,6a,6b,8a,11,14b-hexamethyl-14-oxo-11-((2-(trimethylsilyl)ethoxy)carbonyl)-1,2,3,4,4a,5,6,6a,6b,7,8,8a,9,10,11,12,12a,14,14a,14b-icosahydropicene-4-carboxylic Acid (358-5)

A mixture of 358-4 (45 mg, 0.055 mmol) and Pd/C (10%, 45 mg, 0.42 mmol, 7.7 equiv) in EtOAc was stirred for 1 h at room temperature under hydrogen atmosphere. The reaction mixture was filtered and the filter cake washed with EtOAc. The filtrate was concentrated under reduced pressure. The crude product 358-5 was used in the next step directly without further purification.

Synthesis of 9-((5-methyl-2-oxo-1,3-dioxol-4-yl)methyl) 2-(2-(trimethylsilyl)ethyl) (2S,4aS,6aS,6bR,8aR,9S,10S,12aS,12bR,14bR)-10-((R)-3-(ethoxycarbonyl)pyrrolidin-1-yl)-2,4a,6a,6b,9,12a-hexamethyl-13-oxo-1,2,3,4,4a,5,6,6a,6b,7,8,8a,9,10,11,12,12a,12b,13,14b-icosahydropicene-2,9-dicarboxylate (358-6)

A solution of 358-5 (40 mg, 0.055 mmol), 4-(chloromethyl)-5-methyl-2H-1,3-dioxol-2-one (32.7 mg, 0.22 mmol, 4 equiv), K$_2$CO$_3$ (22.8 mg, 0.17 mmol, 3 equiv), and KI (4.6 mg, 0.028 mmol, 0.5 equiv) in DMF was stirred for 1 h at 60° C. The reaction mixture was cooled and extracted with EtOAc. The combined organic layers were washed with brine, dried over anhydrous Na$_2$SO$_4$, filtered, and concentrated. The residue was purified by prep-TLC (petroleum ether:EtOAc 5:1) to afford 358-6 (30 mg, 65%) as a yellow oil.

Synthesis of (2S,4aS,6aS,6bR,8aR,9S,10S,12aS,12bR,14bR)-10-((R)-3-(ethoxycarbonyl)pyrrolidin-1-yl)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic Acid (358-7)

A solution of 358-6 (30 mg, 0.036 mmol) and TFA (0.5 mL) in CH$_2$Cl$_2$ was stirred for 3 h at room temperature. The reaction mixture was concentrated. The crude product was purified by prep-HPLC with the following conditions: Column, XBridge CSH OBD, 30*150 mm, 5 μm; mobile phase, water (0.05% TFA) and CH$_3$CN (25% to 50% over 8 min); detector, UV 254 nM. This resulted in 358-7 (9.9 mg, 37%) as an off-white solid. MS (ES, m/z) [M+1]$^+$=738.30; $^1$H NMR (400 MHz, methanol-d$_4$) δ 5.63 (s, 1H), 5.35 (s, 1H), 4.22 (m, 2H), 3.84 (s, 2H), 2.94 (m, 2H), 2.50 (s, 2H), 2.21 (m, 9H), 1.87 (m, 10H), 1.61-1.33 (m, 22H), 1.19-0.97 (m, 16H), 0.86 (s, 4H).

Example 103 (2S,4aS,6aS,6bR,8aR,9S,10S,12aS,12bR,14bR)-10-((R)-3-(ethoxycarbonyl)piperidin-1-yl)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,1142,12a,12b,13,14b-icosahydropicene-2-carboxylic Acid (359-1)

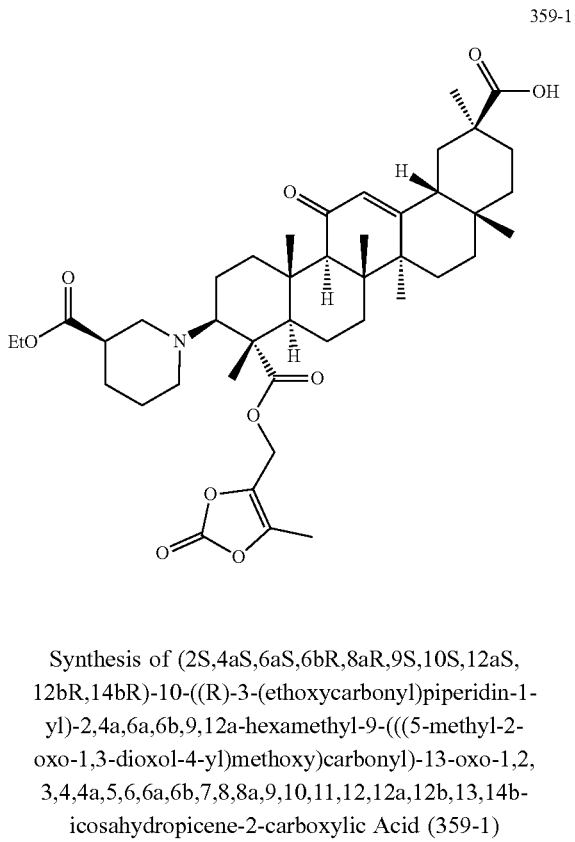

359-1

Synthesis of (2S,4aS,6aS,6bR,8aR,9S,10S,12aS,12bR,14bR)-10-((R)-3-(ethoxycarbonyl)piperidin-1-yl)-2,4a,6a,6b,9,12a-hexamethyl-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic Acid (359-1)

The title compound 359-1 was prepared through the same synthetic route as 358-7, beginning with 358-2 and ethyl (3R)-nipecotate. The crude product was purified by prep-HPLC with the following conditions: column, XBridge CSH OBD, 30*150 mm, 5 μm; mobile phase, water (0.05% TFA) and CH$_3$CN (28% to 45% over 8 min); detector, UV 254 nm. This resulted in 359-1 (9.4 mg, 36%) as an off-white solid. MS (ES, m/z): [M+1]$^+$=752.50; $^1$H NMR (400 MHz, methanol-d$_4$) δ 5.64 (s, 1H), 5.75 (s, 1H), 5.11 (s, 1H), 4.22 (s, 2H), 3.94 (s, 1H), 3.01 (m, 3H), 2.50 (s, 1H), 2.01 (m, 14H), 1.67 (m, 3H), 1.61-1.33 (m, 11H), 1.22 (m, 5H), 1.19-0.97 (m, 12H), 0.86 (s, 3H).

Example 104 (2S,4aS,6aS,6bR,8aR,9S,10S,12aS, 12bR,14bR)-10-((S)-3-(ethoxycarbonyl)piperidin-1-yl)-2,4a,6a,6b,9,12a-hexamethyl-9-(((5-methyl-2-oxo-1,3-dioxol-4-yl)methoxy)carbonyl)-13-oxo-1,2, 3,4,4a,5,6,6a,6b,7,8,8a,9,10,1142,12a,12b,13,14b-icosahydropicene-2-carboxylic Acid (360-1)

Example 105 (2S,4aS,6aS,6bR,8aR,9S,10S,12aS, 12bR,14bR)-10-(4-(ethoxycarbonyl)piperidin-1-yl)-9-(((5-ethyl-2-oxo-1,3-dioxol-4-yl)methoxy)carbonyl)-2,4a,6a,6b,9,12a-hexamethyl-13-oxo-1,2,3,4,4a, 5,6,6a,6b,7,8,8a,9,10,1142,12a,12b,13,14b-icosahydropicene-2-carboxylic Acid (361-1)

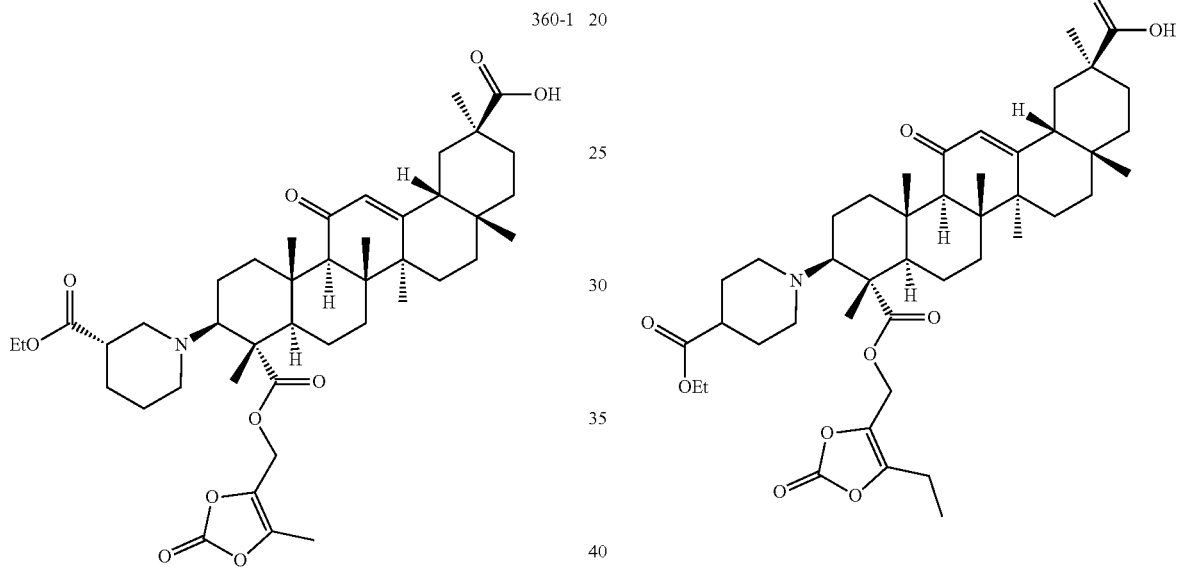

Synthesis of (2S,4aS,6aS,6bR,8aR,9S,10S,12aS, 12bR,14bR)-10-((S)-3-(ethoxycarbonyl)piperidin-1-yl)-2,4a,6a,6b,9,12a-hexamethyl-9-(((5-methyl-2-oxo-1,3-dioxol-4-yl)methoxy)carbonyl)-13-oxo-1,2, 3,4,4a,5,6,6a,6b,7,8,8a,9,10,11,12,12a,12b,13,14b-icosahydropicene-2-carboxylic Acid (360-1)

The title compound 360-1 was prepared through the same synthetic route as 358-7, beginning with 358-2 and ethyl (3S')-nipecotate. The crude product was purified by prep-HPLC with the following conditions: column, XBridge CSH OBD, 30*150 mm, 5 μm; mobile phase, water (0.05% TFA) and CH$_3$CN (25% to 45% over 10 min); detector, UV 254 nm. This resulted in 360-1 (7.0 mg, 26%) as an off-white solid. MS (ES, m/z): [M+1]$^+$=752.50; $^1$H NMR (400 MHz, methanol-d$_4$) δ 5.64 (s, 1H), 5.75 (s, 1H), 5.11 (s, 1H), 4.22 (s, 2H), 3.94 (s, 1H), 3.01 (m, 3H), 2.50 (s, 1H), 2.01 (m, 14H), 1.67 (m, 3H), 1.61-1.33 (m, 11H), 1.22 (m, 5H), 1.19-0.97 (m, 12H), 0.86 (s, 3H).

Synthesis of (2S,4aS,6aS,6bR,8aR,9S,10S,12aS, 12bR,14bR)-10-(4-(ethoxycarbonyl)piperidin-1-yl)-9-(((5-ethyl-2-oxo-1,3-dioxol-4-yl)methoxy)carbonyl)-2,4a,6a,6b,9,12a-hexamethyl-13-oxo-1,2,3,4,4a, 5,6,6a,6b,7,8,8a,9,10,11,12,12a,12b,13,14b-icosahydropicene-2-carboxylic Acid (361-1)

The title compound 361-1 was prepared through the same synthetic route as 358-7, beginning with 358-2 and ethyl isonipecotate and 4-(bromomethyl)-5-ethyl-2H-1,3-dioxol-2-one. The crude product was purified by prep-HPLC with the following conditions: column, XBridge CSH OBD, 30*150 mm, 5 μm; mobile phase, water (0.05% TFA) and CH$_3$CN (40% to 57% over 8 min); detector, UV 254 nm. This resulted in 361-1 (3.7 mg, 14%) as an off-white solid. MS (ES, m/z): [M+1]$^+$=752.35; $^1$H NMR (400 MHz, methanol-d$_4$) δ 0.85 (s, 3H), 0.92 (t, J=6.8 Hz, 1H), 1.00-1.50 (m, 29H), 1.51-1.78 (m, 3H), 1.79-2.10 (m, 6H), 2.11-2.31 (m, 4H), 2.55 (s, 1H), 2.65 (q, 7=7.5 Hz, 3H), 3.00 (d, J=13.6 Hz, 1H), 3.08-3.29 (m, 2H), 3.73 (s, 3H), 3.89 (s, 1H), 5.09 (d, J=14.0 Hz, 1H), 5.19 (d, J=14.0 Hz, 1H), 5.63 (s, 1H).

Example 106 (2S,4aS,6aS,6bR,8aR,9S,10S,12aS, 12bR,14bR)-10-(4-(ethoxycarbonyl)piperidin-1-yl)-2,4a,6a,6b,9,12a-hexamethyl-9-(((5-methyl-2-oxo-1, 3-dioxol-4-yl)methoxy)carbonyl)-13-oxo-1,2,3,4,4a, 5,6,6a,6b,7,8,8a,9,10,1142,12a,12b,13,14b-icosahydropicene-2-carboxylic Acid (362-1)

Synthesis of (2S,4aS,6aS,6bR,8aR,9S,10S,12aS, 12bR,14bR)-10-(4-(ethoxycarbonyl)piperidin-1-yl)-2,4a,6a,6b,9,12a-hexamethyl-9-(((5-methyl-2-oxo-1, 3-dioxol-4-yl)methoxy)carbonyl)-13-oxo-1,2,3,4,4a, 5,6,6a,6b,7,8,8a,9,10,11,12,12a,12b,13,14b-icosahydropicene-2-carboxylic Acid (362-1)

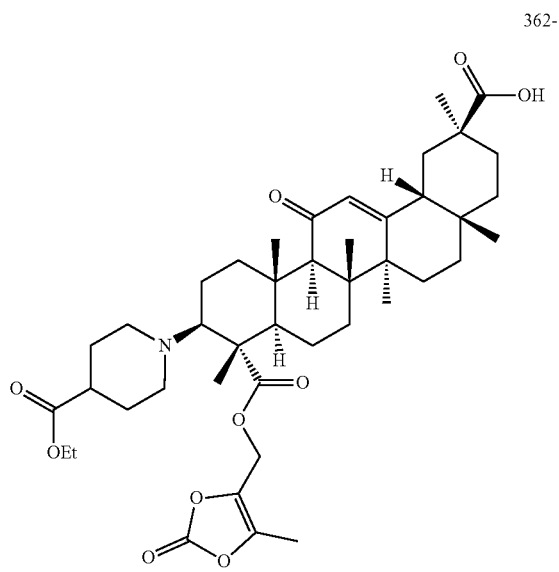

362-1

The title compound 362-1 was prepared through the same synthetic route as 358-7, beginning with 358-2 and ethyl isonipecotate. The crude product was purified by prep-HPLC with the following conditions: column, XSelect CSH OBD, 19*150 mm, 5 μm; mobile phase, water (0.05% TFA) and CH$_3$CN (41% to 47% over 8 min); detector, UV 254 nm. This resulted in 362-1 (2.0 mg, 9%) as an off-white solid. MS (ES, m/z): [M+1]$^+$=752.30; $^1$H NMR (400 MHz, methanol-d$_4$) δ 0.85 (s, 3H), 1.01-1.57 (m, 29H), 1.60-2.38 (m, 14H), 2.55 (s, 1H), 2.65-2.88 (m, 1H), 3.00 (d, J=13.6 Hz, 1H), 3.18-3.30 (m, 3H), 3.38-3.99 (m, 3H), 4.19 (d, J=6.4 Hz, 2H), 5.08 (d, J=14.0 Hz, 1H), 5.20 (d, J=14.0 Hz, 1H), 5.63 (s, 1H).

Example 107 (2S,4aS,6aS,6bR,8aR,9S,10S,12aS, 12bR,14bR)-9-acetamido-2,4a,6a,6b,9,12a-hexamethyl-10-((((5-methyl-2-oxo-1,3-dioxol-4-yl) methoxy)carbonyl)oxy)-13-oxo-1,2,3,4,4a,5,6,6a,6b, 7,8,8a,9,10,1142,12a,12b,13,14b-icosahydropicene-2-carboxylic Acid (363-5)

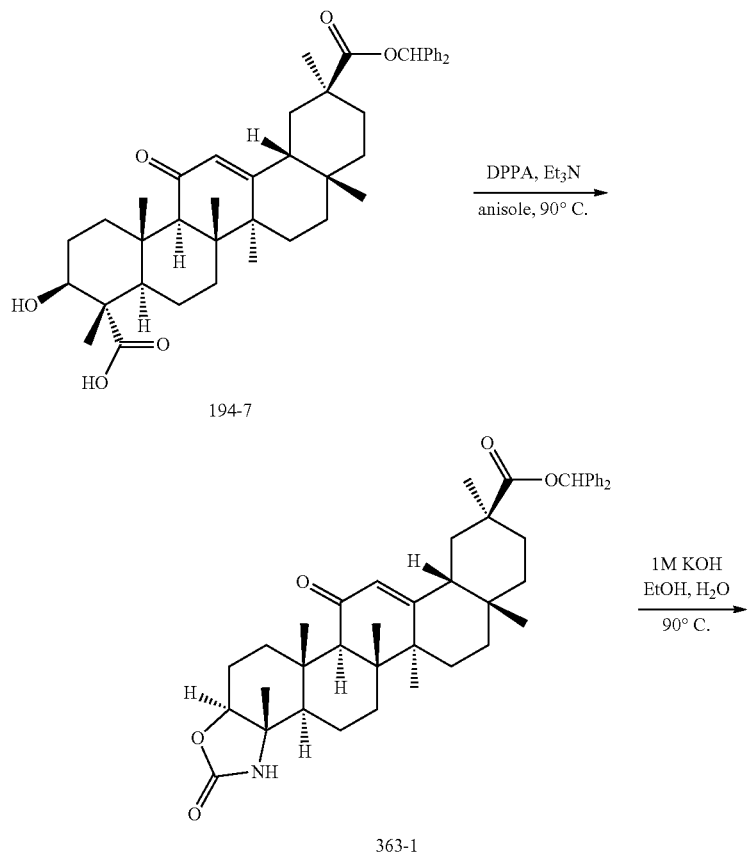

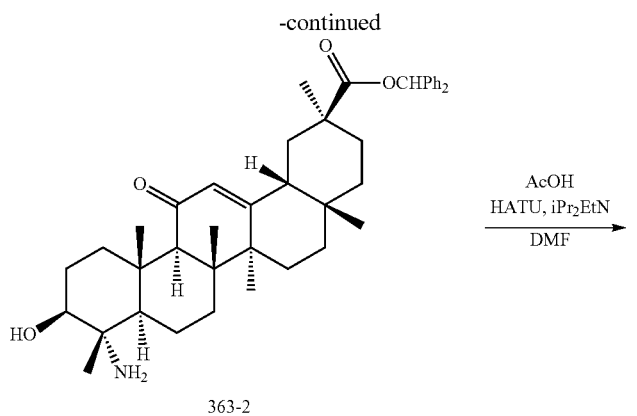
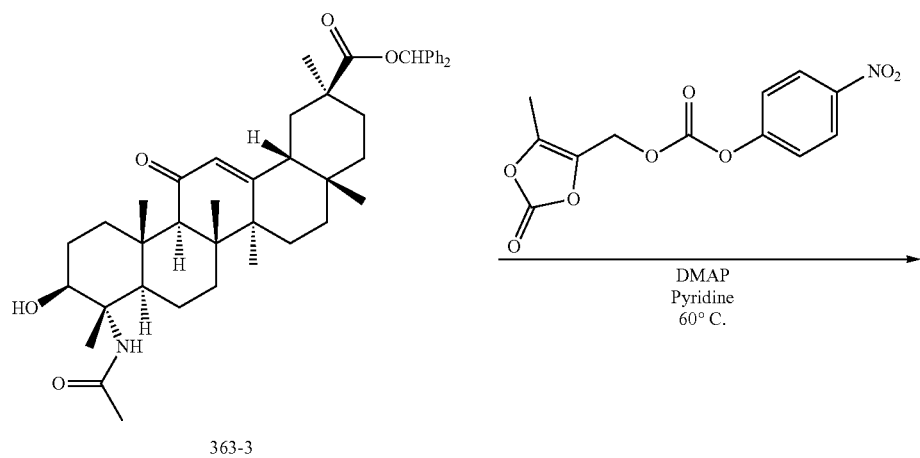
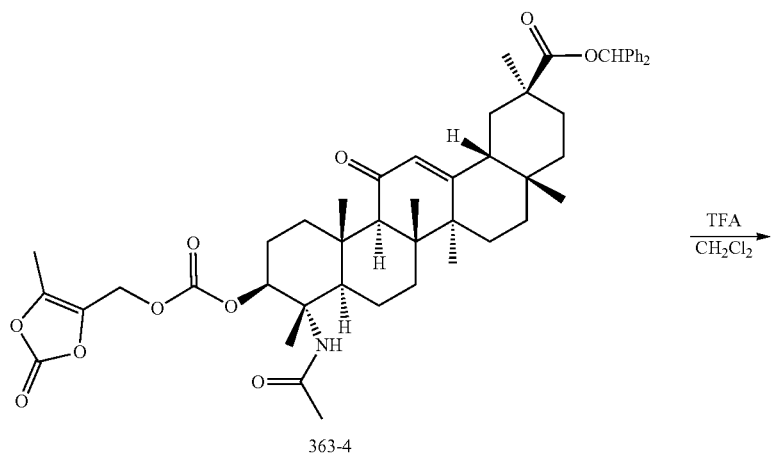

-continued

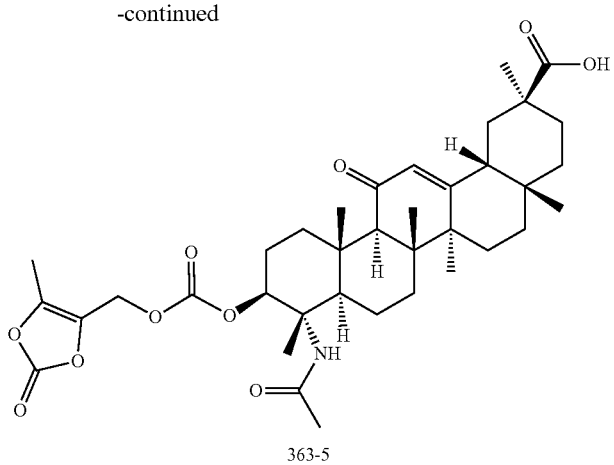

363-5

Synthesis of benzhydryl (3aS,3bR,5aR,5bS,7aS, 10S,11aR,13aR,13bS,15aS)-3a,5a,5b,7a,10,13b-hexamethyl-2,13-dioxo-2,3,3a,3b,4,5,5a,5b,6,7,7a,8, 9,10,11,11a,13,13a,13b,14,15,15a-docosahydropiceno[4,3-d]oxazole-10-carboxylate (363-1)

A mixture of 194-7 (1 g, 1.5 mmol), DPPA (0.7 g, 2.6 mmol, 1.7 equiv), and Et₃N (0.4 g, 3.75 mmol, 2.5 equiv) in anisole (10 mL) was stirred for 1.5 h at 90° C. The reaction mixture was concentrated under reduced pressure. The residue was purified by silica gel column chromatography eluting with petroleum ether:ethyl acetate (1:1) to afford 363-1 (1 g, 100%) as a light yellow solid.

Synthesis of benzhydryl (2S,4aS,6aS,6bR,8aR,9S, 10S,12aS,12bR,14bR)-9-amino-10-hydroxy-2,4a,6a, 6b,9,12a-hexamethyl-13-oxo-1,2,3,4,4a,5,6,6a,6b,7, 8,8a,9,10,11,12,12a,12b,13,14b-icosahydropicene-2-carboxylate (363-2)

A mixture of 363-1 (600 mg, 0.90 mmol) and KOH (12 mL, 1 M in 2:1 EtOH:H₂O) was stirred for 1 h at 90° C. The reaction mixture was cooled and extracted with ethyl acetate. The combined organic layers were washed with brine, dried over anhydrous Na₂SO₄, filtered, and concentrated. The residue was purified by prep-TLC (5:1 CH₂Cl₂: MeOH) to afford 363-2 (400 mg, 69%) as a light yellow solid.

Synthesis of benzhydryl (2S,4aS,6aS,6bR,8aR,9S, 10S,12aS,12bR,14bR)-9-acetamido-10-hydroxy-2, 4a,6a,6b,9,12a-hexamethyl-13-oxo-1,2,3,4,4a,5,6,6a, 6b,7,8,8a,9,10,11,12,12a,12b,13,14b-icosahydropicene-2-carboxylate (363-3)

To a stirred mixture of 363-2 (400 mg, 0.63 mmol), HATU (358 mg, 0.94 mmol, 1.5 equiv), and iPr₂EtN (324 mg, 2.5 mmol, 4 equiv) in DMF was added AcOH (75.3 mg, 1.25 mmol, 2 equiv) dropwise in portions at room temperature. The reaction mixture was stirred for 3 h at room temperature. The residue was purified by prep-TLC (1:1 petroleum ether:ethyl acetate) to afford 363-3 (300 mg, 70%) as a light yellow solid.

Synthesis of benzhydryl (2S,4aS,6aS,6bR,8aR,9S, 10S,12aS,12bR,14bR)-9-acetamido-2,4a,6a,6b,9, 12a-hexamethyl-10-((((5-methyl-2-oxo-1,3-dioxol-4-yl)methoxy)carbonyl)oxy)-13-oxo-1,2,3,4,4a,5,6, 6a,6b,7,8,8a,9,10,11,12,12a,12b,13,14b-icosahydropicene-2-carboxylate (363-4)

A mixture of 363-3 (200 mg, 0.29 mmol), (5-methyl-2-oxo-2H-1,3-dioxol-4-yl) methyl 4-nitrophenyl carbonate (434 mg, 1.5 mmol, 5 equiv), and DMAP (90 mg, 0.74 mmol, 2.5 equiv) in pyridine was stirred overnight at 60° C. The reaction mixture was concentrated under reduced pressure. The residue was purified by prep-TLC (3:1 petroleum ether:ethyl acetate) to afford 363-4 (120 mg, 49%) as a light yellow solid.

Synthesis of (2S,4aS,6aS,6bR,8aR,9S,10S, 12aS, 12bR, 14bR)-9-acetamido-2,4a,6a,6b,9,12a-hexamethyl-10-((((5-methyl-2-oxo-1,3-dioxol-4-yl) methoxy)carbonyl)oxy)-13-oxo-1,2,3,4,4a,5,6,6a,6b, 7,8,8a,9,10,11,12,12a,12b,13,14b-icosahydropicene-2-carboxylic acid (363-5)

A mixture of 363-4 (100 mg, 0.12 mmol) and TFA (0.1 mL, 1.35 mmol) in CF₂Cl₂ was stirred for 1 h at room temperature. The crude product was purified by prep-HPLC with the following conditions: column, XSelect CSH OBD 30*150 mm, 5 μm; mobile phase, water (0.05% TFA) and CH₃CN (52% phase B up to 63% in 8 min); detector, UV. This resulted in 363-5 (27.7 mg, 35%) as a light yellow solid. MS (ES, m/z): [M+1]⁺=670.30; ¹H NMR (300 MHz, methanol-d₄) δ 5.76-5.59 (m, 2H), 5.07-4.89 (m, 2H), 2.78 (d, J=13.6 Hz, 1H), 2.60 (d, J=10.3 Hz, 2H), 2.20 (s, 5H), 2.05-1.63 (m, 9H), 1.55 (d, J=7.9 Hz, 2H), 1.44 (d, J=8.2 Hz, 7H), 1.17 (dd, J=11.0, 6.7 Hz, 15H), 0.85 (s, 3H).

Example 108 (2S,4aS,6aS,6bR,8aR,9S,10S,12aS,12bR,14bR)-2,4a,6a,6b,9,12a-hexamethyl-9-(((5-methyl-2-oxo-1,3-dioxol-4-yl)methoxy)carbonyl)-10-((R)-5-methyl-2-oxooxazolidin-3-yl)-13-oxo-1,2,3,4,4a,5,6,6a,6b,7,8,8a,9,10,11,12,12a,12b,13,14b-icosahydropicene-2-carboxylic Acid (364-5)

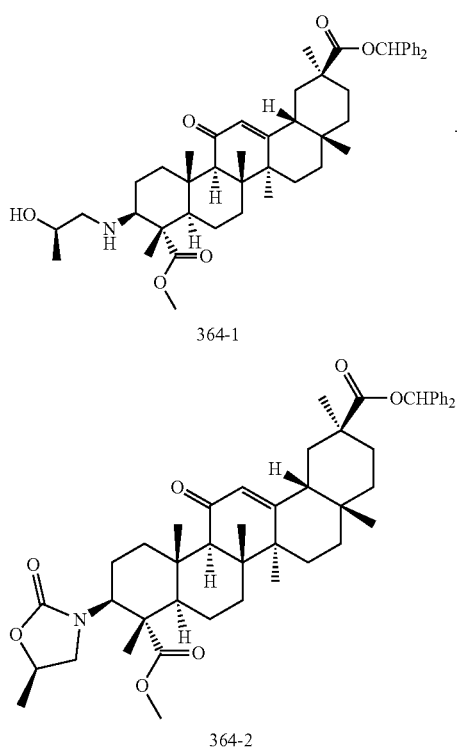

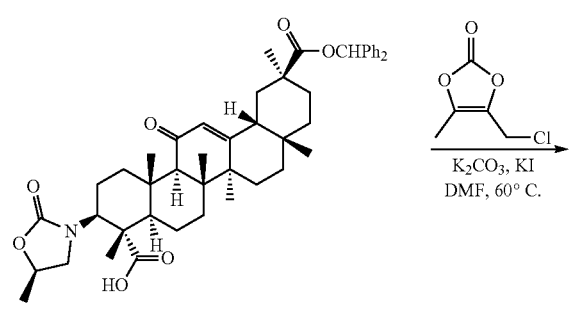

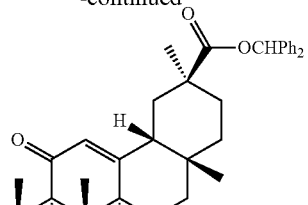

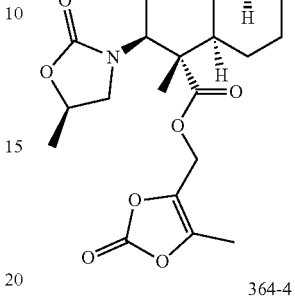

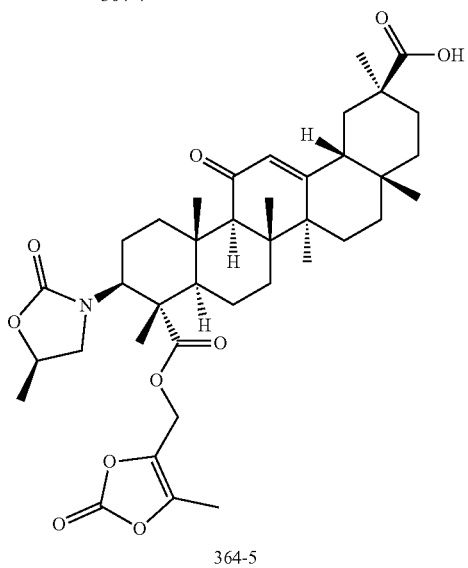

Synthesis of 2-benzhydryl 9-methyl (2S,4aS,6aS,6bR,8aR,9S,10S,12aS,12bR,14bR)-10-(((R)-2-hydroxypropyl)amino)-2,4a,6a,6b,9,12a-hexamethyl-13-oxo-1,2,3,4,4a,5,6,6a,6b,7,8,8a,9,10,11,12,12a,12b,13,14b-icosahydropicene-2,9-dicarboxylate (364-1)

Into a 25-mL round-bottom flask was placed 357-2 (300 mg), EtOH (2.8 mL), (2R)-2-methyloxirane (31 mg, 1.3 equiv). The reaction slurry was stirred for overnight at 40° C. The reaction mixture was cooled and concentrated. The residue was applied onto a silica gel column with ethyl acetate:petroleum ether (1:1). This resulted in 140 mg of 364-1 as a yellow oil.

Synthesis of 2-benzhydryl 9-methyl (2S,4aS,6aS,6bR,8aR,9S,10S,12aS,12bR,14bR)-2,4a,6a,6b,9,12a-hexamethyl-10-((R)-5-methyl-2-oxooxazolidin-3-yl)-13-oxo-1,2,3,4,4a,5,6,6a,6b,7,8,8a,9,10,11,12,12a,12b,13,14b-icosahydropicene-2,9-dicarboxylate (364-2)

Into a 50-mL round-bottom flask was placed 364-1 (340 mg), toluene (5 mL), CDI (187 mg, 2 equiv), and DMAP (111 mg, 2.5 equiv). The reaction slurry was stirred for 1.5 h at room temperature. The reaction mixture was diluted with water and extracted with 3×30 mL of ethyl acetate. The combined organic layers were washed with brine, dried over anhydrous $Na_2SO_4$, filtered, and concentrated. The residue was applied onto a silica gel column with ethyl acetate: petroleum ether (1:1) to provide 140 mg of 364-2 as a brown oil.

Synthesis of (3S,4S,4aR,6aR,6bS,8aS,11S,12aR, 14aR,14bS)-11-((benzhydryloxy)carbonyl)-4,6a,6b, 8a,11,14b-hexamethyl-3-((R)-5-methyl-2-oxooxazo-lidin-3-yl)-14-oxo-1,2,3,4,4a,5,6,6a,6b,7,8,8a,9,10, 11,12,12a,14,14a,14b-icosahydropicene-4-carboxylic Acid (364-3)

Into a 25-mL round-bottom flask was placed 364-2 (134 mg), pyridine (1.3 mL), and LiI (235 mg, 10 equiv). The reaction slurry was stirred for overnight at 130° C. in an oil bath. The reaction mixture was cooled and extracted with 3×30 mL of $CH_2Cl_2$. The combined organic layers were washed with 2×50 ml of 1 M $HCl_{(aq)}$ and 3×50 mL of brine, dried over anhydrous $Na_2SO_4$, filtered, and concentrated. The residue was applied onto a silica gel column with $CH_2Cl_2$/methanol (10:1) to provide 110 mg of 364-3 as a white solid.

Synthesis of 2-benzhydryl 9-((5-methyl-2-oxo-1,3-dioxol-4-yl)methyl) (2S,4aS,6aS,6bR,8aR,9S,10S, 12aS,12bR,14bR)-2,4a,6a,6b,9,12a-hexamethyl-10-((R)-5-methyl-2-oxooxazolidin-3-yl)-13-oxo-1,2,3,4, 4a,5,6,6a,6b,7,8,8a,9,10,11,12,12a,12b,13,14b-icosahydropicene-2,9-dicarboxylate (364-4)

Into a 25-mL round-bottom flask was 364-3 (60 mg), DMF (0.6 mL), KI (7 mg, 0.5 equiv), $K_2CO_3$ (24 mg, 3 equiv), and 4-(chloromethyl)-5-methyl-2H-1,3-dioxol-2-one (18 mg, 1.5 equiv). The reaction slurry was stirred overnight at room temperature. The reaction mixture was diluted with 50 mL of ethyl acetate and water. The layers were separated and the aqueous was extracted with 3×30 mL of ethyl acetate. The combined organic layers were washed with 3 x 100 ml of brine, dried over anhydrous $Na_2SO_4$, filtered, and concentrated. The residue was applied onto a silica gel column with ethyl acetate:petroleum ether (1:1) to provide 50 mg of 364-4 as a yellow solid.

Synthesis of (2S,4aS,6aS,6bR,8aR,9S,10S,12aS, 12bR,14bR)-2,4a,6a,6b,9,12a-hexamethyl-9-(((5-methyl-2-oxo-1,3-dioxol-4-yl)methoxy)carbonyl)-10-((R)-5-methyl-2-oxooxazolidin-3-yl)-13-oxo-1,2, 3,4,4a,5,6,6a,6b,7,8,8a,9,10,11,12,12a,12b,13,14b-icosahydropicene-2-carboxylic Acid (364-5)

Into a 25-mL round-bottom flask was placed 364-4 (60 mg), $CH_2Cl_2$ (1 mL), and TFA (0.2 mL). The reaction slurry was stirred for 40 min at room temperature then concentrated. The crude product (60 mg) was purified by prep-HPLC with the following conditions: column, XSelect CSH OBD, 30*150 mm, 5 μm; mobile phase, water (0.05% TFA) and $CH_3CN$ (65% phase B up to 70% in 8 min); Detector, UV. 10.9 mg product was obtained and concentrated. This resulted in 10.9 mg of 364-5 as a white solid. MS (ES, m/z): $[M+1]^+$=696; $^1H$ NMR (400 MHz, methanol-$d_4$) δ 0.83-0.87 (s, 3H), 0.87-0.94 (d, J=13.6 Hz, 1H), 1.03-1.11 (d, J=14.2 Hz, 1H), 1.14-1.23 (m, 8H), 1.24-1.27 (s, 3H), 1.27-1.37 (d, J=11.5 Hz, 3H), 1.37-1.45 (dd, J=3.9, 15.5 Hz, 6H), 1.46- 1.50 (s, 3H), 1.55-1.70 (m, 1H), 1.70-1.82 (m, 1H), 1.82-1.91 (dd, J=6.5, 12.5 Hz, 2H), 1.94-2.10 (m, 1H), 2.17-2.21 (s, 3H), 2.21-2.27 (d, J=13.5 Hz, 1H), 2.59-2.63 (s, 1H), 2.86-2.94 (d, J=13.6 Hz, 1H), 3.21-3.30 (t, J=8.9 Hz, 1H), 3.74-3.83 (t, J=8.3 Hz, 1H), 4.07-4.16 (dd, J=4.1, 12.9 Hz, 1H), 4.58-4.68 (q, J=7.7 Hz, 1H), 4.69-4.77 (d, J=13.9 Hz, 1H), 5.05-5.13 (d, J=14.0 Hz, 1H), 5.61-5.65 (s, 1H).

Example 109 (2S,4aS,6aS,6bR,8aR,9S,10S,12aS, 12bR,14bR)-10-(2,5-dioxoimidazolidin-1-yl)-2,4a, 6a,6b,9,12a-hexamethyl-9-(((5-methyl-2-oxo-1,3-dioxol-4-yl)methoxy)carbonyl)-13-oxo-1,2,3,4,4a,5, 6,6a,6b,7,8,8a,9,10,1142,12a,12b,13,14b-icosahydropicene-2-carboxylic Acid (365-8)

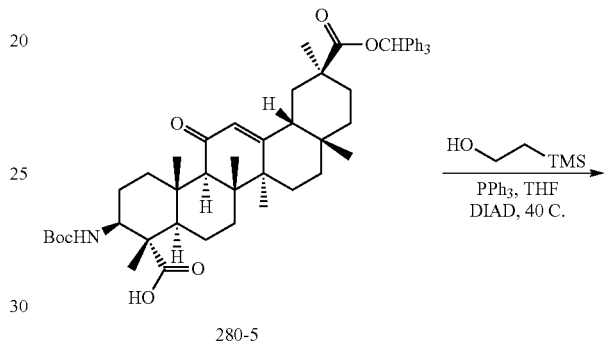

337
-continued

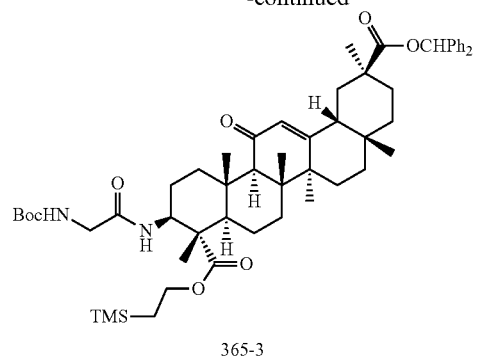
365-3

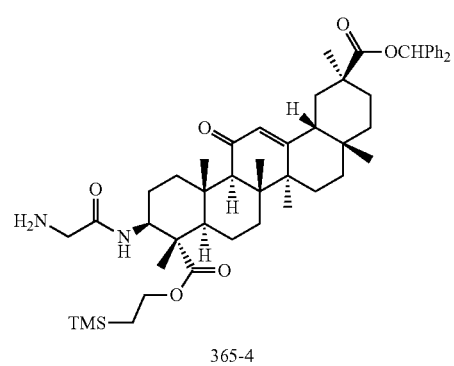
365-4

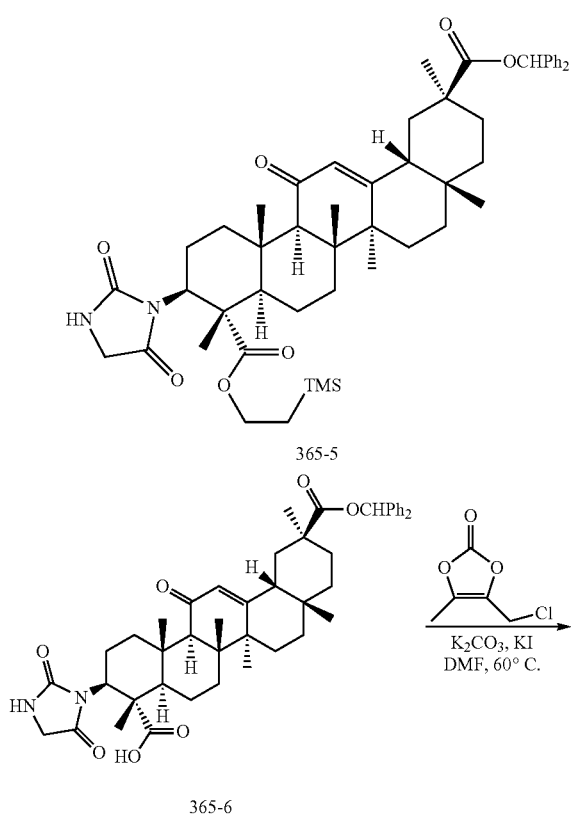
365-5

365-6

338
-continued

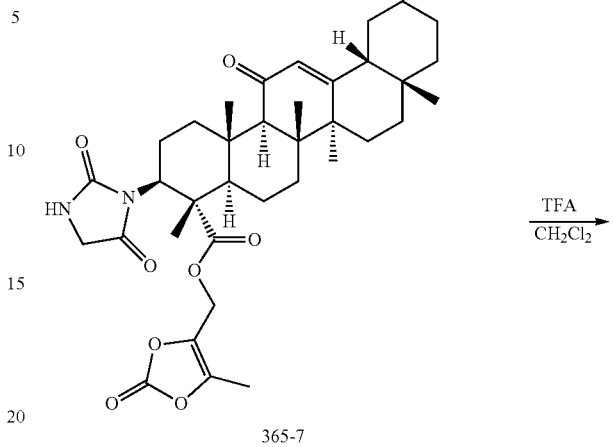
365-7

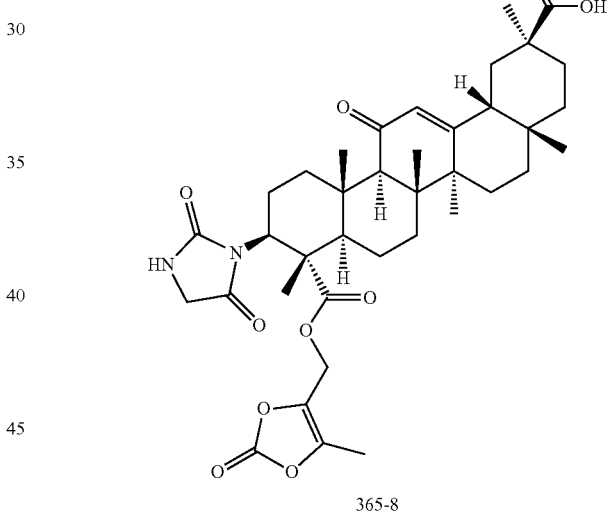
365-8

Synthesis of 2-benzhydryl 9-(2-(trimethylsilyl) ethyl) (2S,4aS,6aS,6bR,8aR,9S,10S,12aS,12bR, 14bR)-10-((tert-butoxycarbonyl)amino)-2,4a,6a,6b, 9,12a-hexamethyl-13-oxo-1,2,3,4,4a,5,6,6a,6b,7,8, 8a,9,10,11,12,12a,12b,13,14b-icosahydropicene-2,9-dicarboxylate (365-1)

Into a 8-mL vial was placed 280-5 (450 mg, 0.59 mmol), THF (1.5 mL), PPh$_3$ (240 mg, 0.92 mmol, 1.6 equiv), and 2-(trimethylsilyl)ethan-1-ol (0.45 mL, 3 mmol, 5 equiv) followed by DIAD (0.18 mL, 0.92 mmol, 1.6 equiv) dropwise with stirring at 40° C. The reaction slurry was stirred for 2 h at 40° C. The resulting mixture was concentrated and the residue applied onto a silica gel column with ethyl acetate:petroleum ether (1:2) to provide 400 mg of 365-1 as a white solid.

Synthesis of 2-benzhydryl 9-(2-(trimethylsilyl) ethyl) (2S,4aS,6aS,6bR,8aR,9S,10S,12aS,12bR, 14bR)-10-amino-2,4a,6a,6b,9,12a-hexamethyl-13-oxo-1,2,3,4,4a,5,6,6a,6b,7,8,8a,9,10,11,12,12a,12b, 13,14b-icosahydropicene-2,9-dicarboxylate (365-2)

Into a 250-mL round-bottom flask was placed 365-1 (400 mg, 0.46 mmol), $CH_2Cl_2$ (24 mL), and 2,6-lutidine (0.27 mL, 2.3 mmol, 5 equiv) followed by the addition of TMSOTf (0.34 mL, 1.85 mmol, 4 equiv) at 0° C. The reaction slurry was stirred for 1 h at room temperature. The reaction mixture was washed with 2×30 ml of 0.5 M $HCl_{(aq)}$. The organic layer was washed with 2×30 mL of brine, dried over anhydrous $Na_2SO_4$, filtered, and concentrated to provide 300 mg of crude 365-2 as a light yellow solid.

Synthesis of 2-benzhydryl 9-(2-(trimethylsilyl) ethyl) (2S,4aS,6aS,6bR,8aR,9S,10S,12aS,12bR, 14bR)-10-(2-((tert-butoxycarbonyl)amino)acetamido)-2,4a,6a,6b,9,12a-hexamethyl-13-oxo-1,2,3,4, 4a,5,6,6a,6b,7,8,8a,9,10,11,12,12a,12b,13,14b-icosahydropicene-2,9-dicarboxylate (365-3)

Into a 50-mL round-bottom flask was placed 365-2 (300 mg, 0.39 mmol), $CH_2Cl_2$ (6 mL), Boc-glycine (205 mg, 1.17 mmol, 3 equiv), EDCI (225 mg, 1.17 mmol, 3.00 equiv), and DMAP (143 mg, 1.17 mmol, 3.00 equiv). The reaction slurry was stirred for 1 h at room temperature then concentrated. The residue was applied onto a silica gel column with ethyl acetate/petroleum ether (1:2) to provide 320 mg of 365-3 as a light yellow solid.

Synthesis of 2-benzhydryl 9-(2-(trimethylsilyl) ethyl) (2S,4aS,6aS,6bR,8aR,9S,10S,12aS,12bR, 14bR)-10-(2-aminoacetamido)-2,4a,6a,6b,9,12a-hexamethyl-13-oxo-1,2,3,4,4a,5,6,6a,6b,7,8,8a,9,10, 11,12,12a,12b,13,14b-icosahydropicene-2,9-dicarboxylate (365-4)

Into a 100-mL round-bottom flask was placed 365-3 (260 mg, 0.28 mmol), $CH_2Cl_2$ (13 mL), and 2,6-lutidine (0.16 mg, 1.4 mmol, 5 equiv) followed by the addition of TMSOTf (0.20 mL, 1.1 mmol, 4 equiv) at 0° C. The reaction slurry was stirred for 1 h at room temperature. The reaction mixture was washed with 2×50 ml of 0.5 M $HCl_{(aq)}$ and 2×50 mL of brine, dried over anhydrous $Na_2SO_4$, filtered, and concentrated to provide 240 mg of 365-4 as a light yellow solid.

Synthesis of 2-benzhydryl 9-(2-(trimethylsilyl) ethyl) (2S,4aS,6aS,6bR,8aR,9S,10S,12aS,12bR, 14bR)-10-(2,5-dioxoimidazolidin-1-yl)-2,4a,6a,6b,9, 12a-hexamethyl-13-oxo-1,2,3,4,4a,5,6,6a,6b,7,8,8a, 9,10,11,12,12a,12b,13,14b-icosahydropicene-2,9-dicarboxylate (365-5)

Into a 100-mL round-bottom flask was placed 365-4 (288 mg, 0.35 mmol), toluene (12 mL), DMAP (86 mg, 0.7 mmol, 2 equiv), and CDI (141 mg, 0.87 mmol, 2.5 equiv). The reaction slurry was stirred overnight at 100° C. The reaction mixture was concentrated and the residue applied onto a silica gel column with ethyl acetate:petroleum ether (1:2) to provide 210 mg of 365-5 as a white solid.

Synthesis of (3S,4S,4aR,6aR,6bS,8aS,11S,12aR, 14aR,14bS)-11-((benzhydryloxy)carbonyl)-3-(2,5-dioxoimidazolidin-1-yl)-4,6a,6b,8a,11,14b-hexamethyl-14-oxo-1,2,3,4,4a,5,6,6a,6b,7,8,8a,9,10,11,12, 12a,14,14a,14b-icosahydropicene-4-carboxylic Acid (365-6)

Into a 50-mL round-bottom flask was placed 365-5 (170 mg, 0.20 mmol), THF (5.5 mL), and TBAF (1.8 mL, 1 mmol, 5 equiv). The resulting solution was stirred overnight at room temperature then concentrated. The residue was applied onto a silica gel column with $CH_2Cl_2$:methanol (10:1) to provide 150 mg of 365-6 as a white solid.

Synthesis of 2-benzhydryl 9-((5-methyl-2-oxo-1,3-dioxol-4-yl)methyl) (2S,4aS,6aS,6bR,8aR,9S,10S, 12aS,12bR,14bR)-10-(2,5-dioxoimidazolidin-1-yl)-2,4a,6a,6b,9,12a-hexamethyl-13-oxo-1,2,3,4,4a,5,6, 6a,6b,7,8,8a,9,10,11,12,12a,12b,13,14b-icosahydropicene-2,9-dicarboxylate (365-7)

Into a 25-mL round-bottom flask, was placed 365-6 (130 mg, 0.17 mmol), DMF (3 mL), 4-(bromomethyl)-5-methyl-2/7-1,3-dioxol-2-one (50 mg, 0.26 mmol, 1.5 equiv), $K_2CO_3$ (72 mg, 0.52 mmol, 3 equiv), and KI (14 mg, 0.09 mmol, 0.5 equiv). The reaction slurry was stirred for 3 h at room temperature. The resulting solution was diluted with 50 mL of ethyl acetate and 50 mL of water. The mixture was extracted with 2×50 mL of ethyl acetate. The combined organic layers were washed with 3×50 ml of brine, dried over anhydrous $Na_2SO_4$, filtered, and concentrated. The residue was applied onto a silica gel column with ethyl acetate:petroleum ether (1:1) to provide 135 mg of 365-7 as a white solid.

Synthesis of (2S,4aS,6aS,6bR,8aR,9S,10S,12aS, 12bR,14bR)-10-(2,5-dioxoimidazolidin-1-yl)-2,4a, 6a,6b,9,12a-hexamethyl-9-(((5-methyl-2-oxo-1,3-dioxol-4-yl)methoxy)carbonyl)-13-oxo-1,2,3,4,4a,5, 6,6a,6b,7,8,8a,9,10,11,12,12a,12b,13,14b-icosahydropicene-2-carboxylic Acid (365-8)

Into a 8-mL vial was placed 365-7 (100 mg, 0.12 mmol), $CH_2Cl_2$ (2 mL), and TFA (0.2 mL). The reaction slurry was stirred for 30 min at room temperature then concentrated. The crude product was purified by prep-HPLC with the following conditions: column, XSelect CSH OBD, 30*150 mm, 5 μm; mobile phase, water (0.05% TFA) and $CH_3CN$ (40% phase B up to 45% in 8 min); Detector, UV. This resulted in 54.3 mg of 365-8 as a white solid. MS (ES, m/z) [M+1]$^+$=695; $^1$H NMR (300 MHz, methanol-$d_4$) δ 0.86 (s, 3H), 0.93 (d, J=12.6 Hz, 1H), 1.08 (d, J=14.2 Hz, 1H), 1.19 (d, J=8.3 Hz, 6H), 1.25 (d, J=2.3 Hz, 7H), 1.46 (d, J=17.5 Hz, 6H), 1.77 (d, J=13.2 Hz, 1H), 1.93 (q, J=14.7, 13.4 Hz, 4H), 2.21 (s, 3H), 2.25 (s, 1H), 2.62 (s, 1H), 2.90 (d, J=13.4 Hz, 1H), 3.07 (d, J=13.3 Hz, 1H), 3.87 (s, 2H), 4.28 (dd, J=13.0, 4.0 Hz, 1H), 4.75 (d, J=13.9 Hz, 1H), 5.00 (d, J=13.9 Hz, 1H), 5.63 (s, 1H).

Example 110 (2S,4aS,6aS,6bR,8aR,9S,10S,12aS, 12bR,14bR)-2,4a,6a,6b,9,12a-hexamethyl-10-((R)-4-methyl-2,5-dioxoimidazolidin-1-yl)-9-(((5-methyl-2-oxo-1,3-dioxol-4-yl)methoxy)carbonyl)-13-oxo-1,2,3,4,4a,5,6,6a,6b,7,8,8a,9,10,1142,12a,12b,13,14b-icosahydropicene-2-carboxylic Acid (366-1)

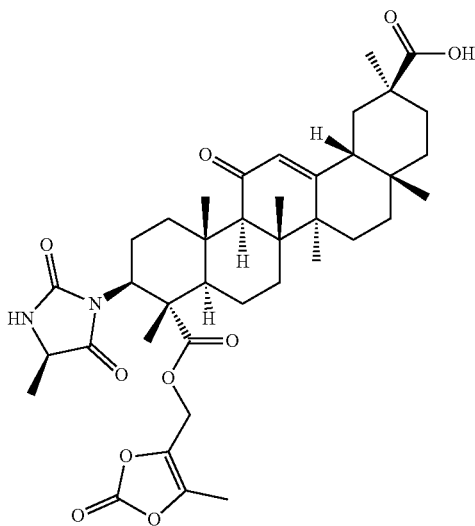

366-1

Synthesis of (2S,4aS,6aS,6bR,8aR,9S,10S,12aS, 12bR,14bR)-2,4a,6a,6b,9,12a-hexamethyl-10-((R)-4-methyl-2,5-dioxoimidazolidin-1-yl)-9-(((5-methyl-2-oxo-1,3-dioxol-4-yl)methoxy)carbonyl)-13-oxo-1,2,3,4,4a,5,6,6a,6b,7,8,8a,9,10,11,12,12a,12b,13,14b-icosahydropicene-2-carboxylic Acid (366-1)

The title compound was prepared using the methods from the synthesis of 365-8, beginning with 365-2 and Boc-(R)-alanine. The crude product was purified by prep-HPLC with the following conditions: column, XSelect CSH OBD, 30*150 mm, 5 μm; mobile phase, water (0.05% TFA) and $CH_3CN$ (45% phase B up to 55% in 8 min); detector, UV 254 nM. This resulted in 14.1 mg (35%) of 366-1 as a white solid. MS (ES, m/z): [M+1]$^+$=709; $^1$H NMR (300 MHz, methanol-d$_4$) δ 0.86 (s, 3H), 0.93 (s, 2H), 1.08 (d, J=15.2 Hz, 1H), 1.14-1.28 (m, 14H), 1.28-1.38 (m, 3H), 1.46 (d, J=17.6 Hz, 8H), 1.67 (d, J=12.9 Hz, 1H), 1.77 (d, J=13.2 Hz, 1H), 1.90 (t, J=14.4 Hz, 5H), 2.21 (d, J=1.5 Hz, 4H), 2.62 (s, 1H), 2.90 (d, J=13.0 Hz, 1H), 3.05 (d, J=14.7 Hz, 2H), 3.26 (s, 1H), 3.97 (dd, J=6.9, 4.1 Hz, 1H), 4.25 (s, 1H), 4.75 (dd, J=13.9, 6.1 Hz, 1H), 4.99 (dd, J=13.9, 9.5 Hz, 1H), 5.63 (s, 1H).

Example 111 2-(3-((1-PEGSK-1H-1,2,3-triazol-4-yl)methoxy)-4-nitrobenzyl) 9-((5-methyl-2-oxo-1,3-dioxol-4-yl)methyl) (2S,4aS,6aS,6bR,8aR,9S,10S, 12aS,12bR,14bR)-10-((2,5,8,11-tetraoxatetradecan-14-oyl)oxy)-2,4a,6a,6b,9,12a-hexamethyl-13-oxo-1,2,3,4,4a,5,6,6a,6b,7,8,8a,9,10,11,12,12a,12b,13,14b-icosahydropicene-2,9-dicarboxylate (605-2)

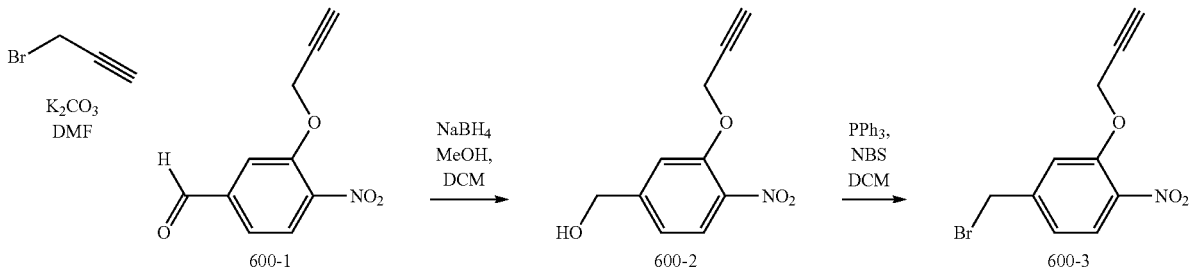

-continued
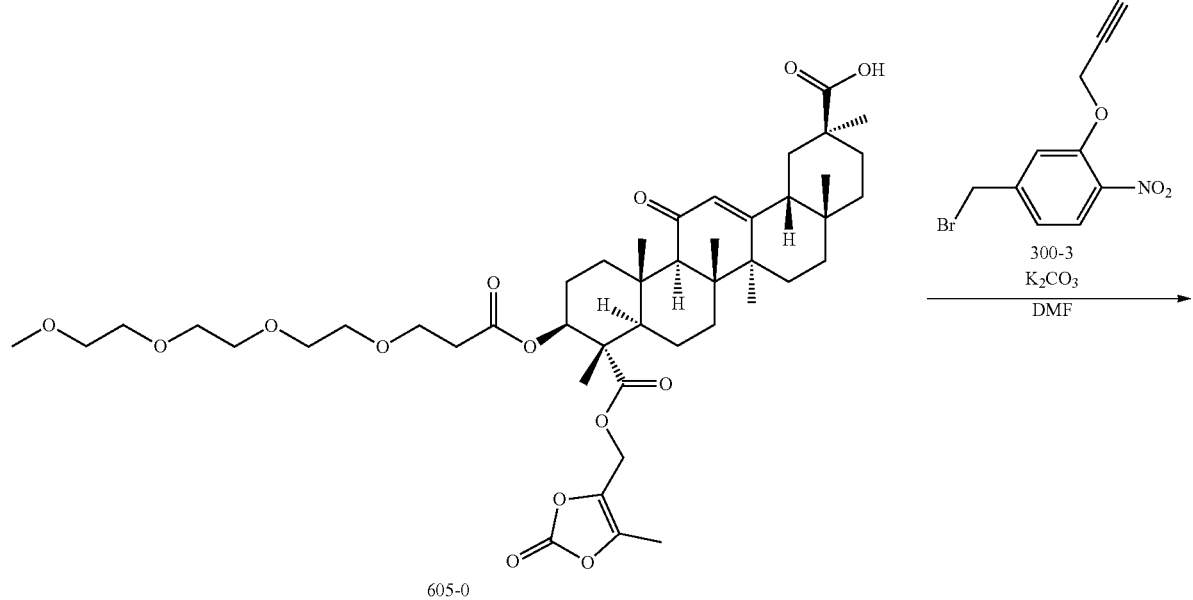
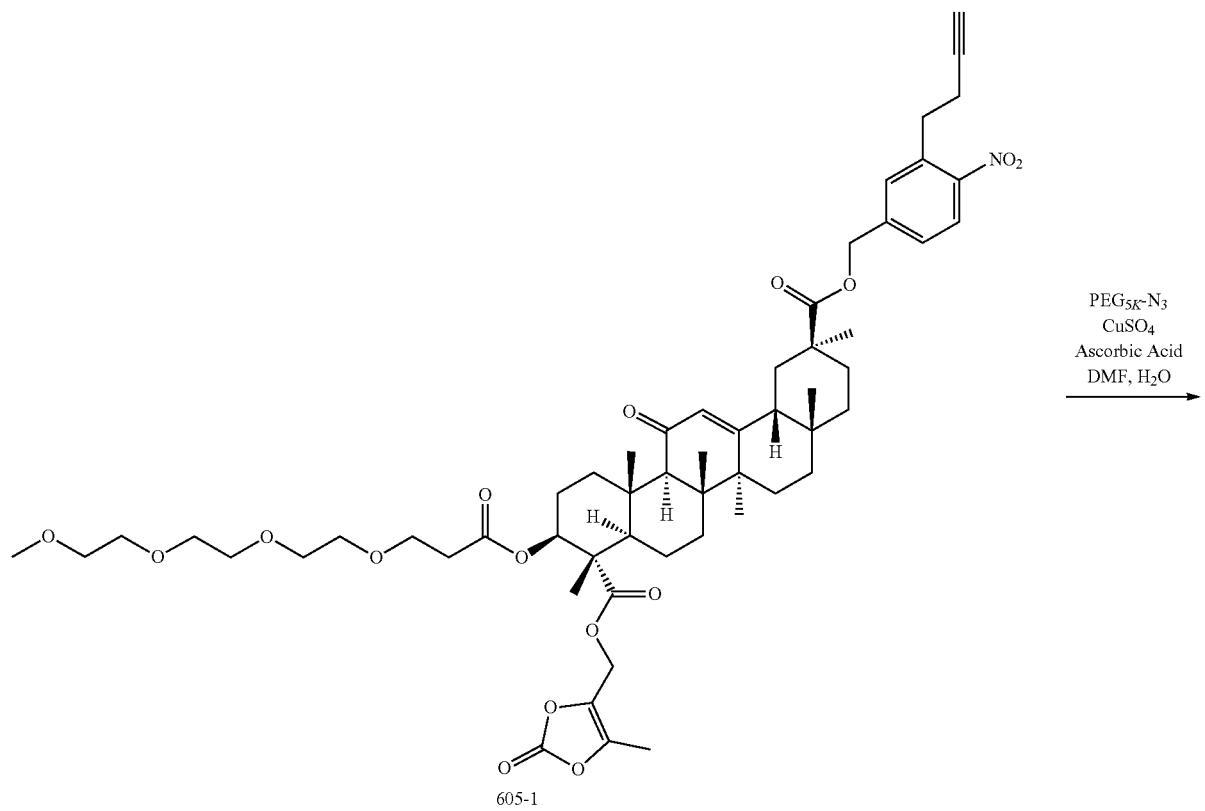

-continued

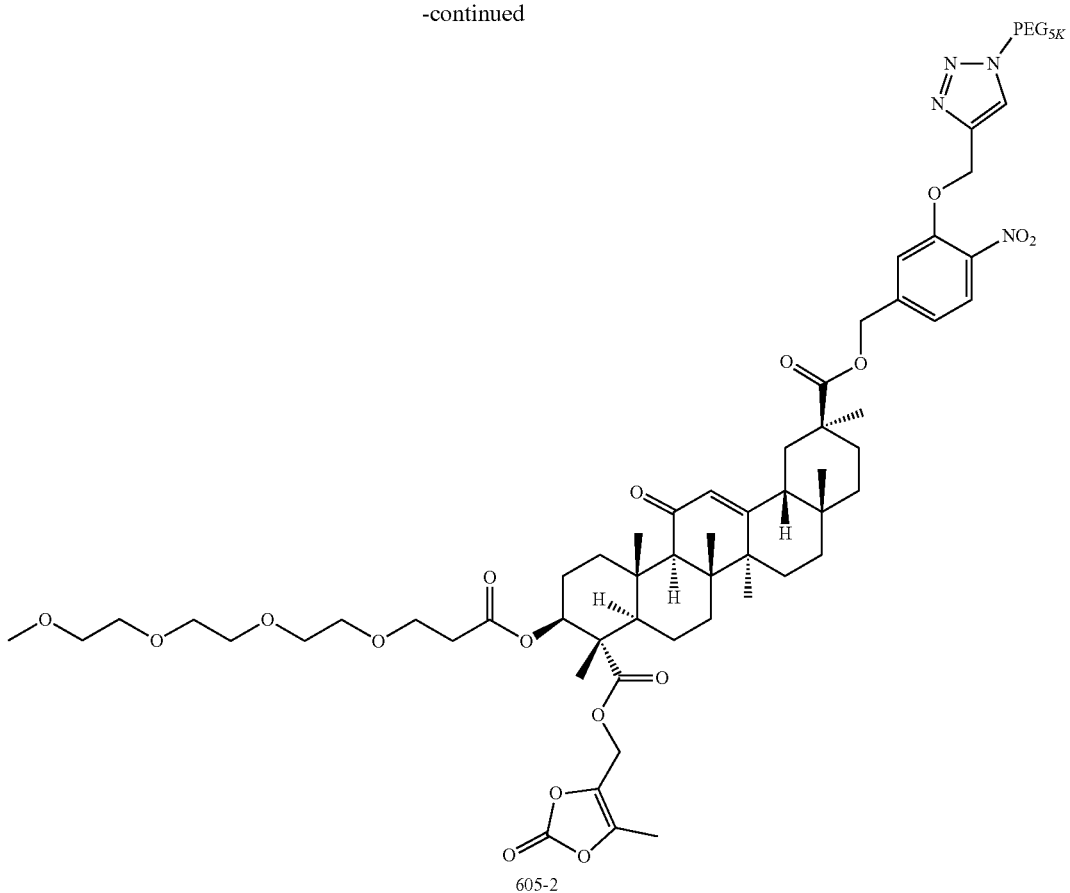
605-2

Synthesis of 4-Nitro-3-(prop-2-yn-1-yloxy)benzaldehyde (600-1)

3-Hydroxy-4-nitrobenzaldehyde (5 g, 0.0299 mol), propargyl bromide (1.05 equiv., 3.50 mL of 80% solution in toluene, 0.0314 mol) and potassium carbonate (1.3 equiv., 5.37 g, 0.0389 mol) in DMF (50 mL) were heated at 65° C. for 2 hours. The reaction was diluted with water (200 mL) and extracted with EtOAc (3×50 mL). The extract was washed with brine, dried (MgSO$_4$) and evaporated. The residue was purified by flash column chromatography (CH$_2$Cl$_2$/Hexane) to give product as an off-white solid (5.83 g, 95%).

Synthesis of (4-nitro-3-(prop-2-yn-1-yloxy)phenyl)methanol (600-2)

Sodium borohydride (1.3 equiv., 1.72 g, 0.0454 mol) was added portionwise to 600-1 (7.17 g, 0.0349 mol) in 10% MeOH/CH$_2$Cl$_2$ (50 mL) at 0° C. and then allowed to warm to rt. The reaction mixture was carefully quenched with 2N HCl. The organic layer was separated, washed with brine, dried (MgSO4) and evaporated to give product suitable for use directly in the next step (6.51 g, 90%).

Synthesis of 4-(Bromomethyl)-1-nitro-2-(prop-2-yn-1-yloxy)benzene (600-3)

N-Bromosuccinimide (1.20 equiv., 4.29 g, 0.0241 mol) was added to 600-2 (4.17 g, 0.0201 mol) and triphenylphosphine (1.5 equiv., 7.91 g, 0.0302 mol) in CH$_2$Cl$_2$ (60 mL) at 0° C. The reaction was allowed to warm to rt and stirred for 30 minutes. The mixture was evaporated and the residue purified by flash column chromatography (EtOAc/Hexane) to give product as a light yellow solid (4.23 g, 78%).

Synthesis of 9-((5-methyl-2-oxo-1,3-dioxol-4-yl)methyl) 2-(4-nitro-3-(prop-2-yn-1-yloxy)benzyl) (2S,4aS,6aS,6bR,8aR,9S,10S,12aS,12bR,14bR)-10-((2,5,8,11-tetraoxatetradecan-14-oyl)oxy)-2,4a,6a,6b,9,12a-hexamethyl-13-oxo-1,2,3,4,4a,5,6,6a,6b,7,8,8a,9,10,11,12,12a,12b,13,14b-icosahydropicene-2,9-dicarboxylate (605-1)

605-0 (0.075 g, 0.0903 mmol), 600-3 (0.027 g, 0.0993 mmol) and potassium carbonate (0.019 g, 0.135 mmol, 1.5 eqiuv.) in DMF (3 mL) were heated at 65° C. for 2 hours. The reaction was diluted with water (20 mL) and extracted with EtOAc. The extract was washed with brine, dried (MgSO$_4$) and evaporated. The residue was purified by flash column chromatography (EtOAc) to give 605-1 as a white solid (90 mg, 98%). MS (ES, m/z) [M+H]$^+$=1020.

Synthesis of 2-(3-((1-PEG$_{5K}$-1H-1,2,3-triazol-4-yl)methoxy)-4-nitrobenzyl) 9-((5-methyl-2-oxo-1,3-dioxol-4-yl)methyl)(2S,4aS,6aS,6bR,8aR,9S,10S,12aS,12bR,14bR)-10-((2,5,8,11-tetraoxatetradecan-14-oyl)oxy)-2,4a,6a,6b,9,12a-hexamethyl-13-oxo-1,2,3,4,4a,5,6,6a,6b,7,8,8a,9,10,11,12,12a,12b,13,14b-icosahydropicene-2,9-dicarboxylate (605-2)

The addition of copper sulfate (5 mg) in water (0.6 mL) to 305-1 (0.090 g, 0.0882 mmol, 1.3 equiv), PEG$_{5K}$-Azide (Average MW=5000)(0.339 g, 0.0679 mmol) and ascorbic acid (10 mg) in DMF (3 mL), followed by addition of fresh ascorbic acid (10 mg) after 1 hour and again (5 mg) at 2 hours gave 0.37 g (90%) product as a white solid. $^1$H NMR (400 MHz, relaxation time=10 sec, DMSO-$d_6$) δ 8.20 (s, 1H), 7.89 (d, J=8 Hz, 1H), 7.60 (s, 1H), 7.12 (d, J=8 Hz, 1H), 5.18-5.38 (m, 5H), 4.54 (t, J=8 Hz, 2H), 4.38-4.50 (m, 1H), 4.18-4.30 (m, 1H), 3.82 (t, J=8 Hz, 2H), 3.60 (m, 2H); 3.46 (s, 444H), 3.38 (s, 3H), 3.24 (s, 3H), 2.79-2.90 (m, 1H), 2.60 (s, 1H), 2.54 (q, J=6.4 Hz, 2H), 2.13-2.28 (m, 2H), 1.83-2.01 (m, 4H), 1.62-1.82 (m, 5H), 1.47-1.53 (m, 6H), 1.39-1.46 (m, 4H), 1.24-1.30 (m, 5H), 1.20 (s, 6H), 1.16 (s, 3H), 1.06 (d, j+10.4 Hz, 2H), 0.85 (s, 3H).

Example 112 HSD2 Activity

Human descending colon epithelial stem cells were cultured as 3D organoids in accordance with Sato et al Gastroenterology. 2011 November; 141(5): 1762-72. Organoids were dissociated using TrypLE Express (life technologies) and plated on 96-well transwells (corning) in supplemented basal media (SBM—advanced DMEM/F12 containing 10 mM HEPES, 1:100 Glutamax, 1:100 penicillin/streptomycin, 1:100N2, 1:50 B27, 1 mM N-acetylcysteine, 10 nM [Leu15]-gastrin I) containing 100 ng/mL Wnt3A (W), 50 ng/mL EGF (E), 100 ng/mL Noggin (N), 500 ng/mL RSpondinl (R), 500 nM A83-01 (S) and 2.5 uM thiazovivin (T). Cultures were differentiated using SBM containing ENRA and 30 nM aldosterone on day 3, and cultures were used for assay on day 6 or 7. Compounds were diluted in DMSO and serial dilutions prepared by titrating in DMSO. Compounds were then diluted into DMEM/F12. Transwell plates containing descending colon cultures were washed twice with DMEM/F12 and compound was added to the apical compartment. Cells were incubated with test compound for 30 minutes at 37° C., 5% $CO_2$ to equilibrate across the cell membrane. A second compound plate was prepared in which the serially diluted compounds in DMSO were diluted into DMEM/F12 containing 40 nM cortisol. Following the 30 minute pre-incubation step, the apical media was aspirated and compounds diluted in DMEM/F12 with 40 nM cortisol were added to the apical side of the transwell. The plate was then incubated for four hours at 37° C., 5% $CO_2$. Cortisol levels were measured using a cortisol HTRF assay kit as described by the manufacturer (Cisbio). Concentration-response curves were then plotted and $IC_{50}$ (and $pIC_{50}$) values were determined using least squares non-linear regression. Glycyrrhetinic acid had a $pIC_{50}$ of 6.6.

Inhibition of HSD2 activity as measured by the inhibition of the conversion of cortisone to cortisol. Compounds of the invention demonstrated greater HSD2 inhibition compared to the corresponding acid metabolite (chemically named).

| Compound | $pIC_{50}$ |
| --- | --- |
| (2S,4aS,6aS,6bR,8aS,10S,12aS,12bR,14bR)-2,4a,6a,6b,9,9,12a-heptamethyl-13-oxo-1,2,3,4,4a,5,6,6a,6b,7,8,8a,9,10,11,12,12a,12b,13,14b-icosahydropicene-2,10-dicarboxylic acid | 5.5 |
| 178-1 | 6.3 |
| 176-2 | 6.3 |
| 700-1 | 6.1 |

| Compound | $pIC_{50}$ |
| --- | --- |
| (2S,4aS,6aS,6bR,8aR,9S,10S,12aS,12bR,14bR)-2,4a,6a,6b,9,12a-hexamethyl-10-{[2-(methylsulfanyl)acetyl]oxy}-13-oxo-1,2,3,4,4a,5,6,6a,6b,7,8,8a,9,10,11,12,12a,12b,13,14b-icosahydropicene-2,9-dicarboxylic acid | 5.4 |
| 194-10 | 8 |
| 195-2 | 6.3 |
| 701-1 | 7 |

| Compound | $pIC_{50}$ |
| --- | --- |
| (2S,4aS,6aS,6bR,8aR,9S,10S,12aS,12bR,14bR)-10-[(2-methanesulfonylacetyl)oxy]-2,4a,6a,6b,9,12a-hexamethyl-13-oxo-1,2,3,4,4a,5,6,6a,6b,7,8,8a,9,10,11,12,12a,12b,13,14b-icosahydropicene-2,9-dicarboxylic acid | <5 |
| 195-2 | 6.3 |

| Compound | $pIC_{50}$ |
| --- | --- |
| (2S,4aS,6aS,6bR,8aR,9S,10S,12aS,12bR,14bR)-10-(benzoyloxy)-2,4a,6a,6b,9,12a-hexamethyl-13-oxo-1,2,3,4,4a,5,6,6a,6b,7,8,8a,9,10,11,12,12a,12b,13,14b-icosahydropicene-2,9-dicarboxylic acid | 6.6 |
| 197-2 | 7.9 |

| Compound | $pIC_{50}$ |
| --- | --- |
| (2S,4aS,6aS,6bR,8aR,9S,10S,12aS,12bR,14bR)-10-(cyclopropanecarbonyloxy)-2,4a,6a,6b,9,12a-hexamethyl-13-oxo-1,2,3,4,4a,5,6,6a,6b,7,8,8a,9,10,11,12,12a,12b,13,14b-icosahydropicene-2,9-dicarboxylic acid | 5.8 |
| 198-2 | 7.7 |

| Compound | $pIC_{50}$ |
| --- | --- |
| (2S,4aS,6aS,6bR,8aR,9S,10S,12aS,12bR,14bR)-10-(methoxymethoxy)-2,4a,6a,6b,9,12a-hexamethyl-13-oxo-1,2,3,4,4a,5,6,6a,6b,7,8,8a,9,10,11,12,12a,12b,13,14b-icosahydropicene-2,9-dicarboxylic acid | 5.1 |
| 205-2 | 6.4 |
| 258-2 | 6.9 |

| Compound | $pIC_{50}$ |
| --- | --- |
| (2S,4aS,6aS,6bR,8aR,9S,10S,12aS,12bR,14bR)-10-(acetyloxy)-2,4a,6a,6b,9,12a-hexamethyl-13-oxo-1,2,3,4,4a,5,6,6a,6b,7,8,8a,9,10,11,12,12a,12b,13,14b-icosahydropicene-2,9-dicarboxylic acid | 5.9 |
| 209-3 | |
| 702-1 | 6.4 |
| 703-1 | 6.1 |
| 704-1 | 6.3 |
| 316-1 | 7.5 |
| 705-1 | 6.6 |
| 706-1 | 6.7 |
| 707-1 | 7.1 |
| 209-3 | 7.2 |
| 243-1 | 7.5 |

| Compound | pIC$_{50}$ |
|---|---|
| (2S,4aS,6aS,6bR,9R,10S,12aS,12bR,14bR)-9-[(carboxymethoxy)methyl]-10-hydroxy-2,4a,6a,6b,9,12a-hexamethyl-13-oxo-1,2,3,4,4a,5,6,6a,6b,7,8,8a,9,10,11,12,12a,12b,13,14b-icosahydropicene-2-carboxylic acid | <5 |
| 240-8 | 5 |

| Compound | pIC$_{50}$ |
|---|---|
| (2S,4aS,6aS,6bR,8aR,9S,10S,12aS,12bR,14bR)-10-[(2-hydroxyacetyl)oxy]-2,4a,6a,6b,9,12a-hexamethyl-13-oxo-1,2,3,4,4a,5,6,6a,6b,7,8,8a,9,10,11,12,12a,12b,13,14b-icosahydropicene-2,9-dicarboxylic acid | 5.9 |
| 244-1 | 6.8 |

| Compound | pIC$_{50}$ |
|---|---|
| (2S,4aS,6aS,6bR,8aR,9S,10S,12aS,12bR,14bR)-10-[(2-methoxyacetyl)oxy]-2,4a,6a,6b,9,12a-hexamethyl-13-oxo-1,2,3,4,4a,5,6,6a,6b,7,8,8a,9,10,11,12,12a,12b,13,14b-icosahydropicene-2,9-dicarboxylic acid | <5 |
| 708-1 | 6.3 |
| 709-1 | 7.2 |

| Compound | pIC$_{50}$ |
|---|---|
| (2S,4aS,6aS,6bR,8aR,10S,12aS,12bR,14bR)-10-(carboxymethoxy)-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxylic acid | 5.4 |
| 710-1 | 6 |
| 711-1 | 5.8 |
| 712-1 | 5 |

| Compound | pIC$_{50}$ |
|---|---|
| (2S,4aS,6aS,6bR,8aR,9S,10S,12aS,12bR,14bR)-10-[(methoxycarbonyl)amino]-2,4a,6a,6b,9,12a-hexamethyl-13-oxo-1,2,3,4,4a,5,6,6a,6b,7,8,8a,9,10,11,12,12a,12b,13,14b-icosahydropicene-2,9-dicarboxylic acid | <5 |
| 281-3 | 6.7 |

| Compound | pIC$_{50}$ |
|---|---|
| (2S,4aS,6aS,6bR,8aR,9S,10S,12aS,12bR,14bR)-2,4a,6a,6b,9,12a-hexamethyl-10-({[2-(morpholin-4-yl)ethyl]carbamoyl}oxy)-13-oxo-1,2,3,4,4a,5,6,6a,6b,7,8,8a,9,10,11,12,12a,12b,13,14b-icosahydropicene-2,9-dicarboxylic acid | <5 |
| 286-4 | 6.9 |

| Compound | pIC$_{50}$ |
|---|---|
| (2S,4aS,6aS,6bR,8aR,9S,10S,12aS,12bR,14bR)-10-{[2-(dimethylamino)acetyl]oxy}-2,4a,6a,6b,9,12a-hexamethyl-13-oxo-1,2,3,4,4a,5,6,6a,6b,7,8,8a,9,10,11,12,12a,12b,13,14b-icosahydropicene-2,9-dicarboxylic acid | <5 |
| 290-2 | 6.6 |

| Compound | pIC$_{50}$ |
|---|---|
| (2S,4aS,6aS,6bR,8aR,9S,10S,12aS,12bR,14bR)-10-[4-(ethoxycarbonyl)-5-methoxy-1H-pyrazol-1-yl]-2,4a,6a,6b,9,12a-hexamethyl-13-oxo-1,2,3,4,4a,5,6,6a,6b,7,8,8a,9,10,11,12,12a,12b,13,14b-icosahydropicene-2,9-dicarboxylic acid | 5.6 |
| 713-1 | 6.9 |

| Compound | pIC$_{50}$ |
|---|---|
| (2S,4aS,6aS,6bR,8aR,9S,10S,12aS,12bR,14bR)-2,4a,6a,6b,9,12a-hexamethyl-13-oxo-10-(2,5,8,11-tetraoxatetradecanoyloxy)-1,2,3,4,4a,5,6,6a,6b,7,8,8a,9,10,11,12,12a,12b,13,14b-icosahydropicene-2,9-dicarboxylic acid | <5 |
| 605-2 | 6.9 |

Example 113 Stability Assays

Sample were analyzed on an Agilent 6410 triple-quadrapole LC-MS system consisting of an Agilent 1260 LC with a Phenomenex Gemini 5 μm column (NX-C18, 110A, 30×2 mm) and the mass spectrometer with an electrospray interface running under a positive ionization mode. Mobile phases were 0.1% formic acid in water and 0.1% formic acid in acetonitrile.

Plasma Stability—Plasma from pooled male rat or human (purchased from BioreclamationIVT, LLC) were pre-warmed to 37° C. Compounds were then added to the plasma samples to make a final concentration of 1 μM and vortexed. Duplicate samples of 100 μL each were taken out at Time 0, 10, 20, 30 and 60 min for extraction and analysis. Extraction and analysis of parent drug were by addition of 300 μL of acetonitrile containing 500 ng/mL of internal standard (labetalol), vortexing, and centrifugation. 150 μL of the supernatant was added to 100 μL of deionized water and 10 μL injected onto LC/MS.

Liver S9 Homogenate Stability—Liver S9 homogenate from pooled male rat or human (purchased from Xenotech, LLC, 20 mg protein/mL) was diluted with 0.05M KH$_2$PO$_4$, pH 7.4 buffer to make 0.8 mg protein/mL and pre-warmed to 37° C. Compounds were then added to the homogenate samples to make a final concentration of 1 μM and vortexed. Duplicate samples of 100 μL each were taken out at Time 0, 5, 15, 30 and 120 min for extraction and analysis. Extraction and analysis of parent drug were by addition of 300 μL of acetonitrile containing 100 ng/mL of internal standard (labetalol), vortexing, and centrifugation. 150 μL of the supernatant was added to 100 μL of deionized water and 10 μL injected onto LC/MS.

Liver Microsomal Stability—Liver microsome from pooled male rat or human (purchased from Xenotech, LLC, 20 mg protein/mL) was diluted with 0.05M KH$_2$PO$_4$, pH 7.4 buffer containing 5 mM MgCh to make 0.5 mg protein/mL and pre-warmed to 37° C. Compounds were then added to the homogenate samples to make a final concentration of 1 μM and vortexed. NADPH in 0.05M KH$_2$PO$_4$, pH 7.4 buffer was then added to make the final concentration of 2 mM to start the reaction. Duplicate samples of 100 μL each were taken out at Time 0, 3, 6, 10, 15, 20 and 30 min for extraction and analysis. Extraction and analysis of parent drug were by addition of 100 μL of acetonitrile containing 100 ng/mL of internal standard (labetalol), vortexing, and centrifugation.

10 µL of the supernatant was injected onto LC/MS. An incubation without the NADPH addition was used as a control for the experiment.

Cecal-Colonic Extract Stability—Female rats (non-fasted) were euthanized and the cecum and colon taken out and weighed. The intestinal contents in the cecum and colon were flushed out with 20 mL deionized water and the tissues re-weighed. Deionized water was added to the cecal-colonic content mixture to make a 10 X w/v dilution. The mixture was then homogenized by a Polytron homogenizer for 2 minutes and centrifuged at 5000 rpm in a Beckman Allegra 25r centrifuge for 10 minutes. The supernatant was taken out and warmed to 37° C. in a shaking water. 1.5 mL Aliquots were then added compounds to make a final concentration of 1 µM and vortexed. Duplicate samples of 100 µL each were taken out at Time 0, 10, 20, 40, 60 and 180 min for extraction and analysis. Extraction and analysis of parent drug were by addition of 300 µL of acetonitrile containing 500 ng/mL of internal standard (labetalol), vortexing, and centrifugation. 150 µL of the supernatant was added to 100 µL of deionized water and 10 µL injected onto LC/MS.

The invention claimed is:

1. A compound of formula I or a salt thereof:

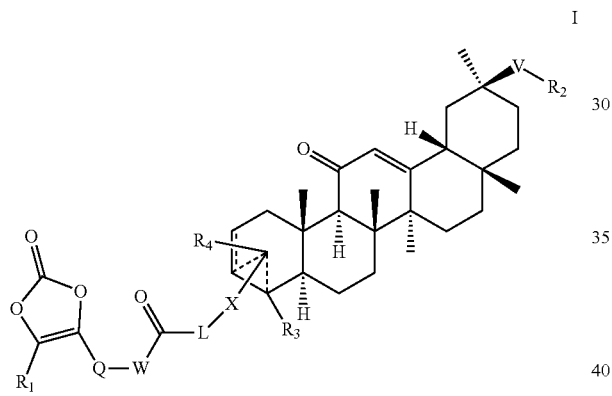

I wherein,

X is a bond, —O—, —C(O)—, —N($R_x$)—, —C(O)N($R_x$)—, —N($R_x$)—C(O)—, —S(O)$_n$—N($R_x$)— or —N($R_x$)—S(O)$_n$—;

L is a bond, alkylene wherein one or more non-adjacent methylene groups of said alkylene are replaced with —O—; divalent aryl or divalent heteroaryl; or L is alkylene-Y-alkylene wherein Y is O, $NR_x$, S, SO, $SO_2$ or a divalent heterocycle; wherein said alkylene groups are optionally substituted with OH, —C(O)O—$R_1$, alkyl or alkyl substituted with OH or —C(O)O—$R_1$; and wherein a carbon of said alkylene groups and $R_x$ optionally together form a heterocycle; provided that when X is other than a bond, then L is other than a bond;

W is O or S;

Q is a bond or alkylene;

$R_1$ is H, alkyl, a carbocycle or a heterocycle wherein said alkyl, carbocycle and heterocycle are each optionally substituted with halogen, OH, amino, oxo, carboxy, acyloxy, alkoxycarbonyl, alkoxyacyloxy, alkoxycarbonyloxy, aminocarbonyl, a carbocycle optionally substituted with alkyl, haloalkyl, oxo, amino and halogen and a heterocycle optionally substituted with alkyl, oxo, amino and halogen; and a carbocycle or heterocycle optionally substituted with alkyl, haloalkyl, oxo, amino and halogen;

V is —C(O)O—, —C(O)O—(CHR$_5$)—O—C(O)—, —C(O)O—(CHR$_5$)—O—C(O)—O—, —C(O)O—(CH$_2$)$_n$—Y—C(O)N(R$_5$)—, —C(O)N(R$_5$)—O—, —NH—C(O)—N(R$_5$)— or NH—S(O)$_n$—; wherein Y is a divalent heterocycle optionally substituted with alkyl, halogen, OH, amino, carboxyl and oxo;

$R_2$ is H or $R_5$;

$R_3$ is absent or alkyl;

$R_4$ is absent, H, OH, =O, —$R_6$, —O—$R_6$, —C(O)O—$R_6$, —O—C(O)—$R_6$, —O—C(O)—O—$R_6$, —O—C(O)—NR$_5$R$_6$, —NR$_5$R$_6$, —NR$_5$—C(O)—R$_6$, —NR$_5$—C(O)—O—R$_6$, —NR$_5$—SO$_2$—R$_6$, =N—O—R$_5$;

$R_5$ is H or alkyl optionally substituted with a carbocycle or heterocycle wherein said carbocycle and heterocycle are optionally substituted with halogen, OH, oxo and alkyl;

$R_6$ is H, alkyl, a carbocycle, a heterocycle wherein said alkyl, carbocycle and heterocycle are optionally substituted with halogen, OH, SH, alkylthio, —S(O)-alkyl, —SO$_2$-alkyl, amino, —NHC(O)-alkyl, oxo, alkyl, carboxyl, acyl, acyloxy, alkoxy, alkoxycarbonyl, a carbocycle optionally substituted with halogen, OH, amino or alkyl, or a heterocycle optionally substituted with halogen, OH, amino or alkyl; and wherein one or more non-adjacent methylene groups in each of said alkyl groups of $R_6$ are optionally replaced with —O— or —S—;

$R_x$ is H, —C(O)O—$R_1$, or alkyl optionally substituted with —C(O)O—$R_1$; and n is 1 or 2.

2. The compound of claim 1, having the structure of any one of Ia-Io:

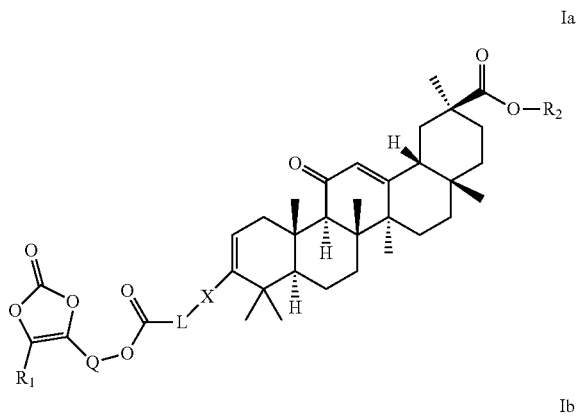

Ia

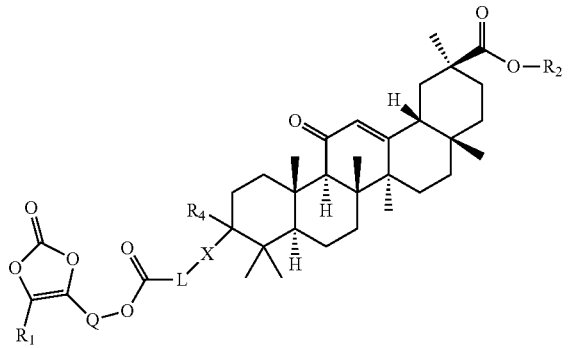

Ib

Ic
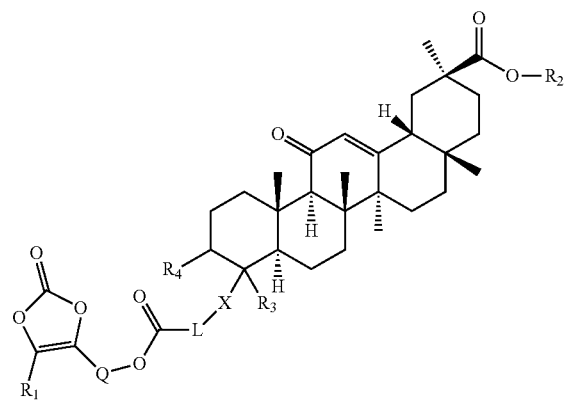
Ig
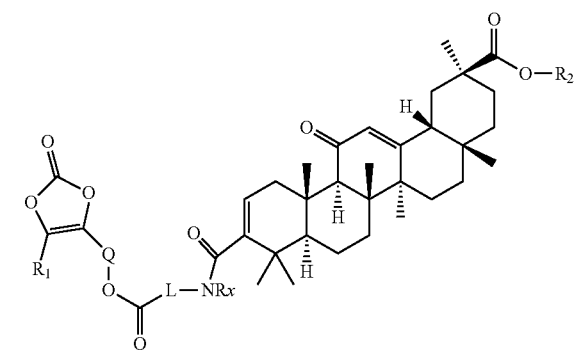
Id
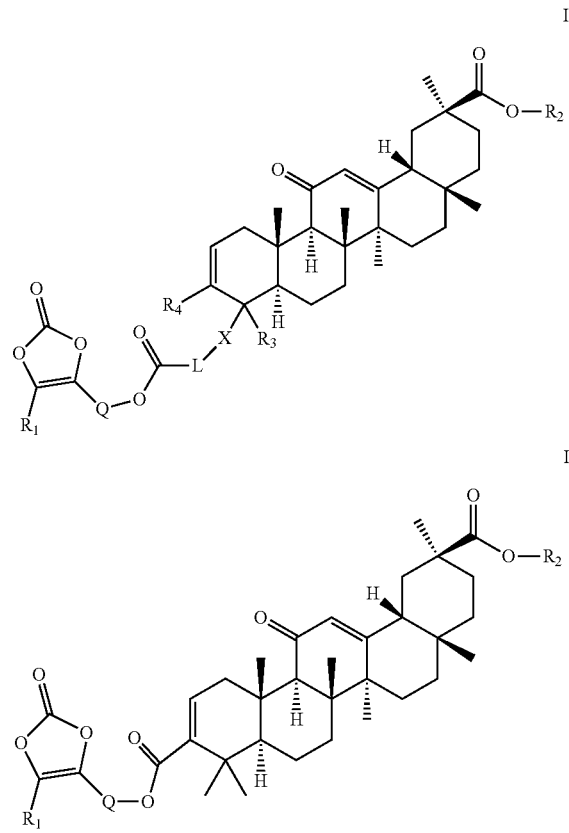
Ih
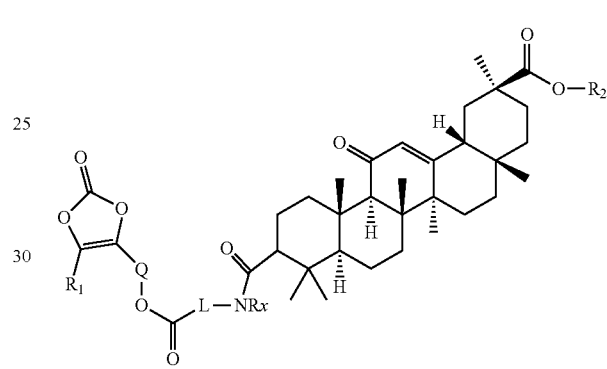
Ie
Ii
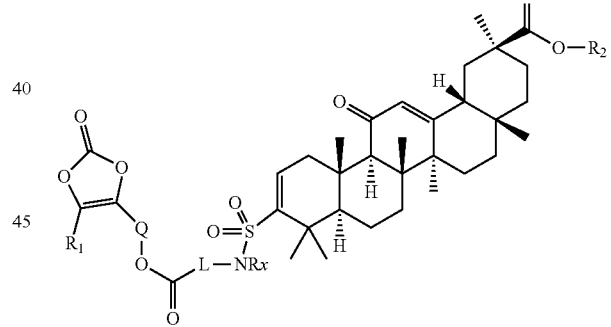
If
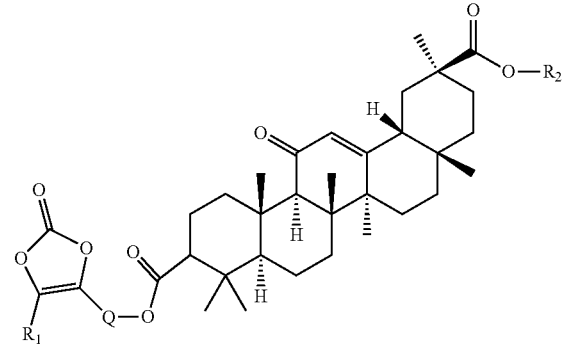
Ij
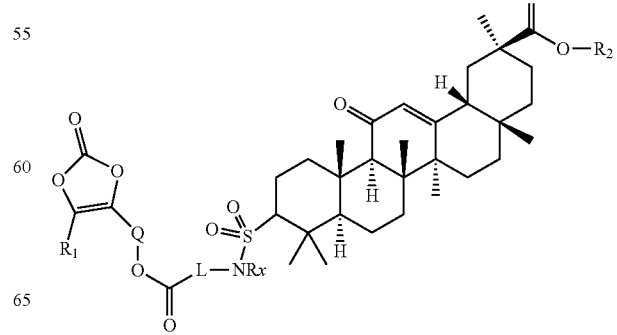
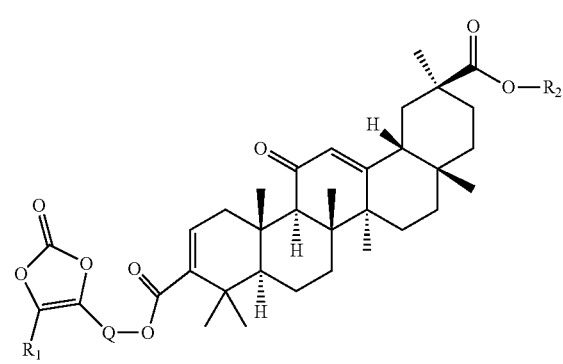

Ik
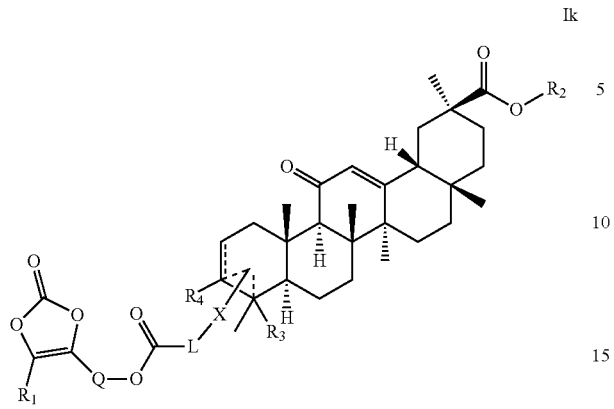
Lo
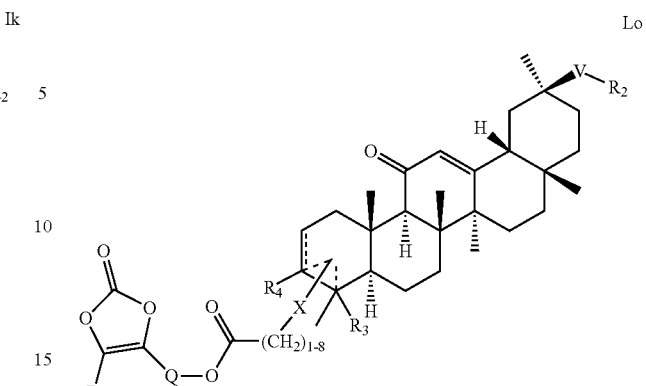
or Formula Ia'-If':
Il
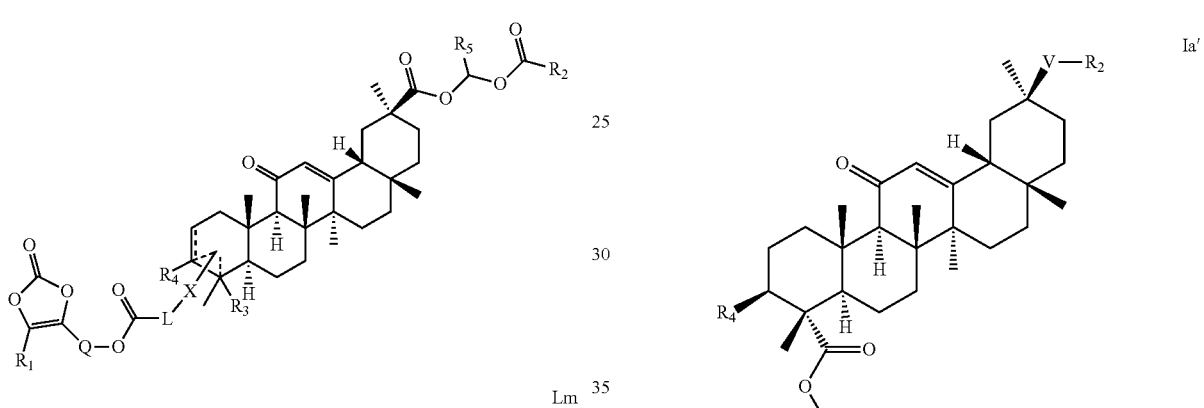
Ia'
Lm
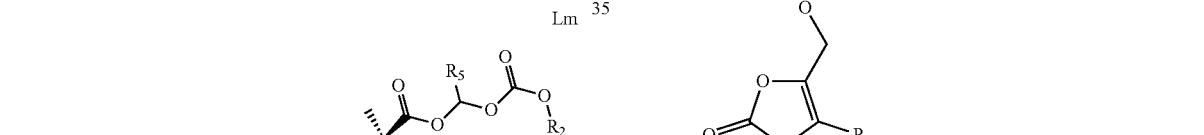
Ln
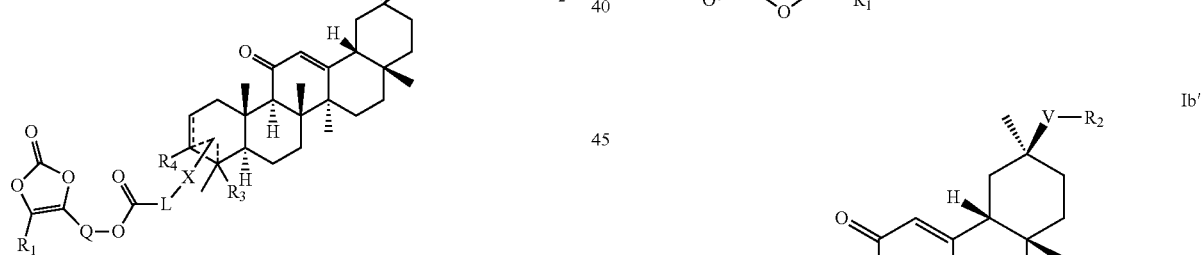
Ib'
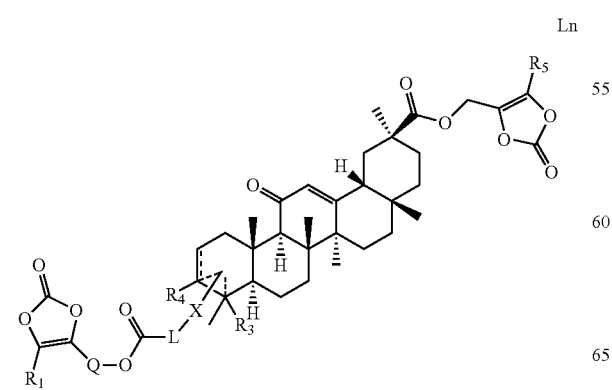

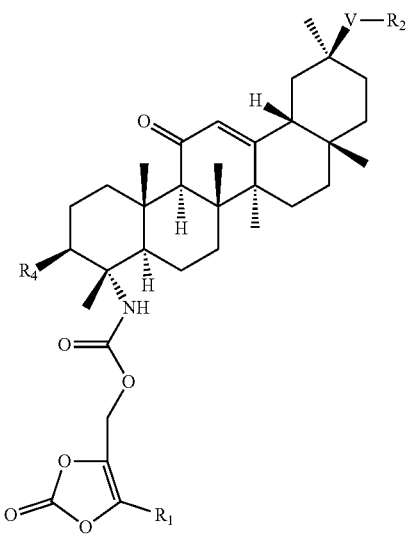

Ic'

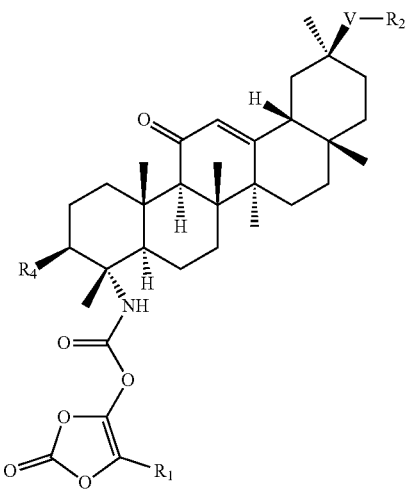

Id'

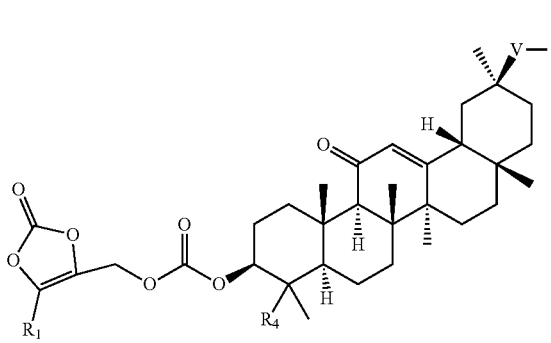

Ie'

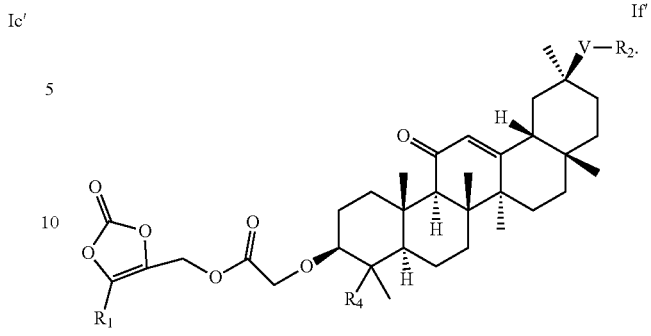

If'

3. The compound of claim 1, wherein V is —C(O)—O— and $R_2$ is H.

4. The compound of claim 1, wherein $R_1$ is methyl, ethyl or isopropyl.

5. The compound of claim 1, wherein X and L are both bonds.

6. The compound as claimed claim 1, wherein Q is O.

7. The compound as claimed in claim 1, wherein $R_3$ is methyl.

8. The compound as claimed in claim 1, wherein $R_4$ is —O—C(O)—$R_6$ and $R_6$ is alkyl, carbocycle or heterocycle; wherein said alkyl is optionally substituted with hydroxyl, halogen carboxy, alkoxy, alkylthio, amino, NHC(O)-alkyl, a heterocycle optionally substituted with alkyl; and said carbocycle and heterocycle are optionally substituted with halogen, hydroxyl and alkyl, wherein said alkyl is optionally substituted with hydroxyl, halogen carboxy; and wherein one or more non-adjacent methylene groups is replaced with —O—.

9. The compound as claimed in claim 1, wherein $R_4$ is $NH_2$, alkoxy, OH, =N—O-alkyl, =N—OH.

10. The compound as claimed in claim 1, wherein $R_4$ is $R_6$ and $R_6$ is phenyl optionally substituted with alkoxy.

11. The compound as claimed in claim 1, wherein $R_4$ is $R_6$ and $R_6$ is a heterocycle optionally substituted with halogen, alkyl, oxo and alkoxycarbonyl.

12. The compound as claimed in claim 1, wherein $R_4$ is —NHC(O)—$R_6$.

13. The compound as claimed in claim 1, claim 1, wherein $R_4$ is —NHC(O)—O—$R_6$.

14. The compound as claimed in claim 1, wherein $R_4$ is —O—C(O)—O—$R_6$.

15. The compound as claimed in claim 1, wherein $R_4$ is O—$R_6$.

16. The compound as claimed in claim 1, wherein $R_4$ is —$NR_5R_6$.

17. The compound as claimed in claim 1, wherein $R_4$ is —O—C(O)—$R_6$ and $R_6$ is methyl, ethyl or cyclopropyl.

18. A method of inhibiting conversion of cortisol to cortisone by 11β-HSD2 comprising contacting 11β-HSD2 with a compound of claim 1.

19. A method for treating a disease or condition mediated by the conversion of cortisol to cortisone by 11β-HSD2 in a mammal, comprising administering to said mammal an effective amount of a compound as claimed in claim 1.

20. A method for promoting potassium ion secretion into the colonic lumen of a mammal, comprising administering to said mammal an effective amount of a compound as claimed in claim 1.

21. A method for treating hyperkalemia in a mammal, comprising administering to said mammal an effective amount of a compound as claimed in claim 1.

22. A pharmaceutical composition comprising a compound as claimed in claim 1 and a pharmaceutically acceptable carrier, diluent or excipient.

* * * * *